US006656716B1

(12) United States Patent
Plowman et al.

(10) Patent No.: US 6,656,716 B1
(45) Date of Patent: Dec. 2, 2003

(54) POLYPEPTIDE FRAGMENTS OF HUMAN PAK5 PROTEIN KINASE

(75) Inventors: Gregory Plowman, San Carlos, CA (US); Ricardo Martinez, Foster City, CA (US); David Whyte, Belmont, CA (US)

(73) Assignee: Sugen, Inc., South San Francisco, CA (US)

( * ) Notice: Subject to any disclaimer, the term of this patent is extended or adjusted under 35 U.S.C. 154(b) by 0 days.

(21) Appl. No.: 09/688,188

(22) Filed: Oct. 16, 2000

Related U.S. Application Data

(62) Division of application No. 09/291,417, filed on Apr. 13, 1999.
(60) Provisional application No. 60/081,784, filed on Apr. 14, 1998.

(51) Int. Cl.$^7$ .................................................. C12N 9/12
(52) U.S. Cl. ........................ 435/194; 530/300; 530/350
(58) Field of Search ................................ 530/300, 350; 435/194

(56) References Cited

U.S. PATENT DOCUMENTS

| | | | |
|---|---|---|---|
| 4,343,940 A | 8/1982 | Kreighbaum | |
| 4,376,110 A | 3/1983 | David et al. | |
| 4,447,608 A | 5/1984 | Jones | |
| 4,757,072 A | 7/1988 | Kabbe | |
| 4,945,050 A | 7/1990 | Sanford | |
| 5,217,999 A | 6/1993 | Levitzki | |
| 5,302,606 A | 4/1994 | Spada | |
| 5,316,553 A | 5/1994 | Kaul | |
| 5,330,992 A | 7/1994 | Eissenstat | |
| 6,013,500 A | * 1/2000 | Minden | |

FOREIGN PATENT DOCUMENTS

| | | |
|---|---|---|
| EP | 0 520 722 A1 | 6/1992 |
| EP | 0 562 734 A1 | 9/1993 |
| EP | 0 566 226 A1 | 10/1993 |
| WO | 91/15495 | 10/1991 |
| WO | 92/20642 | 11/1992 |
| WO | 92/21660 | 12/1992 |
| WO | 93/09236 | 5/1993 |
| WO | 94/03427 | 2/1994 |
| WO | 94/14808 | 7/1994 |
| WO | 96/22976 | 8/1996 |
| WO | WO 97 42212 | 11/1997 |
| WO | WO 99 02699 | 1/1999 |
| WO | WO 99 07854 | 2/1999 |
| WO | WO 99 15635 | 4/1999 |
| WO | WO 99 32637 | 7/1999 |

OTHER PUBLICATIONS

GenBank Accession No. AAD01210. serine/threonine kinase [homo sapiens]. Melnick MB. Publicly available Jan. 5, 1999.*

Abe et al., "Molecular Characterization of a Novel Metabotropic Glutamate Receptor mGluR5 Coupled to Inositol Phosphate/Ca$^{2+}$ Signal," *J. Biol. Chem.* 267(19):13361–13368 (1992).

Abo et al., "PAK4, A Novel Effector fo Cdc42Hs, is Implicated in the Reorganization of the Actin Cytoskeleton and in the Formation of Filopodia," *EMBO J.* 17:6527–6540 (1998).

Allen et al., "Modulation of CD4 by suramin," *Clin. Exp. Immunol.* 91:141–146 (1993).

Allen et al., "PAK3 Mutation in Nonsyndromic X–linked Mental Retardation," *Nat. Genet.* 20:25–30 (1998).

Altschul et al., "Basic Local Alignment Search Tool," *J. Mol. Biol.* 215:403–410 (1990).

Altschul et al., "Gapped Blast and PSI–Blast: A New Generation of Protein Database Search Programs," *Nucleic Acids Research* 25:3389–3402 (1997).

Anafi et al., "Tyrphostin–Induced Inhibition of p210$^{bcr-abl}$ Tyrosine Kinase Activity Induces K562 to Differentiate," *Blood* 82:3524–3529 (1993).

Anafi et al., "SH2/SH3 Adaptor Proteins Can Link Tyrosine Kinases to a Ste20–Related Protein Kinase, HPK1*," *J. Biol. Chem.* 272:27804–27811 (1997).

Andrews et al. (American Veterinary Medicine Association Panel on Euthanasia),"1993 Report of the AVMA Panel on Euthanasia," *J. American Veterinary Medicine Association* 202(2):229–249 (1993).

Bagrodia et al., "Identification of a Mouse p21Cdc42/Rac Activated Kinase," *J. Biol. Chem* 270:22731–22737 (1995).

Baker et al., "Induction of acetylcholine receptor clustering by native polystyrene beads," *Journal of Cell Science* 102:543–555 (1992).

Barker et al., "In vitro activity of non–glutamate containing quinazoline–based thymidylate synthase inhibitors," *Proceedings of the American Association for Cancer Research* 32:327 at abstract No. 1939 (1991).

Bayer et al., "The Avidin–Biotin Complex in Affinity Cytochemistry," *Methods in Enzymology* 62:308–319 (1979).

Benoist and Chambon, "In vivo sequence requirements of the SV40 early promoter region," *Nature* 290:304–310 (1981).

Berger and Wahl, "Screening Colonies of Plaques with Radioactive Nucleic Acid Probes," *Meth. Enzym.* 152:415–423.

(List continued on next page.)

*Primary Examiner*—Ponnathapu Achutamurthy
*Assistant Examiner*—Kathleen Kerr
(74) *Attorney, Agent, or Firm*—Beth A. Burrous; Foley & Lardner

(57) ABSTRACT

The present invention related to the novel human kinase polypeptides STLK2, STLK3, STLK4, STLK5, STLK6, STLK7, ZC1, ZC2, ZC3, ZC4, KHS2, SULU1, SULU2, SULU3, GEK2, PAK4, and PAK5, nucleotide sequences encoding the novel kinase polypeptides, as well as various products and methods useful for the diagnosis and treatment of various kinase-related diseases and conditions.

15 Claims, 76 Drawing Sheets

OTHER PUBLICATIONS

Bertino, "Toward Improved Selectivity in Cancer Chemotherapy: The Richard and Hinda Rosenthal Foundation Award Lecture," *Cancer Research* 39:293–304 (1979).

Bilder et al., "Tyrphostins inhibit PDGF–induced DNA synthesis and associated early events in smooth muscle cells," *Am. J. Physiol.* 260(Cell Physiol.29):C721–C730 (1991).

Bollon and Stauver, "DNA Transformation Efficiency of Various Bacterial and Yeast Host–Vector Systems," *Journal of Clinical Hematology and Oncology* 10(2&3):39–48 (1980).

Botstein et al., "Making Mutations in vitro and Putting Them Back into Yeast," *Miami Winter Symposia—From Gene to Protein: Translation into Biotechnology*, edited by Ahmad et al., Academic Press, 19:265–274 (1982).

Brinster et al., "Factors Affecting the Efficiency of Introducing Foreign DNA into Mice by Microinjecting Eggs," *Proc. Natl. Acad. Sci. USA* 82:4438–4442 (1985).

Broach, "The Yeast Plasmid $2\mu$ Circle," *Cell* 28:203–204 (1982).

Broach, "The Yeast Plasmid $2\mu$ Circle," in *The Molecular Biology of the Yeast Saccharomyces: Life Cycle and Inheritance*, Cold Spring Harbor Laboratory, Cold Spring Harbor, NY, pp. 445–470 (1981).

Brown et al., "Human Ste20 Homologue hPAK1 Links GTPases to the JNK MAP Kinase Pathway," *Current Biol.* 6:598–605 (1996).

Brunton et al., "Anti–tumour activity of novel tryphostins in breast cancer cells," *Proceedings of the American Association for Cancer Research* 33:558 at abstract No. 3335 (1992).

Brycakaert et al., "Inhibition of Platelet–Derived Growth Factor–Induced Mitogenesis and Tyrosine Kinase Activity in Cultured Bone Marrow Fibroblasts by Tyrphostins," *Exp. Cell Research* 199:255–261 (1992).

Buccione et al., "The Acceleration of Anterograde Membrane Traffic is an Immediate Event Following the Activation of Multiple Plasms Membrane Receptors," *Mol. Bio. Cell* 6:291 (1995).

Bullock and Petrusz (eds.), *Techniques in Immunocytochemistry*, Academic Press, Orlando, FL: vol. 1 (1982), vol. 2 (1983), vol. 3 (Table of Contents Only).

Burbelo et al., "A Conserved Binding Motif Defines Numerous Candidate Target Proteins for Both Cdc42 and Rac GTPases," *J. Biol. Chem.* 270:29071–290740 (1995).

Burke et al., "Arylamides of Hydroxylated Isoquinolines as Protein–Tyrosine Kinase Inhibitors," *Bioorganic & Medical Chemistry Letters* 2(12):1771–1774 (1992).

Burke et al., "Bicyclic Compounds as Ring–Constrained Inhibitors of Protein–Tyrosine Kinase $p56^{lck\ 1}$," *Journal of Medicinal Chemistry* 36(4):425–432 (1993).

Campbell, *Monoclonal Antibody Technology: Laboratory Techniques in Biochemistry and Molecular Biology*, vol. 13, Elsevier Science Publishers, Amsterdam, The Netherlands (1984) (Table of Contents Only).

Capecchi, "Altering the Genome by Homologous Recombination," *Science* 244:1288–1292 (1989).

Capecchi, "High Efficiency Transformation by Direct Microinjection of DNA into Cultured Mammalian Cells," *Cell* 22:479–488 (1980).

Cenatiempo, "Prokaryotic gene expression in vitro: transcription–translation coupled systems," *Biochimie* 68:505–515 (1986).

Chard, *An Introduction ot Radioimmunoassay and Related Techniques*, Elsevier Science Publishers, Amsterdam, The Netherlands (1986) (Table of Contents Only).

Chater et al., "Streptomyces ØC31–Like Phages: Cloning Vectors, Genome Changes and Host Range," in *Sixth International Symposium on Actinomycetes Biology*, edited by Szabe et al., Akademiai Kaido, Budapest, Hungary, pp. 45–52 (1986).

Chen and Okayama, "High–Efficiency Transformation of Mammalian Cells by Plasmid DNA," *Molecular and Cellular Biology* 7(8):2745–2752 (1987).

Chomczynski and Sacchi, "Single–Step Method of RNA Isolation by Acid Guanidinium Thiocyanate–Phenol–Chloroform Extraction," *Analytical Biochemistry* 162:156–159 (1987).

Chu et al., "Electroporation for the efficient transfection of mammalian cells with DNA," *Nucleic Acids Research* 15:1311–1326 (1987).

Cullen, "HIV–1: Is Nef a PAK Animal?" *Curr. Biol.* 6:1557–1559 (1996).

Curiel et al., "Gene Transfer to Respiratory Epithelial Cells via the Receptor–mediated Endocytosis Pathway," *Am. J. Respir. Cell. Mol. Biol.* 6:247–252 (1992).

Curtin et al., "Inhibition of the growth of human hepatocellular carcinoma in vitro and in athymic mice by a quinazoline inhibitor of thymidylate synthase, CB3717," *Br. J. Cancer* 53:361–368 (1986).

Daniels et al., "Membrane Targeting of p21–Activated Kinase 1 (PAK1) Induces Neurite Outgrowth from PC12 Cells," *EMBO J.* 17:754–764 (1998).

Diener et al., "Activation of the c–Jun N–terminal Kinase Pathway by a Novel Protein Kinase Related to Human Germinal Center Kinase," *Proc. Natl. Acad. Sci.* 94:9687–9692 (1997).

Dolle et al., "5,7–Dimethoxy–3–(4–pyridinyl)quinoline is a Potent and Selective Inhibitor of Human Vascular β–Type Platelet–Derived Growth Factor Receptor Tyrosine Kinase," *J. Med. Chem.* 37:2627–2629 (1994).

Dong et al., "Activation of tumoricidal properties in macrophages by lipopolysaccharide requires protein–tyrosine kinase activity," *Journal of Leukocyte Biology* 53:53–60 (1993).

Dong et al., "Protein Tyrosine Kinase Inhibitors Decrease Induction of Nitric Oxide Synthase Activity in Lipopolysaccharide–Responsive and Lipopolysaccharide–Nonresponsive Murine Macrophages," *The Journal of Immunology* 151(5):2717–2724 (1993).

Dreborg et al., "Ch. 10—The chemistry and standardization of allergens," in *Handbook of Experimental Immunology—Vol. 1: Immunochemistry*, 4th Ed., edited by Weir et al., Balckwell Scientific Publications, Oxford, England, pp. 10.1–10.28 (1986).

Engvall and Perlmann, "Enzyme–Linked Immunosorbent Assay, ELISA. III. Quantitation of Specific Antibodies by Enzyme–Labeled Anti–Immunoglobulin in Antigen–Coated Tubes," *J. Immunology* 109:129–135 (1972).

Faure et al., "A Member of the Ste20/PAK Family of Protein Kinases is Involved in Both Arrest of Xenopus Oocytes at G2/Prophase of the First Meitic Cell Cycle and in prevention of Apoptosis," *EMBO J.* 16:5550–61 (1997).

Felgner et al., "Lipofection: A Highly Efficient, Lipid–mediated DNA–transfection Procedure," *Proc. Natl. Acad. Sci. USA* 84:7413–7417 (1987).

Felgner and Felgner, "Cationic Liposome–Mediated Transfection," *Nature* 337:387–388 (1989).

Fernandes et al., "Biochemical and Antitumor Effects of 5,8–Dideazaisopteroylglutamate, a Unique Quniazoline Inhibitor of Thymidylate Synthase," *Cancer Research* 43:1117–1123 (1983).

Ferris et al., "Synthesis of Quinazoline Nucleosides from Ribose and Anthranilonitrile. Application of Phase–Transfer Catalysis in Nucleoside Synthesis," *J. Org. Chem.* 44(2):173–178 (1979).

Frost et al., "Cross–Cascade Activation of ERKs and Ternary Complex Factors by Rho Family Proteins," *EMBO J.* 16:6426–6438 (1997).

Frost et al., "Differential Effects of PAK1–activating Mutations Reveal Activity–dependent and –independent Effects on Cytoskleletal Regulation," *J. Biol Chem.* 273:28191–28198 (1998).

Fry et al., "A Specific Inhibitor of the Epidermal Growth Factor Receptor Tyrosine Kinase," *Science* 265:1093–1095 (1994).

Galisteo et al., "The Adaptor Protein Nck Links Receptor Tyrosine Kinases with the Serine–Threonine Kinase Pak1," *J. Biol. Chem.* 271:20997–21000 (1996).

Gazit et al., "Tyrphostins 1. Synthesis and Biological Activity of Protein Tyrosine Kinase Inhibitors," *J. Med. Chem.* 32:2344–2352 (1989).

Gazit et al., "Tyrphostins. 3. Structure–Activity Relationship Studies of a α–Substituted Benzylidenemalononitrile 5–S–Aryltyrphostins," *J. Med. Chem.* 36:3556–3564 (1993).

Gerard et al., "cDNA Synthesis by Cloned Moloney Murine Leukemia Virus Reverse Transcriptase Lacking Rnase H Activity," *Focus* 11(4):66–69 (1989).

Gilman et al., "Isolation of sigma–28–specific promoters from Bacillus subtilis DNA," *Gene* 32:11–20 (1984).

Glick and Whitney, "Factors affecting the expression of foreign proteins in *Escherichia coli*," *Journal of Industrial Microbiology* 1:277–282 (1987).

Goding, "Conjugation of Antibodies with Fluorochromes: Modifications to the Standard Methods," *J. Immunological Methods* 13:215–226 (1976).

Gold et al., "Translational Initiation in Prokaryotes," *Ann. Rev. Microbiol.* 35:365–403 (1981).

Gottesman, "Bacterial Regulation: Global Regulatory Networks," *Ann. Rev. Genet.* 18:415–441 (1984).

Gryczan, "Ch. 10—Molecular Cloning in Bacillus subtilis," in *The Molecular Biology of the Bacilli*, edited by Dubnau, Academic Press, New York, pp. 307–329 (1982).

Hamer and Walling, "Regulation In Vivo of a Cloned Mammalian Gene: Cadmium Induces the Transcription of a Mouse Metallothionein Gene in SV40 Vectors," *J. of Molecular and Applied Genetics* 1:273–288 (1982) (also referred to as Hammer).

Hammer et al., "Spontaneous Inflammatory Disease in Transgenic Rats Expressing HLA–B27 and Human $\beta_2$m: An Animal Model of HLA–B27–Associated Human Disorders," *Cell* 63:1099–1112 (1990).

Hirst et al., "Predicting Leucine Zipper Structures From Sequence," *Protein Engineering* 9:657–662 (1996).

Houdebine and Chourrout, "Transgenesis in Fish," *Experientia* 47:891–897 (1991).

Hu et al., "Human HPK1, a Novel Human Hematopoietic Progenitor Kinase that Activates the JNK/SAPK Kinase Cascade," *Genes and Dev.* 10:2251–2264 (1996).

Hurby et al., in *Synthetic Peptides: A User's Guide*, edited by Grant, Washington University School of Medicine, W.H. Freeman and Company, New York, pp. 289–307 (1992).

Hutchison et al., "Isolation of TAO1, a Protein Kinase That Activated MEKs in Stress–activated Protein Kinase Cascades," *J. Biol. Chem.* 273:28625–28632 (1998).

Innis et al., *PCR Protocols: A Guide to Methods and Applications*, edited by Michael A. Innis et al., Academic Press, San Diego (1990) (Table of Contents Only).

Izaki, *Japanese Journal of Bacteriology* 33(6):729–742 (1978).

Jackman et al., "ICI D1694, a Quinazoline Antifolate Thymidylate Synthase Inhibitor That Is a Potent Inhibitor of L1210 Tumor Cell Growth in Vitro and in Vivo: A New Agent for Clinical Study," *Cancer Research* 51:5579–5586 (1991).

Jasny, "Insect Viruses Invade Biotechnology," *Science* 238:1653 (1987).

John and Twitty, "Plasmids as Epidemiologic Markers in Nosocomial Gram–Negative Bacilli: Experience at a University and Review of the Literature," *Reviews of Infectious Diseases* 8:693–704 (1986).

Johnston and Hopper, "Isolation of the yeast regulatory gene GAL4 and anlaysis of its dosage effects on the galactose/melibiose regulon," *Proc. Natl. Acad. Sci. USA* 79:6971–6975 (1982).

Jones et al., "Quinazoline Antifolates Inhibiting Thymidylate Synthase: Varation of the Amino Acid," *J. Med. Chem.* 29:1114–1118 (1986).

Joyner et al., "Production of a mutation in mouse En–2 gene by homologous recombination in embryonic stem cells," *Nature* 338:153–156 (1989).

Kasprzak et al., "Location of a Contact Site Between Actin and Myosin in the Three–Dimensional Structure of the Acto–S1 Complex," *Biochemistry* 28:9230–9238 (1989).

Kaur et al., "Tyrphostin induced growth inhibition: correlation with effect on $p210^{bcr-alb}$ autokinase activity in K562 chronic myelogenous leukemia," *Anti–Cancer Drugs* 5:213–222 (1994).

Kendall and Cohen, "Plasmid Transfer in Streptomyces lividans: Identification of a kil–kor System Associated with the Transfer Region of PIJ101," *Journal of Bacteriology* 169:4177–4183 (1987).

Kiefer et al., "HPK1, a Hematopoietic Protein Kinase Activating the SAPK/JNK Pathway," *EMBO J.* 15:7013–7025 (1996).

King et al., "Site–specific dephosphorylation and deactivation of the human insulin receptor tyrosine kinase by particulate and soluble phosphotyrosyl protein phosphatases," *Biochem. J.* 275:413–418 (1991).

King et al., "The Protein Kinase Pak3 Positively Regulates Raf–1 Activity Through Phosphorylation of Serin 338," *Nature* 396:180–183 (1998).

Knaus et al., "Regulation of Human Leukocyte p21–Activated Kinases Through G Protein–Coupled Receptors," *Science* 269:221–223 (1995).

Knuutila et al., "DNA Copy Number Amplifications in Human Neoplasms: Review of Comparative Genomic Hybridization Studies," *Am. J. Pathol* 152:1107–1123 (1998).

Kohler and Milstein, "Continuous cultures of fused cells secreting antibody of predefined specificity," *Nature* 256:495–497 (1975).

Kozak, "An analysis of 5'–noncoding sequences from 699 vertebrate messenger RNAs," *Nucleic Acids Research* 15:8125–8148 (1987).

Kumar et al., "Novel Homologues of CSBP/p38 MAP Kinase: Activation, Substrate Specificity and Sensitivity to Inhibition by Pyridinyl Imidazoles," *Biochem. Biophys. Res. Commun.* 235:533–528 (1997).

Kuo et al., "Effects of signalling transduction modulators on the transformed phenotypes in v–H–ras–transformed NIH 3T3 cells," *Cancer Letters* 74:197–202 (1993).

Kuramochi et al., "LOK Is a Novel Mouse STE20–like Protein Kinase That Is Expressed Predominantly in Lymphocytes," *J. Biol. Chem.* 272:22679–22684 (1997).

Lee and Skibo, "Active–Site–Directed Reductive Alkylation of Xanthine Oxidase by Imidazo[4,5–g]quinazoline–4,9–diones Functionalized with a Leaving Group," *Biochemistry* 26:7355–7362 (1987).

Leeuw et al., "Interaction of a G–protein β–subunit with a Conserved Sequence in Ste20/PAK Family Protein Kinases," *Nature* 391:191–195 (1998).

Lemus et al., "Studies of Extended Quinone Methides. Synthesis and Physical Studies of Purine–like Monofunctional and Bifunctional Imidazo[4,5–g]quinazoline Reductive Alkylating Agents," *J. Org. Chem.* 54:3611–3618 (1989).

Levitzki, "Tyrphostins; tyrosine kinase blockers as novel antiproliferative agents and dissectors of signal transduction," *FASEB J.* 6:3275–3282 (1992).

Ley and Seng, "Synthesis Using Benzofuorxan," *Synthesis* 1975:415–422 (1975).

Lu et al., "CDC42 and Rac1 are implicated in the Activation of the Nef–associated Kinase and Replication of HIV–1," *Current Biology* 6:1677–1684 (1996).

Lui et al., "A Drosophila TNF–receptor–associated Factor (TRAF) Binds the Ste20 Kinase Misshapen and Activates Jun Kinase," *Curr. Biol.* 9:101–104 (1999).

Lupas et al., "Predicting Coiled Coils from Protein Sequences," *Science* 252:1162–1164 (1991).

Lupas, "Prediction and Analysis of Coiled–Coil Structures," *Meth. Enzymology* 266:513–525 (1996).

Lutz et al., "The Distribution of Two hnRNP–Associated Proteins Defined by a Monoclonal Antibody Is Altered in Heat–Shocked HeLa Cells," *Experimental Cell Research* 175:109–124 (1988).

Lyall et al., "Tyrphostins Inhibit Epidermal Growth Factor (EGF)–Receptor Tyrosine Kinase Activity in Living Cells an EGF–stimulated Cell Proliferation," *J. Biol. Chem.* 264:14503–14509 (1989).

Madaule et al., "A Novel Partner for the GTP–bound Forms of rho and rac," *FEBS Letters* 377:243–238 (1995).

MaGuire et al., "A New Series of PDGF Receptor Tyrosine Kinase Inhibitors: 3–Substituted Quinoline Derivatives," *J. Med. Chem.* 37:2129–2137 (1994).

Maniatis, "Ch. 11—Recombinant DNA Procedures in the Study of Eukaryotic Genes," in *Cell Biology: A Comprehensive Treatise, vol. 3, Gene Sequence Expression,* Academic Press, NY, pp. 563–608 (1980).

Manser et al., "A Brain Serine/Threonine Protein Kinase Activated by Cdc42 and Rac1," *Nature* 367:40–46 (1994).

Manser et al., "PAK Kinases are Directly Coupled to the PIX Family of Nucleotide Exchange Factors," *Mol. Cell* 1:183–192 (1998).

Mark et al., "Instabiity of Dinucleotide Repeats in Hodgkins's Disease," *Am. J. Hematol.* 57:148–152 (1998).

Maxwell et al., "$^{19}$F Nuclear Magnetic Resonance Imaging of Drug Distribution in Vivo: The Diposition of an Antifolate Anticancer Drug in Mice," *Magnetic Resonance in Medicine* 17:189–196 (1991).

McKnight, "Functional Relationships between Transcriptional Control Signals of the Thymidine Kinase Gene of Herpes Simplex Virus," *Cell* 31:355–365 (1982).

Miller et al., "An Insect Baculovirus Host–Vector System for High–Level Expression of Foreign Genes," in *Genetic Engineering: Principles and Methods,* edited by Setlow et al., Plenum Press, 8:277–298 (1986).

Miller, "Human gene therapy comes of age," *Nature* 357:455–460 (1992).

Mini et al., "Cytotoxic Effects of Folate Antagonists against Methotrexate–resistant Human Leukemic Lymphoblast CCRF–CEM Cell Lines," *Cancer Research* 45:325–330 (1985).

Nelson et al., "Detection of Acridinium Esters by Chemiluminescence," *Nonisotopic DNA Probe Techniques,* ed. Larry J. Kricka, (San Diego: Academic Press, Inc.) pp. 275–310 (1992).

Nikolic et al., "The p35/Cdk5 Kinase is a Neuron–Specific Rac Effector that Inhibits Pak1 Activity," *Nature* 395:194–198 (1998).

Okayama and Berg, "A cDNA Cloning Vector That Permits Expression of cDNA Inserts in Mammalian Cells," *Molecular and Cellular Biology* 3:280–289 (1983).

Osada et al., "A Domain Containing the Cdc42/Rac Interactive Binding (CRIB) Region of p65 PAK Inhibits Transcriptional Activation and Cell Tranformation Mediated by the Ras–Rac Pathway," *FEBS Letters* 404:227–233 (1997).

Peterson and Barnes, "Genistein and Biochanin A Inhibit the Growth of Human Prostate Cancer Cells but not Epidermal Growth Factor Receptor Tyrosine Autophosphorylation," *The Prostate* 22:335–345 (1993).

Phillips and Castle, "Quino[1,2–c]quinazolines. I. Synthesis of Quino[1,2–c]quinazolinium Derivatives and the Related Indazolo[2,3–a]quinoline Derivatives as Analogs of the Antitumor Benzo[c]phenanthridine Alkaloids," *J. Heterocyclic Chemistry* 17:1489–1496 (1980).

Pillemer et al., "Insulin Dependence of Murine Lymphoic T–Cell Leukemia," *Brit. J. Cancer* 50:80–85 (1992).

Pombo et al., "Activation of a Human Ste20–like Kinase by Oxidant Stress Defines a Novel Response Pathway," *EMBO J.* 17:4537–4546 (1996).

Pombo et al., "Activation of the SAPK Pathway by the Human STE20 Homologue Germinal Centre Kinase," *Nature* 377:750–754 (1995).

Pombo et al., "Activation of the Ste20–like Oxidant Stress Response Kinase–1 During the Initial Stages of Chemical Anoxia–induced Necrotic Cell Death," *J. Biol. Chem.* 272:29372–29379 (1997).

Posner et al., "Kinetics of Inhibition by Tyrphostins of the Tyrosine Kinase Activity of the Epidermal Growth Factor Receptor and Analysis by a New Computer Program," *Molecular Pharmacology* 45:673–683 1994.

Pursel et al., "Genetic Engineering of Livestock," *Science* 244:1281–1288 (1989).

Qian et al., "Dominant–negative Zeta–associated Protein 70 Inhibits T Cell Antigen Receptor Signaling," *J. Exp. Med.* 183:611–620 (1996).

Qian et al., "Purification and Cloning of a Protein Kinase that Phosphorylates and Activates the Polo–Like Kinase Plx1," *Science* 282:1701–1704 (1998).

Reece et al., "Pharmacokinetics of Trimetrexate Administered by Five–Day Continuous Infusion to Patients with Advanced Cancer," *Cancer Research* 47:2996–2999 (1987).

Ren et al., "In its Active Form, the GTP–Binding Protein rab8 Interacts with a Stress–Activated Protein Kinase," *Proc. Natl. Acad. Sci.* 93:5151–5155 (1996).

Rendu et al., "Inhibition of Platelet activation by Tyrosine Kinase Inhibitors," *Biochemical Pharmacology* 44(5):881–888 (1992).

Robertson, *Teratocarcinomas and embryonic stem cells: a practical approach,* IRL Press (1987) (Table of Contents).

Roe et al., "Tousled Is a Nuclear Serine/Threonine Protein Kinase that Requires a Coiled–coil Region for Oligomerization and Catalytic Activity," *J. Biol. Chem.* 272:5838–5845 (1997).

Rubin, "Drosophila melanogaster as an Experimental Organism," *Science* 240:1453–1459 (1988).

Rudel and Bokoch, "Membrane and Morphological Changes in Apoptotic Cells Regulated by Caspase–Mediated Activation of Pak2," *Science* 276:1571–4 (1997).

Sambrook, Maniatis and Fritsch, *Molecular Cloning: A Laboratory Manual, $2^{nd}$ Edition,* Cold Spring Harbor Laboratory Press (1989) (Table of Contents—All Three Volumes).

Sauro and Thomas, "Decreased Sensitivity of Aorta from Hypertensive Rats to Vasorelaxation by Tyrphostin," *Life Sciences* 53:PL371–376 (1993).

Sauro and Thomas, "Tyrphostin Attenuates Platelet–Dervied Growth Factor–Induced Contraction in Aortic Smooth Muscle Through Inhibition of Protein Tyrosine Kinase(s)," *The Journal of Pharamacology and Experimental Therapeutics* 267:1119–1125 (1993).

Schinkmann and Blenis, "Cloning and Characterization of a Human STE20–like Protein Kinase with Unusual Cofactor Requirements," *J. Biol. Chem.* 272:28695–28703 (1997).

Schlesinger et al., "The Tao of MEKK," *Frontiers in Bioscience* 3:D1181–6 (1998).

Sculier et al., "Role of an Intensive Care Unit (ICU) in a Medical Onocology Department," *Cancer Immunol. and Immunotherapy* 23:A65 at abstract No. 257 (1986).

Shi and Kehrl, "Activation of Stress–activated Protein Kinase/c–Jun N–terminal Kinase, but Not NF–κB, by the Tumor Necrosis Factor (TNF) Receptor 1 Through a TNF Receptor–associated Factor 2– and Germinal Center Kinase Related–depndent Pathway," *J. Biol. Chem.* 272:32102–32107 (1997).

Sikora and Grzelakowska–Sztabert, "Quinazoline CB 3717 and CB 3703 Inhibitors of Folate Retention and Metabolism in Ehrlich Ascites Carcinoma Cells and Some Organs of the Host–Mouse," *Cancer Letters* 23:289–295 (1984).

Sikora et al., "Development of an Assay for the Estimation of $N^{10}$–Propargyl–5,8–dideazafolic Acid Polyglutamates in Tumor Cells," *Analytical Biochemistry* 172:344–355 (1988).

Silver et al., "Amino terminus of the yeast GAL4 gene product is sufficient for nuclear localization," *Proc. Natl. Acad. Sci. USA* 81:5951–5955 (1984).

Simons et al., "Gene Transfer into Sheep," *Bio/Technology* 6:179–182 (1988) (also referred to as Simms or Simmons).

Smith and Waterman, "Identification of Common Molecular Subsequences," *J. Mol. Biol.* 147:195–197 (1981).

St. Groth and Scheidegger, "Production of Monoclonal Antibodies: Strategy and Tactics," *J. Immunol. Methods* 35:1–21 (1980).

Sternberger et al., "The Unlabeled Antibody Enzyme Method of Immunohistochemistry: Preparation and Properties of Soluble Antigen–Antibody Complex (Horseradish Peroxidase–Antihorseradish Peroxidase) and its Use in Idnetification of Spirochetes," *J. Histochemistry and Cytochemistry* 18(5):315–333 (1970).

Su et al., "NIK is a New Ste20–related Kinase that Binds NCK and MEKK1 and Activates the SAPK/JNK Cascade via a Conserved Regulatory Domain," *EMBO J.* 16:1279–1290 (1997).

Su et al., "The Drosophila Ste20–related Kinase Misshapen is Required for Embryonic Dorsal Closure and Acts Through a JNK MAPK Module on an Evolutionarily Coserved Signaling Pathway," *Genes Dev.* 12:2371–2380 (1998).

Sudol, "Structure and Function of the WW Domain," *Prog. Biochys. Mol. Bio.* 65:113–132 (1996).

Swantek et al., "Jun N–Terminal Kinase/Stress–Activated Protein Kinase (JNK/SAPK) Is Required for Lipopolysaccharide Stimulation of Tumor Necrosis Factor Alpha (TNF–α) Translation: Glucocorticoids Inhibit TNF–α Translation by Blocking JNK/SAPK," *Mol. Cell. Biol.* 6274–6282 (1997).

Szczepanowska et al., "Identification by Mass Spectrometry of the Phosphorylated Residue Responsible for Activation of the Catalytic Domain of Myosin I Heavy Chain Kinase, A Member of the PAK/STE20 Family," *Proc. Natl. Acad. Sci.* 94:8503–8508 (1997).

Tang et al., "Kinase–Deficient Pak1 Mutants Inhibit Ras Transformation of Rat–1 Fibroblasts," *Mol. Cell. Biol.* 17:4454–4464 (1997).

Tijssen, *Practice and Theory of Enzyme Immunoassays: Laboratory Techniques in Biochemistry and Molecular Biology,* vol. 15, Elsevier Sciences Publishers, Amsterdam, The Netherlands (1985) (Table of Contents Only).

Treisman et al., "Misshapen Encodes a Protein Kianse Involved in Cell Shape Control in Drosophila," *Gene* 186:119–125 (1997).

Ulmanen et al., "Transcription and Translation of Foreign Genes in Bacillus subtilis by the Aid of a Secretion Vector," *Journal of Bacteriology* 162:176–182 (1985).

Van Arsdale and Ware,"TNF Receptor Signal Transduction," *J. Immunol.* 153:3043–3050 (1994).

Wang et al., "Activation of the Hematopoietic Progenitor Kinase–1 (HPK1)–dependent, Stress–activated c–Jun N–terminal Kinase (JNK) Pathway by Transforming Growth Factor β (TGF–β)–activated Kinase (TAK1) a Kinase Mediator of TGF β Signal Transduction," *J. Biol. Chem.* 272:22771–22775 (1997).

Ward et al., "Construction and characterisation of a series of multi–copy promoter–probe plasmid vectors for Streptomyces using the aminoglycoside phosphotransferase gene from Tn5 as indicator," *Mol. Gen. Genet.* 203:468–478 (1986).

Wilchek and Jakoby, "The Literature on Affinity Chromatography," *Methods in Enzymology* 34:3–10 (1974) (also referred to as Jacoby).

Wolbring et al., "Inhibition of GTP–utilizing Enzymes by Tyrphostins," *J. Biol. Chem.* 269:22470–22472 (1994).

Wu et al., "Molecular Charaterization of Ste20p, a Potential Mitogea–activated protein or Extracellular Signal–regulated Kinase Kinase (MEK)Kinase Kinase from *Saccharomyces cerevisiae*," J. Biol. Chem. 270:15984–15992 (1995).

Xu et al., "Three–dimensional Structure of the Tyrosine Kinase c–Src," *Nature* 385:595–602 (1997).

Yablonski et al., "A Nck–Pak1 Signaling Module is Required for T–cell Receptor–mediated Activation of NFAT, but not of JNK," *EMBO J.* 17:5647–5657 (1998).

Yan et al., "Activation of Stress–activated Protein Kinase by MEKK1 Phosphorylation of its Activator SEK1," *Nature* 372:798–800 (1994).

Yanagisawa et al., "A Novel Serine/Threonine Kinase Gene, Gek, 1, Is Expressed in Meiotic Testicular Germ Cells and Primordial Germ Cells," *Mol. Reprod. and Dev.* 45:411–420 (1996).

Yang et al., "In Vivo and In Vitro Gene Transfer to Mammalian Somatic Cells by Particle Bombardment," *Proc. Natl. Acad. Sci. USA* 87:9568–9572 (1990).

Yao et al., "A Novel Human STE20–Related Protein Kinase, HGK, That Specifically Activates the c–Jun N–terminal Kinase Signaling Pathway," *J. Biol. Chem.* 274:2118–25 (1999).

Yoneda et al., "The Antiproliferative Effects of Tyrosine Kinase Inhibitors Tyrphostins on a Human Squamous Cell Carcinoma in Vitro and in Nude Mice," *Cancer Research* 51:4430–4435 (1991).

Yuan, "Transducing Signals of Life and Death," *Curr. Opinion in Cell. Biol.* 9:247–251 (1997).

Zhang et al., "Rho Family GTPases Regulate p38 Mitogen–activated Protein Kinase Through the Downstream Mediator Pak1," *J. Biol. Chem.* 270:23934–23936 (1995).

Zhu and Hedgecock, "Mig–15 Encodes a Novel Ser/Thr Protein Kinase of the Ste–20/p65PAK Family," *Worm Breeder's Gazette* 14:76 (1997).

Bucher et al., "A Flexible Motif Search Technique Based On Generalized Profiles", Computers And Chemistry, Gb, Pergamon Press, Oxford, vol. 20, No. 1, pp. 3–23, 1996.

Database EMBL [Online], ID: AF099989, Johnston et al., "SPAK: A Novel Ste–20 Related Kinase Expressed In The Pancreas", Nov. 11 1998.

Database EMBL [Online], ID: AF017635, Baytel et al., "Homo Sapiens DCHT mRNA, Complete CDs", Sep. 23, 1997.

Database EMBL [Online], ID: MMAA20708, Marra et al., "mp54a01.r1 Soares 2NbMT Mus Musculus cDNA Clone 573000 5'", Nov. 21, 1996.

Database EMBL [Online], ID: HS130B11B, Fujiwara et al., "Human Fetal Brain cDNA 5'–end GEN–130B11", Aug. 25, 1995.

Database EMBL [Online], ID: A766905, NCI–CGAP:"... Homo Sapiens cDNA Clone Image:1301771 Similar To TR:Q42341 Q42341 Serine–Threonine Protein Kinase ...", 30 Jan. 1998.

Su et al., "NIK Is A New Ste20–Related Kinase That Binds NCK and MEKK1 and Activates The SAPK/JNK Cascade Via A Conserved Regulatory Domain", The EMBO Journal, vol. 16, No. 6, pp. 1279–1290, 1997.

Database EMBL [Online], ID: AB011123, Ohara et al., "Homo Sapiens mRNA For KIAA0551 Protein, Partial CDs", Apr. 10, 1998.

Database EMBL [Online], ID: AA865818, NCI–CGAP:"... Homo Sapiens cDNA Clone Image:1456752 3' Similar To TR:P97820 P97820NIK ... ", Mar. 16, 1998.

Database EMBL [Online], ID: HS571200, Hillier et al., "yr32h11.r1 Homo Sapiens cDNA Clone 207045 5' ", Sep. 15, 1995.

Database EMBL [Online], ID: HS1254577, Hillier et al., "... Homo Sapiens cDNA Clone 796310 5' Similar To WP:ZC504.4 CE02384 Serine/Threonine Protein Kinase", Jun. 13, 1997.

Database EMBL [Online], ID: AA885355, NCI–CGAP: "... Homo Sapiens cDNA Clone Image:1460315 3' Similar to AP:T17E9.1 CEO1405", Mar. 30, 1998.

Database EMBL [Online], ID: AA576724, NCI–CGAP: "... Homo Sapiens cDNA Clone Image:1074607", Sep. 11, 1997.

Database EMBL [Online], ID: MM1266197, Marra et al., "... Mus Musculus cDNA Clone 805425 5' Similar To WP:T17E9.1 CE01405", Jun. 22, 1997.

Database EMBL [Online], ID: HS1259479, NCI–CGAP: ". . . Homo Sapiens cDNA Clone Image:814858 3' Similar To TR:G881958 C881958 MESS1", Jun. 20, 1997.

Database EMBL [Online], ID: HS1254308, NCI–CGAP: ". . . Homo Sapiens cDNA Clone Image:814858 5' Similar To WP:T19A5.2 CE07510 Serine. Threonine Kinase", Jun. 16, 1997.

Database EMBL [Online], ID: AB015718, Kuramochi et al., "Homo Sapiens LOK mRNA For Protein Kinase, Complete CDs", Dec. 14, 1998.

Database EMBL [Online], ID: AA634299, Hillier et al., "... Homo Sapiens cDNA Clone 743770 3'", Oct. 31, 1997.

* cited by examiner

| | | |
|---|---|---|
| STE20_h | - - - - - - - - - - - - - - - - - - - - - - - MAHLRGFANQHSRV - - - DPEELFTKLDRIGKGSFGEVYKGIDNHTK | 43 |
| MST3_h | - - - - - - - - - - - - - - - - - - - MAHSPVQSGLPGMQNLKADPEELFTKLEKIGKGSFGEVFKGIDNRTQ | 47 |
| STLK2_h | - - - - - - - - - - - - - - - - - - - MAHSPVAVQVPGMQNNIADPEELFTKLERIGKGSFGEVFKGIDNRTQ | 47 |
| STLK3_h | TAAPAPAAPAAPAPAPAPAPAAQAVGWPICRDAYELQEVIGSGATAVVQAALCKPRQ | 57 |
| | | |
| STE20_h | EVVAIKIIDLEEAEDEIEDIQQEITVLSQCDSPYITRYFGSYLKSTKLWIIMEYLGG | 100 |
| MST3_h | KVVAIKIIDLEEAEDEIEDIQQEITVLSQCDSPYVTKYYGSYLKDTKLWIIMEYLGG | 104 |
| STLK2_h | QVVAIKIIDLEEAEDEIEDIQQEITVLSQCDSPYVTKYYGSYLKGSKLWIIMEYLGG | 104 |
| STLK3_h | ERVAIKRINLEKCQTSMDELLKEIQAMSQCSHPNVVTYYTSFVVKDELWLVMKLLSG | 114 |
| | | |
| STE20_h | GSALDLLKPGP - - - - - - - - - - LEETYIATILREILKGLDYLHSERKIHRDIKAANVLL | 148 |
| MST3_h | GSALDLLEPGP - - - - - - - - - - LDETQIATILREILKGLDYLHSEKKIHRDIKAANVLL | 152 |
| STLK2_h | GSALDLLRAGP - - - - - - - - - - FDEFQIATMLKEILKEVLEGLDYLHSEKKIHRDIKAANVLL | 152 |
| STLK3_h | GSMLDIIKYIVNRGEHKNGVLEEAIIATILKEVLEGLDYLHRNGQIHRDLKAGNILL | 171 |
| STLK4_h | - - - - - - - - - - - - - - KSGVLDXSTIATILREVLEGLIEYLHKXGQIHRDVKAGNILX | 41 |
| | | |
| STE20_h | SEQGDVKLADFGV - A - - - - - - - GQLTDTQIKRNTFVGTPFWMAPEVIKQSA - YDFKADI | 198 |
| MST3_h | SEHGEVKLADFGV - A - - - - - - - GQLTDTQIKRNTFVGTPFWMAPEVIKQSA - YDSKADI | 202 |
| STLK2_h | SEQGDVKLADFGV - A - - - - - - - GQLTDTQIKRNTFVGTPFWMAPEVIQQSA - YDSKADI | 202 |
| STLK3_h | GEDGSVQIADFGVSAFLATGGDVTRNKV - RKTFVGTPCWMAPEVMEQVRGYDFKADM | 227 |
| STLK4_h | GEDGSVQIADFGVSAFLATGGDITRNKV - RKTFVGTPCWMAPEVMEQVRGYDFKADI | 97 |

Fig. 1A

```
STE20_h   WSLGITAIELAKGEPPNSDLHPMRVLFLIPKNSPPTLE-G-------QHSKPFKEF   246
MST3_h    WSLGITAIELARGEPPHSELHPMKVLFLIPKNNPPTLE-G-------NYSKPLKEF   250
STLK2_h   WSLGITAIELAKGEPPNSDMHPMRVLFLIPKNNPPTLV-G-------DFTKSFKEF   250
STLK3_h   WSFGITAIELATGAAPYHKYPPMKVLMLTLQNDPPTLETGVEDKEMKKYGKSFRKL  284
STLK4_h   WSFGITAIELATGAAPYHKYPPMKVLMLTLQNDPPSLETGVQDKEMLKKYGKSFRKM  154

STE20_h   VEACLNKDPRFRPTAKELLKHKFITRYTKKTSFLTELIDRYKR-              289
MST3_h    VEACLNKEPSFRPTAKELLKHKFILRNAKKTSYLTELIDRYKR-              293
STLK2_h   IDACLNKDPSFRPTAKELLKHKFIVKNSKKTSYLTELIDRFKR-              293
STLK3_h   LSLCLQKDPSKRPTAAELLKCKFFQKAKNREYLIEKLLTRTPDIAQRAKKVRRVPGS 341
STLK4_h   ISLCLQKDPEKRPTAAELLRHKFFQKAKNKEFLQEKTLQRAPTISERAKKVRRVPGS 211

STE20_h   ---WKSEGHGEESS-SEDSDIDGEAEDGEQGPIW-----                    319
MST3_h    ---WKAEQSHDDS-SEDSDAETDGQASGGSDSG-----                    323
STLK2_h   ---WKAEGHSDDESDSEGSDSESTSRENNTHPEW----                    324
STLK3_h   SGHLHKTEDGDWEWSDDEMDEK-SEEGKAAFSQEKRRVKEE-----            382
STLK4_h   SGRLHKTEDGGWEWSDDEFDEE-SEEGKAISQLRSPRVKESISNSELFPTTDPVGT  267

STE20_h   ------TFPPTIRPSPHSKLHKGTALHSSQKPAEPVK                     350
MST3_h    ------DWIFTIREKDPKNLENGALQPSDLDRNKMKD                     354
STLK2_h   ------SFTTVRKKPDPKKVQNGAEQDLVQTLS---                      351
STLK3_h   ------NPEIAVSASTIPEQIQSLSVHDSQGPPNANE                     413
STLK4_h   LLQVPEQISAHLPQPAGQIATQPTQVSLPPTAEPAKTAQALSSGSGSQETKIP----  320
```

Fig. 1B

```
STE20_h   RQ--PRSQCLSTLVRPVFGELKEKHKQSGGSVGALEELENAFSLAEESCPGISDKLM   405
MST3_h    IPKRPFSQCLSTIISPLFAELKEKSQACGGNLGSIEELRGAIYLAEEACPGISDTMV   411
STLK2_h   -----CLSMIITPAFAELKQQDENNASRNQAIEELEKSIAVAEAACPGITDKMV      400
STLK3_h   DY--REASSCAVNLVLRLRNSRKELNDIRFEFTPGRDTADGVSQELFSAGLVDGHDV   468
STLK4_h   ----ISLVLRLRNSKELNDIRFEFTPGRDTAEGVSQELISAGLVDGRDL           366

STE20_h   VHLVERVQRFSHNRNHLTSTR                                        426
MST3_h    AQLVQRLQRYSLSGGGTSSH                                         431
STLK2_h   KKLIEKFQKCSADESP                                             416
STLK3_h   VIVAANLQKIVDDPKALKTLTFKLASGCDGSEIPDEVKLIGFAQLSVS              516
STLK4_h   VIVAANLQKIVEEPQSNRSVTFKLASGVEGSDIPDDGKLIGFAQLSIS              414
```

Fig. 1C

| | | | |
|---|---|---|---|
| Ste20_h | MAHLRGFANQHSRV- - - - - - - - - - - - - -DPEELFTKLDRIGKGSFGEVYKGIDNHTK | 43 |
| T19A5.2_ce | MTTTSSDELPRQADDDSMKWDRIYIQKLDPEVIFTKQERIGRGSFGEVYKGIDNRTG | 57 |
| Pak_sp | - - - - - - - - - - - - - - - - - - - - - - - - - - - - LLYRNFVKIGQGASGDVYJSARQVGIN | 26 |
| STLK5_h | - - - - - - - - - - - - - - - - - - - - - - - - - - - - - - - - - - - - - - - - - - - - - - - - - - - - - - - - - - - - | 0 |
| | | |
| Ste20_h | EVVAIKIIDLEEAEDEIEDIQQEITVLSQCDSPYITRYFGSYLKSTKLWIIMEYLGG | 100 |
| T19A5.2_ce | RVVAIKIIDLEQAEDEIEDIQQEIQVLSQCDSQYVTKYFGSFLKGSKLWIIMEYLGG | 114 |
| Pak_sp | LSVAIKKMNINQQPKKEF - HVNEILVMKSHHHKNIVNFIDTFFYKSELMVMEYMRG | 82 |
| STLK5_h | - - - - - - - - - - - - - - - - - - - - - - - - - - - - - - - - - - - - - - - - - - - - - - - - - - - - - - - - - - - - | 0 |
| | | |
| Ste20_h | GSALDLLKPGPLEETYIATILREILKGLDYLHSERKIHRDIKAANVLLSEQGDVKLA | 157 |
| T19A5.2_ce | GSALDLTKSGKLDESHIAVILREILKGLEYLHSERKIHRDIKAANVLVSEHGDVKVA | 171 |
| Pak_sp | GSLTEVVTNNTLSEGQIAAICKETLEGLQHLHENGIVHRDIKSDNILLSLQGDIKLT | 139 |
| STLK5_h | - - LICTHFMDGMNELAIAYILQGVLKALDYIHHMGYVHRSVKASHILISVDGKVYL | 55 |
| | | |
| Ste20_h | DFGVAGQLTDTQIKRNTFVGTPF- - - - - - WMAPEVIKQSA - - YDFKADIWSLGITA | 205 |
| T19A5.2_ce | DFGVAGQLTETVKKRITFVGSPF- - - - - - WMAPELIKQSS - - YDYKADIWSLGITA | 219 |
| Pak_sp | DFGFCAQIDSNMTKRTTMVGTPY- - - - - - WMAPEVTRKE - - YGFKVDVWSLGIMA | 187 |
| STLK5_h | GLRSNLSMISAGQRQRVVHDFPKYSVKVLPWLSPEVLQGYDAKSDIYSVGITA | 112 |
| | | |
| Ste20_h | IELAKGEPPNSDLHPMRVLFLIPK-NSPPTLEG-Q - - - - - - - - - - - - - - - - - - - - | 238 |
| T19A5.2_ce | IELANGEPPHSDLHPMRVLFLIPK-NPPPVLQGSQ - - - - - - - - - - - - - - - - - - - | 253 |
| Pak_sp | IEMVEGEPPYLNENPLRALYLIATIGTPKISRPEL - - - - - - - - - - - - - - - - - - - | 222 |
| STLK5_h | CELANGHVPFKDMPATQMLLEKLN-GTVPCLLD-TSTIPAEELTMSPSRSVANSGLS | 167 |

Fig. 2A

```
Ste20_h     - - - - - - - - - - - - - - - - - - - - - - - - - - - - H S K P F K E F V E A C L N K D P R F R P T A K E L L K H K F I T R   272
T19A5.2_ce  - - - - - - - - - - - - - - - - - - - - - - - - - - - - W S K P F K E F V E M C L N K D P E N R P S A S T L L K H Q F I K R   287
Pak_sp      - - - - - - - - - - - - - - - - - - - - - - - - - - - - L S S V F H D F L S K S L T V N P K Q R P S G E L L R H P F L K Q   256
STLK5_h     D S L T T S T P R P S N G D S P H Y H R T F S P H F H H F V E Q C L Q R N P D A R P S A S T L L N H S F F K Q   224

Ste20_h     Y T K K T S F L T E L I D R Y K R W K S E G H G E E S S S E D S D I D G E A E D G E Q G P I W T F P P T I R P S P   329
T19A5.2_ce  A K K N S - - - - I L V D L I E R A A E Y R L R T G V S S D S D L D E D S D G G G G T S K W D Y - P T V R G P R   338
Pak_sp      A V P V S - - - - - S L I P L I K S I H H S G K                                                                   275
STLK5_h     - -                                                                                                              224

Ste20_h     H S K L H K G T A L H S S Q K P A E P V K R Q P R S Q C L S T L V R P V - - - - - F G E L K E K H K Q S G - - G S   379
T19A5.2_ce  V S A D D D G T V R Q R T D R P R A Q V D R R S P S G S P G G T I V R G - - - - - S P Q V A A V A E Q L R - - N S   388
Pak_sp      - - - I K R R A - S E A L P E L L R P V T P I T N F - E G S Q S Q D H S G I F G L                                 260
STLK5_h     - -                                                                                                              224

Ste20_h     V G A L E E L E N A F S L A E E S C P G I S D K L M V H L V E R V Q R F S H N R N H L T S T R                     426
T19A5.2_ce  X X A L D Q L R H V F R D V E D S C P G I C N E L I E E L M Q R I A V P Q V S Q S D L D A A I R R L T T P P S     443
STLK5_h     V T N L E E L E V D D W E F                                                                                       274
```

```
ZC504.4_ce  MRALFLIPRNPPPKLKRNKKWTKKFETFIETVLVKDYHQRPYTGALLRHPFIKEQPHEQT   296
NIK_m       MRALFLIPRNPPPRLK-SKKWSKKFFSFIEGCLVKNYMQRPSTEQLLKHPFIRDQPNERQ   296
ZC1_h       MRALFLIPRNPPPRLK-SKKWSKKFFSFIEGCLVKNYMQRPSTEQLLKHPFIRDQPNERQ   297
ZC2_h       MRALFLIPRNPAPRLK-SKKWSKKFQSFIESCLVKNHSQRPATEQLMKHPFIRDQPNERQ   263
ZC3_h       MRALFLIPRNPPPRLK-SKKWSKKFTDFIDTCLIKTYLSRPPTEQLLKFPFIRDQPTERQ   263

ZC504.4_ce  IRHSIKEHIDRNRVKKQDADYEYSGSEDDEPSPNNRDDSESS---SMIPMDNTLRKGFIQ   353
NIK_m       VRIQLKDHIDRTRKKRGEKDETEYEYSGSEEEEEVPEQEGEPSSIVNVPGESTLRRDFL   356
ZC1_h       VRIQLKDHIDRTRKKRGEKDETEYEYSGSEEEEEVPEQEGEPSSIVNVPGESTLRRDFL   357
ZC2_h       VRIQLKDHIDRTKKKRGEKEETEYEYSGS--NDSGEPSSILNLPRESTLRRDFL        321
ZC3_h       VRIQLKDHIDRSRKKRGEKEETEYEYSGS-EEEDDSHGEEGEPSSIMNVPGESTLRIEFL  322

ZC504.4_ce  KLQESSRGFAEPGAQQLRRLPQQPAPAPFQYQQSRYVEPRRESSEVKLRAVSSRGAADGP  413
NIK_m       RLQQENKERSEALRRQQLLQEQQL------REQEEYKRQLLAERQKRI--           398
ZC1_h       RLQQENKERSEALRRQQLLQEQQL------REQEEYKRQLLAERQKRI--           399
ZC2_h       RLQLANKERSEALRRQQ----LEQQQ----RENEEHKRQLLAERQKRI--           361
ZC3_h       RLQQENKSNSEALKQQQQQLQQQQQQ----RQPEAHIKHLLHQRQRRI--           364

ZC504.4_ce  RHSPASRPRPRSPQQSHPAIAPHLADLANYEKRRSEREEERRRERERQAHHAMPIARVSASV  473
NIK_m       EQQKEQRRLEEQQRREAQRRQQEREQQEREQQEREQQEEKRRLEELERRKEEERRRAEEEKR  458
ZC1_h       EQQKEQRRLEEQQRREARRQQEREQQEREQQEREQQEEKRRLEELERRKEEERRRAEEEKR  459
ZC2_h       EQQKEQRRLEEQQRREQREKELRKQQERQRRHYEEQMRR--         ---EEEERR   404
ZC3_h       EEQKFERRVEEQQRREREQRKLQEKEQRRLEDMQAL--            ---RREEERR  409
```

Fig. 3B

```
ZC504.4_ce  PAPQQSRKMSEPLLITHVKPEDLDVLASELSKMGG------------------------------  508
NIK_m                 RVEREQEYIRRRQLEEEQRHLETLQQQLLQEQAMLL------------------------------  493
ZC1_h                 RVEREQEYIRRRQLEEEQRHLEVLQQQLLQEQAMLLECRWREMEEHRQAERLQRLQQEQA     519
ZC2_h                 RAEHEQEYKRKQLEEQ-------------------------RQAERLQRLKQERD          435
ZC3_h                 QAEREQEYIRHRLEEEQRQLEILQQQLLQEQAILLEYKRKQLEEQRQSERLQRLQQEHA      469

ZC504.4_ce  ----HHNGRSREES-MSPPPPAPPPREASISSITDTIDVGELDNGAQAEWDDLKDIMM       561
NIK_m       ----HDHRRPHAQ|-QQPPPPQQQQDRSKPSFHAPEPKPHYDPADRAREVIQWSHLASLKN  548
ZC1_h       YLLSLQHDHRRPHPQHSQQPPPPQQQERSKPSFHAPEPKAHYEPADRAREVEDRFRKTNHS  579
ZC2_h       YLVSLQHQR-------------QEQRPVEKKPLYHYKEGMSPSEKPAWAKEVEERSRLNRQS  484
ZC3_h       YLKSLQQQQQQQLQK-QQQQLLPGDRKPLYHYGRGMNPADKPAWAREVEERTRMNKQQ     528

ZC504.4_ce  NGEGTLRG-------------------PNKPLPPTPTDGENTLVSDVRRNGNG-----    595
NIK_m       NYSPVSRSHSFSDPSPKFAHHHLRSQDPCPPSRSEGLSQSSDSKSEVPEPTQK------  599
ZC1_h       SPEAQSKQ-----------------TGRVLEPPVPSRSESFSNGNSESVHPALQRPAE-  620
ZC2_h       SPAMPHKV-----------------ANRLSDPNLPPRSESFSISGVQPARTPMLRPVDPQIPH  531
ZC3_h       NSPLAKSK-----------------PGS-TGPEPPIPQASPGPPGPLSQTPPMQRPVEPQEGPH  574

ZC504.4_ce  -------------------------------------                          595
NIK_m       -------------------------------------                          599
ZC1_h       -------------------------------------                          620
ZC2_h       LVAVKSQGPALTASQSV------HEQPTKGLSGFQEALNVT------SHRVEMPRQ        575
ZC3_h       KSLVAHRVPLKPYAAPVPRSQSLQDQPTRNLAAFPASHDPDPAIPAPTATPSARGAVIRQ    634
```

| | | |
|---|---|---|
| ZC504.4_ce | - - - - - - - - - - - - - - - - - - - - - - - - - - - - - - - - - - - - - - - - - - - - - - - - - - - - - - - - - - - - - | 755 |
| NIK_m | E G A D D S T S G P E D T R A A S S P N L S N G E T E S V K T M I V H D D V E S E P A M T P - - S K E G T L I V - - | 831 |
| ZC1_h | E G A D E S T S G P E D T R A A S S L N L S N G E T E S V K T M I V H D D V E S E P A M T P - - S K E G T L I V - - | 837 |
| ZC2_h | E T H D G T V A V S D I P R L I P T G A P G S N E Q Y N V G M V G T H G L E T S H A D S F S G S I S R E G T L M I R E T | 845 |
| ZC3_h | G P A E G S - - - - - - - - - - - - - - R D T P G G R D G D T D S V S T M V H D V E E I T G T Q P P - - - Y G G G T M V V Q R T | 885 |
| ZC504.4_ce | - - - - - - - - - - - - - - - - - - - - - - - - - - - - - - - - - - - - - - - - - - - - - - - - - - - - - - - - - - - - - | 755 |
| NIK_m | - - - - - - - - - - - - - - - - - - - - - - - - - - - - - - - - - - - - R Q T Q S A S S T L Q K H K | 845 |
| ZC1_h | - - - - - - - - - - - - - - - - - - - - - - - - - - - - - - - - - - - - R R T Q S A S S T L Q K H K | 851 |
| ZC2_h | S G E K K R S G H S D S N G F A G H I N L P D L V Q Q S H S P A G T P T E G L G R V S T H S Q E M D S G T E Y G M G S S | 905 |
| ZC3_h | P E E E R N L L H A D S N G Y T - - - N L P D V V Q P S H S P T E N S K G Q S P P S K D G S G D Y Q S R G L V K A P G - | 941 |
| ZC504.4_ce | - - - - - - - - - - - - - - - - - - - - - - - - - - - - - - - - - - - R P Q D I - - - - N Q V Q V N V T P N S N | 772 |
| NIK_m | S S S S F T P F I D P R L L Q I S P S S G T T V T S V V G F S C D G L R P E A I R Q D P T - - - - R K G S V V N V N P T | 901 |
| ZC1_h | S S S S F T P F I D P R L L Q I S P S S G T T V T S V V G F S C D G M R P E A I R Q D P T - - - - R K G S V V N V N P T | 907 |
| ZC2_h | T K A S F T P F V D P R V Y Q T S P T D E D E E S S A A A L F T G E L L R Q E Q A K L N E A R K I S V V N V N P T | 965 |
| ZC3_h | - K I S S F T M F V D L G I Y Q P G G S G D S I P I T A L V G G E G T R L D Q L Q Y D V - - - - - - R K G S V V N V N P T | 994 |
| ZC4_h | - - - - - - - - - - - - - - - - - - - - - - - - - - - - - - - - - - - - - - - - - N V N P L | 5 |
| ZC504.4_ce | G T P A E N D A P E I R K Y K K K F S G E I L C A A L W G V N L L I G T D S G L M L L D R S G Q G K V Y P L I S R R R F | 832 |
| NIK_m | N T R P Q S D T P E I R K Y K K R F N S E I L C A A L W G V N L L V G T E S G L M L L D R S G Q G K V Y P L I N R R R F | 961 |
| ZC1_h | N T R P Q S D T P E I R K Y K K R F N S E I L C A A L W G V N L L V G T E S G L M L L D R S G Q G K V Y P L I N R R R F | 967 |
| ZC2_h | N I R P H S D T P E I R K Y K K R F N S E I L C A A L W G V N L L V G T E N G L M L L D R S G Q G K V Y Y N L I N R R R F | 1025 |
| ZC3_h | N T R A H S E T P E I R K Y K K R F N S E I L C A A L W G V N L L L G T E N G L M L L D R S G Q G K V Y G L I G R R R F | 1054 |
| ZC4_h | Y V S P A C K K P L I H M Y E K E F T S E I C C G S L W G V N L L L G T R S N L Y L M D R S G K A D I T K L I R R R P F | 65 |

```
ZC504.4_ce  L C Y D N E G V Y V N T Y G R M T K N V V L Q W G E M P S S V A Y I S T G Q I M G W G N K A I E I R S V D T G H L D G V   1064
NIK_m       V C Y E D E G V Y V N T Y G R I T K D V V L Q W G E M P T S V A Y I R S N Q T M G W G E K A I E I R S V E T G H L D G V   1188
ZC1_h       V C Y E D E G V Y V N T Y G R I T K D V V L Q W G E M P T S V A Y I R S N Q T M G W G E K A I E I R S V E T G H L D G V   1194
ZC2_h       V C Y E D E G V Y V N T Y G R I T K D V V L Q W G E M P T S V A Y I H S N Q I M G W G E K A I E I R S V E T G H L D G Y   1252
ZC3_h       L C Y E D E G V Y V N T Y G R I I K D V V L Q W G E M P T S V A Y I C S N Q I M G W G E K A I E I R S V E T G H L D G V   1281
ZC4_h       L T F N A E A L S V E A N E Q L F K K I L E M N K D I P S I A F E C T D R T T G W G Q K A I E V R S L Q S R V L E S E     300

ZC504.4_ce  F M H K K A Q K L K F L C E R N D K V F F S S A K G G S C Q I Y F M T L N K P G L T N W                                 1109
NIK_m       F M H K R A Q R L K F L C G R N D K V F F S S V R S G G S S Q V Y F M T L G R T S L L S W                                 1233
ZC1_h       F M H K R A Q R L K F L C E R N D K V F F S S V R S G G S S Q V Y F M T L G R T S L L S W                                 1239
ZC2_h       F M H K R A Q R L K F L C E R N D K V F F A S V R S G G S S Q V F F M T L N R S M M N W                                 1297
ZC3_h       F M H K R A Q R L K F L C E R N D K V F F A S V R S G G S S Q V Y F M T L N R N R I M N W                                 1326
ZC4_h       L K R R S I K K L R E L C T R G D K L E F T S T L R N H H S R V Y F M T L G K L E E L Q S N Y D V                         349
```

Fig. 3G

```
KHS1_h    5  LRPAADILRRNPQQDYELVQRVGSGTYGDVYKARNVHTGELAAVKIIKLEPGDDFSLIQQ   64
KHS2_h    1  MNPGFDLSRRNPQEDFELIQRIGSGTYGDVYKARNVNTGELAAIKVIKLEPGEDFAVVQQ   60

KHS1_h   65  EIFMVKECKHCNIVAYFGSYLSREKLWICMEYCGGGSLQDIYHVTGPLSELQIAYVCRET  124
KHS2_h   61  EIIMMKDCKHPNIVAYFGSYLRRDKLWICMEFCGGGSLQDIYHVTGPLSELQIAYVSRET  120

KHS1_h  125  LQGLAYLHTKGKMHRDIKGANILLTDHGDVKLADFGVAAKITATIAKRKSFIGTPYWMAP  184
KHS2_h  121  LQGLYYLHSKGKMHRDIKGANILLTDNGHVKLADFGVSAQITATIAKRKSFIGTPYWMAP  180

KHS1_h  185  EVAAVEKNGGYNQLCDIWAVGITAIELGELQPPMFDLHPMRALFLMSKSNFQPPKLKDKT  244
KHS2_h  181  EVAAVERKGGYNQLCDLWAVGITAIELAELQPPMFDLHPMRALFLMTKSNFQPPKLKDKM  240

KHS1_h  245  KWSSTFHNFVKIALTKNPKKRPTAERLLTHTFVAQPGLSRALAVELLDKVNNPDNHAHYT  304
KHS2_h  241  KWSNSFHHFVKMALTKNPKKRPTAEKLLQHPFVTQH-LTRSLAIELLDKVNNPD-HSTYH  298

KHS1_h  305  EADDDDFEPHAIIRHTIRSTNRNARAERTASEINFDKLQFEPPLRKETEARDEMGLS---  361
KHS2_h  299  DFDDDDPEPLVAVPHRIHSTSRNVREEKTRSEITFGQVKFDPPLRKETEPHHELPDSDGF  358
```

Fig. 4A

```
KHS1_h  362 ----------SDPNFMLQWNP-----FV-------------------D 375
KHS2_h  359 LDSSEEIYYTARSNLDLQLEYGQGHQGGYFLGANKSLLKSVEEELHQRGHVAHLEDDEGD 418

KHS1_h  376 GANTGKSTSKRAIPPLPPKPRISSYPED-NFPDEEKASTIKHCP--DSESRAPQILRRQ 432
KHS2_h  419 DDESKHSTLKAKIPPPLPPKPPKSIFIPQEMHSTEDENQGTIKRCPMSGSPAKPSQVPPRP 478

KHS1_h  433 SSPSCGPVAETSSIGNGDGISKL-MSENTEGSA-------QAPQLPRKNDKRDFPKPAIN 484
KHS2_h  479 PPPR---LPPHKPVALGNGMSSFQLMGERDGSLCQQQNEHRGTNLSRK-EKKDVPKPISN 534

KHS1_h  485 GLPPTPKVLMGACFSKVFDGCPLKINCATSWIHPDTKDQYIIFGTEDGIYTLNLNELHEA 544
KHS2_h  535 GLPPTPKVHMGACFSKVFNGCPLKIHCASSWINPDTRDQYLIFGAEEGIYTLNLNELHET 594

KHS1_h  545 TMEQLFPRKCTWLYVINNTLMSLSEGKTFQLYSHNLIALFEHAK-KPGLAAHIQTHRFPD 603
KHS2_h  595 SMEQLFPRRCTWLYVMNNCLLSIS-GKASQLYSHNLPGLFDYARQMQKLPVAIPAHKLPD 653

KHS1_h  604 RILPRKFALTTKIPDTKGCHKCCIVRNPYTGHKYLCGALQSGIVLLQWYEPMQKFMLIKH 663
KHS2_h  654 RILPRKFSVSAKIPETKWCQKCCVRNPYTGHKYLCGALQTSIVLLEWVEPMQKFMLIKH 713
```

Fig. 4B

```
              *           *    .    *    .    *    .    *    .    *    .    *    .
KHS1_h  664  FDFPLPSPLNVFEMLVIPEQEYPMVCVAISKGTESNQVVQFETINLNSASSWFTEIGAGS  723
KHS2_h  714  IDFPIPCPLRMFEMLVVPEQEYPLVCVGVSRGRDFNQVVRFETVNPNSTSSWFTE--SDT  771
              *  *  * ***** * * *    ****  *      ***** *** *   ****  .
              *    .    *    .    *    .    *    .    *    .    *    .
KHS1_h  724  QQLDSIHVTQLERDTVLVCLDKFVKIVNLQGKLKSSKKLASELSFDFRIESVVCLQDSVL  783
KHS2_h  772  PQTNVTHVTQLERDTILVCLDCCIKIVNLQGRLKSSRKLSSELTFDFQIESIVCLQDSVL  831
               *   ********.*****  .******.****.***.** ***.***.*******
              *    .    *    .    *    .    *    .    *    .    *    .
KHS1_h  784  AFWKHGMQGKSFKSDEVTQEISDETRVFRLLGSDRVVVLESRPTENPTAHSNLYILAGHE  843
KHS2_h  832  AFWKHGNQGRSFRSNEVTQEISDSTRIFRLLGSDRVVVLESRPTDNPTANSNLYILAGHE  891
             ******.**.**.*.*******. *.**********.******.***.*********
              *  *
KHS1_h  844  NSY  846
KHS2_h  892  NSY  894
```

Fig. 4C

| | | |
|---|---|---|
| SULU_ce | MAPAVLQKPGVIKDPSIAALFSNKDPEQRYQDLREIGHSFGAVYFAYDKKNEQTVAIKK | 60 |
| SULU1_h | ----MRKGVLKDPEIDDLFYKDDPEELFIGLHEIGHSFGAVYFATNAHTNEVVAIKK | 54 |
| SULU3_m | --MPSTNRAGSLKDPEIAELFFKEDPEKLFTDLREIGHSFGAVYFARDVRTNEVVAIKK | 58 |

| | | |
|---|---|---|
| SULU_ce | MNFSGKQAVEKWNDILKEVSFLNTVVHPHIVDYKACFLKDTTCWLVMEYCIGSAADIVDV | 120 |
| SULU1_h | MSYSGKQTHEKWQDILKEVKFLRQLKHPNTIEYKGCYLKEHTAWLVMEYCLGSASDLLEV | 114 |
| SULU3_m | MSYSGKQSTEKWQDIIKEVKFLQRIKHPNSIEYKGCYLREHTAWLVMEYCLGSASDLLEV | 118 |

| | | |
|---|---|---|
| SULU_ce | LRKGMREVEIAAICSQTLDALRYLHSLKRIHRDIKAGNILLSDHAIVKLADFGSASLVDP | 180 |
| SULU1_h | HKKPLQEVEIAAITHGALHGLAYLHSHALIHRDIKAGNILLTEPGQVKLADFGSASMASP | 174 |
| SULU3_m | HKKPLQEVEIAAITHGALQGLAYLHSHTMIHRDIKAGNILLTEPGQVKLADFGSASMASP | 178 |

| | | |
|---|---|---|
| SULU_ce | AQTFIGTPFFMAPEVILAMDEGHYTDRADIWSLGITCIELAERRPPLFSMNAMSALYHIA | 240 |
| SULU1_h | ANSFVGTPYWMAPEVILAMDEGQYDGKVDIWSLGITCIELAERKPPLFNMNAMSALYHIA | 234 |
| SULU3_m | ANSFVGTPYWMAPEVILAMDEGQYDGKVDVWSLGITCIELAERKPPLFNMNAMSALYHIA | 238 |
| SULU3_h | ----------------------------IIELAERKPPLFNMNAMSALYHIA | 24 |

| | | |
|---|---|---|
| SULU_ce | QNDPPTLSPIDTSEQPEWSLEFVQFIDKCLRKPAEERMSAEECFRHPFIQRSRPSDTIQE | 300 |
| SULU1_h | QNDSPTLQSN-----EWTDSFRREVDYCLQKIPQERPTSAELLRHDFVRRDRPLRVLID | 288 |
| SULU3_m | ANSESPTLQSNMN-----EWSDYFRNFVDSCLQKIPQDRPTSEELLKHMFVLRERPETVLID | 284 |
| SULU3_h | ----DSCLQKIPQDRPTSEELLKHIFVLRERPETVLID | 78 |

| | | |
|---|---|---|
| SULU_ce | LIQRTKNMVLELDNFQYKKMRKLMYLDETEGKEGSEGNGASDDLDFHGNEANSIGRAGDS | 360 |
| SULU1_h | LIQRTKDAVRELDNLQYRKMKKILF---------------------------------- | 313 |
| SULU3_m | LIQRTKDAVRELDNLQYRKMKKLLF---------------------------------- | 309 |
| SULU3_h | LIQRTKDAVRELDNLQYRKMKKLLF---------------------------------- | 103 |

Fig. 5A

```
SULU_ce  ASSRSASLTSFRSMQSSGGAGLLVSTNTTGAMDNVHGSSGYGNGSSTTSSARRPPIPS  420
SULU1_h  -----------------------------------------------QETRNGPLNES  324
SULU3_m  -----------------------------------------------QEAHNGPAVEA  320
SULU3_h  -----------------------------------------------QEAHNGPAVEA  114

SULU_ce  QMLSSTSTSGVGTMPSHGSVGASITAIAVNPTPSPSEPIPTSQPTSKSESS-SILETAHD  479
SULU1_h  QEDEEDSEHGTSLNREMDSLGSNHSIPSMSVSTGSQSSSVNSMQEVMDESSSELVMMHDD  384
SULU3_m  QEEEEEQDHGVGRTGTVNSVGSNQSIPSMSIISASSSQSSSSVNSLPDASDDKS-ELDMMEGD  379
SULU3_h  QEEEEEQDHGVGRTGTVNSVGSNQSIPSMSIISASSSQSSSSVNSLPDVSDDKS-ELDMMEGD  173

SULU_ce  DPLDTSI-----------------------RAPVKDLHMPHRAVKERIATLQNHKFATLRSQRII  521
SULU1_h  ESTINSSSVVHKKDHVFTRDEAGHGDPRPEPRPTQSVQSALHYRNRERFATIKSASLV  444
SULU3_m  HTVMSNSSVIHLKPEEENYQEEGDPRTRASDPQSPPQVSRHKSHYRNREHFATIRTASLV  439
SULU3_h  HTVMSNSSVIHLKPEEENYREEGDPRTRASDPQSPPQVSRHKSHYRNREHFATIRTASLV  233

SULU_ce  NQEEEYTKENNMYEQMSKYKHLRQAHHKELQQFEERCALDREQLRVKMDRELEQLTTTY  581
SULU1_h  TRQIHEHEQENELREQMSGYKRMRRQHQKQLIALENKLKAEMDEHRLKLQKEVETHANNS  504
SULU3_m  TRQMQEHEQDSELREQMSGYKRMRRQHQKQLMTLENKLKAEMDEHRLRLDKDLETQRNNF  499
SULU3_h  TRQMQEHEQDSELREQMSGYKRMRRQHQKQLMTLENKLKAEMDEHRLRLDKDLETCRNNF  293

SULU_ce  SKEKMRVRCSQNNELDKRKKDIEDGEKKMKKTKNSQNQQQMKLYSAQQLKEYKYNKEAQK  641
SULU1_h  SIELEKLAKKQVAIIEKEAKVAAADEKKFQQQILAQQKKDLTTFLESQKKQYKICKEKIK  564
SULU3_m  AAEMEKLIKKHQAAMEKEAKVMANEEKKFQQHIQAQQKKELNSFLESQKREYKLRKEQLK  559
SULU3_h  AAEMEKLIKKHQAAMEKEAKVMSNEEKKFQQHIQAQQKKELNSFLESQKREYKLRKEQLK  353
```

Fig. 5B

```
SULU_ce   TR LRSLNM-PRSTYENAMKEVKADLNRVKDARENDFDEKLRAELEDEIVRYRRQQLSNLH  700
SULU1_h   EEMNEDHSTPKKEKQERISKHKENLQHTAEEEAHLLTQQRLYYDKNCRFFKRKIMIKRH      624
SULU3_m   EELNENQSTPKKEKQEWLSKQKENIQHFQAEEEANLLRRQRQYLELECRRFKRRMLGRH      619
SULU3_h   EELNENQSTPKKEKQEWLSKQKENIQHFQAEEEANLLRRQRQYLELECRRFKRRMLGRH      413

SULU_ce   QLEEQLDDEDVNVQERQMDTRHGLLSKQHEMTRDLEIQHLNELHAMKKRHLETQHEAESA     760
SULU1_h   EVEQQNIREELNKKRTQKEMEHAMLIRHDESTRELEYRQLHTLQKLRMDLIRLQHQTELE     684
SULU3_m   NLEQDLVREELNKRQTQKDLEHAMLLRQHESMQELEFRHLNTIQKMRCELIRLQHQTELT     679
SULU3_h   NLEQDLVREELNKRQTQKDLEHAMLLRQHESMQELEFRHLNTIQKMRCELIRLQHQTELT     473

SULU_ce   SQNEYTQRQQDELRKKHAMQSRQQPRDLKIQEAQIRKQYRQVVKTQTRQFKLYLTQMVQV     820
SULU1_h   NQLEYNKRREREELHRKHVMGLRQQPKNLKAMEMQIKKQFQDTCKVQTKQYKALKNHQLEV    744
SULU3_m   NQLEYNKRREREELRRKHVMEVRQQPKSLKSKELQIKKQFQDTCKIQTRQYKALRNHLLET    739
SULU3_h   NQLEYNKRREREELRRKHVMEVRQQPKSLKSKELQIKKQFQDTCKIQTRQYKALRNHLLET    533

SULU_ce   VPKDEQKKELTSRLKQDQMQKVALLASQYESQIKKMVQDKTVKLESWQEDEQRVLSEKLEK    880
SULU1_h   TPKNEHKTILKTLKDEQTRKLAILAEQYEQSINEMMASQALRLDEAQEAECQALRLQLQQ     804
SULU3_m   TPKNEHKAI                                                       748
SULU3_h   TPKSEHKAVLKRLKEEQTRKLAILAEQYDHSINEMLSTQALRLDEAQEAECQVLKMQLQQ     593

SULU_ce   ELEELIAYQKKTRATLEEIKKERTALEEREQMGEMRRLKKEQI                     940
SULU1_h   EMELLNAYQSKIKMQTEAQHERELQKLEQRVSLRRAHLEQKIEELAALQKERSERIKNL     864
SULU3_h   ELELLNAYQSKIKMQAEAQHDRELRELEQRVSLRRALLEQKIEEMLALQNERTERIRSL     653
```

Fig. 5C

```
SULU_ce    RD RHSQ ERHRLENHFV RTGSTSRSSGGIAPGVGNSSSIQMAM              982
SULU1_h    LER QER EIETFDMESLRMGFGNLVTLDFPKEDYR                       898
SULU3_h    LER QAR EIEAFDSESMRLGFSNMVLSNLSPEAFSHSYPGASGWSHNPTGGPGPHWGHPMG 713

SULU3_h    GPPQAWGHPMQGGPQPWGHPSGPMQGVPRGSSMGVRNSPQALRRTASGGRTEQGMSRSTS 773

SULU3_h    VTSQISNGSHMSYT                                              787
```

Fig. 5D

```
LOK_m      1 MAFANFRRILRLSTFEKRKSREYEHVRRDLDPNDVWEIVGELGDGAFGKVYKAKNKETGA     60
GEK2_h     1 MAFANFRRILRLSTFEKRKSREYEHVRRDLDPNEVWEIVGELGDGAFGKVYKAKNKETGA     60

LOK_m     61 LAAAKVIETKSEEELEDYIVEIEILATCDHPYIVKLLGAYYYDGKLWIMIEFCPGGAVDA    120
GEK2_h    61 LAAAKVIETKSEEELEDYIVEIEILATCDHPYIVKLLGAYYHDGKLWIMIEFCPGGAVDA    120

LOK_m    121 IMLELDRGLTEPQIQVVCRQMLEALNFLHGKRIIHRDLKAGNVLMTLEGDIRLADFGVSA    180
GEK2_h   121 IMLELDRGLTEPQIQVVCRQMLEALNFLHSKRIIHRDLKAGNVLMTLEGDIRLADFGVSA    180

LOK_m    181 KNLKTLQKRDSFIGTPYWMAPEVVLCETMKDAPYDYKADIWSLGITLIEMAQIEPPHHEL    240
GEK2_h   181 KNLKTLQKRDSFIGTPYWMAPEVVMCETMKDTPYDYKADIWSLGITLIEMAQIEPPHHEL    240

LOK_m    241 NPMRVLLKIAKSDPPTLLTPSKWSVEFRDFLKIALDKNPETRPSAAQLLQHPFVSRVTSN    300
GEK2_h   241 NPMRVLLKIAKSDPPTLLTPSKWSVEFRDFLKIALDKNPETRPSAAQLLEHPFVSSITSN    300

LOK_m    301 KALRELVAEAKAEVMEEIEDGREDGEEEDAVDAVPPLVNHTQDSANVTQPSLDSNKLLQD    360
GEK2_h   301 KALRELVAEAKAEVMEEIEDGRDEGEEEDAVDAASTLENHTQNSSEVSPPSLNADKPLEE    360
```

Fig. 6A

```
LOK_m  361 S-STPLPPSQPQEPVNGPCSQPSGDGPLQTTSPADGLSKNDNDLKVPVPLRKSRPLSMDA 419
GEK2_h 361 SPSTPLAPSQSQDSVNEPCSQPSGDRSLQTTSPPVVAPGNENGLAVPVPLRKSRPVSMDA 420

LOK_m  420 RIQMDEEKQIPDQDENPSPAASKSQKANQSRPNSSALETLGGEALTNGGLELPSSVTPSH 479
GEK2_h 421 RIQVAQEKQVAEQGGDLSPAANRSQKASQSRPNSSALETLGGEKLANGSLEPPAQAAPGP 480

LOK_m  480 SKRASDCSNLSTSESMDYGTSLSADLSLSLNKETGSLSLKGSKLHNKTLKRTRRFVVDGVEV 539
GEK2_h 481 SKRDSDCSSLCTSESMDYGTNLSTDLSLNKEMGSLSIKDPKLYKKTLKRTRKFVVDGVEV 540

LOK_m  540 SITTSKIISEDEKKDEEMRFLRRQELRELRLLQKEEHRNQTQLSSKHELQLEQMHKRFEQ 599
GEK2_h 541 SITTSKIISEDEKKDEEMRFLRRQELRELRLLQKEEHRNQTQLSNKHELQLEQMHKRFEQ 600

LOK_m  600 EINAKKKFYDVELENLERQQKQQVEKMEQDHSVRRKEEAKRIRLEQDRDYAKFQEQLKQM 659
GEK2_h 601 EINAKKKFFDTELENLERQQKQQVEKMEQDHAVRRREEARRIRLEQDRDYTRFQEQLKLM 660

LOK_m  660 KKEVKSEVEKLPRQQRKESMKQKMEEHSQKKQRLDRDFVAKQKEDLELAMRKLTTENRRE 719
GEK2_h 661 KKEVKNEVEKLPRQQRKESMKQKMEEHTQKKQLLDRDFVAKQKEDLELAMKRLTTDNRRE 720
```

Fig. 6B

```
LOK_m  720 ICDKERDCLSKKQELLRDREAALWEMEEHQLQERHQLVKQQLKDQYFLQRHDLLRKHEKE 779
GEK2_h 721 ICDKERECLMKKQELLRDREAALWEMEEHQLQERHQLVKQQLKDQYFLQRHELLRKHEKE 780

LOK_m  780 REQMQRYNQRMMEQLKVRQQQEKARLPKIQRSDGETRMAMYKKSLHINGAGSASEQREKI 839
GEK2_h 781 REQMQRYNQRMIEQLKVRQQQEKARLPKIQRSEGKTRMAMYKKSLHINGGGSAAEQREKI 840

LOK_m  840 KQFSQQEEKRQKAERLQQQKHEHQMRDMVAQCESNMSELQQLQNEKCYLLVEHETQKLK 899
GEK2_h 841 KQFSQQEEKRQKSERLQQQQKHENQMRDMLAQCESNMSELQQLQNEKCHLLVEHETQKLK 900

LOK_m  900 ALDESHNQSLKE 911
GEK2_h 901 ALDESHNQNLKE 912
```

Fig. 6C

```
PAK1_h   MSNNGLDIQDKPPAPPMRNTSTMIGAGSKDAGTLNHGSKPLPPNPEEKKKKDRFYRSIL-    59
PAK65_h  MEETQQKSHLELLSA--------------NHSLKPLPSVPEEKKPRHKIISIFS-        40
PAK3_m   -MSDSLDNEEKPPAPPLR-----------MNSNNRDSSALNHSSKPLPMAPEEKNKKARLRSIFPG   54

PAK1_h   PGDKTNKKKEKERPEISLPSDFEHTIHVGFDAVTGEFTGMPEQWARLLQTSNITKS---       115
PAK65_h  GTEKGSKKKEKERPEISPPSDFEHTIHVGFDTVTGEFTGMPEQWARLLQTSNITKL---        96
PAK3_m   GGDKTNKKKEKERPEISLPSDFEHTIHVGFDAVTGEFTGIPEQWARLLQTSNITKL---       110
PAK4_h   ---MFRKKKKKRPEISAPQNFQHRVHTSFDPKEGKFVGLPPQWQNILDTLRRPKPVVDP        56

PAK1_h   -------------------------------------------------------------    115
PAK65_h  -------------------------------------------------------------     96
PAK3_m   -------------------------------------------------------------    110
PAK4_h   SRITRVQLQPMKTVVRGSAMPVDGYISGLLNDIQKLSVISSNTLRGRSPTSRRRAQSLGL    116

PAK1_h   -------------------------------------------------------------    115
PAK65_h  -------------------------------------------------------------     96
PAK3_m   -------------------------------------------------------------    110
PAK4_h   LGDEHWATDPDMYLQSPQSERTDPHGLYLSCNGGTPAGHKQMPWPEPQSPRVLPNGLAAK    176

PAK1_h   ---------------------------------EQKKNPQAVLDV                   127
PAK65_h  ---------------------------------EQKKNPQAVLDV                   108
PAK3_m   ---------------------------------EQKKNPQAVLDV                   122
PAK4_h   AQSLGPAEFQGASQRCLQLGACLQSSPPGASPPTGTNRHGMKAAKHGSEEARPQSCLVGS    236
```

```
PAK1_h   LEFYNSKKTSNSQKYMSFT--DKSAEDYNSSNALNVKAVSETPAVPPVSEDEDDDDDAT  185
PAK65_h  LKFYDS---NTVKQKYLSFT--PPEKDGFPSGTPALNAKGTEAPAVVT----EEEDDDEET  160
PAK3_m   LKFYDSKETVNNQKYMSFTSGDKSAHGYIAAHQSNTKTGSEPPLAPPVSEEEDEEEEEEE  182
PAK4_h   ATGRPGEGSPSPKTRESSLKRRLFRSMFLSTAATAPPSSSKPGPPPPQSKPNSSFRPPQK  296
PAK5_h   -----------------------------------------ASGAKLAAGRPFNT  14

PAK1_h   ----PPPVIAPRPEHTKSVYTRSVIEPLPVTPTRDVATSPISPTENNTTPPDALTLNTEK  241
PAK65_h  ----APPVIAPRPDHTKSIYTRSVIDPVPAPVGDSHVDGAAKSL-------DK  202
PAK3_m   DDNEPPPVIAPRPEHTKSIYTRSVVESIASPAAPNKEDIPPSAENANSTTLYR----NTDR  239
PAK4_h   DNPPSLVAKAQSLPSDQPVGTFSPLTTSDTSSPQKSLRTAPATGQLPGRSSPA----GSPR  353
PAK5_h   YPRADTDHPSRGAQGEPHDVAPNGPSAGGLAIPQSSSSSRPPTRARGAPSPGVLGPHAS  74

PAK1_h   QKKKPKMSDEEILEK-----------------------------------LRSIVSVGDPKKKYTRFEKI  276
PAK65_h  QKKKTKMTDEEIHEK-----------------------------------LRTIVSIGDPKKKYTRYEKI  237
PAK3_m   QRKKSKMTDEEILEK-----------------------------------LRSIVSVGDPKKKYTRLEKI  274
PAK4_h   TWHAQISTSNLYLPQDPTVAKGALAGEDTGVVTHEQFKAALRMVVDQGDPRLLLDSYVKI  413
PAK5_h   EPQLAPPACTPAAPAVPGPPGPRSPQREPQRVSHEQFRAALQLVVDPGDPRSYLDNFIKI  134

PAK1_h   GQGASGTVYTAMDVATGQEVAIKQMNLQQQPKKELIINEILVMRENKNPNIVNYLDSYLV  336
PAK65_h  GQGASGTVFTAIDVALGQEVAIKQMNLQKQPKKELIINEILVMRENKNPNIVNYLDSYLV  297
PAK3_m   GQGASGTVYTAMDVATGQEVAIKQMNLQQQPKKELIINEILVMRENKNPNIVNYLDSYLV  334
PAK4_h   GEGSTGIVCLAREKHSGRQVAVKMMDLRKQQRRELLFNEVVIMRDYQHFNVVEMYKSYLV  473
PAK5_h   GEGSTGIVCIATVRSSGKLVAVKKMDLRKQQRRELLFNEVVIMRDYQHENVVEMYNSYLV  194
```

Fig. 7C

SEQ ID NO: 5   STLK2 human  Nterm=1-21   kin=22-274
Cterm=275-416
MAHSPVAVQVPGMQNNIADPEELFTKLERIGKGSFGEVFKGIDNRTQQVVAIKIIDLEEA
EDEIEDIQQEITVLSQCDSSYVTKYYGSYLKGSKLWIIMEYLGGGSALDLLRAGPFDEFQ
IATMLKEILKGLDYLHSEKKIHRDIKAANVLLSEQGDVKLADFGVAGQLTDTQIKRNTFV
GTPFWMAPEVIQQSAYDSKADIWSLGITAIELAKGEPPNSDMHPMRVLFLIPKNNPPTLV
GDFTKSFKEFIDACLNKDPSFRPTAKELLKHKFIVKNSKKTSYLTELIDRFKRWKAEGHS
DDESDSEGSDSESTSRENNTHPEWSFTTVRKKPDPKKVQNGAEQDLVQTLSCLSMIITPA
FAELKQQDENNASRNQAIEELEKSIAVAEAACPGITDKMVKKLIEKFQKCSADESP SEQ ID NO: 6   STLK3 human  Nterm=1-31  kin=32-308   Cterm=309-489
(insert=327-352) tail=490-516
TAAPAPAAPAAPAPAPAPAPAAQAVGWPICRDAYELQEVIGSGATAVVQAALCKPRQERV
AIKRINLEKCQTSMDELLKEIQAMSQCSHPNVVTYYTSFVVKDELWLVMKLLSGGSMLDI
IKYIVNRGEHKNGVLEEAIIATILKEVLEGLDYLHRNGQIHRDLKAGNILLGEDGSVQIA
DFGVSAFLATGGDVTRNKVRKTFVGTPCWMAPEVMEQVRGYDFKADMWSFGITAIELATG
AAPYHKYPPMKVLMLTLQNDPPTLETGVEDKEMMKKYGKSFRKLLSLCLQKDPSKRPTAA
ELLKCKFFQKAKNREYLIEKLLTRTPDIAQRAKKVRRVPGSSGHLHKTEDGDWEWSDDEM
DEKSEEGKAAFSQEKSRRVKEENPEIAVSASTIPEQIQSLSVHDSQGPPNANEDYREASS
CAVNLVLRLRNSRKELNDIRFEFTPGRDTADGVSQELFSAGLVDGHDVVIVAANLQKIVD
DPKALKTLTFKLASGCDGSEIPDEVKLIGFAQLSVS SEQ ID NO: 7   STLK4 human  Nterm=absent, kin=1-178, Ctail=179-414,
insert1=198-222, insert2=253-293
KSGVLDXSTIATILREVLEGLEYLHKXGQIHRDVKAGNILXGEDGSVQIADFGVSAFLAT
GGDITRNKVRKTFVGTPCWMAPEVMEQVRGYDFKADIWSFGITAIELATGAAPYHKYPPM
KVLMLTLQNDPPSLETGVQDKEMLKKYGKSFRKMISLCLQKDPEKRPTAAELLRHKFFQK
AKNKEFLQEKTLQRAPTISERAKKVRRVPGSSGRLHKTEDGGWEWSDDEFDEESEEGKAA
ISQLRSPRVKESISNSELFPTTDPVGTLLQVPEQISAHLPQPAGQIATQPTQVSLPPTAE
PAKTAQALSSGSGSQETKIPISLVLRLRNSKKELNDIRFEFTPGRDTAEGVSQELISAGL
VDGRDLVIVAANLQKIVEEPQSNRSVTFKLASGVEGSDIPDDGKLIGFAQLSIS SEQ ID NO: 8   STLK5 human  Nterm=absent, kin=1-222(lacks N-term),
Ctail=224-274
LICTHFMDGMNELAIAYILQGVLKALDYIHHMGYVHRSVKASHILISVDGKVYLSGLRSN
LSMISHGQRQRVVHDFPKYSVKVLPWLSPEVLQQNLQGYDAKSDIYSVGITACELANGHV
PFKDMPATQMLLEKLNGTVPCLLDTSTIPAEELTMSPSRSVANSGLSDSLTTSTPRPSNG
DSPSHPYHRTFSPHFHHFVEQCLQRNPDARPSASTLLNHSFFKQIKRRASEALPELLRPV

Fig. 8A

TPITNFEGSQSQDHSGIFGLVTNLEELEVDDWEF

SEQ ID NO: 13  ZC1 human 1/5/98 Nterm=1-22 kin=23-289
coiled-coil=290-526 pro=527-640 B=641-896 Rab/Rac-BD=897-1239
MANDSPAKSLVDIDLSSLRDPAGIFELVEVVGNGTYGQVYKGRHVKTGQLAAIKVMDVTE
DEEEEIKLEINMLKKYSHHRNIATYYGAFIKKSPPGHDDQLWLVMEFCGAGSITDLVKNT
KGNTLKEDWIAYISREILRGLAHLHIHHVIHRDIKGQNVLLTENAEVKLVDFGVSAQLDR
TVGRRNTFIGTPYWMAPEVIACDENPDATYDYRSDLWSCGITAIEMAEGAPPLCDMHPMR
ALFLIPRNPPPRLKSKKWSKKFFSFIEGCLVKNYMQRPSTEQLLKHPFIRDQPNERQVRI
QLKDHIDRTRKKRGEKDETEYEYSGSEEEEEVPEQEGEPSSIVNVPGESTLRRDFLRLQ
QENKERSEALRRQQLLQEQQLREQEEYKRQLLAERQKRIEQQKEQRRRLEEQQRREREAR
RQQEREQRRREQEEKRRLEELERRRKEEEERRAEEEKRRVEREQEYIRRQLEEEQRHLE
VLQQQLLQEQAMLLECRWREMEEHRQAERLQRQLQQEQAYLLSLQHDHRRPHPQHSQQPP
PPQQERSKPSFHAPEPKAHYEPADRAREVEDRFRKTNHSSPEAQSKQTGRVLEPPVPSRS
ESFSNGNSESVHPALQRPAEPQVPVRTTSRSPVLSRRDSPLQGSGQQNSQAGQRNSTSIE
PRLLWERVEKLVPRPGSGSSSGSSNSGSQPGSHPGSQSGSGERFRVRSSSKSEGSPSQRL
ENAVKKPEDKKEVFRPLKPADLTALAKELRAVEDVRPPHKVTDYSSSSEESGTTDEEDDD
VEQEGADESTSGPEDTRAASSLNLSNGETESVKTMIVHDDVESEPAMTPSKEGTLIVRRT
QSASSTLQKHKSSSSFTPFIDPRLLQISPSSGTTVTSVVGFSCDGMRPEAIRQDPTRKGS
VVNVNPTNTRPQSDTPEIRKYKKRFNSEILCAALWGVNLLVGTESGLMLLDRSGQGKVYP
LINRRRFQQMDVLEGLNVLVTISGKKDKLRVYYLSWLRNKILHNDPEVEKKQGWTTVGDL
EGCVHYKVVKYERIKFLVIALKSSVEVYAWAPKPYHKFMAFKSFGELVHKPLLVDLTVEE
GQRLKVIYGSCAGFHAVDVDSGSVYDIYLPTHIQCSIKPHAIIILPNTDGMELLVCYEDE
GVYVNTYGRITKDVVLQWGEMPTSVAYIRSNQTMGWGEKAIEIRSVETGHLDGVFMHKRA
QRLKFLCERNDKVFFASVRSGGSSQVYFMTLGRTSLLSW SEQ ID NO: 14  ZC2 human Nterm=missing kin=1-255 coiled-coil=256-442
pro=443-626 B=627-954 Rab/RacBD=955-1297
AFGEVYEGRHVKTGQLAAIKVMDVTGDEEEEIKQEINMLKKYSHHRNIATYYGAFIKKNP
PGMDDQLWLVMEFCGAGSVTDLIKNTKGNTLKEEWIAYICREILRGLSHLHQHKVIHRDI
KGQNVLLTENAEVKLVDFGVSAQLDRTVGRRNTFIGTPYWMAPEVIACDENPDATYDFKS
DLWSLGITAIEMAEGAPPLCDMHPMRALFLIPRNPAPRLKSKKWSKKFQSFIESCLVKNH
SQRPATEQLMKHPFIRDQPNERQVRIQLKDHIDRTKKKRGEKDETEYEYSGSEEEEEEND
SGEPSSILNLPRESTLRRDFLRLQLANKERSEALRRQQLEQQQRENEEHKRQLLAERQKR
IEEQKEQRRRLEEQQRREKELRKQQEREQRRHYEEQMRREEERRAEHEQEYKRKQLEEQ
RQAERLQRQLKQERDYLVSLQHQRQEQRPVEKKPLYHYKEGMSPSEKPAWAKEVEERSRL
NRQSSPAMPHKVANRISDPNLPPRSESFSISGVQPARTPPMLRPVDPQIPHLVAVKSQGP
ALTASQSVHEQPTKGLSGFQEALNVTSHRVEMPRQNSDPTSENPPLPTRIEKFDRSSWLR

Fig. 8B

QEEDIPPKVPQRTTSISPALARKNSPGNGSALGPRLGSQPIRASNPDLRRTEPILESPLQ
RTSSGSSSSSSTPSSQPSSQGGSQPGSQAGSSERTRVRANSKSEGSPVLPHEPAKVKPEE
SRDITRPSRPASYKKAIDEDLTALAKELRELRIEETNRPMKKVTDYSSSSEESESSEEEE
EDGESETHDGTVAVSDIPRLIPTGAPGSNEQYNVGMVGTHGLETSHADSFSGSISREGTL
MIRETSGEKKRSGHSDSNGFAGHINLPDLVQQSHSPAGTPTEGLGRVSTHSQEMDSGTEY
GMGSSTKASFTPFVDPRVYQTSPTDEDEEDEESSAAALFTGELLRQEQAKLNEARKISVV
NVNPTNIRPHSDTPEIRKYKKRFNSEILCAALWGVNLLVGTENGLMLLDRSGQGKVYNLI
NRRRFQQMDVLEGLNVLVTISGKKNKLRVYYLSWLRNRILHNDPEVEKKQGWITVGDLEG
CIHYKVVKYERIKFLVIALKNAVEIYAWAPKPYHKFMAFKSFADLQHKPLLVDLTVEEGQ
RLKVIFGSHTGFHVIDVDSGNSYDIYTPSHIQGNITPHAIVILPKTDGMEMLVCYEDEGV
YVNTYGRITKDVVLQWGEMPTSVAYIHSNQIMGWGEKAIEIRSVETGHLDGVFMHKRAQR
LKFLCERNDKVFFASVRSGGSSQVFFMTLNRNSMMNW

SEQ ID NO: 15   ZC3 human kin=1-255 coiled-coil=256-476 pro=477-680
B=681-983 Rab/RacBD =984-1326
AFGEVYEGRHVKTGQLAAIKVMDVTEDEEEEIKQEINMLKKYSHHRNIATYYGAFIKKSP
PGNDDQLWLVMEFCGAGSVTDLVKNTKGNALKEDCIAYICREILRGLAHLHAHKVIHRDI
KGQNVLLTENAEVKLVDFGVSAQLDRTVGRRNTFIGTPYWMAPEVIACDENPDATYDYRS
DIWSLGITAIEMAEGAPPLCDMHPMRALFLIPRNPPPRLKSKKWSKKFIDFIDTCLIKTY
LSRPPTEQLLKFPFIRDQPTERQVRIQLKDHIDRSRKKRGEKEETEYEYSGSEEEDDSHG
EEGEPSSIMNVPGESTLRREFLRLQQENKSNSEALKQQQQLQQQQQRDPEAHIKHLLHQR
QRRIEEQKEERRRVEEQQRREREQRKLQEKEQQRRLEDMQALRREEERRQAEREQEYIRH
RLEEEQRQLEILQQQLLQEQALLLEYKRKQLEEQRQSERLQRQLQQEHAYLKSLQQQQQQ
QQLQKQQQQQLLPGDRKPLYHYGRGMNPADKPAWAREVEERTRMNKQQNSPLAKSKPGST
GPEPPIPQASPGPPGPLSQTPPMQRPVEPQEGPHKSLVAHRVPLKPYAAPVPRSQSLQDQ
PTRNLAAFPASHDPDPAIPAPTATPSARGAVIRQNSDPTSEGPGPSPNPPAWVRPDNEAP
PKVPQRTSSIATALNTSGAGGSRPAQAVRARPRSNSAWQIYLQRRAERGTPKPPGPPAQP
PGPPNASSNPDLRRSDPGWERSDSVLPASHGHLPQAGSLERNRVGVSSKPDSSPVLSPGN
KAKPDDHRSRPGRPADFVLLKERTLDEAPRPPKKAMDYSSSSEEVESSEDDEEEGEGGPA
EGSRDTPGGRDGDTDSVSTMVVHDVEEITGTQPPYGGGTMVVQRTPEEERNLLHADSNGY
TNLPDVVQPSHSPTENSKGQSPPSKDGSGDYQSRGLVKAPGKSSFTMFVDLGIYQPGGSG
DSIPITALVGGEGTRLDQLQYDVRKGSVVNVNPTNTRAHSETPEIRKYKKRFNSEILCAA
LWGVNLLVGTENGLMLLDRSGQGKVYGLIGRRRFQQMDVLEGLNLLITISGKRNKLRVYY
LSWLRNKILHNDPEVEKKQGWTTVGDMEGCGHYRVVKYERIKFLVIALKSSVEVYAWAPK
PYHKFMAFKSFADLPHRPLLVDLTVEEGQRLKVIYGSSAGFHAVDVDSGNSYDIYIPVHI
QSQITPHAIIFLPNTDGMEMLLCYEDEGVYVNTYGRIIKDVVLQWGEMPTSVAYICSNQI
MGWGEKAIEIRSVETGHLDGVFMHKRAQRLKFLCERNDKVFFASVRSGGSSQVYFMTLNR
NRIMNW

Fig. 8C

SEQ ID NO: 16   ZC4 human Nterm kin coiled-coil pro B=missing
Rab/RacBD=1-349
NVNPLYVSPACKKPLIHMYEKEFTSEICCGSLWGVNLLLGTRSNLYLMDRSGKADITKLI
RRRPFRQIQVLEPLNLLITISGHKNRLRVYHLTWLRNKILNNDPESKRRQEEMLKTEEAC
KAIDKLTGCEHFSVLQHEETTYIAIALKSSIHLYAWAPKSFDESTAIKVFPTLDHKPVTV
DLAIGSEKRLKIFFSSADGYHLIDAESEVMSDVTLPKNPLEIIIPQNIIILPDCLGIGMM
LTFNAEALSVEANEQLFKKILEMWKDIPSSIAFECTQRTTGWGQKAIEVRSLQSRVLESE
LKRRSIKKLRFLCTRGDKLFFTSTLRNHHSRVYFMTLGKLEELQSNYDV SEQ ID NO: 18   KHS2 human Nterm=1-13   kin=14-273   A=274-346
Pro=347-534 RabBD =535-894
MNPGFDLSRRNPQEDFELIQRIGSGTYGDVYKARNVNTGELAAIKVIKLEPGEDFAVVQQ
EIIMMKDCKHPNIVAYFGSYLRRDKLWICMEFCGGGSLQDIYHVTGPLSELQIAYVSRET
LQGLYYLHSKGKMHRDIKGANILLTDNGHVKLADFGVSAQITATIAKRKSFIGTPYWMAP
EVAAVERKGGYNQLCDLWAVGITAIELAELQPPMFDLHPMRALFLMTKSNFQPPKLKDKM
KWSNSFHHFVKMALTKNPKKRPTAEKLLQHPFVTQHLTRSLAIELLDKVNNPDHSTYHDF
DDDDPEPLVAVPHRIHSTSRNVREEKTRSEITFGQVKFDPPLRKETEPHHELPDSDGFLD
SSEEIYYTARSNLDLQLEYGQGHQGGYFLGANKSLLKSVEEELHQRGHVAHLEDDEGDDD
ESKHSTLKAKIPPPLPPKPKSIFIPQEMHSTEDENQGTIKRCPMSGSPAKPSQVPPRPPP
PRLPPHKPVALGNGMSSFQLNGERDGSLCQQQNEHRGTNLSRKEKKDVPKPISNGLPPTP
KVHMGACFSKVFNGCPLKIHCASSWINPDTRDQYLIFGAEEGIYTLNLNELHETSMEQLF
PRRCTWLYVMNNCLLSISGKASQLYSHNLPGLFDYARQMQKLPVAIPAHKLPDRILPRKF
SVSAKIPETKWCQKCCVVRNPYTGHKYLCGALQTSIVLLEWVEPMQKFMLIKHIDFPIPC
PLRMFEMLVVPEQEYPLVCVGVSRGRDFNQVVRFETVNPNSTSSWFTESDTPQTNVTHVT
QLERDTILVCLDCCIKIVNLQGRLKSSRKLSSELTFDFQIESIVCLQDSVLAFWKHGMQG
RSFRSNEVTQEISDSTRIFRLLGSDRVVVLESRPTDNPTANSNLYILAGHENSY SEQ ID NO: 22   SULU1 human N=1-21 kin=22-277 A=278-427
coiled-coil1=428-637 B=638-751 coiled-coil2=752-898
MRKGVLKDPEIDDLFYKDDPEELFIGLHEIGHGSFGAVYFATNAHTNEVVAIKKMSYSGK
QTHEKWQDILKEVKFLRQLKHPNTIEYKGCYLKEHTAWLVMEYCLGSASDLLEVHKKPLQ
EVEIAAITHGALHGLAYLHSHALIHRDIKAGNILLTEPGQVKLADFGSASMASPANSFVG
TPYWMAPEVILAMDEGQYDGKVDIWSLGITCIELAERKPPLFNMNAMSALYHIAQNDSPT
LQSNEWTDSFRRFVDYCLQKIPQERPTSAELLRHDFVRRDRPLRVLIDLIQRTKDAVREL
DNLQYRKMKKILFQETRNGPLNESQEDEEDSEHGTSLNREMDSLGSNHSIPSMSVSTGSQ
SSSVNSMQEVMDESSSELVMMHDDESTINSSSSVVHKKDHVFTRDEAGHGDPRPEPRPTQ
SVQSQALHYRNRERFATIKSASLVTRQIHEHEQENELREQMSGYKRMRRQHQKQLIALEN
KLKAEMDEHRLKLQKEVETHANNSSIELEKLAKKQVAIIEKEAKVAAADEKKFQQQILAQ

Fig. 8D

```
QKKDLTTFLESQKKQYKICKEKIKEEMNEDHSTPKKEKQERISKHKENLQHTQAEEEAHL
LTQQRLYYDKNCRFFKRKIMIKRHEVEQQNIREELNKKRTQKEMEHAMLIRHDESTRELE
YRQLHTLQKLRMDLIRLQHQTELENQLEYNKRRERELHRKHVMGLRQQPKNLKAMEMQIK
KQFQDTCKVQTKQYKALKNHQLEVTPKNEHKTILKTLKDEQTRKLAILAEQYEQSINEMM
ASQALRLDEAQEAECQALRLQLQQEMELLNAYQSKIKMQTEAQHERELQKLEQRVSLRRA
HLEQKIEEELAALQKERSERIKNLLERQEREIETFDMESLRMGFGNLVTLDFPKEDYR
```

SEQ ID NO: 23  SULU3 human Nterm=missing kin partial=1-66 A=67-215
coiled-coil1=216-425 B=426-539 coiled-coil2=540-786 Ctail=687-786

```
IELAERKPPLFNMNAMSALYHIAQNESPTLQSNEWSDYFRNFVDSCLQKIPQDRPTSEEL
LKHIFVLRERPETVLIDLIQRTKDAVRELDNLQYRKMKKLLFQEAHNGPAVEAQEEEEEQ
DHGVGRTGTVNSVGSNQSIPSMSISASSQSSSVNSLPDVSDDKSELDMMEGDHTVMSNSS
VIHLKPEEENYREEGDPRTRASDPQSPPQVSRHKSHYRNREHFATIRTASLVTRQMQEHE
QDSELREQMSGYKRMRRQHQKQLMTLENKLKAEMDEHRLRLDKDLETQRNNFAAEMEKLI
KKHQAAMEKEAKVMSNEEKKFQQHIQAQQKKELNSFLESQKREYKLRKEQLKEELNENQS
TPKKEKQEWLSKQKENIQHFQAEEEANLLRRQRQYLELECRRFKRRMLLGRHNLEQDLVR
EELNKRQTQKDLEHAMLLRQHESMQELEFRHLNTIQKMRCELIRLQHQTELTNQLEYNKR
RERELRRKHVMEVRQQPKSLKSKELQIKKQFQDTCKIQTRQYKALRNHLLETTPKSEHKA
VLKRLKEEQTRKLAILAEQYDHSINEMLSTQALRLDEAQEAECQVLKMQLQQELELLNAY
QSKIKMQAEAQHDRELRELEQRVSLRRALLEQKIEEEMLALQNERTERIRSLLERQAREI
EAFDSESMRLGFSNMVLSNLSPEAFSHSYPGASGWSHNPTGGPGPHWGHPMGGPPQAWGH
PMQGGPQPWGHPSGPMQGVPRGSSMGVRNSPQALRRTASGGRTEQGMSRSTSVTSQISNG
SHMSYT
```

SEQ ID NO: 24  SULU3 murine Nterm=1-25 kin=26-273  A=274-422
cc1=423-632 B=633-748 cc2=missing

```
MPSTNRAGSLKDPEIAELFFKEDPEKLFTDLREIGHGSFGAVYFARDVRTNEVVAIKKMS
YSGKQSTEKWQDIIKEVKFLQRIKHPNSIEYKGCYLREHTAWLVMEYCLGSASDLLEVHK
KPLQEVEIAAITHGALQGLAYLHSHTMIHRDIKAGNILLTEPGQVKLADFGSASMASPAN
SFVGTPYWMAPEVILAMDEGQYDGKVDVWSLGITCIELAERKPPLFNMNAMSALYHIAQN
ESPTLQSNMNDSCLQKIPQDRPTSEELLKHMFVLRERPETVLIDLIQRTKDAVRELDNLQ
YRKMKKLLFQEAHNGPAVEAQEEEEQDHGVGRTGTVNSVGSNQSIPSMSISASSQSSSV
NSLPDASDDKSELDMMEGDHTVMSNSSVIHLKPEEENYQEEGDPRTRASDPQSPPQVSRH
KSHYRNREHFATIRTASLVTRQMQEHEQDSELREQMSGYKRMRRQHQKQLMTLENKLKAE
MDEHRLRLDKDLETQRNNFAAEMEKLIKKHQAAMEKEAKVMANEEKKFQQHIQAQQKKEL
NSFLESQKREYKLRKEQLKEELNENQSTPKKEKQEWLSKQKENIQHFQAEEEANLLRRQR
QYLELECRRFKRRMLLGRHNLEQDLVREELNKRQTQKDLEHAMLLRQHESMQELEFRHLN
TIQKMRCELIRLQHQTELTNQLEYNKRRERELRRKHVMEVRQQPKSLKSKELQIKKQFQD
```

Fig. 8E

TCKIQTRQYKALRNHLLETTPKNEHKAI

SEQ ID NO: 26  GEK2 human N=1-33 kin=34-294 A=295-337 B=338-472 215
coiled-coil1=473-724 215 coiled-coil2=725-912
MAFANFRRILRLSTFEKRKSREYEHVRRDLDPNEVWEIVGELGDGAFGKVYKAKNKETGA
LAAAKVIETKSEEELEDYIVEIEILATCDHPYIVKLLGAYYHDGKLWIMIEFCPGGAVDA
IMLELDRGLTEPQIQVVCRQMLEALNFLHSKRIIHRDLKAGNVLMTLEGDIRLADFGVSA
KNLKTLQKRDSFIGTPYWMAPEVVMCETMKDTPYDYKADIWSLGITLIEMAQIEPPHHEL
NPMRVLLKIAKSDPPTLLTPSKWSVEFRDFLKIALDKNPETRPSAAQLLEHPFVSSITSN
KALRELVAEAKAEVMEEIEDGRDEGEEEDAVDAASTLENHTQNSSEVSPPSLNADKPLEE
SPSTPLAPSQSQDSVNEPCSQPSGDRSLQTTSPPVVAPGNENGLAVPVPLRKSRPVSMDA
RIQVAQEKQVAEQGGDLSPAANRSQKASQSRPNSSALETLGGEKLANGSLEPPAQAAPGP
SKRDSDCSSLCTSESMDYGTNLSTDLSLNKEMGSLSIKDPKLYKKTLKRTRKFVVDGVEV
SITTSKIISEDEKKDEEMRFLRRQELRELRLLQKEEHRNQTQLSNKHELQLEQMHKRFEQ
EINAKKKFFDTELENLERQQKQQVEKMEQDHAVRRREEARRIRLEQDRDYTRFQEQLKLM
KKEVKNEVEKLPRQQRKESMKQKMEEHTQKKQLLDRDFVAKQKEDLELAMKRLTTDNRRE
ICDKERECLMKKQELLRDREAALWEMEEHQLQERHQLVKQQLKDQYFLQRHELLRKHEKE
REQMQRYNQRMIEQLKVRQQQEKARLPKIQRSEGKTRMAMYKKSLHINGGGSAAEQREKI
KQFSQQEEKRQKSERLQQQQKHENQMRDMLAQCESNMSELQQLQNEKCHLLVEHETQKLK
ALDESHNQNLKE SEQ ID NO: 29  PAK4 human Rac=1-51 A=52-224 Nterm=225-393
kin=394-658 Ctail=659-681 residues 13-23
(SAPQNFQHRVH)= Cdc42 /Rac-binding motif
MFRKKKKKRPEISAPQNFQHRVHTSFDPKEGKFVGLPPQWQNILDTLRRPKPVVDPSRIT
RVQLQPMKTVVRGSAMPVDGYISGLLNDIQKLSVISSNTLRGRSPTSRRRAQSLGLLGDE
HWATDPDMYLQSPQSERTDPHGLYLSCNGGTPAGHKQMPWPEPQSPRVLPNGLAAKAQSL
GPAEFQGASQRCLQLGACLQSSPPGASPPTGTNRHGMKAAKHGSEEARPQSCLVGSATGR
PGGEGSPSPKTRESSLKRRLFRSMFLSTAATAPPSSSKPGPPPQSKPNSSFRPPQKDNPP
SLVAKAQSLPSDQPVGTFSPLTTSDTSSPQKSLRTAPATGQLPGRSSPAGSPRTWHAQIS
TSNLYLPQDPTVAKGALAGEDTGVVTHEQFKAALRMVVDQGDPRLLLDSYVKIGEGSTGI
VCLAREKHSGRQVAVKMMDLRKQQRRELLFNEVVIMRDYQHFNVVEMYKSYLVGEELWVL
MEFLQGGALTDIVSQVRLNEEQIATVCEAVLQALAYLHAQGVIHRDIKSDSILLTLDGRV
KLSDFGFCAQISKDVPKRKSLVGTPYWMAPEVISRSLYATEVDIWSLGIMVIEMVDGEPP
YFSDSPVQAMKRLRDSPPPKLKNSHKVSPVLRDFLERMLVRDPQERATAQELLDHPFLLQ
TGLPECLVPLIQLYRKQTSTC

Fig. 8F

SEQ ID NO: 30  PAK5 human Rac A=missing Nterm partial=1-114
kin=115-379 Ctail=380-398
ASGAKLAAGRPFNTYPRADTDHPSRGAQGEPHDVAPNGPSAGGLAIPQSSSSSSRPPTRA
RGAPSPGVLGPHASEPQLAPPACTPAAPAVPGPPGPRSPQREPQRVSHEQFRAALQLVVD
PGDPRSYLDNFIKIGEGSTGIVCIATVRSSGKLVAVKKMDLRKQQRRELLFNEVVIMRDY
QHENVVEMYNSYLVGDELWVVMEFLEGGALTDIVTHTRMNEEQIAAVCLAVLQALSVLHA
QGVIHRDIKSDSILLTHDGRVKLSDFGFCAQVSKEVPRRKSLVGTPYWMAPELISRLPYG
PEVDIWSLGIMVIEMVDGEPPYFNEPPLKAMKMIRDNLPPRLKNLHKVSPSLKGFLDRLL
VRDPAQRATAAELLKHPFLAKAGPPASIVPLMRQNRTR

Fig. 8G

SEQ ID NO: 1  STLK2 HUMAN
TAACAGCCCACCTCCTAGCCCCGGGCTACGCGCCGCCAGCCCAGTAACCCCACTTTTGTG
TGTCCTCCCAGGCCCCGATCGAAAAGCCTGGGAGGGCCGCCGAACTACCCCGGAGGGAG
GAGCCAGTCCGAACCCAAGGCGCCACCGCCGCAGAAGCGGAGCGAGGCAGCATTCGCCTC
CATGGCCCACTCGCCGGTGGCTGTCCAAGTGCCTGGGATGCAGAATAACATAGCTGATCC
AGAAGAACTGTTCACAAAATTAGAGCGCATTGGGAAAGGCTCATTTGGGGAAGTTTTCAA
AGGAATTGATAACCGTACCCAGCAAGTCGTTGCTATTAAAATCATAGACCTTGAGGAAGC
CGAAGATGAAATAGAAGACATTCAGCAAGAAATAACTGTCTTGAGTCAATGTGACAGCTC
ATATGTAACAAAATACTATGGGTCATATTTAAAGGGGTCTAAATTATGGATAATAATGGA
ATACCTGGGCGGTGGTTCAGCACTGGATCTTCTTCGAGCTGGTCCATTTGATGAGTTCCA
GATTGCTACCATGCTAAAGGAAATTTTAAAAGGTCTGGACTATCTGCATTCAGAAAAGAA
AATTCACCGAGACATAAAAGCTGCCAATGTCTTGCTCTCAGAACAAGGAGATGTTAAACT
TGCTGATTTTGGAGTTGCTGGTCAGCTGACAGATACACAGATTAAAAGAAATACCTTTGT
GGGAACTCCATTTTGGATGGCTCCTGAAGTTATTCAACAGTCAGCTTATGACTCAAAAGC
TGACATTTGGTCATTGGGAATTACTGCTATTGAACTAGCCAAGGGAGAGCCACCTAACTC
CGATATGCATCCAATGAGAGTTCTGTTTCTTATTCCCAAAAACAATCCTCCAACTCTTGT
TGGAGACTTTACTAAGTCTTTTAAGGAGTTTATTGATGCTTGCCTGAACAAAGATCCATC
ATTTCGTCCTACAGCAAAAGAACTTCTGAAACACAAATTCATTGTAAAAAATTCAAAGAA
GACTTCTTATCTGACTGAACTGATAGATCGTTTTAAGAGATGGAAGGCAGAAGGACACAG
TGATGATGAATCTGATTCCGAGGGCTCTGATTCGGAATCTACCAGCAGGGAAAACAATAC
TCATCCTGAATGGAGCTTTACCACCGTACGAAAGAAGCCTGATCCAAAGAAAGTACAGAA
TGGGGCAGAGCAAGATCTTGTGCAAACCCTGAGTTGTTTGTCTATGATAATCACACCTGC
ATTTGCTGAACTTAAACAGCAGGACGAGAATAACGCTAGCAGGAATCAGGCGATTGAAGA
ACTCGAGAAAGTATTGCTGTGGCTGAAGCCGCCTGTCCCGGCATCACAGATAAAATGGT
GAAGAAACTAATTGAAAAATTTCAAAAGTGTTCAGCAGACGAATCCCCCTAAGAAACTTA
TTATTGGCTTCTGTTTCATATGGACCCAGAGAGCCCCACCAAACCTACGTCAAGATTAAC
AATGCTTAACCCATGAGCTCCATGTGCCTTTTGGATCTTTGCAACACTGAAGATTTGGAA
GAAGCTATTAAACTATTTTGTGATGGCGTTTATCATTTATATTTTGAAAGGATTATTTT
GTAAGGAATAACTTTTAATACTATAGTTTCACCTGTATTCTAGTAAATGTTGAGACACCG
TTTTGCTTTTAAGTATCCCTATTTCTTAAGTTACGAGGATGAATACCTTTCACATTTTGA
TCTTTAGTTGACTCTACAGTCATGAAACATACAGGTCTTTCAAAGTCATTCTCAATATTC
AGCTTTTGTAAATTATCAAGCTTCAAAAGCTTTTTTTAAAAAAAAAAACATGCATATT
CTAAAAATGACTATTGGTGGGGAGGTGTAAATAAGTCATACCTTCTTAAAACAGAAAATT
TAAGTAAAGTCTTTTAAATGAAACCTGTAAAAGTATTGACTCTTCTACCAAGTTGGTATG
ATATTCCAGGCAGCTCAATGATTATCACATTTGAGACCCTGTGTTTGAAGCATTTACAGG
CAATGTACAGCAACAGAGGTACCTCTTGGTGTATAGTATTTACATTCTCTTTTAGGTAGA
AGAGGCAATTTTACCCTTATTTCACATGGTTAGAAATTTAAAGCAAGATCATTTACCCAA

Fig. 9A

GGATAGGTGTTTGGTAATGTTGAAGGAGTTAGTCTGGCTTCATGTTTTACATCTTCAACT
AAAATCCCATACTATCTGCTTGGATTTGGAGAGCCAAAAAATAAAGCTGATTGTCATGTG
ATTAAATATCTGATCAACAGGTATGAATATAACTTAAATCAGCATATTTTTGCCATGGTA
ATAAATTGTCCTATAAACTATTTATATATTTTGTTCTTCATAATTATCACTAATAAGCA
TCAGTTTGTTGTTTTAAAAGGATATTTAAGTGAGCATTTTCTAGTTCATATGAAAATAA
CCATAGTACAGGATGATTTCTGTCCACACAAAGGTTAAATTAGATTGCACAGTTAATTTT
CACTTATATTTATGGTACTATTATGTGGGTGATGCCTTTTCTTTTAAGCCCAGTACATA
TATTATGCCTGCCTAAGTTCTGAACTGGGGCTGTATTTCAGTAGTTGTAGAATTATTGAT
ATTTAGTTTTGATAGCTAATGTTTAATTGTTTGGATCTGCACAGTTTGGTTTTTGCACAA
AAGTCATTTAAAAAAATCTGAGTAATTGTCAAATATTAAAAGAAAGATATTCTTCCTGTA
AGGAATACAGTTTTTAGTCAAAGTGGCCATTACATCCTCTTTTAATTTACATAATACAG
ATACTTGAGAAAGTTGTTGTGGTGTTGTATGCCAAGAAAATTCTTTTTATTGGTGCCTAT
ATTGTAACAATTATTTTAATGCATTGTATTTGAAGTAACGGTTCAGTTAAATTTTTCA
CCTGCTGTGTAACTGAAACACAATTACAGTTTATAATCATCTGTAGAAGTCTGGAGATAA
TTTTGCAACTCATGTTATGGGTTAAATGAATATTTTGTAAAAGTAAAAGCAACAAATTT
ATAAATTGATTATTTGAAACTTTACAACACAATTGCATCCCAAATACAAATTGTATTGCT
TATTCATTATAGCTATTCGTCCTGTAATCTGTTTCTAGGTGAAGCATACTCCAGTGTTTT
AGGGGTTTTGAAAATAAATATTTAAATTTCACAGTCAAAAAAAAAAAAAAAAAAAAAAA
AAAAAAAAAAAAAAAAAAAAAAAAAA

SEQ ID NO: 2   STLK3 HUMAN
GACAGCAGCGCCGGCCCCGGCAGCTCCCGCGGCCCCGGCCCCGGCCCCGGCCCCGGCCCC
GGCGGCACAGGCTGTCGGCTGGCCCATCTGCAGGGACGCGTACGAGCTGCAGGAGGTTAT
CGGCAGTGGAGCTACTGCTGTGGTTCAGGCAGCCCTATGCAAACCCAGGCAAGAACGTGT
AGCAATAAAACGGATCAACTTGGAAAAATGCCAGACCAGTATGGATGAACTATTAAAAGA
AATTCAAGCCATGAGTCAGTGCAGCCATCCCAACGTAGTGACCTATTACACCTCTTTTGT
GGTCAAAGATGAACTTTGGCTGGTCATGAATTACTAAGTGGAGGTTCAATGTTGGATAT
CATAAAATACATTGTCAACCGAGGAGAACACAAGAATGGAGTTCTGGAAGAGGCAATAAT
AGCAACAATTCTTAAAGAGGTTTTGGAAGGCTTAGACTATCTACACAGAAACGGTCAGAT
TCACAGGGATTTGAAAGCTGGTAATATTCTTCTGGGTGAGGATGGTTCAGTACAAATAGC
AGATTTTGGGGTAAGTGCGTTCCTAGCAACAGGGGGTGATGTTACCCGAAATAAAGTAAG
AAAAACATTCGTTGGCACCCCATGTTGGATGGCTCCTGAAGTCATGGAACAGGTGAGAGG
CTATGACTTCAAGGCTGACATGTGGAGTTTTGGAATAACTGCCATTGAATTAGCAACAGG
AGCAGCGCCTTATCACAAATATCCTCCCATGAAAGTGTTAATGTTGACTTTGCAAAATGA
TCCACCCACTTTGGAAACAGGGGTAGAGGATAAAGAAATGATGAAAAGTACGGCAAGTC
CTTTAGAAAATTACTTTCACTGTGTCTTCAGAAAGATCCTTCCAAAAGGCCCACAGCAGC
AGAACTTTTAAAATGCAAATTCTTCCAGAAAGCCAAGAACAGAGAGTACCTGATTGAGAA
GCTGCTTACAAGAACACCAGACATAGCCCAAAGAGCCAAAAAGGTAAGAAGAGTTCCTGG

Fig. 9B

```
GTCAAGTGGTCACCTTCATAAAACCGAAGACGGGGACTGGGAGTGGAGTGACGACGAGAT
GGATGAGAAGAGCGAAGAAGGGAAAGCAGCTTTTCTCAGGAAAAGTCACGAAGAGTAAA
AGAAGAAAATCCAGAGATTGCAGTGAGTGCCAGCACCATCCCCGAACAAATACAGTCCCT
CTCTGTGCACGACTCTCAGGGCCCACCCAATGCTAATGAAGACTACAGAGAAGCTTCTTC
TTGTGCCGTGAACCTCGTTTTGAGATTAAGAAACTCCAGAAAGGAACTTAATGACATACG
ATTTGAGTTTACTCCAGGAAGAGATACAGCAGATGGTGTATCTCAGGAGCTCTTCTCTGC
TGGCTTGGTGGATGGTCACGATGTAGTTATAGTGGCTGCTAATTTACAGAAGATTGTAGA
TGATCCCAAAGCTTTAAAAACATTGACATTTAAGTTGGCTTCTGGCTGTGATGGGTCGGA
GATTCCTGATGAAGTGAAGCTGATTGGGTTTGCTCAGTTGAGTGTCAGCTGATGTATGTC
CCTTGATGTCACCCTGATCTGTCATGCCCCACCGCCACCCCTACTCCCTTCAACCCTCCC
TCTTTCTGCCCATTTCCTCCCACCCCCTCACTCCCATTTCCTAGCAAAATCAGAAGATTG
TGAAGAGGCCGGCTTCAACAAAATGGGATAAAAAAATAATTTTTAAAACTTACAACACT
CCGAGTTCTGCTTTATTCTCTAGCAATCCACAGTACAAGAACAAGCAAATGCCACAGCTG
CACGACTGTTGCTCATTTTTCCAAAAGCTATTTAATATTCTTAGCAATCAATTTGGATAT
CCCTTAAGTGAAAAGAATCTGAAATACACTCAGGTGGTCTTATTTATTGGCAACAAAGG
AATTTTCTATCCAGAAGCCTATTTCTCCTTTCATTGTTGTTATTTCTGTTATAATACTTT
AATTGTACATCTGACAATACTGCCTCTTTTATGTTGTATTTAGAAATTAATATACTTATA
AAATTAAGATTTATTAGCCAAACTTGAATTCTAGTTTTAAAACTGACTGTGAATTTTATT
TTTCATATATTTATGCATTACACACCTTAGCTATAAGAAAAAAGGGTTTTGATTATATG
CTTCTTGCAGTTAATCTCGTTATTTAAACAAAAGTTTTGGGTCTATCTTTGGAGTATTT
GTAACTTCTAAATTTTGAAATGACTGAATTAGGAATTTGGATGCTTATTCTTTTAGTCTG
TTTGCCTAAAAACCAATTTACAATCTGACTGTCTCTTGGGAGAGGGAGGTGCCTTGCAAA
CTTTCACATTAAGAATGTGCCTGAGGCTGCTTTACTCTGGAATAGTCTCAGATCTAAAAT
TTCCTCTATATAAGGTGGCATATGTTAAGTTTTGCTTCATTGGACCGTTTAGAATGCTAT
GTAAAATGTTGCCATTCTGTTAGATTGCTAACTATATACCCATCTCTGATTTGGCTCTCC
TTAAGTGATAGGATTTGTTATTCTAAAGGTGATAAACTTGAAAATATCAGAATCTGAGTT
TTACTTGAAATTTTGCAGAATACCCAGGTGGAGTGAAAATTGGAAGGGTTTTGTGCAATG
ACTAAAAGGTAAAACGCTGTTAAGGTTCAAGAATCAATACTTTCAACCCAAGTAGCCCTC
TGCTTGACTGTATATTATGGAACTAGTAAACCTTAGGATTTTGAAAATTGGAGTCTAATC
TTTCAAGGAGGTGGGCTCCCAGGATGGTACCATTGCTCTTTCCTAGCTAACCCTAGATAT
GGCAGCTCTTTAATGTACTTCAAAAGCAAATATATATTACTAAGGAAAAAAGTTATTT
ATAATTGCCTTGTCATAATTGTTAAGGTGTTCTAGAGCCATTTGCATACAATTTAATGTA
ATTTCATTCCATTCTATTGTTTACACAACGATTACTCGAAGATGACTGCAAAGGTAAAAG
GAAAATAAAAGTGTATTGCACAATGAAAAA

SEQ ID NO: 3 STLK4 HUMAN
CAAAAGTGGAGTCCTAGATGANTCTACCATTGCTACGATACTCCGAGAAGTACTGGAAGG
GCTGGAATATCTGCATAAAANTGGACAGATCCACAGAGATGTGAAAGCTGGAAACATTCT
```

Fig. 9C

```
TNTTGGAGAAGATGGCTCAGTACAGATTTCAGACTTTGGGGTTAGTGCTTTTTTAGCAAC
TGGTGGTGATATTACCCGAAATAAAGTGAGAAAGACCTTTGTTGGCACCCCTTGTTGGAT
GGCACCTGAAGTTATGGAACAGGTCCGTGGTTATGATTTCAAAGCTGATATTTGGAGTTT
TGGAATTACAGCAATTGAATTGGCTACAGGGGCGGCTCCTTATCATAAATATCCACCAAT
GAAGGTTTTAATGCTGACACTGCAGAACGATCCTCCTTCTTTGGAAACTGGTGTTCAAGA
TAAAGAAATGCTGAAAAAATATGGAAAATCATTTAGAAAATGATTTCATTGTGCCTTCA
AAAAGATCCAGAAAAAGACCAACAGCAGCAGAACTATTAAGGCACAAATTTTTCCAGAA
AGCAAAGAATAAAGAATTTCTTCAAGAAAAACATTGCAGAGAGCACCAACCATTTCTGA
AAGAGCAAAAAGGTTCGGAGAGTACCAGGTTCCAGTGGGCGTCTTCATAAGACAGAGGA
TGGAGGCTGGGAGTGGAGTGATGATGAATTTGATGAAGAAAGTGAGGAAGGGAAAGCAGC
AATTTCACAACTCAGGTCTCCCCGAGTGAAAGAATCAATATCAAATTCTGAGCTCTTTCC
AACAACTGATCCTGTGGGTACTTTGCTCCAAGTTCCAGAACAGATCTCTGCTCATCTACC
TCAGCCAGCTGGGCAGATTGCTACACAGCCAACTCAAGTCTCTCTCCCACCCACCGCAGA
GCCAGCAAAAACAGCTCAGGCTTTGTCTTCAGGATCAGGTTCACAAGAAACCAAGATCCC
AATCAGTCTAGTACTAAGATTAAGGAATTCCAAAAAAGAACTAAATGATATTCGATTTGA
ATTTACTCCTGGGAGAGATACAGCAGAGGGTGTCTCTCAGGAACTCATTTCTGCTGGCCT
GGTCGACGGAAGGGATTTAGTAATAGTGGCAGCTAATTTGCAGAAAATTGTGGAAGAACC
TCAGTCAAATCGATCTGTCACTTTCAAACTGGCATCTGGTGTCGAAGGCTCAGATATTCC
TGATGATGGTAAACTGATAGGATTTGCCCAGCTCAGCATCAGCTAAACCACAACCCTGGA
AGAGGCGGCCTAAGGAGATTCCACACATGCGTATCTCTGTTGCTTCTATTGGCCTAAACC
CACTACTGCCAAAGAACCCAGCAACAAACCTCCCGGCTAGGAGCTTTAGAAGTCTTTATG
TTCTTCCTGCCATCATTCCTCCTTTTCCCACAGGGAAAGAAAGTTGGATCACTAGTGGC
CAGCATCCCCAGAGTTCCGTTAGTAAACTTACTTCATATGTCCCCTGTCTTCCTCCATCT
GAGAAGTGGCCCATGTGCTTCAAGGCCCAGGAGGGAGATCTGTCAGCTCATTCTTGCCTT
ACTCCAATGATGGCCCAGGTGGAAAAGTAGCAGCTGTATCGGGCTTCCTCATCCTGCCTG
TTCCCCCACACCTGCCAGGATATGGACATCTTGGGATATCTCTTTACCACTGAAGTAGAA
TTGATTGTTCAGCTGGAGCCCAGAGAATTTAATTTAATGTTTTTTCTTTGTACCTGATGT
GAATTCTAGCAACCTTTGTTAGGAAAAGCACAGCCTCAGATGGAGGCAGCCTAAACTGT
GTTCTTGTTTTGTTCATGGTGTTTCTAAGCGTTTTGCTGAAGCTGCTCTCAGGCACCCCC
TTCTTCATTGCTCTCTCCAGAAAGGGTTGCTAGCCTTAACTTCAGCTGGTGCAAAACATC
TGACTGTAGCCGAACTTCAGCCATCAGATCCTTCAAAGTGGAACTTTGGATTGTTTTTAC
AGACAACATCGAGTAATGGCTTGTAAATGTGAATTTTGCCAGAGGTGGTTTTTGAACAGG
AAAATCATAATTCATATCATTGGAGAAGTATTTATTTTCAAATATCAAATTGAAGAAAAA
CTCAATCCTCCCATGAAAATCAGTTCGCCTGGCCTCCAAGTCGTGAGGAAATGGGTATGC
AAGGCTGAGATTTCTACAGCAATAAAGGAGACACACACTGGGCCAGAGAGGCCTGCCTTC
TGCCTGCTCTCCTGCACTGACCCTTTGGAGGGGGTCTCTGTGTGCTGAAGCTAACTCAAG
ATGGAAAGTGAAACCACATGTGCCGTGACCTTTAGGTTTTATGAGTAGACAGTGTTCATT
TGATTTTCTACAGAAATAATATAAATTATTCTTTAGGTTTAAAAAGAGCACTCATAATG
```

Fig. 9D

CAATATGTGAATAATCAGTGAGGTTGATTTTTCTTTTTTCCTACCGTTTCATAGTCTTTG
TCTAACTGCTAGTAACCCTACCGAGTTTTATATATGAGTGGGATACTCAATCTGGCCTTA
AAAAGATACACAAGATGGGCTGTGGGTCCCTGGAAGGGGGAGAGTTGCCCTTTACAGA
ATCACTCGAGCCCTTTCCAGCACTGTTGGTCTGATGAACAAGGTTGTTTTACCTTATTTT
CTCTTGGAACATATCTGAAAACCTTCCCCACAAATAACTTGTCACACCTTTTGTTTCATT
CTGAGTCTTTAGTTTTAGTCATGGGCTTTCTTCACCTGCTCTAGGTGCAAAGGCATGTTG
GGAAAGAGATGGATGTTGGGGAGGAAGAGAGGAGATGGATTTCAGTTGGGAGTTAGGAGG
AGAGTAGGTGAGATGATCAGACACCGGAGTTCAACGTCCCAGCAGTCTTGGTAAAGGAG
GGAGCCTGCTGAGCCAGGAGGGAGAAAAGAAGATTGACCAGCTTGCTAGAAAATACTTA
GCTTTTCTTTTTCTTTTTTGTGGAGGGGGACGGAGAGGAACAAGGATGGGGAGGTAGG
AATGAGGTATAGAAAGAGATAGCATCTTCTTTGGCACAAGACTAGTGGCTTACCGCTTA
CCTTAGAGTTTTGTTTTTTTTTTTCAAACCCATCAAAATCTACTTATTTATGAATCCAA
GGGGTGGCAGCATCACTCTGTTCTAGCATTCTTTGTGGAGATGGTCTGGTGCCTAGCTGG
GAGTGAGCAGCAGCCCATCCCCTGTTCACTTTCTCTAGCCCATCATTACCTGTGAACTGC
AGTGGGGCAGTCATGGCAAATAGAATTGGGCTGGGGTTTCTCCTTCTTTTCAGTTCATTG
TTTGCCCTGCTAGGAATTAGAAGACAGACACCATGTCCCAGGACAGTGTTACTTCTTCTG
CATGATGTGTGGTAGACTCCCTTTGCTGGCTTGTGCAGTGATACTGAGAAATACATGAA
CAGAAACTGCCCAGGTGGAACAGCACGTAACCTAGTGAGTGACTGTACTCCTTTCTAGGA
ATGCTGATTCAGAGTGCACCTCTTTGACTAGGTCCCAGGATCCCCTTGTCCCTGGAGTAG
GGACTAACTATAGCACAAGTAATATGTGCCAATGCTATTTGTGAAATGTTTGGTCTTTC
TAAACGACTAAAGGATTTGTTGGGTTTTGCTTAAGTTTTGAACCAAATCCTAGAGCCAG
CTGATAATATTTAATAATCTGGAGGAGAGAATAATGATGTACCAATAAGTGGAGATTCCT
CCTTATGATGTATGCTAGGTTATGGAAGATGTAAAATATTCAACTTTTCCTCCTTTTT
TGGACTTTGTATTTTACTGCATGTTTTCTTCATTTTTAATCAATAAAGAGTAAATTGTCA
AAAAAAAAAAAAAAAAA

SEQ ID NO: 4  STLK5 HUMAN
CTCATCTGTACACACTTCATGGATGGCATGAATGAGCTGGCGATTGCTTACATCCTGCAG
GGGGTGCTGAAGGCCCTCGACTACATCCACCACATGGGATATGTACACAGGAGTGTCAAA
GCCAGCCACATCCTGATCTCTGTGGATGGGAAGGTCTACCTGTCTGGTTTGCGCAGCAAC
CTCAGCATGATAAGCCATGGGCAGCGGCAGCGAGTGGTCCACGATTTTCCCAAGTACAGT
GTCAAGGTTCTGCCGTGGCTCAGCCCCGAGGTCCTCCAGCAGAATCTCCAGGGTTATGAT
GCCAAGTCTGACATCTACAGTGTGGGAATCACAGCCTGTGAACTGGCCAACGGCCATGTC
CCCTTTAAGGATATGCCTGCCACCCAGATGCTGCTAGAGAAACTGAACGGCACAGTGCCC
TGCCTGTTGGATACCAGCACCATCCCGCTGAGGAGCTGACCATGAGCCCTTCGCGCTCA
GTGGCCAACTCTGGCCTGAGTGACAGCCTGACCACCAGCACCCCCGGCCCTCCAACGGT
GACTCGCCCTCCCACCCCTACCACCGAACCTTCTCCCCCACTTCCACCACTTTGTGGAG
CAGTGCCTTCAGCGCAACCCGGATGCCAGGCCCAGTGCCAGCACCCTCCTGAACCACTCT

Fig. 9E

```
TTCTTCAAGCAGATCAAGCGACGTGCCTCAGAGGCTTTGCCCGAATTGCTTCGTCCTGTC
ACCCCCATCACCAATTTTGAGGGCAGCCAGTCTCAGGACCACAGTGGAATCTTTGGCCTG
GTAACAAACCTGGAAGAGCTGGAGGTGGACGATTGGGAGTTCTGAGCCTCTGCAAACTGT
GCGCATTCTCCAGCCAGGGATGCAGAGGCCACCCAGAGGCCCTTCCTGAGGGCCGGCCAC
ATTCCCGCCCTCCTGGGCAGATTGGGTAGAAAGGACATTCTTCCAGGAAAGTTGACTGCT
GACTGATTGGGAAAGAAAATCCTGGAGAGATACTTCACTGCTCCAAGGCTTTTGAGACAC
AAGGGAATCTCAACAACCAGGGATCAGGAGGGTCCAAAGCCGACATTCCCAGTCCTGTGA
GCTCAGGTGACCTCCTCCGCAGAAGAGAGATGCTGCTCTGGCCCTGGGAGCTGAATTCCA
AGCCCAGGGTTTGGCTCCTTAAACCCGAGGACCGCCACCTCTTCCCAGTGCTTGCGACCA
GCCTCATTCTATTTAACTTTGCTCTCAGATGCCTCAGATGCTATAGGTCAGTGAAAGGGC
AAGTAGTAAGCTGCCTGCCTCCCTTCCCTCAGACCTCTCCCTCATAATTCCAGAGAAGGG
CATTTCTGTCTTTTAAGCACAGACTAAGGCTGGAACAGTCCATCCTTATCCCTCTTCTG
GCTTGGGCCCTGACACCTAAGTCTTTCCCACGGTTTATGTGTGTGCCTCATTCCTTTCCC
ACCAAGAATCCATCTTAGCGCCTCCTGCCAGCTGCCCTGGTGCTTTCTCCAAGGGCCATC
AGTGTCTTGCCTAGCTTGAGGGCTTAAGTCCTTATGCTGTGTTAGTTTCGTTGTCAGAAC
AAATTAAAATTTTCAGAGACGCTG

SEQ ID NO: 9  ZC1 HUMAN
GAGACCATGGCGAACGACTCTCCCGCGAAAAGTCTGGTGGACATCGACCTCTCCTCCCTG
CGGGATCCTGCTGGGATTTTTGAGCTGGTGGAAGTGGTTGGAAATGGCACCTATGGACAA
GTCTATAAGGGTCGACATGTTAAAACGGGTCAGTTGGCAGCCATCAAAGTTATGGATGTC
ACTGAGGATGAAGAGGAAGAAATCAAACTGGAGATAAATATGCTAAAGAAATACTCTCAT
CACAGAAACATTGCAACATATTATGGTGCTTTCATCAAAAAGAGCCCTCCAGGACATGAT
GACCAACTCTGGCTTGTTATGGAGTTCTGTGGGGCTGGGTCCATTACAGACCTTGTGAAG
AACACCAAAGGGAACACACTCAAAGAAGACTGGATCGCTTACATCTCCAGAGAAATCCTG
AGGGGACTGGCACATCTTCACATTCATCATGTGATTCACCGGGATATCAAGGGCCAGAAT
GTGTTGCTGACTGAGAATGCAGAGGTGAAACTTGTTGACTTTGGTGTGAGTGCTCAGCTG
GACAGGACTGTGGGGCGGAGAAATACGTTCATAGGCACTCCCTACTGGATGGCTCCTGAG
GTCATCGCCTGTGATGAGAACCCAGATGCCACCTATGATTACAGAAGTGATCTTTGGTCT
TGTGGCATTACAGCCATTGAGATGGCAGAAGGTGCTCCCCCTCTCTGTGACATGCATCCA
ATGAGAGCACTGTTTCTCATTCCCAGAAACCCTCCTCCCCGGCTGAAGTCAAAAAAATGG
TCGAAGAAGTTTTTTAGTTTTATAGAAGGGTGCCTGGTGAAGAATTACATGCAGCGGCCC
TCTACAGAGCAGCTTTTGAAACATCCTTTTATAAGGGATCAGCCAAATGAAAGGCAAGTT
AGAATCCAGCTTAAGGATCATATAGATCGTACCAGGAAGAAGAGAGGCGAGAAAGATGAA
ACTGAGTATGAGTACAGTGGGAGTGAGGAAGAAGAGGAGGAAGTGCCTGAACAGGAAGGA
GAGCCAAGTTCCATTGTGAACGTGCCTGGTGAGTCTACTCTTCGCCGAGATTTCCTGAGA
CTGCAGCAGGAGAACAAGGAACGTTCCGAGGCTCTTCGGAGACAACAGTTACTACAGGAG
CAACAGCTCCGGGAGCAGGAAGAATATAAAAGGCAACTGCTGGCAGAGAGACAGAAGCGG
```

Fig. 9F

```
ATTGAGCAGCAGAAAGAACAGAGGCGACGGCTAGAAGAGCAACAAAGGAGAGAGCGGGAA
GCTAGAAGGCAGCAGGAACGTGAACAGCGAAGGAGAGAACAAGAAGAAAAGAGGCGTCTA
GAGGAGTTGGAGAGAAGGCGCAAAGAAGAAGAGGAGAGGAGACGGGCAGAAGAAGAAAAG
AGGAGAGTTGAAAGAGAACAGGAGTATATCAGGCGACAGCTAGAAGAGGAGCAGCGGCAC
TTGGAAGTCCTTCAGCAGCAGCTGCTCCAGGAGCAGGCCATGTTACTGGAGTGCCGATGG
CGGGAGATGGAGGAGCACCGGCAGGCAGAGAGGCTCCAGAGGCAGTTGCAACAAGAACAA
GCATATCCTGTCTCTACAGCATGACCATAGGAGGCCGCACCCGCAGCACTCGCAGCAG
CCGCCACCACCGCAGCAGGAAAGGAGCAAGCCAAGCTTCCATGCTCCCGAGCCCAAAGCC
CACTACGAGCCTGCTGACCGAGCGCGAGAGGTGGAAGATAGATTTAGGAAAACTAACCAC
AGCTCCCCTGAAGCCCAGTCTAAGCAGACAGGCAGAGTATTGGAGCCACCAGTGCCTTCC
CGATCAGAGTCTTTTTCCAATGGCAACTCCGAGTCTGTGCATCCGCCCTGCAGAGACCA
GCGGAGCCACAGGTTCCTGTGAGAACAACATCTCGCTCCCTGTTCTGTCCCGTCGAGAT
TCCCCACTGCAGGGCAGTGGGCAGCAGAATAGCCAGGCAGGACAGAGAAACTCCACCAGT
ATTGAGCCCAGGCTTCTGTGGGAGAGAGTGGAGAAGCTGGTGCCCAGACCTGGCAGTGGC
AGCTCCTCAGGGTCCAGCAACTCAGGATCCCAGCCCGGGTCTCACCCTGGGTCTCAGAGT
GGCTCCGGGGAACGCTTCAGAGTGAGATCATCATCCAAGTCTGAAGGCTCTCCATCTCAG
CGCCTGGAAAATGCAGTGAAAAAACCTGAAGATAAAAGGAAGTTTTCAGACCCCTCAAG
CCTGCTGATCTGACCGCACTGGCCAAAGAGCTTCGAGCAGTGGAAGATGTACGGCCACCT
CACAAAGTAACGGACTACTCCTCATCCAGTGAGGAGTCGGGGACGACGGATGAGGAGGAC
GACGATGTGGAGCAGGAAGGGGCTGACGAGTCCACCTCAGGACCAGAGGACACCAGAGCA
GCGTCATCTCTGAATTTGAGCAATGGTGAAACGGAATCTGTGAAAACCATGATTGTCCAT
GATGATGTAGAAAGTGAGCCGGCCATGACCCCATCCAAGGAGGGCACTCTAATCGTCCGC
CGGACTCAGTCCGCTAGTAGCACACTCCAGAAACACAAATCTTCCTCCTCCTTTACACCT
TTTATAGACCCCAGATTACTACAGATTTCTCCATCTAGCGGAACAACAGTGACATCTGTG
GTGGGATTTTCCTGTGATGGGATGAGACCAGAAGCCATAAGGCAAGATCCTACCCGGAAA
GGCTCAGTGGTCAATGTGAATCCTACCAACACTAGGCCACAGAGTGACACCCCGGAGATT
CGTAAATACAAGAAGAGGTTTAACTCTGAGATTCTGTGTGCTGCCTTATGGGGAGTGAAT
TGCTAGTGGGTACAGAGAGTGGCCTGATGCTGCTGGACAGAAGTGGCCAAGGGAAGGTC
TATCCTCTTATCAACCGAAGACGATTTCAACAAATGGACGTACTTGAGGGCTTGAATGTC
TTGGTGACAATATCTGGCAAAAGGATAAGTTACGTGTCTACTATTTGTCCTGGTTAAGA
AATAAAATACTTCACAATGATCCAGAAGTTGAGAAGAAGCAGGGATGGACAACCGTAGGG
GATTTGGAAGGATGTGTACATTATAAAGTTGTAAAATATGAAAGAATCAAATTTCTGGTG
ATTGCTTTGAAGAGTTCTGTGGAAGTCTATGCGTGGGCACCAAAGCCATATCACAAATTT
ATGGCCTTTAAGTCATTTGGAGAATTGGTACATAAGCCATTACTGGTGGATCTCACTGTT
GAGGAAGGCCAGAGGTTGAAAGTGATCTATGGATCCTGTGCTGGATTCCATGCTGTTGAT
GTGGATTCAGGATCAGTCTATGACATTTATCTACCAACACATATCCAGTGTAGCATCAAA
CCCCATGCAATCATCATCCTCCCAATACAGATGGAATGGAGCTTCTGGTGTGCTATGAA
GATGAGGGGGTTTATGTAAACACATATGGAAGGATCACCAAGGATGTAGTTCTACAGTGG
```

Fig. 9G

```
GGAGAGATGCCTACATCAGTAGCATATATTCGATCCAATCAGACAATGGGCTGGGGAGAG
AAGGCCATAGAGATCCGATCTGTGGAAACTGGTCACTTGGATGGTGTGTTCATGCACAAA
AGGGCTCAAAGACTAAAATTCTTGTGTGAACGCAATGACAAGGTGTTCTTTGCCTCTGTT
CGGTCTGGTGGCAGCAGTCAGGTTTATTTCATGACCTTAGGCAGGACTTCTCTTCTGAGC
TGGTAGAAGCAGTGTGATCCAGGGATTACTGGCCTCCAGAGTCTTCAAGATCCTGAGAAC
TTGGAATTCCTTGTAACT
```

SEQ ID NO: 10  ZC2 HUMAN
```
GCTTTCGGGGAGGTCTATGAGGGTCGTCATGTCAAAACGGGCCAGCTTGCAGCCATCAAG
GTTATGGATGTCACAGGGGATGAAGAGGAAGAAATCAAACAAGAAATTAACATGTTGAAG
AAATATTCTCATCACCGGAATATTGCTACATACTATGGTGCTTTTATCAAAAAGAACCCA
CCAGGCATGGATGACCAACTTTGGTTGGTGATGGAGTTTTGTGGTGCTGGCTCTGTCACC
GACCTGATCAAGAACACAAAAGGTAACACGTTGAAAGAGGAGTGGATTGCATACATCTGC
AGGGAAATCTTACGGGGCTGAGTCACCTGCACCAGCATAAAGTGATTCATCGAGATATT
AAAGGGCAAAATGTCTTGCTGACTGAAAATGCAGAAGTTAAACTAGTGGACTTTGGAGTC
AGTGCTCAGCTTGATCGAACAGTGGGCAGGAGGAATACTTTCATTGGAACTCCCTACTGG
ATGGCACCAGAAGTTATTGCCTGTGATGAAAACCCAGATGCCACATATGATTTCAAGAGT
GACTTGTGGTCTTTGGGTATCACCGCCATTGAAATGGCAGAAGGTGCTCCCCCTCTCTGT
GACATGCACCCCATGAGAGCTCTCTTCCTCATCCCCCGGAATCCAGCGCCTCGGCTGAAG
TCTAAGAAGTGGTCAAAAAAATTCCAGTCATTTATTGAGAGCTGCTTGGTAAAGAATCAC
AGCCAGCGACCAGCAACAGAACAATTGATGAAGCATCCATTTATACGAGACCAACCTAAT
GAGCGACAGGTCCGCATTCAACTCAAGGACCATATTGATAGAACAAAGAAGAAGCGAGGA
GAAAAAGATGAGACAGAGTATGAGTACAGTGGAAGTGAGGAAGAAGAGGAGGAGAATGAC
TCAGGAGAGCCCAGCTCCATCCTGAATCTGCCAAGGGAGTCGACGCTGCGGAGGGACTTT
CTGAGGCTGCAGCTGGCCAACAAGGAGCGTTCTGAGGCCCTACGGAGGCAGCAGCTGGAG
CAGCAGCAGCGGGAGAATGAGGAGCACAAGCGGCAGCTGCTGGCCGAGCGTCAGAAGCGC
ATCGAGGAGCAGAAAGAGCAGAGGCGGCGGCTGGAGGAGCAACAAAGGCGAGAGAAGGAG
CTGCGGAAGCAGCAGGAGAGGGAGCAGCGCCGGCACTATGAGGAGCAGATGCGCCGGGAG
GAGGAGAGGAGGCGTGCGGAGCATGAACAGGAATATAAGCGCAAACAATTGGAAGAACAG
AGACAAGCAGAAAGACTGCAGAGGCAGCTAAAGCAAGAAAGAGACTACTTAGTTTCCCTT
CAGCATCAGCGGCAGGAGCAGAGGCCTGTGGAGAAGAAGCCACTGTACCATTACAAAGAA
GGAATGAGTCCTAGTGAGAAGCCAGCATGGGCCAAGGAGGTAGAAGAACGGTCAAGGCTC
AACCGGCAAAGTTCCCCTGCCATGCCTCACAAGGTTGCCAACAGGATATCTGACCCCAAC
CTGCCCCCAAGGTCGGAGTCCTTCAGCATTAGTGGAGTTCAGCCTGCTCGAACACCCCCC
ATGCTCAGACCAGTCGATCCCCAGATCCCACATCTGGTAGCTGTAAAATCCCAGGGACCT
GCCTTGACCGCCTCCCAGTCAGTGCACGAGCAGCCCACAAAGGGCCTCTCTGGGTTTCAG
GAGGCTCTGAACGTGACCTCCCACCGCGTGGAGATGCCACGCCAGAACTCAGATCCCACC
TCGGAAAATCCTCCTCTCCCCACTCGCATTGAAAAGTTTGACCGAAGCTCTTGGTTACGA
```

Fig. 9H

```
CAGGAAGAAGACATTCCACCAAAGGTGCCTCAAAGAACAACTTCTATATCCCCAGCATTA
GCCAGAAAGAATTCTCCTGGGAATGGTAGTGCTCTGGGACCCAGACTAGGATCTCAACCC
ATCAGAGCAAGCAACCCTGATCTCCGGAGAACTGAGCCCATCTTGGAGAGCCCCTTGCAG
AGGACCAGCAGTGGCAGTTCCTCCAGCTCCAGCACCCTAGCTCCCAGCCCAGCTCCCAA
GGAGGCTCCAGCCTGGATCACAAGCAGGATCCAGTGAACGCACCAGAGTTCGAGCCAAC
AGTAAGTCAGAAGGATCACCTGTGCTCCCCATGAGCCTGCCAAGGTGAAACCAGAAGAA
TCCAGGGACATTACCCGGCCCAGTCGACCAGCTAGCTACAAAAAAGCTATAGATGAGGAT
CTGACGGCATTAGCCAAAGAACTAAGAGAACTCCGGATTGAAGAAACAAACCGCCCAATG
AAGAAGGTGACTGATTACTCCTCCTCCAGTGAGGAGTCAGAAAGTAGCGAGGAAGAGGAG
GAAGATGGAGAGAGCGAGACCCATGATGGGACAGTGGCTGTCAGCGACATACCCAGACTG
ATACCAACAGGAGCTCCAGGCAGCAACGAGCAGTACAATGTGGGAATGGTGGGGACGCAT
GGGCTGGAGACCTCTCATGCGGACAGTTTCAGCGGCAGTATTTCAAGAGAAGGAACCTTG
ATGATTAGAGAGACGTCTGGAGAGAAGAAGCGATCTGGCCACAGTGACAGCAATGGCTTT
GCTGGCCACATCAACCTCCCTGACCTGGTGCAGCAGAGCCATTCTCCAGCTGGAACCCCG
ACTGAGGGACTGGGGCGCGTCTCAACCCATTCCCAGGAGATGGACTCTGGGACTGAATAT
GGCATGGGGAGCAGCACCAAAGCCTCCTTCACCCCCTTTGTGGACCCCAGAGTATACCAG
ACGTCTCCCACTGATGAAGATGAAGAGGATGAGGAATCATCAGCCGCAGCTCTGTTTACT
GGCGAACTTCTTAGGCAAGAACAGGCCAAACTCAATGAAGCAAGAAAGATTTCGGTGGTA
AATGTAAACCCAACCAACATTCGGCCTCATAGCGACACACCAGAAATCAGAAAATACAAG
AAACGATTCAACTCAGAAATACTTTGTGCAGCTCTGTGGGGTGTAAACCTTCTGGTGGGG
ACTGAAAATGGCCTGATGCTTTTGGACCGAAGTGGGCAAGGCAAAGTCTATAATCTGATC
AACCGGAGGCGATTTCAGCAGATGGATGTGCTAGAGGGACTGAATGTCCTTGTGACAATT
TCAGGAAAGAAGAATAAGCTACGAGTTTACTATCTTTCATGGTTAAGAAACAGAATACTA
CATAATGACCCAGAAGTAGAAAAGAAACAAGGCTGGATCACTGTTGGGGACTTGGAAGGC
TGTATACATTATAAAGTTGTTAAATATGAAAGGATCAAATTTTTGGTGATTGCCTTAAAG
AATGCTGTGGAAATATATGCTTGGGCTCCTAAACCGTATCATAAATTCATGGCATTTAAG
TCTTTTGCAGATCTCCAGCACAAGCCTCTGCTAGTTGATCTCACGGTAGAAGAAGGTCAA
AGATTAAAGGTTATTTTGGTTCACACACTGGTTTCCATGTAATTGATGTTGATTCAGGA
AACTCTTATGATATCTACACACCATCTCATATTCAGGGCAATATCACTCCTCATGCTATT
GTCATCTTGCCTAAAACAGATGGAATGGAAATGCTTGTTTGCTATGAGGATGAGGGGGTG
TATGTAAACACCTATGGCCGGATAACTAAGGATGTGGTGCTCCAATGGGGAGAAATGCCC
ACGTCTGTGGCCTACATTCATTCCAATCAGATAATGGGCTGGGGCGAGAAAGCTATTGAG
ATCCGGTCAGTGGAAACAGGACATTTGGATGGAGTATTTATGCATAAGCGAGCTCAAAGG
TTAAAGTTTCTATGTGAAAGAAATGATAAGGTATTTTTGCATCCGTGCGATCTGGAGGA
AGTAGCCAAGTGTTTTTCATGACCCTCAACAGAAATTCCATGATGAACTGGTAACAGAAG
AGCACTTGGCACTTATCTTCATGGCGTTATTTCTAATTTAAAAGAACATAACTCATGTGG
ACTTATGCCAGTCTAGAGGCAGAATCAGAAGGCTTGGTTGAACATATCGCTTTCCCTTTT
TCCTCTCCCTCCGCCCCTCCCAGTACAGTCCATCT
```

Fig. 9 I

SEQ ID NO: 11   ZC3 HUMAN
GCATTTGGGGAGGTGTATGAGGGTCGGCATGTCAAGACGGGGCAGCTGGCTGCCATCAAG
GTCATGGATGTCACGGAGGACGAGGAGGAAGAGATCAAACAGGAGATCAACATGCTGAAA
AAGTACTCTCACCACCGCAACATCGCCACCTACTACGGAGCCTTCATCAAGAAGAGCCCC
CCGGGAAACGATGACCAGCTCTGGCTGGTGATGGAGTTCTGTGGTGCTGGTTCAGTGACT
GACCTGGTAAAGAACACAAAAGGCAACGCCCTGAAGGAGGACTGTATCGCCTATATCTGC
AGGGAGATCCTCAGGGGTCTGGCCCATCTCCATGCCCACAAGGTGATCCATCGAGACATC
AAGGGGCAGAATGTGCTGCTGACAGAGAATGCTGAGGTCAAGCTAGTGGATTTTGGGGTG
AGTGCTCAGCTGGACCGCACCGTGGGCAGACGGAACACTTTCATTGGGACTCCCTACTGG
ATGGCTCCAGAGGTCATCGCCTGTGATGAGAACCCTGATGCCACCTATGATTACAGGAGT
GATATTTGGTCTCTAGGAATCACAGCCATCGAGATGGCAGAGGGAGCCCCCCCTCTGTGT
GACATGCACCCCATGCGAGCCCTCTTCCTCATTCCTCGGAACCCTCCGCCCAGGCTCAAG
TCCAAGAAGTGGTCTAAGAAGTTCATTGACTTCATTGACACATGTCTCATCAAGACTTAC
CTGAGCCGCCCACCCACGGAGCAGCTACTGAAGTTTCCCTTCATCCGGGACCAGCCCACG
GAGCGGCAGGTCCGCATCCAGCTTAAGGACCACATTGACCGATCCCGGAAGAAGCGGGGT
GAGAAGAGGAGACAGAATATGAGTACAGCGGCAGCGAGGAGGAAGATGACAGCCATGGA
GAGGAAGGAGAGCCAAGCTCCATCATGAACGTGCCTGGAGAGTCGACTCTACGCCGGGAG
TTTCTCCGGCTCCAGCAGGAAAATAAGAGCAACTCAGAGGCTTTAAAACAGCAGCAGCAG
CTGCAGCAGCAGCAGCAGCGAGACCCCGAGGCACACATCAAACACCTGCTGCACCAGCGG
CAGCGGCGCATAGAGGAGCAGAAGGAGGAGCGGCGCCGCGTGGAGGAGCAACAGCGGCGG
GAGCGGGAGCAGCGGAAGCTGCAGGAGAAGGAGCAGCAGCGGCGGCTGGAGGACATGCAG
GCTCTGCGGCGGGAGGAGGAGCGGCGGCAGGCGGAGCGCGAGCAGGAATATATTCGTCAC
AGGCTAGAGGAGGAGCAGCGACAGCTCGAGATCCTTCAGCAACAGCTGCTCCAGGAACAG
GCCCTGCTGCTGGAATACAAGCGGAAGCAGCTGGAGGAGCAGCGGCAGTCAGAACGTCTC
CAGAGGCAGCTGCAGCAGGAGCATGCCTACCTCAAGTCCCTGCAGCAGCAGCAACAGCAG
CAGCAGCTTCAGAAACAACAGCAGCAGCAGCTCCTGCCTGGGGACAGGAAGCCCCTGTAC
CATTATGGTCGGGGCATGAATCCCGCTGACAAACCAGCCTGGGCCCGAGAGGTAGAAGAG
AGAACAAGGATGAACAAGCAGCAGAACTCTCCCTTGGCCAAGAGCAAGCCAGGCAGCACG
GGGCCTGAGCCCCCCATCCCCCAGGCCTCCCCAGGGCCCCAGGACCCCTTTCCCAGACT
CCTCCTATGCAGAGGCCGGTGGAGCCCCAGGAGGGACCGCACAAGAGCCTGGTGGCACAC
CGGGTCCCACTGAAGCCATATGCAGCACCTGTACCCCGATCCCAGTCCCTGCAGGACCAG
CCCACCCGAAACCTGGCTGCCTTCCCAGCCTCCCATGACCCCGACCCTGCCATCCCCGCA
CCCACTGCCACGCCCAGTGCCCGAGGAGCTGTCATCCGCCAGAATTCAGACCCCACCTCT
GAAGGACCTGGCCCCAGCCCGAATCCCCCAGCCTGGGTCCGCCCAGATAACGAGGCCCCA
CCCAAGGTGCCTCAGAGGACCTCATCTATCGCCACTGCCCTTAACACCAGTGGGGCCGGA
GGGTCCCGGCCAGCCCAGGCAGTCCGTGCCAGACCTCGCAGCAACTCCGCCTGGCAAATC
TATCTGCAAAGGCGGGCAGAGCGGGGCACCCCAAAGCCTCCAGGGCCCCCTGCTCAGCCC
CCTGGCCCGCCCAACGCCTCTAGTAACCCCGACCTCAGGAGGAGCGACCCTGGCTGGGAA

Fig. 9J

```
CGCTCGGACAGCGTCCTTCCAGCCTCTCACGGGCACCTCCCCCAGGCTGGCTCACTGGAG
CGGAACCGCGTGGGAGTCTCCTCCAAACCGGACAGCTCCCCTGTGCTCTCCCCTGGGAAT
AAAGCCAAGCCCGACGACCACCGCTCACGGCCAGGCCGGCCCGCAGACTTTGTGTTGCTG
AAAGAGCGGACTCTGGACGAGGCCCCTCGGCCTCCCAAGAAGGCCATGGACTACTCGTCG
TCCAGCGAGGAGGTGGAAAGCAGTGAGGACGACGAGGAGGAAGGCGAAGGCGGGCCAGCA
GAGGGGAGCAGAGATACCCCTGGGGGCCGCGATGGGGATACAGACAGCGTCAGCACCATG
GTGGTCCACGACGTCGAGGAGATCACCGGGACCCAGCCCCCATACGGGGGCGGCACCATG
GTGGTCCAGCGCACCCCTGAAGAGGAGCGGAACCTGCTGCATGCTGACAGCAATGGGTAC
ACAAACCTGCCTGACGTGGTCCAGCCCAGCCACTCACCCACCGAGAACAGCAAAGGCCAA
AGCCCACCCTCGAAGGATGGGAGTGGTGACTACCAGTCTCGTGGGCTGGTAAAGGCCCCT
GGCAAGAGCTCGTTCACGATGTTTGTGGATCTAGGGATCTACCAGCCTGGAGGCAGTGGG
GACAGCATCCCCATCACAGCCCTAGTGGGTGGAGAGGGCACTCGGCTCGACCAGCTGCAG
TACGACGTGAGGAAGGGTTCTGTGGTCAACGTGAATCCCACCAACACCCGGGCCCACAGT
GAGACCCCTGAGATCCGGAAGTACAAGAAGCGATTCAACTCCGAGATCCTCTGTGCAGCC
CTTTGGGGGGTCAACCTGCTGGTGGGCACGGAGAACGGGCTGATGTTGCTGGACCGAAGT
GGGCAGGGCAAGGTGTATGGACTCATTGGGCGGCGACGCTTCCAGCAGATGGATGTGCTG
GAGGGGCTCAACCTGCTCATCACCATCTCAGGGAAAAGGAACAAACTGCGGGTGTATTAC
TTGTCCTGGCTCCGGAACAAGATTCTGCACAATGACCCAGAAGTGGAGAAGAAGCAGGGC
TGGACCACCGTGGGGGACATGGAGGGCTGCGGGCACTACCGTGTTGTGAAATACGAGCGG
ATTAAGTTCCTGGTCATCGCCCTCAAGAGCTCCGTGGAGGTGTATGCCTGGGCCCCCAAA
CCCTACCACAAATTCATGGCCTTCAAGTCCTTTGCCGACCTCCCCCACCGCCCTCTGCTG
GTCGACCTGACAGTAGAGGAGGGGCAGCGGCTCAAGGTCATCTATGGCTCCAGTGCTGGC
TTCCATGCTGTGGATGTCGACTCGGGGAACAGCTATGACATCTACATCCCTGTGCACATC
CAGAGCCAGATCACGCCCCATGCCATCATCTTCCTCCCCAACACCGACGGCATGGAGATG
CTGCTGTGCTACGAGGACGAGGGTGTCTACGTCAACACGTACGGGCGCATCATTAAGGAT
GTGGTGCTGCAGTGGGGGGAGATGCCTACTTCTGTGGCCTACATCTGCTCCAACCAGATA
ATGGGCTGGGGTGAGAAAGCCATTGAGATCCGCTCTGTGGAGACGGGCCACCTCGACGGG
GTCTTCATGCACAAACGAGCTCAGAGGCTCAAGTTCCTGTGTGAGCGGAATGACAAGGTG
TTTTTTGCCTCAGTCCGCTCTGGGGGCAGCAGCCAAGTTTACTTCATGACTCTGAACCGT
AACCGCATCATGAACTGGTGACGGGGCCCTGGGCTGGGGCTGTCCCACACTGGACCCAGC
TCTCCCCCTGCAGCCAGGCTTCCCGGGCCGCCCCTCTTTCCCCTCCCTGGGCTTTTGCTT
TTACTGGTTTGATTTCACTGGAGCCTGCTGGGAACGTGACCTCTGACCCCTGA

SEQ ID NO: 12   ZC4 HUMAN
CAATGTTAACCCACTCTATGTCTCTCCTGCATGTAAAAAACCACTAATCCACATGTATGA
AAAGGAGTTCACTTCTGAGATCTGCTGTGGTTCTTTGTGGGGAGTCAATTTGCTGTTGGG
AACCCGATCTAATCTATATCTGATGGACAGAAGTGGAAAGGCTGACATTACTAAACTTAT
AAGGCGAAGACCATTCCGCCAGATTCAAGTCTTAGAGCCACTCAATTTGCTGATTACCAT
```

Fig. 9K

```
CTCAGGTCATAAGAACAGACTTCGGGTGTATCATCTGACCTGGTTGAGGAACAAGATTTT
GAATAATGATCCAGAAAGTAAAAGAAGGCAAGAAGAAATGCTGAAGACAGAGGAAGCCTG
CAAAGCTATTGATAAGTTAACAGGCTGTGAACACTTCAGTGTCCTCCAACATGAAGAAAC
AACATATATTGCAATTGCTTTGAAATCATCAATTCACCTTTATGCATGGGCACCAAAGTC
CTTTGATGAAAGCACTGCTATTAAAGTATTTCCAACACTTGATCATAAGCCAGTGACAGT
TGACCTGGCTATTGGTTCTGAAAAAGACTAAAGATTTTCTTCAGCTCAGCAGATGGATA
TCACCTCATCGATGCAGAATCTGAGGTTATGTCTGATGTGACCCTGCCAAAGAATCCCCT
GGAAATCATTATACCACAGAATATCATCATTTTACCTGATTGCTTGGGAATTGGCATGAT
GCTCACCTTCAATGCTGAAGCCCTCTCTGTGGAAGCAAATGAACAACTCTTCAAGAAGAT
CCTTGAAATGTGGAAAGACATACCATCTTCTATAGCTTTTGAATGTACACAGCGAACCAC
AGGATGGGGCCAAAAGGCCATTGAAGTGCGCTCTTTGCAATCCAGGGTTCTGGAAAGTGA
GCTGAAGCGCAGGTCAATTAAGAAGCTGAGATTCCTGTGCACCCGGGGTGACAAGCTGTT
CTTTACCTCTACCCTGCGCAATCACCACAGCCGGGTTTACTTCATGACACTTGGAAAACT
TGAAGAGCTCCAAAGCAATTATGATGTCTAAAAGTTTCCAGTGATTTATTACCACATTAT
AAACATCATGTATAGGCAGTCTGCATCTTCAGATTTCAGAGATTAAATGAGTATTCAGTT
TTATTTTTAGTAAAGATTAAATCCAAAACTTTACTTTTAATGTAGCACAGAATAGTTTTA
ATGAGAAATGCAGCTTTATGTATAAAATTAACTATAGCAAGCTCTAGGTACTCCAATGGT
GTACAATGTCTTTTGCACAAACTTTGTAACTTTTGTTACTGTGAATTCAAACATTACTCT
TTGGACAGTTTGGACAGTATCTGTATTCAGATTTTACAACATGGAGTAAAGAAACCTGTT
ATGAATTAGATTACAAGCAGCCTTCAAAAGAATTGGCACTGGGATAAGATTTTTCAGAAA
AGAAAAACATCGGCAAACT

SEQ ID NO: 17   KHS2 HUMAN
CCGCCATGAACCCCGGCTTCGATTTGTCCCGCCGGAACCCGCAGGAGGACTTCGAGCTGA
TTCAGCGCATCGGCAGCGGCACCTACGGCGACGTCTACAAGGCACGGAATGTTAACACTG
GTGAATTAGCAGCAATTAAAGTAATAAAATTGGAACCAGGAGAAGACTTTGCAGTTGTGC
AGCAAGAAATTATTATGATGAAAGACTGTAAACACCCAAATATTGTTGCTTATTTTGGAA
GCTATCTCAGGCGAGATAAGCTTTGGATTTGCATGGAGTTTTGTGGAGGTGGTTCTTTAC
AGGATATTTATCACGTAACTGGACCTCTGTCAGAACTGCAAATTGCATATGTTAGCAGAG
AAACACTGCAGGGATTATATTATCTTCACAGTAAAGGAAAAATGCACAGAGATATAAAGG
GAGCTAACATTCTATTAACGGATAATGGTCATGTGAAATTGGCTGATTTTGGAGTATCTG
CACAGATAACAGCTACAATTGCCAAACGGAAGTCTTTCATTGGCACACCATATTGGATGG
CTCCAGAAGTTGCAGCTGTTGAGAGGAAGGGGGGTTACAATCAACTCTGTGATCTCTGGG
CAGTGGGAATCACTGCCATAGAACTTGCAGAGCTTCAGCCTCCTATGTTTGACTTACACC
CAATGAGAGCATTATTTCTAATGACAAAAGCAATTTTCAGCCTCCTAAACTAAAGGATA
AAATGAAATGGTCAAATAGTTTTCATCACTTTGTGAAAATGGCACTTACCAAAAATCCGA
AAAAAGACCTACTGCTGAAAAATTATTACAGCATCCTTTTGTAACACAACATTTGACAC
GGTCTTTGGCAATCGAGCTGTTGGATAAAGTAAATAATCCAGATCATTCCACTTACCATG
```

Fig. 9L

```
ATTTCGATGATGATGATCCTGAGCCTCTTGTTGCTGTACCACATAGAATTCACTCAACAA
GTAGAAACGTGAGAGAAGAAAAAACACGCTCAGAGATAACCTTTGGCCAAGTGAAATTTG
ATCCACCCTTAAGAAAGGAGACAGAACCACATCATGAACTTCCCGACAGTGATGGTTTTT
TGGACAGTTCAGAAGAAATATACTACACTGCAAGATCTAATCTGGATCTGCAACTGGAAT
ATGGACAAGGACACCAAGGTGGTTACTTTTTAGGTGCAAACAAGAGTCTTCTCAAGTCTG
TTGAAGAAGAATTGCATCAGCGAGGACACGTCGCACATTTAGAAGATGATGAAGGAGATG
ATGATGAATCTAAACACTCAACTCTGAAAGCAAAAATTCCACCTCCTTTGCCACCAAAGC
CTAAGTCTATCTTCATACCACAGGAAATGCATTCTACTGAGGATGAAAATCAAGGAACAA
TCAAGAGATGTCCCATGTCAGGGAGCCCAGCAAAGCCATCCCAAGTTCCACCTAGACCAC
CACCTCCCAGATTACCCCCACACAAACCTGTTGCCTTAGGAAATGGAATGAGCTCCTTCC
AGTTAAATGGTGAACGAGATGGCTCATTATGTCAACAACAGAATGAACATAGAGGCACAA
ACCTTTCAAGAAAGAAAAGAAAGATGTACCAAAGCCTATTAGTAATGGTCTTCCTCCAA
CACCTAAAGTGCATATGGGTGCATGTTTTCAAAAGTTTTAATGGGTGTCCCTTGAAAA
TTCACTGTGCATCATCATGGATAAACCCAGATACAAGAGATCAGTACTTGATATTTGGTG
CCGAAGAAGGGATTTATACCCTCAATCTTAATGAACTTCATGAAACATCAATGGAACAGC
TATTCCCTCGAAGGTGTACATGGTTGTATGTAATGAACAATTGCTTGCTATCAATATCTG
GTAAAGCTTCTCAGCTTTATTCCCATAATTTACCAGGGCTTTTTGATTATGCAAGACAAA
TGCAAAAGTTACCTGTTGCTATTCCAGCACACAAACTCCCTGACAGAATACTGCCAAGGA
AATTTTCTGTATCAGCAAAAATCCCTGAAACCAAATGGTGCCAGAAGTGTTGTGTTGTAA
GAAATCCTTACACGGGCCATAAATACCTATGTGGAGCACTTCAGACTAGCATTGTTCTAT
TAGAATGGGTTGAACCAATGCAGAAATTTATGTTAATTAAGCACATAGATTTTCCTATAC
CATGTCCACTTAGAATGTTTGAAATGCTGGTAGTTCCTGAACAGGAGTACCCTTTAGTTT
GTGTTGGTGTCAGTAGAGGTAGAGACTTCAACCAAGTGGTTCGATTTGAGACGGTCAATC
CAAATTCTACCTCTTCATGGTTTACAGAATCAGATACCCCACAGACAAATGTTACTCATG
TAACCCAACTGGAGAGAGATACCATCCTTGTATGCTTGGACTGTTGTATAAAAATAGTAA
ATCTCCAAGGAAGATTAAAATCTAGCAGGAAATTGTCATCAGAACTCACCTTTGATTTCC
AGATTGAATCAATAGTGTGCCTACAAGACAGTGTGCTAGCTTTCTGGAAACATGGAATGC
AAGGTAGAAGTTTTAGATCTAATGAGGTAACACAAGAAATTTCAGATAGCACAAGAATTT
TCAGGCTGCTTGGATCTGACAGGGTCGTGGTTTTGGAAAGTAGGCCAACTGATAACCCCA
CAGCAAATAGCAATTTGTACATCCTGGCGGGTCATGAAACAGTTACTGAGAATTGTTGT
GCTTTGACAGTTAACTCTAGAAAGAAGAACACTACCACTGCAACATTAATGGATGCTTG
AAGCTGTACAAAAGCTGCAGTAACCTGTCTTCAGTTACTTTGTAATTTATTGTGGCATGA
GATAAGATGGGGAAAATTTTGTTTTAAGTGGTATGGATATATTTAGCATATTGAACCACA
CAAGTGCTTAATTCATTGTTATGTAATCTTTGTACATATAGGCAGTATTTTTTCTGTGAA
ACTTCATATTGCTGAAGACATACACTAAGAATTTATGTAGATAATGTACTTTTATGAGAT
GTACAAGTAAGTGTCTTATCTGTACAGATGTAAATGTTGATGAAAATGCAATTGGGGTTA
ATATTTAAGAATTCTTTAGTATATTCTTGGGTGTGGCTATATTACAAAATGGGATGCTG
GCAATGAAACAATACATTTAACACTATTGTATTTTTATTATATGTAATTTAGTAATATGA
```

Fig. 9M

```
ATATAAATCTTGTAACTTTTAAAATTGTAATGGAGGCTGTAATCATTTTATAATCTTTTT
AATTTTAATGCAAGTACACTGGTGTTTATATTTGCACAAAGTATTGATATGTGATGTATT
AAGTCACAAAAGTAAGCTGTGACATTGTCTATAAGCATTTGGCTCCACAAATGTATTTGG
ATTGTTTTCTATGTGAAGCAAACCAATTATAATTAACCACATGTTGTAGTAACTGGTCTT
TTTATATTTAAGCAGAATCCTGTAAGATTGCTTGTCTTTGCTTAAAAACAATACCTTTGA
ACATTTTTGAATCACAGAATAGCGGTACCATGATAGAATACTGCAATTGTGGTCAGAATT
ACAGTATGCACAAAGAATTAATTAGCATTATTAAAGAGTCCTCACTAAACATTTCATATG
ATCACACTGAAGAACTGTAACATTCCATAGAGTGAAGTGGTTCAAATTTCTCTTGGAATT
TTTACTTTTGTTGGCCTTATTTATGATCCTTTTCATATTTCTTTTGACTTAGAGTATTA
ATACATGGCCAAAATAATTTAGTTACTACCTCATACAAACAATATAATGGTTACTACACA
TCACAGGAACTTAGTTTTGGTTTAAGTCATTTTTGATTGCTTTTTCCAATGGAATATGT
ATATACCAGGTTTTAGCAAAATGCACACTTTTGGCTCTTTTGGTATATGTTCTTTATAT
TTAATGTGAGTATATACACTAAGAACAAACTAAATTGTGATTTATGATCTTCATTTATT
TTAATGATAATGGTTTTAAAATATGTTCCTGATTGTACATATTGTAAAATAAACATGTTT
TTT

SEQ ID NO: 19  SULU1 HUMAN
GGGAGGGTCCTTGTGGCGCCGGGCGGCGGGGTCCTGCGTGGAGAGTGGGACGCAACGCCG
AGACCGCGAGCAGAGGCTGCGCACAGCCGGATCCGGCACTCAGCGACCGGACCCAAGGAT
CCGCCGGGGAACAAGCCACAGGAGAGCGACTCAGGAACAAGTGTGGGAGAGGAAGCGGCG
GCGGCGGCGCCGGGCCCGGGGGTGGTGACAGCAGGTCTGAGGTTGCATCATAAATACAAA
GGACTGAAGTTATAAAGAGAAAAGAGAAGTTTGCTGCTAAAATGAATCTGAGCAATATG
GAATATTTTGTGCCACACACAAAAAGGTACTGAAGATTTACCCCCCAAAAAAAATTGTCA
ATGAGAAATAAAGCTAACTGATATCAAAAGCAGAGCCTGCTCTACTGGCCATCATGCGT
AAAGGGGTGCTGAAGGACCCAGAGATTGACGATCTATTCTACAAAGATGATCCTGAGGAA
CTTTTTATTGGTTTGCATGAAATTGGACATGGAAGTTTTGGAGCAGTTTATTTTGCTACA
AATGCTCACACCAATGAGGTGGTGGCAATTAAGAAGATGTCCTATAGTGGGAAGCAGACC
CATGAGAAATGGCAAGATATTCTTAAGGAAGTTAAATTTTTACGACAATTGAAGCATCCT
AATACTATTGAGTACAAAGGCTGTTACTTGAAAGAACACACTGCTTGGTTGGTGATGGAA
TATTGCTTAGGCTCAGCCTCTGATTTATTAGAAGTTCATAAAAAACCACTTCAGGAAGTG
GAGATCGCTGCCATTACTCATGGAGCCTTGCATGGACTAGCCTACCTACATTCTCATGCA
TTGATTCATAGGGATATTAAAGCAGGAAATATTCTTCTAACAGAGCCAGGTCAGGTAAAA
CTAGCTGATTTTGGATCTGCTTCAATGGCTTCTCCTGCCAACTCCTTCGTGGGCACACCT
TACTGGATGGCTCCAGAGGTGATCTTAGCTATGGATGAAGGACAGTATGATGGGAAAGTT
GATATTTGGTCACTTGGCATCACTTGTATTGAATTGGCGGAACGGAAGCCGCCCCTTTTC
AACATGAATGCAATGAGTGCCTTATATCACATTGCCCAGAATGACTCCCCAACGTTACAG
TCTAATGAATGGACAGACTCCTTTAGGAGATTTGTTGATTACTGCTTGCAGAAAATACCT
CAGGAAAGGCCAACATCAGCAGAACTATTAAGGCATGACTTTGTTCGACGAGACCGGCCA
```

Fig. 9N

```
CTACGTGTCCTCATTGACCTCATACAGAGGACAAAAGATGCAGTTCGTGAGCTAGATAAC
CTACAGTACCGAAAAATGAAAAAATACTTTTCCAAGAGACACGGAATGGACCCTTGAAT
GAGTCACAGGAGGATGAGGAAGACAGTGAACATGGAACCAGCCTGAACAGGGAAATGGAC
AGCCTGGGCAGCAACCATTCCATTCCAAGCATGTCCGTGAGCACAGGCAGCCAGAGCAGC
AGTGTGAACAGCATGCAGGAAGTCATGGACGAGAGCAGTTCCGAACTTGTCATGATGCAC
GATGACGAAAGCACAATCAATTCCAGCTCCTCCGTCGTGCATAAGAAAGATCATGTATTC
ACAAGGGATGAGGCGGGCCACGGCGATCCCAGGCCTGAGCCGCGGCCTACCCAGTCAGTT
CAGAGCCAGGCCCTCCACTACCGGAACAGAGAGCGCTTTGCCACGATCAAATCAGCATCT
TTGGTTACACGACAGATCCATGAGCATGAGCAGGAGAACGAGTTGCGGGAACAGATGTCA
GGTTATAAGCGGATGCGGCGCCAGCACCAGAAGCAGCTGATCGCCCTGGAGAACAAGCTG
AAGGCTGAGATGGACGAGCACCGCCTCAAGCTACAGAAGGAGGTGGAGACGCATGCCAAC
AACTCGTCCATCGAGCTGGAGAAGCTGGCCAAGAAGCAAGTGGCTATCATAGAAAAGGAG
GCAAAGGTAGCTGCAGCAGATGAGAAGAAGTTCCAGCAACAGATCTTGGCCCAGCAGAAG
AAAGATTTGACAACTTTCTTAGAAAGTCAGAAGAAGCAGTATAAGATTTGTAAGGAAAAA
ATAAAAGAGGAAATGAATGAGGACCATAGCACACCCAAGAAAGAGAAGCAAGAGCGGATC
TCCAAACATAAAGAGAACTTGCAGCACACACAGGCTGAAGAGGAAGCCCACCTTCTCACT
CAACAGAGACTGTACTACGACAAAAATTGTCGTTTCTTCAAGCGGAAAATAATGATCAAG
CGGCACGAGGTGGAGCAGCAGAACATTCGGGAGGAACTAAATAAAAGAGGACCCAGAAG
GAGATGGAGCATGCCATGCTAATCCGGCACGACGAGTCCACCCGAGAGCTAGAGTACAGG
CAGCTGCACACGTTACAGAAGCTACGCATGGATCTGATCCGTTTACAGCACCAGACGGAA
CTGGAAAACCAGCTGGAGTACAATAAGAGGCGAGAAAGAGAACTGCACAGAAAGCATGTC
ATGGGACTTCGGCAACAGCCAAAAAACTTAAAGGCCATGGAAATGCAAATTAAAAAACAG
TTTCAGGACACTTGCAAAGTACAGACCAAACAGTATAAAGCACTCAAGAATCACCAGTTG
GAAGTTACTCCAAAGAATGAGCACAAAACAATCTTAAAGACACTGAAAGATGAGCAGACA
AGAAAACTTGCCATTTTGGCAGAGCAGTATGAACAGAGTATAAATGAAATGATGGCCTCT
CAAGCGTTACGGCTAGATGAGGCTCAAGAAGCAGAATGCCAGGCCTTGAGGCTACAGCTC
CAGCAGGAAATGGAGCTGCTCAACGCCTACCAGAGCAAAATCAAGATGCAAACAGAGGCA
CAACATGAACGTGAGCTCCAGAAGCTAGAGCAGAGAGTGTCTCTGCGCAGAGCACACCTT
GAGCAGAAGATTGAAGAGGAGCTGGCTGCCCTTCAGAAGGAACGCAGCGAGAGAATAAAG
AACCTATTGGAAAGGCAAGAGCGAGAGATTGAAACTTTTGACATGGAGAGCCTCAGAATG
GGATTTGGGAATTTGGTTACATTAGATTTTCCTAAGGAGGACTACAGATGAGATTAAATT
TTTTGCCATTTACAAAAAAAAAAAAAAAAGAAAACAGAAAAAAATTCAGACCCTGCAA
AACCACATTCCCCATTTTAACGGGCGTTGCTCTCACTCTCTCTCTCTCTTACTCTTACTG
ACATCGTGTCGGACTAGTGCCTGTTTATTCTTACTCCATCAGGGGCCCCCTTCCTCCCCC
CGTGTCAACTTTCAGTGCTGGCCAAAACCTGGCCGTCTCTTCTATTCACAGTACACGTCA
CAGTATTGATGTGATTCAAAATGTTTCAGTGAAAACTTTGGAGACAGTTTTAACAAAACC
AATAAACCAACAACAAAAAAGTGGATGTATATTGCTTTAAGCAATCACTCATTACCACC
AATCTGTGAAAGTAAAGCAAAAAATAATAATAATAAATGCCAAGGGGGAGAGAGACACAA
```

Fig. 9 O

TATCCGCAGCCTTACACCTTAACTAGCTGCTGCATTATTTTATTTTATTTTATTTTTTG
GTATTTATTCATCAGGAATAAAAAAAACAAAGTTTTATTAAAGATTGAAAATTTGATACA
TTTTACAGAAACTAATTGTGATGTACATATCAGTGGTGACATATTATTACTTTTTTGGGG
ACGGGGGGTGGGTGGGGTGAAGAGATCTTGTGATTTTAAGAACCTGCTGGCAAGAGTT
AACTTGTCTTCAGCATATTCTGATTGTATCATAATCATTTCTGCTGTTGCAGAGGATGT
GAATACACTTAAGGAGCTCACAGAATCCCAGTAGCACAAATTGGGCTTTGGCAAATCGTG
TATTTTGTGTATAGAAGGAATTTAAGGAGAGGTATTACTTATTTTCATATTGTATTTTAA
CTGTTTCTCTGATCAAATTTTTTACTTCCTCCTCCTGTTCCTCCCCACCTCCCTCCTTT
TCCAGTTCAGTATTTGGAGTTCAACACTGTCTCTCAATCAGATCATCTTGATCTTTTTCT
TTATCTCCCTTCCCCTTCCTAAGTCCCATTTCTTGGTCATAAATATTGCATTATTCACAC
TTTCAAACTGTGTATTTTCTTACAATAAAAAATGATGAAAAAAAAAAAAAAAAAA

SEQ ID NO: 20 SULU3 HUMAN
TATTGAATTGGCGGAACGGAAGCCTCCTTTATTTAATATGAATGCAATGAGTGCCTTATA
TCACATAGCCCAAAATGAATCCCCTACACTACAGTCTAATGAATGGTCTGATTATTTTCG
CAACTTTGTAGATTCTTGCCTCCAGAAAATCCCTCAAGATCGACCTACATCAGAGGAACT
TTTAAAGCACATATTTGTTCTTCGGGAGCGCCCTGAAACCGTGTTAATAGATCTCATTCA
GAGGACAAAGGATGCAGTAAGAGAGCTGGACAATCTGCAGTATCGAAAGATGAAGAAACT
CCTTTTCCAGGAGGCACATAATGGACCAGCAGTAGAAGCACAGGAAGAAGAAGAGGAACA
AGATCATGGTGTTGGCCGGACAGGAACAGTTAATAGTGTTGGAAGTAATCAATCCATTCC
CAGCATGTCCATCAGTGCCAGCAGCCAAAGCAGTAGTGTTAACAGTCTTCCAGATGTCTC
AGATGACAAGAGTGAGCTAGACATGATGGAGGGAGACCACACAGTGATGTCTAACAGTTC
TGTTATCCATTTAAAACCAGAGGAAGAAAATTACAGAGAAGAGGGAGATCCTAGAACAAG
AGCATCAGATCCACAATCTCCACCCCAAGTATCTCGTCACAAATCACACTATCGTAATCG
AGAACACTTTGCTACTATACGGACAGCATCACTGGTTACGAGGCAAATGCAAGAACATGA
GCAGGACTCTGAGCTTAGAGAACAAATGTCTGGCTATAAGCGAATGAGGCGACAACATCA
AAAGCAACTGATGACTCTGGAAAACAAGCTAAGGCTGAGATGGATGAACATCGCCTCAG
ATTAGACAAAGATCTTGAAACTCAGCGTAACAATTTTGCTGCAGAAATGGAGAAACTTAT
CAAGAAACACCAGGCTGCCATGGAGAAAGAGGCTAAAGTGATGTCCAATGAAGAGAAAA
ATTTCAGCAACATATTCAGGCCCAACAGAAGAAAGAACTGAATAGTTTTCTCGAGTCCCA
GAAAAGAGAGTATAAACTTCGAAAAGAGCAGCTTAAGAGGAGCTAAATGAAAACCAGAG
TACCCCAAAAAAGAAAACAGGAGTGGCTTTCAAAGCAGAAGGAGAATATACAGCATTT
CCAAGCAGAAGAAGAAGCTAACCTTCTTCGACGTCAAAGACAATACCTAGAGCTGGAATG
CCGTCGCTTCAAGAGAAGAATGTTACTTGGGCGTCATAACTTAGAGCAGGACCTTGTCAG
GGAGGAGTTAAACAAAAGACAGACTCAGAAGGACTTAGAGCATGCCATGCTACTCCGACA
GCATGAATCTATGCAAGAACTGGAGTTCCGCCACCTCAACACAATTCAGAAGATGCGCTG
TGAGTTGATCAGATTACAGCATCAAACTGAGCTCACTAACCAGCTGGAATATAATAAGCG
AAGAGAACGAGAACTAAGACGAAAGCATGTCATGGAAGTTCGACAACAGCCTAAGAGTTT

Fig. 9P

```
GAAGTCTAAAGAACTCCAAATAAAAAGCAGTTTCAGGATACCTGCAAAATCCAAACCAG
ACAGTACAAAGCATTAAGAAATCACCTGCTGGAGACTACACCAAAGAGTGAGCACAAAGC
TGTTCTGAAACGGCTCAAGGAGGAACAGACCCGGAAATTAGCTATCTTGGCTGAGCAGTA
TGATCACAGCATTAATGAAATGCTCTCCACACAAGCCCTGCGTTTGGATGAAGCACAGGA
AGCAGAGTGCCAGGTTTTGAAGATGCAGCTGCAGCAGGAACTGGAGCTGTTGAATGCGTA
TCAGAGCAAAATCAAGATGCAAGCTGAGGCACAACATGATCGAGAGCTTCGCGAGCTTGA
ACAGAGGGTCTCCCTCCGGAGGGCACTCTTAGAACAAAAGATTGAAGAAGAGATGTTGGC
TTTGCAGAATGAGCGCACAGAACGAATACGAAGCCTGTTGGAACGTCAAGCCAGAGAGAT
TGAAGCTTTTGACTCTGAAAGCATGAGACTAGGTTTTAGTAATATGGTCCTTTCTAATCT
CTCCCCTGAGGCATTCAGCCACAGCTACCCGGGAGCTTCTGGTTGGTCACACAACCCTAC
TGGGGGTCCAGGACCTCACTGGGGTCATCCCATGGGTGGCCCACCACAAGCTTGGGGCCA
TCCAATGCAAGGTGGACCCCAGCCATGGGGTCACCCTTCAGGGCCAATGCAAGGGGTACC
TCGAGGTAGCAGTATGGGAGTCCGCAATAGCCCCCAGGCTCTGAGGCGGACAGCTTCTGG
GGGACGGACGGAGCAGGGCATGAGCAGAAGCACGAGTGTCACTTCACAAATATCCAATGG
GTCACACATGTCTTATACATAACTTAATAATTGAGAGTGGCAATTCCGCTGGAGCTGTCT
GCCAAAAGAAACTGCCTACAGACATCATCACAGCAGCCTCCTCACTTGGGTACTACAGTG
TGGAAGCTGAGTGCATATGGTATATTTTATTCATTTTTGTAAAGCGTTCTGTTTTGTGTT
TACTAATTGGGATGTCATAGTACTTGGCTGCCGGGTTTGTTTGTTTTGGGGAAATTTTG
AAAAGTGGAGTTGATATTAAAAATAAATGTGTATGTGTGTACATATATATACACACACAT
ACACATATATTATGCATGTGGTGAAAAGAATTGGCTAGATAGGGGATTTTTCTGAACACT
GCAAAAATAGAACGTAGCAAAATGGCTTCAGTTATCACTTTTGGGTGTCTGTATCCTAAG
AAGTTTCTGAAAAGATCTAAAGCCTTTTTATCCCATATCCCAAATTCTTATGAGCCACTC
ACAGCAGGCAGCATATGTTGAAATAAGTTATTACTGGTACACACCTGCATTGCCTCACCA
GTGTATTTATTTGTTATTAAATTGATCTGACTTCTCAGCCTCATTTGGACTAAAAAAGA
AAGCAGAAATCCATGAACACATTGCTTCTCGGCCTTTTGGCTAAGATCAAGTGTAGAAAT
CCATGAACACTAAAGGACTTCATTGATTTTTTCAGAGAGTAGAAAACAACTTAGTTTTTC
TTTTTTCCTGAATGCGTCATAGGCTTGTGAGTGATTTTTGTCCATTCAATTGTGCCTTCT
TTGTATTATGATAAGATGGGGGTACTTAAGGAGATCACAAGTTGTGTGAGGATTGCATTA
ACAAACCTATGAGCCTTCAATGGGGAAGACCAGAAGGGTGAGAGGGGCCCTGAAAGTTCA
TATGGTGGGTATGTCCCGCAGCAGAGTGAGGAGATGAAGCTTACGTGTCCTGACGTTTTG
TTGCTTATACTGTGATATCTCATCCTAGCTAAGCTCTATAATGCCCAAGACCCCAAACAG
TACTTTTACTTTGTTTGTACAAAAACAAAGACATATAGCCAATACAAATCAAATGCCGGA
GGTGTTTGATGCCATATTTGCAAATTGCCATCTATTGAATTCTCGTCACACTACATAGA
CATAATTGTTATCTCCTTTTGGCTTATGTGATTTTCTGTTTACAAGTAGAATAGCCAATT
ATTTAAATGTTTAGTTGCCACAGTGAACCAGGAGTCACTGAGCCAATGACTTTACCAGCT
GCTGACTAATCTTCATCACCACTGTAGATTTTGCTGCATGTGCAGGTCCTCTATTTTTAA
TTGCTGTTTTCGTTGCTGCAGTACTTTACAAACTTCTAGTTCGTTGAGACTTAGTGACCA
TTTGGCATCAAGTTAACATCACACAATAGGAAACACCACTTCCACAAGTCTCAAGCCTCA
```

Fig. 9Q

GTGCTAAAGTACTACTGAAAAGGAACTAGGAAGTTTGGCCAATT

SEQ ID NO: 21 SULU3 MURINE
GCAGGATGCCATCAACTAACAGAGCAGGCAGTCTAAAGGACCCTGAAATTGCAGAGCTCT
TCTTCAAAGAAGATCCGGAAAAGCTCTTCACAGATCTCAGAGAAATCGGCCATGGGAGCT
TTGGAGCAGTATATTTTGCACGAGATGTGCGTACTAATGAAGTGGTGGCCATCAAGAAAA
TGTCTTATAGTGGAAAGCAGTCTACTGAGAAATGGCAGGATATTATTAAGGAAGTCAAGT
TTCTACAAAGAATAAAACATCCCAACAGTATAGAATACAAAGGCTGCTATTTACGTGAAC
ACACAGCATGGCTTGTAATGGAATATTGTTTAGGATCTGCTTCAGATTTATTAGAAGTTC
ATAAAAAGCCATTACAAGAAGTGGAAATAGCAGCAATTACACATGGTGCTCTCCAGGGAC
TAGCTTATTTACATTCTCATACCATGATCCATAGAGATATCAAAGCAGGAAATATCCTTC
TGACAGAACCAGGCCAAGTGAAACTTGCTGACTTTGGATCTGCTTCCATGGCTTCCCCTG
CCAATTCTTTTGTGGGAACACCATATTGGATGGCCCCAGAAGTAATTTTAGCCATGGATG
AAGGACAGTATGATGGCAAAGTTGATGTATGGTCTCTTGGAATAACGTGTATTGAATTAG
CCGAGAGGAAGCCTCCTTTATTTAATATGAATGCAATGAGTGCCTTATATCACATAGCCC
AAAATGAATCCCCTACACTACAATCTAATATGAATGATTCTTGCCTCCAGAAAATCCCTC
AAGATCGCCCTACATCAGAGGAACTTTTAAAGCACATGTTTGTTCTTCGAGAGCGCCCTG
AAACAGTGTTAATAGATCTTATTCAAGGACAAAGGATGCAGTAAGAGAGCTGGACAATC
TGCAGTATCGAAAGATGAAGAAACTCCTTTTCCAGGAGGCACATAATGGGCCAGCGGTAG
AAGCACAGGAAGAAGAGGAGGAGCAAGATCATGGTGTTGGCCGAACAGGAACAGTGAATA
GTGTTGGAAGCAATCAGTCTATCCCTAGTATGTCTATCAGTGCCAGCAGTCAAAGCAGCA
GTGTTAATAGTCTTCCAGATGCATCAGATGACAAGAGTGAGCTAGACATGATGGAGGGAG
ACCATACAGTGATGTCTAACAGTTCTGTCATCCACTTAAAACCTGAGGAGGAAAATTACC
AGGAAGAAGGAGATCCTAGAACAAGAGCATCAGACCCACAGTCTCCCCCTCAGGTGTCTC
GTCACAAGTCACATTATCGTAATAGAGAACACTTTGCAACCATACGAACAGCATCACTGG
TTACAAGACAGATGCAAGAACATGAGCAGGACTCTGAACTTAGAGAACAGATGTCTGGTT
ATAAGCGGATGAGGCGACAGCATCAAAAGCAGCTGATGACGCTGGAAAATAAACTGAAGG
CAGAGATGGACGAACATCGGCTCAGATTAGACAAAGATCTTGAAACTCAGCGTAACAATT
TCGCTGCAGAAATGGAGAAACTTATTAAGAAACACCAAGCTGCTATGGAAAAGAGGCTA
AAGTGATGGCCAATGAGGAGAAAAAATTCCAGCAACACATTCAGGCTCAACAGAAAAAG
AACTGAATAGCTTTTTGGAGTCTCAAAAAGAGAATATAAACTTCGCAAAGAGCAGCTTA
AGGAGGAGCTGAATGAAAACCAGAGCACACCTAAAAAAGAAAAGCAGGAATGGCTTTCAA
AGCAGAAGGAGAATATACAGCATTTTCAGGCAGAAGAAGAAGCTAATCTTCTTCGACGTC
AAAGGCAGTATCTAGAGCTAGAATGTCGTCGCTTCAAAAGAAGAATGTTACTTGGGCGAC
ATAACTTGGAACAGGACCTTGTCAGGGAGGAGTTAAACAAAGGCAGACTCAAAAGGACT
TGGAACATGCAATGCTATTGCGACAGCATGAATCAATGCAAGAACTGGAGTTTCGCCATC
TCAACACTATTCAGAAGATGCGCTGTGAGTTGATCAGACTGCAGCATCAAACTGAGCTCA
CTAACCAGCTAGAGTACAATAAGAGAAGGGAACGGGAACTGAGGCGAAAACATGTCATGG

Fig. 9R

AAGTTCGACAACAACCTAAGAGTCTGAAGTCTAAAGAACTCCAAATAAAAAAGCAGTTTC
AGGATACCTGCAAAATTCAAACCAGACAGTACAAAGCATTAAGGAATCACCTACTGGAGA
CTACACCAAAGAATGAGCACAAAGCAATC

SEQ ID NO: 25 GEK2 HUMAN
CGAAGCCACAGCCCGAGCCCGAGCCCGAGCCCGAGCCGGCGCCACCGCGCCCCCGGCCAT
GGCTTTTGCCAATTTCCGCCGCATCCTGCGCCTGTCTACCTTCGAGAAGAGAAAGTCCCG
CGAATATGAGCACGTCCGCCGCGACCTGGACCCCAACGAGGTGTGGGAGATCGTGGGCGA
GCTGGGCGACGGCGCCTTCGGCAAGGTTTACAAGGCCAAGAATAAGGAGACGGGTGCTTT
GGCTGCGGCCAAAGTCATTGAAACCAAGAGTGAGGAGGAGCTGGAGGACTACATCGTGGA
GATTGAGATCCTGGCCACCTGCGACCACCCCTACATTGTGAAGCTCCTGGGAGCCTACTA
TCACGACGGGAAGCTGTGGATCATGATTGAGTTCTGTCCAGGGGGAGCCGTGGACGCCAT
CATGCTGGAGCTGGACAGAGGCCTCACGGAGCCCCAGATACAGGTGGTTTGCCGCCAGAT
GCTAGAAGCCCTCAACTTCCTGCACAGCAAGAGGATCATCCACCGAGATCTGAAAGCTGG
CAACGTGCTGATGACCCTCGAGGGAGACATCAGGCTGGCTGACTTTGGTGTGTCTGCCAA
GAATCTGAAGACTCTACAGAAACGAGATTCCTTCATCGGCACGCCTTACTGGATGGCCCC
CGAGGTGGTCATGTGTGAGACCATGAAAGACACGCCCTACGACTACAAGCCGACATCTG
GTCCCTGGGCATCACGCTGATTGAGATGGCCCAGATCGAGCCGCCACACCACGAGCTCAA
CCCCATGCGGGTCCTGCTAAAGATCGCCAAGTCGGACCCTCCCACGCTGCTCACGCCCTC
CAAGTGGTCTGTAGAGTTCCGTGACTTCCTGAAGATAGCCCTGGATAAGAACCCAGAAAC
CCGACCCAGTGCCGCGCAGCTGCTGGAGCATCCCTTCGTCAGCAGCATCACCAGTAACAA
GGCTCTGCGGGAGCTGGTGGCTGAGGCCAAGGCCGAGGTGATGGAAGAGATCGAAGACGG
CCGGGATGAGGGGGAAGAGGAGGACGCCGTGGATGCCGCCTCCACCCTGGAGAACCATAC
TCAGAACTCCTCTGAGGTGAGTCCGCCAAGCCTCAATGCTGACAAGCCTCTCGAGGAGTC
ACCTTCCACCCCGCTGGCACCCAGCCAGTCTCAGGACAGTGTGAATGAGCCCTGCAGCCA
GCCCTCTGGGGACAGATCCCTCCAAACCACCAGTCCCCCAGTCGTGGCCCCTGGAAATGA
GAACGGCCTGGCAGTGCCTGTGCCCCTGCGGAAGTCCCGACCCGTGTCAATGGATGCCAG
AATTCAGGTAGCCCAGGAGAAGCAAGTTGCTGAGCAGGGTGGGACCTCAGCCCAGCAGC
CAACAGATCTCAAAAGGCCAGCCAGAGCCGGCCCAACAGCAGCGCCCTGGAGACCTTGGG
TGGGGAGAAGCTGGCCAATGGCAGCCTGGAGCCACCTGCCCAGGCAGCTCCAGGGCCTTC
CAAGAGGGACTCGGACTGCAGCAGCCTCTGCACCTCTGAGAGCATGGACTATGGTACCAA
TCTCTCCACTGACCTGTCGCTGAACAAAGAGATGGGCTCTCTGTCCATCAAGGACCCGAA
ACTGTACAAAAAACCCTCAAGCGGACACGCAAATTTGTGGTGGATGGTGTGGAGGTGAG
CATCACCACCTCCAAGATCATCAGCGAAGATGAGAAGAAGGATGAGGAGATGAGATTTCT
CAGGCGCCAGGAACTCCGAGAGCTTCGGCTGCTCCAGAAAGAAGAGCATCGGAACCAGAC
CCAGCTGAGTAACAAGCATGAGCTGCAGCTGGAGCAAATGCATAAACGTTTTGAACAGGA
AATCAACGCCAAGAAGAAGTTCTTTGACACGGAATTAGAGAACCTGGAGCGTCAGCAAAA
GCAGCAAGTGGAGAAGATGGAGCAAGACCATGCCGTGCGCCGCCGGGAGGAGGCCAGGCG

Fig. 9S

GATCCGCCTGGAGCAGGATCGGGACTACACCAGGTTCCAAGAGCAGCTCAAACTGATGAA
GAAAGAGGTGAAGAACGAGGTGGAGAAGCTCCCCCGACAGCAGCGGAAGGAAAGCATGAA
GCAGAAGATGGAGGAGCACACGCAGAAAAAGCAGCTTCTTGACCGGGACTTTGTAGCCAA
GCAGAAGGAGGACCTGGAGCTGGCCATGAAGAGGCTCACCACCGACAACAGGCGGGAGAT
CTGTGACAAGGAGCGCGAGTGCCTCATGAAGAAGCAGGAGCTCCTTCGAGACCGGGAAGC
AGCCCTGTGGGAGATGGAAGAGCACCAGCTGCAGGAGAGGCACCAGCTGGTGAAGCAGCA
GCTCAAAGACCAGTACTTCCTCCAGCGGCACGAGCTGCTGCGCAAGCATGAGAAGGAGCG
GGAGCAGATGCAGCGCTACAACCAGCGCATGATAGAGCAGCTGAAGGTGCGGCAGCAACA
GGAAAAGGCGCGGCTGCCCAAGATCCAGAGGAGTGAGGGCAAGACGCGCATGGCCATGTA
CAAGAAGAGCCTCCACATCAACGGCGGGGGCAGCGCAGCTGAGCAGCGTGAGAAGATCAA
GCAGTTCTCCCAGCAGGAGGAGAAGAGGCAGAAGTCGGAGCGGCTGCAGCAACAGCAGAA
ACACGAGAACCAGATGCGGGACATGCTGGCGCAGTGCGAGAGCAACATGAGCGAGCTGCA
GCAGCTGCAGAATGAAAAGTGCCACCTCCTGGTAGAGCACGAAACCCAGAAACTGAAGGC
CCTGGATGAGAGCCATAACCAGAACCTGAAGGAAT

SEQ ID NO: 27  PAK4 HUMAN
CGTTCCTGGGCTTCCCGCTCCGCAGGCCTGCGGAGGACTGGCCCAGCAAGGTCCCAGGTC
TTCCCTCTCCTTAGCGCCTAAGAGAGAGGCCCAGTGCGGGTGAGGAGTCGCGAGGAAGAG
GCGGAAGGCGCCGGAAGGCACCATGTTCCGCAAGAAAAAGAAGAAACGCCCTGAGATCTC
AGCGCCACAGAACTTCCAGCACCGTGTCCACACCTCCTTCGACCCCAAAGAAGGCAAGTT
TGTGGGCCTCCCCCCACAATGGCAGAACATCCTGGACACACTGCGGCGCCCCAAGCCCGT
GGTGGACCCTTCGCGAATCACACGGGTGCAGCTCCAGCCCATGAAGACAGTGGTGCGGGG
CAGCGCGATGCCTGTGGATGGCTACATCTCGGGGCTGCTCAACGACATCCAGAAGTTGTC
AGTCATCAGCTCCAACACCCTGCGTGGCCGCAGCCCCACCAGCCGGCGGCGGGCACAGTC
CCTGGGGCTGCTGGGGGATGAGCACTGGGCCACCGACCCAGACATGTACCTCCAGAGCCC
CCAGTCTGAGCGCACTGACCCCCACGGCCTCTACCTCAGCTGCAACGGGGGCACACCAGC
AGGCCACAAGCAGATGCCGTGGCCCGAGCCACAGAGCCCACGGGTCCTGCCCAATGGGCT
GGCTGCAAAGGCACAGTCCCTGGGCCCCGCCGAGTTTCAGGGTGCCTCGCAGCGCTGTCT
GCAGCTGGGTGCCTGCCTGCAGAGCTCCCCACCAGGAGCCTCGCCCCCACGGGCACCAA
TAGGCATGGAATGAAGGCTGCCAAGCATGGCTCTGAGGAGGCCCGGCCACAGTCCTGCCT
GGTGGGCTCAGCCACAGGCAGGCCAGGTGGGGAAGGCAGCCCTAGCCCTAAGACCCGGGA
GAGCAGCCTGAAGCGCAGGCTATTCCGAAGCATGTTCCTGTCCACTGCTGCCACAGCCCC
TCCAAGCAGCAGCAAGCCAGGCCCTCCACCACAGAGCAAGCCCAACTCCTCTTTCCGACC
GCCGCAGAAAGACAACCCCCCAAGCCTGGTGGCCAAGGCCCAGTCCTTGCCCTCGGACCA
GCCGGTGGGGACCTTCAGCCCTCTGACCACTTCGGATACCAGCAGCCCCCAGAAGTCCCT
CCGCACAGCCCCGGCCACAGGCCAGCTTCCAGGCCGGTCTTCCCCAGCGGGATCCCCCCG
CACCTGGCACGCCCAGATCAGCACCAGCAACCTGTACCTGCCCCAGGACCCCACGGTTGC
CAAGGGTGCCCTGGCTGGTGAGGACACAGGTGTTGTGACACATGAGCAGTTCAAGGCTGC

Fig. 9T

```
GCTCAGGATGGTGGTGGACCAGGGTGACCCCGGCTGCTGCTGGACAGCTACGTGAAGAT
TGGCGAGGGCTCCACCGGCATCGTCTGCTTGGCCCGGGAGAAGCACTCGGGCCGCCAGGT
GGCCGTCAAGATGATGGACCTCAGGAAGCAGCAGCGCAGGGAGCTGCTCTTCAACGAGGT
GGTGATCATGCGGGACTACCAGCACTTCAACGTGGTGGAGATGTACAAGAGCTACCTGGT
GGGCGAGGAGCTGTGGGTGCTCATGGAGTTCCTGCAGGGAGGAGCCCTCACAGACATCGT
CTCCCAAGTCAGGCTGAATGAGGAGCAGATTGCCACTGTGTGTGAGGCTGTGCTGCAGGC
CCTGGCCTACCTGCATGCTCAGGGTGTCATCCACCGGGACATCAAGAGTGACTCCATCCT
GCTGACCCTCGATGGCAGGGTGAAGCTCTCGGACTTCGGATTCTGTGCTCAGATCAGCAA
AGACGTCCCTAAGAGGAAGTCCCTGGTGGGAACCCCCTACTGGATGGCTCCTGAAGTGAT
CTCCAGGTCTTTGTATGCCACTGAGGTGGATATCTGGTCTCTGGGCATCATGGTGATTGA
GATGGTAGATGGGGAGCCACCGTACTTCAGTGACTCCCAGTGCAAGCCATGAAGAGGCT
CCGGGACAGCCCCCACCCAAGCTGAAAAACTCTCACAAGGTCTCCCCAGTGCTGCGAGA
CTTCCTGGAGCGGATGCTGGTGCGGGACCCCAAGAGAGAGCCACAGCCCAGGAGCTCCT
AGACCACCCCTTCCTGCTGCAGACAGGGCTACCTGAGTGCCTGGTGCCCCTGATCCAGCT
CTACCGAAAGCAGACCTCCACCTGCTGAGCCCACCCCAAGTATGCCTGCCACCTACGCCC
ACAGGCAGGGCACACTGGGCAGCCAGCCTGCCGGCAGGACTTGCCTGCCTCCTCCTCTCA
GTATTCTCTCCAAAGATTGAAATGTGAAGCCCCAGCCCCACCCTCTGCCCTTCAGCCTAC
TGGGCCAGGCCGGACCTGCCCCCTCAGTGTCTCTCCCTCCCGAGTCCCCAGATGGAGACC
CCTTTCTACAGGATGACCCCTTGATATTTGCACAGGGATATTTCTAAGAAACGCAGAGGC
CAGCGTTCCTGGCCTCTGCAGCCAACACAGTAGAAAAGGCTGCTGTGGTTTTTTAAAGGC
AGTTGTCCACTAGTGTCCTAGGCCACTGCAGAGGGCAGACTGCTGGTCTCCACAGATACC
TGCTGTTCTCAGCTCCAGCTTCAAACCTCGAGTCTCGAGAGGGCCACGGGGTGGTTTTTA
TGACCGGAATCCCGCTTCCTCCCTCACGTCTGATGTCCTGAAGGTGCAGTCCCACCTGTA
CAGCCCCTCCCCGCCAAGAACTGTGAATGGCCTGCTCCAGGCCATGGCTGGGGGCAGGGA
GTGAGGGACAATTTCTGAGTGAAAGAGAAAGAATGGGGTCGGTGGTGAAGGTGCTCTCA
CTTTACAGAATGGAGAGAACATCGTGTGTGTGTGTGTGTGTGTGTGTGTGTGTGTGTGTG
TGTGTGTGTGTGTGTGTGTGTGTGTAAGGGGAGGAAAGCCACCTTGACAGCCCAGGTC
CCTCCAGGTCACCCACAGCCAGTTTCAGGAAGGCTGCCCCTCTCTCCCACTAAGTTCTGG
CCTGAAGGGACCTGCTTTCTTGGCCTGGCTTCCACCTCTCCACTCCTGTGTCTACCTGGC
CAGTGGAGTGGTCCATGCTAAGTCTAACACTCCTGGGAGCTCAGGAGGCTTCTGAGCTTC
TCCTGTACTGTGCATCGTGAGGGCCAGAGACAGGAATGTAAGGATTGGCAACTGTGTTAC
CTTTCAAGTTTATCTCAATAACCAGGTCATCAGGGACCCATTGTTCTCTTCAGAACCCTA
TCTGGGAGAGAAGGCGAACCACCTCCGGGTTTCCATCATGTCAAGGTCACAGGCATCCAT
GTGTGCAAACCATCTGCCCCAGCTGCCTCCACAGACTGCTGTCTCCTTGTCCTCCTCGGC
CCTGCCCCACTTCAGGGCTGCTGTGAGATGGAATTCCAGGAAGAACTTCAGGTGTCTGG
ACCCTTTCTATCTAGATAATATTTTTAGATTCTTCTGCTCCCTAGTGACCTACCTGGGGG
CAAAGAAATTGCAAGGACTTTTTTTTAAGGGTCAGAGTTTTCAAAACAAAAGCATCTTCC
CTAGAAATTTTTGTGAATTGTTTGCACTTGTGCCTGTTTTAAATTAAATTGAGTGTTCAA
```

Fig. 9U

AGCC

SEQ ID NO: 28  PAK5 HUMAN
GGCCAGTGGGGCGAAACTGGCAGCTGGCCGGCCCTTTAACACCTACCCGAGGGCTGACAC
GGACCACCCATCCCGGGGTGCCCAGGGGGAGCCTCATGACGTGGCCCCTAACGGGCCATC
AGCGGGGGGCCTGGCCATCCCCCAGTCCTCCTCCTCCTCCTCCCGGCCTCCCACCCGAGC
CCGAGGTGCCCCCAGCCCTGGAGTGCTGGGACCCCACGCCTCAGAGCCCCAGCTGGCCCC
TCCAGCCTGCACCCCGCCGCCCTGCTGTTCCTGGGCCCCTGGCCCCGCTCACCACA
GCGGGAGCCACAGCGAGTATCCCATGAGCAGTTCCGGGCTGCCCTGCAGCTGGTGGTGGA
CCCAGGCGACCCCCGCTCCTACCTGGACAACTTCATCAAGATTGGCGAGGGCTCCACGGG
CATCGTGTGCATCGCCACCGTGCGCAGCTCGGGCAAGCTGGTGGCCGTCAAGAAGATGGA
CCTGCGCAAGCAGCAGAGGCGCGAGCTGCTCTTCAACGAGGTGGTAATCATGAGGGACTA
CCAGCACGAGAATGTGGTGGAGATGTACAACAGCTACCTGGTGGGGACGAGCTCTGGGT
GGTCATGGAGTTCCTGGAAGGAGGCGCCCTCACCGACATCGTCACCCACACCAGGATGAA
CGAGGAGCAGATCGCGGCCGTGTGCCTTGCAGTGCTGCAGGCCCTGTCGGTGCTCCACGC
CCAGGGCGTCATCCACCGGGACATCAAGAGCGACTCGATCCTGCTGACCCATGATGGCAG
GGTGAAGCTGTCAGACTTTGGGTTCTGCGCCCAGGTGAGCAAGGAAGTGCCCCGAAGGAA
GTCGCTGGTCGGCACGCCCTACTGGATGGCCCCAGAGCTCATCTCCCGCCTTCCCTACGG
GCCAGAGGTAGACATCTGGTCGCTGGGGATAATGGTGATTGAGATGGTGGACGGAGAGCC
CCCCTACTTCAACGAGCCACCCCTCAAAGCCATGAAGATGATTCGGGACAACCTGCCACC
CCGACTGAAGAACCTGCACAAGGTGTCGCCATCCCTGAAGGGCTTCCTGGACCGCCTGCT
GGTGCGAGACCCTGCCCAGCGGGCCACGGCAGCCGAGCTGCTGAAGCACCCATTCCTGGC
CAAGGCAGGGCCGCCTGCCAGCATCGTGCCCCTCATGCGCCAGAACCGCACCAGATGAGG
CCCAGCGCCCTTCCCCTCAACCAAAGAGCCCCCCGGGTCACCCCGCCCCACTGAGGCC
AGTAGGGGGCCAGGCCTCCCACTCCTCCCAGCCCGGGAGATGCTCCGCGTGGCACCACCC
TCCTTGCTGGGGGTAGATGAGACCCTACTACTGAACTCCAGTTTTGATCTCGTGACTTTT
AGAAAAACACAGGGACTCGTGGGAGCAAGCGAGGCTCCCAGGACCCCCACCCTCTGGGAC
AGGCCCTCCCCCATGTTCTTCTGTCTCCAGGAAGGGCAGCGGCCCTCCCATCACTGGAAG
TCTGCAGTGGGGGTCGCTGGGGGTGGAGAGAACACTAAGAGGTGAACATGTATGAGTGTG
TGCACGCGTGTGAGTGTGCATGTGTGTGTGTGCAAAGGTCCAGCCACCCCGTCCTCCA
GCCCGCAAGGGGTGTCTGGCGCCTTGCCTGACACCCAGCCCCCTCTCCCCCTGAGCCATT
GTGGGGGTCGATCATGAATGTCCGAAGAGTGGCCTTTTCCCGTAGCCCTGCGCCCCCTTT
CTGTGGCTGGATGGGGAGACAGGTCAGGGCCCCCCACCCTCTCCAGCCCCTGCAGCAAAT
GACTACTGCACCTGGACAGCCTCCTCTTTTCTAGAAGTCTATTTATATTGTCATTTTATA
ACACTCTAGCCCCTGCCCTTATTGGGGGACAGATGGTCCCTGTCCTGCGGGGTGGCCCTG
GCAGAACCACTGCCTGAAGAACCAGGTTCCTGCCCGGTCAGCGCAGCCCCAGCCCGCCCA
CCCCTGCCTCGAGTTAGTTTTACAATTAAAACATTGTCTTGTTTTGTGAAAAAAAAAAA
AAAAAAAAA

Fig. 9V

>STLK5_h
MSSFLPEGGCYELLTVIGKGFEDLMTVNLARYKPTGEYVTVRRINLEACSNEMVTFLQGELHVSKLFNHPNIVPYRATFI
ADNELWVVTSFMAYGSAKDLICTHFMDGMNELAIAYILQGVLKALDYIHHMGYVHRSVKASHILISVDGKVYLSGLRSNL
SMISHGQRQRVVHDFFPKYSVKVLPWLSPEVLQQNLQGYDAKSDIYSVGITACELANGHVPFKDMPATQMLLEKLNGTVPC
LLDTSTIPAEELTMSPSRSVANSGLSDSLTTSTPRPSNGDSPSHPYHRTFSPHFHHFVEQCLQRNPDARPSASTLLNHSF
FKQIKRRASEALPELLRPVTPITNFEGSQSQDHSGIFGLVTNLEELEVDDWEF

>STLK6_h
MSLLDCFCTSRTQVESLRPEKQSETSIHQYLVDEPTLSWSRPSTRASEVLCSTNVSHYELQVEIGRGFDNLTSVHLARHT
PTGTLVTIKITNLENCNEERLKALQKAVILSHFFRHPNITTYWTVFTVGSWLWVISPFMAYGSASQLLRTYFPEGMSETL
IRNILFGAVRGLNYLHQNGCIHRSIKASHILISGDGLVTLSGLSHLHSLVKHGQRHRAVYDFPQFSTSVQPWLSPELLRQ
DLHGYNVKSDIYSVGITACELASGQVPFQDMHRTQMLLQKLKGPPYSPLDISIFPQSESRMKNSQSGVDSGIGESVLVSS
GTHTVNSDRLHTPSSKTFSPAFFSLVQLCLQQDPEKRPSASSLLSHVFFKQMKEESQDSILSLLPPAYNKPSISLPPVLP
WTEPECDFPDEKDSYWEF

>STLK7_h
NRDDYELQEVIGSGATAVVQAAYCAPKKEKVAIKRINLEKCQTSMDELLKEIQAMSQCHHPNIVSYYTSFVVKDELWLVM
KLLSGGSVLDIIKHIVAKGEHKS

>ZC4_h
MAGPGGWRDREVTDLGHLPDPTGIFSLDKTIGLGTYGRIYLGLHEKTGAFTAVKVMNARKDEEEDLRTELNLLRKYSFHK
NIVSFYGAFFKLSPPGQRHQLWMVMELCAAGSVTDVVRMTSNQSLKEDWIAYICREILQGLAHLHAHRVIHRDIKGQNVL
LTHNAEVKLVDFGVSAQVSRTNGRRNSFIGTPYWMAPEVIDCDEDPRRSYDYRSDVWSVGITAIEMAEGAPPLCNLQPLE
ALFVILRESAPTVKSSGWSRKFHNFMEKCTIKNFLFRPTSANMLQHPFVRDIKNERHVVESLTRHLTGIIKKRQKKEQAR
EKKSKVSTLRQALAKRLSPKRFRAKSSWRPEKLELSDLEARRQRRQRRWEDIFNQHEEELRQVDKDKEDESSDNDEVFHS

Fig. 10A

```
>PAK5_h
MFGKRKKKRVEISAPSNFEHRVHTGFDQHEQKFTGLPRQWQSLIEESARRPKPLVDPACITSIQPGAPKTIVRGSKGAKDG
ALTLLLDEFENMSVTRSNSLRRDSPPPPARARQENGMPEEPATTARGGPGKAGSRGRFAGHSEAGGGSGDRRRAGPEKRP
KSSREGSGGPQESSRDKRPLSGPDVGTPQPAGLASGAKLAAGRPFNTYPRADTDHPSRGAQGEPHDVAPNGPSAGGLAIP
QSSSSSSRPPTRARGAPSPGVLGPHASEPQLAPPACTPAAPAVPGPPGPQREPQRVSHEQFRAALQLVVDPGDPRSY
LDNFIKIGEGSTGIVCIATVRSSGKLVAVKKMDLRKQQRRELLFNEVVIMRDYQHENVVEMYNSYLVGDELWVMEFLEG
GALTDIVTHTRMNEEQIAAVCLAVLQALSVLHAQGVIHRDIKSDSILLTHDGRVKLSDFGFCAQVSKEVPRRKSLVGTPY
WMAPELISRLPYGPEVDIWSLGIMVIEMVDGEPPYFNEPPLKAMKIRDNLPPRLKNLHKVSPSLKGFLDRLLVRDPAQR
ATAAELLKHPFLAKAGPPASIVPLMRQNRTR

>GEK2_h
MAFANFRRILRLSTFEKRKSREYEHVRRDLDPNEWEIVGELGDGAFGKVYKAKNKETGALAAAKVIETKSEEELEDYIV
EIEILATCDHPYIVKLLGAYYHDGKLWIMIEFCPGGAVDAIMLELDRGLTEPQIQVVCRQMLEALNFLHSKRIIHRDLKA
```

Fig. 10B

GNVLMTLEGDIRLADFGVSAKNLKTLQKRDSFIGTPYWMAPEVVMCETMKDTPYDYKADIWSLGITLIEMAQIEPPHHEL
NPMRVLLKIAKSDPPTLLTPSKWSVEFRDFLKIALDKNPETRPSAAQLLEHPFVSSITSNKALRELVAEAKAEVMEEIED
GRDEGEEEDAVDAASTLENHTQNSSEVSPPSLNADKPLEESPSTPLAPSQSQDSVNEPCSQPSGDRSLQTTSPPVVAPGN
ENGLAVPVPLRKSRPVSMDARIQVAQEKQVAEQGGDLSPAANRSQKASQSRPNSSALETLGGEKLANGSLEPPAQAAPGP
SKRDSDCSSLCTSESMDYGTNLSTDLSLNKEMGSLSIKDPKLYKKTLKRTRKFVVDGVEVSITTSKIISEDEKKDEEMRF
LRRQELRELRLLQKEEHRNQTQLSNKHELQLEQMHKRFEQEINAKKKFFDTELENLERQQKQQVEKMEQDHAVRRREEAR
RIRLEQDRDYTRFQEQLKLMKKEVKNEVEKLPRQQRKESMKQKMEEHTQKKQLLDRDFVAKQKEDLELAMKRLTTDNRRE
ICDKERECLMKKQELLRDREAALWEMEEHQLQERHQLVKQQLKDQYFLQRHELLRKHEKEREQMQRYNQRMIEQLKVRQQ
QEKARLPKIQRSEGKTRMAMYKKSLHINGGSAAEQREKIKQFSQQEEKRQKSERLQQQKHENQMRDMLAQCESNMSEL
QQLQNEKCHLLVEHETQKLKALDESHNQNLKEWRDKLRPRKKALEEDLNQKKREQEMFFKLSEEAECPNPSTPSKAAKFF
PYSSGDAS

Fig. 10C

```
>STLK5_h
GGCCAAGACGGTCGGGCTGCTTGCTAACTCCAGGAACAGGTTTAAGTTTTTGAAACTGAAGTAGGTCTACACAGTAGGA
ACTCATGTCATTTCTTGTAAGTAAAACCAGAGCGAATCAGGCGGTGGGTCTCGGAAAAGTTCATTGTTGAGGGCTTAAGAG
ATTTGGAACTATTTGGAGAGGAGGGTGTTACGAGCTGAGCTGCTCAGAGTCAATAGCATCCTTAAACAGGAGGTCATGAGTAGCTT
TCTGCCAGAGGAGGGAGGGTGTTACGAGCTGACTGTGACTGATGGATTTGAGGACCTGATGTGAATCTAGCAA
GGTACAAACCAACAGGAGAGTACGTGACTGTAGGAGGATTAACCTTGTTCAATGAGATGGTAACATTCTTG
CAGGGCGAGCTGCATGTCACATTCATGCATGGCATAGGGGGTGCTGAAGGCCCTCATGGATGCATGAATGA
GCTGTGGGTTGCTTACATCCTGATCTCTGTGATGGGTTATGCCTGCAAGTCTGCAAAGATCTCATGGGATATGTACACAGGAGT
AGCTCAAAGCCAGCCACACATCCTGATCTCTGTGATGGGTTATGCCTGCAAGATGCCTGTTTGCGCAGCAACCTCAGCATGATAAG
GTCATGGGCTGGATATAGCATCTAAGGATATATGCCTGAGGGAGCCCTTCGCGTGCAACTCTGCCTGAGTGACAGCCTGACCA
CCATGTCTCCTGAAGGAATCTCCAGGGTTATGCCTGATGAGCCCTCGCCTGCCAACGTGACTGCCTCTCCCCACTTCTTCCACCACTTT
CAGCACCACCGGCCTTCAGCCAGAGGCATTCGCCCAACGTGACTGCCTGACTGCCCCAACCGACACCCCCGAACCTTCTCCCAACCACCTT
CCAGCCGAGCCCCGGGCCTTCAGCAGAGGCATTCGGCCTGAATTGCTTGCCTGTCCTGTCACCCCATCACCAATTTTGAGGGCAGCCAGTCTC
GTGGAGCAGCGTGCCTGCCTCAGCAGCGTGACTGACTGCCTGAATTGCTTGCCTGTCACCCCATCACCAATTTTGAGGGCAGCCAGTCTC
CAAGCGACGTGCCTGCCTCAGCAGCGTGACTGACTGCCCCGATGAACAACCAGGGATGATTGGGACGATTGGGAGTTCGAGCCACTTCCGCCCTCCT
AGGATCAGATGGGAATCTTTCCAGCAGGATGCAGAGGCACCCAGAGGCCCCTTCTGACTGCTGCCACCGCCACCCTTTGACTGCTGCACATCAGA
AACCTGTGCGCATTTGGGTAGAAGGCTTTCAGGAAAAGGACCTGACCTGACCGACCACCTCTGCGACCAGCCCTCCTTTGGCAAGCCGACATTCCCAGTC
GGGCAGATTGGGTAGAAGGCTTTCAGGAAAAGGACCTGACCTGACCGACCACCTCTGCGACCAGCCCTCCTTTGGCAAGCCGACATTCCCAGTC
TCACTGCTCCAAGGCTTTTGAGAATCCTCCCGGCCACCTCCTTGCCGACCAGCGCATCCCGGAGGCAAGCCAATGCCAGATCCCAATTCCCATCATTTTCAGATGCCT
CTGTGAGCTCAGGGGTGACCCTCAAGGACCCTCCCGGCCACCTCTTGCCGACCAGCGCCCTCCTTTCTCTCAGACCTTCTATTTAACTTTGCTCTCAGATGCCT
CAGATGCCTATAGGTCAGTGAAGGGCAAAGGGCAGACCGCCGCCACCGCCACCTCCTCCTTCCCTTTCCTTTGACCTTCTATTTAACTTTGCTCTCAGATGCCT
GAAGGGCATTTCTGTCTGTTTTAAGCACAGAGACTAAGGCTGGAACAGTCATAAGGCTAAGACTAAGGCTAAGACTAAGACTCCCTTCTCTTCTTTCTCTGAC
```

Fig. 11A

>STLK6_h
AAGGAAGATAAAACAAAAGCCTTCTTCTTTGGAATAGATGGATTTTTGTCACTTTCTGTGTGAACTAAAGTGATTCAATGTCT
CTTTTGGATTGCTTCTGCACTTCAAGAACACCAAGTTGAATCACTCAGACCTGAAAAACAGTCTGAAACCAGTATCCATCA
ATACTTGGTTGATGAGCTCCAAGTTCCTCAACCCTTTCCTGGTCACGTCACGTAGAGCCAGTGAGTACTATGTTCACCAACGTTT
CTCACTATGAGCTCCAAGTAGAAATAGGAGAAGAGGATTTGACAACTTGACTTCTGTCCATCTTGCACGGCATACTCCACG
GGAACACTGGTAACTTTTTCCGGCATCCAATATTACAACTTATTGAGGACCTTTCACTGTTGGCAGCTTTACAGAAAGCCGTGAT
TCTATCCCACTTTTCCGGCATCCAATATTACAACTTATTGAGGACCTTTCACTGTTGGCAGCTGGCTTTGGGTTATTT
CTTCCATTTATGGCCTGGTTCAGCAGTCGTGAGAGGCCTAGCCTGTATTCTGCACATCTGCATAGTTTGGTTAAGCATGAGAGTTAATAAGA
AACATTCTCTTTGGTTGAAGCGTGATGATCAGATGCTTGAACTGATCTTGAACTGATCTTGAACTGGCTATTCACAGGAGTATTAAAGCCAGCA
TATCCTCATTCTGTATGATCAGATGCTTGAAGTCAGATGCTCGAATGTATCCCATCTGCAGCTGGCTGAATTAGCCCATGGAGAATTAGCCCATTGGATCATCAGTGAACTACTCTTTCCTC
ATAGGGCTGTGTATATAGAATCAGATGCTTGAAGTCAGATGCTCAGATGCTCGAATGTATCTCGGCTGAATTAGCCCATGGAGAATTAGCCCATTGGATGTGCTTGTCTCCAGTGGAACT
CATGGGTATAATGTGAAGCATAGAATCAGATGCTTGAAGTCAGATGCTTAGAAGTCAGTGTATCCCTCAAAACTTTATTGTCCCAGCTAGCAGCAGTTATTACAGAAGAAGAAA
AATCAGAATCCATAAATAGTGACCGATTACAGAAAGAAAATTCCGATTACAGATGAAAAAATTCCGATTACAGAAAATAGTCCAGCTCTTCCAAACTTTATTGTCCCAGCTAGCAGCAGTTATTACAGAAGAAGAAA
CACACAGTAAATAGTGACCGATTACAGATGAAAAATTCCGATTACAGAAAATAGTAGTCCATCAGCAAGCAGCAGCAGCAGCAGCAGTTATTACAGAAGAAGAAA
TTTGCAACAAGATCCTGAGAAGCAGCAGCAAGCAAGCAGTTTATTGTCCATCAATAACAAGCCATCTCCAGTTTATTGTCCATCAATAACAAGCCATCTCCAGTTTATTGTTCTTCAAACAGATGAAGAAGAAA
GCCAGGATTCAATACTTTCACTGTTGCCTCTGCTGTTTCACTGTTGCCTCTGCTGTTTTCTTCTTGCCTCCAGTTTATTGTTCTTCAAACAGATGAAGAAGAAA
GAGCCAGAATGTGATTTCCTGATGAAAAGAAAAGACTCATCTGGGAATTCATGGCTGCCAATTCATCATTTTATGTCCTATATA
CTTGACACTTTCCTTGCTGTGCTGTCTCGTCTCGTCTTGTCTCCTCTGCTGTGTGTCCCTCTGTTAGTCCCCTCTGTTGTAGTCCCCTCTGTTGTAGTCCCCTCTGTTGTAGTCCCCACCAGTTTGTAGTCCTCCCCACCAGTTTGTAGTCCCCAGTCCTACACCAGTCCAGTACT
GCACTGGACAAGGAAACATCAGAATTACTAATTACTAATTACTAATTACTAATTACTAGTCCAGCACCAGTTTGTAGTCCTCCCCACAGGGGGGAAACACCAGTTTGTAGTCCACACAGAGTACT
ATGACAAGGAAACATCAGAATTACTAATTACTAATTACTAGTAGTCATTATTCTGGAATTTTTCTAAGCTGTGACTAACTCTT
ACCTAAGTCTTTCCCACGGTTTATGTGTGTGCCTCATTCCTTTCCCACCAAGAATCCATCTTAGCGCCTCCTGCCAGCTG
CCCTGGTGCTTTCTCCAAGGGCCATCAGTCAGTGTCTCTTGCCTAGCTTCTTGCCTTGAGGGCTTAAGTCCTTAGTTCGTTGT
CAGAACAAATTAAAATTTTCAGAGACGCTG

Fig. 11B

TTTATCTCTCAATATAATTTTTCAGTATTTTGCTGTCCCTTGGGAATGGGCCCTCAGAGGAC
AGTGCTTCCAGACCCTTTTCTGTAGAGGGAAATGTTTGTGCTATTCTTCTGTTAATACTTATGGTAACACCTAAC
ACATCAGACACCTTTTCACATTAAATGATTCACTGTGAAATATACAGAAATTGTAATTTGCTTTTTTAAAAAGGGCTAA
TGAGCCTCACTGAGTCAATGCCATCATCCTAATATTGTATCTTACTACACATCTTTTGTGTGGCAAAAGATGAGCTGTGGCTTGTCA
AGTAACACTTTCCTACTTATGTAAATTATAGATCCTAAATTCACGCACCCCGTGGGAGCTCAATAAAGATTACTGAATT
G

>STLK7_h
TCAACAGGGACGATTACGAGCTGCAGGAGGTCGGAGGAGGTCACGGATCTCGGGCCACCTGCCGGATCCAACTTGCCAGGAATATTCTCACT
AAAAGGAGAGAAAGTGGCAATCAAAGGATAAACCTTGAGAAATTGAGCAGACTTCATGAGAAGACTTATTACAGCTGTTA
AGCCATGAGTCAATGCCAAATCCATCATCCTAATATTGTATCTTACTACACATCTTTTGTGTGGCAAAAGGGAACACAAAGT
TGAAGCTGCTAAGTGGAGTTCTGTTCTGGATATTATTAAGCACATTGTGGCAAAAGGGAACACAAAGT

>ZC4_h
ATGGCGGGACCTGGGGGCTGGAGGCCTTGGCCTCGTAAGGATGAGGAGGATCTCAGGAGACATTTTCAAGCTGAGTGACTGACTGCAGGTT
AGATAAAACCATTGGCCCTTGGCCTCGTAAGGATGAGGAGGATCTCAGGAGACATTTTCAAGCTGAGTGACTGACTGCAGGTT
AAGTGATGAACGCTCGTTCTTCGTATGAGGATCATTTTCAAGCTGAGTGACTGACTGACTGCAGGTT
AAGTGATGAACGCTCGTTCTTCGTATGAGGATCATTTTCAAGCTGAGTGACTTGGATGGTGATGCTTATATCT
ATGTGCAGCAGGTTCGGTCAGTAGTGTCACTTGAGAATGACGCCACAGGTAATCAGAGTTAAACCGGACATCAAAGGTCAGAATGTGCTG
CCGAGAACGGAATCCTTAGGCCTTAGCTGAAGTAACTGGATGTTTGATTTCACCTGCACCTGACCACGGTGAGGACCCAGGTGAAGAGCCCCTCCCTCGTGTAAGCGGATGGTCCCGATGTCTGCCAAATCTCTGCTCTCCCACAGTGACTGACTGCAAATCCAGCGGATGGTTCCCACATTTCATGGA
CTGACTTCATTGGGACACCATATGCTGTCTGTATTTTGCGGGAATTCCCTGTTCCGTTCTGCTACTTCTGCAAACATGCTTCAACACCCATTGTTCGGGATATAAAAA
AAGTGTACGATAAAAAAATTTCCTGTTCCGTTCTGCTACTTCTGCAAACATGCTTCAACACCCATTGTTCGGGATATAAAAA

```
CATAAGAACAGACTTCGGGTGTATCATCTGACCTGGTTGAGGAACAAGATTTTGAATAATGATCCAGAAAGTAAAGAAG
GCAAGAAGAAATGCTGAAGACAGAGGAAGCCTGCAAAGCTATTGATAAGTTAACAGGCTGTGAACACTTCAGTGTCCTCC
AACATGAAGAAACAACATATTAAAGTATTTCCAACACTTCACCTTTATGCATGGGCACCAAAGTCCTTTGAT
GAAAGCACTGCTATTAATTTCTTCAGTCAGCAGATCATAAGCCAGTGACAGTTGACCTGGCTATTGTCTGATGTGAAAAG
ACTAAAGATTTCCCTGAAGCCCTCTGTGGAAATCATTATACCACAGAATATCATTACCTGATTGCTTGGGAATTGTGGAAAGACATACCATC
CAAAGAATCCCTGAAGCCCTCTGTGGAAGCGAAATGAACAACTCCTTCAAGAAGATCCTGAAATGTGCGCTCTTTGCAATCCAGG
TTCAATGCTGAAGCTTTTGAATGTACACAGCGCAGGTCAATTAAGAAGCTGAGATTCCTGTGCACCGGGGTGACAAGCTGTTCTTTACC
TTCTATAGCTTTGAATGTACACAGCGCAGGTCAATTAAGAAGCTGAGATTCCTGTGCACCGGGGTGACAAGCTGTTCTTTACC
TCTACCCTGCGCAATCACCAGCCGGGTTTACTTCATGACACTTGGAAAACTTGAAGAGCTCCAAAGCAATTATGATGT
CTAA

>PAK5_h
CGGGAGTGTCCGCGTGGTGCGGTGCAAGAGAGCTGAAGGAGGCGCGAGGGCGCGGAGTTCCAGGCCGAGCAGTTAGGC
CGCGAGCGACTGCCGGCCGCCGAGCCGCGATGAGTAACCCGAAGCCCTAGAGGAGTGGTCACCTGCCTGAGGGCACTTCTGTC
CCACCAGCATCAGAGACCGCAGCACCGGCCTTCGACAGCCCCTCGACCCCGCGCCTCGGCAGGAAGAAGCGGTGGAGATCTCCGC
CGTCCAACTTCGAGGATGAGGACGGCGTGTCGCACGGGCAGACTCTTCACGGGCTGCGCCATCATCCAGTCCCAGTGGGCTGCCAG
AGCCTGATCGTCGTGCGGGCAGCCGGGCCCCCAAGCCTCGTGTCTGGCAGGTTTGAGACGAGTTTGAGAACATGTCGG
CAAGACCATCGTGCCAACTGGCTCCAACCGGCCAGGGGGCGGCCAGGAAAATGGGCGCGAGGCGGGTGGCGG
TGACACGCTACCAGGGGCCCAGGGAAGACAGCCGCCAGGAAGCCAGGCCTGCTCGCTGCTTCGCCGGTTCGCCGGAGGGCCCAGGAGAG
CCGGCCACCACCGGCAGGCGACGGCCCCTCTCCCAGGGCTGCTGGTTCTGGCCGCCAAGTCTTCCCAGCCTCACCCAGCCCCCATCAGGCCTCC
CAGTGGTGACAAACGCCGGCCCTTTAACACCCTACCCTGACACCGGACACGGACGTGTCGACGTGCTGAGGGCTGACCCCATCCCGGGGTGCCCAGGGGAGCCCTCATGACGT
CCGTGGCCCGCCGCTAACGGGCCCATCAGCGGGGGCCTCCGCTCCCTGCCTCCACCCGAGCCC
```

```
>GEK2_h
CGAGCCCACAGCCCGAGCCCGAGCCCGAGCCCGGCGCCCCGGCCGGCCCATGGCTTTTGCCAATTTCCGCC
GCATCCTCGCGCTGTCTCTACCTTCGAGAAGAGAAAGTCCCGGAATATGAGCGCGTCCGCGCCTTGACCCCCAACGAG
GTGTGGGAGATCGTGGGCGAGCTGGGCGACGGCGCCTTTCGGCCAAGGTTTACAAGGCCAAGTCGTCCGCGGGTGCTTT
GGCTGCGGCCAAAGTCATTGTGAAGTCCTGGGAGCTCATATCACGGACTACATCGTGGAGATTGAGATCCTGGCCACCT
GCGACCACCTGAACATCATGCGTCTGAAGCTCATCTGCACAGCAAGCTGTGTGATACAGGTGGTTTGCCGCCAGAT
GGGGGAGCCCTCAACTTCCTGGACGTGGAAAGAGGATCATCACCGAGATCTGAAAGCTGGCAACGTGCTGATGACCTCG
GCTAGAAGACATCAGGCTGCCCCCGAGGTGCTTCTGCACAGCTCTACAGAGACTCTAAGAGATTCTTCATCGGC
ACGCCTTACTGGCATCACGCTGATTGAGATGGCCCAGATCGAGCTCAACCCACCGACCCCTAGAGTTCCGTTGTAA
GTCCCTGGCATCCGGGACCCCAGAAACCCAGAAACCGACAGGCCGACATGCCGCCAGTGCTGCTGGAGCATCCAGTAACAA
AGATCGCCAAGCCTGGGAGAACAGAGTCCTGACCCTGCCTTCCACCTTCCAAACCCGCTGGAGGTGACAGTGTGAAATGAGGAGAACAGCAAGTTGCTGAGCGACAAAGAGAGGA
CTGGATAAGAACCCAGAAACCGACAGGCCGACATGCCGCCAGTGCTGCTGGAGCATCCAGTAACAAAGATCGCCAAGCCT
GGCTCTGCGGACAGAGTCCTGACCCTGCCTTCCACCTTCCAAACCCGCTGGAGGTGACAGTGTGAAATGAGGAGAACAGCAAGTT
AGGACGAAGCTGGGAGATGCCGAGGCGTGGATGCCGAGGCCGAACCATACTCAGAATCTCGTGAGGTGACAGTGTGAAATGAGGAGAACAGCAAGTTGCTGAGCGACCTTGCCTG
GACAAGCTCTGGGATGTCCGAGGAGACAGAGTCCTGACCCTGCCTTCCACCTTCCAAACCCGCTGGAGGTGACAGTGTGAAATGAGGAGAACAGCAAGTTGCTGAGCGACCTTGCCTG
GCCCTCTGCCCCCTGCGGAAGCTCTGGGATGTCCGAGGAGACAGAGTCCTGACCCTGCCTTCCACCTTCCAAACCCGCTGGAGGT
TGCCCCCTGCCAGCTGCCAATGGCCAGCGCCAGTGCCCAAGGCCACCTGCCCAAGGCCCTTCCACCTGCCGTTGTGCA
GGGGAGAAGCTGGCCACCTGGCCAATGGCCAGCGCCATGGTACCAATCTTGTAAGCGGACAACCCTCAAGAGGAACCAGAG
TGGGGCAGCTGGCCACCTGGCCAATGGCCAGCGCCATGGTACCAATCTTGTAAGCGGACAACCCTCAAGAGGAACCAGAG
GCCAGCAAGCTGGGAGAATGCCGAGAAACCGAGAAATCATCAGCGGAAAAAGATGAGAACGATCGGAGTAACAGAGAAATG
CTGTCCATCAAGGACCTCCCAAGAACCCAAGAATCATCAGCGGAAAAAGATGAGAACGATCGGAGTAACAGAGAAATG
AGCTTCGGCTGCTGTCCAGAAACAGGAAATCAACGCCAAGAAGAAGTTCTTTGACACACGGAGAACCTCAGCGAG
CATAAACGTTTTGAACAGGAAATCAACGCCAAGAAGAAGTTCTTTGACACACGGAGAACCTCAGCGTCAGCAGAAA
```

Fig. 11G

```
GCAGCAAGTGGAGAAGATGGAGCAAGACCATGCCGTGCGCCGCCGGAGGAGGCCAGGCGGATCCGCCTGGAGCAGGATC
GGGACTACACCAGGTTCCAAGAGCAGCAGCTCAAACTGATGAAGAACGAGGTGAAGAACCAGAGTGGAGAAGCTCCCCGACAG
CAGCGGAAGGAAAAGCCATGAAGCAGAAGATGGAGGAGCACACCAGAAAAAGCAGCTTCTTGACCGGGACTTTGTAGCCAA
GCAGAAGGAGGACCTGGCCATGAAGCAGGAGCTCTCAGACGCGGAGATCTGTGACAAGGAGCGCGAGT
GCCTCATGAAGCAGGAGCAGGAGCTCTCCTTCAAAGACCAGTCTGGGAAGAGCACCAGCTGACAAGCTGCAGGAGAGG
CACCAGCTGGTGAAGCAGCGCGTACAACCAGCAGCATGATAGAGCAGCCTGCTGCCAAGCATGAGAAGGAGGAGCG
GGAGCAGATGCAGCGGAGTGAGGGCAAGCGCGCATGCCCAGCAGGAAGAAAGGCGCGGCTGCCCA
AGATCCAGAGGAGTGAGAAGATCGCGGGGACATCAAGCTGGAGCTGCAGCCCTCCACATCAACGGCGGCTGCAGCAGCTGCAGCT
GAGCAGCGCTGAGAACCAGAGATGCCGGTAGAGCACGCAGCAGCAGAGTCGAGCTGCAGCAGCCAGAACCAGAACAGCAGAA
ACACGAGAACCAGATGCCGGTAGAGCACGCAGAAACCCAGAAACTGAAGGCCCTGGATGAGAGCCATAACCAGAAGCGGAGCCGGAGCAGGAATGAAAAGT
GCCACCTCCTGGTTCGGCCGCCGCGAGCATCAAGCAGCACGAAAAGGCTCTCGGAAGAGGATCTGAACCAAGCAGGAGATGTTCTTCAAGCT
GACAAGCTTCGGCCGCCGCCAAACCCCACCCCTTCCCACCCAAGCCCGCCAAGTTCTTCCCCTACAGTCTTCCCTGGGATGCTT
GAGCGAGGAGGCGGAGTGCC
CC
```

```
STLK6_h  L S P E L L R Q D L H G Y N V K S D I Y S V G I T A C E L A S G Q V P F Q D M H R T Q M L L Q K L K  282
STLK5_h  L S P E V L Q Q N L Q G Y D A K S D I Y S V G I T A C E L A N G H V P F K D M P A T Q M L L E K L N  200
SPAK_h   M A P E V M E Q - V R G Y D F K A D M W S F G I T A I E L A T G A A P Y H K Y P P M K V L M L T L Q  289

STLK6_h  G P P Y S P L D I S I F P Q S E S R M K N S Q S G V D S G I G E S V L V S S G T H T V N S D R L H T  332
STLK5_h  G T V P C L L D T S T I P A E E L T M S P S R S V A N S G L S D S - L T T S T P R P S N G D S P S H  249
SPAK_h   N D P P T - - - - - - - - - - - - - - - - - - - - - - - - - - - - - - - - - - - L E T G V - - E D  301

STLK6_h  P S - S K T F S P A F F S L V Q L C L Q Q D P E K R P S A S S L L S H V F F K Q M K E E S Q D S I L  381
STLK5_h  P Y - H R I F S P H F H H F V E Q C L Q R N P D A R P S A S T L L N H S F F K Q I K R R A S E A L P  298
SPAK_h   K E M M K K Y G K S F R K L L S L C L Q K D P S K R P T A E L L K C K F F Q K A K N R E Y - - L I  349

STLK6_h  S L L P P A Y N K P S I S L P P V L P W T E P - - - - - E C D F P D E K D S Y W E F                    418
STLK5_h  E L L R P V - - T P I T N F E G S Q S Q D H S G I F G L V T N L E E L E V D D W E F                    338
SPAK_h   E K L L T R T P D I A Q R A K K V R R V P G S - - - - - S G H L H K T E D G D W E W S D D E M D E K  394

SPAK_h   S E E G K A A F S Q E K S R R V K E E N P E I A V S A S T I P E Q I Q S L S V H D S Q G P P N A N E  444

SPAK_h   D Y R E A S S C A V N L V L R L R N S R K E L N D I R F E F T P G R D T A D G V S Q E L F S A G L V  494

SPAK_h   D G H D V V I V A A N L Q K I V D D P K A L K T L T F K L A S G C D G S E I P D E V K L I G F A Q L  544

SPAK_h   S V S                                                                                                547
```

Fig. 12B

```
PAK1_h U51120  MSNNGLDIQDKPPAPPMRNTSTMIGAGSKDAGTLNHGSKPLPPNPEEKKKDRFYRSILP  60
PAK4_h         ------------------------------------------------------------   0
PAK5_h         ------------------------------------------------------------   0

PAK1_h U51120  GDKTNKKKEKERPEISLPSDFEHTIHVGFDAVT-GEFTGMPEQWARLLQTSNITKS----  115
PAK4_h         ---MFRKKKKKRPEISAPQNFQHRVHTSFDPKEGKFVGLPPQWQNTLD-TLRRPKPVVDP   56
PAK5_h         ---MF-GKRKKKRVEISAPSNFEHRVHTGFDQHEQKFITGLPRQWQSLIEESARRPKPLVDP  56

PAK1_h U51120  SRITRVQLQPMKTVVRGSAMPVDGYITSGLLNDIQKLSVISSNTLRGRSPTSRRRAQSLGL  115
PAK4_h         ACITSIIQPGAPKTIIVRGSKGAKDGALTLLLDEFENMSVTRSNSLRRDSPPPPARAR--  116
PAK5_h         ------------------------------------------------------------  112

PAK1_h U51120  LGDEHWATDPDMYLQSPQSERTDPHGLYLSCNGGTPAGHKQMPWPEPQSPRVLPNGLAAK  176
PAK4_h         ------------------------------QENGMPEEPATTARGGPGK-----------  131
PAK5_h         ------------------------------------------------------------  115

PAK1_h U51120  -----EQKKNPQAVLDV-------------------------------------------  127
PAK4_h         AQSLGPAEFQGASQRCLQLGACLQSSPPGASPPTGTNRHGMKAAKHGSEEARPQSCLVGS  236
PAK5_h         AGSRGR----FAGHSEAGGGSGDRRRAGPEKRPKSSREGSGPQESSRDKRP--LSGP--  183

PAK1_h U51120  ------------------------------------AEDYNSSNALNVKA-----VSETPAVPPVS  174
PAK4_h         ATGRPGGEGSPSPKTRESSLKRRLFRSMFLSTAATAPPSSSKPGPQSKPNSSFRPPQK--  296
PAK5_h         DVGTPQPAGLAISGAKLAAG-----RPFNTYPRADTDHPSRGAQGEPHDVAPNGP---  232
```

```
PAK1_h  U51120    QHQFLKIAKPLSSLTPLIAAKEATKNNH
PAK4_h            DHPFLLQTGLPECLVPLIQLYRKQTSTC
PAK5_h            KHPFLAKAGPPASIVPLMRQNRTR
```

RESIDUES THAT MATCH THE CONSENSUS NAMED CONSENSUS #1 EXACTLY.

BOX RESIDUES THAT MATCH THE CONSENSUS EXACTLY.

Fig. 13C

```
ZC4_h.pro  MAGPGGWRDREVTDLGHLPDPTGIFSLDKTIGLGTYGRIYLGLHEKTGAF  50
ZC1_h.pro  MANDSPAKSLVDIDLSSLRDPAGIFELVEVVGNGTYGQVYKGRHVKTGQL  50

ZC4_h.pro  TAVKVMNARKDEEEDLRTELNLLRKYSFHKNIVSFYGAFFKLSPPGQRHQ  100
ZC1_h.pro  AAIKVMDVTEDEEEEIKLEINMLKKYSHHRNIATYYGAFIKKSPPGHDDQ  100

ZC4_h.pro  LWMVMELCAAGSVTDVVRMTSNQSLKEDWIAYICREILQGLAHLHAHRVI  150
ZC1_h.pro  LWLVMEFCGAGSITDLVKNTLKEDWIAYISREILRGLAHLHIHHVI      150

ZC4_h.pro  HRDIKGQNVLLTHNAEVKLVDFGVSAQVSRTNGRRNSFIGTPYWMAPEVI  200
ZC1_h.pro  HRDIKGQNVLLTENAEVKLVDFGVSAQLDRTVGRRNTFIGTPYWMAPEVI  200

ZC4_h.pro  DCDEDPRRSYDYRSDVWSYGITAIEMAEGAPPLCNLQPLEALFVILRESA  250
ZC1_h.pro  ACDENPDATYDYRSDLWSCGITAIEMAEGAPPLCDMHPMRALFLIPRNPP  250

ZC4_h.pro  PTVKSSGWSRKFHNFMEKCTIKNELFRPTSANMLQHPFVRDIKNERHVVE  300
ZC1_h.pro  PRLKSKKWSKKEFSEIEGCLVKNYMQRPSTEQLLKHPFIRDQPNERQVRI  300

ZC4_h.pro  SLTRHLTGIIKKR-----------QKKEQAREKKS                324
ZC1_h.pro  QLKDHIDRTRKKRGEKDETEYEYSGSEEEEVPEQEGEPSSIVNVPGES   350

ZC4_h.pro  KVSTLRQALAKRLSPKRFRAKSSWRPEKLELSDLEARRQRRWEDIFN    374
ZC1_h.pro  TLRRDFLRLQQENKERSEALRRQQLLQEQQUREQEEYKRQLLAERQKRIE 400

ZC4_h.pro  QHEELRQVDKDKEDESSDNDEVFHSIQAEVQIEPLKPYISNPKKIEVQE  424
ZC1_h.pro  QQKEQRRRLEEQQRRREARRQQEREQRREQEEKRRLEELERRKEEE    450
```

Fig. 14A

```
ZC4_h.pro  RSPSVPNNQDHAHHVKFSSSVPQRSLLEQAQKPIDIRQRSSQNRQNWLAA  474
ZC1_h.pro  RRRAEEEKRRVEREQEYIRRQLEEEQRHLEVLQQQLLQEQAMLLECRWRE   500

ZC4_h.pro  SGDSKHKILAGKTQSYCLTIYISEVKKEEFQEGMNQKCQGAQVGLGPEGH   524
ZC1_h.pro  MEEHRQAERLQRQLQQEQAYLLLSLQHDHRRPHPQHSQQPPPQQERSKPS   550

ZC4_h.pro  CIWQLGESSSEEESPVTGRRSQSSPPYSTIDQKLLVDIHVPDGFKVGKIS   574
ZC1_h.pro  FHAPEPKAHYEPADRAREVEDRFRKTNHSSPEAQSKQTGRVLEPPVPSRS   600

ZC4_h.pro  PPVYLTNEWGYNALSEIFRNDWLTPAPVIOPPEEDGDYVELYDASADTD   624
ZC1_h.pro  ESFSNGNSESVHPALQRPAEPQVPVRTTSRSPVLSRRDSPLQGSGQQNSQ   650

ZC4_h.pro  GDDDDESNDTFEEDTYDHANGNDDLDNQVDQANDVCKDHDDDNKFVDDVN   674
ZC1_h.pro  AGQRNSTSIEPRLLWERVEKLVPRPGSGSSSGSSNSGSQPGSHPGSQSGS   700

ZC4_h.pro  NNYYEAPSCPRASYGRDGSCKQDGYDGSRGKEEAYRGYGSHTANRSHGGS   724
ZC1_h.pro  GERFRVRSSSKSEGSPSQRLENAVKKPEDKKEVFRPLKPADLTALAKELR   750

ZC4_h.pro  AASEDNAAIGDQEEHAANIGSERRGSEGDGGKGVVRTSEESGALGLNGEE   774
ZC1_h.pro  AVEDVRPPHKVTDYSSSSEESGTTDEEEDDVEQEGADESTSGPEDTRAAS   800

ZC4_h.pro  NCSEIDGPGLKRPASQDFEYLQEEPGGNEASNAIDSGAAPSAPDHESDN   824
ZC1_h.pro  SLNLSNGETESVKTMIVHDDVESEPAMTPSKEGTLIVRRTQSASSTLQKH   850

ZC4_h.pro  KDISESSTQSDFSANHSSPSKGSGMSADANFASAILYAGFVEVPEESPKQ   874
ZC1_h.pro  KSSSSFTPFIDPRLLQISPSSGTTVTSVVGFSCDGMRPE--AIRQDPTRK   898
```

Fig. 14B

```
ZC4_h.pro  P S E V N V N P L Y V S P A C K K P L I H M Y E K E F T S E I C C G S L W G V N L L L G T R S N L Y        924
ZC1_h.pro  G S V V N V N P T N T R P Q S D T P E I R K Y K K R E N S E I L C A A L W G V N L L V G T E S G L M        948

ZC4_h.pro  L M D R S G K A D I T K L I R R P F R Q I Q V L E P L N L L I T I S G H K N R L R V Y H L T W L R        974
ZC1_h.pro  L L D R S G Q G K V Y P L I N R R F Q Q M D V L E G L N V L V T I S G K K D K L R V Y Y L S W L R        998

ZC4_h.pro  N K I L N N D P E S K R R Q E - E M L K T E E A C K A I D K L T G C E H F S V L Q H E E T T Y I A I       1023
ZC1_h.pro  N K I L H N D P E V E K K Q G W T - - - - - - T V G D L E G C V H Y K V V K Y E R I K F L V I           1039

ZC4_h.pro  A L K S S I H L Y A W A P K S F D E S T A I K V F P T L D H K P V T V D L A I G S E K R L K I F F S     1073
ZC1_h.pro  A L K S S V E V Y A W A P K P Y H K F M A F K S E G E L V H K P L L V D L T V E E G Q R L K V I Y G     1089

ZC4_h.pro  S A D G Y H L I D A E S E V M S D V T L P K N P L E I I I P Q N I I I L P D C L G I G M M L T F N A     1123
ZC1_h.pro  S C A G F H A V D V D S G S V Y D I Y L P T H I Q C S I K P H A I I I L P N T D G M E L L V C Y E D     1139

ZC4_h.pro  E A L S V E A N E Q L F K K I L E M W K D I P S S I A F E C T Q R T T G W G Q K A I E V R S L Q S R     1173
ZC1_h.pro  E G V Y V N T Y G R I T K D V V L Q W G E M P T S V A Y I R S N Q T M G W G E K A I E I R S V E T G     1189

ZC4_h.pro  V L E S E L K R R S I K K L R F L C T R G D K L F F T S T L R N H H S R V Y F M T L G K L E E L Q S     1223
ZC1_h.pro  H L D G V F M H K R A Q R L K F L C E R N D K V F F A S V R S G G S S Q V Y F M T L G R T S L L S W     1239

ZC4_h.pro  N Y D V                                                                                              1227
ZC1_h.pro                                                                                                     1239
```

▮ BOX RESIDUES THAT MATCH ZC4_h.pro EXACTLY.

Fig. 14C

```
Db = LOK1_m
Qy = GEK2_h

Db    1 MAFANFRRILRLSTFEKRKSREYEHVRRDLDPNDVWEIVGELGDGAFGKVYKAKNKETGA   60
Qy    1 MAFANFRRILRLSTFEKRKSREYEHVRRDLDPNEVWEIVGELGDGAFGKVYKAKNKETGA   60

Db   61 LAAAKVIETKSEEELEDYIVEIEILATCDHPYIVKLLGAYYYDGKLWIMIEFCPGGAVDA  120
Qy   61 LAAAKVIETKSEEELEDYIVEIEILATCDHPYIVKLLGAYYHDGKLWIMIEFCPGGAVDA  120

Db  121 IMLELDRGLTEPQIQVVCRQMLEALNFLHGKRIIHRDLKAGNVLMTLEGDIRLADFGVSA  180
Qy  121 IMLELDRGLTEPQIQVVCRQMLEALNFLHSKRIIHRDLKAGNVLMTLEGDIRLADFGVSA  180

Db  181 KNLKTLQKRDSFIGTPYWMAPEVVLCETMKDAPYDYKADIWSLGITLIEMAQIEPPHHEL  240
Qy  181 KNLKTLQKRDSFIGTPYWMAPEVVMCETMKDTPYDYKADIWSLGITLIEMAQIEPPHHEL  240

Db  241 NPMRVLLKIAKSDPPTLLTPSKWSVEFRDFLKIALDKNPETRPSAAQLLQHPFVSRVTSN  300
Qy  241 NPMRVLLKIAKSDPPTLLTPSKWSVEFRDFLKIALDKNPETRPSAAQLLEHPFVSSITSN  300

Db  301 KALRELVAEAKAEVMEEIEDGREDGEEEDAVDAVPPLVNHTQDSANVTQPSLDSNKLLQD  360
Qy  301 KALRELVAEAKAEVMEEIEDGRDEGEEEDAVDAASTLENHTQNSSEVSPPSLNADKPLEE  360
```

Fig. 15A

```
Db  361 S-STPLPPSQPQEPVNGPCSQPSGDGPLQTTSPADGLSKNDNDLKVPVPLRKSRPLSMDA 419
Qy  361 SPSTPLAPSQSQDSVNEPCSQPSGDRSLQTTSPPVVAPGNENGLAVPVPLRKSRPVSMDA 420

Db  420 RIQMDEEKQIPDQDENPSPAASKSQKANQSRPNSSALETLGGEALTNGGLELPSSVTPSH 479
Qy  421 RIQVAQEKQVAEQGGDLSPAANRSQKASQSRPNSSALETLGGEKLANGSLEPPAQAAPGP 480

Db  480 SKRASDCSNLSTSESMDYGTSLSADLSLNKETGSLSLKGSKLHNKTLKRTRRFVVDGVEV 539
Qy  481 SKRDSDCSSLCTSESMDYGTNLSTDLSLNKEMGSLSIKDPKLYKKTLKRTRKFVVDGVEV 540

Db  540 SITTSKIISEDEKKDEEMRFLRRQELRELRLLQKEEHRNQTQLSSKHELQLEQMHKRFEQ 599
Qy  541 SITTSKIISEDEKKDEEMRFLRRQELRELRLLQKEEHRNQTQLSNKHELQLEQMHKRFEQ 600

Db  600 EINAKKKFYDVELENLERQQKQQVEKMEQDHSVRRKEEAKRIRLEQDRDYAKFQEQLKQM 659
Qy  601 EINAKKKFFDTELENLERQQKQQVEKMEQDHAVRRREEARRIRLEQDRDYTRFQEQLKLM 660

Db  660 KKEVKSEVEKLPRQQRKESMKQKMEEHSQKKQRLDRDFVAKQKEDLELAMRKLTTENRRE 719
Qy  661 KKEVKNEVEKLPRQQRKESMKQKMEEHTQKKQLLDRDFVAKQKEDLELAMKRLTTDNRRE 720
```

Fig. 15B

```
Db  720 ICDKERDCLSKKQELLRDREAALWEMEEHQLQERHQLVKQQLKDQYFLQRHDLLRKHEKE 779
Qy  721 ICDKERECLMKKQELLRDREAALWEMEEHQLQERHQLVKQQLKDQYFLQRHELLRKHEKE 780

Db  780 REQMQRYNQRMMEQLKVRQQQEKARLPKIQRSDGETRMAMYKKSLHINGAGSASEQREKI 839
Qy  781 REQMQRYNQRMIEQLKVRQQQEKARLPKIQRSEGKTRMAMYKKSLHINGGGSAAEQREKI 840

Db  840 KQFSQQEEKRQKAERLQQQQKHEHQMRDMVAQCESNMSELQQLQNEKCYLLVEHETQKLK 899
Qy  841 KQFSQQEEKRQKSERLQQQQKHENQMRDMLAQCESNMSELQQLQNEKCHLLVEHETQKLK 900

Db  900 ALDESHNQSLKEWRDKLRPRKKALEEDLNQKKREQEMFFKLSEEAE-PRPTTPSKASNFF 958
Qy  901 ALDESHNQNLKEWRDKLRPRKKALEEDLNQKKREQEMFFKLSEEAECPNPSTPSKAAKFF 960

Db  959 PYSSGDAS 966
Qy  961 PYSSGDAS 968
```

Fig. 15C

SEQUENCE LISTING

<160> NUMBER OF SEQ ID NOS: 155

<210> SEQ ID NO 1
<211> LENGTH: 3268
<212> TYPE: DNA
<213> ORGANISM: Homo sapiens

<400> SEQUENCE: 1

```
taacagccca cctcctagcc ccgggctacg cgccgccagc ccagtaaccc cacttttgtg      60
tgtcctccca ggccccgatc gaaaagcctg ggagggccgc cgaactaccc ccggagggag     120
gagccagtcc gaacccaagg cgccaccgcc gcagaagcgg agcgaggcag cattcgcctc     180
catggcccac tcgccggtgg ctgtccaagt gcctgggat cagaataaca tagctgatcc      240
agaagaactg ttcacaaaat tagagcgcat tgggaaaggc tcatttgggg aagttttcaa     300
aggaattgat aaccgtaccc agcaagtcgt tgctattaaa atcatagacc ttgaggaagc     360
cgaagatgaa atagaagaca ttcagcaaga aataactgtc ttgagtcaat gtgacagctc     420
atatgtaaca aaatactatg ggtcatattt aaagggtct aaattatgga taataatgga      480
atacctgggc ggtggttcag cactggatct tcttcgagct ggtccatttg atgagttcca     540
gattgctacc atgctaaagg aaattttaaa aggtctggac tatctgcatt cagaaaagaa     600
aattcaccga gacataaaag ctgccaatgt cttgctctca gaacaaggag atgttaaact     660 tgctgattt ggagttgctg gtcagctgac agatacacag attaaaagaa ataccttgt      720 gggaactcca tttttggatgg ctcctgaagt tattcaacag tcagcttatg actcaaaagc     780
tgacatttgg tcattgggaa ttactgctat tgaactagcc aagggagagc cacctaactc     840
cgatatgcat ccaatgagag ttctgtttct tattcccaaa aacaatcctc caactcttgt     900
tggagacttt actaagtctt ttaaggagtt tattgatgct tgcctgaaca aagatccatc     960
atttcgtcct acagcaaaag aacttctgaa acacaaattc attgtaaaaa attcaaagaa    1020
gacttcttat ctgactgaac tgatagatcg ttttaagaga tggaaggcag aaggacacag    1080
tgatgatgaa tctgattccg agggctctga ttcggaatct accagcaggg aaaacaatac    1140
tcatcctgaa tggagcttta ccaccgtacg aaagaagcct gatccaaaga aagtacagaa    1200 tgggcagag caagatcttg tgcaaaccct gagttgtttg tctatgataa tcacacctgc    1260
```

-continued

| | |
|---|---|
| atttgctgaa cttaaacagc aggacgagaa taacgctagc aggaatcagg cgattgaaga | 1320 |
| actcgagaaa agtattgctg tggctgaagc cgcctgtccc ggcatcacag ataaaatggt | 1380 |
| gaagaaacta attgaaaaat ttcaaaagtg ttcagcagac gaatccccct aagaaactta | 1440 |
| ttattggctt ctgtttcata tggacccaga gagccccacc aaacctacgt caagattaac | 1500 |
| aatgcttaac ccatgagctc catgtgcctt ttggatcttt gcaacactga agatttggaa | 1560 |
| gaagctatta aactattttg tgatggcgtt tatcatttta tattttgaaa ggattatttt | 1620 |
| gtaaggaata acttttaata ctatagtttc acctgtattc tagtaaatgt tgagacaccg | 1680 |
| ttttgctttt aagtatccct atttcttaag ttacgaggat gaatacctt cacattttga | 1740 |
| tctttagttg actctacagt catgaaacat acaggtcttt caaagtcatt ctcaatattc | 1800 |
| agcttttgta aattatcaag cttcaaaaag cttttttta aaaaaaaaa catgcatatt | 1860 |
| ctaaaaatga ctattggtgg ggaggtgtaa ataagtcata ccttcttaaa acagaaaatt | 1920 |
| taagtaaagt cttttaaatg aaacctgtaa aagtattgac tcttctacca agttggtatg | 1980 |
| atattccagg cagctcaatg attatcacat ttgagaccct gtgtttgaag catttacagg | 2040 |
| caatgtacag caacagaggt acctcttggt gtatagtatt tacattctct tttaggtaga | 2100 |
| agaggcaatt ttacccttat ttcacatggt tagaaattta agcaagatc atttacccaa | 2160 |
| ggataggtgt ttggtaatgt tgaaggagtt agtctggctt catgttttac atcttcaact | 2220 |
| aaaatcccat actatctgct tggatttgga gagccaaaaa ataaagctga ttgtcatgtg | 2280 |
| attaaatatc tgatcaacag gtatgaatat aacttaaatc agcatatttt tgccatggta | 2340 |
| ataaattgtc ctataaacta tttatatatt tttgttcttc ataattatca ctaataagca | 2400 |
| tcagtttgtt gttttttaaaa ggatatttaa gtgagcattt tctagttcat atgaaaataa | 2460 |
| ccatagtaca ggatgatttc tgtccacaca aaggttaaat tagattgcac agttaatttt | 2520 |
| cacttatatt tatggtacta ttatgtgggt gatgcctttt tcttttaagc ccagtacata | 2580 |
| tattatgcct gcctaagttc tgaactgggg ctgtatttca gtagttgtag aattattgat | 2640 |
| atttagtttt gatagctaat gtttaattgt ttggatctgc acagtttggt ttttgcacaa | 2700 |
| aagtcattta aaaaaatctg agtaattgtc aaatattaaa agaaagatat tcttcctgta | 2760 |
| aggaatacag tttttagtca agtggccat tacatcctct ttttaattta cataatacag | 2820 |
| atacttgaga aagttgttgt ggtgttgtat gccaagaaaa ttcttttttat tggtgcctat | 2880 |
| attgtaacaa ttatttttaa tgcattgtat tttgaagtaa cggttcagtt aaattttca | 2940 |
| cctgctgtgt aactgaaaca caattacagt ttataatcat ctgtagaagt ctggagataa | 3000 |
| ttttgcaact catgttatgg gttaaatgaa tattttgta aaagtaaaag caacaaattt | 3060 |
| ataaattgat tatttgaaac tttacaacac aattgcatcc caaatacaaa ttgtattgct | 3120 |
| tattcattat agctattcgt cctgtaatct gtttctaggt gaagcatact ccagtgtttt | 3180 |
| aggggttttg aaaataaata tttaaatttc acagtcaaaa aaaaaaaa aaaaaaaaa | 3240 |
| aaaaaaaa aaaaaaaaa aaaaaaa | 3268 |

<210> SEQ ID NO 2
<211> LENGTH: 3030
<212> TYPE: DNA
<213> ORGANISM: Homo sapiens

<400> SEQUENCE: 2

| | |
|---|---|
| gacagcagcg ccggccccgg cagctcccgc ggccccggcc ccggcccgg cccggcccc | 60 |

```
ggcggcacag gctgtcggct ggcccatctg cagggacgcg tacgagctgc aggaggttat      120
cggcagtgga gctactgctg tggttcaggc agccctatgc aaacccaggc aagaacgtgt      180
agcaataaaa cggatcaact tggaaaaatg ccagaccagt atggatgaac tattaaaaga      240
aattcaagcc atgagtcagt gcagccatcc caacgtagtg acctattaca cctcttttgt      300
ggtcaaagat gaactttggc tggtcatgaa attactaagt ggaggttcaa tgttggatat      360
cataaaatac attgtcaacc gaggagaaca aagaatggaa gttctggaag aggcaataat      420
agcaacaatt cttaaagagg ttttggaagg cttagactat ctacacagaa acggtcagat      480
tcacagggat ttgaaagctg gtaatattct tctgggtgag gatggttcag tacaaatagc      540
agattttggg gtaagtgcgt tcctagcaac agggggtgat gttacccgaa ataaagtaag      600
aaaaacattc gttggcaccc catgttggat ggctcctgaa gtcatggaac aggtgagagg      660
ctatgacttc aaggctgaca tgtggagttt tggaataact gccattgaat tagcaacagg      720
agcagcgcct tatcacaaat atcctcccat gaaagtgtta atgttgactt tgcaaaatga      780
tccacccact ttgaaacagg ggtagagga taaagaaatg atgaaaaagt acggcaagtc      840
ctttagaaaa ttactttcac tgtgtcttca gaaagatcct tccaaaaggc ccacagcagc      900
agaactttta aaatgcaaat tcttccagaa agccaagaac agagagtacc tgattgagaa      960
gctgcttaca agaacaccag acatagccca aagagccaaa aagtaagaa gagttcctgg     1020 gtcaagtggt caccttcata aaccgaagac cggggactgg gagtggagtg acgacgagat     1080
ggatgagaag agcgaagaag ggaaagcagc ttttttctcag gaaagtcac gaagagtaaa     1140 agaagaaaat ccagagattg cagtgagtgc cagcaccatc cccgaacaaa tacagtccct     1200
ctctgtgcac gactctcagg gcccacccaa tgctaatgaa gactacagag aagcttcttc     1260
ttgtgccgtg aacctcgttt tgagattaag aaactccaga aggaactta atgacatacg     1320 atttgagttt actccaggaa gagatacagc agatggtgta tctcaggagc tcttctctgc     1380
tggcttggtg gatggtcacg atgtagttat agtggctgct aatttacaga agattgtaga     1440
tgatcccaaa gctttaaaaa cattgacatt taagttggct tctggctgtg atgggtcgga     1500
gattcctgat gaagtgaagc tgattgggtt tgctcagttg agtgtcagct gatgtatgtc     1560
ccttgatgtc accctgatct gtcatgcccc accgccaccc ctactccctt caaccctccc     1620
tctttctgcc catttcctcc caccccctca ctcccatttc ctagcaaaat cagaagattg     1680
tgaagaggcc ggcttcaaca aaatgggata aaaaaataat tttttaaaac ttacaacact     1740
ccgagttctg ctttattctc tagcaatcca cagtacaaga acaagcaaat gccacagctg     1800
cacgactgtt gctcattttt ccaaaagcta tttaatattc ttagcaatca atttggatat     1860
cccttaagtg aaaagaatct gaaatacact caggtggtct tatttattgg caacaaaagg     1920
aattttctat ccagaagcct atttctcctt tcattgttgt tatttctgtt ataatacttt     1980
aattgtacat ctgacaatac tgcctctttt atgttgtatt tagaaattaa tatacttata     2040
aaattaagat ttattagcca aacttgaatt ctagttttaa aactgactgt gaattttatt     2100
tttcatatat ttatgcatta cacaccttag ctataagaaa aaagggtttt tgattatatg     2160
cttcttgcag ttaatctcgt tatttaaaca aaagttttg ggtctatctt tggagtattt     2220
gtaacttcta aattttgaaa tgactgaatt aggaatttgg atgcttattc ttttagtctg     2280
tttgcctaaa aaccaattta caatctgact gtctcttggg agagggaggt gccttgcaaa     2340 cttttcacatt aagaatgtgc ctgaggctgc tttactctgg aatagtctca gatctaaaat     2400
ttcctctata aaggtggca tatgttaagt tttgcttcat tggaccgttt agaatgctat     2460
```

-continued

```
gtaaaatgtt gccattctgt tagattgcta actatatacc catctctgat ttggctctcc      2520
ttaagtgata ggatttgtta ttctaaaggt gataaacttg aaaatatcag aatctgagtt      2580
ttacttgaaa ttttgcagaa tacccaggtg gagtgaaaat tggaagggtt ttgtgcaatg      2640
actaaaaggt aaaacgctgt taaggttcaa gaatcaatac tttcaaccca agtagccctc      2700
tgcttgactg tatattatgg aactagtaaa ccttaggatt ttgaaaattg gagtctaatc      2760
tttcaaggag gtgggctccc aggatggtac cattgctctt tcctagctaa ccctagatat      2820
ggcagctctt taatgtactt caaaaagcaa atatatatta ctaaggaaaa aaagttatt      2880 ataattgcct tgtcataatt gttaaggtgt tctagagcca tttgcataca atttaatgta      2940
atttcattcc attctattgt ttacacaacg attactcgaa gatgactgca aagtaaaag      3000 gaaaataaaa gtgtattgca caatgaaaaa                                       3030
```

<210> SEQ ID NO 3
<211> LENGTH: 3857
<212> TYPE: DNA
<213> ORGANISM: Homo sapiens
<220> FEATURE:
<221> NAME/KEY: modified_base
<222> LOCATION: (22)
<223> OTHER INFORMATION: a, t, c, g, other or unknown
<220> FEATURE:
<221> NAME/KEY: modified_base
<222> LOCATION: (81)
<223> OTHER INFORMATION: a, t, c, g, other or unknown
<220> FEATURE:
<221> NAME/KEY: modified_base
<222> LOCATION: (122)
<223> OTHER INFORMATION: a, t, c, g, other or unknown

<400> SEQUENCE: 3

```
caaaagtgga gtcctagatg antctaccat tgctacgata ctccgagaag tactggaagg      60
gctggaatat ctgcataaaa ntggacagat ccacagagat gtgaaagctg gaaacattct     120
tnttggagaa gatggctcag tacagatttc agactttggg gttagtgctt ttttagcaac     180
tggtggtgat attacccgaa ataaagtgag aaagaccttt gttggcaccc cttgttggat     240
ggcacctgaa gttatggaac aggtccgtgg ttatgatttc aaagctgata tttggagttt     300
tggaattaca gcaattgaat tggctacagg ggcggctcct tatcataaat atccaccaat     360
gaaggtttta atgctgacac tgcagaacga tcctccttct ttggaaactg gtgttcaaga     420
taaagaaatg ctgaaaaaat atggaaaatc atttagaaaa atgatttcat tgtgccttca     480
aaaagatcca gaaaaaagac caacagcagc agaactatta aggcacaaat ttttccagaa     540
agcaaagaat aaagaatttc ttcaagaaaa aacattgcag agagcaccaa ccatttctga     600
aagagcaaaa aaggttcgga gagtaccagg ttccagtggg cgtcttcata agacagagga     660
tggaggctgg gagtggagtg atgatgaatt tgatgaagaa agtgaggaag ggaaagcagc     720
aatttcacaa ctcaggtctc cccgagtgaa agaatcaata tcaaattctg agctctttcc     780
aacaactgat cctgtgggta ctttgctcca agttccagaa cagatctctg ctcatctacc     840
tcagccagct gggcagattg ctacacagcc aactcaagtc tctctcccac ccaccgcaga     900
gccagcaaaa acagctcagg ctttgtcttc aggatcaggt tcacaagaaa ccaagatccc     960
aatcagtcta gtactaagat taaggaattc caaaaaagaa ctaaatgata ttcgatttga    1020
atttactcct gggagagata cagcagaggg tgtctctcag gaactcattt ctgctggcct    1080
ggtcgacgga agggatttag taatagtggc agctaatttg cagaaaattg tggaagaacc    1140
```

-continued

```
tcagtcaaat cgatctgtca ctttcaaact ggcatctggt gtcgaaggct cagatattcc    1200
tgatgatggt aaactgatag gatttgccca gctcagcatc agctaaacca caaccctgga    1260
agaggcggcc taaggagatt ccacacatgc gtatctctgt tgcttctatt ggcctaaacc    1320
cactactgcc aaagaaccca gcaacaaacc tcccggctag gagctttaga agtctttatg    1380
ttcttcctgc catcattcct ccttttccca cagggaaaga aaagttggat cactagtggc    1440
cagcatcccc agagttccgt tagtaaactt acttcatatg tcccctgtct tcctccatct    1500
gagaagtggc ccatgtgctt caaggcccag gagggagatc tgtcagctca ttcttgcctt    1560
actccaatga tggcccaggt ggaaaagtag cagctgtatc gggcttcctc atcctgcctg    1620
ttcccccaca cctgccagga tatggacatc ttgggatatc tctttaccac tgaagtagaa    1680
ttgattgttc agctggagcc cagagaattt aatttaatgt ttttttctttg tacctgatgt    1740 gaattctagc aacctttgtt aggaaaaagc acagcctcag atggaggcag cctaaactgt    1800
gttcttgttt tgttcatggt gtttctaagc gttttgctga agctgctctc aggcaccccc    1860
ttcttcattg ctctctccag aaaggggttgc tagccttaac ttcagctggt gcaaaacatc    1920
tgactgtagc cgaacttcag ccatcagatc cttcaaagtg gaactttgga ttgttttttac    1980 agacaacatc gagtaatggc ttgtaaatgt gaattttgcc agaggtggtt tttgaacagg    2040
aaaatcataa ttcatatcat tggagaagta tttattttca aatatcaaat tgaagaaaaa    2100
ctcaatcctc ccatgaaaat cagttcgcct ggcctccaag tcgtgaggaa atgggtatgc    2160
aaggctgaga tttctacagc aataaaggag acacacactg gccagagag gcctgccttc    2220 tgcctgctct cctgcactga ccctttggag ggggtctctg tgtgctgaag ctaactcaag    2280
atggaaagtg aaaccacatg tgccgtgacc tttaggtttt atgagtagac agtgttcatt    2340
tgattttcta cagaaataat ataaattatt ctttaggttt aaaaaagagc actcataatg    2400
caatatgtga ataatcagtg aggttgattt ttctttttc ctaccgtttc atagtctttg    2460
tctaactgct agtaacccta ccgagttttta tatatgagtg ggatactcaa tctggcctta    2520
aaaagataca caaagatggg ctgtgggtcc ctggaaaggg ggagagttgc cctttacaga    2580
atcactcgag ccctttccag cactgttggt ctgatgaaca aggttgtttt accttatttt    2640
ctcttggaac atatctgaaa accttcccca caaataactt gtcacacctt ttgtttcatt    2700
ctgagtcttt agttttagtc atgggctttc ttcacctgct ctaggtgcaa aggcatgttg    2760
ggaaagagat ggatgttggg gaggaagaga ggagatggat ttcagttggg agttaggagg    2820
agagtaggtg agatgatcag acaccggagt tcaacgtccc agcagtcttg gtaaaaggag    2880
ggagcctgct gagccaggag ggagaaaaga agattgacca gcttgctaga aaaatactta    2940
gcttttcttt ttcttttttt gtggaggggg gacggagagg aacaaggatg gggaggtagg    3000
aatgaggtat agaaaagaga tagcatcttc tttggcacaa gactagtggc ttaccgctta    3060
ccttagagtt ttgttttttt tttttcaaac ccatcaaaat ctacttattt atgaatccaa    3120
ggggtggcag catcactctg ttctagcatt cttttgtggag atggtctggt gcctagctgg    3180
gagtgagcag cagcccatcc cctgttcact ttctctagcc catcattacc tgtgaactgc    3240
agtggggcag tcatggcaaa tagaattggg ctggggtttc tccttctttt cagttcattg    3300
tttgccctgc taggaattag aagacagaca ccatgtccca ggacagtgtt acttcttctg    3360
catgatgtgt ggtagactcc ctttgctggc ttgtgcagtg atactgagaa aatacatgaa    3420
cagaaactgc ccaggtggaa cagcacgtaa cctagtgagt gactgtactc ctttctagga    3480
atgctgattc agagtgcacc tctttgacta ggtcccagga tcccctttgtc cctggagtag    3540
```

```
ggactaacta tagcacaaag taatatgtgc caatgctatt tgtgaaatgt ttggtctttc    3600
taaacgacta aaggatttgt tgggtttttg cttaagtttt gaaccaaatc ctagagccag    3660
ctgataatat ttaataatct ggaggagaga ataatgatgt accaataagt ggagattcct    3720
ccttatgatg tatgctaggt tatggaagat gtaaaatatt caactttttc ctccttttt    3780 tggactttgt attttactgc atgttttctt cattttaat caataaagag taaattgtca    3840
aaaaaaaaaa aaaaaa                                                    3857

<210> SEQ ID NO 4
<211> LENGTH: 1584
<212> TYPE: DNA
<213> ORGANISM: Homo sapiens

<400> SEQUENCE: 4
ctcatctgta cacacttcat ggatggcatg aatgagctgg cgattgctta catcctgcag      60
ggggtgctga aggccctcga ctacatccac cacatgggat atgtacacag gagtgtcaaa     120
gccagccaca tcctgatctc tgtggatggg aaggtctacc tgtctggttt gcgcagcaac     180
ctcagcatga taagccatgg gcagcggcag cgagtggtcc acgatttccc caagtacagt     240
gtcaaggttc tgccgtggct cagccccgag gtcctccagc agaatctcca gggttatgat     300
gccaagtctg acatctacag tgtgggaatc acagcctgtg aactggccaa cggccatgtc     360
ccctttaagg atatgcctgc cacccagatg ctgctagaga aactgaacgg cacagtgccc     420
tgcctgttgg ataccagcac catccccgct gaggagctga ccatgagccc ttcgcgctca     480
gtggccaact ctggcctgag tgacagcctg accaccagca cccccggcc ctccaacggt     540 gactcgccct cccacccta ccaccgaacc ttctcccccc acttccacca ctttgtggag     600
cagtgccttc agcgcaaccc ggatgccagg cccagtgcca gcaccctcct gaaccactct     660
ttcttcaagc agatcaagcg acgtgcctca gaggctttgc ccgaattgct tcgtcctgtc     720 accccccatca ccaattttga gggcagccag tctcaggacc acagtggaat ctttggcctg     780
gtaacaaacc tggaagagct ggaggtggac gattgggagt tctgagcctc tgcaaactgt     840
gcgcattctc cagccaggga tgcagaggcc acccagaggc ccttcctgag gccggccac     900 attcccgccc tcctgggcag attgggtaga aaggacattc ttccaggaaa gttgactgct     960
gactgattgg gaaagaaaat cctgagaga tacttcactg ctccaaggct tttgagacac    1020
aagggaatct caacaaccag ggatcaggag ggtccaaagc cgacattccc agtcctgtga    1080
gctcaggtga cctcctccgc agaagagaga tgctgtctg gccctgggag ctgaattcca    1140
agcccagggt ttggctcctt aaacccgagg accgccacct cttcccagtg cttgcgacca    1200
gcctcattct atttaacttt gctctcagat gcctcagatg ctataggtca gtgaaagggc    1260
aagtagtaag ctgcctgcct cccttccctc agacctctcc ctcataattc cagagaaggg    1320
catttctgtc ttttaagca cagactaagg ctggaacagt ccatccttat ccctcttctg    1380
gcttgggccc tgcacctaa gtctttccca cggtttatgt gtgtgcctca ttcctttccc    1440
accaagaatc catcttagcg cctcctgcca gctgccctgg tgctttctcc aagggccatc    1500
agtgtcttgc ctagcttgag ggcttaagtc cttatgctgt gttagtttcg ttgtcagaac    1560
aaattaaaat tttcagagac gctg                                          1584

<210> SEQ ID NO 5
<211> LENGTH: 416
<212> TYPE: PRT
```

-continued

```
<213> ORGANISM: Homo sapiens

<400> SEQUENCE: 5

Met Ala His Ser Pro Val Ala Val Gln Val Pro Gly Met Gln Asn Asn
  1               5                  10                  15

Ile Ala Asp Pro Glu Glu Leu Phe Thr Lys Leu Glu Arg Ile Gly Lys
             20                  25                  30

Gly Ser Phe Gly Glu Val Phe Lys Gly Ile Asp Asn Arg Thr Gln Gln
         35                  40                  45

Val Val Ala Ile Lys Ile Ile Asp Leu Glu Glu Ala Glu Asp Glu Ile
     50                  55                  60

Glu Asp Ile Gln Gln Glu Ile Thr Val Leu Ser Gln Cys Asp Ser Ser
 65                  70                  75                  80

Tyr Val Thr Lys Tyr Tyr Gly Ser Tyr Leu Lys Gly Ser Lys Leu Trp
                 85                  90                  95

Ile Ile Met Glu Tyr Leu Gly Gly Gly Ser Ala Leu Asp Leu Leu Arg
            100                 105                 110

Ala Gly Pro Phe Asp Glu Phe Gln Ile Ala Thr Met Leu Lys Glu Ile
        115                 120                 125

Leu Lys Gly Leu Asp Tyr Leu His Ser Glu Lys Lys Ile His Arg Asp
    130                 135                 140

Ile Lys Ala Ala Asn Val Leu Leu Ser Glu Gln Gly Asp Val Lys Leu
145                 150                 155                 160

Ala Asp Phe Gly Val Ala Gly Gln Leu Thr Asp Thr Gln Ile Lys Arg
                165                 170                 175

Asn Thr Phe Val Gly Thr Pro Phe Trp Met Ala Pro Glu Val Ile Gln
            180                 185                 190

Gln Ser Ala Tyr Asp Ser Lys Ala Asp Ile Trp Ser Leu Gly Ile Thr
        195                 200                 205

Ala Ile Glu Leu Ala Lys Gly Glu Pro Pro Asn Ser Asp Met His Pro
    210                 215                 220

Met Arg Val Leu Phe Leu Ile Pro Lys Asn Asn Pro Pro Thr Leu Val
225                 230                 235                 240

Gly Asp Phe Thr Lys Ser Phe Lys Glu Phe Ile Asp Ala Cys Leu Asn
                245                 250                 255

Lys Asp Pro Ser Phe Arg Pro Thr Ala Lys Glu Leu Leu Lys His Lys
            260                 265                 270

Phe Ile Val Lys Asn Ser Lys Lys Thr Ser Tyr Leu Thr Glu Leu Ile
        275                 280                 285

Asp Arg Phe Lys Arg Trp Lys Ala Glu Gly His Ser Asp Asp Glu Ser
    290                 295                 300

Asp Ser Glu Gly Ser Asp Ser Glu Ser Thr Ser Arg Glu Asn Asn Thr
305                 310                 315                 320

His Pro Glu Trp Ser Phe Thr Thr Val Arg Lys Lys Pro Asp Pro Lys
                325                 330                 335

Lys Val Gln Asn Gly Ala Glu Gln Asp Leu Val Gln Thr Leu Ser Cys
            340                 345                 350

Leu Ser Met Ile Ile Thr Pro Ala Phe Ala Glu Leu Lys Gln Gln Asp
        355                 360                 365

Glu Asn Asn Ala Ser Arg Asn Gln Ala Ile Glu Glu Leu Glu Lys Ser
    370                 375                 380

Ile Ala Val Ala Glu Ala Ala Cys Pro Gly Ile Thr Asp Lys Met Val
385                 390                 395                 400
```

```
Lys Lys Leu Ile Glu Lys Phe Gln Lys Cys Ser Ala Asp Glu Ser Pro
            405                 410                 415

<210> SEQ ID NO 6
<211> LENGTH: 516
<212> TYPE: PRT
<213> ORGANISM: Homo sapiens

<400> SEQUENCE: 6

Thr Ala Ala Pro Ala Pro Ala Ala Pro Ala Pro Ala Pro Ala Pro
  1               5                  10                  15

Ala Pro Ala Pro Ala Ala Gln Ala Val Gly Trp Pro Ile Cys Arg Asp
                 20                  25                  30

Ala Tyr Glu Leu Gln Glu Val Ile Gly Ser Gly Ala Thr Ala Val Val
             35                  40                  45

Gln Ala Ala Leu Cys Lys Pro Arg Gln Glu Arg Val Ala Ile Lys Arg
 50                  55                  60

Ile Asn Leu Glu Lys Cys Gln Thr Ser Met Asp Glu Leu Leu Lys Glu
 65                  70                  75                  80

Ile Gln Ala Met Ser Gln Cys Ser His Pro Asn Val Val Thr Tyr Tyr
                 85                  90                  95

Thr Ser Phe Val Val Lys Asp Glu Leu Trp Leu Val Met Lys Leu Leu
            100                 105                 110

Ser Gly Gly Ser Met Leu Asp Ile Ile Lys Tyr Ile Val Asn Arg Gly
        115                 120                 125

Glu His Lys Asn Gly Val Leu Glu Glu Ala Ile Ile Ala Thr Ile Leu
    130                 135                 140

Lys Glu Val Leu Glu Gly Leu Asp Tyr Leu His Arg Asn Gly Gln Ile
145                 150                 155                 160

His Arg Asp Leu Lys Ala Gly Asn Ile Leu Leu Gly Glu Asp Gly Ser
                165                 170                 175

Val Gln Ile Ala Asp Phe Gly Val Ser Ala Phe Leu Ala Thr Gly Gly
            180                 185                 190

Asp Val Thr Arg Asn Lys Val Arg Lys Thr Phe Val Gly Thr Pro Cys
        195                 200                 205

Trp Met Ala Pro Glu Val Met Glu Gln Val Arg Gly Tyr Asp Phe Lys
    210                 215                 220

Ala Asp Met Trp Ser Phe Gly Ile Thr Ala Ile Glu Leu Ala Thr Gly
225                 230                 235                 240

Ala Ala Pro Tyr His Lys Tyr Pro Pro Met Lys Val Leu Met Leu Thr
                245                 250                 255

Leu Gln Asn Asp Pro Pro Thr Leu Glu Thr Gly Val Glu Asp Lys Glu
            260                 265                 270

Met Met Lys Lys Tyr Gly Lys Ser Phe Arg Lys Leu Leu Ser Leu Cys
        275                 280                 285

Leu Gln Lys Asp Pro Ser Lys Arg Pro Thr Ala Ala Glu Leu Leu Lys
    290                 295                 300

Cys Lys Phe Phe Gln Lys Ala Lys Asn Arg Glu Tyr Leu Ile Glu Lys
305                 310                 315                 320

Leu Leu Thr Arg Thr Pro Asp Ile Ala Gln Arg Ala Lys Lys Val Arg
                325                 330                 335

Arg Val Pro Gly Ser Ser Gly His Leu His Lys Thr Glu Asp Gly Asp
            340                 345                 350

Trp Glu Trp Ser Asp Asp Glu Met Asp Glu Lys Ser Glu Glu Gly Lys
        355                 360                 365
```

-continued

```
Ala Ala Phe Ser Gln Glu Lys Ser Arg Arg Val Lys Glu Glu Asn Pro
    370                 375                 380

Glu Ile Ala Val Ser Ala Ser Thr Ile Pro Glu Gln Ile Gln Ser Leu
385                 390                 395                 400

Ser Val His Asp Ser Gln Gly Pro Pro Asn Ala Asn Glu Asp Tyr Arg
                405                 410                 415

Glu Ala Ser Ser Cys Ala Val Asn Leu Val Leu Arg Leu Arg Asn Ser
                420                 425                 430

Arg Lys Glu Leu Asn Asp Ile Arg Phe Glu Phe Thr Pro Gly Arg Asp
            435                 440                 445

Thr Ala Asp Gly Val Ser Gln Glu Leu Phe Ser Ala Gly Leu Val Asp
450                 455                 460

Gly His Asp Val Val Ile Val Ala Ala Asn Leu Gln Lys Ile Val Asp
465                 470                 475                 480

Asp Pro Lys Ala Leu Lys Thr Leu Thr Phe Lys Leu Ala Ser Gly Cys
                485                 490                 495

Asp Gly Ser Glu Ile Pro Asp Glu Val Lys Leu Ile Gly Phe Ala Gln
                500                 505                 510

Leu Ser Val Ser
        515

<210> SEQ ID NO 7
<211> LENGTH: 414
<212> TYPE: PRT
<213> ORGANISM: Homo sapiens
<220> FEATURE:
<221> NAME/KEY: MOD_RES
<222> LOCATION: (7)
<223> OTHER INFORMATION: Any amino acid
<220> FEATURE:
<221> NAME/KEY: MOD_RES
<222> LOCATION: (27)
<223> OTHER INFORMATION: Any amino acid
<220> FEATURE:
<221> NAME/KEY: MOD_RES
<222> LOCATION: (41)
<223> OTHER INFORMATION: Any amino acid

<400> SEQUENCE: 7

Lys Ser Gly Val Leu Asp Xaa Ser Thr Ile Ala Thr Ile Leu Arg Glu
  1               5                  10                  15

Val Leu Glu Gly Leu Glu Tyr Leu His Lys Xaa Gly Gln Ile His Arg
                20                  25                  30

Asp Val Lys Ala Gly Asn Ile Leu Xaa Gly Glu Asp Gly Ser Val Gln
            35                  40                  45

Ile Ala Asp Phe Gly Val Ser Ala Phe Leu Ala Thr Gly Gly Asp Ile
    50                  55                  60

Thr Arg Asn Lys Val Arg Lys Thr Phe Val Gly Thr Pro Cys Trp Met
65                  70                  75                  80

Ala Pro Glu Val Met Glu Gln Val Arg Gly Tyr Asp Phe Lys Ala Asp
                85                  90                  95

Ile Trp Ser Phe Gly Ile Thr Ala Ile Glu Leu Ala Thr Gly Ala Ala
                100                 105                 110

Pro Tyr His Lys Tyr Pro Pro Met Lys Val Leu Met Leu Thr Leu Gln
            115                 120                 125

Asn Asp Pro Pro Ser Leu Glu Thr Gly Val Gln Asp Lys Glu Met Leu
    130                 135                 140

Lys Lys Tyr Gly Lys Ser Phe Arg Lys Met Ile Ser Leu Cys Leu Gln
```

```
                145                 150                 155                 160
Lys Asp Pro Glu Lys Arg Pro Thr Ala Ala Glu Leu Leu Arg His Lys
                    165                 170                 175

Phe Phe Gln Lys Ala Lys Asn Lys Glu Phe Leu Gln Glu Lys Thr Leu
                180                 185                 190

Gln Arg Ala Pro Thr Ile Ser Glu Arg Ala Lys Lys Val Arg Arg Val
            195                 200                 205

Pro Gly Ser Ser Gly Arg Leu His Lys Thr Glu Asp Gly Gly Trp Glu
        210                 215                 220

Trp Ser Asp Asp Glu Phe Asp Glu Glu Ser Glu Gly Lys Ala Ala
225                 230                 235                 240

Ile Ser Gln Leu Arg Ser Pro Arg Val Lys Glu Ser Ile Ser Asn Ser
                245                 250                 255

Glu Leu Phe Pro Thr Thr Asp Pro Val Gly Thr Leu Leu Gln Val Pro
                260                 265                 270

Glu Gln Ile Ser Ala His Leu Pro Gln Pro Ala Gly Gln Ile Ala Thr
                275                 280                 285

Gln Pro Thr Gln Val Ser Leu Pro Pro Thr Ala Glu Pro Ala Lys Thr
                290                 295                 300

Ala Gln Ala Leu Ser Ser Gly Ser Gly Ser Gln Glu Thr Lys Ile Pro
305                 310                 315                 320

Ile Ser Leu Val Leu Arg Leu Arg Asn Ser Lys Lys Glu Leu Asn Asp
                325                 330                 335

Ile Arg Phe Glu Phe Thr Pro Gly Arg Asp Thr Ala Glu Gly Val Ser
                340                 345                 350

Gln Glu Leu Ile Ser Ala Gly Leu Val Asp Gly Arg Asp Leu Val Ile
                355                 360                 365

Val Ala Ala Asn Leu Gln Lys Ile Val Glu Glu Pro Gln Ser Asn Arg
370                 375                 380

Ser Val Thr Phe Lys Leu Ala Ser Gly Val Glu Gly Ser Asp Ile Pro
385                 390                 395                 400

Asp Asp Gly Lys Leu Ile Gly Phe Ala Gln Leu Ser Ile Ser
                405                 410

<210> SEQ ID NO 8
<211> LENGTH: 274
<212> TYPE: PRT
<213> ORGANISM: Homo sapiens

<400> SEQUENCE: 8

Leu Ile Cys Thr His Phe Met Asp Gly Met Asn Glu Leu Ala Ile Ala
  1               5                  10                  15

Tyr Ile Leu Gln Gly Val Leu Lys Ala Leu Asp Tyr Ile His His Met
                 20                  25                  30

Gly Tyr Val His Arg Ser Val Lys Ala Ser His Ile Leu Ile Ser Val
             35                  40                  45

Asp Gly Lys Val Tyr Leu Ser Gly Leu Arg Ser Asn Leu Ser Met Ile
         50                  55                  60

Ser His Gly Gln Arg Gln Arg Val Val His Asp Phe Pro Lys Tyr Ser
65                  70                  75                  80

Val Lys Val Leu Pro Trp Leu Ser Pro Glu Val Leu Gln Gln Asn Leu
                 85                  90                  95

Gln Gly Tyr Asp Ala Lys Ser Asp Ile Tyr Ser Val Gly Ile Thr Ala
                100                 105                 110
```

```
Cys Glu Leu Ala Asn Gly His Val Pro Phe Lys Asp Met Pro Ala Thr
        115                 120                 125
Gln Met Leu Leu Glu Lys Leu Asn Gly Thr Val Pro Cys Leu Leu Asp
    130                 135                 140
Thr Ser Thr Ile Pro Ala Glu Glu Leu Thr Met Ser Pro Ser Arg Ser
145                 150                 155                 160
Val Ala Asn Ser Gly Leu Ser Asp Ser Leu Thr Thr Ser Thr Pro Arg
                165                 170                 175
Pro Ser Asn Gly Asp Ser Pro Ser His Pro Tyr His Arg Thr Phe Ser
            180                 185                 190
Pro His Phe His His Phe Val Glu Gln Cys Leu Gln Arg Asn Pro Asp
        195                 200                 205
Ala Arg Pro Ser Ala Ser Thr Leu Leu Asn His Ser Phe Phe Lys Gln
    210                 215                 220
Ile Lys Arg Arg Ala Ser Glu Ala Leu Pro Glu Leu Leu Arg Pro Val
225                 230                 235                 240
Thr Pro Ile Thr Asn Phe Glu Gly Ser Gln Ser Gln Asp His Ser Gly
                245                 250                 255
Ile Phe Gly Leu Val Thr Asn Leu Glu Glu Leu Glu Val Asp Asp Trp
            260                 265                 270
Glu Phe

<210> SEQ ID NO 9
<211> LENGTH: 3798
<212> TYPE: DNA
<213> ORGANISM: Homo sapiens

<400> SEQUENCE: 9
gagaccatgg cgaacgactc tcccgcgaaa agtctggtgg acatcgacct ctcctccctg      60
cgggatcctg ctgggatttt tgagctggtg gaagtggttg gaaatggcac ctatggacaa     120
gtctataagg gtcgacatgt taaaacgggt cagttggcag ccatcaaagt tatggatgtc     180
actgaggatg aagaggaaga atcaaactg agataaaata tgctaaagaa atactctcat      240
cacagaaaca ttgcaacata ttatggtgct ttcatcaaaa agagccctcc aggacatgat     300
gaccaactct ggcttgttat ggagttctgt ggggctgggt ccattacaga ccttgtgaag     360
aacaccaaag ggaacacact caaagaagac tggatcgctt acatctccag agaaatcctg     420
aggggactgg cacatcttca cattcatcat gtgattcacc gggatatcaa gggccagaat     480
gtgttgctga ctgagaatgc agaggtgaaa cttgttgact ttggtgtgag tgctcagctg     540
gacaggactg tggggcggag aaatacgttc ataggcactc cctactggat ggctcctgag     600
gtcatcgcct gtgatgagaa cccagatgcc acctatgatt acagaagtga tctttggtct     660
tgtggcatta cagccattga gatggcagaa ggtgctcccc ctctctgtga catgcatcca     720
atgagagcac tgtttctcat tcccagaaac cctcctcccc ggctgaagtc aaaaaaatgg     780
tcgaagaagt tttttagttt tatagaaggg tgcctggtga agaattacat gcagcggccc     840
tctacagagc agcttttgaa acatcctttt ataagggatc agccaaatga aaggcaagtt     900
agaatccagc ttaaggatca tatagatcgt accaggaaga gagaggcga gaaagatgaa      960
actgagtatg agtacagtgg gagtgaggaa gaagaggagg aagtgcctga caggaagga    1020
gagccaagtt ccattgtgaa cgtgcctggt gagtctactc ttcgccgaga tttcctgaga    1080
ctgcagcagg agaacaagga acgttccgag gctcttcgga gacaacagtt actacaggag    1140
caacagctcc gggagcagga agaatataaa aggcaactgc tggcagagag acagaagcgg    1200
```

```
attgagcagc agaaagaaca gaggcgacgg ctagaagagc aacaaaggag agagcgggaa    1260
gctagaaggc agcaggaacg tgaacagcga aggagagaac aagaagaaaa gaggcgtcta    1320
gaggagttgg agagaaggcg caaagaagaa gaggagagga gacgggcaga agaagaaaag    1380
aggagagttg aaagaaaca ggagtatatc aggcgacagc tagaagagga gcagcggcac    1440
ttggaagtcc ttcagcagca gctgctccag gagcaggcca tgttactgga gtgccgatgg    1500
cgggagatgg aggagcaccg gcaggcgagg aggctccaga ggcagttgca acaagaacaa    1560
gcatatctcc tgtctctaca gcatgaccat ggaggccgc acccgcagca ctcgcagcag    1620
ccgccaccac cgcagcagga aaggagcaag ccaagcttcc atgctcccga gcccaaagcc    1680
cactacgagc ctgctgaccg agcgcgagag gtggaagata gatttaggaa aactaaccac    1740
agctcccctg aagcccagtc taagcagaca ggcagagtat ggagccacc agtgccttcc    1800 cgatcagagt cttttccaa tggcaactcc gagtctgtgc atccgccct gcagagacca    1860 gcggagccac aggttcctgt gagaacaaca tctcgctccc ctgttctgtc ccgtcgagat    1920
tccccactgc agggcagtgg gcagcagaat agccaggcag acagagaaa ctccaccagt    1980 attgagccca ggcttctgtg ggagagagtg gagaagctgg tgcccagacc tggcagtggc    2040
agctcctcag ggtccagcaa ctcaggatcc cagcccgggt ctcaccctgg gtctcagagt    2100
ggctccgggg aacgcttcag agtgagatca tcatccaagt ctgaaggctc tccatctcag    2160
cgcctggaaa atgcagtgaa aaacctgaa gataaaaagg aagttttcag acccctcaag    2220
cctgctgatc tgaccgcact ggccaaagag cttcgagcag tggaagatgt acggccacct    2280
cacaaagtaa cggactactc ctcatccagt gaggagtcgg ggacgacgga tgaggaggac    2340
gacgatgtgg agcaggaagg ggctgacgag tccacctcag gaccagagga caccagagca    2400
gcgtcatctc tgaatttgag caatggtgaa acggaatctg tgaaaaccat gattgtccat    2460
gatgatgtag aaagtgagcc ggccatgacc ccatccaagg agggcactct aatcgtccgc    2520
cggactcagt ccgctagtag cacactccag aaacacaaat cttcctcctc ctttacacct    2580
tttatagacc ccagattact acagatttct ccatctagcg gaacaacagt gacatctgtg    2640
gtgggatttt cctgtgatgg gatgagacca gaagccataa gcaagatcc tacccggaaa    2700 ggctcagtgg tcaatgtgaa tcctaccaac actaggccac agagtgacac cccggagatt    2760
cgtaaataca agaagaggtt taactctgag attctgtgtg ctgccttatg gggagtgaat    2820
ttgctagtgg gtacagagag tggcctgatg ctgctggaca gaagtggcca agggaaggtc    2880
tatcctctta tcaaccgaag acgatttcaa caaatggacg tacttgaggg cttgaatgtc    2940
ttggtgacaa tatctggcaa aaaggataag ttacgtgtct actatttgtc ctggttaaga    3000
aataaaatac ttcacaatga tccagaagtt gagaagaagc agggatggac aaccgtaggg    3060
gatttggaag gatgtgtaca ttataaagtt gtaaaatatg aaagaatcaa atttctggtg    3120
attgctttga agagttctgt ggaagtctat gcgtgggcac caaagccata tcacaaattt    3180
atggccttta agtcatttgg agaattggta cataagccat tactggtgga tctcactgtt    3240
gaggaaggcc agaggttgaa agtgatctat ggatcctgtg ctggattcca tgctgttgat    3300
gtggattcag gatcagtcta tgacatttat ctaccaacac atatccagtg tagcatcaaa    3360
ccccatgcaa tcatcatcct ccccaataca gatggaatgg agcttctggt gtgctatgaa    3420
gatgaggggg tttatgtaaa cacatatgga aggatcacca aggatgtagt tctacagtgg    3480
ggagagatgc ctacatcagt agcatatatt cgatccaatc agacaatggg ctggggagag    3540
```

```
aaggccatag agatccgatc tgtggaaact ggtcacttgg atggtgtgtt catgcacaaa    3600
agggctcaaa gactaaaatt cttgtgtgaa cgcaatgaca aggtgttctt tgcctctgtt    3660
cggtctggtg gcagcagtca ggtttatttc atgaccttag caggacttc tcttctgagc     3720 tggtagaagc agtgtgatcc agggattact ggcctccaga gtcttcaaga tcctgagaac    3780
ttggaattcc ttgtaact                                                  3798

<210> SEQ ID NO 10
<211> LENGTH: 4055
<212> TYPE: DNA
<213> ORGANISM: Homo sapiens

<400> SEQUENCE: 10
gctttcgggg aggtctatga gggtcgtcat gtcaaaacgg gccagcttgc agccatcaag      60
gttatggatg tcacagggga tgaagaggaa gaaatcaaac aagaaattaa catgttgaag     120
aaatattctc atcaccggaa tattgctaca tactatggtg cttttatcaa aaagaaccca     180
ccaggcatgg atgaccaact ttggttggtg atggagtttt gtggtgctgg ctctgtcacc     240
gacctgatca agaacacaaa aggtaacacg ttgaaagagg agtggattgc atacatctgc     300
agggaaatct tacgggggct gagtcacctg caccagcata agtgattca tcgagatatt      360 aaagggcaaa atgtcttgct gactgaaaat gcagaagtta aactagtgga ctttggagtc     420
agtgctcagc ttgatcgaac agtgggcagg aggaatactt tcattggaac tccctactgg     480
atggcaccag aagttattgc ctgtgatgaa acccagatg ccacatatga tttcaagagt      540
gacttgtggt ctttgggtat caccgccatt gaaatggcag aaggtgctcc ccctctctgt     600
gacatgcacc ccatgagagc tctcttcctc atccccggga atccagcgcc tcggctgaag    660
tctaagaagt ggtcaaaaaa attccagtca tttattgaga gctgcttggt aaagaatcac    720
agccagcgac cagcaacaga acaattgatg aagcatccat ttatacgaga ccaacctaat    780
gagcgacagg tccgcattca actcaaggac catattgata gaacaaagaa gaagcgagga    840 gaaaagatg agacagagta tgagtacagt ggaagtgagg aagaagagga ggagaatgac    900
tcaggagagc ccagctccat cctgaatctg ccaagggagt cgacgctgcg gagggacttt    960
ctgaggctgc agctggccaa caaggagcgt tctgaggccc tacggaggca gcagctggag   1020
cagcagcagc gggagaatga ggagcacaag cggcagctgc tggccgagcg tcagaagcgc   1080
atcgaggagc agaaagagca gaggcggcg ctggaggagc aacaaaggcg agagaaggag    1140
ctgcggaagc agcaggagag ggagcagcgc cggcactatg aggagcagat gcgccgggag   1200
gaggagagga ggcgtgcgga gcatgaacag gaatataagc gcaaacaatt ggaagaacag   1260
agacaagcag aaagactgca gaggcagcta aagcaagaaa gagactactt agtttccctt   1320
cagcatcagc ggcaggagca gaggcctgtg gagaagaagc cactgtacca ttacaaagaa   1380
ggaatgagtc ctagtgagaa gccagcatgg gccaaggagg tagaagaacg gtcaaggctc   1440
aaccggcaaa gttcccctgc catgcctcac aaggttgcca acaggatatc tgaccccaac   1500
ctgcccccaa ggtcggagtc cttcagcatt agtggagttc agcctgctcg aacaccccc    1560 atgctcagac cagtcgatcc ccagatccca catctggtag ctgtaaaatc ccagggacct   1620
gccttgaccg cctcccagtc agtgcacgag cagcccacaa agggcctctc tgggtttcag   1680
gaggctctga acgtgacctc ccaccgcgtg gagatgccac gccagaactc agatcccacc   1740
tcggaaaatc ctcctctccc cactcgcatt gaaaagtttg accgaagctc ttggttacga   1800
caggaagaag acattccacc aaaggtgcct caaagaacaa cttctatatc cccagcatta   1860
```

```
gccagaaaga attctcctgg gaatggtagt gctctgggac ccagactagg atctcaaccc    1920
atcagagcaa gcaaccctga tctccggaga actgagccca tcttggagag ccccttgcag    1980
aggaccagca gtggcagttc ctccagctcc agcacccta gctcccagcc cagctcccaa     2040
ggaggctccc agcctggatc acaagcagga tccagtgaac gcaccagagt tcgagccaac    2100
agtaagtcag aaggatcacc tgtgctcccc catgagcctg ccaaggtgaa accagaagaa    2160
tccagggaca ttaccggcc cagtcgacca gctagctaca aaaagctat agatgaggat      2220 ctgacggcat tagccaaaga actaagagaa ctccggattg aagaaacaaa ccgcccaatg    2280
aagaaggtga ctgattactc ctcctccagt gaggagtcag aaagtagcga ggaagaggag    2340
gaagatggag agagcgagac ccatgatggg acagtggctg tcagcgacat acccagactg    2400
ataccaacag gagctccagg cagcaacgag cagtacaatg tgggaatggt ggggacgcat    2460
gggctggaga cctctcatgc ggacagtttc agcggcagta tttcaagaga aggaaccttg    2520
atgattagag agacgtctgg agagaagaag cgatctggcc acagtgacag caatggcttt    2580
gctggccaca tcaacctccc tgacctggtg cagcagagcc attctccagc tggaaccccg    2640
actgagggac tggggcgcgt ctcaacccat tcccaggaga tggactctgg gactgaatat    2700
ggcatgggga gcagcaccaa agcctccttc acccccttg tggaccccag agtataccag     2760
acgtctccca ctgatgaaga tgaagaggat gaggaatcat cagccgcagc tctgtttact    2820
ggcgaacttc ttaggcaaga acaggccaaa ctcaatgaag caagaaagat ttcggtggta    2880
aatgtaaacc caaccaacat tcggcctcat agcgacacac cagaaatcag aaaatacaag    2940
aaacgattca actcagaaat actttgtgca gctctgtggg gtgtaaacct tctggtgggg    3000
actgaaaatg gcctgatgct tttggaccga agtgggcaag gcaaagtcta taatctgatc    3060
aaccggaggc gatttcagca gatggatgtg ctagagggac tgaatgtcct tgtgacaatt    3120
tcaggaaaga agaataagct acgagtttac tatctttcat ggttaagaaa cagaatacta    3180
cataatgacc cagaagtaga aaagaaacaa ggctggatca ctgttgggga cttgaaggc     3240 tgtatacatt ataaagttgt taaatatgaa aggatcaaat ttttggtgat tgccttaaag    3300
aatgctgtgg aaatatatgc ttgggctcct aaaccgtatc ataaattcat ggcatttaag    3360
tcttttgcag atctccagca caagcctctg ctagttgatc tcacggtaga agaaggtcaa    3420
agattaaagg ttattttttgg ttcacacact ggtttccatg taattgatgt tgattcagga   3480
aactcttatg atatctacac accatctcat attcagggca atatcactcc tcatgctatt    3540
gtcatcttgc ctaaaacaga tggaatggaa atgcttgttt gctatgagga tgaggggtg    3600 tatgtaaaca cctatggccg gataactaag gatgtggtgc tccaatgggg agaaatgccc    3660
acgtctgtgg cctacattca ttccaatcag ataatgggct ggggcgagaa agctattgag    3720
atccggtcag tggaaacagg acatttggat ggagtattta tgcataagcg agctcaaagg    3780
ttaaagtttc tatgtgaaag aaatgataag gtatttttttg catccgtgcg atctggagga   3840
agtagccaag tgtttttcat gaccctcaac agaaattcca tgatgaactg gtaacagaag    3900
agcacttggc acttatcttc atggcgttat ttctaattta aaagaacata actcatgtgg    3960
acttatgcca gtctagaggc agaatcagaa ggcttggttg aacatatcgc tttccctttt    4020 tcctctcct ccgcccctcc cagtacagtc catct                                4055
```

<210> SEQ ID NO 11
<211> LENGTH: 4133
<212> TYPE: DNA

-continued

<213> ORGANISM: Homo sapiens

<400> SEQUENCE: 11

```
gcatttgggg aggtgtatga gggtcggcat gtcaagacgg ggcagctggc tgccatcaag      60
gtcatggatg tcacggagga cgaggaggaa gagatcaaac aggagatcaa catgctgaaa     120
aagtactctc accaccgcaa catcgccacc tactacggag ccttcatcaa gaagagcccc     180
ccgggaaacg atgaccagct ctggctggtg atggagttct gtggtgctgg ttcagtgact     240
gacctggtaa agaacacaaa aggcaacgcc ctgaaggagg actgtatcgc ctatatctgc     300
agggagatcc tcagggtct ggcccatctc catgcccaca agtgatcca tcgagacatc       360
aaggggcaga atgtgctgct gacagagaat gctgaggtca agctagtgga ttttggggtg     420
agtgctcagc tggaccgcac cgtgggcaga cggaacactt tcattgggac tccctactgg     480
atggctccag aggtcatcgc ctgtgatgag aaccctgatg ccacctatga ttacaggagt     540
gatatttggt ctctaggaat cacagccatc gagatggcag agggagcccc ccctctgtgt     600
gacatgcacc ccatgcgagc cctcttcctc attcctcgga accctccgcc caggctcaag     660
tccaagaagt ggtctaagaa gttcattgac ttcattgaca catgtctcat caagacttac     720
ctgagccgcc cacccacgga gcagctactg aagtttccct tcatccggga ccagcccacg     780
gagcggcagg tccgcatcca gcttaaggac cacattgacc gatcccggaa gaagcggggt     840
gagaaagagg agacagaata tgagtacagc ggcagcgagg aggaagatga cagccatgga     900
gaggaaggag agccaagctc catcatgaac gtgcctggag agtcgactct acgccgggag     960
tttctccggc tccagcagga aaataagagc aactcagagg ctttaaaaca gcagcagcag    1020
ctgcagcagc agcagcagcg agaccccgag gcacacatca acacctgct gcaccagcgg     1080
cagcggcgca tagaggagca aaggaggag cggcgccgcg tggaggagca acagcggcgg     1140
gagcgggagc agcggaagct gcaggagaag gagcagcagc ggcggctgga ggacatgcag    1200
gctctgcggc gggaggagga gcggcggcag gcggagcgcg agcaggaata tattcgtcac    1260
aggctagagg aggagcagcg acagctcgag atccttcagc aacagctgct ccaggaacag    1320
gccctgctgc tggaatacaa gcggaagcag ctggaggagc agcggcagtc agaacgtctc    1380
cagaggcagc tgcagcagga gcatgcctac ctcaagtccc tgcagcagca gcaacagcag    1440
cagcagcttc agaaacaaca gcagcagcag ctcctgcctg gggacaggaa gcccctgtac    1500
cattatggtc ggggcatgaa tcccgctgac aaaccagcct gggcccgaga ggtagaagag    1560
agaacaagga tgaacaagca gcagaactct cccttggcca agagcaagcc aggcagcacg    1620
gggcctgagc ccccatccc caggcctcc caggggccc caggaccct ttcccagact         1680
cctcctatgc agaggccggt ggagccccag gagggaccgc acaagagcct ggtggcacac    1740
cgggtcccac tgaagccata tgcagcacct gtacccgat cccagtccct gcaggaccag     1800
cccacccgaa acctggctgc cttcccagcc tccatgacc ccgaccctgc catccccgca      1860
cccactgcca cgcccagtgc ccgaggagct gtcatccgcc agaattcaga ccccacctct    1920
gaaggacctg gccccagccc gaatccccca gcctgggtcc gcccagataa cgaggcccca    1980
cccaaggtgc ctcagaggac ctcatctatc gccactgccc ttaacaccag tggggccgga    2040
gggtcccggc cagcccaggc agtccgtgcc agacctcgca gcaactccgc ctggcaaatc    2100
tatctgcaaa ggcgggcaga gcggggcacc ccaaagcctc cagggccccc tgctcagccc    2160
cctggcccgc ccaacgcctc tagtaacccc gacctcagga ggagcgaccc tggctgggaa    2220
cgctcggaca gcgtccttcc agcctctcac gggcacctcc cccaggctgg ctcactggag    2280
```

```
cggaaccgcg tgggagtctc ctccaaaccg gacagctccc ctgtgctctc ccctgggaat   2340
aaagccaagc ccgacgacca ccgctcacgg ccaggccggc ccgcagactt tgtgttgctg   2400
aaagagcgga ctctggacga ggcccctcgg cctcccaaga aggccatgga ctactcgtcg   2460
tccagcgagg aggtggaaag cagtgaggac gacgaggagg aaggcgaagg cgggccagca   2520
gaggggagca gagataccgc tgggggccgc gatgggggata cagacagcgt cagcaccatg   2580
gtggtccacg acgtcgagga gatcaccggg acccagcccc catacggggg cggcaccatg   2640
gtggtccagc gcaccctga agaggagcgg aacctgctgc atgctgacag caatgggtac   2700
acaaacctgc ctgacgtggt ccagcccagc cactcaccca ccgagaacag caaaggccaa   2760
agcccaccct cgaaggatgg gagtggtgac taccagtctc gtgggctggt aaaggcccct   2820
ggcaagagct cgttcacgat gtttgtggat ctagggatct accagcctgg aggcagtggg   2880
gacagcatcc ccatcacagc cctagtgggt ggagagggca ctcggctcga ccagctgcag   2940
tacgacgtga ggaagggttc tgtggtcaac gtgaatccca ccaacacccg ggcccacagt   3000
gagacccctg agatccggaa gtacaagaag cgattcaact ccgagatcct ctgtgcagcc   3060
ctttgggggg tcaacctgct ggtgggcacg gagaacgggc tgatgttgct ggaccgaagt   3120
gggcagggca aggtgtatgg actcattggg cggcgacgct ccagcagat ggatgtgctg   3180 gagggggctca acctgctcat caccatctca gggaaaagga acaaactgcg ggtgtattac   3240
ttgtcctggc tccggaacaa gattctgcac aatgacccag aagtgagaa gaagcagggc   3300 tggaccaccg tggggggacat ggaggggctgc gggcactacc gtgttgtgaa atacgagcgg   3360
attaagttcc tggtcatcgc cctcaagagc tccgtggagg tgtatgcctg ggcccccaaa   3420
ccctaccaca aattcatggc cttcaagtcc tttgccgacc tcccccaccg ccctctgctg   3480
gtcgacctga cagtagagga ggggcagcgg ctcaaggtca tctatggctc cagtgctggc   3540
ttccatgctg tggatgtcga ctcggggaac agctatgaca tctacatccc tgtgcacatc   3600
cagagccaga tcacgcccca tgccatcatc ttcctcccca acaccgacgg catggagatg   3660
ctgctgtgct acgaggacga gggtgtctac gtcaacacgt acgggcgcat cattaaggat   3720
gtggtgctgc agtgggggga gatgcctact tctgtggcct acatctgctc caaccagata   3780
atgggctggg gtgagaaagc cattgagatc cgctctgtgg agacgggcca cctcgacggg   3840
gtcttcatgc acaaacgagc tcagaggctc aagttcctgt gtgagcggaa tgacaaggtg   3900
ttttttgcct cagtccgctc tgggggcagc agccaagttt acttcatgac tctgaaccgt   3960
aaccgcatca tgaactggtg acggggccct gggctgggc tgtcccacac tggacccagc   4020 tctcccctg cagccaggct tcccggggccg cccctctttc ccctcctgg gcttttgctt   4080 ttactggttt gatttcactg gagcctgctg ggaacgtgac ctctgacccc tga          4133
```

<210> SEQ ID NO 12
<211> LENGTH: 1459
<212> TYPE: DNA
<213> ORGANISM: Homo sapiens

<400> SEQUENCE: 12

```
caatgttaac ccactctatg tctctcctgc atgtaaaaaa ccactaatcc acatgtatga     60
aaaggagttc acttctgaga tctgctgtgg ttctttgtgg ggagtcaatt tgctgttggg    120
aacccgatct aatctatatc tgatggacag aagtggaaag gctgacatta ctaaacttat    180
aaggcgaaga ccattccgcc agattcaagt cttagagcca ctcaatttgc tgattaccat    240
```

```
                                                                -continued ctcaggtcat aagaacagac ttcgggtgta tcatctgacc tggttgagga caagattttt      300
gaataatgat ccagaaagta aagaaggca agaagaaatg ctgaagacag aggaagcctg       360
caaagctatt gataagttaa caggctgtga cacttcagt gtcctccaac atgaagaaac       420
aacatatatt gcaattgctt tgaaatcatc aattcacctt tatgcatggg caccaaagtc     480
ctttgatgaa agcactgcta ttaaagtatt tccaacactt gatcataagc cagtgacagt     540
tgacctggct attggttctg aaaaaagact aaagattttc ttcagctcag cagatggata    600
tcacctcatc gatgcagaat ctgaggttat gtctgatgtg accctgccaa gaatcccct      660 ggaaatcatt ataccacaga atatcatcat tttacctgat tgcttgggaa ttggcatgat    720
gctcaccttc aatgctgaag ccctctctgt ggaagcaaat gaacaactct tcaagaagat    780
ccttgaaatg tggaaagaca taccatcttc tatagctttt gaatgtacac agcgaaccac   840
aggatggggc caaaaggcca ttgaagtgcg ctctttgcaa tccagggttc tggaaagtga    900
gctgaagcgc aggtcaatta agaagctgag attcctgtgc acccgggtg acaagctgtt     960 ctttaccctct accctgcgca atcaccacag ccgggtttac ttcatgacac ttggaaaact  1020
tgaagagctc caaagcaatt atgatgtcta aaagtttcca gtgatttatt accacattat   1080
aaacatcatg tataggcagt ctgcatcttc agatttcaga gattaaatga gtattcagtt    1140 ttattttag taaagattaa atccaaaact ttacttttaa tgtagcacag aatagtttta     1200
atgagaaatg cagctttatg tataaaatta actatagcaa gctctaggta ctccaatggt   1260
gtacaatgtc ttttgcacaa actttgtaac ttttgttact gtgaattcaa acattactct   1320
ttggacagtt tggacagtat ctgtattcag attttacaac atggagtaaa gaaacctgtt  1380
atgaattaga ttacaagcag ccttcaaaag aattggcact gggataagat ttttcagaaa  1440
agaaaaacat cggcaaact                                                1459

<210> SEQ ID NO 13
<211> LENGTH: 1239
<212> TYPE: PRT
<213> ORGANISM: Homo sapiens

<400> SEQUENCE: 13

Met Ala Asn Asp Ser Pro Ala Lys Ser Leu Val Asp Ile Asp Leu Ser
 1               5                  10                  15

Ser Leu Arg Asp Pro Ala Gly Ile Phe Glu Leu Val Glu Val Val Gly
             20                  25                  30

Asn Gly Thr Tyr Gly Gln Val Tyr Lys Gly Arg His Val Lys Thr Gly
         35                  40                  45

Gln Leu Ala Ala Ile Lys Val Met Asp Val Thr Glu Asp Glu Glu Glu
     50                  55                  60

Glu Ile Lys Leu Glu Ile Asn Met Leu Lys Lys Tyr Ser His His Arg
 65                  70                  75                  80

Asn Ile Ala Thr Tyr Tyr Gly Ala Phe Ile Lys Lys Ser Pro Pro Gly
                 85                  90                  95

His Asp Asp Gln Leu Trp Leu Val Met Glu Phe Cys Gly Ala Gly Ser
            100                 105                 110

Ile Thr Asp Leu Val Lys Asn Thr Lys Gly Asn Thr Leu Lys Glu Asp
        115                 120                 125

Trp Ile Ala Tyr Ile Ser Arg Glu Ile Arg Gly Leu Ala His Leu
    130                 135                 140

His Ile His His Val Ile His Arg Asp Ile Lys Gly Gln Asn Val Leu
145                 150                 155                 160
```

-continued

```
Leu Thr Glu Asn Ala Glu Val Lys Leu Val Asp Phe Gly Val Ser Ala
                165                 170                 175
Gln Leu Asp Arg Thr Val Gly Arg Arg Asn Thr Phe Ile Gly Thr Pro
            180                 185                 190
Tyr Trp Met Ala Pro Glu Val Ile Ala Cys Asp Glu Asn Pro Asp Ala
        195                 200                 205
Thr Tyr Asp Tyr Arg Ser Asp Leu Trp Ser Cys Gly Ile Thr Ala Ile
    210                 215                 220
Glu Met Ala Glu Gly Ala Pro Pro Leu Cys Asp Met His Pro Met Arg
225                 230                 235                 240
Ala Leu Phe Leu Ile Pro Arg Asn Pro Pro Arg Leu Lys Ser Lys
                245                 250                 255
Lys Trp Ser Lys Lys Phe Phe Ser Phe Ile Glu Gly Cys Leu Val Lys
                260                 265                 270
Asn Tyr Met Gln Arg Pro Ser Thr Glu Gln Leu Leu Lys His Pro Phe
            275                 280                 285
Ile Arg Asp Gln Pro Asn Glu Arg Gln Val Arg Ile Gln Leu Lys Asp
        290                 295                 300
His Ile Asp Arg Thr Arg Lys Lys Arg Gly Glu Lys Asp Glu Thr Glu
305                 310                 315                 320
Tyr Glu Tyr Ser Gly Ser Glu Glu Glu Glu Val Pro Glu Gln
                325                 330                 335
Glu Gly Glu Pro Ser Ser Ile Val Asn Val Pro Gly Glu Ser Thr Leu
                340                 345                 350
Arg Arg Asp Phe Leu Arg Leu Gln Gln Glu Asn Lys Glu Arg Ser Glu
            355                 360                 365
Ala Leu Arg Arg Gln Gln Leu Leu Gln Glu Gln Leu Arg Glu Gln
        370                 375                 380
Glu Glu Tyr Lys Arg Gln Leu Leu Ala Glu Arg Gln Lys Arg Ile Glu
385                 390                 395                 400
Gln Gln Lys Glu Gln Arg Arg Leu Glu Glu Gln Arg Arg Glu
                405                 410                 415
Arg Glu Ala Arg Arg Gln Gln Glu Arg Glu Gln Arg Arg Glu Gln
                420                 425                 430
Glu Glu Lys Arg Arg Leu Glu Glu Leu Glu Arg Arg Lys Glu Glu
            435                 440                 445
Glu Glu Arg Arg Arg Ala Glu Glu Lys Arg Arg Val Glu Arg Glu
        450                 455                 460
Gln Glu Tyr Ile Arg Arg Gln Leu Glu Glu Gln Arg His Leu Glu
465                 470                 475                 480
Val Leu Gln Gln Gln Leu Leu Gln Glu Gln Ala Met Leu Leu Glu Cys
                485                 490                 495
Arg Trp Arg Glu Met Glu Glu His Gln Ala Glu Arg Leu Gln Arg
            500                 505                 510
Gln Leu Gln Gln Glu Gln Ala Tyr Leu Leu Ser Leu Gln His Asp His
            515                 520                 525
Arg Arg Pro His Pro Gln His Ser Gln Pro Pro Pro Gln Gln
        530                 535                 540
Glu Arg Ser Lys Pro Ser Phe His Ala Pro Glu Pro Lys Ala His Tyr
545                 550                 555                 560
Glu Pro Ala Asp Arg Ala Arg Glu Val Glu Asp Arg Phe Arg Lys Thr
                565                 570                 575
```

-continued

```
Asn His Ser Ser Pro Glu Ala Gln Ser Lys Gln Thr Gly Arg Val Leu
            580                 585                 590

Glu Pro Pro Val Pro Ser Arg Ser Glu Ser Phe Ser Asn Gly Asn Ser
            595                 600             605

Glu Ser Val His Pro Ala Leu Gln Arg Pro Ala Glu Pro Gln Val Pro
            610                 615                 620

Val Arg Thr Thr Ser Arg Ser Pro Val Leu Ser Arg Arg Asp Ser Pro
625                 630                 635                 640

Leu Gln Gly Ser Gly Gln Gln Asn Ser Gln Ala Gly Gln Arg Asn Ser
                    645                 650                 655

Thr Ser Ile Glu Pro Arg Leu Leu Trp Glu Arg Val Glu Lys Leu Val
            660                 665                 670

Pro Arg Pro Gly Ser Gly Ser Ser Gly Ser Ser Asn Ser Gly Ser
            675                 680                 685

Gln Pro Gly Ser His Pro Gly Ser Gln Ser Gly Ser Gly Glu Arg Phe
            690                 695                 700

Arg Val Arg Ser Ser Lys Ser Glu Gly Ser Pro Ser Gln Arg Leu
705                 710                 715                 720

Glu Asn Ala Val Lys Lys Pro Glu Asp Lys Lys Glu Val Phe Arg Pro
                    725                 730                 735

Leu Lys Pro Ala Asp Leu Thr Ala Leu Ala Lys Glu Leu Arg Ala Val
                740                 745                 750

Glu Asp Val Arg Pro Pro His Lys Val Thr Asp Tyr Ser Ser Ser Ser
                755                 760                 765

Glu Glu Ser Gly Thr Thr Asp Glu Glu Asp Asp Val Glu Gln Glu
770                 775                 780

Gly Ala Asp Glu Ser Thr Ser Gly Pro Glu Asp Thr Arg Ala Ala Ser
785                 790                 795                 800

Ser Leu Asn Leu Ser Asn Gly Glu Thr Glu Ser Val Lys Thr Met Ile
                    805                 810                 815

Val His Asp Asp Val Glu Ser Glu Pro Ala Met Thr Pro Ser Lys Glu
                820                 825                 830

Gly Thr Leu Ile Val Arg Arg Thr Gln Ser Ala Ser Ser Thr Leu Gln
                835                 840                 845

Lys His Lys Ser Ser Ser Ser Phe Thr Pro Phe Ile Asp Pro Arg Leu
    850                 855                 860

Leu Gln Ile Ser Pro Ser Ser Gly Thr Thr Val Thr Ser Val Val Gly
865                 870                 875                 880

Phe Ser Cys Asp Gly Met Arg Pro Glu Ala Ile Arg Gln Asp Pro Thr
                885                 890                 895

Arg Lys Gly Ser Val Val Asn Val Asn Pro Thr Asn Thr Arg Pro Gln
                900                 905                 910

Ser Asp Thr Pro Glu Ile Arg Lys Tyr Lys Lys Arg Phe Asn Ser Glu
            915                 920                 925

Ile Leu Cys Ala Ala Leu Trp Gly Val Asn Leu Leu Val Gly Thr Glu
        930                 935                 940

Ser Gly Leu Met Leu Leu Asp Arg Ser Gly Gln Gly Lys Val Tyr Pro
945                 950                 955                 960

Leu Ile Asn Arg Arg Phe Gln Gln Met Asp Val Leu Glu Gly Leu
                    965                 970                 975

Asn Val Leu Val Thr Ile Ser Gly Lys Lys Asp Lys Leu Arg Val Tyr
                980                 985                 990

Tyr Leu Ser Trp Leu Arg Asn Lys Ile Leu His Asn Asp Pro Glu Val
```

-continued

```
                995                 1000                1005
Glu Lys Lys Gln Gly Trp Thr Thr Val Gly Asp Leu Glu Gly Cys Val
    1010                1015                1020

His Tyr Lys Val Val Lys Tyr Glu Arg Ile Lys Phe Leu Val Ile Ala
1025                1030                1035                1040

Leu Lys Ser Ser Val Glu Val Tyr Ala Trp Ala Pro Lys Pro Tyr His
            1045                1050                1055

Lys Phe Met Ala Phe Lys Ser Phe Gly Glu Leu Val His Lys Pro Leu
        1060                1065                1070

Leu Val Asp Leu Thr Val Glu Glu Gly Gln Arg Leu Lys Val Ile Tyr
    1075                1080                1085

Gly Ser Cys Ala Gly Phe His Ala Val Asp Val Asp Ser Gly Ser Val
    1090                1095                1100

Tyr Asp Ile Tyr Leu Pro Thr His Ile Gln Cys Ser Ile Lys Pro His
1105                1110                1115                1120

Ala Ile Ile Ile Leu Pro Asn Thr Asp Gly Met Glu Leu Leu Val Cys
            1125                1130                1135

Tyr Glu Asp Glu Gly Val Tyr Val Asn Thr Tyr Gly Arg Ile Thr Lys
        1140                1145                1150

Asp Val Val Leu Gln Trp Gly Glu Met Pro Thr Ser Val Ala Tyr Ile
    1155                1160                1165

Arg Ser Asn Gln Thr Met Gly Trp Gly Glu Lys Ala Ile Glu Ile Arg
    1170                1175                1180

Ser Val Glu Thr Gly His Leu Asp Gly Val Phe Met His Lys Arg Ala
1185                1190                1195                1200

Gln Arg Leu Lys Phe Leu Cys Gly Arg Asn Asp Lys Val Phe Phe Ala
            1205                1210                1215

Ser Val Arg Ser Gly Gly Ser Ser Gln Val Tyr Phe Met Thr Leu Gly
        1220                1225                1230

Arg Thr Ser Leu Leu Ser Trp
        1235
```

<210> SEQ ID NO 14
<211> LENGTH: 1297
<212> TYPE: PRT
<213> ORGANISM: Homo sapiens

<400> SEQUENCE: 14

```
Ala Phe Gly Glu Val Tyr Glu Gly Arg His Val Lys Thr Gly Gln Leu
  1               5                  10                  15

Ala Ala Ile Lys Val Met Asp Val Thr Gly Asp Glu Glu Glu Glu Ile
                20                  25                  30

Lys Gln Glu Ile Asn Met Leu Lys Lys Tyr Ser His His Arg Asn Ile
            35                  40                  45

Ala Thr Tyr Tyr Gly Ala Phe Ile Lys Lys Asn Pro Pro Gly Met Asp
        50                  55                  60

Asp Gln Leu Trp Leu Val Met Glu Phe Cys Gly Ala Gly Ser Val Thr
    65                  70                  75                  80

Asp Leu Ile Lys Asn Thr Lys Gly Asn Thr Leu Lys Glu Glu Trp Ile
                85                  90                  95

Ala Tyr Ile Cys Arg Glu Ile Leu Arg Gly Leu Ser His Leu His Gln
                100                 105                 110

His Lys Val Ile His Arg Asp Ile Lys Gly Gln Asn Val Leu Leu Thr
            115                 120                 125
```

-continued

```
Glu Asn Ala Glu Val Lys Leu Val Asp Phe Gly Val Ser Ala Gln Leu
    130                 135                 140
Asp Arg Thr Val Gly Arg Arg Asn Thr Phe Ile Gly Thr Pro Tyr Trp
145                 150                 155                 160
Met Ala Pro Glu Val Ile Ala Cys Asp Glu Asn Pro Asp Ala Thr Tyr
                165                 170                 175
Asp Phe Lys Ser Asp Leu Trp Ser Leu Gly Ile Thr Ala Ile Glu Met
            180                 185                 190
Ala Glu Gly Ala Pro Pro Leu Cys Asp Met His Pro Met Arg Ala Leu
        195                 200                 205
Phe Leu Ile Pro Arg Asn Pro Ala Pro Arg Leu Lys Ser Lys Lys Trp
    210                 215                 220
Ser Lys Lys Phe Gln Ser Phe Ile Glu Ser Cys Leu Val Lys Asn His
225                 230                 235                 240
Ser Gln Arg Pro Ala Thr Glu Gln Leu Met Lys His Pro Phe Ile Arg
                245                 250                 255
Asp Gln Pro Asn Glu Arg Gln Val Arg Ile Gln Leu Lys Asp His Ile
            260                 265                 270
Asp Arg Thr Lys Lys Lys Arg Gly Glu Lys Asp Glu Thr Glu Tyr Glu
        275                 280                 285
Tyr Ser Gly Ser Glu Glu Glu Glu Glu Asn Asp Ser Gly Glu Pro
    290                 295                 300
Ser Ser Ile Leu Asn Leu Pro Arg Glu Ser Thr Leu Arg Arg Asp Phe
305                 310                 315                 320
Leu Arg Leu Gln Leu Ala Asn Lys Glu Arg Ser Glu Ala Leu Arg Arg
                325                 330                 335
Gln Gln Leu Glu Gln Gln Arg Glu Asn Glu His Lys Arg Gln
            340                 345                 350
Leu Leu Ala Glu Arg Gln Lys Arg Ile Glu Gln Lys Glu Gln Arg
        355                 360                 365
Arg Arg Leu Glu Glu Gln Gln Arg Arg Glu Lys Glu Leu Arg Lys Gln
    370                 375                 380
Gln Glu Arg Glu Gln Arg Arg His Tyr Glu Glu Gln Met Arg Arg Glu
385                 390                 395                 400
Glu Glu Arg Arg Arg Ala Glu His Glu Gln Glu Tyr Lys Arg Lys Gln
                405                 410                 415
Leu Glu Glu Gln Arg Gln Ala Glu Arg Leu Gln Arg Gln Leu Lys Gln
            420                 425                 430
Glu Arg Asp Tyr Leu Val Ser Leu Gln His Gln Arg Gln Glu Gln Arg
        435                 440                 445
Pro Val Glu Lys Lys Pro Leu Tyr His Tyr Lys Glu Gly Met Ser Pro
    450                 455                 460
Ser Glu Lys Pro Ala Trp Ala Lys Glu Val Glu Glu Arg Ser Arg Leu
465                 470                 475                 480
Asn Arg Gln Ser Ser Pro Ala Met Pro His Lys Val Ala Asn Arg Ile
                485                 490                 495
Ser Asp Pro Asn Leu Pro Pro Arg Ser Glu Ser Phe Ser Ile Ser Gly
            500                 505                 510
Val Gln Pro Ala Arg Thr Pro Met Leu Arg Pro Val Asp Pro Gln
        515                 520                 525
Ile Pro His Leu Val Ala Val Lys Ser Gln Gly Pro Ala Leu Thr Ala
    530                 535                 540
Ser Gln Ser Val His Glu Gln Pro Thr Lys Gly Leu Ser Gly Phe Gln
```

-continued

```
545                 550                 555                 560
Glu Ala Leu Asn Val Thr Ser His Arg Val Glu Met Pro Arg Gln Asn
                565                 570                 575
Ser Asp Pro Thr Ser Glu Asn Pro Pro Leu Pro Thr Arg Ile Glu Lys
                580                 585                 590
Phe Asp Arg Ser Ser Trp Leu Arg Gln Glu Glu Asp Ile Pro Pro Lys
                595                 600                 605
Val Pro Gln Arg Thr Thr Ser Ile Ser Pro Ala Leu Ala Arg Lys Asn
            610                 615                 620
Ser Pro Gly Asn Gly Ser Ala Leu Gly Pro Arg Leu Gly Ser Gln Pro
625                 630                 635                 640
Ile Arg Ala Ser Asn Pro Asp Leu Arg Arg Thr Glu Pro Ile Leu Glu
                645                 650                 655
Ser Pro Leu Gln Arg Thr Ser Ser Gly Ser Ser Ser Ser Ser Ser Thr
                660                 665                 670
Pro Ser Ser Gln Pro Ser Ser Gln Gly Gly Ser Gln Pro Gly Ser Gln
            675                 680                 685
Ala Gly Ser Ser Glu Arg Thr Arg Val Arg Ala Asn Ser Lys Ser Glu
        690                 695                 700
Gly Ser Pro Val Leu Pro His Glu Pro Ala Lys Val Lys Pro Glu Glu
705                 710                 715                 720
Ser Arg Asp Ile Thr Arg Pro Ser Arg Pro Ala Ser Tyr Lys Lys Ala
                725                 730                 735
Ile Asp Glu Asp Leu Thr Ala Leu Ala Lys Glu Leu Arg Glu Leu Arg
                740                 745                 750
Ile Glu Glu Thr Asn Arg Pro Met Lys Lys Val Thr Asp Tyr Ser Ser
            755                 760                 765
Ser Ser Glu Glu Ser Glu Ser Ser Glu Glu Glu Glu Asp Gly Glu
770                 775                 780
Ser Glu Thr His Asp Gly Thr Val Ala Val Ser Asp Ile Pro Arg Leu
785                 790                 795                 800
Ile Pro Thr Gly Ala Pro Gly Ser Asn Glu Gln Tyr Asn Val Gly Met
                805                 810                 815
Val Gly Thr His Gly Leu Glu Thr Ser His Ala Asp Ser Phe Ser Gly
                820                 825                 830
Ser Ile Ser Arg Glu Gly Thr Leu Met Ile Arg Glu Thr Ser Gly Glu
            835                 840                 845
Lys Lys Arg Ser Gly His Ser Asp Ser Asn Gly Phe Ala Gly His Ile
850                 855                 860
Asn Leu Pro Asp Leu Val Gln Gln Ser His Ser Pro Ala Gly Thr Pro
865                 870                 875                 880
Thr Glu Gly Leu Gly Arg Val Ser Thr His Ser Gln Glu Met Asp Ser
                885                 890                 895
Gly Thr Glu Tyr Gly Met Gly Ser Ser Thr Lys Ala Ser Phe Thr Pro
            900                 905                 910
Phe Val Asp Pro Arg Val Tyr Gln Thr Ser Pro Thr Asp Glu Asp Glu
            915                 920                 925
Glu Asp Glu Glu Ser Ser Ala Ala Ala Leu Phe Thr Gly Glu Leu Leu
        930                 935                 940
Arg Gln Glu Gln Ala Lys Leu Asn Glu Ala Arg Lys Ile Ser Val Val
945                 950                 955                 960
Asn Val Asn Pro Thr Asn Ile Arg Pro His Ser Asp Thr Pro Glu Ile
                965                 970                 975
```

-continued

```
Arg Lys Tyr Lys Lys Arg Phe Asn Ser Glu Ile Leu Cys Ala Ala Leu
            980                 985                 990
Trp Gly Val Asn Leu Leu Val Gly Thr Glu Asn Gly Leu Met Leu Leu
            995                 1000                1005
Asp Arg Ser Gly Gln Gly Lys Val Tyr Asn Leu Ile Asn Arg Arg Arg
    1010                1015                1020
Phe Gln Gln Met Asp Val Leu Glu Gly Leu Asn Val Leu Val Thr Ile
1025                1030                1035                1040
Ser Gly Lys Lys Asn Lys Leu Arg Val Tyr Tyr Leu Ser Trp Leu Arg
            1045                1050                1055
Asn Arg Ile Leu His Asn Asp Pro Glu Val Glu Lys Lys Gln Gly Trp
            1060                1065                1070
Ile Thr Val Gly Asp Leu Glu Gly Cys Ile His Tyr Lys Val Val Lys
            1075                1080                1085
Tyr Glu Arg Ile Lys Phe Leu Val Ile Ala Leu Lys Asn Ala Val Glu
            1090                1095                1100
Ile Tyr Ala Trp Ala Pro Lys Pro Tyr His Lys Phe Met Ala Phe Lys
1105                1110                1115                1120
Ser Phe Ala Asp Leu Gln His Lys Pro Leu Leu Val Asp Leu Thr Val
            1125                1130                1135
Glu Glu Gly Gln Arg Leu Lys Val Ile Phe Gly Ser His Thr Gly Phe
            1140                1145                1150
His Val Ile Asp Val Asp Ser Gly Asn Ser Tyr Asp Ile Tyr Thr Pro
            1155                1160                1165
Ser His Ile Gln Gly Asn Ile Thr Pro His Ala Ile Val Ile Leu Pro
    1170                1175                1180
Lys Thr Asp Gly Met Glu Met Leu Val Cys Tyr Glu Asp Glu Gly Val
1185                1190                1195                1200
Tyr Val Asn Thr Tyr Gly Arg Ile Thr Lys Asp Val Val Leu Gln Trp
            1205                1210                1215
Gly Glu Met Pro Thr Ser Val Ala Tyr Ile His Ser Asn Gln Ile Met
            1220                1225                1230
Gly Trp Gly Glu Lys Ala Ile Glu Ile Arg Ser Val Glu Thr Gly His
            1235                1240                1245
Leu Asp Gly Val Phe Met His Lys Arg Ala Gln Arg Leu Lys Phe Leu
1250                1255                1260
Cys Glu Arg Asn Asp Lys Val Phe Phe Ala Ser Val Arg Ser Gly Gly
1265                1270                1275                1280
Ser Ser Gln Val Phe Phe Met Thr Leu Asn Arg Asn Ser Met Met Asn
            1285                1290                1295
Trp
```

<210> SEQ ID NO 15
<211> LENGTH: 1326
<212> TYPE: PRT
<213> ORGANISM: Homo sapiens

<400> SEQUENCE: 15

```
Ala Phe Gly Glu Val Tyr Glu Gly Arg His Val Lys Thr Gly Gln Leu
  1               5                  10                  15
Ala Ala Ile Lys Val Met Asp Val Thr Glu Asp Glu Glu Glu Glu Ile
            20                  25                  30
Lys Gln Glu Ile Asn Met Leu Lys Lys Tyr Ser His His Arg Asn Ile
            35                  40                  45
```

-continued

```
Ala Thr Tyr Tyr Gly Ala Phe Ile Lys Lys Ser Pro Pro Gly Asn Asp
 50                  55                  60

Asp Gln Leu Trp Leu Val Met Glu Phe Cys Gly Ala Gly Ser Val Thr
 65                  70                  75                  80

Asp Leu Val Lys Asn Thr Lys Gly Asn Ala Leu Lys Glu Asp Cys Ile
                 85                  90                  95

Ala Tyr Ile Cys Arg Glu Ile Leu Arg Gly Leu Ala His Leu His Ala
            100                 105                 110

His Lys Val Ile His Arg Asp Ile Lys Gly Gln Asn Val Leu Leu Thr
        115                 120                 125

Glu Asn Ala Glu Val Lys Leu Val Asp Phe Gly Val Ser Ala Gln Leu
130                 135                 140

Asp Arg Thr Val Gly Arg Arg Asn Thr Phe Ile Gly Thr Pro Tyr Trp
145                 150                 155                 160

Met Ala Pro Glu Val Ile Ala Cys Asp Glu Asn Pro Asp Ala Thr Tyr
                165                 170                 175

Asp Tyr Arg Ser Asp Ile Trp Ser Leu Gly Ile Thr Ala Ile Glu Met
            180                 185                 190

Ala Glu Gly Ala Pro Pro Leu Cys Asp Met His Pro Met Arg Ala Leu
        195                 200                 205

Phe Leu Ile Pro Arg Asn Pro Pro Arg Leu Lys Ser Lys Lys Trp
210                 215                 220

Ser Lys Lys Phe Ile Asp Phe Ile Asp Thr Cys Leu Ile Lys Thr Tyr
225                 230                 235                 240

Leu Ser Arg Pro Pro Thr Glu Gln Leu Leu Lys Phe Pro Phe Ile Arg
                245                 250                 255

Asp Gln Pro Thr Glu Arg Gln Val Arg Ile Gln Leu Lys Asp His Ile
            260                 265                 270

Asp Arg Ser Arg Lys Lys Arg Gly Glu Lys Glu Thr Glu Tyr Glu
        275                 280                 285

Tyr Ser Gly Ser Glu Glu Glu Asp Asp Ser His Gly Glu Glu Gly Glu
290                 295                 300

Pro Ser Ser Ile Met Asn Val Pro Gly Glu Ser Thr Leu Arg Arg Glu
305                 310                 315                 320

Phe Leu Arg Leu Gln Gln Glu Asn Lys Ser Asn Ser Glu Ala Leu Lys
                325                 330                 335

Gln Gln Gln Gln Leu Gln Gln Gln Gln Arg Asp Pro Glu Ala His
            340                 345                 350

Ile Lys His Leu Leu His Gln Arg Gln Arg Ile Glu Gly Gln Lys
        355                 360                 365

Glu Glu Arg Arg Arg Val Glu Glu Gln Arg Arg Glu Arg Glu Gln
370                 375                 380

Arg Lys Leu Gln Glu Lys Glu Gln Arg Arg Leu Glu Asp Met Gln
385                 390                 395                 400

Ala Leu Arg Arg Glu Glu Glu Arg Arg Gln Ala Glu Arg Glu Gln Glu
                405                 410                 415

Tyr Ile Arg His Arg Leu Glu Glu Glu Gln Arg Gln Leu Glu Ile Leu
            420                 425                 430

Gln Gln Gln Leu Leu Gln Glu Ala Leu Leu Glu Tyr Lys Arg
        435                 440                 445

Lys Gln Leu Glu Glu Gln Arg Gln Ser Glu Arg Leu Gln Arg Gln Leu
450                 455                 460
```

-continued

```
Gln Gln Glu His Ala Tyr Leu Lys Ser Leu Gln Gln Gln Gln Gln
465                 470                 475                 480

Gln Gln Leu Gln Lys Gln Gln Gln Gln Leu Leu Pro Gly Asp Arg
            485                 490                 495

Lys Pro Leu Tyr His Tyr Gly Arg Gly Met Asn Pro Ala Asp Lys Pro
                500                 505                 510

Ala Trp Ala Arg Glu Val Glu Arg Thr Arg Met Asn Lys Gln Gln
            515                 520                 525

Asn Ser Pro Leu Ala Lys Ser Lys Pro Gly Ser Thr Gly Pro Glu Pro
530                 535                 540

Pro Ile Pro Gln Ala Ser Pro Gly Pro Gly Pro Leu Ser Gln Thr
545                 550                 555                 560

Pro Pro Met Gln Arg Pro Val Glu Pro Gln Glu Gly Pro His Lys Ser
                565                 570                 575

Leu Val Ala His Arg Val Pro Leu Lys Pro Tyr Ala Ala Pro Val Pro
                580                 585                 590

Arg Ser Gln Ser Leu Gln Asp Gln Pro Thr Arg Asn Leu Ala Ala Phe
                595                 600                 605

Pro Ala Ser His Asp Pro Asp Pro Ala Ile Pro Ala Pro Thr Ala Thr
610                 615                 620

Pro Ser Ala Arg Gly Ala Val Ile Arg Gln Asn Ser Asp Pro Thr Ser
625                 630                 635                 640

Glu Gly Pro Gly Pro Ser Pro Asn Pro Pro Ala Trp Val Arg Pro Asp
                645                 650                 655

Asn Glu Ala Pro Pro Lys Val Pro Gln Arg Thr Ser Ser Ile Ala Thr
                660                 665                 670

Ala Leu Asn Thr Ser Gly Ala Gly Gly Ser Arg Pro Ala Gln Ala Val
            675                 680                 685

Arg Ala Arg Pro Arg Ser Asn Ser Ala Trp Gln Ile Tyr Leu Gln Arg
690                 695                 700

Arg Ala Glu Arg Gly Thr Pro Lys Pro Pro Gly Pro Pro Ala Gln Pro
705                 710                 715                 720

Pro Gly Pro Pro Asn Ala Ser Ser Asn Pro Asp Leu Arg Arg Ser Asp
                725                 730                 735

Pro Gly Trp Glu Arg Ser Asp Ser Val Leu Pro Ala Ser His Gly His
            740                 745                 750

Leu Pro Gln Ala Gly Ser Leu Glu Arg Asn Arg Val Gly Val Ser Ser
            755                 760                 765

Lys Pro Asp Ser Ser Pro Val Leu Ser Pro Gly Asn Lys Ala Lys Pro
770                 775                 780

Asp Asp His Arg Ser Arg Pro Gly Arg Pro Ala Asp Phe Val Leu Leu
785                 790                 795                 800

Lys Glu Arg Thr Leu Asp Glu Ala Pro Arg Pro Lys Lys Ala Met
            805                 810                 815

Asp Tyr Ser Ser Ser Ser Glu Glu Val Glu Ser Ser Glu Asp Asp Glu
                820                 825                 830

Glu Glu Gly Glu Gly Gly Pro Ala Glu Gly Ser Arg Asp Thr Pro Gly
            835                 840                 845

Gly Arg Asp Gly Asp Thr Asp Ser Val Ser Thr Met Val Val His Asp
            850                 855                 860

Val Glu Glu Ile Thr Gly Thr Gln Pro Pro Tyr Gly Gly Gly Thr Met
865                 870                 875                 880

Val Val Gln Arg Thr Pro Glu Glu Glu Arg Asn Leu Leu His Ala Asp
```

-continued

```
                    885                 890                 895
Ser Asn Gly Tyr Thr Asn Leu Pro Asp Val Val Gln Pro Ser His Ser
                900                 905                 910
Pro Thr Glu Asn Ser Lys Gly Gln Ser Pro Ser Lys Asp Gly Ser
            915                 920                 925
Gly Asp Tyr Gln Ser Arg Gly Leu Val Lys Ala Pro Gly Lys Ser Ser
        930                 935                 940
Phe Thr Met Phe Val Asp Leu Gly Ile Tyr Gln Pro Gly Gly Ser Gly
945                 950                 955                 960
Asp Ser Ile Pro Ile Thr Ala Leu Val Gly Glu Gly Thr Arg Leu
                965                 970                 975
Asp Gln Leu Gln Tyr Asp Val Arg Lys Gly Ser Val Val Asn Val Asn
            980                 985                 990
Pro Thr Asn Thr Arg Ala His Ser Glu Thr Pro Glu Ile Arg Lys Tyr
        995                 1000                1005
Lys Lys Arg Phe Asn Ser Glu Ile Leu Cys Ala Ala Leu Trp Gly Val
    1010                1015                1020
Asn Leu Leu Val Gly Thr Glu Asn Gly Leu Met Leu Leu Asp Arg Ser
1025                1030                1035                1040
Gly Gln Gly Lys Val Tyr Gly Leu Ile Gly Arg Arg Arg Phe Gln Gln
            1045                1050                1055
Met Asp Val Leu Glu Gly Leu Asn Leu Leu Ile Thr Ile Ser Gly Lys
        1060                1065                1070
Arg Asn Lys Leu Arg Val Tyr Tyr Leu Ser Trp Leu Arg Asn Lys Ile
            1075                1080                1085
Leu His Asn Asp Pro Glu Val Glu Lys Lys Gln Gly Trp Thr Thr Val
    1090                1095                1100
Gly Asp Met Glu Gly Cys Gly His Tyr Arg Val Val Lys Tyr Glu Arg
1105                1110                1115                1120
Ile Lys Phe Leu Val Ile Ala Leu Lys Ser Ser Val Glu Val Tyr Ala
            1125                1130                1135
Trp Ala Pro Lys Pro Tyr His Lys Phe Met Ala Phe Lys Ser Phe Ala
        1140                1145                1150
Asp Leu Pro His Arg Pro Leu Leu Val Asp Leu Thr Val Glu Glu Gly
            1155                1160                1165
Gln Arg Leu Lys Val Ile Tyr Gly Ser Ser Ala Gly Phe His Ala Val
    1170                1175                1180
Asp Val Asp Ser Gly Asn Ser Tyr Asp Ile Tyr Ile Pro Val His Ile
1185                1190                1195                1200
Gln Ser Gln Ile Thr Pro His Ala Ile Ile Phe Leu Pro Asn Thr Asp
            1205                1210                1215
Gly Met Glu Met Leu Leu Cys Tyr Glu Asp Glu Gly Val Tyr Val Asn
        1220                1225                1230
Thr Tyr Gly Arg Ile Ile Lys Asp Val Val Leu Gln Trp Gly Glu Met
            1235                1240                1245
Pro Thr Ser Val Ala Tyr Ile Cys Ser Asn Gln Ile Met Gly Trp Gly
    1250                1255                1260
Glu Lys Ala Ile Glu Ile Arg Ser Val Glu Thr Gly His Leu Asp Gly
1265                1270                1275                1280
Val Phe Met His Lys Arg Ala Gln Arg Leu Lys Phe Leu Cys Glu Arg
            1285                1290                1295
Asn Asp Lys Val Phe Phe Ala Ser Val Arg Ser Gly Gly Ser Ser Gln
        1300                1305                1310
```

```
Val Tyr Phe Met Thr Leu Asn Arg Asn Arg Ile Met Asn Trp
        1315                1320                1325

<210> SEQ ID NO 16
<211> LENGTH: 349
<212> TYPE: PRT
<213> ORGANISM: Homo sapiens

<400> SEQUENCE: 16

Asn Val Asn Pro Leu Tyr Val Ser Pro Ala Cys Lys Lys Pro Leu Ile
  1               5                  10                  15

His Met Tyr Glu Lys Glu Phe Thr Ser Glu Ile Cys Cys Gly Ser Leu
             20                  25                  30

Trp Gly Val Asn Leu Leu Leu Gly Thr Arg Ser Asn Leu Tyr Leu Met
         35                  40                  45

Asp Arg Ser Gly Lys Ala Asp Ile Thr Lys Leu Ile Arg Arg Arg Pro
     50                  55                  60

Phe Arg Gln Ile Gln Val Leu Glu Pro Leu Asn Leu Leu Ile Thr Ile
 65                  70                  75                  80

Ser Gly His Lys Asn Arg Leu Arg Val Tyr His Leu Thr Trp Leu Arg
                 85                  90                  95

Asn Lys Ile Leu Asn Asn Asp Pro Glu Ser Lys Arg Arg Gln Glu Glu
            100                 105                 110

Met Leu Lys Thr Glu Glu Ala Cys Lys Ala Ile Asp Lys Leu Thr Gly
        115                 120                 125

Cys Glu His Phe Ser Val Leu Gln His Glu Glu Thr Thr Tyr Ile Ala
130                 135                 140

Ile Ala Leu Lys Ser Ser Ile His Leu Tyr Ala Trp Ala Pro Lys Ser
145                 150                 155                 160

Phe Asp Glu Ser Thr Ala Ile Lys Val Phe Pro Thr Leu Asp His Lys
                165                 170                 175

Pro Val Thr Val Asp Leu Ala Ile Gly Ser Glu Lys Arg Leu Lys Ile
            180                 185                 190

Phe Phe Ser Ser Ala Asp Gly Tyr His Leu Ile Asp Ala Glu Ser Glu
        195                 200                 205

Val Met Ser Asp Val Thr Leu Pro Lys Asn Pro Leu Glu Ile Ile Ile
    210                 215                 220

Pro Gln Asn Ile Ile Ile Leu Pro Asp Cys Leu Gly Ile Gly Met Met
225                 230                 235                 240

Leu Thr Phe Asn Ala Glu Ala Leu Ser Val Glu Ala Asn Glu Gln Leu
                245                 250                 255

Phe Lys Lys Ile Leu Glu Met Trp Lys Asp Ile Pro Ser Ser Ile Ala
            260                 265                 270

Phe Glu Cys Thr Gln Arg Thr Thr Gly Trp Gly Gln Lys Ala Ile Glu
        275                 280                 285

Val Arg Ser Leu Gln Ser Arg Val Leu Glu Ser Glu Leu Lys Arg Arg
    290                 295                 300

Ser Ile Lys Lys Leu Arg Phe Leu Cys Thr Arg Gly Asp Lys Leu Phe
305                 310                 315                 320

Phe Thr Ser Thr Leu Arg Asn His His Ser Arg Val Tyr Phe Met Thr
                325                 330                 335

Leu Gly Lys Leu Glu Glu Leu Gln Ser Asn Tyr Asp Val
            340                 345
```

```
<210> SEQ ID NO 17
<211> LENGTH: 4023
<212> TYPE: DNA
<213> ORGANISM: Homo sapiens

<400> SEQUENCE: 17
ccgccatgaa ccccggcttc gatttgtccc gccggaaccc gcaggaggac ttcgagctga      60
ttcagcgcat cggcagcggc acctacggcg acgtctacaa ggcacggaat gttaacactg     120
gtgaattagc agcaattaaa gtaataaaat tggaaccagg agaagacttt gcagttgtgc     180
agcaagaaat tattatgatg aaagactgta acacccaaa tattgttgct tattttggaa      240
gctatctcag gcgagataag ctttggattt gcatggagtt ttgtggaggt ggttctttac     300
aggatattta tcacgtaact ggacctctgt cagaactgca aattgcatat gttagcagag     360
aaacactgca gggattatat tatcttcaca gtaaaggaaa aatgcacaga gatataaagg     420
gagctaacat tctattaacg gataatggtc atgtgaaatt ggctgatttt ggagtatctg     480
cacagataac agctacaatt gccaaacgga agtctttcat tggcacacca tattggatgg     540
ctccagaagt tgcagctgtt gagaggaagg ggggttacaa tcaactctgt gatctctggg     600
cagtgggaat cactgccata gaacttgcag agcttcagcc tcctatgttt gacttacacc     660
caatgagagc attatttcta atgacaaaaa gcaattttca gcctcctaaa ctaaaggata     720
aaatgaaatg gtcaaatagt tttcatcact ttgtgaaaat ggcacttacc aaaaatccga     780
aaaaagacc tactgctgaa aaattattac agcatccttt tgtaacacaa catttgacac     840
ggtctttggc aatcgagctg ttggataaag taaataatcc agatcattcc acttaccatg     900
atttcgatga tgatgatcct gagcctcttg ttgctgtacc acatagaatt cactcaacaa     960
gtagaaacgt gagagaagaa aaaacacgct cagagataac ctttggccaa gtgaaatttg    1020
atccacccctt aagaaggag acagaaccac atcatgaact tcccgacagt gatggttttt    1080
tggacagttc agaagaaata tactacactg caagatctaa tctggatctg caactggaat    1140
atggacaagg acaccaaggt ggttactttt taggtgcaaa caagagtctt ctcaagtctg    1200
ttgaagaaga attgcatcag cgaggacacg tcgcacattt agaagatgat gaaggagatg    1260
atgatgaatc taaacactca actctgaaag caaaaattcc acctcctttg ccaccaaagc    1320
ctaagtctat cttcatacca caggaaatgc attctactga ggatgaaaat caaggaacaa    1380
tcaagagatg tcccatgtca gggagcccag caaagccatc ccaagttcca cctagaccac    1440
cacctcccag attaccccca cacaaacctg ttgccttagg aaatggaatg agctccttcc    1500
agttaaatgg tgaacgagat ggctcattat gtcaacaaca gaatgaacat agaggcacaa    1560
acctttcaag aaaagaaaag aaagatgtac caaagcctat tagtaatggt cttcctccaa    1620
cacctaaagt gcatatgggt gcatgttttt caaaagtttt taatgggtgt cccttgaaaa    1680
ttcactgtgc atcatcatgg ataaacccag atacaagaga tcagtacttg atatttggtg    1740
ccgaagaagg gatttatacc ctcaatctta tgaacttca tgaaacatca atggaacagc    1800
tattccctcg aagtgtaca tggttgtatg taatgaacaa ttgcttgcta tcaatatctg    1860
gtaaagcttc tcagctttat tcccataatt taccagggct ttttgattat gcaagacaaa    1920
tgcaaaagtt acctgttgct attccagcac acaaactccc tgacagaata ctgccaagga    1980
aattttctgt atcagcaaaa atccctgaaa ccaaatggtg ccagaagtgt tgtgttgtaa    2040
gaatccttta cacgggccat aaatacctat gtggagcact tcagactagc attgttctat    2100
tagaatgggt tgaaccaatg cagaaattta tgttaattaa gcacatagat tttcctatac    2160
```

```
                                                                -continued catgtccact  tagaatgttt  gaaatgctgg  tagttcctga  acaggagtac  cctttagttt   2220
gtgttggtgt  cagtagaggt  agagacttca  accaagtggt  tcgatttgag  acggtcaatc   2280
caaattctac  ctcttcatgg  tttacagaat  cagataccc   acagacaaat  gttactcatg   2340
taacccaact  ggagagagat  accatccttg  tatgcttgga  ctgttgtata  aaatagtaa    2400 atctccaagg  aagattaaaa  tctagcagga  aattgtcatc  agaactcacc  tttgatttcc   2460
agattgaatc  aatagtgtgc  ctacaagaca  gtgtgctagc  tttctggaaa  catggaatgc   2520
aaggtagaag  ttttagatct  aatgaggtaa  cacaagaaat  tcagatagc   acaagaattt   2580 tcaggctgct  tggatctgac  agggtcgtgg  ttttggaaag  taggccaact  gataacccca   2640
cagcaaatag  caatttgtac  atcctggcgg  gtcatgaaaa  cagttactga  gaattgttgt   2700
gctttgacag  ttaactctag  aaagaaagaa  cactaccact  gcaacattaa  tggatgcttg   2760
aagctgtaca  aaagctgcag  taacctgtct  tcagttactt  tgtaatttat  tgtggcatga   2820
gataagatgg  ggaaaatttt  gttttaagtg  gtatggatat  atttagcata  ttgaaccaca   2880
caagtgctta  attcattgtt  atgtaatctt  tgtacatata  ggcagtattt  tttctgtgaa   2940
acttcatatt  gctgaagaca  tacactaaga  atttatgtag  ataatgtact  tttatgagat   3000
gtacaagtaa  gtgtcttatc  tgtacagatg  taaatgttga  tgaaaatgca  attggggtta   3060
atattttaag  aattctttag  tatattcttg  ggtgtggcta  tattacaaaa  tgggatgctg   3120
gcaatgaaac  aatacattta  acactattgt  atttttatta  tatgtaattt  agtaatatga   3180
atataaatct  tgtaacttt   aaaattgtaa  tggaggctgt  aatcatttta  taatctttt    3240 aatttttaatg  caagtacact  ggtgtttata  tttgcacaaa  gtattgatat  gtgatgtatt  3300
aagtcacaaa  agtaagctgt  gacattgtct  ataagcattt  ggctccacaa  atgtatttgg   3360
attgttttct  atgtgaagca  aaccaattat  aattaaccac  atgttgtagt  aactggtctt   3420
tttatattta  agcagaatcc  tgtaagattg  cttgtctttg  cttaaaaaca  atacctttga   3480 acattttga   atcacagaat  agcggtacca  tgatagaata  ctgcaattgt  ggtcagaatt   3540
acagtatgca  caaagaatta  attagcatta  ttaaagagtc  ctcactaaac  atttcatatg   3600
atcacactga  agaactgtaa  cattccatag  agtgaagtgg  ttcaaatttc  tcttggaatt   3660 tttactttg   ttggccttat  tttatgatcc  ttttcatatt  tctttgact   tagagtatta   3720 atacatggcc  aaaataattt  agttactacc  tcatacaaac  aatataatgg  ttactacaca   3780
tcacaggaac  ttagttttgg  tttaagtcat  ttttgattgc  tttttccaa   tggaatatgt   3840 ataccagg    ttttagcaaa  atgcacactt  ttggctcttt  ttggtatatg  ttctttatat   3900
tttaatgtga  gtatatacac  taagaacaaa  ctaaattgtg  atttatgatc  ttcatttatt   3960
ttaatgataa  tggttttaaa  atatgttcct  gattgtacat  attgtaaaat  aaacatgttt   4020
ttt                                                                     4023
```

<210> SEQ ID NO 18
<211> LENGTH: 894
<212> TYPE: PRT
<213> ORGANISM: Homo sapiens

<400> SEQUENCE: 18

```
Met Asn Pro Gly Phe Asp Leu Ser Arg Arg Asn Pro Gln Glu Asp Phe
  1               5                  10                  15

Glu Leu Ile Gln Arg Ile Gly Ser Gly Thr Tyr Gly Asp Val Tyr Lys
             20                  25                  30

Ala Arg Asn Val Asn Thr Gly Glu Leu Ala Ala Ile Lys Val Ile Lys
```

-continued

```
                 35                  40                  45
Leu Glu Pro Gly Glu Asp Phe Ala Val Gln Gln Glu Ile Ile Met
         50                  55                  60
Met Lys Asp Cys Lys His Pro Asn Ile Val Ala Tyr Phe Gly Ser Tyr
 65                  70                  75                  80
Leu Arg Arg Asp Lys Leu Trp Ile Cys Met Glu Phe Cys Gly Gly
                 85                  90                  95
Ser Leu Gln Asp Ile Tyr His Val Thr Gly Pro Leu Ser Glu Leu Gln
                100                 105                 110
Ile Ala Tyr Val Ser Arg Glu Thr Leu Gln Gly Leu Tyr Tyr Leu His
                115                 120                 125
Ser Lys Gly Lys Met His Arg Asp Ile Lys Gly Ala Asn Ile Leu Leu
        130                 135                 140
Thr Asp Asn Gly His Val Lys Leu Ala Asp Phe Gly Val Ser Ala Gln
145                 150                 155                 160
Ile Thr Ala Thr Ile Ala Lys Arg Lys Ser Phe Ile Gly Thr Pro Tyr
                    165                 170                 175
Trp Met Ala Pro Glu Val Ala Ala Val Glu Arg Lys Gly Gly Tyr Asn
            180                 185                 190
Gln Leu Cys Asp Leu Trp Ala Val Gly Ile Thr Ala Ile Glu Leu Ala
        195                 200                 205
Glu Leu Gln Pro Pro Met Phe Asp Leu His Pro Met Arg Ala Leu Phe
210                 215                 220
Leu Met Thr Lys Ser Asn Phe Gln Pro Pro Lys Leu Lys Asp Lys Met
225                 230                 235                 240
Lys Trp Ser Asn Ser Phe His His Phe Val Lys Met Ala Leu Thr Lys
                    245                 250                 255
Asn Pro Lys Lys Arg Pro Thr Ala Glu Lys Leu Leu Gln His Pro Phe
                260                 265                 270
Val Thr Gln His Leu Thr Arg Ser Leu Ala Ile Glu Leu Leu Asp Lys
            275                 280                 285
Val Asn Asn Pro Asp His Ser Thr Tyr His Asp Phe Asp Asp Asp
        290                 295                 300
Pro Glu Pro Leu Val Ala Val Pro His Arg Ile His Ser Thr Ser Arg
305                 310                 315                 320
Asn Val Arg Glu Glu Lys Thr Arg Ser Glu Ile Thr Phe Gly Gln Val
                    325                 330                 335
Lys Phe Asp Pro Pro Leu Arg Lys Glu Thr Glu Pro His His Glu Leu
                340                 345                 350
Pro Asp Ser Asp Gly Phe Leu Asp Ser Ser Glu Ile Tyr Tyr Thr
            355                 360                 365
Ala Arg Ser Asn Leu Asp Leu Gln Leu Glu Tyr Gly Gln Gly His Gln
        370                 375                 380
Gly Gly Tyr Phe Leu Gly Ala Asn Lys Ser Leu Leu Lys Ser Val Glu
385                 390                 395                 400
Glu Glu Leu His Gln Arg Gly His Val Ala His Leu Glu Asp Asp Glu
                    405                 410                 415
Gly Asp Asp Asp Glu Ser Lys His Ser Thr Leu Lys Ala Lys Ile Pro
                420                 425                 430
Pro Pro Leu Pro Pro Lys Pro Lys Ser Ile Phe Ile Pro Gln Glu Met
            435                 440                 445
His Ser Thr Glu Asp Glu Asn Gln Gly Thr Ile Lys Arg Cys Pro Met
450                 455                 460
```

-continued

```
Ser Gly Ser Pro Ala Lys Pro Ser Gln Val Pro Pro Arg Pro Pro
465                 470                 475                 480

Pro Arg Leu Pro Pro His Lys Pro Val Ala Leu Gly Asn Gly Met Ser
            485                 490                 495

Ser Phe Gln Leu Asn Gly Glu Arg Asp Gly Ser Leu Cys Gln Gln Gln
        500                 505                 510

Asn Glu His Arg Gly Thr Asn Leu Ser Arg Lys Glu Lys Lys Asp Val
    515                 520                 525

Pro Lys Pro Ile Ser Asn Gly Leu Pro Pro Thr Pro Lys Val His Met
530                 535                 540

Gly Ala Cys Phe Ser Lys Val Phe Asn Gly Cys Pro Leu Lys Ile His
545                 550                 555                 560

Cys Ala Ser Ser Trp Ile Asn Pro Asp Thr Arg Asp Gln Tyr Leu Ile
                565                 570                 575

Phe Gly Ala Glu Gly Ile Tyr Thr Leu Asn Leu Asn Glu Leu His
            580                 585                 590

Glu Thr Ser Met Glu Gln Leu Phe Pro Arg Arg Cys Thr Trp Leu Tyr
        595                 600                 605

Val Met Asn Asn Cys Leu Leu Ser Ile Ser Gly Lys Ala Ser Gln Leu
    610                 615                 620

Tyr Ser His Asn Leu Pro Gly Leu Phe Asp Tyr Ala Arg Gln Met Gln
625                 630                 635                 640

Lys Leu Pro Val Ala Ile Pro Ala His Lys Leu Pro Asp Arg Ile Leu
                645                 650                 655

Pro Arg Lys Phe Ser Val Ser Ala Lys Ile Pro Glu Thr Lys Trp Cys
            660                 665                 670

Gln Lys Cys Cys Val Val Arg Asn Pro Tyr Thr Gly His Lys Tyr Leu
        675                 680                 685

Cys Gly Ala Leu Gln Thr Ser Ile Val Leu Leu Glu Trp Val Glu Pro
    690                 695                 700

Met Gln Lys Phe Met Leu Ile Lys His Ile Asp Phe Pro Ile Pro Cys
705                 710                 715                 720

Pro Leu Arg Met Phe Glu Met Leu Val Val Pro Glu Gln Glu Tyr Pro
                725                 730                 735

Leu Val Cys Val Gly Val Ser Arg Gly Arg Asp Phe Asn Gln Val Val
            740                 745                 750

Arg Phe Glu Thr Val Asn Pro Asn Ser Thr Ser Ser Trp Phe Thr Glu
        755                 760                 765

Ser Asp Thr Pro Gln Thr Asn Val Thr His Val Thr Gln Leu Glu Arg
    770                 775                 780

Asp Thr Ile Leu Val Cys Leu Asp Cys Cys Ile Lys Ile Val Asn Leu
785                 790                 795                 800

Gln Gly Arg Leu Lys Ser Ser Arg Lys Leu Ser Ser Glu Leu Thr Phe
                805                 810                 815

Asp Phe Gln Ile Glu Ser Ile Val Cys Leu Gln Asp Ser Val Leu Ala
            820                 825                 830

Phe Trp Lys His Gly Met Gln Gly Arg Ser Phe Arg Ser Asn Glu Val
        835                 840                 845

Thr Gln Glu Ile Ser Asp Ser Thr Arg Ile Phe Arg Leu Leu Gly Ser
    850                 855                 860

Asp Arg Val Val Val Leu Glu Ser Arg Pro Thr Asp Asn Pro Thr Ala
865                 870                 875                 880
```

Asn Ser Asn Leu Tyr Ile Leu Ala Gly His Glu Asn Ser Tyr
            885                 890

<210> SEQ ID NO 19
<211> LENGTH: 4196
<212> TYPE: DNA
<213> ORGANISM: Homo sapiens

<400> SEQUENCE: 19

| | | | | | |
|---|---|---|---|---|---|
| gggagggtcc | ttgtggcgcc | gggcggcggg | gtcctgcgtg | gagagtggga | cgcaacgccg | 60 |
| agaccgcgag | cagaggctgc | gcacagccgg | atccggcact | cagcgaccgg | acccaaggat | 120 |
| ccgccgggga | acaagccaca | ggagagcgac | tcaggaacaa | gtgtgggaga | ggaagcggcg | 180 |
| gcggcggcgc | cgggcccggg | ggtggtgaca | gcaggtctga | ggttgcatca | taaatacaaa | 240 |
| ggactgaagt | tataaaagag | aaaagagaag | tttgctgcta | aaatgaatct | gagcaatatg | 300 |
| gaatattttg | tgccacacac | aaaaaggtac | tgaagattta | cccccaaaa | aaaattgtca | 360 |
| atgagaaata | aagctaactg | atatcaaaaa | gcagagcctg | ctctactggc | catcatgcgt | 420 |
| aaagggtgc | tgaaggaccc | agagattgac | gatctattct | acaaagatga | tcctgaggaa | 480 |
| ctttttattg | gtttgcatga | aattggacat | ggaagttttg | gagcagttta | ttttgctaca | 540 |
| aatgctcaca | ccaatgaggt | ggtggcaatt | aagaagatgt | cctatagtgg | gaagcagacc | 600 |
| catgagaaat | ggcaagatat | tcttaaggaa | gttaaatttt | tacgacaatt | gaagcatcct | 660 |
| aatactattg | agtacaaagg | ctgttacttg | aaagaacaca | ctgcttggtt | ggtgatggaa | 720 |
| tattgcttag | gctcagcctc | tgatttatta | gaagttcata | aaaaaccact | tcaggaagtg | 780 |
| gagatcgctg | ccattactca | tggagccttg | catggactag | cctacctaca | ttctcatgca | 840 |
| ttgattcata | gggatattaa | agcaggaaat | attcttctaa | cagagccagg | tcaggtaaaa | 900 |
| ctagctgatt | ttggatctgc | ttcaatggct | tctcctgcca | actccttcgt | gggcacacct | 960 |
| tactggatgg | ctccagaggt | gatcttagct | atggatgaag | acagtatga | tgggaaagtt | 1020 |
| gatatttggt | cacttggcat | cacttgtatt | gaattggcgg | aacggaagcc | gccccttttc | 1080 |
| aacatgaatg | caatgagtgc | cttatatcac | attgcccaga | atgactcccc | aacgttacag | 1140 |
| tctaatgaat | ggacagactc | ctttaggaga | tttgttgatt | actgcttgca | gaaaatacct | 1200 |
| caggaaaggc | caacatcagc | agaactatta | aggcatgact | tgttcgacg | agaccggcca | 1260 |
| ctacgtgtcc | tcattgacct | catacagagg | acaaaagatg | cagttcgtga | gctagataac | 1320 |
| ctacagtacc | gaaaaatgaa | aaaaatactt | ttccaagaga | cacggaatgg | acccttgaat | 1380 |
| gagtcacagg | aggatgagga | agacagtgaa | catggaacca | gcctgaacag | ggaaatggac | 1440 |
| agcctgggca | gcaaccattc | cattccaagc | atgtccgtga | gcacaggcag | ccagagcagc | 1500 |
| agtgtgaaca | gcatgcagga | agtcatggac | gagagcagtt | ccgaacttgt | catgatgcac | 1560 |
| gatgacgaaa | gcaacatcaa | ttccagctcc | tccgtcgtgc | ataagaaaga | tcatgtattc | 1620 |
| acaagggatg | aggcgggcca | cggcgatccc | aggcctgagc | cgcggcctac | ccagtcagtt | 1680 |
| cagagccagg | ccctccacta | ccggaacaga | gagcgctttg | ccacgatcaa | atcagcatct | 1740 |
| ttggttacac | gacagatcca | tgagcatgag | caggagaacg | agttgcggga | acagatgtca | 1800 |
| ggttataagc | ggatgcggcg | ccagcaccag | aagcagctga | tcgccctgga | gaacaagctg | 1860 |
| aaggctgaga | tggacgagca | ccgcctcaag | ctacagaagg | aggtggagac | gcatgccaac | 1920 |
| aactcgtcca | tcgagctgga | gaagctggcc | aagaagcaag | tggctatcat | agaaaaggag | 1980 |
| gcaaaggtag | ctgcagcaga | tgagaagaag | ttccagcaac | agatcttggc | ccagcagaag | 2040 |

-continued

```
aaagatttga caactttctt agaaagtcag aagaagcagt ataagatttg taaggaaaaa    2100
ataaaagagg aaatgaatga ggaccatagc acacccaaga aagagaagca agagcggatc    2160
tccaaacata aagagaactt gcagcacaca caggctgaag aggaagccca ccttctcact    2220
caacagagac tgtactacga caaaaattgt cgtttcttca agcggaaaat aatgatcaag    2280
cggcacgagg tggagcagca gaacattcgg gaggaactaa ataaaaagag gacccagaag    2340
gagatggagc atgccatgct aatccggcac gacgagtcca cccgagagct agagtacagg    2400
cagctgcaca cgttacagaa gctacgcatg gatctgatcc gtttacagca ccagacggaa    2460
ctggaaaacc agctggagta caataagagg cgagaaagag aactgcacag aaagcatgtc    2520
atgggacttc ggcaacagcc aaaaaactta aaggccatgg aaatgcaaat taaaaaacag    2580
tttcaggaca cttgcaaagt acagaccaaa cagtataaag cactcaagaa tcaccagttg    2640
gaagttactc caaagaatga gcacaaaaca atcttaaaga cactgaaaga tgagcagaca    2700
agaaaacttg ccattttggc agagcagtat gaacagagta taaatgaaat gatggcctct    2760
caagcgttac ggctagatga ggctcaagaa gcagaatgcc aggccttgag gctacagctc    2820
cagcaggaaa tggagctgct caacgcctac cagagcaaaa tcaagatgca aacagaggca    2880
caacatgaac gtgagctcca gaagctagag cagagagtgt ctctgcgcag agcacacctt    2940
gagcagaaga ttgaagagga gctggctgcc cttcagaagg aacgcagcga gagaataaag    3000
aacctattgg aaaggcaaga gcgagagatt gaaactttg acatggagag cctcagaatg    3060
ggatttggga atttggttac attagatttt cctaaggagg actacagatg agattaaatt    3120
ttttgccatt tacaaaaaaa aaaaaaaaaa agaaaacaga aaaaaattca gaccctgcaa    3180
aaccacattc cccattttaa cgggcgttgc tctcactctc tctctctctt actcttactg    3240
acatcgtgtc ggactagtgc ctgtttattc ttactccatc aggggccccc ttcctccccc    3300
cgtgtcaact ttcagtgctg gccaaaacct ggccgtctct tctattcaca gtacgtca     3360 cagtattgat gtgattcaaa atgtttcagt gaaactttg gagacagttt taacaaaacc    3420
aataaaccaa caacaaaaaa agtggatgta tattgcttta agcaatcact cattaccacc    3480
aatctgtgaa agtaaagcaa aaaataataa taataaatgc caaggggggag agagacacaa    3540 tatccgcagc cttacacctt aactagctgc tgcattattt tattttattt tattttttg    3600 gtatttattc atcaggaata aaaaaaacaa agttttatta aagattgaaa atttgataca    3660
ttttacagaa actaattgtg atgtacatat cagtggtgac atattattac ttttttgggg    3720
acggggggtg ggtggggtga agagatcttg tgattttaa gaacctgctg gcaagagttt    3780
aacttgtctt cagcatattc tgattgtatc ataatcattt tctgctgttg cagaggatgt    3840
gaatacactt aaggagctca cagaatccca gtagcacaaa ttgggctttg gcaaatcgtg    3900
tattttgtgt atagaaggaa tttaaggaga ggtattactt attttcatat tgtattttaa    3960
ctgtttctct gatcaaattt ttttacttcc tcctcctgtt cctccccacc tccctccttt    4020
tccagttcag tatttggagt tcaacactgt ctctcaatca gatcatcttg atcttttct    4080 ttatctccct tccccttcct aagtcccatt tcttggtcat aaatattgca ttattcacac    4140
tttcaaactg tgtattttct tacaataaaa aatgatgaaa aaaaaaaaa aaaaaa       4196
```

<210> SEQ ID NO 20
<211> LENGTH: 3824
<212> TYPE: DNA
<213> ORGANISM: Homo sapiens
<400> SEQUENCE: 20

-continued

```
tattgaattg gcggaacgga agcctccttt atttaatatg aatgcaatga gtgccttata    60
tcacatagcc caaaatgaat cccctacact acagtctaat gaatggtctg attattttcg   120
caactttgta gattcttgcc tccagaaaat ccctcaagat cgacctacat cagaggaact   180
tttaaagcac atatttgttc ttcgggagcg ccctgaaacc gtgttaatag atctcattca   240
gaggacaaag gatgcagtaa gagagctgga caatctgcag tatcgaaaga tgaagaaact   300 cctttttccag gaggcacata atggaccagc agtagaagca caggaagaag aagaggaaca   360
agatcatggt gttggccgga caggaacagt taatagtgtt ggaagtaatc aatccattcc   420
cagcatgtcc atcagtgcca gcagccaaag cagtagtgtt aacagtcttc cagatgtctc   480
agatgacaag agtgagctag acatgatgga gggagaccac acagtgatgt ctaacagttc   540
tgttatccat ttaaaaccag aggaagaaaa ttacagagaa gagggagatc ctagaacaag   600
agcatcagat ccacaatctc caccccaagt atctcgtcac aaatcacact atcgtaatcg   660
agaacacttt gctactatac ggacagcatc actggttacg aggcaaatgc aagaacatga   720
gcaggactct gagcttagag aacaaatgtc tggctataag cgaatgaggc gacaacatca   780
aaagcaactg atgactctgg aaaacaagct aaaggctgag atggatgaac atcgcctcag   840
attagacaaa gatcttgaaa ctcagcgtaa caattttgct gcagaaatgg agaaacttat   900
caagaaacac caggctgcca tggagaaaga ggctaaagtg atgtccaatg aagagaaaaa   960
atttcagcaa catattcagg cccaacagaa gaaagaactg aatagttttc tcgagtccca  1020
gaaaagagag tataaacttc gaaaagagca gcttaaagag gagctaaatg aaaaccagag  1080 taccccccaaa aaagaaaaac aggagtggct ttcaaagcag aaggagaata tacagcattt  1140
ccaagcagaa gaagaagcta accttcttcg acgtcaaaga caatacctag agctggaatg  1200
ccgtcgcttc aagagaagaa tgttacttgg gcgtcataac ttagagcagg accttgtcag  1260
ggaggagtta aacaaaagac agactcagaa ggacttagag catgccatgc tactccgaca  1320
gcatgaatct atgcaagaac tggagttccg ccacctcaac acaattcaga gatgcgctg   1380 tgagttgatc agattacagc atcaaactga gctcactaac cagctggaat ataataagcg  1440
aagagaacga gaactaagac gaaagcatgt catggaagtt cgacaacagc ctaagagttt  1500
gaagtctaaa gaactccaaa taaaaaagca gtttcaggat acctgcaaaa tccaaaccag  1560
acagtacaaa gcattaagaa atcacctgct ggagactaca ccaaagagtg agcacaaagc  1620
tgttctgaaa cggctcaagg aggaacagac ccggaaatta gctatcttgg ctgagcagta  1680
tgatcacagc attaatgaaa tgctctccac acaagccctg cgtttggatg aagcacagga  1740
agcagagtgc caggttttga agatgcagct gcagcaggaa ctggagctgt tgaatgcgta  1800
tcagagcaaa atcaagatgc aagctgaggc acaacatgat cgagagcttc gcgagcttga  1860
acagagggtc tccctccgga gggcactctt agaacaaaag attgaagaag atgttggc    1920 tttgcagaat gagcgcacag aacgaatacg aagcctgttg gaacgtcaag ccagagagat  1980
tgaagctttt gactctgaaa gcatgagact aggttttagt aatatggtcc tttctaatct  2040
ctcccctgag gcattcagcc acagctaccc gggagcttct ggttggtcac acaaccctac  2100
tgggggtcca ggacctcact gggtcatccc catggtggc ccaccacaag cttggggcca   2160
tccaatgcaa ggtggacccc agccatgggg tcacccttca gggccaatgc aagggtacc   2220 tcgaggtagc agtatgggag tccgcaatag ccccaggct ctgaggcgga cagcttctgg   2280
gggacggacg gagcagggca tgagcagaag cacgagtgtc acttcacaaa tatccaatgg  2340
```

-continued

```
gtcacacatg tcttatacat aacttaataa ttgagagtgg caattccgct ggagctgtct      2400
gccaaaagaa actgcctaca gacatcatca cagcagcctc ctcacttggg tactacagtg      2460
tggaagctga gtgcatatgg tatattttat tcattttttgt aaagcgttct gttttgtgtt     2520
tactaattgg gatgtcatag tacttggctg ccgggtttgt ttgttttttgg ggaaattttg     2580 aaaagtggag ttgatattaa aaataaatgt gtatgtgtgt acatatatat acacacacat      2640
acacatatat tatgcatgtg gtgaaaagaa ttggctagat aggggatttt tctgaacact      2700
gcaaaaatag aacgtagcaa aatggcttca gttatcactt ttgggtgtct gtatcctaag      2760
aagtttctga aaagatctaa agcctttttta tcccatatcc caaattctta tgagccactc     2820
acagcaggca gcatatgttg aaataagtta ttactggtac acacctgcat tgcctcacca      2880
gtgtatttat ttgttattaa attgatctga cttctcagcc tcatttggac taaaaaaga      2940 aagcagaaat ccatgaacac attgcttctc ggccttttgg ctaagatcaa gtgtagaaat      3000
ccatgaacac taaaggactt cattgatttt ttcagagagt agaaacaac ttagttttttc     3060 tttttttcctg aatgcgtcat aggcttgtga gtgattttttg tccattcaat tgtgccttct    3120
ttgtattatg ataagatggg ggtacttaag gagatcacaa gttgtgtgag gattgcatta     3180
acaaacctat gagccttcaa tggggaagac cagaagggtg agaggggccc tgaaagttca     3240
tatggtgggt atgtcccgca gcagagtgag gagatgaagc ttacgtgtcc tgacgttttg     3300
ttgcttatac tgtgatatct catcctagct aagctctata atgcccaaga ccccaaacag     3360
tacttttact ttgtttgtac aaaaacaaag acatatagcc aatacaaatc aaatgccgga     3420
ggtgtttgat gccatatttg caaattgcca tctattgaaa ttctcgtcac actacataga     3480
cataattgtt atctccttttt ggcttatgtg attttctgtt tacaagtaga atagccaatt    3540
atttaaatgt ttagttgcca cagtgaacca ggagtcactg agccaatgac tttaccagct     3600
gctgactaat cttcatcacc actgtagatt ttgctgcatg tgcaggtcct ctatttttaa     3660 ttgctgttttt cgttgctgca gtactttaca aacttctagt tcgttgagac ttagtgacca    3720
tttggcatca agttaacatc acacaatagg aaacaccact tccacaagtc tcaagcctca    3780
gtgctaaagt actactgaaa aggaactagg aagtttggcc aatt                      3824
```

<210> SEQ ID NO 21
<211> LENGTH: 2249
<212> TYPE: DNA
<213> ORGANISM: Murine sp.

<400> SEQUENCE: 21

```
gcaggatgcc atcaactaac agagcaggca gtctaaagga ccctgaaatt gcagagctct       60
tcttcaaaga agatccggaa aagctcttca cagatctcag agaaatcggc catgggagct      120
ttggagcagt atattttgca cgagatgtgc gtactaatga agtggtggcc atcaagaaaa      180
tgtcttatag tggaaagcag tctactgaga aatggcagga tattattaag gaagtcaagt      240
ttctacaaag aataaaacat cccaacagta tagaatacaa aggctgctat ttacgtgaac      300
acacagcatg gcttgtaatg gaatattgtt taggatctgc ttcagattta ttagaagttc      360
ataaaaagcc attacaagaa gtggaaatag cagcaattac acatggtgct ctccagggac      420
tagcttattt acattctcat accatgatcc atagagatat caaagcagga aatatccttc      480
tgacagaacc aggccaagtg aaacttgctg actttggatc tgcttccatg gcttcccctg      540
ccaattcttt tgtgggaaca ccatattgga tggccccaga agtaatttta gccatggatg      600
aaggacagta tgatggcaaa gttgatgtat ggtctcttgg aataacgtgt attgaattag      660
```

-continued

```
ccgagaggaa gcctccttta tttaatatga atgcaatgag tgccttatat cacatagccc    720
aaaatgaatc ccctacacta caatctaata tgaatgattc ttgcctccag aaaatccctc    780
aagatcgccc tacatcagag gaacttttaa agcacatgtt tgttcttcga gagcgccctg    840
aaacagtgtt aatagatctt attcaaagga caaaggatgc agtaagagag ctggacaatc    900
tgcagtatcg aaagatgaag aaactccttt tccaggaggc acataatggg ccagcggtag    960
aagcacagga agaagaggag gagcaagatc atggtgttgg ccgaacagga acagtgaata   1020
gtgttggaag caatcagtct atccctagta tgtctatcag tgccagcagt caaagcagca   1080
gtgttaatag tcttccagat gcatcagatg acaagagtga gctagacatg atggagggag   1140
accatacagt gatgtctaac agttctgtca tccacttaaa acctgaggag gaaaattacc   1200
aggaagaagg agatcctaga caagagcat cagacccaca gtctcccct caggtgtctc      1260 gtcacaagtc acattatcgt aatagagaac actttgcaac catacgaaca gcatcactgg   1320
ttacaagaca gatgcaagaa catgagcagg actctgaact tagagaacag atgtctggtt   1380
ataagcggat gaggcgacag catcaaaagc agctgatgac gctggaaaat aaactgaagg   1440
cagagatgga cgaacatcgg ctcagattag acaaagatct tgaaactcag cgtaacaatt   1500
tcgctgcaga aatggagaaa cttattaaga acaccaagc tgctatggaa aaagaggcta    1560
aagtgatggc caatgaggag aaaaaattcc agcaacacat tcaggctcaa cagaaaaaag   1620
aactgaatag cttttttggag tctcaaaaaa gagaatataa acttcgcaaa gagcagctta   1680
aggaggagct gaatgaaaac cagagcacac ctaaaaaaga aaagcaggaa tggctttcaa   1740
agcagaagga gaatatacag cattttcagg cagaagaaga agctaatctt cttcgacgtc   1800
aaaggcagta tctagagcta gaatgtcgtc gcttcaaaag aagaatgtta cttgggcgac   1860
ataacttgga acaggacctt gtcagggagg agttaaacaa aagcagact caaaaggact     1920 tggaacatgc aatgctattg cgacagcatg aatcaatgca agaactggag tttcgccatc   1980
tcaacactat tcagaagatg cgctgtgagt tgatcagact gcagcatcaa actgagctca   2040
ctaaccagct agagtacaat aagagaaggg aacgggaact gaggcgaaaa catgtcatgg   2100
aagttcgaca caacctaag agtctgaagt ctaaagaact ccaaataaaa agcagtttc     2160 aggatacctg caaaattcaa accagacagt acaaagcatt aaggaatcac ctactggaga   2220
ctacaccaaa gaatgagcac aaagcaatc                                     2249
```

<210> SEQ ID NO 22
<211> LENGTH: 898
<212> TYPE: PRT
<213> ORGANISM: Homo sapiens

<400> SEQUENCE: 22

```
Met Arg Lys Gly Val Leu Lys Asp Pro Glu Ile Asp Asp Leu Phe Tyr
 1               5                  10                  15

Lys Asp Asp Pro Glu Glu Leu Phe Ile Gly Leu His Glu Ile Gly His
                20                  25                  30

Gly Ser Phe Gly Ala Val Tyr Phe Ala Thr Asn Ala His Thr Asn Glu
            35                  40                  45

Val Val Ala Ile Lys Lys Met Ser Tyr Ser Gly Lys Gln Thr His Glu
        50                  55                  60

Lys Trp Gln Asp Ile Leu Lys Glu Val Lys Phe Leu Arg Gln Leu Lys
    65                  70                  75                  80

His Pro Asn Thr Ile Glu Tyr Lys Gly Cys Tyr Leu Lys Glu His Thr
```

```
                    85                  90                  95
Ala Trp Leu Val Met Glu Tyr Cys Leu Gly Ser Ala Ser Asp Leu Leu
                100                 105                 110

Glu Val His Lys Lys Pro Leu Gln Glu Val Glu Ile Ala Ala Ile Thr
                115                 120                 125

His Gly Ala Leu His Gly Leu Ala Tyr Leu His Ser His Ala Leu Ile
            130                 135                 140

His Arg Asp Ile Lys Ala Gly Asn Ile Leu Leu Thr Glu Pro Gly Gln
145                 150                 155                 160

Val Lys Leu Ala Asp Phe Gly Ser Ala Ser Met Ala Ser Pro Ala Asn
                165                 170                 175

Ser Phe Val Gly Thr Pro Tyr Trp Met Ala Pro Glu Val Ile Leu Ala
            180                 185                 190

Met Asp Glu Gly Gln Tyr Asp Gly Lys Val Asp Ile Trp Ser Leu Gly
            195                 200                 205

Ile Thr Cys Ile Glu Leu Ala Glu Arg Lys Pro Pro Leu Phe Asn Met
        210                 215                 220

Asn Ala Met Ser Ala Leu Tyr His Ile Ala Gln Asn Asp Ser Pro Thr
225                 230                 235                 240

Leu Gln Ser Asn Glu Trp Thr Asp Ser Phe Arg Arg Phe Val Asp Tyr
                245                 250                 255

Cys Leu Gln Lys Ile Pro Gln Glu Arg Pro Thr Ser Ala Glu Leu Leu
                260                 265                 270

Arg His Asp Phe Val Arg Arg Asp Arg Pro Leu Arg Val Leu Ile Asp
            275                 280                 285

Leu Ile Gln Arg Thr Lys Asp Ala Val Arg Glu Leu Asp Asn Leu Gln
        290                 295                 300

Tyr Arg Lys Met Lys Lys Ile Leu Phe Gln Glu Thr Arg Asn Gly Pro
305                 310                 315                 320

Leu Asn Glu Ser Gln Glu Asp Glu Glu Asp Ser Glu His Gly Thr Ser
                325                 330                 335

Leu Asn Arg Glu Met Asp Ser Leu Gly Ser Asn His Ser Ile Pro Ser
            340                 345                 350

Met Ser Val Ser Thr Gly Ser Gln Ser Ser Ser Val Asn Ser Met Gln
            355                 360                 365

Glu Val Met Asp Glu Ser Ser Ser Glu Leu Val Met Met His Asp Asp
            370                 375                 380

Glu Ser Thr Ile Asn Ser Ser Ser Val Val His Lys Lys Asp His
385                 390                 395                 400

Val Phe Thr Arg Asp Glu Ala Gly His Gly Asp Pro Arg Pro Glu Pro
            405                 410                 415

Arg Pro Thr Gln Ser Val Gln Ser Gln Ala Leu His Tyr Arg Asn Arg
            420                 425                 430

Glu Arg Phe Ala Thr Ile Lys Ser Ala Ser Leu Val Thr Arg Gln Ile
            435                 440                 445

His Glu His Glu Gln Glu Asn Glu Leu Arg Glu Gln Met Ser Gly Tyr
        450                 455                 460

Lys Arg Met Arg Arg Gln His Gln Lys Gln Leu Ile Ala Leu Glu Asn
465                 470                 475                 480

Lys Leu Lys Ala Glu Met Asp Glu His Arg Leu Lys Leu Gln Lys Glu
                485                 490                 495

Val Glu Thr His Ala Asn Asn Ser Ser Ile Glu Leu Glu Lys Leu Ala
                500                 505                 510
```

-continued

```
Lys Lys Gln Val Ala Ile Ile Glu Lys Glu Ala Lys Val Ala Ala Ala
            515                 520                 525
Asp Glu Lys Lys Phe Gln Gln Gln Ile Leu Ala Gln Gln Lys Lys Asp
    530                 535                 540
Leu Thr Thr Phe Leu Glu Ser Gln Lys Gln Tyr Lys Ile Cys Lys
545                 550                 555                 560
Glu Lys Ile Lys Glu Glu Met Asn Glu Asp His Ser Thr Pro Lys Lys
                565                 570                 575
Glu Lys Gln Glu Arg Ile Ser Lys His Lys Glu Asn Leu Gln His Thr
            580                 585                 590
Gln Ala Glu Glu Ala His Leu Leu Thr Gln Gln Arg Leu Tyr Tyr
            595                 600                 605
Asp Lys Asn Cys Arg Phe Phe Lys Arg Lys Ile Met Ile Lys Arg His
    610                 615                 620
Glu Val Glu Gln Gln Asn Ile Arg Glu Glu Leu Asn Lys Lys Arg Thr
625                 630                 635                 640
Gln Lys Glu Met Glu His Ala Met Leu Ile Arg His Asp Glu Ser Thr
                645                 650                 655
Arg Glu Leu Glu Tyr Arg Gln Leu His Thr Leu Gln Lys Leu Arg Met
            660                 665                 670
Asp Leu Ile Arg Leu Gln His Gln Thr Glu Leu Glu Asn Gln Leu Glu
    675                 680                 685
Tyr Asn Lys Arg Arg Glu Arg Glu Leu His Arg Lys His Val Met Gly
    690                 695                 700
Leu Arg Gln Gln Pro Lys Asn Leu Lys Ala Met Glu Met Gln Ile Lys
705                 710                 715                 720
Lys Gln Phe Gln Asp Thr Cys Lys Val Gln Thr Lys Gln Tyr Lys Ala
                725                 730                 735
Leu Lys Asn His Gln Leu Glu Val Thr Pro Lys Asn Glu His Lys Thr
            740                 745                 750
Ile Leu Lys Thr Leu Lys Asp Glu Gln Thr Arg Lys Leu Ala Ile Leu
            755                 760                 765
Ala Glu Gln Tyr Glu Gln Ser Ile Asn Glu Met Met Ala Ser Gln Ala
    770                 775                 780
Leu Arg Leu Asp Glu Ala Gln Glu Ala Glu Cys Gln Ala Leu Arg Leu
785                 790                 795                 800
Gln Leu Gln Gln Glu Met Glu Leu Leu Asn Ala Tyr Gln Ser Lys Ile
                805                 810                 815
Lys Met Gln Thr Glu Ala Gln His Glu Arg Glu Leu Gln Lys Leu Glu
            820                 825                 830
Gln Arg Val Ser Leu Arg Arg Ala His Leu Glu Gln Lys Ile Glu Glu
            835                 840                 845
Glu Leu Ala Ala Leu Gln Lys Glu Arg Ser Glu Arg Ile Lys Asn Leu
    850                 855                 860
Leu Glu Arg Gln Glu Arg Glu Ile Glu Thr Phe Asp Met Glu Ser Leu
865                 870                 875                 880
Arg Met Gly Phe Gly Asn Leu Val Thr Leu Asp Phe Pro Lys Glu Asp
                885                 890                 895
Tyr Arg

<210> SEQ ID NO 23
<211> LENGTH: 786
<212> TYPE: PRT
```

```
<213> ORGANISM: Homo sapiens

<400> SEQUENCE: 23

Ile Glu Leu Ala Glu Arg Lys Pro Pro Leu Phe Asn Met Asn Ala Met
  1               5                  10                  15

Ser Ala Leu Tyr His Ile Ala Gln Asn Glu Ser Pro Thr Leu Gln Ser
             20                  25                  30

Asn Glu Trp Ser Asp Tyr Phe Arg Asn Phe Val Asp Ser Cys Leu Gln
         35                  40                  45

Lys Ile Pro Gln Asp Arg Pro Thr Ser Glu Glu Leu Leu Lys His Ile
     50                  55                  60

Phe Val Leu Arg Glu Arg Pro Glu Thr Val Leu Ile Asp Leu Ile Gln
 65                  70                  75                  80

Arg Thr Lys Asp Ala Val Arg Glu Leu Asp Asn Leu Gln Tyr Arg Lys
                 85                  90                  95

Met Lys Lys Leu Leu Phe Gln Glu Ala His Asn Gly Pro Ala Val Glu
            100                 105                 110

Ala Gln Glu Glu Glu Glu Gln Asp His Gly Val Gly Arg Thr Gly
            115                 120                 125

Thr Val Asn Ser Val Gly Ser Asn Gln Ser Ile Pro Ser Met Ser Ile
130                 135                 140

Ser Ala Ser Ser Gln Ser Ser Val Asn Ser Leu Pro Asp Val Ser
145                 150                 155                 160

Asp Asp Lys Ser Glu Leu Asp Met Met Glu Gly Asp His Thr Val Met
                165                 170                 175

Ser Asn Ser Ser Val Ile His Leu Lys Pro Glu Glu Asn Tyr Arg
            180                 185                 190

Glu Glu Gly Asp Pro Arg Thr Arg Ala Ser Asp Pro Gln Ser Pro Pro
            195                 200                 205

Gln Val Ser Arg His Lys Ser His Tyr Arg Asn Arg Glu His Phe Ala
            210                 215                 220

Thr Ile Arg Thr Ala Ser Leu Val Thr Arg Gln Met Gln Glu His Glu
225                 230                 235                 240

Gln Asp Ser Glu Leu Arg Glu Gln Met Ser Gly Tyr Lys Arg Met Arg
                245                 250                 255

Arg Gln His Gln Lys Gln Leu Met Thr Leu Glu Asn Lys Leu Lys Ala
            260                 265                 270

Glu Met Asp Glu His Arg Leu Arg Leu Asp Lys Asp Leu Glu Thr Gln
            275                 280                 285

Arg Asn Asn Phe Ala Ala Glu Met Glu Lys Leu Ile Lys His Gln
            290                 295                 300

Ala Ala Met Glu Lys Glu Ala Lys Val Met Ser Asn Glu Glu Lys Lys
305                 310                 315                 320

Phe Gln Gln His Ile Gln Ala Gln Gln Lys Glu Leu Asn Ser Phe
                325                 330                 335

Leu Glu Ser Gln Lys Arg Glu Tyr Lys Leu Arg Lys Glu Gln Leu Lys
            340                 345                 350

Glu Glu Leu Asn Glu Asn Gln Ser Thr Pro Lys Lys Glu Lys Gln Glu
            355                 360                 365

Trp Leu Ser Lys Gln Lys Glu Asn Ile Gln His Phe Gln Ala Glu Glu
            370                 375                 380

Glu Ala Asn Leu Leu Arg Arg Gln Arg Gln Tyr Leu Glu Leu Glu Cys
385                 390                 395                 400
```

```
Arg Arg Phe Lys Arg Arg Met Leu Leu Gly Arg His Asn Leu Glu Gln
            405                 410                 415
Asp Leu Val Arg Glu Glu Leu Asn Lys Arg Gln Thr Gln Lys Asp Leu
            420                 425                 430
Glu His Ala Met Leu Leu Arg Gln His Glu Ser Met Gln Glu Leu Glu
            435                 440                 445
Phe Arg His Leu Asn Thr Ile Gln Lys Met Arg Cys Glu Leu Ile Arg
            450                 455                 460
Leu Gln His Gln Thr Glu Leu Thr Asn Gln Leu Glu Tyr Asn Lys Arg
465                 470                 475                 480
Arg Glu Arg Glu Leu Arg Arg Lys His Val Met Glu Val Arg Gln Gln
                485                 490                 495
Pro Lys Ser Leu Lys Ser Lys Glu Leu Gln Ile Lys Lys Gln Phe Gln
                500                 505                 510
Asp Thr Cys Lys Ile Gln Thr Arg Gln Tyr Lys Ala Leu Arg Asn His
                515                 520                 525
Leu Leu Glu Thr Thr Pro Lys Ser Glu His Lys Ala Val Leu Lys Arg
            530                 535                 540
Leu Lys Glu Glu Gln Thr Arg Lys Leu Ala Ile Leu Ala Glu Gln Tyr
545                 550                 555                 560
Asp His Ser Ile Asn Glu Met Leu Ser Thr Gln Ala Leu Arg Leu Asp
                565                 570                 575
Glu Ala Gln Glu Ala Glu Cys Gln Val Leu Lys Met Gln Leu Gln Gln
                580                 585                 590
Glu Leu Glu Leu Leu Asn Ala Tyr Gln Ser Lys Ile Lys Met Gln Ala
            595                 600                 605
Glu Ala Gln His Asp Arg Glu Leu Arg Glu Leu Glu Gln Arg Val Ser
            610                 615                 620
Leu Arg Arg Ala Leu Leu Glu Gln Lys Ile Glu Glu Glu Met Leu Ala
625                 630                 635                 640
Leu Gln Asn Glu Arg Thr Glu Arg Ile Arg Ser Leu Leu Glu Arg Gln
                645                 650                 655
Ala Arg Glu Ile Glu Ala Phe Asp Ser Glu Ser Met Arg Leu Gly Phe
                660                 665                 670
Ser Asn Met Val Leu Ser Asn Leu Ser Pro Glu Ala Phe Ser His Ser
            675                 680                 685
Tyr Pro Gly Ala Ser Gly Trp Ser His Asn Pro Thr Gly Gly Pro Gly
            690                 695                 700
Pro His Trp Gly His Pro Met Gly Gly Pro Pro Gln Ala Trp Gly His
705                 710                 715                 720
Pro Met Gln Gly Gly Pro Gln Pro Trp Gly His Pro Ser Gly Pro Met
                725                 730                 735
Gln Gly Val Pro Arg Gly Ser Ser Met Gly Val Arg Asn Ser Pro Gln
                740                 745                 750
Ala Leu Arg Arg Thr Ala Ser Gly Gly Arg Thr Glu Gln Gly Met Ser
            755                 760                 765
Arg Ser Thr Ser Val Thr Ser Gln Ile Ser Asn Gly Ser His Met Ser
770                 775                 780
Tyr Thr
785

<210> SEQ ID NO 24
<211> LENGTH: 748
<212> TYPE: PRT
```

```
<213> ORGANISM: Murine sp.

<400> SEQUENCE: 24

Met Pro Ser Thr Asn Arg Ala Gly Ser Leu Lys Asp Pro Glu Ile Ala
  1               5                  10                  15

Glu Leu Phe Phe Lys Glu Asp Pro Glu Lys Leu Phe Thr Asp Leu Arg
             20                  25                  30

Glu Ile Gly His Gly Ser Phe Gly Ala Val Tyr Phe Ala Arg Asp Val
         35                  40                  45

Arg Thr Asn Glu Val Val Ala Ile Lys Lys Met Ser Tyr Ser Gly Lys
     50                  55                  60

Gln Ser Thr Glu Lys Trp Gln Asp Ile Ile Lys Glu Val Lys Phe Leu
 65                  70                  75                  80

Gln Arg Ile Lys His Pro Asn Ser Ile Glu Tyr Lys Gly Cys Tyr Leu
                 85                  90                  95

Arg Glu His Thr Ala Trp Leu Val Met Glu Tyr Cys Leu Gly Ser Ala
                100                 105                 110

Ser Asp Leu Leu Glu Val His Lys Lys Pro Leu Gln Glu Val Glu Ile
            115                 120                 125

Ala Ala Ile Thr His Gly Ala Leu Gln Gly Leu Ala Tyr Leu His Ser
        130                 135                 140

His Thr Met Ile His Arg Asp Ile Lys Ala Gly Asn Ile Leu Leu Thr
145                 150                 155                 160

Glu Pro Gly Gln Val Lys Leu Ala Asp Phe Gly Ser Ala Ser Met Ala
                165                 170                 175

Ser Pro Ala Asn Ser Phe Val Gly Thr Pro Tyr Trp Met Ala Pro Glu
            180                 185                 190

Val Ile Leu Ala Met Asp Glu Gly Gln Tyr Asp Gly Lys Val Asp Val
        195                 200                 205

Trp Ser Leu Gly Ile Thr Cys Ile Glu Leu Ala Glu Arg Lys Pro Pro
210                 215                 220

Leu Phe Asn Met Asn Ala Met Ser Ala Leu Tyr His Ile Ala Gln Asn
225                 230                 235                 240

Glu Ser Pro Thr Leu Gln Ser Asn Met Asn Asp Ser Cys Leu Gln Lys
                245                 250                 255

Ile Pro Gln Asp Arg Pro Thr Ser Glu Glu Leu Leu Lys His Met Phe
            260                 265                 270

Val Leu Arg Glu Arg Pro Glu Thr Val Leu Ile Asp Leu Ile Gln Arg
        275                 280                 285

Thr Lys Asp Ala Val Arg Glu Leu Asp Asn Leu Gln Tyr Arg Lys Met
    290                 295                 300

Lys Lys Leu Leu Phe Gln Glu Ala His Asn Gly Pro Ala Val Glu Ala
305                 310                 315                 320

Gln Glu Glu Glu Glu Gln Asp His Gly Val Gly Arg Thr Gly Thr
                325                 330                 335

Val Asn Ser Val Gly Ser Asn Gln Ser Ile Pro Ser Met Ser Ile Ser
            340                 345                 350

Ala Ser Ser Gln Ser Ser Val Asn Ser Leu Pro Asp Ala Ser Asp
        355                 360                 365

Asp Lys Ser Glu Leu Asp Met Met Glu Gly Asp His Thr Val Met Ser
    370                 375                 380

Asn Ser Ser Val Ile His Leu Lys Pro Glu Glu Asn Tyr Gln Glu
385                 390                 395                 400
```

```
Glu Gly Asp Pro Arg Thr Arg Ala Ser Asp Pro Gln Ser Pro Pro Gln
                405                 410                 415

Val Ser Arg His Lys Ser His Tyr Arg Asn Arg Glu His Phe Ala Thr
            420                 425                 430

Ile Arg Thr Ala Ser Leu Val Thr Arg Gln Met Gln Glu His Glu Gln
        435                 440                 445

Asp Ser Glu Leu Arg Glu Gln Met Ser Gly Tyr Lys Arg Met Arg Arg
    450                 455                 460

Gln His Gln Lys Gln Leu Met Thr Leu Glu Asn Lys Leu Lys Ala Glu
465                 470                 475                 480

Met Asp Glu His Arg Leu Arg Leu Asp Lys Asp Leu Glu Thr Gln Arg
                485                 490                 495

Asn Asn Phe Ala Ala Glu Met Glu Lys Leu Ile Lys His Gln Ala
            500                 505                 510

Ala Met Glu Lys Glu Ala Lys Val Met Ala Asn Glu Glu Lys Lys Phe
            515                 520                 525

Gln Gln His Ile Gln Ala Gln Gln Lys Lys Glu Leu Asn Ser Phe Leu
        530                 535                 540

Glu Ser Gln Lys Arg Glu Tyr Lys Leu Arg Lys Glu Gln Leu Lys Glu
545                 550                 555                 560

Glu Leu Asn Glu Asn Gln Ser Thr Pro Lys Lys Glu Lys Gln Glu Trp
                565                 570                 575

Leu Ser Lys Gln Lys Glu Asn Ile Gln His Phe Gln Ala Glu Glu Glu
            580                 585                 590

Ala Asn Leu Leu Arg Arg Gln Arg Gln Tyr Leu Glu Leu Glu Cys Arg
        595                 600                 605

Arg Phe Lys Arg Arg Met Leu Leu Gly Arg His Asn Leu Glu Gln Asp
    610                 615                 620

Leu Val Arg Glu Glu Leu Asn Lys Arg Gln Thr Gln Lys Asp Leu Glu
625                 630                 635                 640

His Ala Met Leu Leu Arg Gln His Glu Ser Met Gln Glu Leu Glu Phe
                645                 650                 655

Arg His Leu Asn Thr Ile Gln Lys Met Arg Cys Glu Leu Ile Arg Leu
            660                 665                 670

Gln His Gln Thr Glu Leu Thr Asn Gln Leu Glu Tyr Asn Lys Arg Arg
        675                 680                 685

Glu Arg Glu Leu Arg Arg Lys His Val Met Glu Val Arg Gln Gln Pro
    690                 695                 700

Lys Ser Leu Lys Ser Lys Glu Leu Gln Ile Lys Lys Gln Phe Gln Asp
705                 710                 715                 720

Thr Cys Lys Ile Gln Thr Arg Gln Tyr Lys Ala Leu Arg Asn His Leu
                725                 730                 735

Leu Glu Thr Thr Pro Lys Asn Glu His Lys Ala Ile
            740                 745

<210> SEQ ID NO 25
<211> LENGTH: 2795
<212> TYPE: DNA
<213> ORGANISM: Homo sapiens

<400> SEQUENCE: 25
cgaagccaca gcccgagccc gagcccgagc ccgagccggc gccaccgcgc ccccggccat      60
ggcttttgcc aatttccgcc gcatcctgcg cctgtctacc ttcgagaaga gaaagtcccg     120
cgaatatgag cacgtccgcc gcgacctgga ccccaacgag gtgtgggaga tcgtgggcga    180
```

-continued

```
gctgggcgac ggcgccttcg gcaaggttta caaggccaag aataaggaga cgggtgcttt      240
ggctgcggcc aaagtcattg aaaccaagag tgaggaggag ctggaggact acatcgtgga      300
gattgagatc ctggccacct gcgaccaccc ctacattgtg aagctcctgg agcctacta      360 tcacgacggg aagctgtgga tcatgattga gttctgtcca gggggagccg tggacgccat      420
catgctggag ctggacagag gcctcacgga gccccagata caggtggttt gccgccagat      480
gctagaagcc ctcaacttcc tgcacagcaa gaggatcatc caccgagatc tgaaagctgg      540
caacgtgctg atgaccctcg agggagacat caggctggct gactttggtg tgtctgccaa      600
gaatctgaag actctacaga aacgagattc cttcatcggc acgccttact ggatggcccc      660
cgaggtggtc atgtgtgaga ccatgaaaga cacgccctac gactacaaag ccgacatctg      720
gtccctgggc atcacgctga ttgagatggc ccagatcgag ccgccacacc acgagctcaa      780
ccccatgcgg gtcctgctaa agatcgccaa gtcggaccct cccacgctgc tcacgccctc      840
caagtggtct gtagagttcc gtgacttcct gaagatagcc ctggataaga cccagaaac      900 ccgacccagt gccgcgcagc tgctggagca tcccttcgtc agcagcatca ccagtaacaa      960
ggctctgcgg gagctggtgg ctgaggccaa ggccgaggtg atggaagaga tcgaagacgg     1020
ccgggatgag gggaagagg aggacgccgt ggatgccgcc tccaccctgg agaaccatac     1080
tcagaactcc tctgaggtga gtccgccaag cctcaatgct gacaagcctc tcgaggagtc     1140
accttccacc ccgctggcac ccagccagtc tcaggacagt gtgaatgagc cctgcagcca     1200
gccctctggg gacagatccc tccaaaccac cagtccccca gtcgtggccc ctggaaatga     1260
gaacggcctg gcagtgcctg tgccccgcg gaagtcccga cccgtgtcaa tggatgccag     1320
aattcaggta gcccaggaga agcaagttgc tgagcagggt ggggacctca gcccagcagc     1380
caacagatct caaaaggcca gcagagccg gcccaacagc agcgccctgg agaccttggg     1440
tggggagaag ctggccaatg gcagcctgga gccacctgcc aggcagctc cagggccttc     1500 caagagggac tcggactgca gcagcctctg cacctctgag agcatggact atggtaccaa     1560
tctctccact gacctgtcgc tgaacaaaga gatgggctct ctgtccatca aggacccgaa     1620
actgtacaaa aaaccctca gcggacacg caaatttgtg gtggatggtg tggaggtgag     1680
catcaccacc tccaagatca tcagcgaaga tgagaagaag gatgaggaga tgagatttct     1740
caggcgccag gaactccgag agcttcggct gctccagaaa gaagagcatc ggaaccagac     1800
ccagctgagt aacaagcatg agctgcagct ggagcaaatg cataaacgtt ttgaacagga     1860
aatcaacgcc aagaagaagt tctttgacac ggaattagag aacctggagc gtcagcaaaa     1920
gcagcaagtg gagaagatgg agcaagacca tgccgtgcgc cgccgggagg aggccaggcg     1980
gatccgcctg gagcaggatc gggactacac caggttccaa gagcagctca actgatgaa     2040 gaaagaggtg aagaacgagg tggagaagct cccccgacag cagcggaagg aaagcatgaa     2100
gcagaagatg gaggagcaca cgcagaaaaa gcagcttctt gaccgggact ttgtagccaa     2160
gcagaaggag gacctggagc tggccatgaa gaggctcacc accgacaaca ggcgggagat     2220
ctgtgacaag gagcgcgagt gcctcatgaa gaagcaggag ctccttcgag accgggaagc     2280
agccctgtgg gagatggaag agcaccagct gcaggagagg caccagctgg tgaagcagca     2340
gctcaaagac cagtacttcc tccagcggca cgagctgctg cgcaagcatg agaaggagcg     2400
ggagcagatg cagcgctaca accagcgcat gatagagcag ctgaaggtgc ggcagcaaca     2460
ggaaaaggcg cggctgccca gatccagag gagtgagggc aagacgcgca tggccatgta     2520
```

-continued

```
caagaagagc ctccacatca acggcggggg cagcgcagct gagcagcgtg agaagatcaa    2580
gcagttctcc cagcaggagg agaagaggca gaagtcggag cggctgcagc aacagcagaa    2640
acacgagaac cagatgcggg acatgctggc gcagtgcgag agcaacatga gcagctgca     2700 gcagctgcag aatgaaaagt gccacctcct ggtagagcac gaaacccaga aactgaaggc    2760
cctggatgag agccataacc agaacctgaa ggaat                               2795
```

<210> SEQ ID NO 26
<211> LENGTH: 912
<212> TYPE: PRT
<213> ORGANISM: Homo sapiens

<400> SEQUENCE: 26

```
Met Ala Phe Ala Asn Phe Arg Arg Ile Leu Arg Leu Ser Thr Phe Glu
 1               5                  10                  15

Lys Arg Lys Ser Arg Glu Tyr Glu His Val Arg Arg Asp Leu Asp Pro
            20                  25                  30

Asn Glu Val Trp Glu Ile Val Gly Glu Leu Gly Asp Gly Ala Phe Gly
        35                  40                  45

Lys Val Tyr Lys Ala Lys Asn Lys Glu Thr Gly Ala Leu Ala Ala Ala
    50                  55                  60

Lys Val Ile Glu Thr Lys Ser Glu Glu Leu Glu Asp Tyr Ile Val
65                  70                  75                  80

Glu Ile Glu Ile Leu Ala Thr Cys Asp His Pro Tyr Ile Val Lys Leu
                85                  90                  95

Leu Gly Ala Tyr Tyr His Asp Gly Lys Leu Trp Ile Met Ile Glu Phe
            100                 105                 110

Cys Pro Gly Gly Ala Val Asp Ala Ile Met Leu Glu Leu Asp Arg Gly
        115                 120                 125

Leu Thr Glu Pro Gln Ile Gln Val Val Cys Arg Gln Met Leu Glu Ala
    130                 135                 140

Leu Asn Phe Leu His Ser Lys Arg Ile Ile His Arg Asp Leu Lys Ala
145                 150                 155                 160

Gly Asn Val Leu Met Thr Leu Glu Gly Asp Ile Arg Leu Ala Asp Phe
                165                 170                 175

Gly Val Ser Ala Lys Asn Leu Lys Thr Leu Gln Lys Arg Asp Ser Phe
            180                 185                 190

Ile Gly Thr Pro Tyr Trp Met Ala Pro Glu Val Val Met Cys Glu Thr
        195                 200                 205

Met Lys Asp Thr Pro Tyr Asp Tyr Lys Ala Asp Ile Trp Ser Leu Gly
    210                 215                 220

Ile Thr Leu Ile Glu Met Ala Gln Ile Glu Pro Pro His His Glu Leu
225                 230                 235                 240

Asn Pro Met Arg Val Leu Leu Lys Ile Ala Lys Ser Asp Pro Pro Thr
                245                 250                 255

Leu Leu Thr Pro Ser Lys Trp Ser Val Glu Phe Arg Asp Phe Leu Lys
            260                 265                 270

Ile Ala Leu Asp Lys Asn Pro Glu Thr Arg Pro Ser Ala Ala Gln Leu
        275                 280                 285

Leu Glu His Pro Phe Val Ser Ser Ile Thr Ser Asn Lys Ala Leu Arg
    290                 295                 300

Glu Leu Val Ala Glu Ala Lys Ala Glu Val Met Glu Glu Ile Glu Asp
305                 310                 315                 320

Gly Arg Asp Glu Gly Glu Glu Glu Asp Ala Val Asp Ala Ala Ser Thr
```

```
                      325                 330                 335
Leu Glu Asn His Thr Gln Asn Ser Ser Glu Val Ser Pro Pro Ser Leu
            340                 345                 350
Asn Ala Asp Lys Pro Leu Glu Ser Pro Ser Thr Pro Leu Ala Pro
            355                 360                 365
Ser Gln Ser Gln Asp Ser Val Asn Glu Pro Cys Ser Gln Pro Ser Gly
            370                 375                 380
Asp Arg Ser Leu Gln Thr Thr Ser Pro Pro Val Val Ala Pro Gly Asn
385                 390                 395                 400
Glu Asn Gly Leu Ala Val Pro Val Pro Leu Arg Lys Ser Arg Pro Val
                405                 410                 415
Ser Met Asp Ala Arg Ile Gln Val Ala Gln Glu Lys Gln Val Ala Glu
            420                 425                 430
Gln Gly Gly Asp Leu Ser Pro Ala Ala Asn Arg Ser Gln Lys Ala Ser
            435                 440                 445
Gln Ser Arg Pro Asn Ser Ser Ala Leu Glu Thr Leu Gly Gly Glu Lys
    450                 455                 460
Leu Ala Asn Gly Ser Leu Glu Pro Pro Ala Gln Ala Ala Pro Gly Pro
465                 470                 475                 480
Ser Lys Arg Asp Ser Asp Cys Ser Ser Leu Cys Thr Ser Glu Ser Met
                485                 490                 495
Asp Tyr Gly Thr Asn Leu Ser Thr Asp Leu Ser Leu Asn Lys Glu Met
            500                 505                 510
Gly Ser Leu Ser Ile Lys Asp Pro Lys Leu Tyr Lys Lys Thr Leu Lys
            515                 520                 525
Arg Thr Arg Lys Phe Val Val Asp Gly Val Glu Val Ser Ile Thr Thr
    530                 535                 540
Ser Lys Ile Ile Ser Glu Asp Glu Lys Lys Asp Glu Glu Met Arg Phe
545                 550                 555                 560
Leu Arg Arg Gln Glu Leu Arg Glu Leu Arg Leu Leu Gln Lys Glu Glu
                565                 570                 575
His Arg Asn Gln Thr Gln Leu Ser Asn Lys His Glu Leu Gln Leu Glu
            580                 585                 590
Gln Met His Lys Arg Phe Glu Gln Glu Ile Asn Ala Lys Lys Lys Phe
    595                 600                 605
Phe Asp Thr Glu Leu Glu Asn Leu Glu Arg Gln Gln Lys Gln Gln Val
    610                 615                 620
Glu Lys Met Glu Gln Asp His Ala Val Arg Arg Arg Glu Glu Ala Arg
625                 630                 635                 640
Arg Ile Arg Leu Glu Gln Asp Arg Asp Tyr Thr Arg Phe Gln Glu Gln
                645                 650                 655
Leu Lys Leu Met Lys Lys Glu Val Lys Asn Glu Val Glu Lys Leu Pro
            660                 665                 670
Arg Gln Gln Arg Lys Glu Ser Met Lys Gln Lys Met Glu Glu His Thr
            675                 680                 685
Gln Lys Lys Gln Leu Leu Asp Arg Asp Phe Val Ala Lys Gln Lys Glu
    690                 695                 700
Asp Leu Glu Leu Ala Met Lys Arg Leu Thr Thr Asp Asn Arg Arg Glu
705                 710                 715                 720
Ile Cys Asp Lys Glu Arg Glu Cys Leu Met Lys Lys Gln Glu Leu Leu
                725                 730                 735
Arg Asp Arg Glu Ala Ala Leu Trp Glu Met Glu Glu His Gln Leu Gln
            740                 745                 750
```

```
Glu Arg His Gln Leu Val Lys Gln Gln Leu Lys Asp Gln Tyr Phe Leu
            755                 760                 765

Gln Arg His Glu Leu Leu Arg Lys His Glu Lys Glu Arg Glu Gln Met
        770                 775                 780

Gln Arg Tyr Asn Gln Arg Met Ile Glu Gln Leu Lys Val Arg Gln Gln
785                 790                 795                 800

Gln Glu Lys Ala Arg Leu Pro Lys Ile Gln Arg Ser Glu Gly Lys Thr
                805                 810                 815

Arg Met Ala Met Tyr Lys Lys Ser Leu His Ile Asn Gly Gly Gly Ser
            820                 825                 830

Ala Ala Glu Gln Arg Glu Lys Ile Lys Gln Phe Ser Gln Gln Glu Glu
            835                 840                 845

Lys Arg Gln Lys Ser Glu Arg Leu Gln Gln Gln Lys His Glu Asn
    850                 855                 860

Gln Met Arg Asp Met Leu Ala Gln Cys Glu Ser Asn Met Ser Glu Leu
865                 870                 875                 880

Gln Gln Leu Gln Asn Glu Lys Cys His Leu Leu Val Glu His Glu Thr
                885                 890                 895

Gln Lys Leu Lys Ala Leu Asp Glu Ser His Asn Gln Asn Leu Lys Glu
            900                 905                 910

<210> SEQ ID NO 27
<211> LENGTH: 3604
<212> TYPE: DNA
<213> ORGANISM: Homo sapiens

<400> SEQUENCE: 27
cgttcctggg cttcccgctc cgcaggcctg cggaggactg gcccagcaag gtcccaggtc      60
ttccctctcc ttagcgccta agagagaggc ccagtgcggg tgaggagtcg cgaggaagag     120
gcggaaggcg ccggaaggca ccatgttccg caagaaaaag aagaaacgcc ctgagatctc     180
agcgccacag aacttccagc accgtgtcca cacctccttc gaccccaaag aaggcaagtt     240
tgtgggcctc cccccacaat ggcagaacat cctggacaca ctgcggcgcc ccaagcccgt     300
ggtggaccct tcgcgaatca cacgggtgca gctccagccc atgaagacag tggtgcgggg     360
cagcgcgatg cctgtggatg gctacatctc ggggctgctc aacgacatcc agaagttgtc     420
agtcatcagc tccaacaccc tgcgtggccg cagccccacc agccggcggc gggcacagtc     480
cctggggctg ctgggggatg agcactgggc caccgaccca gacatgtacc tccagagccc     540
ccagtctgag cgcactgacc cccacggcct ctacctcagc tgcaacgggg gcacaccagc     600
aggccacaag cagatgccgt ggcccgagcc acagagccca cgggtcctgc ccaatgggct     660
ggctgcaaag gcacagtccc tgggccccgc cgagtttcag ggtgcctcgc agcgctgtct     720
gcagctgggt gcctgcctgc agagctcccc accaggagcc tcgcccccca cgggcaccaa     780
taggcatgga atgaaggctg ccaagcatgg ctctgaggag gcccggccac agtcctgcct     840
ggtgggctca gccacaggca ggccaggtgg ggaaggcagc cctagcccta agacccggga     900
gagcagcctg aagcgcaggc tattccgaag catgttcctg tccactgctg ccacagcccc     960
tccaagcagc agcaagccag gccctccacc acagagcaag cccaactcct ctttccgacc    1020
gccgcagaaa gacaaccccc caagcctggt ggccaaggcc cagtccttgc cctcggacca    1080
gccggtgggg accttcagcc ctctgaccac ttcggatacc agcagccccc agaagtccct    1140
ccgcacagcc ccggccacag gccagcttcc aggccggtct tccccagcgg gatcccccg    1200
```

```
                                                    -continued cacctggcac gcccagatca gcaccagcaa cctgtacctg ccccaggacc ccacggttgc      1260
caagggtgcc ctggctggtg aggacacagg tgttgtgaca catgagcagt tcaaggctgc      1320
gctcaggatg gtggtggacc agggtgaccc ccggctgctg ctggacagct acgtgaagat      1380
tggcgagggc tccaccggca tcgtctgctt ggcccgggag aagcactcgg gccgccaggt      1440
ggccgtcaag atgatggacc tcaggaagca gcagcgcagg gagctgctct tcaacgaggt      1500
ggtgatcatg cgggactacc agcacttcaa cgtggtggag atgtacaaga gctacctggt      1560
gggcgaggag ctgtgggtgc tcatggagtt cctgcaggga ggagccctca cagacatcgt      1620
ctcccaagtc aggctgaatg aggagcagat tgccactgtg tgtgaggctg tgctgcaggc      1680
cctggcctac ctgcatgctc agggtgtcat ccaccgggac atcaagagtg actccatcct      1740
gctgaccctc gatggcaggg tgaagctctc ggacttcgga ttctgtgctc agatcagcaa      1800
agacgtccct aagaggaagt ccctggtggg aacccctac tggatggctc ctgaagtgat      1860
ctccaggtct ttgtatgcca ctgaggtgga tatctggtct ctgggcatca tggtgattga      1920
gatggtagat ggggagccac cgtacttcag tgactcccca gtgcaagcca tgaagaggct      1980
ccgggacagc cccccaccca agctgaaaaa ctctcacaag gtctccccag tgctgcgaga      2040
cttcctggag cggatgctgg tgcgggaccc ccaagagaga gccacagccc aggagctcct      2100
agaccacccc ttcctgctgc agacagggct acctgagtgc ctggtgcccc tgatccagct      2160
ctaccgaaag cagacctcca cctgctgagc ccaccccaag tatgcctgcc acctacgccc      2220
acaggcaggg cacactgggc agccagcctg ccggcaggac ttgcctgcct cctcctctca      2280
gtattctctc caaagattga aatgtgaagc cccagcccca ccctctgccc ttcagcctac      2340
tgggccaggc cggacctgcc ccctcagtgt ctctccctcc cgagtcccca gatggagacc      2400
cctttctaca ggatgacccc ttgatatttg cacagggata tttctaagaa acgcagaggc      2460
cagcgttcct ggcctctgca gccaacacag tagaaaaggc tgctgtggtt ttttaaaggc      2520
agttgtccac tagtgtccta ggccactgca gagggcagac tgctggtctc cacagatacc      2580
tgctgttctc agctccagct tcaaacctcg agtctcgaga gggccacggg gtggttttta      2640
tgaccggaat cccgcttcct ccctcacgtc tgatgtcctg aaggtgcagt cccacctgta      2700
cagcccctcc ccgccaagaa ctgtgaatgg cctgctccag gccatggctg ggggcaggga      2760
gtgaggggac aatttctgag tgaaagagaa agaatggggt cggtggtgaa ggtgctctca      2820
ctttacagaa tggagagaac atcgtgtgtg tgtgtgtgtg tgtgtgtgtg tgtgtgtgtg      2880
tgtgtgtgtg tgtgtgtgtg tgtgtgtaag gggaggaaag ccaccttgac agcccaggtc      2940
cctccaggtc acccacagcc agtttcagga aggctgcccc tctctcccac taagttctgg      3000
cctgaaggga cctgctttct tggcctggct tccacctctc cactcctgtg tctacctggc      3060
cagtggagtg gtccatgcta agtctaacac tcctgggagc tcaggaggct tctgagcttc      3120
tcctgtactg tgcatcgtga gggccagaga caggaatgta aggattggca actgtgttac      3180
ctttcaagtt tatctcaata accaggtcat cagggaccca ttgttctctt cagaacccta      3240
tctgggagag aaggcgaacc acctccgggt tccatcatg tcaaggtcac aggcatccat      3300
gtgtgcaaac catctgcccc agctgcctcc acagactgct gtctccttgt cctcctcggc      3360
cctgccccac ttcagggctg ctgtgagatg gaattccagg aaagaacttc aggtgtctgg      3420 acccttctcta tctagataat attttagat tcttctgctc cctagtgacc tacctggggg      3480
caaagaaatt gcaaggactt ttttttaagg gtcagagttt tcaaaacaaa agcatcttcc      3540
ctagaaattt ttgtgaattg tttgcacttg tgcctgtttt aaattaaatt gagtgttcaa      3600
```

| | |
|---|---:|
| agcc | 3604 |

<210> SEQ ID NO 28
<211> LENGTH: 2050
<212> TYPE: DNA
<213> ORGANISM: Homo sapiens

<400> SEQUENCE: 28

| | | | | | |
|---|---|---|---|---|---:|
| ggccagtggg | gcgaaactgg | cagctggccg | gcccctttaac | acctacccga | gggctgacac | 60 |
| ggaccaccca | tcccggggtg | cccaggggga | gcctcatgac | gtggccccta | acgggccatc | 120 |
| agcgggggc | ctggccatcc | cccagtcctc | ctcctcctcc | tcccggcctc | ccacccgagc | 180 |
| ccgaggtgcc | cccagccctg | gagtgctggg | accccacgcc | tcagagcccc | agctggcccc | 240 |
| tccagcctgc | accccgccg | ccctgctgt | tcctgggccc | cctggccccc | gctcaccaca | 300 |
| gcgggagcca | cagcgagtat | cccatgagca | gttccgggct | gccctgcagc | tggtggtgga | 360 |
| cccaggcgac | ccccgctcct | acctggacaa | cttcatcaag | attggcgagg | gctccacggg | 420 |
| catcgtgtgc | atcgccaccg | tgcgcagctc | gggcaagctg | gtggccgtca | agaagatgga | 480 |
| cctgcgcaag | cagcagaggc | gcgagctgct | cttcaacgag | gtggtaatca | tgagggacta | 540 |
| ccagcacgag | aatgtggtgg | agatgtacaa | cagctacctg | gtggggacg | agctctgggt | 600 |
| ggtcatggag | ttcctggaag | gaggcgccct | caccgacatc | gtcacccaca | ccaggatgaa | 660 |
| cgaggagcag | atcgcggccg | tgtgcctttgc | agtgctgcag | gccctgtcgg | tgctccacgc | 720 |
| ccagggcgtc | atccaccggg | acatcaagag | cgactcgatc | ctgctgaccc | atgatggcag | 780 |
| ggtgaagctg | tcagactttg | ggttctgcgc | ccaggtgagc | aaggaagtgc | ccgaaggaa | 840 |
| gtcgctggtc | ggcacgccct | actggatggc | cccagagctc | atctcccgcc | ttccctacgg | 900 |
| gccagaggta | gacatctggt | cgctggggat | aatggtgatt | gagatggtgg | acggagagcc | 960 |
| cccctacttc | aacgagccac | ccctcaaagc | catgaagatg | attcgggaca | acctgccacc | 1020 |
| ccgactgaag | aacctgcaca | aggtgtcgcc | atcccctgaag | ggcttcctgg | accgcctgct | 1080 |
| ggtgcgagac | cctgcccagc | gggccacggc | agccgagctg | ctgaagcacc | cattcctggc | 1140 |
| caaggcaggg | ccgcctgcca | gcatcgtgcc | cctcatgcgc | cagaaccgca | ccagatgagg | 1200 |
| cccagcgccc | ttcccctcaa | ccaaagagcc | ccccgggtc | accccgccc | cactgaggcc | 1260 |
| agtaggggc | caggcctccc | actcctccca | gcccgggaga | tgctccgcgt | ggcaccaccc | 1320 |
| tccttgctgg | gggtagatga | gaccctacta | ctgaactcca | gtttgatct | cgtgactttt | 1380 |
| agaaaacac | agggactcgt | gggagcaagc | gaggctccca | ggaccccac | cctctgggac | 1440 |
| aggccctccc | ccatgttctt | ctgtctccag | gaagggcagc | ggccctccca | tcactggaag | 1500 |
| tctgcagtgg | gggtcgctgg | gggtggagag | aacactaaga | ggtgaacatg | tatgagtgtg | 1560 |
| tgcacgcgtg | tgagtgtgca | tgtgtgtgtg | tgtgcaaagg | tccagccacc | ccgtcctcca | 1620 |
| gcccgcaagg | ggtgtctggc | gccttgcctg | acacccagcc | cctctcccc | ctgagccatt | 1680 |
| gtggggtcg | atcatgaatg | tccgaagagt | ggccttttcc | cgtagccctg | cgccccttt | 1740 |
| ctgtggctgg | atggggagac | aggtcagggc | ccccaccct | ctccagcccc | tgcagcaaat | 1800 |
| gactactgca | cctggacagc | ctcctctttt | ctagaagtct | atttatattg | tcattttata | 1860 |
| acactctagc | cctgcccctt | attggggggac | agatggtccc | tgtcctgcgg | ggtggccctg | 1920 |
| gcagaaccac | tgcctgaaga | accaggttcc | tgccccgtca | gcgcagcccc | agcccgccca | 1980 |
| cccctgcctc | gagttagttt | tacaattaaa | acattgtctt | gttttgtgaa | aaaaaaaaaa | 2040 | aaaaaaaaaa                                                                          2050

<210> SEQ ID NO 29
<211> LENGTH: 681
<212> TYPE: PRT
<213> ORGANISM: Homo sapiens

<400> SEQUENCE: 29

Met Phe Arg Lys Lys Lys Lys Arg Pro Glu Ile Ser Ala Pro Gln
 1               5                  10                  15

Asn Phe Gln His Arg Val His Thr Ser Phe Asp Pro Lys Glu Lys
                20                  25                  30

Phe Val Gly Leu Pro Pro Gln Trp Gln Asn Ile Leu Asp Thr Leu Arg
                35                  40                  45

Arg Pro Lys Pro Val Val Asp Pro Ser Arg Ile Thr Arg Val Gln Leu
     50                  55                  60

Gln Pro Met Lys Thr Val Val Arg Gly Ser Ala Met Pro Val Asp Gly
 65                  70                  75                  80

Tyr Ile Ser Gly Leu Leu Asn Asp Ile Gln Lys Leu Ser Val Ile Ser
                    85                  90                  95

Ser Asn Thr Leu Arg Gly Arg Ser Pro Thr Ser Arg Arg Ala Gln
                100                 105                 110

Ser Leu Gly Leu Leu Gly Asp Glu His Trp Ala Thr Asp Pro Asp Met
                115                 120                 125

Tyr Leu Gln Ser Pro Gln Ser Glu Arg Thr Asp Pro His Gly Leu Tyr
            130                 135                 140

Leu Ser Cys Asn Gly Gly Thr Pro Ala Gly His Lys Gln Met Pro Trp
145                 150                 155                 160

Pro Glu Pro Gln Ser Pro Arg Val Leu Pro Asn Gly Leu Ala Ala Lys
                165                 170                 175

Ala Gln Ser Leu Gly Pro Ala Glu Phe Gln Gly Ala Ser Gln Arg Cys
                180                 185                 190

Leu Gln Leu Gly Ala Cys Leu Gln Ser Ser Pro Pro Gly Ala Ser Pro
            195                 200                 205

Pro Thr Gly Thr Asn Arg His Gly Met Lys Ala Ala Lys His Gly Ser
    210                 215                 220

Glu Glu Ala Arg Pro Gln Ser Cys Leu Val Gly Ser Ala Thr Gly Arg
225                 230                 235                 240

Pro Gly Gly Glu Gly Ser Pro Ser Pro Lys Thr Arg Glu Ser Ser Leu
                245                 250                 255

Lys Arg Arg Leu Phe Arg Ser Met Phe Leu Ser Thr Ala Ala Thr Ala
                260                 265                 270

Pro Pro Ser Ser Ser Lys Pro Gly Pro Pro Gln Ser Lys Pro Asn
            275                 280                 285

Ser Ser Phe Arg Pro Pro Gln Lys Asp Asn Pro Pro Ser Leu Val Ala
    290                 295                 300

Lys Ala Gln Ser Leu Pro Ser Asp Gln Pro Val Gly Thr Phe Ser Pro
305                 310                 315                 320

Leu Thr Thr Ser Asp Thr Ser Ser Pro Gln Lys Ser Leu Arg Thr Ala
                325                 330                 335

Pro Ala Thr Gly Gln Leu Pro Gly Arg Ser Ser Pro Ala Gly Ser Pro
                340                 345                 350

Arg Thr Trp His Ala Gln Ile Ser Thr Ser Asn Leu Tyr Leu Pro Gln
            355                 360                 365

-continued

```
Asp Pro Thr Val Ala Lys Gly Ala Leu Ala Gly Glu Asp Thr Gly Val
    370                 375                 380

Val Thr His Glu Gln Phe Lys Ala Ala Leu Arg Met Val Val Asp Gln
385                 390                 395                 400

Gly Asp Pro Arg Leu Leu Asp Ser Tyr Val Lys Ile Gly Glu Gly
                405                 410                 415

Ser Thr Gly Ile Val Cys Leu Ala Arg Glu Lys His Ser Gly Arg Gln
            420                 425                 430

Val Ala Val Lys Met Met Asp Leu Arg Lys Gln Gln Arg Arg Glu Leu
            435                 440                 445

Leu Phe Asn Glu Val Val Ile Met Arg Asp Tyr Gln His Phe Asn Val
    450                 455                 460

Val Glu Met Tyr Lys Ser Tyr Leu Val Gly Glu Leu Trp Val Leu
465                 470                 475                 480

Met Glu Phe Leu Gln Gly Gly Ala Leu Thr Asp Ile Val Ser Gln Val
                485                 490                 495

Arg Leu Asn Glu Glu Gln Ile Ala Thr Val Cys Glu Ala Val Leu Gln
            500                 505                 510

Ala Leu Ala Tyr Leu His Ala Gln Gly Val Ile His Arg Asp Ile Lys
        515                 520                 525

Ser Asp Ser Ile Leu Leu Thr Leu Asp Gly Arg Val Lys Leu Ser Asp
    530                 535                 540

Phe Gly Phe Cys Ala Gln Ile Ser Lys Asp Val Pro Lys Arg Lys Ser
545                 550                 555                 560

Leu Val Gly Thr Pro Tyr Trp Met Ala Pro Glu Val Ile Ser Arg Ser
                565                 570                 575

Leu Tyr Ala Thr Glu Val Asp Ile Trp Ser Leu Gly Ile Met Val Ile
            580                 585                 590

Glu Met Val Asp Gly Glu Pro Pro Tyr Phe Ser Asp Ser Pro Val Gln
        595                 600                 605

Ala Met Lys Arg Leu Arg Asp Ser Pro Pro Lys Leu Lys Asn Ser
    610                 615                 620

His Lys Val Ser Pro Val Leu Arg Asp Phe Leu Glu Arg Met Leu Val
625                 630                 635                 640

Arg Asp Pro Gln Glu Arg Ala Thr Ala Gln Glu Leu Leu Asp His Pro
                645                 650                 655

Phe Leu Leu Gln Thr Gly Leu Pro Glu Cys Leu Val Pro Leu Ile Gln
            660                 665                 670

Leu Tyr Arg Lys Gln Thr Ser Thr Cys
        675                 680

<210> SEQ ID NO 30
<211> LENGTH: 398
<212> TYPE: PRT
<213> ORGANISM: Homo sapiens

<400> SEQUENCE: 30

Ala Ser Gly Ala Lys Leu Ala Ala Gly Arg Pro Phe Asn Thr Tyr Pro
  1                 5                  10                  15

Arg Ala Asp Thr Asp His Pro Ser Arg Gly Ala Gln Gly Glu Pro His
                20                  25                  30

Asp Val Ala Pro Asn Gly Pro Ser Ala Gly Gly Leu Ala Ile Pro Gln
            35                  40                  45

Ser Ser Ser Ser Ser Ser Arg Pro Pro Thr Arg Ala Arg Gly Ala Pro
     50                  55                  60
```

-continued

```
Ser Pro Gly Val Leu Gly Pro His Ala Ser Glu Pro Gln Leu Ala Pro
 65                  70                  75                  80

Pro Ala Cys Thr Pro Ala Ala Pro Ala Val Pro Gly Pro Pro Gly Pro
                 85                  90                  95

Arg Ser Pro Gln Arg Glu Pro Gln Arg Val Ser His Glu Gln Phe Arg
            100                 105                 110

Ala Ala Leu Gln Leu Val Val Asp Pro Gly Asp Pro Arg Ser Tyr Leu
        115                 120                 125

Asp Asn Phe Ile Lys Ile Gly Glu Gly Ser Thr Gly Ile Val Cys Ile
    130                 135                 140

Ala Thr Val Arg Ser Ser Gly Lys Leu Val Ala Val Lys Lys Met Asp
145                 150                 155                 160

Leu Arg Lys Gln Gln Arg Arg Glu Leu Leu Phe Asn Glu Val Val Ile
                165                 170                 175

Met Arg Asp Tyr Gln His Glu Asn Val Val Glu Met Tyr Asn Ser Tyr
            180                 185                 190

Leu Val Gly Asp Glu Leu Trp Val Val Met Glu Phe Leu Glu Gly Gly
        195                 200                 205

Ala Leu Thr Asp Ile Val Thr His Thr Arg Met Asn Glu Glu Gln Ile
    210                 215                 220

Ala Ala Val Cys Leu Ala Val Leu Gln Ala Leu Ser Val Leu His Ala
225                 230                 235                 240

Gln Gly Val Ile His Arg Asp Ile Lys Ser Asp Ser Ile Leu Leu Thr
                245                 250                 255

His Asp Gly Arg Val Lys Leu Ser Asp Phe Gly Phe Cys Ala Gln Val
            260                 265                 270

Ser Lys Glu Val Pro Arg Arg Lys Ser Leu Val Gly Thr Pro Tyr Trp
        275                 280                 285

Met Ala Pro Glu Leu Ile Ser Arg Leu Pro Tyr Gly Pro Glu Val Asp
    290                 295                 300

Ile Trp Ser Leu Gly Ile Met Val Ile Glu Met Val Asp Gly Glu Pro
305                 310                 315                 320

Pro Tyr Phe Asn Glu Pro Pro Leu Lys Ala Met Lys Met Ile Arg Asp
                325                 330                 335

Asn Leu Pro Pro Arg Leu Lys Asn Leu His Lys Val Ser Pro Ser Leu
            340                 345                 350

Lys Gly Phe Leu Asp Arg Leu Leu Val Arg Asp Pro Ala Gln Arg Ala
        355                 360                 365

Thr Ala Ala Glu Leu Leu Lys His Pro Phe Leu Ala Lys Ala Gly Pro
    370                 375                 380

Pro Ala Ser Ile Val Pro Leu Met Arg Gln Asn Arg Thr Arg
385                 390                 395

<210> SEQ ID NO 31
<211> LENGTH: 1001
<212> TYPE: PRT
<213> ORGANISM: Artificial Sequence
<220> FEATURE:
<223> OTHER INFORMATION: Description of Artificial Sequence: Synthetic
      murine/human SULU3

<400> SEQUENCE: 31

Met Pro Ser Thr Asn Arg Ala Gly Ser Leu Lys Asp Pro Glu Ile Ala
  1               5                  10                  15

Glu Leu Phe Phe Lys Glu Asp Pro Glu Lys Leu Phe Thr Asp Leu Arg
```

```
                    20                  25                    30
     Glu Ile Gly His Gly Ser Phe Gly Ala Val Tyr Phe Ala Arg Asp Val
                  35                  40                  45

Arg Thr Asn Glu Val Val Ala Ile Lys Lys Met Ser Tyr Ser Gly Lys
              50                  55                  60

Gln Ser Thr Glu Lys Trp Gln Asp Ile Ile Lys Glu Val Lys Phe Leu
      65                  70                  75                  80

Gln Arg Ile Lys His Pro Asn Ser Ile Glu Tyr Lys Gly Cys Tyr Leu
                          85                  90                  95

Arg Glu His Thr Ala Trp Leu Val Met Glu Tyr Cys Leu Gly Ser Ala
                     100                 105                 110

Ser Asp Leu Leu Glu Val His Lys Lys Pro Leu Gln Glu Val Glu Ile
                 115                 120                 125

Ala Ala Ile Thr His Gly Ala Leu Gln Gly Leu Ala Tyr Leu His Ser
     130                 135                 140

His Thr Met Ile His Arg Asp Ile Lys Ala Gly Asn Ile Leu Leu Thr
     145                 150                 155                 160

Glu Pro Gly Gln Val Lys Leu Ala Asp Phe Gly Ser Ala Ser Met Ala
                         165                 170                 175

Ser Pro Ala Asn Ser Phe Val Gly Thr Pro Tyr Trp Met Ala Pro Glu
                 180                 185                 190

Val Ile Leu Ala Met Asp Glu Gly Gln Tyr Asp Gly Lys Val Asp Val
                     195                 200                 205

Trp Ser Leu Gly Ile Thr Cys Ile Glu Leu Ala Glu Arg Lys Pro Pro
             210                 215                 220

Leu Phe Asn Met Asn Ala Met Ser Ala Leu Tyr His Ile Ala Gln Asn
     225                 230                 235                 240

Glu Ser Pro Thr Leu Gln Ser Asn Glu Trp Ser Asp Tyr Phe Arg Asn
                         245                 250                 255

Phe Val Asp Ser Cys Leu Gln Lys Ile Pro Gln Asp Arg Pro Thr Ser
                 260                 265                 270

Glu Glu Leu Leu Lys His Ile Phe Val Leu Arg Glu Arg Pro Glu Thr
                     275                 280                 285

Val Leu Ile Asp Leu Ile Gln Arg Thr Lys Asp Ala Val Arg Glu Leu
             290                 295                 300

Asp Asn Leu Gln Tyr Arg Lys Met Lys Lys Leu Leu Phe Gln Glu Ala
     305                 310                 315                 320

His Asn Gly Pro Ala Val Glu Ala Gln Glu Glu Glu Glu Glu Gln Asp
                         325                 330                 335

His Gly Val Gly Arg Thr Gly Thr Val Asn Ser Val Gly Ser Asn Gln
                 340                 345                 350

Ser Ile Pro Ser Met Ser Ile Ser Ala Ser Ser Gln Ser Ser Ser Val
                     355                 360                 365

Asn Ser Leu Pro Asp Val Ser Asp Asp Lys Ser Glu Leu Asp Met Met
             370                 375                 380

Glu Gly Asp His Thr Val Met Ser Asn Ser Ser Val Ile His Leu Lys
     385                 390                 395                 400

Pro Glu Glu Glu Asn Tyr Arg Glu Glu Gly Asp Pro Arg Thr Arg Ala
                         405                 410                 415

Ser Asp Pro Gln Ser Pro Pro Gln Val Ser Arg His Lys Ser His Tyr
                 420                 425                 430

Arg Asn Arg Glu His Phe Ala Thr Ile Arg Thr Ala Ser Leu Val Thr
             435                 440                 445
```

-continued

```
Arg Gln Met Gln Glu His Glu Gln Asp Ser Glu Leu Arg Glu Gln Met
    450                 455                 460
Ser Gly Tyr Lys Arg Met Arg Gln His Gln Lys Gln Leu Met Thr
465                 470                 475                 480
Leu Glu Asn Lys Leu Lys Ala Glu Met Asp Glu His Arg Leu Arg Leu
            485                 490                 495
Asp Lys Asp Leu Glu Thr Gln Arg Asn Asn Phe Ala Ala Glu Met Glu
                500                 505                 510
Lys Leu Ile Lys Lys His Gln Ala Ala Met Glu Lys Glu Ala Lys Val
            515                 520                 525
Met Ser Asn Glu Glu Lys Lys Phe Gln Gln His Ile Gln Ala Gln Gln
530                 535                 540
Lys Lys Glu Leu Asn Ser Phe Leu Glu Ser Gln Lys Arg Glu Tyr Lys
545                 550                 555                 560
Leu Arg Lys Glu Gln Leu Lys Glu Glu Leu Asn Glu Asn Gln Ser Thr
                565                 570                 575
Pro Lys Lys Glu Lys Gln Glu Trp Leu Ser Lys Gln Lys Glu Asn Ile
            580                 585                 590
Gln His Phe Gln Ala Glu Glu Ala Asn Leu Leu Arg Arg Gln Arg
            595                 600                 605
Gln Tyr Leu Glu Leu Glu Cys Arg Arg Phe Lys Arg Arg Met Leu Leu
    610                 615                 620
Gly Arg His Asn Leu Glu Gln Asp Leu Val Arg Glu Glu Leu Asn Lys
625                 630                 635                 640
Arg Gln Thr Gln Lys Asp Leu Glu His Ala Met Leu Leu Arg Gln His
                645                 650                 655
Glu Ser Met Gln Glu Leu Glu Phe Arg His Leu Asn Thr Ile Gln Lys
            660                 665                 670
Met Arg Cys Glu Leu Ile Arg Leu Gln His Gln Thr Glu Leu Thr Asn
            675                 680                 685
Gln Leu Glu Tyr Asn Lys Arg Arg Glu Arg Glu Leu Arg Arg Lys His
    690                 695                 700
Val Met Glu Val Arg Gln Gln Pro Lys Ser Leu Lys Ser Lys Glu Leu
705                 710                 715                 720
Gln Ile Lys Lys Gln Phe Gln Asp Thr Cys Lys Ile Gln Thr Arg Gln
                725                 730                 735
Tyr Lys Ala Leu Arg Asn His Leu Leu Glu Thr Thr Pro Lys Ser Glu
            740                 745                 750
His Lys Ala Val Leu Lys Arg Leu Lys Glu Glu Gln Thr Arg Lys Leu
            755                 760                 765
Ala Ile Leu Ala Glu Gln Tyr Asp His Ser Ile Asn Glu Met Leu Ser
770                 775                 780
Thr Gln Ala Leu Arg Leu Asp Glu Ala Gln Glu Ala Glu Cys Gln Val
785                 790                 795                 800
Leu Lys Met Gln Leu Gln Gln Glu Leu Glu Leu Leu Asn Ala Tyr Gln
                805                 810                 815
Ser Lys Ile Lys Met Gln Ala Glu Ala Gln His Asp Arg Glu Leu Arg
            820                 825                 830
Glu Leu Glu Gln Arg Val Ser Leu Arg Arg Ala Leu Leu Glu Gln Lys
        835                 840                 845
Ile Glu Glu Glu Met Leu Ala Leu Gln Asn Glu Arg Thr Glu Arg Ile
850                 855                 860
```

```
Arg Ser Leu Leu Glu Arg Gln Ala Arg Glu Ile Glu Ala Phe Asp Ser
865                 870                 875                 880

Glu Ser Met Arg Leu Gly Phe Ser Asn Met Val Leu Ser Asn Leu Ser
            885                 890                 895

Pro Glu Ala Phe Ser His Ser Tyr Pro Gly Ala Ser Gly Trp Ser His
                900                 905                 910

Asn Pro Thr Gly Gly Pro Gly Pro His Trp Gly His Pro Met Gly Gly
            915                 920                 925

Pro Pro Gln Ala Trp Gly His Pro Met Gln Gly Pro Gln Pro Trp
    930                 935                 940

Gly His Pro Ser Gly Pro Met Gln Val Pro Arg Gly Ser Ser Met
945                 950                 955                 960

Gly Val Arg Asn Ser Pro Gln Ala Leu Arg Arg Thr Ala Ser Gly Gly
                965                 970                 975

Arg Thr Glu Gln Gly Met Ser Arg Ser Thr Ser Val Thr Ser Gln Ile
            980                 985                 990

Ser Asn Gly Ser His Met Ser Tyr Thr
            995                 1000
```

<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (11)
<223> OTHER INFORMATION: a, t, c, g, other or unknown
<220> FEATURE:
<221> NAME/KEY: modified_base
<222> LOCATION: (14)
<223> OTHER INFORMATION: a, t, c, g, other or unknown
<220> FEATURE:
<221> NAME/KEY: modified_base
<222> LOCATION: (20)
<223> OTHER INFORMATION: a, t, c, g, other or unknown

<400> SEQUENCE: 32
ctgaattcgg ngcnttyggn aargt                                25

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (13)
<223> OTHER INFORMATION: a, t, c, g, other or unknown
<220> FEATURE:
<221> NAME/KEY: modified_base
<222> LOCATION: (16)
<223> OTHER INFORMATION: a, t, c, g, other or unknown

<400> SEQUENCE: 33
gctggatccy tcngnggca tcca                                  24

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Primer
<220> FEATURE:

```
<221> NAME/KEY: modified_base
<222> LOCATION: (3)
<223> OTHER INFORMATION: a, t, c, g, other or unknown
<220> FEATURE:
<221> NAME/KEY: modified_base
<222> LOCATION: (9)
<223> OTHER INFORMATION: a, t, c, g, other or unknown
<220> FEATURE:
<221> NAME/KEY: modified_base
<222> LOCATION: (15)
<223> OTHER INFORMATION: a, t, c, g, other or unknown

<400> SEQUENCE: 34
gcnttyggng argtntayga rgg                                        23

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (13)
<223> OTHER INFORMATION: a, t, c, g, other or unknown
<220> FEATURE:
<221> NAME/KEY: modified_base
<222> LOCATION: (16)
<223> OTHER INFORMATION: a, t, c, g, other or unknown

<400> SEQUENCE: 35
gctggatccy tcnggnswca tcca                                       24

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (9)
<223> OTHER INFORMATION: a, t, c, g, other or unknown
<220> FEATURE:
<221> NAME/KEY: modified_base
<222> LOCATION: (15)
<223> OTHER INFORMATION: a, t, c, g, other or unknown
<220> FEATURE:
<221> NAME/KEY: modified_base
<222> LOCATION: (21)
<223> OTHER INFORMATION: a, t, c, g, other or unknown

<400> SEQUENCE: 36
gagttyggng argtnttyyt ngc                                        23

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic
      motif

<400> SEQUENCE: 37

Gly Ala Phe Gly Lys Val
 1               5

<210> SEQ ID NO 38
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      motif

<400> SEQUENCE: 38

Trp Met Pro Pro Glu
  1               5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic
      motif

<400> SEQUENCE: 39

Ala Phe Gly Glu Val Tyr Glu Gly
  1               5

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      motif

<400> SEQUENCE: 40

Trp Met Ser Pro Glu
  1               5

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      motif

<400> SEQUENCE: 41

Glu Phe Gly Glu Val Tyr Glu Gly
  1               5

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 42
cacagaaacg gtcagattca c                                           21

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 43
gatcagggtg acatcaaggg ac                                          22

<210> SEQ ID NO 44
<211> LENGTH: 22
<212> TYPE: DNA
```

<213> ORGANISM: Artificial Sequence
<220> FEATURE:
<223> OTHER INFORMATION: Description of Artificial Sequence: Primer

<400> SEQUENCE: 44
ctcatctgta cacacttcat gg                                    22

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 45
gattcccaca ctgtagatgt c                                     21

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 46
ggccctcgac tacatccacc acat                                  24

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 47
caacgaaact aacacagcat aagg                                  24

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 48
atggcgaacg actctcccgc gaa                                   23

<210> SEQ ID NO 49
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 49
acaccaaaat caacaagttt cacctc                                26

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 50
agttacaagg aattccaagt tct                                   23

<210> SEQ ID NO 51
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 51
atgaagagga agaaatcaaa ctg                                             23

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 52
agatggactg tactgggagg                                                 20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 53
actttgtgca gctctgtggg                                                 20

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 54
aaggttatgg atgtcacagg g                                               21

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 55
ctcacaaggt tgccaacagg                                                 20

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 56
agtccccacc agaaggttta c                                               21

<210> SEQ ID NO 57
<211> LENGTH: 19
<212> TYPE: DNA
<213> ORGANISM: Artificial Sequence
<220> FEATURE:

<223> OTHER INFORMATION: Description of Artificial Sequence: Primer

<400> SEQUENCE: 57 tcagggtca gaggtcacg                                                    19

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 58
cccaaaccct accacaaatt c                                                21

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 59
cccccgggaa acgatgacca                                                  20

<210> SEQ ID NO 60
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 60
agccgctgcc cctcctctac tgt                                              23

<210> SEQ ID NO 61
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 61
accgcaacat cgccacctac tac                                              23

<210> SEQ ID NO 62
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 62
ctcgacgtcg tggaccacc                                                   19

<210> SEQ ID NO 63
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 63
caatgttaac ccactctatg tctc                                             24

```
<210> SEQ ID NO 64
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 64
agtttgccga tgttttcctt ttc                                              23

<210> SEQ ID NO 65
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 65
ccgccatgaa ccccggctt                                                   19

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 66
cgattgccaa agaccgtgtc a                                                21

<210> SEQ ID NO 67
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 67
agaagttgca gctgttgaga gga                                              23

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 68
tatggcccgt gtaaggattt c                                                21

<210> SEQ ID NO 69
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 69
gtgccagaag tgttgtgttg taa                                              23

<210> SEQ ID NO 70
<211> LENGTH: 22
<212> TYPE: DNA
<213> ORGANISM: Artificial Sequence
<220> FEATURE:
<223> OTHER INFORMATION: Description of Artificial Sequence: Primer
```

```
<400> SEQUENCE: 70
tattgaattg gcggaacgga ag                                              22

<210> SEQ ID NO 71
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 71
ttgttttgtg ctcattcttt ggag                                            24

<210> SEQ ID NO 72
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 72
gattgctttg tgctcattct ttgg                                            24

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 73
ttgttctaag agtgccctcc g                                               21

<210> SEQ ID NO 74
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 74
aagaccatgc cgtgcgccg                                                  19

<210> SEQ ID NO 75
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 75
attccttcag gttctggtta tgg                                             23

<210> SEQ ID NO 76

<400> SEQUENCE: 76

000

<210> SEQ ID NO 77

<400> SEQUENCE: 77

000
```

```
<210> SEQ ID NO 78
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide 540A

<400> SEQUENCE: 78

His Gly Asp Pro Arg Pro Glu Pro Arg Pro Thr Gln
 1               5                  10

<210> SEQ ID NO 79
<211> LENGTH: 10
<212> TYPE: PRT
<213> ORGANISM: Artificial Sequence
<220> FEATURE:
<223> OTHER INFORMATION: Description of Artificial Sequence: Syntbetic
      peptide 539A

<400> SEQUENCE: 79

Cys Leu Asp Phe Pro Lys Glu Asp Tyr Arg
 1               5                  10

<210> SEQ ID NO 80

<400> SEQUENCE: 80

000

<210> SEQ ID NO 81
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide 542A

<400> SEQUENCE: 81

Pro Ser Thr Asn Arg Ala Gly Ser Leu Lys Asp Pro Glu Cys
 1               5                  10

<210> SEQ ID NO 82
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide 554A

<400> SEQUENCE: 82

Cys Leu Val Pro Leu Ile Gln Leu Tyr Arg Lys Gln Thr Ser Thr
 1               5                  10                  15

<210> SEQ ID NO 83

<400> SEQUENCE: 83

000

<210> SEQ ID NO 84
<211> LENGTH: 426
<212> TYPE: PRT
<213> ORGANISM: Homo sapiens

<400> SEQUENCE: 84

Met Ala His Leu Arg Gly Phe Ala Asn Gln His Ser Arg Val Asp Pro
 1               5                  10                  15
```

-continued

```
Glu Glu Leu Phe Thr Lys Leu Asp Arg Ile Gly Lys Gly Ser Phe Gly
             20                  25                  30
Glu Val Tyr Lys Gly Ile Asp Asn His Thr Lys Glu Val Val Ala Ile
         35                  40                  45
Lys Ile Ile Asp Leu Glu Glu Ala Glu Asp Glu Ile Glu Asp Ile Gln
     50                  55                  60
Gln Glu Ile Thr Val Leu Ser Gln Cys Asp Ser Pro Tyr Ile Thr Arg
 65                  70                  75                  80
Tyr Phe Gly Ser Tyr Leu Lys Ser Thr Lys Leu Trp Ile Ile Met Glu
                 85                  90                  95
Tyr Leu Gly Gly Gly Ser Ala Leu Asp Leu Leu Lys Pro Gly Pro Leu
            100                 105                 110
Glu Glu Thr Tyr Ile Ala Thr Ile Leu Arg Glu Ile Leu Lys Gly Leu
        115                 120                 125
Asp Tyr Leu His Ser Glu Arg Lys Ile His Arg Asp Ile Lys Ala Ala
    130                 135                 140
Asn Val Leu Leu Ser Glu Gln Gly Asp Val Lys Leu Ala Asp Phe Gly
145                 150                 155                 160
Val Ala Gly Gln Leu Thr Asp Thr Gln Ile Lys Arg Asn Thr Phe Val
                165                 170                 175
Gly Thr Pro Phe Trp Met Ala Pro Glu Val Ile Lys Gln Ser Ala Tyr
            180                 185                 190
Asp Phe Lys Ala Asp Ile Trp Ser Leu Gly Ile Thr Ala Ile Glu Leu
        195                 200                 205
Ala Lys Gly Glu Pro Pro Asn Ser Asp Leu His Pro Met Arg Val Leu
    210                 215                 220
Phe Leu Ile Pro Lys Asn Ser Pro Pro Thr Leu Glu Gly Gln His Ser
225                 230                 235                 240
Lys Pro Phe Lys Glu Phe Val Glu Ala Cys Leu Asn Lys Asp Pro Arg
                245                 250                 255
Phe Arg Pro Thr Ala Lys Glu Leu Leu Lys His Lys Phe Ile Thr Arg
            260                 265                 270
Tyr Thr Lys Lys Thr Ser Phe Leu Thr Glu Leu Ile Asp Arg Tyr Lys
        275                 280                 285
Arg Trp Lys Ser Glu Gly His Gly Glu Glu Ser Ser Ser Glu Asp Ser
    290                 295                 300
Asp Ile Asp Gly Glu Ala Glu Asp Gly Glu Gln Gly Pro Ile Trp Thr
305                 310                 315                 320
Phe Pro Pro Thr Ile Arg Pro Ser Pro His Ser Lys Leu His Lys Gly
                325                 330                 335
Thr Ala Leu His Ser Ser Gln Lys Pro Ala Glu Pro Val Lys Arg Gln
            340                 345                 350
Pro Arg Ser Gln Cys Leu Ser Thr Leu Val Arg Pro Val Phe Gly Glu
        355                 360                 365
Leu Lys Glu Lys His Lys Gln Ser Gly Gly Ser Val Gly Ala Leu Glu
    370                 375                 380
Glu Leu Glu Asn Ala Phe Ser Leu Ala Glu Glu Ser Cys Pro Gly Ile
385                 390                 395                 400
Ser Asp Lys Leu Met Val His Leu Val Glu Arg Val Gln Arg Phe Ser
                405                 410                 415
His Asn Arg Asn His Leu Thr Ser Thr Arg
            420                 425
```

<210> SEQ ID NO 85
<211> LENGTH: 431
<212> TYPE: PRT
<213> ORGANISM: Homo sapiens

<400> SEQUENCE: 85

```
Met Ala His Ser Pro Val Gln Ser Gly Leu Pro Gly Met Gln Asn Leu
 1               5                  10                  15

Lys Ala Asp Pro Glu Glu Leu Phe Thr Lys Leu Glu Lys Ile Gly Lys
            20                  25                  30

Gly Ser Phe Gly Glu Val Phe Lys Gly Ile Asp Asn Arg Thr Gln Lys
        35                  40                  45

Val Val Ala Ile Lys Ile Ile Asp Leu Glu Glu Ala Glu Asp Glu Ile
    50                  55                  60

Glu Asp Ile Gln Gln Glu Ile Thr Val Leu Ser Gln Cys Asp Ser Pro
65                  70                  75                  80

Tyr Val Thr Lys Tyr Tyr Gly Ser Tyr Leu Lys Asp Thr Lys Leu Trp
                85                  90                  95

Ile Ile Met Glu Tyr Leu Gly Gly Gly Ser Ala Leu Asp Leu Leu Glu
            100                 105                 110

Pro Gly Pro Leu Asp Glu Thr Gln Ile Ala Thr Ile Leu Arg Glu Ile
        115                 120                 125

Leu Lys Gly Leu Asp Tyr Leu His Ser Glu Lys Lys Ile His Arg Asp
    130                 135                 140

Ile Lys Ala Ala Asn Val Leu Leu Ser Glu His Gly Glu Val Lys Leu
145                 150                 155                 160

Ala Asp Phe Gly Val Ala Gly Gln Leu Thr Asp Thr Gln Ile Lys Arg
                165                 170                 175

Asn Thr Phe Val Gly Thr Pro Phe Trp Met Ala Pro Glu Val Ile Lys
            180                 185                 190

Gln Ser Ala Tyr Asp Ser Lys Ala Asp Ile Trp Ser Leu Gly Ile Thr
        195                 200                 205

Ala Ile Glu Leu Ala Arg Gly Glu Pro Pro His Ser Glu Leu His Pro
    210                 215                 220

Met Lys Val Leu Phe Leu Ile Pro Lys Asn Asn Pro Pro Thr Leu Glu
225                 230                 235                 240

Gly Asn Tyr Ser Lys Pro Leu Lys Glu Phe Val Glu Ala Cys Leu Asn
                245                 250                 255

Lys Glu Pro Ser Phe Arg Pro Thr Ala Lys Glu Leu Leu Lys His Lys
            260                 265                 270

Phe Ile Leu Arg Asn Ala Lys Lys Thr Ser Tyr Leu Thr Glu Leu Ile
        275                 280                 285

Asp Arg Tyr Lys Arg Trp Lys Ala Glu Gln Ser His Asp Asp Ser Ser
    290                 295                 300

Ser Glu Asp Ser Asp Ala Glu Thr Asp Gly Gln Ala Ser Gly Gly Ser
305                 310                 315                 320

Asp Ser Gly Asp Trp Ile Phe Thr Ile Arg Glu Lys Asp Pro Lys Asn
                325                 330                 335

Leu Glu Asn Gly Ala Leu Gln Pro Ser Asp Leu Asp Arg Asn Lys Met
            340                 345                 350

Lys Asp Ile Pro Lys Arg Pro Phe Ser Gln Cys Leu Ser Thr Ile Ile
        355                 360                 365

Ser Pro Leu Phe Ala Glu Leu Lys Glu Lys Ser Gln Ala Cys Gly Gly
    370                 375                 380
```

-continued

Asn Leu Gly Ser Ile Glu Glu Leu Arg Gly Ala Ile Tyr Leu Ala Glu
385                 390                 395                 400

Glu Ala Cys Pro Gly Ile Ser Asp Thr Met Val Ala Gln Leu Val Gln
            405                 410                 415

Arg Leu Gln Arg Tyr Ser Leu Ser Gly Gly Thr Ser Ser His
        420                 425                 430

<210> SEQ ID NO 86
<211> LENGTH: 443
<212> TYPE: PRT
<213> ORGANISM: Caenorhabditis elegans
<220> FEATURE:
<221> NAME/KEY: MOD_RES
<222> LOCATION: (389)..(390)
<223> OTHER INFORMATION: Any amino acid

<400> SEQUENCE: 86

Met Thr Thr Thr Ser Ser Asp Glu Leu Pro Arg Gln Ala Asp Asp Asp
1               5                   10                  15

Ser Met Lys Trp Asp Arg Ile Tyr Ile Gln Lys Leu Asp Pro Glu Val
            20                  25                  30

Ile Phe Thr Lys Gln Glu Arg Ile Gly Arg Gly Ser Phe Gly Glu Val
        35                  40                  45

Tyr Lys Gly Ile Asp Asn Arg Thr Gly Arg Val Val Ala Ile Lys Ile
    50                  55                  60

Ile Asp Leu Glu Gln Ala Glu Asp Glu Ile Asp Ile Gln Gln Glu
65                  70                  75                  80

Ile Gln Val Leu Ser Gln Cys Asp Ser Gln Tyr Val Thr Lys Tyr Phe
                85                  90                  95

Gly Ser Phe Leu Lys Gly Ser Lys Leu Trp Ile Ile Met Glu Tyr Leu
            100                 105                 110

Gly Gly Gly Ser Ala Leu Asp Leu Thr Lys Ser Gly Lys Leu Asp Glu
        115                 120                 125

Ser His Ile Ala Val Ile Leu Arg Glu Ile Leu Lys Gly Leu Glu Tyr
    130                 135                 140

Leu His Ser Glu Arg Lys Ile His Arg Asp Ile Lys Ala Ala Asn Val
145                 150                 155                 160

Leu Val Ser Glu His Gly Asp Val Lys Val Ala Asp Phe Gly Val Ala
                165                 170                 175

Gly Gln Leu Thr Glu Thr Val Lys Lys Arg Ile Thr Phe Val Gly Ser
            180                 185                 190

Pro Phe Trp Met Ala Pro Glu Leu Ile Lys Gln Ser Ser Tyr Asp Tyr
        195                 200                 205

Lys Ala Asp Ile Trp Ser Leu Gly Ile Thr Ala Ile Glu Leu Ala Asn
    210                 215                 220

Gly Glu Pro Pro His Ser Asp Leu His Pro Met Arg Val Leu Phe Leu
225                 230                 235                 240

Ile Pro Lys Asn Pro Pro Val Leu Gln Gly Ser Gln Trp Ser Lys
                245                 250                 255

Pro Phe Lys Glu Phe Val Glu Met Cys Leu Asn Lys Asp Pro Glu Asn
            260                 265                 270

Arg Pro Ser Ala Ser Thr Leu Leu Lys His Gln Phe Ile Lys Arg Ala
        275                 280                 285

Lys Lys Asn Ser Ile Leu Val Asp Leu Ile Glu Arg Ala Ala Glu Tyr
    290                 295                 300

```
Arg Leu Arg Thr Gly Val Ser Ser Asp Ser Asp Leu Asp Glu Asp Ser
305                 310                 315                 320

Asp Gly Gly Gly Thr Ser Lys Trp Asp Tyr Pro Thr Val Arg Gly
            325                 330                 335

Pro Arg Val Ser Ala Asp Asp Gly Thr Val Arg Gln Arg Thr Asp
            340                 345                 350

Arg Pro Arg Ala Gln Val Asp Arg Arg Ser Pro Ser Gly Ser Pro Gly
            355                 360                 365

Gly Thr Ile Val Arg Gly Ser Pro Gln Val Ala Ala Val Ala Glu Gln
    370                 375                 380

Leu Arg Asn Ser Xaa Xaa Ala Leu Asp Gln Leu Arg His Val Phe Arg
385                 390                 395                 400

Asp Val Glu Asp Ser Cys Pro Gly Ile Cys Asn Glu Leu Ile Glu Glu
            405                 410                 415

Leu Met Gln Arg Ile Ala Val Pro Gln Val Ser Gln Ser Asp Leu Asp
            420                 425                 430

Ala Ala Ile Arg Arg Leu Thr Thr Pro Pro Ser
            435                 440

<210> SEQ ID NO 87
<211> LENGTH: 275
<212> TYPE: PRT
<213> ORGANISM: Saccharomyces pombe

<400> SEQUENCE: 87

Leu Leu Tyr Arg Asn Phe Val Lys Ile Gly Gln Gly Ala Ser Gly Asp
  1               5                  10                  15

Val Tyr Ser Ala Arg Gln Val Gly Thr Asn Leu Ser Val Ala Ile Lys
             20                  25                  30

Lys Met Asn Ile Asn Gln Gln Pro Lys Lys Glu Phe Ile Val Asn Glu
         35                  40                  45

Ile Leu Val Met Lys Ser His His Lys Asn Ile Val Asn Phe Ile
     50                  55                  60

Asp Thr Phe Phe Tyr Lys Ser Glu Leu Trp Met Val Met Glu Tyr Met
 65                  70                  75                  80

Arg Gly Gly Ser Leu Thr Glu Val Val Thr Asn Asn Thr Leu Ser Glu
                 85                  90                  95

Gly Gln Ile Ala Ala Ile Cys Lys Glu Thr Leu Glu Gly Leu Gln His
            100                 105                 110

Leu His Glu Asn Gly Ile Val His Arg Asp Ile Lys Ser Asp Asn Ile
        115                 120                 125

Leu Leu Ser Leu Gln Gly Asp Ile Lys Leu Thr Asp Phe Gly Phe Cys
130                 135                 140

Ala Gln Ile Asp Ser Asn Met Thr Lys Arg Thr Thr Met Val Gly Thr
145                 150                 155                 160

Pro Tyr Trp Met Ala Pro Glu Val Val Thr Arg Lys Glu Tyr Gly Phe
                165                 170                 175

Lys Val Asp Val Trp Ser Leu Gly Ile Met Ala Ile Glu Met Val Glu
            180                 185                 190

Gly Glu Pro Pro Tyr Leu Asn Glu Asn Pro Leu Arg Ala Leu Tyr Leu
        195                 200                 205

Ile Ala Thr Ile Gly Thr Pro Lys Ile Ser Arg Pro Glu Leu Leu Ser
    210                 215                 220

Ser Val Phe His Asp Phe Leu Ser Lys Ser Leu Thr Val Asn Pro Lys
225                 230                 235                 240
```

```
Gln Arg Pro Ser Ser Gly Glu Leu Leu Arg His Pro Phe Leu Lys Gln
                245                 250                 255

Ala Val Pro Val Ser Ser Leu Ile Pro Leu Ile Lys Ser Ile His His
            260                 265                 270

Ser Gly Lys
        275

<210> SEQ ID NO 88
<211> LENGTH: 1109
<212> TYPE: PRT
<213> ORGANISM: Caenorhabditis elegans

<400> SEQUENCE: 88

Met Ser Ser Gly Leu Asp Glu Ile Asp Leu Asn Ser Leu Arg Asp
  1               5                  10                  15

Pro Ala Gly Ile Phe Glu Leu Ile Glu Val Val Gly Asn Gly Thr Tyr
                 20                  25                  30

Gly Gln Val Tyr Lys Gly Arg His Val Lys Thr Ala Gln Leu Ala Ala
             35                  40                  45

Ile Lys Ile Met Asn Ile Asn Glu Asp Glu Glu Asp Glu Ile Lys Leu
 50                  55                  60

Glu Ile Asn Met Leu Lys Lys His Ser His His Arg Asn Val Ala Thr
 65                  70                  75                  80

Tyr Tyr Gly Ala Phe Ile Lys Lys Leu Pro Ser Ser Thr Gly Lys His
                 85                  90                  95

Asp Gln Leu Trp Leu Val Met Glu Phe Cys Gly Ser Gly Ser Ile Thr
            100                 105                 110

Asp Leu Val Lys Asn Thr Lys Gly Gly Ser Leu Lys Glu Glu Trp Ile
            115                 120                 125

Ala Tyr Ile Cys Arg Glu Ile Leu Arg Gly Leu Tyr His Leu His Gln
        130                 135                 140

Ser Lys Val Ile His Arg Asp Ile Lys Gly Gln Asn Val Leu Leu Thr
145                 150                 155                 160

Asp Ser Ala Glu Val Lys Leu Val Asp Phe Gly Val Ser Ala Gln Leu
                165                 170                 175

Asp Lys Thr Val Gly Arg Arg Asn Thr Phe Ile Gly Thr Pro Tyr Trp
            180                 185                 190

Met Ala Pro Glu Val Ile Ala Cys Asp Glu Ser Pro Glu Ala Thr Tyr
        195                 200                 205

Asp Ser Arg Ser Asp Leu Trp Ser Leu Gly Ile Thr Ala Leu Glu Met
    210                 215                 220

Ala Glu Gly His Pro Pro Leu Cys Asp Met His Pro Met Arg Ala Leu
225                 230                 235                 240

Phe Leu Ile Pro Arg Asn Pro Pro Lys Leu Lys Arg Asn Lys Lys
                245                 250                 255

Trp Thr Lys Lys Phe Glu Thr Phe Ile Glu Thr Val Leu Val Lys Asp
            260                 265                 270

Tyr His Gln Arg Pro Tyr Thr Gly Ala Leu Leu Arg His Pro Phe Ile
        275                 280                 285

Lys Glu Gln Pro His Glu Gln Thr Ile Arg His Ser Ile Lys Glu His
    290                 295                 300

Ile Asp Arg Asn Arg Arg Val Lys Lys Asp Ala Asp Tyr Glu Tyr
305                 310                 315                 320

Ser Gly Ser Glu Asp Asp Glu Pro Ser Pro Asn Asn Arg Asp Asp Ser
```

```
                    325                 330                 335
Glu Ser Ser Ser Met Ile Pro Met Asp Asn Thr Leu Arg Lys Gly Phe
                340                 345                 350
Gln Lys Leu Gln Glu Ser Ser Arg Gly Phe Ala Glu Pro Gly Ala Gln
            355                 360                 365
Gln Leu Arg Arg Leu Pro Gln Gln Pro Ala Pro Ala Pro Phe Gln Tyr
        370                 375                 380
Gln Gln Ser Arg Tyr Val Glu Pro Arg Glu Ser Ser Glu Val Lys
385                 390                 395                 400
Leu Arg Ala Val Ser Ser Arg Gly Ala Ala Asp Gly Pro Arg His Ser
                405                 410                 415
Pro Ala Ser Arg Pro Arg Pro Arg Ser Pro Gln Gln Ser His Pro Ala
                420                 425                 430
Ala Pro His Leu Ala Asp Leu Ala Asn Tyr Glu Lys Arg Arg Arg Ser
                435                 440                 445
Glu Arg Glu Glu Arg Arg Glu Arg Glu Arg Gln Ala His His Ala Met
            450                 455                 460
Pro Ile Ala Arg Val Ser Ala Ser Val Pro Ala Pro Gln Gln Ser Arg
465                 470                 475                 480
Lys Met Ser Glu Pro Leu Leu Ile Thr His Val Lys Pro Glu Asp Leu
                485                 490                 495
Asp Val Leu Ala Ser Glu Leu Ser Lys Met Gly Gly His His Asn Gly
                500                 505                 510
Arg Ser Arg Glu Glu Ser Met Ser Pro Pro Pro Ala Pro Pro Pro
            515                 520                 525
Arg Glu Ala Ser Ile Ser Ser Ile Thr Asp Thr Ile Asp Val Gly Glu
            530                 535                 540
Leu Asp Asn Gly Ala Asp Ala Glu Trp Asp Asp Leu Lys Asp Ile Met
545                 550                 555                 560
Met Asn Gly Glu Gly Thr Leu Arg Gly Pro Asn Lys Pro Leu Pro Pro
                565                 570                 575
Thr Pro Thr Asp Gly Glu Asn Thr Leu Val Ser Asp Val Arg Arg Asn
                580                 585                 590
Gly Asn Gly Asn Ser Gly His Gly Ala Tyr Lys Gly Lys Lys Ile Pro
            595                 600                 605
Glu Ile Arg Pro Gly Ile Ile Ser Leu Asp Asp Asp Ser Asp Ser
        610                 615                 620
Asp Asn Glu Glu Gly Asn Glu Pro Leu Met Phe Lys Pro Ile Val Arg
625                 630                 635                 640
Cys Pro Phe Ser Ile Phe Phe Trp Phe Leu Ser Ala Asn Val Ile His
                645                 650                 655
Ser Val Asp Gly Ser Ile Pro Leu Val Lys His Leu Ile Trp Phe Gln
                660                 665                 670
Asn Ala Ser Ser Ser Arg Gly Ala Leu Pro Asp Leu Leu Pro Lys Ser
            675                 680                 685
Pro Asp Leu Arg Arg Gln Ile Asn Asp Gln Thr Arg Gln Met Ser Asp
        690                 695                 700
Asp Arg Ala Asp Glu Gln Pro Asn Gly Phe Gln Asn Ser Asp Ser Arg
705                 710                 715                 720
Ser Ser Ile Gln His Ser Phe Ser Asn Arg Asp Arg Glu Lys Ser Phe
            725                 730                 735
Val Gly Tyr Phe Gly Gly Gly Ala Gly Ala Gly Gly Thr Val Asn
        740                 745                 750
```

```
Arg Pro Gly Arg Pro Gln Asp Ile Asn Gln Val Gln Val Asn Val Thr
            755                 760                 765

Pro Asn Ser Asn Gly Thr Pro Ala Glu Asn Asp Ala Pro Glu Ile Arg
        770                 775                 780

Lys Tyr Lys Lys Lys Phe Ser Gly Glu Ile Leu Cys Ala Ala Leu Trp
785                 790                 795                 800

Gly Val Asn Leu Leu Ile Gly Thr Asp Ser Gly Leu Met Leu Leu Asp
                805                 810                 815

Arg Ser Gly Gln Gly Lys Val Tyr Pro Leu Ile Ser Arg Arg Arg Phe
            820                 825                 830

Asp Gln Met Thr Val Leu Glu Gly Gln Asn Ile Leu Ala Thr Ile Ser
            835                 840                 845

Gly Arg Lys Arg Ile Arg Val Tyr Tyr Leu Ser Trp Leu Arg Gln
            850                 855                 860

Lys Ile Leu Arg Thr Glu Gly Ala Gly Ser Ala Asn Thr Thr Glu Lys
865                 870                 875                 880

Arg Asn Gly Trp Val Asn Val Gly Asp Leu Gln Gly Ala Ile His Phe
                885                 890                 895

Lys Ile Val Arg Tyr Glu Arg Ile Lys Phe Leu Val Val Gly Leu Glu
            900                 905                 910

Ser Ser Ile Glu Ile Tyr Ala Trp Ala Pro Lys Pro Tyr His Lys Phe
            915                 920                 925

Met Ser Phe Lys Ser Phe Gly Ser Leu Ser His Val Pro Leu Ile Val
            930                 935                 940

Asp Leu Thr Val Glu Asp Asn Ala Arg Leu Lys Val Leu Tyr Gly Ser
945                 950                 955                 960

Thr Gly Gly Phe His Ala Ile Asp Leu Asp Ser Ala Ala Val Tyr Asp
                965                 970                 975

Ile Tyr Thr Pro Ala Gln Ser Gly Gln Thr Thr Pro His Cys Ile
            980                 985                 990

Val Val Leu Pro Asn Ser Asn Gly Met Gln Leu Leu Leu Cys Tyr Asp
            995                 1000                1005

Asn Glu Gly Val Tyr Val Asn Thr Tyr Gly Arg Met Thr Lys Asn Val
    1010                1015                1020

Val Leu Gln Trp Gly Glu Met Pro Ser Ser Val Ala Tyr Ile Ser Thr
1025                1030                1035                1040

Gly Gln Ile Met Gly Trp Gly Asn Lys Ala Ile Glu Ile Arg Ser Val
                1045                1050                1055

Asp Thr Gly His Leu Asp Gly Val Phe Met His Lys Lys Ala Gln Lys
            1060                1065                1070

Leu Lys Phe Leu Cys Glu Arg Asn Asp Lys Val Phe Phe Ser Ser Ala
        1075                1080                1085

Lys Gly Gly Gly Ser Cys Gln Ile Tyr Phe Met Thr Leu Asn Lys Pro
    1090                1095                1100

Gly Leu Thr Asn Trp
1105

<210> SEQ ID NO 89
<211> LENGTH: 1233
<212> TYPE: PRT
<213> ORGANISM: Murine sp.

<400> SEQUENCE: 89

Met Ala Asn Asp Ser Pro Ala Lys Ser Leu Val Asp Ile Asp Leu Ser
```

-continued

```
  1               5                   10                  15
Ser Leu Arg Asp Pro Ala Gly Ile Phe Glu Leu Val Glu Val Val Gly
            20                  25                  30

Asn Gly Thr Tyr Gly Gln Val Tyr Lys Gly Arg His Val Lys Thr Val
        35                  40                  45

Thr Ala Ala Ile Lys Val Met Asp Val Thr Glu Asp Glu Glu Glu Glu
    50                  55                  60

Ile Thr Leu Glu Ile Asn Met Leu Lys Lys Tyr Ser His His Arg Asn
65                  70                  75                  80

Ile Ala Thr Tyr Tyr Gly Ala Phe Ile Lys Lys Ser Pro Pro Gly His
                85                  90                  95

Asp Asp Gln Leu Trp Leu Val Met Glu Phe Cys Gly Ala Gly Ser Ile
            100                 105                 110

Thr Asp Leu Val Lys Asn Thr Lys Gly Asn Thr Leu Lys Glu Asp Trp
        115                 120                 125

Ile Ala Tyr Ile Ser Arg Glu Ile Leu Arg Gly Leu Ala His Leu His
    130                 135                 140

Ile His His Val Ile His Arg Asp Ile Lys Gly Gln Asn Val Leu Leu
145                 150                 155                 160

Thr Glu Asn Ala Glu Val Lys Leu Val Asp Phe Gly Val Ser Ala Gln
                165                 170                 175

Leu Asp Arg Thr Val Gly Arg Arg Asn Thr Phe Ile Gly Thr Pro Tyr
            180                 185                 190

Trp Met Ala Pro Glu Val Ile Ala Cys Asp Glu Asn Pro Asp Ala Thr
        195                 200                 205

Tyr Asp Tyr Arg Ser Asp Leu Trp Ser Cys Gly Ile Thr Ala Ile Glu
    210                 215                 220

Met Ala Glu Gly Gly Pro Pro Leu Cys Asp Met His Pro Met Arg Ala
225                 230                 235                 240

Leu Phe Leu Ile Pro Arg Asn Pro Pro Arg Leu Lys Ser Lys Lys
                245                 250                 255

Trp Ser Lys Lys Phe Phe Ser Phe Ile Glu Gly Cys Leu Val Lys Asn
            260                 265                 270

Tyr Met Gln Arg Pro Ser Thr Glu Gln Leu Leu Lys His Pro Phe Ile
        275                 280                 285

Arg Asp Gln Pro Asn Glu Arg Gln Val Arg Ile Gln Leu Lys Asp His
    290                 295                 300

Ile Asp Arg Thr Arg Lys Lys Arg Gly Glu Lys Asp Glu Thr Glu Tyr
305                 310                 315                 320

Glu Tyr Ser Gly Ser Glu Glu Glu Glu Val Pro Glu Gln Glu
                325                 330                 335

Gly Glu Pro Ser Ser Ile Val Asn Val Pro Gly Glu Ser Thr Leu Arg
            340                 345                 350

Arg Asp Phe Leu Arg Leu Gln Gln Glu Asn Lys Glu Arg Ser Glu Ala
        355                 360                 365

Leu Arg Arg Gln Gln Leu Leu Gln Glu Gln Gln Leu Arg Glu Gln Glu
    370                 375                 380

Glu Tyr Lys Arg Gln Leu Leu Ala Glu Arg Gln Lys Arg Ile Glu Gln
385                 390                 395                 400

Gln Lys Glu Gln Arg Arg Arg Leu Glu Glu Gln Gln Arg Arg Glu Arg
                405                 410                 415

Glu Ala Arg Arg Gln Gln Glu Arg Glu Gln Arg Arg Glu Gln Glu
            420                 425                 430
```

-continued

```
Glu Lys Arg Arg Leu Glu Glu Leu Glu Arg Arg Lys Glu Glu
            435                 440                 445
Glu Arg Arg Arg Ala Glu Glu Lys Arg Arg Val Glu Arg Glu Gln
450                 455                 460
Glu Tyr Ile Arg Arg Gln Leu Glu Glu Gln Arg His Leu Glu Ile
465                 470                 475                 480
Leu Gln Gln Gln Leu Leu Gln Glu Gln Ala Met Leu Leu His Asp His
                485                 490                 495
Arg Arg Pro His Ala Gln Gln Pro Pro Pro Gln Gln Gln Asp
            500                 505                 510
Arg Ser Lys Pro Ser Phe His Ala Pro Glu Pro Lys Pro His Tyr Asp
            515                 520                 525
Pro Ala Asp Arg Ala Arg Glu Val Gln Trp Ser His Leu Ala Ser Leu
530                 535                 540
Lys Asn Asn Val Ser Pro Val Ser Arg Ser His Ser Phe Ser Asp Pro
545                 550                 555                 560
Ser Pro Lys Phe Ala His His His Leu Arg Ser Gln Asp Pro Cys Pro
                565                 570                 575
Pro Ser Arg Ser Glu Gly Leu Ser Gln Ser Ser Asp Ser Lys Ser Glu
            580                 585                 590
Val Pro Glu Pro Thr Gln Lys Ala Trp Ser Arg Ser Asp Ser Asp Glu
            595                 600                 605
Val Pro Pro Arg Val Pro Val Arg Thr Thr Ser Arg Ser Pro Val Leu
            610                 615                 620
Ser Arg Arg Asp Ser Pro Leu Gln Gly Gly Gln Gln Asn Ser Gln
625                 630                 635                 640
Ala Gly Gln Arg Asn Ser Thr Ser Ser Ile Glu Pro Arg Leu Leu Trp
                645                 650                 655
Glu Arg Val Glu Lys Leu Val Pro Arg Pro Gly Ser Gly Ser Ser Ser
                660                 665                 670
Gly Ser Ser Asn Ser Gly Ser Gln Pro Gly Ser His Pro Gly Ser Gln
            675                 680                 685
Ser Gly Ser Gly Glu Arg Phe Arg Val Arg Ser Ser Ser Lys Ser Glu
            690                 695                 700
Gly Ser Pro Ser Pro Arg Gln Glu Ser Ala Ala Lys Lys Pro Asp Asp
705                 710                 715                 720
Lys Lys Glu Val Phe Arg Ser Leu Lys Pro Ala Gly Glu Val Asp Leu
                725                 730                 735
Thr Ala Leu Ala Lys Glu Leu Arg Ala Val Glu Asp Val Arg Pro Pro
            740                 745                 750
His Lys Val Thr Asp Tyr Ser Ser Ser Glu Glu Ser Gly Thr Thr
            755                 760                 765
Asp Glu Glu Glu Asp Val Glu Glu Gly Ala Asp Asp Ser Thr
            770                 775                 780
Ser Gly Pro Glu Asp Thr Arg Ala Ala Ser Ser Pro Asn Leu Ser Asn
785                 790                 795                 800
Gly Glu Thr Glu Ser Val Lys Thr Met Ile Val His Asp Asp Val Glu
                805                 810                 815
Ser Glu Pro Ala Met Thr Pro Ser Lys Glu Gly Thr Leu Ile Val Arg
            820                 825                 830
Gln Thr Gln Ser Ala Ser Ser Thr Leu Gln Lys His Lys Ser Ser Ser
            835                 840                 845
```

-continued

```
Ser Phe Thr Pro Phe Ile Asp Pro Arg Leu Leu Gln Ile Ser Pro Ser
    850                 855                 860
Ser Gly Thr Thr Val Thr Ser Val Val Gly Phe Ser Cys Asp Gly Leu
865                 870                 875                 880
Arg Pro Glu Ala Ile Arg Gln Asp Pro Thr Arg Lys Gly Ser Val Val
                885                 890                 895
Asn Val Asn Pro Thr Asn Thr Arg Pro Gln Ser Asp Pro Glu Ile
            900                 905                 910
Arg Lys Tyr Lys Lys Arg Phe Asn Ser Glu Ile Leu Cys Ala Ala Leu
        915                 920                 925
Trp Gly Val Asn Leu Val Gly Thr Glu Ser Gly Leu Met Leu Leu
    930                 935                 940
Asp Arg Ser Gly Gln Gly Lys Val Tyr Pro Leu Ile Ser Arg Arg Arg
945                 950                 955                 960
Phe Gln Gln Met Asp Val Leu Glu Gly Leu Asn Val Leu Val Thr Ile
                965                 970                 975
Ser Gly Lys Lys Asp Lys Leu Arg Val Tyr Tyr Leu Ser Trp Leu Arg
            980                 985                 990
Asn Lys Ile Leu His Asn Asp Pro Glu Val Glu Lys Lys Gln Gly Trp
        995                 1000                1005
Thr Thr Val Gly Asp Leu Glu Gly Cys Val His Tyr Lys Val Val Lys
    1010                1015                1020
Tyr Glu Arg Ile Lys Phe Leu Val Ile Ala Leu Lys Ser Ser Val Glu
1025                1030                1035                1040
Val Tyr Ala Trp Ala Pro Lys Pro Tyr His Lys Phe Met Ala Phe Lys
                1045                1050                1055
Ser Phe Gly Glu Leu Leu His Lys Pro Leu Leu Val Asp Leu Thr Val
            1060                1065                1070
Glu Glu Gly Gln Arg Leu Lys Val Ile Tyr Gly Ser Cys Ala Gly Phe
        1075                1080                1085
His Ala Val Asp Val Asp Ser Gly Ser Val Tyr Asp Ile Tyr Leu Pro
    1090                1095                1100
Thr His Ile Gln Cys Ser Ile Lys Pro His Ala Ile Ile Ile Leu Pro
1105                1110                1115                1120
Asn Thr Asp Gly Met Glu Leu Leu Val Cys Tyr Glu Asp Glu Gly Val
                1125                1130                1135
Tyr Val Asn Thr Tyr Gly Arg Ile Thr Lys Asp Val Val Leu Gln Trp
            1140                1145                1150
Gly Glu Met Pro Thr Ser Val Ala Tyr Ile Arg Ser Asn Gln Thr Met
        1155                1160                1165
Gly Trp Gly Glu Lys Ala Ile Glu Ile Arg Ser Val Glu Thr Gly His
    1170                1175                1180
Leu Asp Gly Val Phe Met His Leu Arg Ala Gln Arg Leu Lys Phe Leu
1185                1190                1195                1200
Cys Gly Arg Asn Asp Lys Val Phe Phe Ser Ser Val Arg Ser Gly Gly
                1205                1210                1215
Ser Ser Gln Val Tyr Phe Met Thr Leu Gly Arg Thr Ser Leu Leu Ser
            1220                1225                1230
Trp
```

<210> SEQ ID NO 90
<211> LENGTH: 982
<212> TYPE: PRT
<213> ORGANISM: Caenorhabditis elegans

<400> SEQUENCE: 90

| | | | | | | | | | | | | | | |
|---|---|---|---|---|---|---|---|---|---|---|---|---|---|---|
|Met|Ala|Pro|Ala|Val|Leu|Asp|Lys|Pro|Gly|Val|Ile|Lys|Asp|Pro|Ser|
|1| | | |5| | | | |10| | | | |15| |
|Ile|Ala|Ala|Leu|Phe|Ser|Asn|Lys|Asp|Pro|Glu|Gln|Arg|Tyr|Gln|Asp|
| | | |20| | | | |25| | | | |30| | |
|Leu|Arg|Glu|Ile|Gly|His|Gly|Ser|Phe|Gly|Ala|Val|Tyr|Phe|Ala|Tyr|
| | |35| | | | |40| | | | |45| | | |
|Asp|Lys|Lys|Asn|Glu|Gln|Thr|Val|Ala|Ile|Lys|Lys|Met|Asn|Phe|Ser|
| |50| | | | |55| | | | |60| | | | |
|Gly|Lys|Gln|Ala|Val|Glu|Lys|Trp|Asn|Asp|Ile|Leu|Lys|Glu|Val|Ser|
|65| | | | |70| | | | |75| | | | |80|
|Phe|Leu|Asn|Thr|Val|Val|His|Pro|His|Ile|Val|Asp|Tyr|Lys|Ala|Cys|
| | | | |85| | | | |90| | | | |95| |
|Phe|Leu|Lys|Asp|Thr|Thr|Cys|Trp|Leu|Val|Met|Glu|Tyr|Cys|Ile|Gly|
| | | |100| | | | |105| | | | |110| | |
|Ser|Ala|Ala|Asp|Ile|Val|Asp|Val|Leu|Arg|Lys|Gly|Met|Arg|Glu|Val|
| | |115| | | | |120| | | | |125| | | |
|Glu|Ile|Ala|Ala|Ile|Cys|Ser|Gln|Thr|Leu|Asp|Ala|Leu|Arg|Tyr|Leu|
| |130| | | | |135| | | | |140| | | | |
|His|Ser|Leu|Lys|Arg|Ile|His|Arg|Asp|Ile|Lys|Ala|Gly|Asn|Ile|Leu|
|145| | | | |150| | | | |155| | | | |160|
|Leu|Ser|Asp|His|Ala|Ile|Val|Lys|Leu|Ala|Asp|Phe|Gly|Ser|Ala|Ser|
| | | | |165| | | | |170| | | | |175| |
|Leu|Val|Asp|Pro|Ala|Gln|Thr|Phe|Ile|Gly|Thr|Pro|Phe|Phe|Met|Ala|
| | | |180| | | | |185| | | | |190| | |
|Pro|Glu|Val|Ile|Leu|Ala|Met|Asp|Glu|Gly|His|Tyr|Thr|Asp|Arg|Ala|
| | |195| | | | |200| | | | |205| | | |
|Asp|Ile|Trp|Ser|Leu|Gly|Ile|Thr|Cys|Ile|Glu|Leu|Ala|Glu|Arg|Arg|
| |210| | | | |215| | | | |220| | | | |
|Pro|Pro|Leu|Phe|Ser|Met|Asn|Ala|Met|Ser|Ala|Leu|Tyr|His|Ile|Ala|
|225| | | | |230| | | | |235| | | | |240|
|Gln|Asn|Asp|Pro|Pro|Thr|Leu|Ser|Pro|Ile|Asp|Thr|Ser|Glu|Gln|Pro|
| | | | |245| | | | |250| | | | |255| |
|Glu|Trp|Ser|Leu|Glu|Phe|Val|Gln|Phe|Ile|Asp|Lys|Cys|Leu|Arg|Lys|
| | | |260| | | | |265| | | | |270| | |
|Pro|Ala|Glu|Glu|Arg|Met|Ser|Ala|Glu|Cys|Phe|Arg|His|Pro|Phe|
| | |275| | | | |280| | | | |285| | | |
|Ile|Gln|Arg|Ser|Arg|Pro|Ser|Asp|Thr|Ile|Gln|Glu|Leu|Ile|Gln|Arg|
| |290| | | | |295| | | | |300| | | | |
|Thr|Lys|Asn|Met|Val|Leu|Glu|Leu|Asp|Asn|Phe|Gln|Tyr|Lys|Lys|Met|
|305| | | | |310| | | | |315| | | | |320|
|Arg|Lys|Leu|Met|Tyr|Leu|Asp|Glu|Thr|Glu|Gly|Lys|Glu|Gly|Ser|Glu|
| | | | |325| | | | |330| | | | |335| |
|Gly|Asn|Gly|Ala|Ser|Asp|Asp|Leu|Asp|Phe|His|Gly|Asn|Glu|Ala|Asn|
| | | |340| | | | |345| | | | |350| | |
|Ser|Ile|Gly|Arg|Ala|Gly|Asp|Ser|Ala|Ser|Arg|Ser|Ala|Ser|Leu|
| | |355| | | | |360| | | | |365| | | |
|Thr|Ser|Phe|Arg|Ser|Met|Gln|Ser|Gly|Gly|Ala|Gly|Leu|Leu|Val|
| |370| | | | |375| | | | |380| | | | |
|Ser|Thr|Asn|Thr|Thr|Gly|Ala|Met|Asp|Asn|Val|His|Gly|Ser|Ser|Gly|
|385| | | | |390| | | | |395| | | | |400|
|Tyr|Gly|Asn|Gly|Ser|Ser|Ser|Thr|Thr|Ser|Ser|Ala|Arg|Arg|Arg|Pro|

```
                    405                 410                 415
Pro Ile Pro Ser Gln Met Leu Ser Ser Thr Ser Thr Ser Gly Val Gly
                420                 425                 430

Thr Met Pro Ser His Gly Ser Val Gly Ala Ser Ile Thr Ala Ile Ala
                435                 440                 445

Val Asn Pro Thr Pro Ser Pro Ser Glu Pro Ile Pro Thr Ser Gln Pro
            450                 455                 460

Thr Ser Lys Ser Glu Ser Ser Ile Leu Glu Thr Ala His Asp Asp
465                 470                 475                 480

Pro Leu Asp Thr Ser Ile Arg Ala Pro Val Lys Asp Leu His Met Pro
                    485                 490                 495

His Arg Ala Val Lys Glu Arg Ile Ala Thr Leu Gln Asn His Lys Phe
                500                 505                 510

Ala Thr Leu Arg Ser Gln Arg Ile Ile Asn Gln Glu Gln Glu Glu Tyr
                515                 520                 525

Thr Lys Glu Asn Asn Met Tyr Glu Gln Met Ser Lys Tyr Lys His Leu
            530                 535                 540

Arg Gln Ala His His Lys Glu Leu Gln Gln Phe Glu Glu Arg Cys Ala
545                 550                 555                 560

Leu Asp Arg Glu Gln Leu Arg Val Lys Met Asp Arg Glu Leu Glu Gln
                    565                 570                 575

Leu Thr Thr Thr Tyr Ser Lys Glu Lys Met Arg Val Arg Cys Ser Gln
                580                 585                 590

Asn Asn Glu Leu Asp Lys Arg Lys Asp Ile Glu Asp Gly Glu Lys
            595                 600                 605

Lys Met Lys Lys Thr Lys Asn Ser Gln Asn Gln Gln Met Lys Leu
                610                 615                 620

Tyr Ser Ala Gln Gln Leu Lys Glu Tyr Lys Tyr Asn Lys Glu Ala Gln
625                 630                 635                 640

Lys Thr Arg Leu Arg Ser Leu Asn Met Pro Arg Ser Thr Tyr Glu Asn
                    645                 650                 655

Ala Met Lys Glu Val Lys Ala Asp Leu Asn Arg Val Lys Asp Ala Arg
                660                 665                 670

Glu Asn Asp Phe Asp Glu Lys Leu Arg Ala Glu Leu Glu Asp Glu Ile
            675                 680                 685

Val Arg Tyr Arg Arg Gln Gln Leu Ser Asn Leu His Gln Leu Glu Glu
    690                 695                 700

Gln Leu Asp Asp Glu Asp Val Asn Val Gln Glu Arg Gln Met Asp Thr
705                 710                 715                 720

Arg His Gly Leu Leu Ser Lys Gln His Glu Met Thr Arg Asp Leu Glu
                    725                 730                 735

Ile Gln His Leu Asn Glu Leu His Ala Met Lys Lys Arg His Leu Glu
                740                 745                 750

Thr Gln His Glu Ala Glu Ser Ala Ser Gln Asn Glu Tyr Thr Gln Arg
            755                 760                 765

Gln Gln Asp Glu Leu Arg Lys Lys His Ala Met Gln Ser Arg Gln Gln
    770                 775                 780

Pro Arg Asp Leu Lys Ile Gln Glu Ala Gln Ile Arg Lys Gln Tyr Arg
785                 790                 795                 800

Gln Val Val Lys Thr Gln Thr Arg Gln Phe Lys Leu Tyr Leu Thr Gln
                    805                 810                 815

Met Val Gln Val Val Pro Lys Asp Glu Gln Lys Glu Leu Thr Ser Arg
                820                 825                 830
```

-continued

Leu Lys Gln Asp Gln Met Gln Lys Val Ala Leu Leu Ala Ser Gln Tyr
            835                 840                 845

Glu Ser Gln Ile Lys Lys Met Val Gln Asp Lys Thr Val Lys Leu Glu
850                 855                 860

Ser Trp Gln Glu Asp Glu Gln Arg Val Leu Ser Glu Lys Leu Glu Lys
865                 870                 875                 880

Glu Leu Glu Glu Leu Ile Ala Tyr Gln Lys Lys Thr Arg Ala Thr Leu
            885                 890                 895

Glu Glu Gln Ile Lys Lys Glu Arg Thr Ala Leu Glu Glu Arg Ile Gly
            900                 905                 910

Thr Arg Arg Ala Met Leu Glu Gln Lys Ile Ile Glu Glu Arg Glu Gln
            915                 920                 925

Met Gly Glu Met Arg Arg Leu Lys Lys Glu Gln Ile Arg Asp Arg His
930                 935                 940

Ser Gln Glu Arg His Arg Leu Glu Asn His Phe Val Arg Thr Gly Ser
945                 950                 955                 960

Thr Ser Arg Ser Ser Gly Gly Ile Ala Pro Gly Val Gly Asn Ser Ser
            965                 970                 975

Ser Ile Gln Met Ala Met
            980

<210> SEQ ID NO 91
<211> LENGTH: 842
<212> TYPE: PRT
<213> ORGANISM: Homo sapiens

<400> SEQUENCE: 91

Leu Arg Pro Ala Ala Asp Ile Leu Arg Arg Asn Pro Gln Gln Asp Tyr
1               5                   10                  15

Glu Leu Val Gln Arg Val Gly Ser Gly Thr Tyr Gly Asp Val Tyr Lys
            20                  25                  30

Ala Arg Asn Val His Thr Gly Glu Leu Ala Ala Val Lys Ile Ile Lys
        35                  40                  45

Leu Glu Pro Gly Asp Asp Phe Ser Leu Ile Gln Gln Glu Ile Phe Met
50                  55                  60

Val Lys Glu Cys Lys His Cys Asn Ile Val Ala Tyr Phe Gly Ser Tyr
65                  70                  75                  80

Leu Ser Arg Glu Lys Leu Trp Ile Cys Met Glu Tyr Cys Gly Gly Gly
            85                  90                  95

Ser Leu Gln Asp Ile Tyr His Val Thr Gly Pro Leu Ser Glu Leu Gln
            100                 105                 110

Ile Ala Tyr Val Cys Arg Glu Thr Leu Gln Gly Leu Ala Tyr Leu His
        115                 120                 125

Thr Lys Gly Lys Met His Arg Asp Ile Lys Gly Ala Asn Ile Leu Leu
130                 135                 140

Thr Asp His Gly Asp Val Lys Leu Ala Asp Phe Gly Val Ala Ala Lys
145                 150                 155                 160

Ile Thr Ala Thr Ile Ala Lys Arg Lys Ser Phe Ile Gly Thr Pro Tyr
            165                 170                 175

Trp Met Ala Pro Glu Val Ala Ala Val Glu Lys Asn Gly Gly Tyr Asn
            180                 185                 190

Gln Leu Cys Asp Ile Trp Ala Val Gly Ile Thr Ala Ile Glu Leu Gly
        195                 200                 205

Glu Leu Gln Pro Pro Met Phe Asp Leu His Pro Met Arg Ala Leu Phe

-continued

```
            210                 215                 220
Leu Met Ser Lys Ser Asn Phe Gln Pro Pro Lys Leu Lys Asp Lys Thr
225                 230                 235                 240

Lys Trp Ser Ser Thr Phe His Asn Phe Val Lys Ile Ala Leu Thr Lys
                245                 250                 255

Asn Pro Lys Lys Arg Pro Thr Ala Glu Arg Leu Leu Thr His Thr Phe
                260                 265                 270

Val Ala Gln Pro Gly Leu Ser Arg Ala Leu Ala Val Glu Leu Leu Asp
                275                 280                 285

Lys Val Asn Asn Pro Asp Asn His Ala His Tyr Thr Glu Ala Asp Asp
                290                 295                 300

Asp Asp Phe Glu Pro His Ala Ile Ile Arg His Thr Ile Arg Ser Thr
305                 310                 315                 320

Asn Arg Asn Ala Arg Ala Glu Arg Thr Ala Ser Glu Ile Asn Phe Asp
                325                 330                 335

Lys Leu Gln Phe Glu Pro Pro Leu Arg Lys Glu Thr Glu Ala Arg Asp
                340                 345                 350

Glu Met Gly Leu Ser Ser Asp Pro Asn Phe Met Leu Gln Trp Asn Pro
                355                 360                 365

Phe Val Asp Gly Ala Asn Thr Gly Lys Ser Thr Ser Lys Arg Ala Ile
370                 375                 380

Pro Pro Pro Leu Pro Pro Lys Pro Arg Ile Ser Ser Tyr Pro Glu Asp
385                 390                 395                 400

Asn Phe Pro Asp Glu Glu Lys Ala Ser Thr Ile Lys His Cys Pro Asp
                405                 410                 415

Ser Glu Ser Arg Ala Pro Gln Ile Leu Arg Arg Gln Ser Ser Pro Ser
                420                 425                 430

Cys Gly Pro Val Ala Glu Thr Ser Ile Gly Asn Gly Asp Gly Ile
                435                 440                 445

Ser Lys Leu Met Ser Glu Asn Thr Glu Gly Ser Ala Gln Ala Pro Gln
                450                 455                 460

Leu Pro Arg Lys Asn Asp Lys Arg Asp Phe Pro Lys Pro Ala Ile Asn
465                 470                 475                 480

Gly Leu Pro Pro Thr Pro Lys Val Leu Met Gly Ala Cys Phe Ser Lys
                485                 490                 495

Val Phe Asp Gly Cys Pro Leu Lys Ile Asn Cys Ala Thr Ser Trp Ile
                500                 505                 510

His Pro Asp Thr Lys Asp Gln Tyr Ile Ile Phe Gly Thr Glu Asp Gly
                515                 520                 525

Ile Tyr Thr Leu Asn Leu Asn Glu Leu His Glu Ala Thr Met Glu Gln
                530                 535                 540

Leu Phe Pro Arg Lys Cys Thr Trp Leu Tyr Val Ile Asn Asn Thr Leu
545                 550                 555                 560

Met Ser Leu Ser Glu Gly Lys Thr Phe Gln Leu Tyr Ser His Asn Leu
                565                 570                 575

Ile Ala Leu Phe Glu His Ala Lys Lys Pro Gly Leu Ala Ala His Ile
                580                 585                 590

Gln Thr His Arg Phe Pro Asp Arg Ile Leu Pro Arg Lys Phe Ala Leu
                595                 600                 605

Thr Thr Lys Ile Pro Asp Thr Lys Gly Cys His Lys Cys Cys Ile Val
                610                 615                 620

Arg Asn Pro Tyr Thr Gly His Lys Tyr Leu Cys Gly Ala Leu Gln Ser
625                 630                 635                 640
```

-continued

```
Gly Ile Val Leu Leu Gln Trp Tyr Glu Pro Met Gln Lys Phe Met Leu
                645                 650                 655
Ile Lys His Phe Asp Phe Pro Leu Pro Ser Pro Leu Asn Val Phe Glu
            660                 665                 670
Met Leu Val Ile Pro Glu Gln Glu Tyr Pro Met Val Cys Val Ala Ile
        675                 680                 685
Ser Lys Gly Thr Glu Ser Asn Gln Val Val Gln Phe Glu Thr Ile Asn
    690                 695                 700
Leu Asn Ser Ala Ser Ser Trp Phe Thr Glu Ile Gly Ala Gly Ser Gln
705                 710                 715                 720
Gln Leu Asp Ser Ile His Val Thr Gln Leu Glu Arg Asp Thr Val Leu
                725                 730                 735
Val Cys Leu Asp Lys Phe Val Lys Ile Val Asn Leu Gln Gly Lys Leu
            740                 745                 750
Lys Ser Ser Lys Lys Leu Ala Ser Glu Leu Ser Phe Asp Phe Arg Ile
        755                 760                 765
Glu Ser Val Val Cys Leu Gln Asp Ser Val Leu Ala Phe Trp Lys His
    770                 775                 780
Gly Met Gln Gly Lys Ser Phe Lys Ser Asp Glu Val Thr Gln Glu Ile
785                 790                 795                 800
Ser Asp Glu Thr Arg Val Phe Arg Leu Leu Gly Ser Asp Arg Val Val
                805                 810                 815
Val Leu Glu Ser Arg Pro Thr Glu Asn Pro Thr Ala His Ser Asn Leu
            820                 825                 830
Tyr Ile Leu Ala Gly His Glu Asn Ser Tyr
        835                 840

<210> SEQ ID NO 92
<211> LENGTH: 911
<212> TYPE: PRT
<213> ORGANISM: Murine sp.

<400> SEQUENCE: 92

Met Ala Phe Ala Asn Phe Arg Arg Ile Leu Arg Leu Ser Thr Phe Glu
 1               5                  10                  15
Lys Arg Lys Ser Arg Glu Tyr Glu His Val Arg Arg Asp Leu Asp Pro
             20                  25                  30
Asn Asp Val Trp Glu Ile Val Gly Glu Leu Gly Asp Gly Ala Phe Gly
         35                  40                  45
Lys Val Tyr Lys Ala Lys Asn Lys Glu Thr Gly Ala Leu Ala Ala Ala
     50                  55                  60
Lys Val Ile Glu Thr Lys Ser Glu Glu Glu Leu Glu Asp Tyr Ile Val
 65                  70                  75                  80
Glu Ile Glu Ile Leu Ala Thr Cys Asp His Pro Tyr Ile Val Lys Leu
                 85                  90                  95
Leu Gly Ala Tyr Tyr Tyr Asp Gly Lys Leu Trp Ile Met Ile Glu Phe
            100                 105                 110
Cys Pro Gly Gly Ala Val Asp Ala Ile Met Leu Glu Leu Asp Arg Gly
        115                 120                 125
Leu Thr Glu Pro Gln Ile Gln Val Val Cys Arg Gln Met Leu Glu Ala
    130                 135                 140
Leu Asn Phe Leu His Gly Lys Arg Ile Ile His Arg Asp Leu Lys Ala
145                 150                 155                 160
Gly Asn Val Leu Met Thr Leu Glu Gly Asp Ile Arg Leu Ala Asp Phe
```

-continued

```
                    165                 170                 175
Gly Val Ser Ala Lys Asn Leu Lys Thr Leu Gln Lys Arg Asp Ser Phe
                180                 185                 190
Ile Gly Thr Pro Tyr Trp Met Ala Pro Glu Val Leu Cys Glu Thr
            195                 200                 205
Met Lys Asp Ala Pro Tyr Asp Tyr Lys Ala Asp Ile Trp Ser Leu Gly
            210                 215                 220
Ile Thr Leu Ile Glu Met Ala Gln Ile Glu Pro Pro His His Glu Leu
225                 230                 235                 240
Asn Pro Met Arg Val Leu Leu Lys Ile Ala Lys Ser Asp Pro Pro Thr
                245                 250                 255
Leu Leu Thr Pro Ser Lys Trp Ser Val Glu Phe Arg Asp Phe Leu Lys
                260                 265                 270
Ile Ala Leu Asp Lys Asn Pro Glu Thr Arg Pro Ser Ala Ala Gln Leu
                275                 280                 285
Leu Gln His Pro Phe Val Ser Arg Val Thr Ser Asn Lys Ala Leu Arg
            290                 295                 300
Glu Leu Val Ala Glu Ala Lys Ala Glu Val Met Glu Glu Ile Glu Asp
305                 310                 315                 320
Gly Arg Glu Asp Gly Glu Glu Asp Ala Val Asp Ala Val Pro Pro
                325                 330                 335
Leu Val Asn His Thr Gln Asp Ser Ala Asn Val Thr Gln Pro Ser Leu
                340                 345                 350
Asp Ser Asn Lys Leu Leu Gln Asp Ser Ser Thr Pro Leu Pro Pro Ser
                355                 360                 365
Gln Pro Gln Glu Pro Val Asn Gly Pro Cys Ser Gln Pro Ser Gly Asp
    370                 375                 380
Gly Pro Leu Gln Thr Thr Ser Pro Ala Asp Gly Leu Ser Lys Asn Asp
385                 390                 395                 400
Asn Asp Leu Lys Val Pro Val Pro Leu Arg Lys Ser Arg Pro Leu Ser
                405                 410                 415
Met Asp Ala Arg Ile Gln Met Asp Glu Glu Lys Gln Ile Pro Asp Gln
                420                 425                 430
Asp Glu Asn Pro Ser Pro Ala Ala Ser Lys Ser Gln Lys Ala Asn Gln
            435                 440                 445
Ser Arg Pro Asn Ser Ser Ala Leu Glu Thr Leu Gly Gly Glu Ala Leu
    450                 455                 460
Thr Asn Gly Gly Leu Glu Leu Pro Ser Ser Val Thr Pro Ser His Ser
465                 470                 475                 480
Lys Arg Ala Ser Asp Cys Ser Asn Leu Ser Thr Ser Glu Ser Met Asp
                485                 490                 495
Tyr Gly Thr Ser Leu Ser Ala Asp Leu Ser Leu Asn Lys Glu Thr Gly
            500                 505                 510
Ser Leu Ser Leu Lys Gly Ser Lys Leu His Asn Lys Thr Leu Lys Arg
            515                 520                 525
Thr Arg Arg Phe Val Val Asp Gly Val Glu Val Ser Ile Thr Thr Ser
            530                 535                 540
Lys Ile Ile Ser Glu Asp Glu Lys Lys Asp Glu Glu Met Arg Phe Leu
545                 550                 555                 560
Arg Arg Gln Glu Leu Arg Glu Leu Arg Leu Leu Gln Lys Glu Glu His
                565                 570                 575
Arg Asn Gln Thr Gln Leu Ser Ser Lys His Glu Leu Gln Leu Glu Gln
            580                 585                 590
```

```
Met His Lys Arg Phe Glu Gln Glu Ile Asn Ala Lys Lys Lys Phe Tyr
            595                 600                 605

Asp Val Glu Leu Glu Asn Leu Glu Arg Gln Gln Lys Gln Gln Val Glu
        610                 615                 620

Lys Met Glu Gln Asp His Ser Val Arg Lys Glu Glu Ala Lys Arg
625                 630                 635                 640

Ile Arg Leu Glu Gln Asp Arg Asp Tyr Ala Lys Phe Gln Glu Gln Leu
                645                 650                 655

Lys Gln Met Lys Lys Glu Val Lys Ser Glu Val Glu Lys Leu Pro Arg
            660                 665                 670

Gln Gln Arg Lys Glu Ser Met Lys Gln Lys Met Glu Glu His Ser Gln
            675                 680                 685

Lys Lys Gln Arg Leu Asp Arg Asp Phe Val Ala Lys Gln Lys Glu Asp
        690                 695                 700

Leu Glu Leu Ala Met Arg Lys Leu Thr Thr Glu Asn Arg Arg Glu Ile
705                 710                 715                 720

Cys Asp Lys Glu Arg Asp Cys Leu Ser Lys Lys Gln Glu Leu Leu Arg
                725                 730                 735

Asp Arg Glu Ala Ala Leu Trp Glu Met Glu Glu His Gln Leu Gln Glu
                740                 745                 750

Arg His Gln Leu Val Lys Gln Gln Leu Lys Asp Gln Tyr Phe Leu Gln
            755                 760                 765

Arg His Asp Leu Leu Arg Lys His Glu Lys Glu Arg Glu Gln Met Gln
770                 775                 780

Arg Tyr Asn Gln Arg Met Met Glu Gln Leu Lys Val Arg Gln Gln Gln
785                 790                 795                 800

Glu Lys Ala Arg Leu Pro Lys Ile Gln Arg Ser Asp Gly Glu Thr Arg
                805                 810                 815

Met Ala Met Tyr Lys Lys Ser Leu His Ile Asn Gly Ala Gly Ser Ala
            820                 825                 830

Ser Glu Gln Arg Glu Lys Ile Lys Gln Phe Ser Gln Gln Glu Glu Lys
        835                 840                 845

Arg Gln Lys Ala Glu Arg Leu Gln Gln Gln Lys His Glu His Gln
        850                 855                 860

Met Arg Asp Met Val Ala Gln Cys Glu Ser Asn Met Ser Glu Leu Gln
865                 870                 875                 880

Gln Leu Gln Asn Glu Lys Cys Tyr Leu Leu Val Glu His Glu Thr Gln
                885                 890                 895

Lys Leu Lys Ala Leu Asp Glu Ser His Asn Gln Ser Leu Lys Glu
            900                 905                 910

<210> SEQ ID NO 93
<211> LENGTH: 545
<212> TYPE: PRT
<213> ORGANISM: Homo sapiens

<400> SEQUENCE: 93

Met Ser Asn Asn Gly Leu Asp Ile Gln Asp Lys Pro Pro Ala Pro Pro
1               5                   10                  15

Met Arg Asn Thr Ser Thr Met Ile Gly Ala Gly Ser Lys Asp Ala Gly
            20                  25                  30

Thr Leu Asn His Gly Ser Lys Pro Leu Pro Pro Asn Pro Glu Glu Lys
        35                  40                  45

Lys Lys Lys Asp Arg Phe Tyr Arg Ser Ile Leu Pro Gly Asp Lys Thr
```

-continued

```
            50                  55                  60
Asn Lys Lys Glu Lys Glu Arg Pro Glu Ile Ser Leu Pro Ser Asp
 65                  70                  75                  80

Phe Glu His Thr Ile His Val Gly Phe Asp Ala Val Thr Gly Glu Phe
                 85                  90                  95

Thr Gly Met Pro Glu Gln Trp Ala Arg Leu Leu Gln Thr Ser Asn Ile
                100                 105                 110

Thr Lys Ser Glu Gln Lys Lys Asn Pro Gln Ala Val Leu Asp Val Leu
                115                 120                 125

Glu Phe Tyr Asn Ser Lys Lys Thr Ser Asn Ser Gln Lys Tyr Met Ser
            130                 135                 140

Phe Thr Asp Lys Ser Ala Glu Asp Tyr Asn Ser Ser Asn Ala Leu Asn
145                 150                 155                 160

Val Lys Ala Val Ser Glu Thr Pro Ala Val Pro Pro Val Ser Glu Asp
                165                 170                 175

Glu Asp Asp Asp Asp Asp Ala Thr Pro Pro Val Ile Ala Pro
            180                 185                 190

Arg Pro Glu His Thr Lys Ser Val Tyr Thr Arg Ser Val Ile Glu Pro
            195                 200                 205

Leu Pro Val Thr Pro Thr Arg Asp Val Ala Thr Ser Pro Ile Ser Pro
        210                 215                 220

Thr Glu Asn Asn Thr Thr Pro Pro Asp Ala Leu Thr Leu Asn Thr Glu
225                 230                 235                 240

Lys Gln Lys Lys Lys Pro Lys Met Ser Asp Glu Ile Leu Glu Lys
                245                 250                 255

Leu Arg Ser Ile Val Ser Val Gly Asp Pro Lys Lys Tyr Thr Arg
            260                 265                 270

Phe Glu Lys Ile Gly Gln Gly Ala Ser Gly Thr Val Tyr Thr Ala Met
            275                 280                 285

Asp Val Ala Thr Gly Gln Glu Val Ala Ile Lys Gln Met Asn Leu Gln
290                 295                 300

Gln Gln Pro Lys Lys Glu Leu Ile Ile Asn Glu Ile Leu Val Met Arg
305                 310                 315                 320

Glu Asn Lys Asn Pro Asn Ile Val Asn Tyr Leu Asp Ser Tyr Leu Val
                325                 330                 335

Gly Asp Glu Leu Trp Val Val Met Glu Tyr Leu Ala Gly Gly Ser Leu
            340                 345                 350

Thr Asp Val Val Thr Glu Thr Cys Met Asp Glu Gly Gln Ile Ala Ala
            355                 360                 365

Val Cys Arg Glu Cys Leu Gln Ala Leu Glu Ser Leu His Ser Asn Gln
370                 375                 380

Val Ile His Arg Asp Ile Lys Ser Asp Asn Ile Leu Leu Gly Met Asp
385                 390                 395                 400

Gly Ser Val Lys Leu Thr Asp Phe Gly Phe Cys Ala Gln Ile Thr Pro
                405                 410                 415

Glu Gln Ser Lys Arg Ser Thr Met Val Gly Thr Pro Tyr Trp Met Ala
                420                 425                 430

Pro Glu Val Val Thr Arg Lys Ala Tyr Gly Pro Lys Val Asp Ile Trp
            435                 440                 445

Ser Leu Gly Ile Met Ala Ile Glu Met Ile Glu Gly Glu Pro Pro Tyr
        450                 455                 460

Leu Asn Glu Asn Pro Leu Arg Ala Leu Tyr Leu Ile Ala Thr Asn Gly
465                 470                 475                 480
```

```
Thr Pro Glu Leu Gln Asn Pro Glu Lys Leu Ser Ala Ile Phe Arg Asp
            485                 490                 495
Phe Leu Asn Arg Cys Leu Glu Met Asp Val Glu Lys Arg Gly Ser Ala
        500                 505                 510
Lys Glu Leu Leu Gln His Gln Phe Leu Lys Ile Ala Lys Pro Leu Ser
    515                 520                 525
Ser Leu Thr Pro Leu Ile Ala Ala Lys Glu Ala Thr Lys Asn Asn
530                 535                 540
His
545

<210> SEQ ID NO 94
<211> LENGTH: 506
<212> TYPE: PRT
<213> ORGANISM: Homo sapiens

<400> SEQUENCE: 94

Met Glu Glu Thr Gln Gln Lys Ser Asn Leu Glu Leu Leu Ser Ala Asn
1               5                   10                  15
His Ser Leu Lys Pro Leu Pro Ser Val Pro Glu Glu Lys Lys Pro Arg
            20                  25                  30
His Lys Ile Ile Ser Ile Phe Ser Gly Thr Glu Lys Gly Ser Lys Lys
        35                  40                  45
Lys Glu Lys Glu Arg Pro Glu Ile Ser Pro Pro Ser Asp Phe Glu His
    50                  55                  60
Thr Ile His Val Gly Phe Asp Thr Val Thr Gly Glu Phe Thr Gly Met
65                  70                  75                  80
Pro Glu Gln Trp Ala Arg Leu Leu Gln Thr Ser Asn Ile Thr Lys Leu
                85                  90                  95
Glu Gln Lys Lys Asn Pro Gln Ala Val Leu Asp Val Leu Lys Phe Tyr
            100                 105                 110
Asp Ser Asn Thr Val Lys Gln Lys Tyr Leu Ser Phe Thr Pro Pro Glu
        115                 120                 125
Lys Asp Gly Phe Pro Ser Gly Thr Pro Ala Leu Asn Ala Lys Gly Thr
    130                 135                 140
Glu Ala Pro Ala Val Val Thr Glu Glu Glu Asp Asp Asp Glu Glu Thr
145                 150                 155                 160
Ala Pro Pro Val Ile Ala Pro Arg Pro Asp His Thr Lys Ser Ile Tyr
                165                 170                 175
Thr Arg Ser Val Ile Asp Pro Val Pro Ala Pro Val Gly Asp Ser His
            180                 185                 190
Val Asp Gly Ala Ala Lys Ser Leu Asp Lys Gln Lys Lys Lys Thr Lys
        195                 200                 205
Met Thr Asp Glu Glu Ile Met Glu Lys Leu Arg Thr Ile Val Ser Ile
    210                 215                 220
Gly Asp Pro Lys Lys Lys Tyr Thr Arg Tyr Glu Lys Ile Gly Gln Gly
225                 230                 235                 240
Ala Ser Gly Thr Val Phe Thr Ala Thr Asp Val Ala Leu Gly Gln Glu
                245                 250                 255
Val Ala Ile Lys Gln Ile Asn Leu Gln Lys Gln Pro Lys Lys Glu Leu
            260                 265                 270
Ile Ile Asn Glu Ile Leu Val Met Lys Glu Leu Lys Asn Pro Asn Ile
        275                 280                 285
Val Asn Phe Leu Asp Ser Tyr Leu Val Gly Asp Glu Leu Phe Val Val
```

-continued

```
                     290                 295                 300
Met Glu Tyr Leu Ala Gly Arg Ser Leu Thr Asp Val Val Thr Glu Thr
305                 310                 315                 320

Cys Met Asp Glu Ala Gln Ile Ala Ala Val Cys Arg Glu Cys Leu Gln
                325                 330                 335

Ala Leu Glu Phe Leu His Ala Asn Gln Val Ile His Arg Asp Ile Lys
            340                 345                 350

Ser Asp Asn Val Leu Leu Gly Met Glu Gly Ser Val Lys Leu Thr Asp
        355                 360                 365

Phe Gly Phe Cys Ala Gln Ile Thr Pro Glu Gln Ser Lys Arg Ser Thr
    370                 375                 380

Met Val Gly Thr Pro Tyr Trp Met Ala Pro Glu Val Val Thr Arg Lys
385                 390                 395                 400

Ala Tyr Gly Pro Lys Val Asp Ile Trp Ser Leu Gly Ile Met Ala Ile
                405                 410                 415

Glu Met Val Glu Gly Glu Pro Pro Tyr Leu Asn Glu Asn Pro Leu Arg
            420                 425                 430

Ala Leu Tyr Leu Ile Ala Thr Asn Gly Thr Pro Glu Leu Gln Asn Pro
        435                 440                 445

Glu Lys Leu Ser Pro Ile Phe Arg Asp Phe Leu Asn Arg Cys Leu Glu
    450                 455                 460

Met Asp Val Glu Lys Arg Gly Ser Ala Lys Glu Leu Leu Gln His Pro
465                 470                 475                 480

Phe Leu Lys Leu Ala Lys Pro Leu Ser Ser Leu Thr Pro Leu Ile Met
                485                 490                 495

Ala Ala Lys Glu Ala Met Lys Ser Asn Arg
            500                 505

<210> SEQ ID NO 95
<211> LENGTH: 544
<212> TYPE: PRT
<213> ORGANISM: Murine sp.

<400> SEQUENCE: 95

Met Ser Asp Ser Leu Asp Asn Glu Glu Lys Pro Pro Ala Pro Pro Leu
1               5                   10                  15

Arg Met Asn Ser Asn Asn Arg Asp Ser Ser Ala Leu Asn His Ser Ser
            20                  25                  30

Lys Pro Leu Pro Met Ala Pro Glu Glu Lys Asn Lys Lys Ala Arg Leu
        35                  40                  45

Arg Ser Ile Phe Pro Gly Gly Gly Asp Lys Thr Asn Lys Lys Lys Glu
    50                  55                  60

Lys Glu Arg Pro Glu Ile Ser Leu Pro Ser Asp Phe Glu His Thr Ile
65                  70                  75                  80

His Val Gly Phe Asp Ala Val Thr Gly Glu Phe Thr Gly Ile Pro Glu
                85                  90                  95

Gln Trp Ala Arg Leu Leu Gln Thr Ser Asn Ile Thr Lys Leu Glu Gln
            100                 105                 110

Lys Lys Asn Pro Gln Ala Val Leu Asp Val Leu Lys Phe Tyr Asp Ser
        115                 120                 125

Lys Glu Thr Val Asn Asn Gln Lys Tyr Met Ser Phe Thr Ser Gly Asp
    130                 135                 140

Lys Ser Ala His Gly Tyr Ile Ala Ala His Gln Ser Asn Thr Lys Thr
145                 150                 155                 160
```

-continued

| | | | | | | | | | | | |
|---|---|---|---|---|---|---|---|---|---|---|---|
|Gly|Ser|Glu|Pro 165|Pro|Leu|Ala|Pro|Val 170|Ser|Glu|Glu|Asp|Glu 175|
|Glu|Glu|Glu|Glu 180|Glu|Glu|Asp|Asp|Asn 185|Glu|Pro|Pro|Val 190|Ile|Ala|
|Pro|Arg|Pro 195|Glu|His|Thr|Lys|Ser 200|Ile|Tyr|Thr|Arg|Ser 205|Val|Val|Glu|
|Ser|Ile 210|Ala|Ser|Pro|Ala|Ala 215|Pro|Asn|Lys|Glu|Asp 220|Ile|Pro|Pro|Ser|
|Ala 225|Glu|Asn|Ala|Asn|Ser 230|Thr|Thr|Leu|Tyr|Arg 235|Asn|Thr|Asp|Arg|Gln 240|
|Arg|Lys|Lys|Ser|Lys 245|Met|Thr|Asp|Glu|Glu 250|Ile|Leu|Glu|Lys|Leu 255|Arg|
|Ser|Ile|Val|Ser 260|Val|Gly|Asp|Pro|Lys 265|Lys|Tyr|Thr|Arg 270|Leu|Glu|
|Lys|Ile|Gly 275|Gln|Gly|Ala|Ser|Gly 280|Thr|Val|Tyr|Thr|Ala 285|Leu|Asp|Ile|
|Ala|Thr 290|Gly|Gln|Glu|Val|Ala 295|Ile|Lys|Gln|Met|Asn 300|Leu|Gln|Gln|Gln|
|Pro 305|Lys|Lys|Glu|Leu|Ile 310|Ile|Asn|Glu|Ile|Leu 315|Val|Met|Arg|Glu|Asn 320|
|Lys|Asn|Pro|Asn|Ile 325|Val|Asn|Tyr|Leu|Asp 330|Ser|Tyr|Leu|Val|Gly 335|Asp|
|Glu|Leu|Trp|Val 340|Val|Met|Glu|Tyr|Leu 345|Ala|Gly|Gly|Ser 350|Leu|Thr|Asp|
|Val|Val|Thr 355|Glu|Thr|Cys|Met|Asp 360|Val|Gly|Gln|Ile|Ala 365|Ala|Val|Cys|
|Arg 370|Glu|Cys|Leu|Gln|Ala 375|Leu|Asp|Phe|Leu|His 380|Ser|Asn|Gln|Val|Ile|
|His 385|Arg|Asp|Ile|Lys|Ser 390|Asp|Asn|Ile|Leu|Leu 395|Gly|Met|Asp|Gly|Ser 400|
|Val|Lys|Leu|Thr|Asp 405|Phe|Gly|Phe|Cys|Ala 410|Gln|Ile|Thr|Pro|Glu 415|Gln|
|Ser|Lys|Arg|Ser 420|Thr|Met|Val|Gly|Thr 425|Pro|Tyr|Trp|Met 430|Ala|Pro|Glu|
|Val|Val|Thr 435|Arg|Lys|Ala|Tyr|Gly 440|Pro|Lys|Val|Asp|Ile 445|Trp|Ser|Leu|
|Gly 450|Ile|Met|Ala|Ile|Glu 455|Met|Val|Glu|Gly|Pro 460|Pro|Tyr|Leu|Asn|
|Glu 465|Asn|Pro|Leu|Arg|Ala 470|Leu|Tyr|Leu|Ile|Ala 475|Thr|Asn|Gly|Thr|Pro 480|
|Glu|Leu|Gln|Asn|Pro 485|Glu|Arg|Leu|Ser|Ala 490|Val|Phe|His|Asp|Phe 495|Leu|
|Asn|Arg|Cys|Leu 500|Glu|Met|Asp|Val|Asp 505|Arg|Arg|Gly|Ser 510|Ala|Lys|Glu|
|Leu|Leu|Gln|His 515|Pro|Phe|Leu|Lys|Leu 520|Ala|Lys|Pro|Leu 525|Ser|Ser|Leu|
|Thr 530|Pro|Leu|Ile|Ile|Ala 535|Ala|Lys|Glu|Ala|Ile 540|Lys|Asn|Ser|Ser|Arg|

<210> SEQ ID NO 96
<211> LENGTH: 2110
<212> TYPE: DNA
<213> ORGANISM: Homo sapiens

<400> SEQUENCE: 96

```
ggccaagacg gtcgggctg cttgctaact ccaggaacag gtttaagttt ttgaaactga      60
agtaggtcta cacagtagga actcatgtca tttcttgtaa gtaaaccaga gcgaatcagg    120
cggtgggtct cggaaaagtt cattgttgag ggcttaagag atttggaact atttggagac    180
caatgatgcg agctcagagt caatagcatc cttctctaaa caggaggtca tgagtagctt    240
tctgccagag ggagggtgtt acgagctgct cactgtgata ggcaaaggat ttgaggacct    300
gatgactgtg aatctagcaa ggtacaaacc aacaggagag tacgtgactg tacggaggat    360
taacctagaa gcttgttcca atgagatggt aacattcttg cagggcgagc tgcatgtctc    420
caaactcttc aaccatccca atatcgtgcc atatcgagcc acttttattg cagacaatga    480
gctgtgggtt gtcacatcat tcatggcata cggttctgca aaagatctca tctgtacaca    540
cttcatggat ggcatgaatg agctggcgat tgcttacatc ctgcagggg tgctgaaggc    600 cctcgactac atccaccaca tgggatatgt acacaggagt gtcaaagcca gccacatcct    660
gatctctgtg gatgggaagg tctacctgtc tggtttgcgc agcaacctca gcatgataag    720
ccatgggcag cggcagcgag tggtccacga ttttcccaag tacagtgtca aggttctgcc    780
gtggctcagc cccgaggtcc tccagcagaa tctccagggt tatgatgcca agtctgacat    840
ctacagtgtg ggaatcacag cctgtgaact ggccaacggc catgtcccct ttaaggatat    900
gcctgccacc cagatgctgc tagagaaact gaacggcaca gtgccctgcc tgttggatac    960
cagcaccatc cccgctgagg agctgaccat gagcccttcg cgctcagtgg ccaactctgg   1020
cctgagtgac agcctgacca ccagcacccc ccggccctcc aacggtgact cgccctccca   1080
cccctaccac cgaaccttct cccccccactt ccaccacttt gtggagcagt gccttcagcg   1140
caacccggat gccaggccca gtgccagcac cctcctgaac cactctttct tcaagcagat   1200
caagcgacgt gcctcagagg cttttgcccga attgcttcgt cctgtcaccc ccatcaccaa   1260
ttttgagggc agccagtctc aggaccacag tggaatcttt ggcctggtaa caaacctgga   1320
agagctggag gtggacgatt gggagttctg agcctctgca aactgtgcgc attctccagc   1380
cagggatgca gaggccaccc agaggccctt cctgagggcc ggccacattc ccgccctcct   1440
gggcagattg ggtagaaagg acattcttcc aggaaagttg actgctgact gattgggaaa   1500
gaaaatcctg gagagatact tcactgctcc aaggcttttg agacacaagg gaatctcaac   1560
aaccagggat caggagggtc caaagccgac attcccagtc ctgtgagctc aggtgacctc   1620
ctccgcagaa gagagatgct gctctggccc tgggagctga attccaagcc cagggtttgg   1680
ctccttaaac ccgaggaccg ccacctcttc ccagtgcttg cgaccagcct cattctatt   1740 aactttgctc tcagatgcct cagatgctat aggtcagtga aagggcaagt agtaagctgc   1800
ctgcctccct tccctcagac ctctcccctca taattccaga aagggcatt tctgtctttt    1860 taagcacaga ctaaggctgg aacagtccat ccttatccct cttctggctt gggccctgac    1920
acctaagtct ttcccacggt ttatgtgtgt gcctcattcc tttcccacca agaatccatc    1980
ttagcgcctc ctgccagctg ccctggtgct ttctccaagg gccatcagtg tcttgcctag    2040
cttgagggct taagtcctta tgctgtgtta gtttcgttgt cagaacaaat taaaatttc     2100 agagacgctg                                                           2110
```

<210> SEQ ID NO 97
<211> LENGTH: 373
<212> TYPE: PRT
<213> ORGANISM: Homo sapiens

```
<400> SEQUENCE: 97

Met Ser Ser Phe Leu Pro Glu Gly Gly Cys Tyr Glu Leu Leu Thr Val
  1               5                  10                  15

Ile Gly Lys Gly Phe Glu Asp Leu Met Thr Val Asn Leu Ala Arg Tyr
             20                  25                  30

Lys Pro Thr Gly Glu Tyr Val Thr Val Arg Arg Ile Asn Leu Glu Ala
             35                  40                  45

Cys Ser Asn Glu Met Val Thr Phe Leu Gln Gly Glu Leu His Val Ser
 50                  55                  60

Lys Leu Phe Asn His Pro Asn Ile Val Pro Tyr Arg Ala Thr Phe Ile
 65                  70                  75                  80

Ala Asp Asn Glu Leu Trp Val Val Thr Ser Phe Met Ala Tyr Gly Ser
                 85                  90                  95

Ala Lys Asp Leu Ile Cys Thr His Phe Met Asp Gly Met Asn Glu Leu
            100                 105                 110

Ala Ile Ala Tyr Ile Leu Gln Gly Val Leu Lys Ala Leu Asp Tyr Ile
            115                 120                 125

His His Met Gly Tyr Val His Arg Ser Val Lys Ala Ser His Ile Leu
    130                 135                 140

Ile Ser Val Asp Gly Lys Val Tyr Leu Ser Gly Leu Arg Ser Asn Leu
145                 150                 155                 160

Ser Met Ile Ser His Gly Gln Arg Gln Arg Val Val His Asp Phe Pro
                165                 170                 175

Lys Tyr Ser Val Lys Val Leu Pro Trp Leu Ser Pro Glu Val Leu Gln
            180                 185                 190

Gln Asn Leu Gln Gly Tyr Asp Ala Lys Ser Asp Ile Tyr Ser Val Gly
        195                 200                 205

Ile Thr Ala Cys Glu Leu Ala Asn Gly His Val Pro Phe Lys Asp Met
    210                 215                 220

Pro Ala Thr Gln Met Leu Leu Glu Lys Leu Asn Gly Thr Val Pro Cys
225                 230                 235                 240

Leu Leu Asp Thr Ser Thr Ile Pro Ala Glu Glu Leu Thr Met Ser Pro
                245                 250                 255

Ser Arg Ser Val Ala Asn Ser Gly Leu Ser Asp Ser Leu Thr Thr Ser
            260                 265                 270

Thr Pro Arg Pro Ser Asn Gly Asp Ser Pro Ser His Pro Tyr His Arg
        275                 280                 285

Thr Phe Ser Pro His Phe His His Phe Val Glu Gln Cys Leu Gln Arg
    290                 295                 300

Asn Pro Asp Ala Arg Pro Ser Ala Ser Thr Leu Leu Asn His Ser Phe
305                 310                 315                 320

Phe Lys Gln Ile Lys Arg Arg Ala Ser Glu Ala Leu Pro Glu Leu Leu
                325                 330                 335

Arg Pro Val Thr Pro Ile Thr Asn Phe Glu Gly Ser Gln Ser Gln Asp
            340                 345                 350

His Ser Gly Ile Phe Gly Leu Val Thr Asn Leu Glu Glu Leu Glu Val
        355                 360                 365

Asp Asp Trp Glu Phe
    370

<210> SEQ ID NO 98
<211> LENGTH: 2001
<212> TYPE: DNA
<213> ORGANISM: Homo sapiens
```

<400> SEQUENCE: 98

```
aaggaagata aaacaaaagc cttctttgga atagatggat ttttgtcact ttctgtgtga       60
actaaagtga ttcaatgtct cttttggatt gcttctgcac ttcaagaaca caagttgaat      120
cactcagacc tgaaaaacag tctgaaacca gtatccatca atacttggtt gatgagccaa      180
ccctttcctg gtcacgtcca tccactagag ccagtgaagt actatgttcc accaacgttt      240
ctcactatga gctccaagta gaataggaa gaggatttga caacttgact tctgtccatc       300
ttgcacggca tactcccacg ggaacactgg taactataaa aattacaaat ctggaaaact      360
gcaatgaaga acgcctgaaa gctttacaga aagccgtgat tctatcccac ttttccggc      420
atcccaatat tacaacttat tggacagttt tcactgttgg cagctggctt tgggttattt      480
ctccatttat ggcctatggt tcagcaagtc aactcttgag gacctatttt cctgaaggaa      540
tgagtgaaac tttaataaga aacattctct ttggagccgt gagagggttg aactatctgc      600
accaaaatgg ctgtattcac aggagtatta agccagcca tatcctcatt ctggtgatg       660
gcctagtgac cctctctggc ctttcccatc tgcatagttt ggttaagcat ggacagaggc      720
atagggctgt gtatgatttc ccacagttca gcacatcagt gcagccgtgg ctgagtccag      780
aactactgag acaggattta catgggtata atgtgaagtc agatatttac agtgttggga      840
ttacagcatg tgaattagcc agtgggcagg tgcctttcca ggacatgcat agaactcaga      900
tgctgttaca gaaactgaaa ggtcctcctt atagcccatt ggatatcagt attttccctc      960
aatcagaatc cagaatgaaa aattcccagt caggtgtaga ctctgggatt ggagaaagtg    1020
tgcttgtctc cagtggaact cacacagtaa atagtgaccg attacacaca ccatcctcaa    1080
aaactttctc tcctgccttc tttagcttgg tacagctctg tttgcaacaa gatcctgaga    1140
aaaggccatc agcaagcagt ttattgtccc atgttttctt caaacagatg aaagaagaa     1200
gccaggattc aatactttca ctgttgcctc ctgcttataa caagccatca atatcattgc    1260
ctccagtgtt accttggact gagccagaat gtgattttcc tgatgaaaaa gactcatact    1320
gggaattcta gggctgccaa atcatttat gtcctatata cttgacactt tctccttgct     1380
gcttttttctt ctgtatttct aggtacaaat accagaatta tacttgaaaa tacagttggt    1440
gcactggaga atctattatt taaaaccact ctgttcaaag gggcaccagt ttgtagtccc    1500
tctgtttcgc acagagtact atgacaagga aacatcagaa ttactaatct agctagtgtc    1560
atttattctg gaattttttt ctaagctgtg actaactctt tttatctctc aatataattt    1620
ttgagccagt taattttttt cagtattttg ctgtcccttg ggaatgggcc ctcagaggac    1680
agtgcttcca agtacatctt ctcccagatt ctctggcctt tttaatgagc tattgttaaa    1740
ccaacaggct agtttatctt acatcagacc cttttctggt agagggaaaa tgtttgtgct    1800
ttcccttttt cttctgttaa tacttatggt aacacctaac tgagcctcac tcacattaaa    1860
tgattcactt gaaatatata cagaaattgt aatttgcttt ttttaaaaa agggggctaa      1920
agtaacactt tcctacttat gtaaattata gatcctaaat tcacgcaccc cgtgggagct    1980
caataaagat ttactgaatt g                                              2001
```

<210> SEQ ID NO 99
<211> LENGTH: 418
<212> TYPE: PRT
<213> ORGANISM: Homo sapiens

<400> SEQUENCE: 99

-continued

```
Met Ser Leu Leu Asp Cys Phe Cys Thr Ser Arg Thr Gln Val Glu Ser
 1               5                  10                  15

Leu Arg Pro Glu Lys Gln Ser Glu Thr Ser Ile His Gln Tyr Leu Val
                20                  25                  30

Asp Glu Pro Thr Leu Ser Trp Ser Arg Pro Ser Thr Arg Ala Ser Glu
            35                  40                  45

Val Leu Cys Ser Thr Asn Val Ser His Tyr Glu Leu Gln Val Glu Ile
        50                  55                  60

Gly Arg Gly Phe Asp Asn Leu Thr Ser Val His Leu Ala Arg His Thr
 65                  70                  75                  80

Pro Thr Gly Thr Leu Val Thr Ile Lys Ile Thr Asn Leu Glu Asn Cys
                85                  90                  95

Asn Glu Glu Arg Leu Lys Ala Leu Gln Lys Ala Val Ile Leu Ser His
                100                 105                 110

Phe Phe Arg His Pro Asn Ile Thr Thr Tyr Trp Thr Val Phe Thr Val
                115                 120                 125

Gly Ser Trp Leu Trp Val Ile Ser Pro Phe Met Ala Tyr Gly Ser Ala
130                 135                 140

Ser Gln Leu Leu Arg Thr Tyr Phe Pro Glu Gly Met Ser Glu Thr Leu
145                 150                 155                 160

Ile Arg Asn Ile Leu Phe Gly Ala Val Arg Gly Leu Asn Tyr Leu His
                165                 170                 175

Gln Asn Gly Cys Ile His Arg Ser Ile Lys Ala Ser His Ile Leu Ile
                180                 185                 190

Ser Gly Asp Gly Leu Val Thr Leu Ser Gly Leu Ser His Leu His Ser
                195                 200                 205

Leu Val Lys His Gly Gln Arg His Arg Ala Val Tyr Asp Phe Pro Gln
                210                 215                 220

Phe Ser Thr Ser Val Gln Pro Trp Leu Ser Pro Glu Leu Leu Arg Gln
225                 230                 235                 240

Asp Leu His Gly Tyr Asn Val Lys Ser Asp Ile Tyr Ser Val Gly Ile
                245                 250                 255

Thr Ala Cys Glu Leu Ala Ser Gly Gln Val Pro Phe Gln Asp Met His
                260                 265                 270

Arg Thr Gln Met Leu Leu Gln Lys Leu Lys Gly Pro Pro Tyr Ser Pro
                275                 280                 285

Leu Asp Ile Ser Ile Phe Pro Gln Ser Glu Ser Arg Met Lys Asn Ser
                290                 295                 300

Gln Ser Gly Val Asp Ser Gly Ile Gly Glu Ser Val Leu Val Ser Ser
305                 310                 315                 320

Gly Thr His Thr Val Asn Ser Asp Arg Leu His Thr Pro Ser Ser Lys
                325                 330                 335

Thr Phe Ser Pro Ala Phe Phe Ser Leu Val Gln Leu Cys Leu Gln Gln
                340                 345                 350

Asp Pro Glu Lys Arg Pro Ser Ala Ser Ser Leu Leu Ser His Val Phe
                355                 360                 365

Phe Lys Gln Met Lys Glu Glu Ser Gln Asp Ser Ile Leu Ser Leu Leu
                370                 375                 380

Pro Pro Ala Tyr Asn Lys Pro Ser Ile Ser Leu Pro Pro Val Leu Pro
385                 390                 395                 400

Trp Thr Glu Pro Glu Cys Asp Phe Pro Asp Glu Lys Asp Ser Tyr Trp
                405                 410                 415

Glu Phe
```

<210> SEQ ID NO 100
<211> LENGTH: 311
<212> TYPE: DNA
<213> ORGANISM: Homo sapiens

<400> SEQUENCE: 100

```
tcaacaggga cgattacgag ctgcaggagg tgatcgggag tggagcaact gctgtagtcc      60
aagcagctta ttgtgcccct aaaaaggaga agtggcaat caaacggata aaccttgaga     120
aatgtcaaac tagcatggat gaactcctga agaaattca agccatgagt caatgccatc     180
atcctaatat tgtatcttac tacacatctt ttgtggtaaa agatgagctg tggcttgtca     240
tgaagctgct aagtggaggt tctgttctgg atattattaa gcacattgtg caaaagggg      300
aacacaaaag t                                                          311
```

<210> SEQ ID NO 101
<211> LENGTH: 103
<212> TYPE: PRT
<213> ORGANISM: Homo sapiens

<400> SEQUENCE: 101

```
Asn Arg Asp Asp Tyr Glu Leu Gln Glu Val Ile Gly Ser Gly Ala Thr
  1               5                  10                  15
Ala Val Val Gln Ala Ala Tyr Cys Ala Pro Lys Lys Glu Lys Val Ala
                 20                  25                  30
Ile Lys Arg Ile Asn Leu Glu Lys Cys Gln Thr Ser Met Asp Glu Leu
             35                  40                  45
Leu Lys Glu Ile Gln Ala Met Ser Gln Cys His His Pro Asn Ile Val
         50                  55                  60
Ser Tyr Tyr Thr Ser Phe Val Val Lys Asp Glu Leu Trp Leu Val Met
 65                  70                  75                  80
Lys Leu Leu Ser Gly Gly Ser Val Leu Asp Ile Ile Lys His Ile Val
                 85                  90                  95
Ala Lys Gly Glu His Lys Ser
            100
```

<210> SEQ ID NO 102
<211> LENGTH: 2806
<212> TYPE: DNA
<213> ORGANISM: Homo sapiens

<400> SEQUENCE: 102

```
cgggagtgtc cgcggtggtg gcggtgcaag agagctgaag gaggcgcgag ggcgcggagt      60
tccaggccga gcagttaggc cgcgagcgac tgcggcgccg agccgatgag taacccgaag     120
cccctagagg agtggtcacc tgcctgaggg cacttctgtc ccaccagcat cagaccaggc     180
cgcaccgagt ccccggcacc atgtttggga gaggaagaa gcgggtggag atctccgcgc     240
cgtccaactt cgagcaccgc gtgcacacgg gcttcgacca gcacgagcag aagttcacgg     300
ggctgccccg ccagtggcag agcctgatcg aggagtcggc tcgccggccc aagcccctcg     360
tcgaccccgc ctgcatcacc tccatccagc ccggggcccc caagaccatc gtgcggggca     420
gcaaggtgc caagatggg gccctcacgc tgctgctgga cgagtttgag aacatgtcgg     480
tgacacgctc caactccctg cggagagaca gccgccgcc gccgccgt ccccgccagg     540
aaaatgggat gccagaggag ccggccacca cggccagagg gggcccaggg aaggcaggca     600
gccgaggccg gttcgccggt cacagcgagg cgggtggcgg cagtggtgac aggcgacggg     660
```

```
cggggccaga gaagaggccc aagtcttcca gggagggctc aggggtccc caggagtcct      720 cccgggacaa acgcccctc tccgggcctg atgtcggcac ccccagcct gctggtctgg      780 ccagtggggc gaaactggca gctggccggc cctttaacac ctacccgagg gctgacacgg    840
accacccatc ccgggggtgcc caggggggagc ctcatgacgt ggcccctaac gggccatcag  900 cgggggggcct ggccatcccc cagtcctcct cctcctcctc ccggcctccc acccgagccc   960
gaggtgcccc cagccctgga gtgctggac cccacgcctc agagcccag ctggcccctc     1020 cagcctgcac cccgccgcc cctgctgttc ctggcccccc tgggccccgc tcaccacagc   1080
gggagccaca gcgagtatcc catgagcagt tccgggctgc cctgcagctg gtggtggacc  1140
caggcgaccc ccgctcctac ctggacaact tcatcaagat ggcgagggc tccacgggca   1200 tcgtgtgcat cgccaccgtg cgcagctcgg gcaagctggt ggccgtcaag aagatggacc  1260
tgcgcaagca gcagaggcgc gagctgctct tcaacgaggt ggtaatcatg agggactacc  1320
agcacgagaa tgtggtggag atgtacaaca gctacctggt gggggacgag ctctgggtgg  1380
tcatggagtt cctggaagga ggcgccctca ccgacatcgt caccacacc aggatgaacg   1440 aggagcagat cgcggccgtg tgccttgcag tgctgcaggc cctgtcggtg ctccacgccc  1500
agggcgtcat ccaccgggac atcaagagcg actcgatcct gctgacccat gatggcaggg  1560
tgaagctgtc agactttggg ttctgcgccc aggtgagcaa ggaagtgccc cgaaggaagt  1620
cgctggtcgg cacgccctac tggatggccc cagagctcat ctcccgcctt ccctacgggc  1680
cagaggtaga catctggtcg ctggggataa tggtgattga gatggtggac ggagagcccc  1740
cctacttcaa cgagccaccc ctcaaagcca tgaagatgat tcgggacaac ctgccacccc  1800
gactgaagaa cctgcacaag gtgtcgccat ccctgaaggg cttcctggac cgcctgctgg  1860
tgcgagaccc tgcccagcgg gccacggcag ccgagctgct gaagcaccca ttcctggcca  1920
aggcagggcc gcctgccagc atcgtgcccc tcatgcgcca gaaccgcacc agatgaggcc  1980 cagcgcccctt cccctcaacc aaagagcccc ccgggtcac cccgcccca ctgaggccag   2040 taggggggcca ggcctcccac tcctcccagc ccgggagatg ctccgcgtgg caccaccctc  2100
cttgctgggg gtagatgaga ccctactact gaactccagt tttgatctcg tgactttttag  2160 aaaaacacag ggactcgtgg gagcaagcga ggctcccagg accccaccc tctgggacag   2220 gccctccccc atgttcttct gtctccagga agggcagcgg ccctcccatc actggaagtc  2280
tgcagtgggg gtcgctgggg gtggagagaa cactaagagg tgaacatgta tgagtgtgtg  2340
cacgcgtgtg agtgtgcatg tgtgtgtgtg tgcaaaggtc cagccacccc gtcctccagc  2400
ccgcaagggg tgtctggcgc cttgcctgac acccagcccc ctctcccct gagccattgt   2460 ggggggtcgat catgaatgtc cgaagagtgg ccttttcccg tagccctgcg cccccttttct 2520 gtggctggat ggggagacag tcagggccc cccaccctct ccagccctg cagcaaatga    2580 ctactgcacc tggacagcct cctctttct agaagtctat ttatattgtc attttataac    2640
actctagccc ctgcccttat tggggacag atggtccctg tcctgcgggg tggccctggc   2700
agaaccactg cctgaagaac caggttcctg cccggtcagc gcagcccag cccgcccacc   2760 cctgcctcga gttagttta caattaaaac attgtcttgt tttgtg                    2806
```

<210> SEQ ID NO 103
<211> LENGTH: 591
<212> TYPE: PRT
<213> ORGANISM: Homo sapiens

```
<400> SEQUENCE: 103

Met Phe Gly Lys Arg Lys Lys Arg Val Glu Ile Ser Ala Pro Ser Asn
  1               5                  10                  15

Phe Glu His Arg Val His Thr Gly Phe Asp Gln His Glu Gln Lys Phe
                 20                  25                  30

Thr Gly Leu Pro Arg Gln Trp Gln Ser Leu Ile Glu Glu Ser Ala Arg
             35                  40                  45

Arg Pro Lys Pro Leu Val Asp Pro Ala Cys Ile Thr Ser Ile Gln Pro
         50                  55                  60

Gly Ala Pro Lys Thr Ile Val Arg Gly Ser Lys Gly Ala Lys Asp Gly
 65                  70                  75                  80

Ala Leu Thr Leu Leu Leu Asp Glu Phe Glu Asn Met Ser Val Thr Arg
                 85                  90                  95

Ser Asn Ser Leu Arg Arg Asp Ser Pro Pro Pro Ala Arg Ala Arg
                100                 105                 110

Gln Glu Asn Gly Met Pro Glu Glu Pro Ala Thr Thr Ala Arg Gly Gly
            115                 120                 125

Pro Gly Lys Ala Gly Ser Arg Gly Arg Phe Ala Gly His Ser Glu Ala
130                 135                 140

Gly Gly Gly Ser Gly Asp Arg Arg Ala Gly Pro Glu Lys Arg Pro
145                 150                 155                 160

Lys Ser Ser Arg Glu Gly Ser Gly Pro Gln Glu Ser Ser Arg Asp
                165                 170                 175

Lys Arg Pro Leu Ser Gly Pro Asp Val Gly Thr Pro Gln Pro Ala Gly
            180                 185                 190

Leu Ala Ser Gly Ala Lys Leu Ala Ala Gly Arg Pro Phe Asn Thr Tyr
            195                 200                 205

Pro Arg Ala Asp Thr Asp His Pro Ser Arg Gly Ala Gln Gly Glu Pro
        210                 215                 220

His Asp Val Ala Pro Asn Gly Pro Ser Ala Gly Leu Ala Ile Pro
225                 230                 235                 240

Gln Ser Ser Ser Ser Ser Arg Pro Pro Thr Arg Ala Arg Gly Ala
                245                 250                 255

Pro Ser Pro Gly Val Leu Gly Pro His Ala Ser Glu Pro Gln Leu Ala
            260                 265                 270

Pro Pro Ala Cys Thr Pro Ala Ala Pro Ala Val Pro Gly Pro Pro Gly
        275                 280                 285

Pro Arg Ser Pro Gln Arg Glu Pro Gln Arg Val Ser His Glu Gln Phe
290                 295                 300

Arg Ala Ala Leu Gln Leu Val Val Asp Pro Gly Asp Pro Arg Ser Tyr
305                 310                 315                 320

Leu Asp Asn Phe Ile Lys Ile Gly Glu Gly Ser Thr Gly Ile Val Cys
                325                 330                 335

Ile Ala Thr Val Arg Ser Ser Gly Lys Leu Val Ala Val Lys Lys Met
            340                 345                 350

Asp Leu Arg Lys Gln Gln Arg Arg Glu Leu Leu Phe Asn Glu Val Val
            355                 360                 365

Ile Met Arg Asp Tyr Gln His Glu Asn Val Val Glu Met Tyr Asn Ser
        370                 375                 380

Tyr Leu Val Gly Asp Glu Leu Trp Val Val Met Glu Phe Leu Glu Gly
385                 390                 395                 400

Gly Ala Leu Thr Asp Ile Val Thr His Thr Arg Met Asn Glu Glu Gln
                405                 410                 415
```

```
            Ile Ala Ala Val Cys Leu Ala Val Leu Gln Ala Leu Ser Val Leu His
                        420                 425                 430

Ala Gln Gly Val Ile His Arg Asp Ile Lys Ser Asp Ser Ile Leu Leu
                    435                 440                 445

Thr His Asp Gly Arg Val Lys Leu Ser Asp Phe Gly Phe Cys Ala Gln
                450                 455                 460

Val Ser Lys Glu Val Pro Arg Arg Lys Ser Leu Val Gly Thr Pro Tyr
            465                 470                 475                 480

Trp Met Ala Pro Glu Leu Ile Ser Arg Leu Pro Tyr Gly Pro Glu Val
                            485                 490                 495

Asp Ile Trp Ser Leu Gly Ile Met Val Ile Glu Met Val Asp Gly Glu
                        500                 505                 510

Pro Pro Tyr Phe Asn Glu Pro Pro Leu Lys Ala Met Lys Met Ile Arg
                    515                 520                 525

Asp Asn Leu Pro Pro Arg Leu Lys Asn Leu His Lys Val Ser Pro Ser
                530                 535                 540

Leu Lys Gly Phe Leu Asp Arg Leu Leu Val Arg Asp Pro Ala Gln Arg
            545                 550                 555                 560

Ala Thr Ala Ala Glu Leu Leu Lys His Pro Phe Leu Ala Lys Ala Gly
                            565                 570                 575

Pro Pro Ala Ser Ile Val Pro Leu Met Arg Gln Asn Arg Thr Arg
                        580                 585                 590

<210> SEQ ID NO 104
<211> LENGTH: 3684
<212> TYPE: DNA
<213> ORGANISM: Homo sapiens

<400> SEQUENCE: 104
atggcgggac ctgggggctg gagggacagg gaggtcacgg atctgggcca cctgccggat     60
ccaactggaa tattctcact agataaaacc attggccttg gtacttatgg cagaatctat    120
ttgggacttc atgagaagac tggtgcattt acagctgtta aagtgatgaa cgctcgtaag    180
gatgaggaag aggatctcag gactgaactc aaccttctga ggaagtactc tttccacaaa    240
aacattgtgt ccttctatgg agcatttttc aagctgagtc ccctggtca gcggcaccaa    300 ctttggatgg tgatggagtt atgtgcagca ggttcggtca ctgatgtagt gagaatgacc    360
agtaatcaga gtttaaaaga agattggatt gcttatatct gccgagaaat ccttcagggc    420
ttagctcacc ttcacgcaca ccgagtaatt caccgggaca tcaaaggtca gaatgtgctg    480
ctgactcata tgctgaagt aaaactggtt gattttggag tgagtgccca ggtgagcaga    540
actaatggaa gaaggaatag tttcattggg acaccatact ggatggcacc tgaggtgatt    600
gactgtgatg aggacccaag acgctcctat gattacagaa gtgatgtgtg gtctgtggga    660
attactgcca ttgaaatggc tgaaggagcc cctcctctgt gtaaccttca accccttgga    720
gctctcttcg ttattttgcg ggaatctgct cccacagtca aatccagcgg atggtcccgt    780
aagttccaca atttcatgga aaagtgtacg ataaaaaatt tcctgtttcg tcctacttct    840
gcaaacatgc ttcaacaccc atttgttcgg gatataaaaa atgaacgaca tgttgttgag    900
tcattaacaa ggcatcttac tggaatcatt aaaaaaagac agaaaaaaga acaggcacgg    960
gagaaaaaat caaagttttc tactctgagg caagcactgg caaaaagact atcaccaaag   1020
aggttcaggg caaagtcatc atggagacct gaaaagcttg aactctcgga tttagaagcc   1080
cgcaggcaaa ggcgccaacg cagatgggaa gatatcttta tcagcatga ggaagaattg   1140
```

-continued

```
agacaagttg ataaagacaa agaagatgaa tcatcagaca atgatgaagt atttcattcg    1200
attcaggctg aagtccagat agagccattg aagccataca tttcaaatcc taaaaaaatt    1260
gaggttcaag agagatctcc ttctgtgcct aacaaccagg atcatgcaca tcatgtcaag    1320
ttctcttcaa gcgttcctca gcggtctctt ttggaacaag ctcagaagcc cattgacatc    1380
agacaaagga gttcgcaaaa tcgtcaaaat tggctggcag catcaggtga ttcaaagcac    1440
aaaattttag caggcaaaac acagagctac tgtttaacaa tttatatttc agaagtcaag    1500
aaagaagaat ttcaagaagg aatgaatcaa agtgtcagg gagcccaagt aggattagga    1560
cctgaaggcc attgtatttg gcaattgggt gaatcttctt ctgaggaaga aagtcctgtg    1620 actgaagga ggtctcagtc atcaccacct tattctacta ttgatcagaa gttgctggtt    1680
gacatccatg ttccagatgg atttaaagta ggaaaaatat caccccctgt atacttgaca    1740
aacgaatggg taggctataa tgcactctct gaaatcttcc ggaatgattg gttaactccg    1800
gcacctgtca ttcagccacc tgaagaggat ggtgattatg ttgaactcta tgatgccagt    1860
gctgatactg atggtgatga tgatgatgag tctaatgata cttttgaaga tacctatgat    1920
catgccaatg gcaatgatga cttggataac caggttgatc aggctaatga tgtttgtaaa    1980
gaccatgatg atgacaacaa taagtttgtt gatgatgtaa ataataatta ttatgaggcg    2040
cctagttgtc caagggcaag ctatggcaga gatggaagct gcaagcaaga tggttatgat    2100
ggaagtcgtg aaaagagga agcctacaga ggctatggaa gccatacagc caatagaagc    2160
catggaggaa gtgcagccag tgaggacaat gcagccattg gagatcagga agaacatgca    2220
gccaatatag gcagtgaaag aagaggcagt gagggtgatg gaggtaaggg agtcgttcga    2280
accagtgaag agagtggagc ccttggactc aatggagaag aaaattgctc agagacagat    2340
ggtccaggat tgaagagacc tgcgtctcag gactttgaat atctacagga ggagccaggt    2400
ggtggaaatg aggcctcaaa tgccattgac tcaggtgctg caccgtcagc acctgatcat    2460
gagagtgaca ataaggacat atcagaatca tcaacacaat cagattttc tgccaatcac    2520 tcatctcctt ccaaaggttc tgggatgtct gctgatgcta actttgccag tgccatctta    2580
tacgctggat tcgtagaagt acctgaggaa tcacctaagc aaccctctga agtcaatgtt    2640
aacccactct atgtctctcc tgcatgtaaa aaaccactaa tccacatgta tgaaaaggag    2700
ttcacttctg agatctgctg tggttctttg tggggagtca atttgctgtt gggaacccga    2760
tctaatctat atctgatgga cagaagtgga aaggctgaca ttactaaaact tataaggcga    2820 agaccattcc gccagattca agtcttagag ccactcaatt tgctgattac catctcaggt    2880
cataagaaca gacttcgggt gtatcatctg acctggttga ggaacaagat tttgaataat    2940
gatccagaaa gtaaaagaag gcaagaagaa atgctgaaga cagaggaagc ctgcaaagct    3000
attgataagt taacaggctg tgaacacttc agtgtcctcc aacatgaaga aacaacatat    3060
attgcaattg ctttgaaatc atcaattcac ctttatgcat gggcaccaaa gtcctttgat    3120
gaaagcactg ctattaaagt atttccaaca cttgatcata agccagtgac agttgacctg    3180
gctattggtt ctgaaaaaag actaaagatt tcttcagct cagcagatgg atatcacctc    3240
atcgatgcag aatctgaggt tatgtctgat gtgaccctgc caaagaatcc cctggaaatc    3300
attataccac agaatatcat cattttacct gattgcttgg gaattggcat gatgctcacc    3360
ttcaatgctg aagccctctc tgtggaagca aatgaacaac tcttcaagaa gatccttgaa    3420
atgtggaaag acataccatc ttctatagct tttgaatgta cacagcgaac cacaggatgg    3480
```

```
ggccaaaagg ccattgaagt gcgctctttg caatccaggg ttctggaaag tgagctgaag    3540
cgcaggtcaa ttaagaagct gagattcctg tgcacccggg gtgacaagct gttctttacc    3600
tctaccctgc gcaatcacca cagccgggtt tacttcatga cacttggaaa acttgaagag    3660
ctccaaagca attatgatgt ctaa                                            3684
```

<210> SEQ ID NO 105
<211> LENGTH: 1227
<212> TYPE: PRT
<213> ORGANISM: Homo sapiens

<400> SEQUENCE: 105

```
Met Ala Gly Pro Gly Gly Trp Arg Asp Arg Glu Val Thr Asp Leu Gly
 1               5                  10                  15

His Leu Pro Asp Pro Thr Gly Ile Phe Ser Leu Asp Lys Thr Ile Gly
                20                  25                  30

Leu Gly Thr Tyr Gly Arg Ile Tyr Leu Gly Leu His Glu Lys Thr Gly
            35                  40                  45

Ala Phe Thr Ala Val Lys Val Met Asn Ala Arg Lys Asp Glu Glu Glu
        50                  55                  60

Asp Leu Arg Thr Glu Leu Asn Leu Leu Arg Lys Tyr Ser Phe His Lys
 65                  70                  75                  80

Asn Ile Val Ser Phe Tyr Gly Ala Phe Phe Lys Leu Ser Pro Pro Gly
                85                  90                  95

Gln Arg His Gln Leu Trp Met Val Met Glu Leu Cys Ala Ala Gly Ser
               100                 105                 110

Val Thr Asp Val Val Arg Met Thr Ser Asn Gln Ser Leu Lys Glu Asp
            115                 120                 125

Trp Ile Ala Tyr Ile Cys Arg Glu Ile Leu Gln Gly Leu Ala His Leu
        130                 135                 140

His Ala His Arg Val Ile His Arg Asp Ile Lys Gly Gln Asn Val Leu
145                 150                 155                 160

Leu Thr His Asn Ala Glu Val Lys Leu Val Asp Phe Gly Val Ser Ala
                165                 170                 175

Gln Val Ser Arg Thr Asn Gly Arg Arg Asn Ser Phe Ile Gly Thr Pro
            180                 185                 190

Tyr Trp Met Ala Pro Glu Val Ile Asp Cys Asp Glu Asp Pro Arg Arg
        195                 200                 205

Ser Tyr Asp Tyr Arg Ser Asp Val Trp Ser Val Gly Ile Thr Ala Ile
    210                 215                 220

Glu Met Ala Glu Gly Ala Pro Pro Leu Cys Asn Leu Gln Pro Leu Glu
225                 230                 235                 240

Ala Leu Phe Val Ile Leu Arg Glu Ser Ala Pro Thr Val Lys Ser Ser
                245                 250                 255

Gly Trp Ser Arg Lys Phe His Asn Phe Met Glu Lys Cys Thr Ile Lys
            260                 265                 270

Asn Phe Leu Phe Arg Pro Thr Ser Ala Asn Met Leu Gln His Pro Phe
        275                 280                 285

Val Arg Asp Ile Lys Asn Glu Arg His Val Val Glu Ser Leu Thr Arg
    290                 295                 300

His Leu Thr Gly Ile Ile Lys Lys Arg Gln Lys Glu Gln Ala Arg
305                 310                 315                 320

Glu Lys Lys Ser Lys Val Ser Thr Leu Arg Gln Ala Leu Ala Lys Arg
                325                 330                 335
```

-continued

```
Leu Ser Pro Lys Arg Phe Arg Ala Lys Ser Ser Trp Arg Pro Glu Lys
            340                 345                 350

Leu Glu Leu Ser Asp Leu Glu Ala Arg Arg Gln Arg Gln Arg Arg
        355                 360                 365

Trp Glu Asp Ile Phe Asn Gln His Glu Glu Leu Arg Gln Val Asp
    370                 375                 380

Lys Asp Lys Glu Asp Glu Ser Ser Asp Asn Asp Glu Val Phe His Ser
385                 390                 395                 400

Ile Gln Ala Glu Val Gln Ile Glu Pro Leu Lys Pro Tyr Ile Ser Asn
                405                 410                 415

Pro Lys Lys Ile Glu Val Gln Glu Arg Ser Pro Ser Val Pro Asn Asn
            420                 425                 430

Gln Asp His Ala His His Val Lys Phe Ser Ser Ser Val Pro Gln Arg
        435                 440                 445

Ser Leu Leu Glu Gln Ala Gln Lys Pro Ile Asp Ile Arg Gln Arg Ser
    450                 455                 460

Ser Gln Asn Arg Gln Asn Trp Leu Ala Ala Ser Gly Asp Ser Lys His
465                 470                 475                 480

Lys Ile Leu Ala Gly Lys Thr Gln Ser Tyr Cys Leu Thr Ile Tyr Ile
                485                 490                 495

Ser Glu Val Lys Lys Glu Glu Phe Gln Glu Gly Met Asn Gln Lys Cys
            500                 505                 510

Gln Gly Ala Gln Val Gly Leu Gly Pro Glu Gly His Cys Ile Trp Gln
        515                 520                 525

Leu Gly Glu Ser Ser Ser Glu Glu Ser Pro Val Thr Gly Arg Arg
    530                 535                 540

Ser Gln Ser Ser Pro Pro Tyr Ser Thr Ile Asp Gln Lys Leu Leu Val
545                 550                 555                 560

Asp Ile His Val Pro Asp Gly Phe Lys Val Gly Lys Ile Ser Pro Pro
                565                 570                 575

Val Tyr Leu Thr Asn Glu Trp Val Gly Tyr Asn Ala Leu Ser Glu Ile
            580                 585                 590

Phe Arg Asn Asp Trp Leu Thr Pro Ala Pro Val Ile Gln Pro Pro Glu
        595                 600                 605

Glu Asp Gly Asp Tyr Val Glu Leu Tyr Asp Ala Ser Ala Asp Thr Asp
    610                 615                 620

Gly Asp Asp Asp Glu Ser Asn Asp Thr Phe Glu Asp Thr Tyr Asp
625                 630                 635                 640

His Ala Asn Gly Asn Asp Asp Leu Asp Asn Gln Val Asp Gln Ala Asn
                645                 650                 655

Asp Val Cys Lys Asp His Asp Asp Asn Lys Phe Val Asp Asp
            660                 665                 670

Val Asn Asn Asn Tyr Tyr Glu Ala Pro Ser Cys Pro Arg Ala Ser Tyr
        675                 680                 685

Gly Arg Asp Gly Ser Cys Lys Gln Asp Gly Tyr Asp Gly Ser Arg Gly
    690                 695                 700

Lys Glu Glu Ala Tyr Arg Gly Tyr Gly Ser His Thr Ala Asn Arg Ser
705                 710                 715                 720

His Gly Gly Ser Ala Ala Ser Glu Asp Asn Ala Ala Ile Gly Asp Gln
                725                 730                 735

Glu Glu His Ala Ala Asn Ile Gly Ser Glu Arg Arg Gly Ser Glu Gly
            740                 745                 750

Asp Gly Gly Lys Gly Val Val Arg Thr Ser Glu Glu Ser Gly Ala Leu
```

```
                755                 760                 765
Gly Leu Asn Gly Glu Glu Asn Cys Ser Glu Thr Asp Gly Pro Gly Leu
            770                 775                 780

Lys Arg Pro Ala Ser Gln Asp Phe Glu Tyr Leu Gln Glu Glu Pro Gly
785                 790                 795                 800

Gly Gly Asn Glu Ala Ser Asn Ala Ile Asp Ser Gly Ala Ala Pro Ser
                805                 810                 815

Ala Pro Asp His Glu Ser Asp Asn Lys Asp Ile Ser Glu Ser Ser Thr
            820                 825                 830

Gln Ser Asp Phe Ser Ala Asn His Ser Ser Pro Ser Lys Gly Ser Gly
            835                 840                 845

Met Ser Ala Asp Ala Asn Phe Ala Ser Ala Ile Leu Tyr Ala Gly Phe
    850                 855                 860

Val Glu Val Pro Glu Glu Ser Pro Lys Gln Pro Ser Glu Val Asn Val
865                 870                 875                 880

Asn Pro Leu Tyr Val Ser Pro Ala Cys Lys Lys Pro Leu Ile His Met
                885                 890                 895

Tyr Glu Lys Glu Phe Thr Ser Glu Ile Cys Cys Gly Ser Leu Trp Gly
            900                 905                 910

Val Asn Leu Leu Leu Gly Thr Arg Ser Asn Leu Tyr Leu Met Asp Arg
            915                 920                 925

Ser Gly Lys Ala Asp Ile Thr Lys Leu Ile Arg Arg Arg Pro Phe Arg
    930                 935                 940

Gln Ile Gln Val Leu Glu Pro Leu Asn Leu Leu Ile Thr Ile Ser Gly
945                 950                 955                 960

His Lys Asn Arg Leu Arg Val Tyr His Leu Thr Trp Leu Arg Asn Lys
                965                 970                 975

Ile Leu Asn Asn Asp Pro Glu Ser Lys Arg Arg Gln Glu Glu Met Leu
            980                 985                 990

Lys Thr Glu Glu Ala Cys Lys Ala Ile Asp Lys Leu Thr Gly Cys Glu
            995                 1000                1005

His Phe Ser Val Leu Gln His Glu Glu Thr Thr Tyr Ile Ala Ile Ala
    1010                1015                1020

Leu Lys Ser Ser Ile His Leu Tyr Ala Trp Ala Pro Lys Ser Phe Asp
1025                1030                1035                1040

Glu Ser Thr Ala Ile Lys Val Phe Pro Thr Leu Asp His Lys Pro Val
                1045                1050                1055

Thr Val Asp Leu Ala Ile Gly Ser Glu Lys Arg Leu Lys Ile Phe Phe
            1060                1065                1070

Ser Ser Ala Asp Gly Tyr His Leu Ile Asp Ala Glu Ser Glu Val Met
            1075                1080                1085

Ser Asp Val Thr Leu Pro Lys Asn Pro Leu Glu Ile Ile Ile Pro Gln
    1090                1095                1100

Asn Ile Ile Ile Leu Pro Asp Cys Leu Gly Ile Gly Met Met Leu Thr
1105                1110                1115                1120

Phe Asn Ala Glu Ala Leu Ser Val Glu Ala Asn Glu Gln Leu Phe Lys
                1125                1130                1135

Lys Ile Leu Glu Met Trp Lys Asp Ile Pro Ser Ser Ile Ala Phe Glu
            1140                1145                1150

Cys Thr Gln Arg Thr Thr Gly Trp Gly Gln Lys Ala Ile Glu Val Arg
    1155                1160                1165

Ser Leu Gln Ser Arg Val Leu Glu Ser Glu Leu Lys Arg Arg Ser Ile
1170                1175                1180
```

Lys Lys Leu Arg Phe Leu Cys Thr Arg Gly Asp Lys Leu Phe Phe Thr
1185                1190                1195                1200

Ser Thr Leu Arg Asn His His Ser Arg Val Tyr Phe Met Thr Leu Gly
            1205                1210                1215

Lys Leu Glu Glu Leu Gln Ser Asn Tyr Asp Val
        1220                1225

<210> SEQ ID NO 106
<211> LENGTH: 2962
<212> TYPE: DNA
<213> ORGANISM: Homo sapiens

<400> SEQUENCE: 106

| | | | | | |
|---|---|---|---|---|---|
| cgaagccaca | gcccgagccc | gagcccgagc | ccgagccggc | gccaccgcgc | ccccggccat | 60 |
| ggcttttgcc | aatttccgcc | gcatcctgcg | cctgtctacc | ttcgagaaga | gaaagtcccg | 120 |
| cgaatatgag | cacgtccgcc | gcgacctgga | ccccaacgag | gtgtgggaga | tcgtgggcga | 180 |
| gctgggcgac | ggcgccttcg | gcaaggttta | caaggccaag | aataaggaga | cgggtgcttt | 240 |
| ggctgcggcc | aaagtcattg | aaaccaagag | tgaggaggag | ctggaggact | acatcgtgga | 300 |
| gattgagatc | ctggccacct | cgaccaccc | ctacattgtg | aagctcctgg | agcctacta | 360 |
| tcacgacggg | aagctgtgga | tcatgattga | gttctgtcca | ggggagccg | tggacgccat | 420 |
| catgctggag | ctggacagag | gcctcacgga | gccccagata | caggtggttt | gccgccagat | 480 |
| gctagaagcc | ctcaacttcc | tgcacagcaa | gaggatcatc | accgagatc | tgaaagctgg | 540 |
| caacgtgctg | atgaccctcg | agggagacat | caggctggct | gactttggtg | tgtctgccaa | 600 |
| gaatctgaag | actctacaga | aacgagattc | cttcatcggc | acgccttact | ggatggcccc | 660 |
| cgaggtggtc | atgtgtgaga | ccatgaaaga | cacgccctac | gactacaaag | ccgacatctg | 720 |
| gtccctgggc | atcacgctga | ttgagatggc | ccagatcgag | ccgccacacc | acgagctcaa | 780 |
| ccccatgcgg | gtcctgctaa | agatcgccaa | gtcggaccct | ccacgctgc | tcacgccctc | 840 |
| caagtggtct | gtagagttcc | gtgacttcct | gaagatagcc | ctggataaga | acccagaaac | 900 |
| ccgacccagt | gccgcgcagc | tgctggagca | tcccttcgtc | agcagcatca | ccagtaacaa | 960 |
| ggctctgcgg | gagctggtgg | ctgaggccaa | ggccgaggtg | atggaagaga | tcgaagacgg | 1020 |
| ccgggatgag | ggggaagagg | aggacgccgt | ggatgccgcc | tccaccctgg | agaaccatac | 1080 |
| tcagaactcc | tctgaggtga | gtccgccaag | cctcaatgct | gacaagcctc | tcgaggagtc | 1140 |
| accttccacc | ccgctggcac | ccagccagtc | tcaggacagt | gtgaatgagc | cctgcagcca | 1200 |
| gccctctggg | gacagatccc | tccaaaccac | cagtcccca | gtcgtggccc | ctggaaatga | 1260 |
| gaacggcctg | gcagtgcctg | tgcccctgcg | gaagtcccga | cccgtgtcaa | tggatgccag | 1320 |
| aattcaggta | gccaggagaa | agcaagttgc | tgagcagggt | ggggacctca | gcccagcagc | 1380 |
| caacagatct | caaaaggcca | gccagagccg | gcccaacagc | agcgccctgg | agaccttggg | 1440 |
| tgggagaag | ctggccaatg | gcagcctgga | gccacctgcc | caggcagctc | cagggccttc | 1500 |
| caagagggac | tcggactgca | gcagcctctg | cacctctgag | agcatggact | atggtaccaa | 1560 |
| tctctccact | gacctgtcgc | tgaacaaaga | gatgggctct | ctgtccatca | aggacccgaa | 1620 |
| actgtacaaa | aaaccctca | gcggacacg | caaatttgtg | gtggatggtg | tggaggtgag | 1680 |
| catcaccacc | tccaagatca | tcagcgaaga | tgagaagaag | gatgaggaga | tgagatttct | 1740 |
| caggcgccag | gaactccgag | agcttcggct | gctccagaaa | gaagagcatc | ggaaccagac | 1800 |
| ccagctgagt | aacaagcatg | agctgcagct | ggagcaaatg | cataaacgtt | ttgaacagga | 1860 |

-continued

```
aatcaacgcc aagaagaagt tctttgacac ggaattagag aacctggagc gtcagcaaaa    1920
gcagcaagtg gagaagatgg agcaagacca tgccgtgcgc cgccgggagg aggccaggcg    1980
gatccgcctg gagcaggatc gggactacac caggttccaa gagcagctca aactgatgaa    2040
gaaagaggtg aagaacgagg tggagaagct cccccgacag cagcggaagg aaagcatgaa    2100
gcagaagatg gaggagcaca cgcagaaaaa gcagcttctt gaccgggact ttgtagccaa    2160
gcagaaggag gacctggagc tggccatgaa gaggctcacc accgacaaca ggcgggagat    2220
ctgtgacaag gagcgcgagt gcctcatgaa gaagcaggag ctccttcgag accgggaagc    2280
agccctgtgg gagatggaag agcaccagct gcaggagagg caccagctgg tgaagcagca    2340
gctcaaagac cagtacttcc tccagcggca cgagctgctg cgcaagcatg agaaggagcg    2400
ggagcagatg cagcgctaca accagcgcat gatagagcag ctgaaggtgc ggcagcaaca    2460
ggaaaaggcg cggctgccca agatccagag gagtgagggc aagacgcgca tggccatgta    2520
caagaagagc ctccacatca cggcgggggg cagcgcagct gagcagcgtg agaagatcaa    2580
gcagttctcc cagcaggagg agaagaggca gaagtcggag cggctgcagc aacagcagaa    2640
acacgagaac cagatgcggg acatgctggc gcagtgcgag agcaacatga gcgagctgca    2700
gcagctgcag aatgaaaagt gccacctcct ggtagacaca gaaacccaga aactgaaggc    2760
cctggatgag agccataacc agaacctgaa ggaatggcgg acaagcttc ggccgcgcaa    2820 gaaggctctg gaagaggatc tgaaccagaa gaagcgggac caggagatgt tcttcaagct    2880
gagcgaggag gcggagtgcc caaacccctc caccccaagc aaggccgcca gttcttccc    2940 ctacagctct ggggatgctt cc    2962
```

<210> SEQ ID NO 107
<211> LENGTH: 968
<212> TYPE: PRT
<213> ORGANISM: Homo sapiens

<400> SEQUENCE: 107

```
Met Ala Phe Ala Asn Phe Arg Arg Ile Leu Arg Leu Ser Thr Phe Glu
  1               5                  10                  15

Lys Arg Lys Ser Arg Glu Tyr Glu His Val Arg Arg Asp Leu Asp Pro
             20                  25                  30

Asn Glu Val Trp Glu Ile Val Gly Glu Leu Gly Asp Gly Ala Phe Gly
         35                  40                  45

Lys Val Tyr Lys Ala Lys Asn Lys Glu Thr Gly Ala Leu Ala Ala Ala
     50                  55                  60

Lys Val Ile Glu Thr Lys Ser Glu Glu Leu Glu Asp Tyr Ile Val
 65                  70                  75                  80

Glu Ile Glu Ile Leu Ala Thr Cys Asp His Pro Tyr Ile Val Lys Leu
                 85                  90                  95

Leu Gly Ala Tyr Tyr His Asp Gly Lys Leu Trp Ile Met Ile Glu Phe
            100                 105                 110

Cys Pro Gly Gly Ala Val Asp Ala Ile Met Leu Glu Leu Asp Arg Gly
        115                 120                 125

Leu Thr Glu Pro Gln Ile Gln Val Val Cys Arg Gln Met Leu Glu Ala
    130                 135                 140

Leu Asn Phe Leu His Ser Lys Arg Ile Ile His Arg Asp Leu Lys Ala
145                 150                 155                 160

Gly Asn Val Leu Met Thr Leu Glu Gly Asp Ile Arg Leu Ala Asp Phe
                165                 170                 175
```

-continued

```
Gly Val Ser Ala Lys Asn Leu Lys Thr Leu Gln Lys Arg Asp Ser Phe
            180                 185                 190

Ile Gly Thr Pro Tyr Trp Met Ala Pro Glu Val Val Met Cys Glu Thr
        195                 200                 205

Met Lys Asp Thr Pro Tyr Asp Tyr Lys Ala Asp Ile Trp Ser Leu Gly
    210                 215                 220

Ile Thr Leu Ile Glu Met Ala Gln Ile Glu Pro Pro His His Glu Leu
225                 230                 235                 240

Asn Pro Met Arg Val Leu Leu Lys Ile Ala Lys Ser Asp Pro Pro Thr
                245                 250                 255

Leu Leu Thr Pro Ser Lys Trp Ser Val Glu Phe Arg Asp Phe Leu Lys
            260                 265                 270

Ile Ala Leu Asp Lys Asn Pro Glu Thr Arg Pro Ser Ala Ala Gln Leu
        275                 280                 285

Leu Glu His Pro Phe Val Ser Ser Ile Thr Ser Asn Lys Ala Leu Arg
    290                 295                 300

Glu Leu Val Ala Glu Ala Lys Ala Glu Val Met Glu Glu Ile Glu Asp
305                 310                 315                 320

Gly Arg Asp Glu Gly Glu Glu Asp Ala Val Asp Ala Ala Ser Thr
                325                 330                 335

Leu Glu Asn His Thr Gln Asn Ser Ser Glu Val Ser Pro Pro Ser Leu
            340                 345                 350

Asn Ala Asp Lys Pro Leu Glu Gly Ser Pro Ser Thr Pro Leu Ala Pro
                355                 360                 365

Ser Gln Ser Gln Asp Ser Val Asn Glu Pro Cys Ser Gln Pro Ser Gly
    370                 375                 380

Asp Arg Ser Leu Gln Thr Thr Ser Pro Pro Val Val Ala Pro Gly Asn
385                 390                 395                 400

Glu Asn Gly Leu Ala Val Pro Val Pro Leu Arg Lys Ser Arg Pro Val
                405                 410                 415

Ser Met Asp Ala Arg Ile Gln Val Ala Gln Glu Lys Gln Val Ala Glu
            420                 425                 430

Gln Gly Gly Asp Leu Ser Pro Ala Ala Asn Arg Ser Gln Lys Ala Ser
        435                 440                 445

Gln Ser Arg Pro Asn Ser Ser Ala Leu Glu Thr Leu Gly Gly Glu Lys
    450                 455                 460

Leu Ala Asn Gly Ser Leu Glu Pro Pro Ala Gln Ala Ala Pro Gly Pro
465                 470                 475                 480

Ser Lys Arg Asp Ser Asp Cys Ser Ser Leu Cys Thr Ser Glu Ser Met
                485                 490                 495

Asp Tyr Gly Thr Asn Leu Ser Thr Asp Leu Ser Leu Asn Lys Glu Met
            500                 505                 510

Gly Ser Leu Ser Ile Lys Asp Pro Lys Leu Tyr Lys Lys Thr Leu Lys
        515                 520                 525

Arg Thr Arg Lys Phe Val Val Asp Gly Val Glu Val Ser Ile Thr Thr
    530                 535                 540

Ser Lys Ile Ile Ser Glu Asp Glu Lys Lys Asp Glu Glu Met Arg Phe
545                 550                 555                 560

Leu Arg Arg Gln Glu Leu Arg Glu Leu Arg Leu Leu Gln Lys Glu Glu
                565                 570                 575

His Arg Asn Gln Thr Gln Leu Ser Asn Lys His Glu Leu Gln Leu Glu
            580                 585                 590
```

```
Gln Met His Lys Arg Phe Glu Gln Glu Ile Asn Ala Lys Lys Lys Phe
                595                 600                 605

Phe Asp Thr Glu Leu Glu Asn Leu Glu Arg Gln Gln Lys Gln Gln Val
610                 615                 620

Glu Lys Met Glu Gln Asp His Ala Val Arg Arg Arg Glu Glu Ala Arg
625                 630                 635                 640

Arg Ile Arg Leu Glu Gln Asp Arg Asp Tyr Thr Arg Phe Gln Glu Gln
                645                 650                 655

Leu Lys Leu Met Lys Lys Glu Val Lys Asn Glu Val Glu Lys Leu Pro
                660                 665                 670

Arg Gln Gln Arg Lys Glu Ser Met Lys Gln Lys Met Glu Glu His Thr
                675                 680                 685

Gln Lys Lys Gln Leu Leu Asp Arg Asp Phe Val Ala Lys Gln Lys Glu
                690                 695                 700

Asp Leu Glu Leu Ala Met Lys Arg Leu Thr Thr Asp Asn Arg Arg Glu
705                 710                 715                 720

Ile Cys Asp Lys Glu Arg Glu Cys Leu Met Lys Lys Gln Glu Leu Leu
                725                 730                 735

Arg Asp Arg Glu Ala Ala Leu Trp Glu Met Glu Glu His Gln Leu Gln
                740                 745                 750

Glu Arg His Gln Leu Val Lys Gln Gln Leu Lys Asp Gln Tyr Phe Leu
                755                 760                 765

Gln Arg His Glu Leu Leu Arg Lys His Glu Lys Glu Arg Glu Gln Met
                770                 775                 780

Gln Arg Tyr Asn Gln Arg Met Ile Glu Gln Leu Lys Val Arg Gln Gln
785                 790                 795                 800

Gln Glu Lys Ala Arg Leu Pro Lys Ile Gln Arg Ser Glu Gly Lys Thr
                805                 810                 815

Arg Met Ala Met Tyr Lys Lys Ser Leu His Ile Asn Gly Gly Gly Ser
                820                 825                 830

Ala Ala Glu Gln Arg Glu Lys Ile Lys Gln Phe Ser Gln Gln Glu Glu
                835                 840                 845

Lys Arg Gln Lys Ser Glu Arg Leu Gln Gln Gln Gln Lys His Glu Asn
850                 855                 860

Gln Met Arg Asp Met Leu Ala Gln Cys Glu Ser Asn Met Ser Glu Leu
865                 870                 875                 880

Gln Gln Leu Gln Asn Glu Lys Cys His Leu Leu Val Glu His Glu Thr
                885                 890                 895

Gln Lys Leu Lys Ala Leu Asp Glu Ser His Asn Gln Asn Leu Lys Glu
                900                 905                 910

Trp Arg Asp Lys Leu Arg Pro Arg Lys Lys Ala Leu Glu Glu Asp Leu
                915                 920                 925

Asn Gln Lys Lys Arg Glu Gln Glu Met Phe Phe Lys Leu Ser Glu Glu
930                 935                 940

Ala Glu Cys Pro Asn Pro Ser Thr Pro Ser Lys Ala Ala Lys Phe Phe
945                 950                 955                 960

Pro Tyr Ser Ser Gly Asp Ala Ser
                965

<210> SEQ ID NO 108
<211> LENGTH: 11
<212> TYPE: PRT
<213> ORGANISM: Homo sapiens
<220> FEATURE:
<221> NAME/KEY: MOD_RES
```

<222> LOCATION: (2)
<223> OTHER INFORMATION: Any amino acid
<220> FEATURE:
<221> NAME/KEY: MOD_RES
<222> LOCATION: (4)
<223> OTHER INFORMATION: Any amino acid
<220> FEATURE:
<221> NAME/KEY: MOD_RES
<222> LOCATION: (6)
<223> OTHER INFORMATION: Any amino acid
<220> FEATURE:
<221> NAME/KEY: MOD_RES
<222> LOCATION: (8)
<223> OTHER INFORMATION: Any amino acid
<220> FEATURE:
<221> NAME/KEY: MOD_RES
<222> LOCATION: (10)
<223> OTHER INFORMATION: Any amino acid

<400> SEQUENCE: 108

Leu Xaa Leu Xaa Leu Xaa Leu Xaa Leu Xaa Leu
 1               5                  10

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 109
gcagcaagtg gagaagatgg                                              20

<210> SEQ ID NO 110
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 110
ggaagcatcc ccagagctgt ag                                           22

<210> SEQ ID NO 111
<211> LENGTH: 12
<212> TYPE: PRT
<213> ORGANISM: Homo sapiens

<400> SEQUENCE: 111

Glu Lys Phe Gln Lys Cys Ser Ala Asp Glu Ser Pro
 1               5                  10

<210> SEQ ID NO 112
<211> LENGTH: 16
<212> TYPE: PRT
<213> ORGANISM: Homo sapiens

<400> SEQUENCE: 112

Ser Ile Ser Asn Ser Glu Leu Phe Pro Thr Thr Asp Pro Val Gly Thr
 1               5                  10                  15

<210> SEQ ID NO 113
<211> LENGTH: 9
<212> TYPE: PRT
<213> ORGANISM: Homo sapiens

<400> SEQUENCE: 113

Leu Asp Phe Pro Lys Glu Asp Tyr Arg

<210> SEQ ID NO 114
<211> LENGTH: 12
<212> TYPE: PRT
<213> ORGANISM: Homo sapiens

<400> SEQUENCE: 114

His Gly Asp Pro Arg Pro Glu Pro Arg Pro Thr Gln
 1               5                  10

<210> SEQ ID NO 115
<211> LENGTH: 14
<212> TYPE: PRT
<213> ORGANISM: Homo sapiens

<400> SEQUENCE: 115

Pro Ser Thr Asn Arg Ala Gly Ser Leu Lys Asp Pro Glu Cys
 1               5                  10

<210> SEQ ID NO 116
<211> LENGTH: 19
<212> TYPE: PRT
<213> ORGANISM: Homo sapiens

<400> SEQUENCE: 116

Asp Pro Arg Thr Arg Ala Ser Asp Pro Gln Ser Pro Pro Gln Val Ser
 1               5                  10                  15

Arg His Lys

<210> SEQ ID NO 117
<211> LENGTH: 16
<212> TYPE: PRT
<213> ORGANISM: Homo sapiens

<400> SEQUENCE: 117

Cys Leu Val Pro Leu Ile Gln Leu Tyr Arg Lys Gln Thr Ser Thr Cys
 1               5                  10                  15

<210> SEQ ID NO 118
<211> LENGTH: 9
<212> TYPE: PRT
<213> ORGANISM: Homo sapiens

<400> SEQUENCE: 118

Pro Leu Met Arg Gln Asn Arg Thr Arg
 1               5

<210> SEQ ID NO 119
<211> LENGTH: 16
<212> TYPE: PRT
<213> ORGANISM: Homo sapiens

<400> SEQUENCE: 119

Ser Gly Asp Arg Arg Arg Ala Gly Pro Glu Lys Arg Pro Lys Ser Ser
 1               5                  10                  15

<210> SEQ ID NO 120
<211> LENGTH: 16
<212> TYPE: PRT
<213> ORGANISM: Homo sapiens

<400> SEQUENCE: 120

Cys Arg Arg Lys Ser Leu Val Gly Thr Pro Tyr Trp Met Ala Pro Glu

-continued

<210> SEQ ID NO 121
<211> LENGTH: 15
<212> TYPE: PRT
<213> ORGANISM: Homo sapiens

<400> SEQUENCE: 121

```
Arg Thr Val Gly Arg Arg Asn Thr Phe Ile Gly Thr Pro Pro Tyr
1               5                   10                  15
```

<210> SEQ ID NO 122
<211> LENGTH: 15
<212> TYPE: PRT
<213> ORGANISM: Homo sapiens

<400> SEQUENCE: 122

```
Lys Arg Lys Ser Phe Ile Gly Thr Pro Tyr Trp Met Ala Pro Glu
1               5                   10                  15
```

<210> SEQ ID NO 123
<211> LENGTH: 15
<212> TYPE: PRT
<213> ORGANISM: Homo sapiens

<400> SEQUENCE: 123

```
Lys Arg Asn Thr Phe Val Gly Thr Pro Phe Trp Met Ala Pro Glu
1               5                   10                  15
```

<210> SEQ ID NO 124
<211> LENGTH: 15
<212> TYPE: PRT
<213> ORGANISM: Homo sapiens

<400> SEQUENCE: 124

```
Pro Ala Asn Ser Phe Val Gly Thr Pro Tyr Trp Met Ala Pro Glu
1               5                   10                  15
```

<210> SEQ ID NO 125
<211> LENGTH: 15
<212> TYPE: PRT
<213> ORGANISM: Homo sapiens

<400> SEQUENCE: 125

```
Arg Arg Asn Thr Phe Ile Gly Thr Pro Tyr Trp Met Ala Pro Glu
1               5                   10                  15
```

<210> SEQ ID NO 126
<211> LENGTH: 15
<212> TYPE: PRT
<213> ORGANISM: Homo sapiens

<400> SEQUENCE: 126

```
Arg Arg Asn Thr Phe Ile Gly Thr Pro Tyr Trp Met Ala Pro Glu
1               5                   10                  15
```

<210> SEQ ID NO 127
<211> LENGTH: 18
<212> TYPE: PRT
<213> ORGANISM: Homo sapiens

<400> SEQUENCE: 127

```
Arg Asn Lys Val Arg Lys Thr Phe Val Gly Thr Pro Cys Trp Met Ala
1               5                   10                  15
```

Pro Glu

<210> SEQ ID NO 128
<211> LENGTH: 22
<212> TYPE: DNA
<213> ORGANISM: Homo sapiens

<400> SEQUENCE: 128
ctcccatttc ctagcaaaat ca                                              22

<210> SEQ ID NO 129
<211> LENGTH: 22
<212> TYPE: DNA
<213> ORGANISM: Homo sapiens

<400> SEQUENCE: 129
agaggcagta ttgtcagatg ta                                              22

<210> SEQ ID NO 130
<211> LENGTH: 22
<212> TYPE: DNA
<213> ORGANISM: Homo sapiens

<400> SEQUENCE: 130
ccacacatgc gtatctctgt tg                                              22

<210> SEQ ID NO 131
<211> LENGTH: 24
<212> TYPE: DNA
<213> ORGANISM: Homo sapiens

<400> SEQUENCE: 131
ttgctagaat tcacatcagg taca                                            24

<210> SEQ ID NO 132
<211> LENGTH: 22
<212> TYPE: DNA
<213> ORGANISM: Homo sapiens

<400> SEQUENCE: 132
atccctggat cacactgctt ct                                              22

<210> SEQ ID NO 133
<211> LENGTH: 22
<212> TYPE: DNA
<213> ORGANISM: Homo sapiens

<400> SEQUENCE: 133
caaggtgttc tttgcctctg tt                                              22

<210> SEQ ID NO 134
<211> LENGTH: 21
<212> TYPE: DNA
<213> ORGANISM: Homo sapiens

<400> SEQUENCE: 134
agatggactg tactgggagg g                                               21

<210> SEQ ID NO 135
<211> LENGTH: 22
<212> TYPE: DNA
<213> ORGANISM: Homo sapiens

<400> SEQUENCE: 135

```
agaagagcac ttggcactta tc                                      22

<210> SEQ ID NO 136
<211> LENGTH: 20
<212> TYPE: DNA
<213> ORGANISM: Homo sapiens

<400> SEQUENCE: 136
catcatgaac tggtgacggg                                         20

<210> SEQ ID NO 137
<211> LENGTH: 23
<212> TYPE: DNA
<213> ORGANISM: Homo sapiens

<400> SEQUENCE: 137
ccagtgaaat caaaccagta aaa                                     23

<210> SEQ ID NO 138
<211> LENGTH: 24
<212> TYPE: DNA
<213> ORGANISM: Homo sapiens

<400> SEQUENCE: 138
caaaacctgg ccgtctcttc tatt                                    24

<210> SEQ ID NO 139
<211> LENGTH: 23
<212> TYPE: DNA
<213> ORGANISM: Homo sapiens

<400> SEQUENCE: 139
atttgtgcta ctgggattct gtg                                     23

<210> SEQ ID NO 140
<211> LENGTH: 24
<212> TYPE: DNA
<213> ORGANISM: Homo sapiens

<400> SEQUENCE: 140
gaatagcggt accatgatag aata                                    24

<210> SEQ ID NO 141
<211> LENGTH: 23
<212> TYPE: DNA
<213> ORGANISM: Homo sapiens

<400> SEQUENCE: 141
taccaaaaag agccaaaagt gtg                                     23

<210> SEQ ID NO 142
<211> LENGTH: 23
<212> TYPE: DNA
<213> ORGANISM: Homo sapiens

<400> SEQUENCE: 142
ctcagtattc tctccaaaga ttg                                     23

<210> SEQ ID NO 143
<211> LENGTH: 23
<212> TYPE: DNA
<213> ORGANISM: Homo sapiens
```

```
<400> SEQUENCE: 143
gatgttctct ccattctgta aag                                              23

<210> SEQ ID NO 144
<211> LENGTH: 21
<212> TYPE: DNA
<213> ORGANISM: Homo sapiens

<400> SEQUENCE: 144
catcactgga agtctgcagt g                                                21

<210> SEQ ID NO 145
<211> LENGTH: 20
<212> TYPE: DNA
<213> ORGANISM: Homo sapiens

<400> SEQUENCE: 145
caggtgcagt agtcatttgc                                                  20

<210> SEQ ID NO 146
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 146
ggagctgtcg tattccagtc                                                  20

<210> SEQ ID NO 147
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 147
aacccctcaa gacccgttta g                                                21

<210> SEQ ID NO 148
<211> LENGTH: 4
<212> TYPE: PRT
<213> ORGANISM: Artificial Sequence
<220> FEATURE:
<223> OTHER INFORMATION: Description of Artificial Sequence: Synthetic
      motif
<220> FEATURE:
<221> NAME/KEY: MOD_RES
<222> LOCATION: (2)
<223> OTHER INFORMATION: Any amino acid
<220> FEATURE:
<221> NAME/KEY: MOD_RES
<222> LOCATION: (3)
<223> OTHER INFORMATION: Any amino acid

<400> SEQUENCE: 148

Pro Xaa Xaa Pro
  1

<210> SEQ ID NO 149
<211> LENGTH: 50
<212> TYPE: PRT
<213> ORGANISM: Artificial Sequence
<220> FEATURE:
<223> OTHER INFORMATION: Description of Artificial Sequence: Synthetic
      leucine zipper
<220> FEATURE:
```

```
<221> NAME/KEY: MOD_RES
<222> LOCATION: (2)..(7)
<223> OTHER INFORMATION: Any amino acid
<220> FEATURE:
<221> NAME/KEY: MOD_RES
<222> LOCATION: (9)..(14)
<223> OTHER INFORMATION: Any amino acid
<220> FEATURE:
<221> NAME/KEY: MOD_RES
<222> LOCATION: (16)..(21)
<223> OTHER INFORMATION: Any amino acid
<220> FEATURE:
<221> NAME/KEY: MOD_RES
<222> LOCATION: (23)..(42)
<223> OTHER INFORMATION: Any amino acid
<220> FEATURE:
<221> NAME/KEY: MOD_RES
<222> LOCATION: (44)..(49)
<223> OTHER INFORMATION: Any amino acid

<400> SEQUENCE: 149

Leu Xaa Xaa Xaa Xaa Xaa Xaa Leu Xaa Xaa Xaa Xaa Xaa Xaa Leu Xaa
 1               5                  10                  15

Xaa Xaa Xaa Xaa Xaa Leu Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Leu Xaa Xaa Xaa Xaa Xaa
        35                  40                  45

Xaa Leu
    50

<210> SEQ ID NO 150
<211> LENGTH: 13
<212> TYPE: PRT
<213> ORGANISM: Artificial Sequence
<220> FEATURE:
<223> OTHER INFORMATION: Description of Artificial Sequence: Synthetic
      Cdc42/Rac-binding motif
<220> FEATURE:
<221> NAME/KEY: MOD_RES
<222> LOCATION: (2)
<223> OTHER INFORMATION: Variable amino acid
<220> FEATURE:
<221> NAME/KEY: MOD_RES
<222> LOCATION: (4)..(9)
<223> OTHER INFORMATION: Four to six variable amino acids
<220> FEATURE:
<221> NAME/KEY: MOD_RES
<222> LOCATION: (11)..(12)
<223> OTHER INFORMATION: Variable amino acid

<400> SEQUENCE: 150

Ser Xaa Pro Xaa Xaa Xaa Xaa Xaa Xaa His Xaa Xaa His
 1               5                  10

<210> SEQ ID NO 151
<211> LENGTH: 787
<212> TYPE: PRT
<213> ORGANISM: Homo sapiens

<400> SEQUENCE: 151

Ile Ile Glu Leu Ala Glu Arg Lys Pro Pro Leu Phe Asn Met Asn Ala
 1               5                  10                  15

Met Ser Ala Leu Tyr His Ile Ala Gln Asn Glu Ser Pro Thr Leu Gln
            20                  25                  30

Ser Asn Glu Trp Ser Asp Tyr Phe Arg Asn Phe Val Asp Ser Cys Leu
        35                  40                  45

Gln Lys Ile Pro Gln Asp Arg Pro Thr Ser Glu Glu Leu Leu Lys His
    50                  55                  60
```

```
Ile Phe Val Leu Arg Glu Arg Pro Glu Thr Val Leu Ile Asp Leu Ile
 65                  70                  75                  80

Gln Arg Thr Lys Asp Ala Val Arg Glu Leu Asp Asn Leu Gln Tyr Arg
             85                  90                  95

Lys Met Lys Lys Leu Leu Phe Gln Ala His Asn Gly Pro Ala Tyr
            100                 105                 110

Glu Ala Gln Glu Glu Glu Glu Gln Asp His Gly Val Gly Arg Thr
        115                 120                 125

Gly Thr Val Asn Ser Val Gly Ser Asn Gln Ser Ile Pro Ser Met Ser
    130                 135                 140

Ile Ser Ala Ser Ser Gln Ser Ser Val Asn Ser Leu Pro Asp Val
145                 150                 155                 160

Ser Asp Asp Lys Ser Glu Leu Asp Met Met Glu Gly Asp His Thr Val
                165                 170                 175

Met Ser Asn Ser Ser Val Ile His Leu Lys Pro Glu Glu Asn Tyr
            180                 185                 190

Arg Glu Glu Gly Asp Pro Arg Thr Arg Ala Ser Asp Pro Gln Ser Pro
        195                 200                 205

Pro Gln Val Ser Arg His Lys Ser His Tyr Arg Asn Arg Glu His Phe
    210                 215                 220

Ala Thr Ile Arg Thr Ala Ser Leu Val Thr Arg Gln Met Gln Glu His
225                 230                 235                 240

Glu Gln Asp Ser Glu Leu Arg Glu Gln Met Ser Gly Tyr Lys Arg Met
                245                 250                 255

Arg Arg Gln His Gln Lys Gln Leu Met Thr Leu Glu Asn Lys Leu Lys
            260                 265                 270

Ala Glu Met Asp Glu His Arg Leu Arg Leu Asp Lys Cys Leu Glu Thr
        275                 280                 285

Gly Arg Asn Asn Phe Ala Ala Glu Met Glu Lys Leu Ile Lys Lys His
    290                 295                 300

Gln Ala Ala Met Glu Lys Glu Ala Lys Val Met Ser Asn Glu Glu Lys
305                 310                 315                 320

Lys Phe Gln Gln His Ile Gln Ala Gln Gln Lys Lys Glu Leu Asn Ser
                325                 330                 335

Phe Leu Glu Ser Gln Lys Arg Glu Tyr Lys Leu Arg Lys Glu Gln Leu
            340                 345                 350

Lys Glu Glu Leu Asn Glu Asn Gln Ser Thr Pro Lys Lys Glu Lys Gln
        355                 360                 365

Glu Trp Leu Ser Lys Gln Lys Glu Asn Ile Gln His Phe Gln Ala Glu
    370                 375                 380

Glu Glu Ala Asn Leu Leu Arg Arg Gln Arg Gln Tyr Leu Glu Leu Glu
385                 390                 395                 400

Cys Arg Arg Phe Lys Arg Arg Met Leu Leu Gly Arg His Asn Leu Glu
                405                 410                 415

Gln Asp Leu Val Arg Glu Glu Leu Asn Lys Arg Gln Thr Gln Lys Asp
            420                 425                 430

Leu Glu His Ala Met Leu Leu Arg Gln His Glu Ser Met Gln Glu Leu
        435                 440                 445

Glu Phe Arg His Leu Asn Thr Ile Gln Lys Met Arg Cys Glu Leu Ile
    450                 455                 460

Arg Leu Gln His Gln Thr Glu Leu Thr Asn Gln Leu Glu Tyr Asn Lys
465                 470                 475                 480
```

-continued

```
Arg Arg Glu Arg Glu Leu Arg Arg Lys His Val Met Glu Val Arg Gln
            485                 490                 495
Gln Pro Lys Ser Leu Lys Ser Lys Glu Leu Gln Ile Lys Lys Gln Phe
        500                 505                 510
Gln Asp Thr Cys Lys Ile Gln Thr Arg Gln Tyr Lys Ala Leu Arg Asn
        515                 520                 525
His Leu Leu Glu Thr Thr Pro Lys Ser Glu His Lys Ala Val Leu Lys
    530                 535                 540
Arg Leu Lys Glu Glu Gln Thr Arg Lys Leu Ala Ile Leu Ala Glu Gln
545                 550                 555                 560
Tyr Asp His Ser Ile Asn Glu Met Leu Ser Thr Gln Ala Leu Arg Leu
                565                 570                 575
Asp Glu Ala Gln Glu Ala Glu Cys Gln Val Leu Lys Met Gln Leu Gln
            580                 585                 590
Gln Glu Leu Glu Leu Leu Asn Ala Tyr Gln Ser Lys Ile Lys Met Gln
        595                 600                 605
Ala Glu Ala Gln His Asp Arg Glu Leu Arg Glu Leu Glu Gln Arg Val
        610                 615                 620
Ser Leu Arg Arg Ala Leu Leu Glu Gln Lys Ile Glu Glu Met Leu
625                 630                 635                 640
Ala Leu Gln Asn Glu Arg Thr Glu Arg Ile Arg Ser Leu Leu Glu Arg
                645                 650                 655
Gln Ala Arg Glu Ile Glu Ala Phe Asp Ser Glu Ser Met Arg Leu Gly
            660                 665                 670
Phe Ser Asn Met Val Leu Ser Asn Leu Ser Pro Glu Ala Phe Ser His
                675                 680                 685
Ser Tyr Pro Gly Ala Ser Gly Trp Ser His Asn Pro Thr Gly Gly Pro
    690                 695                 700
Gly Pro His Trp Gly His Pro Met Gly Gly Pro Pro Gln Ala Trp Gly
705                 710                 715                 720
His Pro Met Gln Gly Gly Pro Gln Pro Trp Gly His Pro Ser Gly Pro
                725                 730                 735
Met Gln Gly Val Pro Arg Gly Ser Ser Met Gly Val Arg Asn Ser Pro
            740                 745                 750
Gln Ala Leu Arg Arg Thr Ala Ser Gly Gly Arg Thr Glu Gln Gly Met
        755                 760                 765
Ser Arg Ser Thr Ser Val Thr Ser Gln Ile Ser Asn Gly Ser His Met
    770                 775                 780
Ser Tyr Thr
785
```

<210> SEQ ID NO 152
<211> LENGTH: 338
<212> TYPE: PRT
<213> ORGANISM: Homo sapiens
<220> FEATURE:
<221> NAME/KEY: MOD_RES
<222> LOCATION: (2)
<223> OTHER INFORMATION: Any amino acid

<400> SEQUENCE: 152

```
His Xaa Glu Tyr Val Pro Val Arg Arg Ile Asn Leu Glu Ala Cys Ser
  1               5                  10                  15
Asn Glu Met Val Thr Ser Cys Arg Ala Ser Cys Met Phe Gln Thr Leu
            20                  25                  30
Asn His Pro Asn Ile Val Pro Tyr Arg Ala Thr Leu Ile Ala Asp Asn
```

-continued

```
            35                  40                  45
Glu Leu Trp Val Val Thr Ser Phe Met Ala Tyr Gly Ser Ala Lys Asp
             50                  55                  60
Leu Ile Cys Thr His Phe Met Asp Gly Met Asn Glu Leu Ala Ile Ala
 65                  70                  75                  80
Tyr Ile Leu Gln Gly Val Leu Lys Ala Leu Asp Tyr Ile His His Asn
                 85                  90                  95
Gly Tyr Val His Arg Ser Val Lys Ala Ser His Ile Leu Ile Ser Val
            100                 105                 110
Asp Gly Lys Val Tyr Leu Ser Gly Leu Arg Ser Asn Leu Ser Met Ile
        115                 120                 125
Ser His Gly Gln Arg Gln Arg Val Val His Asp Phe Pro Lys Tyr Ser
    130                 135                 140
Val Lys Val Leu Pro Trp Leu Ser Pro Glu Val Leu Gln Gln Asn Leu
145                 150                 155                 160
Gln Gly Tyr Asp Ala Lys Ser Asp Ile Tyr Ser Val Gly Ile Thr Ala
                165                 170                 175
Cys Glu Leu Ala Asn Gly His Val Pro Phe Lys Asp Met Pro Ala Thr
            180                 185                 190
Gln Met Leu Leu Glu Lys Leu Asn Gly Thr Val Pro Cys Leu Leu Asp
        195                 200                 205
Thr Ser Thr Ile Pro Ala Glu Glu Leu Thr Met Ser Pro Ser Arg Ser
    210                 215                 220
Val Ala Asn Ser Gly Leu Ser Asp Ser Leu Thr Thr Ser Thr Pro Arg
225                 230                 235                 240
Pro Ser Asn Gly Asp Ser Pro Ser His Pro Tyr His Arg Thr Phe Ser
                245                 250                 255
Pro His Phe His His Phe Val Glu Gln Cys Leu Gln Arg Asn Pro Asp
            260                 265                 270
Ala Arg Pro Ser Ala Ser Thr Leu Leu Asn His Ser Phe Phe Lys Gln
        275                 280                 285
Ile Lys Arg Arg Ala Ser Glu Ala Leu Pro Glu Leu Leu Arg Pro Val
    290                 295                 300
Thr Pro Ile Thr Asn Phe Glu Gly Ser Gln Ser Gln Asp His Ser Gly
305                 310                 315                 320
Ile Phe Gly Leu Val Thr Asn Leu Glu Glu Leu Glu Val Asp Asp Trp
                325                 330                 335
Glu Phe
```

<210> SEQ ID NO 153
<211> LENGTH: 546
<212> TYPE: PRT
<213> ORGANISM: Homo sapiens

<400> SEQUENCE: 153

```
Met Ala Glu Pro Ser Gly Ser Val His Val Gln Leu Pro Gln Gln Ala
  1               5                  10                  15
Ala Pro Val Thr Ala Ala Ala Ala Ala Pro Ala Ala Thr Ala
                 20                  25                  30
Ala Pro Ala Pro Ala Ala Pro Ala Ala Pro Ala Pro Ala Pro Ala Pro
             35                  40                  45
Ala Pro Ala Ala Gln Ala Val Gly Trp Pro Ile Cys Arg Asp Ala Tyr
         50                  55                  60
Glu Leu Gln Glu Val Ile Gly Ser Gly Ala Thr Ala Val Val Gln Ala
```

```
              65                  70                  75                  80
Ala Leu Cys Lys Pro Arg Gln Glu Arg Val Ala Ile Lys Arg Ile Asn
                    85                  90                  95
Leu Glu Lys Cys Gln Thr Ser Met Asp Glu Leu Leu Lys Glu Ile Gln
                100                 105                 110
Ala Met Ser Gln Cys Ser His Pro Asn Val Val Thr Tyr Tyr Thr Ser
            115                 120                 125
Phe Val Val Lys Asp Glu Leu Trp Leu Val Met Lys Leu Leu Ser Gly
        130                 135                 140
Gly Ser Met Leu Asp Ile Ile Lys Tyr Ile Val Asn Arg Gly Glu His
145                 150                 155                 160
Lys Asn Gly Val Leu Glu Glu Ala Ile Ile Ala Thr Ile Leu Lys Glu
                165                 170                 175
Val Leu Glu Gly Leu Asp Tyr Leu His Arg Asn Gly Gln Ile His Arg
                180                 185                 190
Asp Leu Lys Ala Gly Asn Ile Leu Leu Gly Glu Asp Gly Ser Val Gln
            195                 200                 205
Ile Ala Asp Phe Gly Val Ser Ala Phe Leu Ala Thr Gly Gly Asp Val
        210                 215                 220
Thr Arg Asn Lys Val Arg Lys Thr Phe Val Gly Thr Pro Cys Trp Met
225                 230                 235                 240
Ala Pro Glu Val Met Glu Gln Val Arg Gly Tyr Asp Phe Lys Ala Asp
                245                 250                 255
Met Trp Ser Phe Gly Ile Thr Ala Ile Glu Leu Ala Thr Gly Ala Ala
                260                 265                 270
Pro Tyr His Lys Tyr Pro Pro Met Lys Val Leu Met Leu Thr Leu Gln
            275                 280                 285
Asn Asp Pro Pro Thr Leu Glu Thr Gly Val Glu Asp Lys Glu Met Met
        290                 295                 300
Lys Lys Tyr Gly Lys Ser Phe Arg Lys Leu Leu Ser Leu Cys Leu Gln
305                 310                 315                 320
Lys Asp Pro Ser Lys Arg Pro Thr Ala Ala Glu Leu Leu Lys Cys Lys
                325                 330                 335
Phe Phe Gln Lys Ala Lys Asn Arg Glu Tyr Leu Ile Glu Lys Leu Leu
                340                 345                 350
Thr Arg Thr Pro Asp Ile Ala Gln Arg Ala Lys Lys Val Arg Arg Val
            355                 360                 365
Pro Gly Ser Ser Gly His Leu His Lys Thr Glu Asp Gly Asp Trp Glu
        370                 375                 380
Trp Ser Asp Asp Glu Met Asp Glu Lys Ser Glu Glu Gly Lys Ala Ala
385                 390                 395                 400
Phe Ser Gln Glu Lys Ser Arg Arg Val Lys Glu Glu Asn Pro Glu Ile
                405                 410                 415
Ala Val Ser Ala Ser Thr Ile Pro Glu Gln Ile Gln Ser Leu Ser Val
            420                 425                 430
His Asp Ser Gln Gly Pro Pro Asn Ala Asn Glu Asp Tyr Arg Glu Ala
        435                 440                 445
Ser Ser Cys Ala Val Asn Leu Val Leu Arg Leu Arg Asn Ser Arg Lys
    450                 455                 460
Glu Leu Asn Asp Ile Arg Phe Glu Phe Thr Pro Gly Arg Asp Thr Ala
465                 470                 475                 480
Asp Gly Val Ser Gln Glu Leu Phe Ser Ala Gly Leu Val Asp Gly His
                485                 490                 495
```

-continued

```
Asp Val Val Ile Val Ala Ala Asn Leu Gln Lys Ile Val Asp Asp Pro
            500                 505                 510

Lys Ala Leu Lys Thr Leu Thr Phe Lys Leu Ala Ser Gly Cys Asp Gly
            515                 520                 525

Ser Glu Ile Pro Asp Glu Val Lys Leu Ile Gly Phe Ala Gln Leu Ser
            530                 535                 540

Val Ser
545

<210> SEQ ID NO 154
<211> LENGTH: 966
<212> TYPE: PRT
<213> ORGANISM: Murine sp.

<400> SEQUENCE: 154

Met Ala Phe Ala Asn Phe Arg Arg Ile Leu Arg Leu Ser Thr Phe Glu
  1               5                  10                  15

Lys Arg Lys Ser Arg Glu Tyr Glu His Val Arg Arg Asp Leu Asp Pro
                 20                  25                  30

Asn Asp Val Trp Glu Ile Val Gly Glu Leu Gly Asp Gly Ala Phe Gly
             35                  40                  45

Lys Val Tyr Lys Ala Lys Asn Lys Glu Thr Gly Ala Leu Ala Ala Ala
         50                  55                  60

Lys Val Ile Glu Thr Lys Ser Glu Glu Leu Glu Asp Tyr Ile Val
 65                  70                  75                  80

Glu Ile Glu Ile Leu Ala Thr Cys Asp His Pro Tyr Ile Val Lys Leu
                 85                  90                  95

Leu Gly Ala Tyr Tyr Asp Gly Lys Leu Trp Ile Met Ile Glu Phe
                100                 105                 110

Cys Pro Gly Gly Ala Val Asp Ala Ile Met Leu Glu Leu Asp Arg Gly
            115                 120                 125

Leu Thr Glu Pro Gln Ile Gln Val Val Cys Arg Gln Met Leu Glu Ala
        130                 135                 140

Leu Asn Phe Leu His Gly Lys Arg Ile Ile His Arg Asp Leu Lys Ala
145                 150                 155                 160

Gly Asn Val Leu Met Thr Leu Glu Gly Asp Ile Arg Leu Ala Asp Phe
                165                 170                 175

Gly Val Ser Ala Lys Asn Leu Lys Thr Leu Gln Lys Arg Asp Ser Phe
            180                 185                 190

Ile Gly Thr Pro Tyr Trp Met Ala Pro Glu Val Val Leu Cys Glu Thr
        195                 200                 205

Met Lys Asp Ala Pro Tyr Asp Tyr Lys Ala Asp Ile Trp Ser Leu Gly
    210                 215                 220

Ile Thr Leu Ile Glu Met Ala Gln Ile Glu Pro Pro His His Glu Leu
225                 230                 235                 240

Asn Pro Met Arg Val Leu Leu Lys Ile Ala Lys Ser Asp Pro Pro Thr
                245                 250                 255

Leu Leu Thr Pro Ser Lys Trp Ser Val Glu Phe Arg Asp Phe Leu Lys
            260                 265                 270

Ile Ala Leu Asp Lys Asn Pro Glu Thr Arg Pro Ser Ala Ala Gln Leu
        275                 280                 285

Leu Gln His Pro Phe Val Ser Arg Val Thr Ser Asn Lys Ala Leu Arg
    290                 295                 300

Glu Leu Val Ala Glu Ala Lys Ala Glu Val Met Glu Glu Ile Glu Asp
```

-continued

```
305                 310                 315                 320

Gly Arg Glu Asp Gly Glu Glu Glu Asp Ala Val Asp Ala Val Pro Pro
                325                 330                 335

Leu Val Asn His Thr Gln Asp Ser Ala Asn Val Thr Gln Pro Ser Leu
                340                 345                 350

Asp Ser Asn Lys Leu Leu Gln Asp Ser Ser Thr Pro Leu Pro Pro Ser
                355                 360                 365

Gln Pro Gln Glu Pro Val Asn Gly Pro Cys Ser Gln Pro Ser Gly Asp
            370                 375                 380

Gly Pro Leu Gln Thr Thr Ser Pro Ala Asp Gly Leu Ser Lys Asn Asp
385                 390                 395                 400

Asn Asp Leu Lys Val Pro Val Pro Leu Arg Lys Ser Arg Pro Leu Ser
                405                 410                 415

Met Asp Ala Arg Ile Gln Met Asp Glu Glu Lys Gln Ile Pro Asp Gln
                420                 425                 430

Asp Glu Asn Pro Ser Pro Ala Ala Ser Lys Ser Gln Lys Ala Asn Gln
                435                 440                 445

Ser Arg Pro Asn Ser Ser Ala Leu Glu Thr Leu Gly Gly Glu Ala Leu
                450                 455                 460

Thr Asn Gly Gly Leu Glu Leu Pro Ser Ser Val Thr Pro Ser His Ser
465                 470                 475                 480

Lys Arg Ala Ser Asp Cys Ser Asn Leu Ser Thr Ser Glu Ser Met Asp
                485                 490                 495

Tyr Gly Thr Ser Leu Ser Ala Asp Leu Ser Leu Asn Lys Glu Thr Gly
                500                 505                 510

Ser Leu Ser Leu Lys Gly Ser Lys Leu His Asn Lys Thr Leu Lys Arg
                515                 520                 525

Thr Arg Arg Phe Val Val Asp Gly Val Glu Val Ser Ile Thr Thr Ser
                530                 535                 540

Lys Ile Ile Ser Glu Asp Glu Lys Lys Asp Glu Glu Met Arg Phe Leu
545                 550                 555                 560

Arg Arg Gln Glu Leu Arg Glu Leu Arg Leu Leu Gln Lys Glu Glu His
                565                 570                 575

Arg Asn Gln Thr Gln Leu Ser Ser Lys His Glu Leu Gln Leu Glu Gln
                580                 585                 590

Met His Lys Arg Phe Glu Gln Glu Ile Asn Ala Lys Lys Lys Phe Tyr
                595                 600                 605

Asp Val Glu Leu Glu Asn Leu Glu Arg Gln Gln Lys Gln Gln Val Glu
                610                 615                 620

Lys Met Glu Gln Asp His Ser Val Arg Arg Lys Glu Glu Ala Lys Arg
625                 630                 635                 640

Ile Arg Leu Glu Gln Asp Arg Asp Tyr Ala Lys Phe Gln Glu Gln Leu
                645                 650                 655

Lys Gln Met Lys Lys Glu Val Lys Ser Glu Val Glu Lys Leu Pro Arg
                660                 665                 670

Gln Gln Arg Lys Glu Ser Met Lys Gln Lys Met Glu Glu His Ser Gln
                675                 680                 685

Lys Lys Gln Arg Leu Asp Arg Asp Phe Val Ala Lys Gln Lys Glu Asp
                690                 695                 700

Leu Glu Leu Ala Met Arg Lys Leu Thr Thr Glu Asn Arg Arg Glu Ile
705                 710                 715                 720

Cys Asp Lys Glu Arg Asp Cys Leu Ser Lys Lys Gln Glu Leu Leu Arg
                725                 730                 735
```

Asp Arg Glu Ala Ala Leu Trp Glu Met Glu Glu His Gln Leu Gln Glu
            740                 745                 750

Arg His Gln Leu Val Lys Gln Gln Leu Lys Asp Gln Tyr Phe Leu Gln
            755                 760                 765

Arg His Asp Leu Leu Arg Lys His Glu Lys Glu Arg Glu Gln Met Gln
            770                 775                 780

Arg Tyr Asn Gln Arg Met Met Glu Gln Leu Lys Val Arg Gln Gln Gln
785                 790                 795                 800

Glu Lys Ala Arg Leu Pro Lys Ile Gln Arg Ser Asp Gly Glu Thr Arg
            805                 810                 815

Met Ala Met Tyr Lys Lys Ser Leu His Ile Asn Gly Ala Gly Ser Ala
            820                 825                 830

Ser Glu Gln Arg Glu Lys Ile Lys Gln Phe Ser Gln Gln Glu Glu Lys
            835                 840                 845

Arg Gln Lys Ala Glu Arg Leu Gln Gln Gln Lys His Glu His Gln
            850                 855                 860

Met Arg Asp Met Val Ala Gln Cys Glu Ser Asn Met Ser Glu Leu Gln
865                 870                 875                 880

Gln Leu Gln Asn Glu Lys Cys Tyr Leu Leu Val Glu His Glu Thr Gln
            885                 890                 895

Lys Leu Lys Ala Leu Asp Glu Ser His Asn Gln Ser Leu Lys Glu Trp
            900                 905                 910

Arg Asp Lys Leu Arg Pro Arg Lys Lys Ala Leu Glu Glu Asp Leu Asn
            915                 920                 925

Gln Lys Lys Arg Glu Gln Glu Met Phe Phe Lys Leu Ser Glu Glu Ala
            930                 935                 940

Glu Pro Arg Pro Thr Thr Pro Ser Lys Ala Ser Asn Phe Phe Pro Tyr
945                 950                 955                 960

Ser Ser Gly Asp Ala Ser
            965

<210> SEQ ID NO 155
<211> LENGTH: 968
<212> TYPE: PRT
<213> ORGANISM: Homo sapiens

<400> SEQUENCE: 155

Met Ala Phe Ala Asn Phe Arg Arg Ile Leu Arg Leu Ser Thr Phe Glu
1               5                  10                  15

Lys Arg Lys Ser Arg Glu Tyr Glu His Val Arg Arg Asp Leu Asp Pro
            20                  25                  30

Asn Glu Val Trp Glu Ile Val Gly Glu Leu Gly Asp Gly Ala Phe Gly
            35                  40                  45

Lys Val Tyr Lys Ala Lys Asn Lys Glu Thr Gly Ala Leu Ala Ala Ala
        50                  55                  60

Lys Val Ile Glu Thr Lys Ser Glu Glu Glu Leu Glu Asp Tyr Ile Val
65              70                  75                  80

Glu Ile Glu Ile Leu Ala Thr Cys Asp His Pro Tyr Ile Val Lys Leu
            85                  90                  95

Leu Gly Ala Tyr Tyr His Asp Gly Lys Leu Trp Ile Met Ile Glu Phe
            100                 105                 110

Cys Pro Gly Gly Ala Val Asp Ala Ile Met Leu Glu Leu Asp Arg Gly
            115                 120                 125

Leu Thr Glu Pro Gln Ile Gln Val Val Cys Arg Gln Met Leu Glu Ala

-continued

```
            130                 135                 140
Leu Asn Phe Leu His Ser Lys Arg Ile Ile His Arg Asp Leu Lys Ala
145                 150                 155                 160
Gly Asn Val Leu Met Thr Leu Glu Gly Asp Ile Arg Leu Ala Asp Phe
                165                 170                 175
Gly Val Ser Ala Lys Asn Leu Lys Thr Leu Gln Lys Arg Asp Ser Phe
                180                 185                 190
Ile Gly Thr Pro Tyr Trp Met Ala Pro Glu Val Val Met Cys Glu Thr
                195                 200                 205
Met Lys Asp Thr Pro Tyr Asp Tyr Lys Ala Asp Ile Trp Ser Leu Gly
                210                 215                 220
Ile Thr Leu Ile Glu Met Ala Gln Ile Glu Pro Pro His His Glu Leu
225                 230                 235                 240
Asn Pro Met Arg Val Leu Leu Lys Ile Ala Lys Ser Asp Pro Pro Thr
                245                 250                 255
Leu Leu Thr Pro Ser Lys Trp Ser Val Glu Phe Arg Asp Phe Leu Lys
                260                 265                 270
Ile Ala Leu Asp Lys Asn Pro Glu Thr Arg Pro Ser Ala Ala Gln Leu
                275                 280                 285
Leu Glu His Pro Phe Val Ser Ser Ile Thr Ser Asn Lys Ala Leu Arg
                290                 295                 300
Glu Leu Val Ala Glu Ala Lys Ala Glu Val Met Glu Glu Ile Glu Asp
305                 310                 315                 320
Gly Arg Asp Glu Gly Glu Glu Asp Ala Val Asp Ala Ala Ser Thr
                325                 330                 335
Leu Glu Asn His Thr Gln Asn Ser Ser Glu Val Ser Pro Pro Ser Leu
                340                 345                 350
Asn Ala Asp Lys Pro Leu Glu Glu Ser Pro Ser Thr Pro Leu Ala Pro
                355                 360                 365
Ser Gln Ser Gln Asp Ser Val Asn Glu Pro Cys Ser Gln Pro Ser Gly
                370                 375                 380
Asp Arg Ser Leu Gln Thr Thr Ser Pro Pro Val Val Ala Pro Gly Asn
385                 390                 395                 400
Glu Asn Gly Leu Ala Val Pro Val Pro Leu Arg Lys Ser Arg Pro Val
                405                 410                 415
Ser Met Asp Ala Arg Ile Gln Val Ala Gln Glu Lys Gln Val Ala Glu
                420                 425                 430
Gln Gly Gly Asp Leu Ser Pro Ala Ala Asn Arg Ser Gln Lys Ala Ser
                435                 440                 445
Gln Ser Arg Pro Asn Ser Ser Ala Leu Glu Thr Leu Gly Gly Glu Lys
                450                 455                 460
Leu Ala Asn Gly Ser Leu Glu Pro Pro Ala Gln Ala Ala Pro Gly Pro
465                 470                 475                 480
Ser Lys Arg Asp Ser Asp Cys Ser Ser Leu Cys Thr Ser Glu Ser Met
                485                 490                 495
Asp Tyr Gly Thr Asn Leu Ser Thr Asp Leu Ser Leu Asn Lys Glu Met
                500                 505                 510
Gly Ser Leu Ser Ile Lys Asp Pro Lys Leu Tyr Lys Lys Thr Leu Lys
                515                 520                 525
Arg Thr Arg Lys Phe Val Val Asp Gly Val Glu Val Ser Ile Thr Thr
                530                 535                 540
Ser Lys Ile Ile Ser Glu Asp Glu Lys Lys Asp Glu Glu Met Arg Phe
545                 550                 555                 560
```

-continued

```
Leu Arg Arg Gln Glu Leu Arg Glu Leu Arg Leu Gln Lys Glu Glu
                565                 570                 575
His Arg Asn Gln Thr Gln Leu Ser Asn Lys His Glu Leu Gln Leu Glu
                580                 585                 590
Gln Met His Lys Arg Phe Glu Gln Glu Ile Asn Ala Lys Lys Lys Phe
                595                 600                 605
Phe Asp Thr Glu Leu Glu Asn Leu Glu Arg Gln Gln Lys Gln Gln Val
    610                 615                 620
Glu Lys Met Glu Gln Asp His Ala Val Arg Arg Glu Glu Ala Arg
625                 630                 635                 640
Arg Ile Arg Leu Glu Gln Asp Arg Asp Tyr Thr Arg Phe Gln Glu Gln
                645                 650                 655
Leu Lys Leu Met Lys Lys Glu Val Lys Asn Glu Val Glu Lys Leu Pro
                660                 665                 670
Arg Gln Gln Arg Lys Glu Ser Met Lys Gln Lys Met Glu Glu His Thr
                675                 680                 685
Gln Lys Lys Gln Leu Leu Asp Arg Asp Phe Val Ala Lys Gln Lys Glu
    690                 695                 700
Asp Leu Glu Leu Ala Met Lys Arg Leu Thr Thr Asp Asn Arg Arg Glu
705                 710                 715                 720
Ile Cys Asp Lys Glu Arg Glu Cys Leu Met Lys Lys Gln Glu Leu Leu
                725                 730                 735
Arg Asp Arg Glu Ala Ala Leu Trp Glu Met Glu Glu His Gln Leu Gln
                740                 745                 750
Glu Arg His Gln Leu Val Lys Gln Gln Leu Lys Asp Gln Tyr Phe Leu
                755                 760                 765
Gln Arg His Glu Leu Leu Arg Lys His Glu Lys Glu Arg Glu Gln Met
    770                 775                 780
Gln Arg Tyr Asn Gln Arg Met Ile Glu Gln Leu Lys Val Arg Gln Gln
785                 790                 795                 800
Gln Glu Lys Ala Arg Leu Pro Lys Ile Gln Arg Ser Glu Gly Lys Thr
                805                 810                 815
Arg Met Ala Met Tyr Lys Lys Ser Leu His Ile Asn Gly Gly Gly Ser
                820                 825                 830
Ala Ala Glu Gln Arg Glu Lys Ile Lys Gln Phe Ser Gln Gln Glu Glu
                835                 840                 845
Lys Arg Gln Lys Ser Glu Arg Leu Gln Gln Gln Lys His Glu Asn
    850                 855                 860
Gln Met Arg Asp Met Leu Ala Gln Cys Glu Ser Asn Met Ser Glu Leu
865                 870                 875                 880
Gln Gln Leu Gln Asn Glu Lys Cys His Leu Leu Val Glu His Glu Thr
                885                 890                 895
Gln Lys Leu Lys Ala Leu Asp Glu Ser His Asn Gln Asn Leu Lys Glu
                900                 905                 910
Trp Arg Asp Lys Leu Arg Pro Arg Lys Lys Ala Leu Glu Glu Asp Leu
                915                 920                 925
Asn Gln Lys Lys Arg Glu Gln Glu Met Phe Phe Lys Leu Ser Glu Glu
    930                 935                 940
Ala Glu Cys Pro Asn Pro Ser Thr Pro Ser Lys Ala Ala Lys Phe Phe
945                 950                 955                 960
Pro Tyr Ser Ser Gly Asp Ala Ser
                965
```

POLYPEPTIDE FRAGMENTS OF HUMAN PAK5 PROTEIN KINASE

RELATED APPLICATIONS

This application is a divisional of U.S. application Ser. No. 09/291,417, filed Apr. 13, 1999.

The present application also claims priority to U.S. Provisional Patent Application Serial No. 60/081,784 by Plowman and Martinez, entitled STE20-Related Protein kinases, filed Apr. 14, 1998, hereby incorporated by reference herein in its entirety, including any drawings, tables, or figures.

The instant application contains a "lengthy" Sequence Listing which has been submitted via triplicate CD-R in lieu of a printed paper copy, and is hereby incorporated by reference in its entirety. Said CD-R are labeled "CRF", "Copy 1" and "Copy 2", respectively, and each contains only one identical 329 Kb file (38602328.APP).

FIELD OF THE INVENTION

The present invention relates to novel kinase polypeptides, nucleotide sequences encoding the novel kinase polypeptides, as well as various products and methods useful for the diagnosis and treatment of various kinase-related diseases and conditions.

BACKGROUND OF THE INVENTION

The following description of the background of the invention is provided to aid in understanding the invention, but is not admitted to be or to describe prior art to the invention.

Cellular signal transduction is a fundamental mechanism whereby external stimuli that regulate diverse cellular processes are relayed to the interior of cells. One of the key biochemical mechanisms of signal transduction involves the reversible phosphorylation of proteins, which enables regulation of the activity of mature proteins by altering their structure and function.

The best characterized protein kinases in eukaryotes phosphorylate proteins on the hydroxyl moiety of serine, threonine and tyrosine residues. These kinases largely fall into two groups, those specific for phosphorylating serines and threonines, and those specific for phosphorylating tyrosines. Some kinases, referred to as "dual specificity" kinases, are able to phosphorylate on tyrosine as well as serine/threonine residues.

Protein kinases can also be characterized by their location within the cell. Some kinases are transmembrane receptor-type proteins capable of directly altering their catalytic activity in response to the external environment such as the binding of a ligand. Others are non-receptor-type proteins lacking any transmembrane domain. They can be found in a variety of cellular compartments from the inner surface of the cell membrane to the nucleus.

Many kinases are involved in regulatory cascades wherein their substrates may include other kinases whose activities are regulated by their phosphorylation state. Ultimately the activity of some downstream effector is modulated by phosphorylation resulting from activation of such a pathway.

Protein kinases are one of the largest families of eukaryotic proteins with several hundred known members. These proteins share a 250–300 amino acid domain that can be subdivided into 12 distinct subdomains that comprise the common catalytic core structure. These conserved protein motifs have recently been exploited using PCR-based cloning strategies leading to a significant expansion of the known kinases.

Multiple alignment of the sequences in the catalytic domain of protein kinases and subsequent parsimony analysis permits the segregation of related kinases into distinct branches or subfamilies including: tyrosine kinases, cyclic-nucleotide-dependent kinases, calcium/calmodulin kinases, cyclin-dependent kinases and MAP-kinases, serine-threonine kinase receptors, and several other less defined subfamilies.

SUMMARY OF THE INVENTION

Through the use of a targeted PCR cloning strategy and of a "motif extraction" bioinformatics script, mammalian members of the STE20-kinase family have been identified as part of the present invention. Multiple alignment and parsimony analysis of the catalytic domain of all of these STE20-family members reveals that these proteins cluster into 9 distinct subgroups. Classification in this manner has proven highly accurate not only in predicting motifs present in the remaining non-catalytic portion of each protein, but also in their regulation, substrates, and signaling pathways. The present invention includes the partial or complete sequence of new members of the STE20-family, their classification, predicted or deduced protein structure, and a strategy for elucidating their biologic and therapeutic relevance.

Thus, a first aspect of the invention features an isolated, enriched, or purified nucleic acid molecule encoding a kinase polypeptide selected from the group consisting of STLK2, STLK3, STLK4, STLK5, STLK6, STLK7, ZC1, ZC2, ZC3, ZC4, KHS2, SULU1, SULU3, GEK2, PAK4, and PAK5.

By "isolated" in reference to nucleic acid is meant a polymer of nucleotides conjugated to each other, including DNA and RNA, that is isolated from a natural source or that is synthesized. The isolated nucleic acid of the present invention is unique in the sense that it is not found in a pure or separated state in nature. Use of the term "isolated" indicates that a naturally occurring sequence has been removed from its normal cellular (i.e., chromosomal) environment. Thus, the sequence may be in a cell-free solution or placed in a different cellular environment. The term does not imply that the sequence is the only nucleotide chain present, but that it is essentially free (about 90–95% pure at least) of non-nucleotide material naturally associated with it, and thus is distinguished from isolated chromosomes.

By the use of the term "enriched" in reference to nucleic acid is meant that the specific DNA dr RNA sequence constitutes a significantly higher fraction (2–5 fold) of the total DNA or RNA present in the cells or solution of interest than in normal or diseased cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that enriched does not imply that there are no other DNA or RNA sequences present, just that the relative amount of the sequence of interest has been significantly increased. The term "significant" is used to indicate that the level of increase is useful to the person making such an increase, and generally means an increase relative to other nucleic acids of about at least 2 fold, more preferably at least 5 to 10 fold or even more. The term also does not imply that there is no DNA or RNA from other sources. The other source DNA may, for example, comprise DNA from a yeast or bacterial genome, or a cloning vector such as pUC19. This term distinguishes from naturally occurring events, such as viral infection, or tumor type growths, in which the level of one mRNA may be naturally increased relative to other species of mRNA. That is, the term is meant to cover only those situations in which a person has intervened to elevate the proportion of the desired nucleic acid.

It is also advantageous for some purposes that a nucleotide sequence be in purified form. The term "purified" in reference to nucleic acid does not require absolute purity (such as a homogeneous preparation). Instead, it represents an indication that the sequence is relatively more pure than in the natural environment (compared to the natural level this level should be at least 2–5 fold greater, e.g., in terms of mg/mL). Individual clones isolated from a cDNA library may be purified to electrophoretic homogeneity. The claimed DNA molecules obtained from these clones could be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^6$-fold purification of the native message.

Thus, purification of at least one order of magnitude, preferably two or three orders, and more preferably four or five orders of magnitude is expressly contemplated.

By a "kinase polypeptide" is meant 32 (preferably 40, more preferably 45, most preferably 55) or more contiguous amino acids set forth in the amino acid sequence of SEQ ID NO:5, SEQ ID NO:6, or SEQ ID NO:7, or the corresponding full-length amino acid sequence; 250 (preferably 255, more preferably 260, most preferably 270) or more contiguous amino acids set forth in the amino acid sequence SEQ ID NO:13, SEQ ID NO:14, SEQ ID NO:15, or SEQ ID NO:105, or the corresponding full-length amino acid sequence; 27 (preferably 30, more preferably 40, most preferably 45) or more contiguous amino acids set forth in the amino acid sequence SEQ ID NO:18; 16 (preferably 20, more preferably 25, most preferably 35) or more contiguous amino acids set forth in the amino acid sequence SEQ ID NO:22, SEQ ID NO:23, SEQ ID NO:24, SEQ ID NO:29, SEQ ID NO:31, or SEQ ID NO:103 or the corresponding full-length amino acid sequence; 6 (preferably 10, more preferably 15, most preferably 25) or more contiguous amino acids set forth in the amino acid sequence of SEQ ID NO:97 or SEQ ID NO:99, 22 (preferably 30, more preferably 35, most preferably 45) or more contiguous amino acids set forth in the amino acid sequence of SEQ ID NO:101, or the corresponding full-length amino acid sequence; 78 (preferably 80, more preferably 85, most preferably 90) or more contiguous amino acids set forth in the amino acid sequence SEQ ID NO:107 or functional derivatives thereof as described herein. For sequences for which the full-length sequence is not given, the remaining sequences can be determined using methods well-known to those in the art and are intended to be included in the invention. In certain aspects, polypeptides of 100, 200, 300 or more amino acids are preferred. The kinase polypeptide can be encoded by a full-length nucleic acid sequence or any portion of the full-length nucleic acid sequence, so long as a functional activity of the polypeptide is retained, not to include fragments containing only amino acids 1–22 of SEQ ID NO:13 or only amino acids 1–33 of SEQ ID NO:107.

The amino acid sequence will be substantially similar to the sequence shown in SEQ ID NO:5, SEQ ID NO:6, SEQ ID NO:7, SEQ ID NO:13, SEQ ID NO:14, SEQ ID NO:15, SEQ ID NO:18, SEQ ID NO:22, SEQ ID NO:23, SEQ ID NO:24, SEQ ID NO:29, SEQ ID NO:31, SEQ ID NO:97, SEQ ID NO:99, SEQ ID NO:100, SEQ ID NO:103, SEQ ID NO:105, or SEQ ID NO:107, or the corresponding full-length amino acid sequence, or fragments thereof, not to include fragments consisting only of the amino acid sequences 1–22 of SEQ ID NO:13 or 1–33 of SEQ ID NO:107. A sequence that is substantially similar to the sequence of SEQ ID NO:5, SEQ ID NO:6, SEQ ID NO:7, SEQ ID NO:13, SEQ ID NO:14, SEQ ID NO:15, SEQ ID NO:18, SEQ ID NO:22, SEQ ID NO:23, SEQ ID NO:24, SEQ ID NO:29, SEQ ID NO:31, SEQ ID NO:97, SEQ ID NO:99, SEQ ID NO:101, SEQ ID NO:103, SEQ ID NO:105, or SEQ ID NO:107 will preferably have at least 90% identity (more preferably at least 95% and most preferably 99–100%) to the sequence of SEQ ID NO:5, SEQ ID NO:6, SEQ ID NO:7, SEQ ID NO:13, SEQ ID NO:14, SEQ ID NO:15, SEQ ID NO:18, SEQ ID NO:22, SEQ ID NO:23, SEQ ID NO:24, SEQ ID NO:29, SEQ ID NO:31, SEQ ID NO:97, SEQ ID NO:99, SEQ ID NO:101, SEQ ID NO:103, SEQ ID NO:105, or SEQ ID NO:107.

By "identity" is meant a property of sequences that measures their similarity or relationship. Identity is measured by dividing the number of identical residues by the total number of residues and gaps and multiplying the product by 100. "Gaps" are spaces in an alignment that are the result of additons or deletions of amino acids. Thus, two copies of exactly the same sequence have 100% identity, but sequences that are less highly conserved, and have deletions, additions, or replacements, may have a lower degree of identity. Those skilled in the art will recognize that several computer programs are available for determining sequence identity using standard parameters, for example Blast (Altschul, et al. (1997) Nucleic Acids Res. 25:3389–3402), Blast2 (Altschul, et al. (1990) J. mol. biol. 215:403–410), and Smith-Waterman (Smith, et al. (1981) J. Mol. Biol. 147:195–197).

In preferred embodiments, the invention features isolated, enriched, or purified nucleic acid molecules encoding a kinase polypeptide comprising a nucleotide sequence that: (a) encodes a polypeptide having the amino acid sequence set forth in SEQ ID NO:5, SEQ ID NO:6, SEQ ID NO:7, SEQ ID NO:13, SEQ ID NO:14, SEQ ID NO:15, SEQ ID NO:18, SEQ ID NO:22, SEQ ID NO:23, SEQ ID NO:24, SEQ ID NO:29, SEQ ID NO:31, SEQ ID NO:97, SEQ ID NO:99, SEQ ID NO:101, SEQ ID NO:103, SEQ ID NO:105, or SEQ ID NO:107; (b) is the complement of the nucleotide sequence of (a); (c) hybridizes under highly stringent conditions to the nucleotide molecule of (a) and encodes a naturally occurring kinase polypeptide; (d) encodes a kinase polypeptide having the amino acid sequence of SEQ ID NO:5, SEQ ID NO:6, SEQ ID NO:7 SEQ ID NO:13, SEQ ID NO:14, SEQ ID NO:15, SEQ ID NO:18, SEQ ID NO:22, SEQ ID NO:23, SEQ ID NO:24, SEQ ID NO:29, SEQ ID NO:31, SEQ ID NO:97, SEQ ID NO:99, SEQ ID NO:103, SEQ ID NO:105, or SEQ ID NO:107, except that it lacks one or more, but not all, of the following segments of amino acid residues: 1–21, 22–274, or 275–416 of SEQ ID NO:5, 1–31, 32–308, 309–489 or 490–516 of SEQ ID NO:6, 1–178 or 179–414 of SEQ ID NO:7, 1–22, 23–289, 290–526, 527–640, 641–896, or 897–1239 of SEQ ID NO:13, 1–255, 256–442, 443–626, 627–954, or 955–1297 of SEQ ID NO:14, 1–255, 256–476, 477–680, 681–983, or 984–1326 of SEQ ID NO:15, 1–13, 14–273, 274–346, 347–534, or 535–894 of SEQ ID NO:18, 1–21, 22–277, 278–427, 428–637, 638–751, or 752–898 of SEQ ID NO:22, 1–66, 67–215, 216–425, 426–539, 540–786, or 787–887 of SEQ ID NO:23, 1–25, 26–273, 274–422, 423–632, or 633–748 of SEQ ID NO:24, 1–51, 52–224, 225–393, 394–658, or 659–681 of SEQ ID NO:29, 1–25, 26–281, 284–430, 431–640, 641–754, 755–901, or 902–1001 of SEQ ID NO:31, 1–10, 11–321, or 322–373 of SEQ ID NO:97, 1–57, 58–369, or 370–418 of SEQ ID NO:99, 1–52, 53–173, 174–307, 308–572, or 573–591 of SEQ ID NO:103, 1–24, 25–289, 290–397, 398–628, 629–872, or 873–1227 of SEQ ID NO:105, or 1–33, 34–294, 295–337, 338–472, 473–724, or 725–968 of SEQ ID NO:107; (e) is the complement of the nucleotide sequence pf (d); (f) encodes a polypeptide having the amino acid sequence set forth in SEQ ID NO:5, SEQ ID NO:6, SEQ ID NO:7, SEQ ID NO:13, SEQ ID NO:14, SEQ ID NO:15, SEQ ID NO:18, SEQ ID NO:22, SEQ ID NO:23, SEQ ID NO:24, SEQ ID NO:29, SEQ ID NO:31; SEQ ID NO:97, SEQ ID NO:99, SEQ ID NO:103, SEQ ID NO:105, or SEQ ID NO:107 from amino acid residues 1–21, 22–274, or 275–416 of SEQ ID NO:5, 1–31, 32–308, 309–489, or 490–516 of SEQ ID NO:6, 1–178 or 179–414 of SEQ ID NO:7, 23–289, 290–526, 527–640, 641–896, or 897–1239 of SEQ ID NO:13, 1–255, 256–442, 443–626, 627–954, or 955–1297 of SEQ ID NO:14, 1–255, 256–476, 477–680, 681–983, or 984–1326 of SEQ ID NO:15, 1–13, 14–273, 274–346, 347–534, or 535–894 of SEQ ID NO:18, 1–21, 22–277, 278–427, 428–637, 638–751, or 752–898 of SEQ ID NO:22, 1–66, 67–215, 216–425, 426–539, 540–786, or 787–887 of SEQ ID NO:23, 1–25, 26–273, 274–422, 423–632, or 633–748 of SEQ ID NO:24, 1–51, 52–224, 225–393, 394–658, or 659–681 of SEQ ID NO:29, 1–25, 26–281, 282–430, 431–640, 641–754, 755–901, or 902–1001 of SEQ ID NO:31, 1–10, 11–321, or 322–373 of SEQ ID NO:97, 1–57, 58–369, or 370–418 of SEQ ID NO:99, 1–52, 53–173, 174–307, 308–572, or 573–591 of SEQ ID NO:103, 1–24, 25–289, 290–397, 398–628, 629–872, or 873–1227 of SEQ ID NO:105,or 1–33, 34–294, 295–337, 338–472, 473–724, or 725–968 of SEQ ID NO:107; (g) is the complement of the nucleotide sequence of (f); (h) encodes a polypeptide having the amino acid sequence set forth in SEQ ID NO:5, SEQ ID NO:6, SEQ ID NO:7, SEQ ID NO:13, SEQ ID NO:14, SEQ ID NO:15, SEQ ID NO:18, SEQ ID NO:22, SEQ ID NO:23, SEQ ID NO:24, SEQ ID NO:29, SEQ ID NO:31, SEQ ID NO:97, SEQ ID NO:99, SEQ ID NO:101, SEQ ID NO:103, SEQ ID NO:105, or SEQ ID NO:107, except that it lacks one or more of the domains selected from the group consisting of a N-terminal domain, a catalytic domain, a C-terminal domain, a coiled-coil structure region, a proline-rich region, a spacer region, an insert, and a C-terminal tail; or (i) is the complement of the nucleotide sequence of (h).

The term "complement" refers to two nucleotides that can form multiple favorable interactions with one another. For example, adenine is complementary to thymine as they can form two hydrogen bonds. Similarly, guanine and cytosine are complementary since they can form three hydrogen bonds. A nucleotide sequence is the complement of another nucleotide sequence if all of the nucleotides of the first sequence are complementary to all of the nucleotides of the second sequence.

The term "domain" refers to a region of a polypeptide which contains a particular function. For instance, N-terminal or C-terminal domains of signal transduction proteins can serve functions including, but not limited to, binding molecules that localize the signal transduction molecule to different regions of the cell or binding other signaling molecules directly responsible for propagating a particular cellular signal. Some domains can be expressed separately from the rest of the protein and function by themselves, while others must remain part of the intact protein to retain function. The latter are termed functional regions of proteins and also relate to domains.

The term "N-terminal domain" refers to the extracatalytic region located between the initiator methionine and the catalytic domain of the protein kinase. The N-terminal domain can be identified following a Smith-Waterman alignment of the protein sequence against the non-redundant protein database to define the N-terminal boundary of the catalytic domain. Depending on its length, the N-terminal domain may or may not play a regulatory role in kinase function. An example of a protein kinase whose N-terminal domain has been shown to play a regulatory role is PAK65, which contains a CRIB motif used for Cdc42 and rac binding (Burbelo, P. D. et al. (1995) J. Biol. Chem. 270, 29071–290740).

The N-terminal domain spans amino acid residues 1–21 of the sequence set forth in SEQ ID NO:5, amino acid residues 1–31 of the sequence set forth in SEQ ID NO:6, amino acid residues 1–22 of the sequence set forth in SEQ ID NO:13, amino acid residues 1–13 of the sequence set forth in SEQ ID NO:18, amino acid residues 1–21 of the sequence set forth in SEQ ID NO:22, amino acid residues 1–25 of the sequence set forth in SEQ ID NO:24, amino acid residues 1–51 of the sequence set forth in SEQ ID NO:29, amino acid residues 1–25 of the sequence set forth in SEQ ID NO:31, amino acid residues 1–57 of the sequence set forth in SEQ ID NO:99, amino acid residues 1–52 of the sequence set forth in SEQ ID NO:103, amino acid residues 1–24 of the sequence set forth in SEQ ID NO:105, or amino acid residues 1–33 of the sequence set forth in SEQ ID NO:107.

The term "catalytic domain" refers to a region of the protein kinase that is typically 25–300 amino acids long and is responsible for carrying out the phosphate transfer reaction from a high-energy phosphate donor molecule such as ATP or GTP to itself (autophosphorylation) or to other proteins (exogenous phosphorylation). The catalytic domain of protein kinases is made up of 12 subdomains that contain highly conserved amino acid residues, and are responsible for proper polypeptide folding and for catalysis. The catalytic domain can be identified following a Smith-Waterman alignment of the protein sequence against the non-redundant protein database.

The catalytic domain spans amino acid residues 22–274 of the sequence set forth in SEQ ID NO:5, residues 32–308 of the sequence set forth in SEQ ID NO:6, residues 1–178 of the sequence set forth in SEQ ID NO:7, residues 23–289 of the sequence set forth in SEQ ID NO:13, residues 1–255 of the sequence set forth in SEQ ID NO:14, residues 1–255 of the sequence set forth in SEQ ID NO:15, residues 14–273 of the sequence set forth in SEQ ID NO:18, residues 22–277 of the sequence set forth in SEQ ID NO:22, residues 1–66 of the sequence set forth in SEQ ID NO:23, residues 26–273 of the sequence set forth in SEQ ID NO:24, residues 394–658 of the sequence set forth in SEQ ID NO:29, residues 26–281 of the sequence set forth in SEQ ID NO:31, residues 1–278 of the sequence set forth in SEQ ID NO:97, residues 58–369 of the sequence set forth in SEQ ID NO:99, residues 1–103 of the sequence set forth in SEQ ID NO:101, residues 308–572 of the sequence set forth in SEQ ID NO:103, residues 25–289 of the sequence set forth in SEQ ID NO:105, or residues 34–294 of the sequence set forth in SEQ ID NO:107.

The term "catalytic activity", as used herein, defines the rate at which a kinase catalytic domain phosphorylates a substrate. Catalytic activity can be measured, for example, by determining the amount of a substrate converted to a phosphorylated product as a function of time. Catalytic activity can be measured by methods of the invention by holding time constant and determining the concentration of a phosphorylated substrate after a fixed period of time. Phosphorylation of a substrate occurs at the active-site of a protein kinase. The active-site is normally a cavity in which the substrate binds to the protein kinase and is phosphorylated.

The term "substrate" as used herein refers to a molecule phosphorylated by a kinase of the invention. Kinases phosphorylate substrates on serine/threonine or tyrosine amino acids. The molecule may be another protein or a polypeptide.

The term "C-terminal domain" refers to the region located between the catalytic domain or the last (located closest to the C-terminus) functional domain and the carboxy-terminal amino acid residue of the protein kinase. By "functional" domain is meant any region of the polypeptide that may play a regulatory or catalytic role as predicted from amino acid sequence homology to other proteins or by the presence of amino acid sequences that may give rise to specific structural conformations (i.e. coiled-coils). The C-terminal domain can be identified by using a Smith-Waterman alignment of the protein sequence against the non-redundant protein database to define the C-terminal boundary of the catalytic domain or of any functional C-terminal extracatalytic domain. Depending on its length and amino acid composition, the C-terminal domain may or may not play a regulatory role in kinase function. An example of a protein kinase whose C-terminal domain may play a regulatory role is PAK3 which contains a heterotrimeric $G_b$ subunit-binding site near its C-terminus (Leeuw, T. et al (1998) Nature, 391, 191–195).

The C-terminal domain spans amino acid residues 275–416 of the sequence set forth in SEQ ID NO:5, residues 309–489 of the sequence set forth in SEQ ID NO:6, residues 179–414 of the sequence set forth in SEQ ID NO:7, residues 897–1239 of the sequence set forth in SEQ ID NO:13, residues 955–1297 of the sequence set forth in SEQ ID NO:14, residues 984–1326 of the sequence set forth in SEQ ID NO:15, residues 535–894 of the sequence set forth in SEQ ID NO:18, residues 752–898 of the sequence set forth in SEQ ID NO:22, residues 279–330 of the sequence set forth in SEQ ID NO:97, residues 370–418 of the sequence set forth in SEQ ID NO:99, or residues 873–1227 of the sequence set forth in SEQ ID NO:105.

The term "signal transduction pathway" refers to the molecules that propagate an extracellular signal through the cell membrane to become an intracellular signal. This signal can then stimulate a cellular response. The polypeptide molecules involved in signal transduction processes are typically receptor and non-receptor protein tyrosine kinases, receptor and non-receptor protein phosphatases, SRC homology 2 and 3 domains, phosphotyrosine binding proteins (SRC homology 2 (SH2) and phosphotyrosine binding (PTB and PH) domain containing proteins), proline-rich binding proteins (SH3 domain containing proteins), nucleotide exchange factors, and transcription factors.

The term "coiled-coil structure region" as used herein, refers to a polypeptide sequence that has a high probability of adopting a coiled-coil structure as predicted by computer algorithms such as COILS (Lupas, A. (1996) Meth. Enzymology 266:513–525). Coiled-coils are formed by two or three amphipathic α-helices in parallel. Coiled-coils can bind to coiled-coil domains of other polypeptides resulting in homo- or heterodimers (Lupas, A. (1991) Science 252:1162–1164). Coiled-coil-dependent oligomerization has been shown to be necessary for protein function including catalytic activity of serine/threonine kinases (Roe, J. et al. (1997) J. Biol. Chem. 272:5838–5845).

The coiled-coil structure region spans amino acid residues 290–526 of the sequence set forth in SEQ ID NO:13, residues 256–442 of the sequence set forth in SEQ ID NO:14, residues 256–476 of the sequence set forth in SEQ ID NO:15, residues 428–637 of the sequence set forth in SEQ ID NO:22, residues 216–425 or 540–786 of the sequence set forth in SEQ ID NO:23, residues 423–632 of the sequence set forth in SEQ ID NO:24, residues 431–640 or 755–901 of the sequence set forth in SEQ ID NO:31, residues 291–398 or 629–668 of the sequence set forth in SEQ ID NO:105, or residues 473–724 or 725–968 of the sequence set forth in SEQ ID NO:107.

The term "proline-rich region" as used herein, refers to a region of a protein kinase whose proline content over a given amino acid length is higher than the average content of this amino acid found in proteins(i.e., >10%). Proline-rich regions are easily discernable by visual inspection of amino acid sequences and quantitated by standard computer sequence analysis programs such as the DNAStar program EditSeq. Proline-rich regions have been demonstrated to participate in regulatory protein-protein interactions. Among these interactions, those that are most relevant to this invention involve the "PxxP" (SEQ ID NO: 148) proline rich motif found in certain protein kinases (i.e., human PAK1) and the SH3 domain of the adaptor molecule Nck (Galisteo, M. L. et al. (1996) J. Biol. Chem. 271:20997–21000). Other regulatory interactions involving "PxxP" (SEQ ID NO:148) proline-rich motifs include the WW domain (Sudol, M. (1996) Prog. Biochys. Mol. Bio. 65:113–132).

The proline-rich region spans amino acid residues 527–640 of the sequence set forth in SEQ ID NO:13, residues 443–626 of the sequence set forth in SEQ ID NO:14, residues 477–680 of the sequence set forth in SEQ ID NO:15, residues 347–534 of the sequence set forth in SEQ ID NO:18,residues 398–628 of the sequence set forth in SEQ ID NO:105, or residues 338–472 of the sequence set forth in SEQ ID NO:107.

The term "spacer region" as used herein, refers to a region of the protein kinase located between predicted functional domains. The spacer region has no detectable homology to any amino acid sequence in the database, and can be identified by using a Smith-Waterman alignment of the protein sequence against the non-redundant protein database to define the C- and N-terminal boundaries of the flanking functional domains. Spacer regions may or may not play a fundamental role in protein kinase function. Precedence for the regulatory role of spacer regions in kinase function is provided by the role of the src kinase spacer in inter-domain interactions (Xu, W. et al. (1997) Nature 385:595–602).

The spacer region spans amino acid residues 641–896 of the sequence set forth in SEQ ID NO:13, residues 627–954 of the sequence set forth in SEQ ID NO:14, residues 681–983 of the sequence set forth in SEQ ID NO:15, residues 274–346 of the sequence set forth in SEQ ID NO:18, residues 278–427 or 638–751 of the sequence set forth in SEQ ID NO:22, residues 67–215 or 426–539 of the sequence set forth in SEQ ID NO:23, residues 274–422 or 633–748 of the sequence set forth in SEQ ID NO:24, residues 225–393 of the sequence set forth in SEQ ID NO:29, residues 282–430 or 641–754 of the sequence set forth in SEQ ID NO:31, residues 174–307 of the sequence set forth in SEQ ID NO:103, residues 669–872 of the sequence set forth in SEQ ID NO:105, or residues 295–337of the sequence set forth in SEQ ID NO:107.

The term "insert" as used herein refers to a portion of a protein kinase that is absent from a close homolog. Inserts may or may not by the product alternative splicing of exons. Inserts can be identified by using a Smith-Waterman sequence alignment of the protein sequence against the non-redundant protein database, or by means of a multiple sequence alignment of homologous sequences using the DNAStar program Megalign. Inserts may play a functional role by presenting a new interface for protein-protein interactions, or by interfering with such interactions. Inserts span amino acid residues 52–224 of the sequence set forth in SEQ ID NO:29 or residues 53–173 of the sequence set forth in SEQ ID NO:103.

The term "C-terminal tail" as used herein, refers to a C-terminal domain of a protein kinase, that by homology extends or protrudes past the C-terminal amino acid of its closest homolog. C-terminal tails can be identified by using a Smith-Waterman sequence alignment of the protein sequence against the non-redundant protein database, or by means of a multiple sequence alignment of homologous sequences using the DNAStar program Megalign. Depending on its length, a C-terminal tail may or may not play a regulatory role in kinase function.

The C-terminal tail spans amino acid residues 490–516 of the sequence set forth in SEQ ID NO:6, residues 787–887 of the sequence set forth in SEQ ID NO:23, residues 659–681 of the sequence set forth in SEQ ID NO:29, residues 994–1093 of the sequence set forth in SEQ ID NO:31, or residues 573–591 of the sequence set forth in SEQ ID NO:103.

Various low or high stringency hybridization conditions may be used depending upon the specificity and selectivity desired. These conditions are well-known to those skilled in the art. Under stringent hybridization conditions only highly complementary nucleic acid sequences hybridize. Preferably, such conditions prevent hybridization of nucleic acids having more than 1 or 2 mismatches out of 20 contiguous nucleotides, more preferably, such conditions prevent hybridization of nucleic acids having more than 1 or 2 mismatches out of 50 contiguous nucleotides, most preferably, such conditions prevent hybridization of nucleic acids having more than 1 or 2 mismatches out of 100 contiguous nucleotides. In some instances, the conditions may prevent hybridization of nucleic acids having more than 5 mismatches in the full-length sequence.

By stringent hybridization assay conditions is meant hybridization assay conditions at least as stringent as the following: hybridization in 50% formamide, 5×SSC, 50 mM NaH$_2$PO$_4$, pH 6.8, 0.5% SDS, 0.1 mg/mL sonicated salmon sperm DNA, and 5×Denhart solution at 42° C. overnight; washing with 2×SSC, 0.1% SDS at 45° C.; and washing with 0.2×SSC, 0.1% SDS at 45° C. Under some of the most stringent hybridization assay conditions, the second wash can be done with 0.1×SSC at a temperature up to 70° C. (Berger et al. (1987) *Guide to Molecular Cloning Techniques* pg 421, hereby incorporated by reference herein including any figures, tables, or drawings.). However, other applications may require the use of conditions falling between these sets of conditions. Methods of determining the conditions required to achieve desired hybridizations are well-known to those with ordinary skill in the art, and are based on several factors, including but not limited to, the sequences to be hybridized and the samples to be tested.

In other preferred embodiments, the invention features isolated, enriched, or purified nucleic acid molecules encoding kinase polypeptides, further comprising a vector or promoter effective to initiate transcription in a host cell. The invention also features recombinant nucleic acid, preferably in a cell or an organism. The recombinant nucleic acid may contain a sequence set forth in SEQ ID NO:1, SEQ ID NO:2, SEQ ID NO:3, SEQ ID NO:9, SEQ ID NO:10, SEQ ID NO:11, SEQ ID NO:17, SEQ ID NO:19, SEQ ID NO:20, SEQ ID NO:21, SEQ ID NO:27, SEQ ID NO:96, SEQ ID NO:98, SEQ ID NO:100, SEQ ID NO:102,SEQ ID NO:104, or SEQ ID NO:106, or a functional derivative thereof and a vector or a promoter effective to initiate transcription in a host cell. The recombinant nucleic acid can alternatively contain a transcriptional initiation region functional in a cell, a sequence complementary to an RNA sequence encoding a kinase polypeptide and a transcriptional termination region functional in a cell. Specific vectors and host cell combinations are discussed herein.

The term "vector" relates to a single or double-stranded circular nucleic acid molecule that can be transfected into cells and replicated within or independently of a cell genome. A circular double-stranded nucleic acid molecule can be cut and thereby linearized upon treatment with restriction enzymes. An assortment of nucleic acid vectors, restriction enzymes, and the knowledge of the nucleotide sequences cut by restriction enzymes are readily available to those skilled in the art. A nucleic acid molecule encoding a kinase can be inserted into a vector by cutting the vector with restriction enzymes and ligating the two pieces together.

The term "transfecting" defines a number of methods to insert a nucleic acid vector or other nucleic acid molecules into a cellular organism. These methods involve a variety of techniques, such as treating the cells with high concentrations of salt, an electric field, detergent, or DMSO to render the outer membrane or wall of the cells permeable to nucleic acid molecules of interest or use of various viral transduction strategies.

The term "promoter" as used herein, refers to nucleic acid sequence needed for gene sequence expression. Promoter regions vary from organism to organism, but are well known to persons skilled in the art for different organisms. For example, in prokaryotes, the promoter region contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like.

In preferred embodiments, the isolated nucleic acid comprises, consists essentially of, or consists of a nucleic acid sequence set forth in SEQ ID NO:1, SEQ ID NO:2, SEQ ID NO:3, SEQ ID NO:9, SEQ ID NO:10, SEQ ID NO:11, SEQ ID NO:17, SEQ ID NO:19, SEQ ID NO:20, SEQ ID NO:21, SEQ ID NO:27, SEQ ID NO:96, SEQ ID NO:98, SEQ ID NO:100 SEQ ID NO:102, SEQ ID NO:104, or SEQ ID NO:106, or the corresponding full-length sequence, encodes the amino acid sequence of SEQ ID NO:5, SEQ ID NO:6, SEQ ID NO:7, SEQ ID NO:13, SEQ ID NO:14, SEQ ID NO:15, SEQ ID NO:18, SEQ ID NO:22, SEQ ID NO:23, SEQ ID NO:24, SEQ ID NO:29, SEQ ID NO:31, SEQ ID NO:97, SEQ ID NO:99, SEQ ID NO:101, SEQ ID NO:103, SEQ ID NO:105, or SEQ ID NO:107, or the corresponding full-length amino acid sequence, a functional derivative thereof, or at least 40, 45, 50, 60, 100, 200, or 300 contiguous amino acids of SEQ ID NO:5, SEQ ID NO:6, or SEQ ID NO:7, or of the corresponding full-length amino acid sequence; at least 250, 255, 275, 300, or 400 contiguous amino acids of SEQ ID NO:13, SEQ ID NO:14, SEQ ID NO:15, or of the corresponding full-length amino acid sequence; at least 27, 30, 35, 40, 50, 100, 200, or 300 contiguous amino acids of SEQ ID NO:18; at least 16, 25, 35, 50, 100, 200, or 300 contiguous amino acids of SEQ ID NO:22, SEQ ID NO:23, SEQ ID NO:24, SEQ ID NO:29, SEQ ID NO:31, or SEQ ID NO:103, or of the corresponding full-length amino acid sequence; 6 (preferably 10, more preferably 15, most preferably 25) or more contiguous amino acids set forth in the amino acid sequence of SEQ ID NO:97 or SEQ ID NO:99, or the corresponding full-length amino acid sequence; 22 (preferably 30, more preferably 35, most preferably 45) or more contiguous amino acids set forth in the amino acid sequence of SEQ ID NO:101, or the corresponding full-length amino acid sequence; or at least 80, 85, 90, 100, 200, or 300 contiguous amino acids of SEQ ID NO:107, or functional derivatives thereof. The kinase polypeptides, selected from the group consisting of STLK2, STLK3, STLK4, STLK5, STLK6, STLK7, ZC1, ZC2, ZC3, ZC4, KHS2, SULU1, SULU3, GEK2, PAK4, and PAK5, comprise, consist essentially of, or consist of at least at least 40, 45, 50, 60, 100, 200, or 300 contiguous amino acids of SEQ ID NO:5, SEQ ID NO:6, or SEQ ID NO:7; at least 250, 255, 275, 300, or 400 contiguous amino acids of SEQ ID NO:13, SEQ ID NO:14, SEQ ID NO:15, or SEQ ID NO:105; at least 27, 30, 35, 40, 50, 100, 200, or 300 contiguous amino acids of SEQ ID NO:18; at least 35, 40, 45, 50, 100, 200, or 300 contiguous amino acids of SEQ ID NO:22, SEQ ID NO:23, SEQ ID NO:24, SEQ ID NO:29, SEQ ID NO:31 or SEQ ID NO:103; 6 (preferably 10, more preferably 15, most preferably 25) or more contiguous amino acids set forth in the amino acid sequence of SEQ ID NO:97 or SEQ ID NO:99; 22 (preferably 30, more preferably 35, most preferably.45) or more contiguous amino acids set forth in the amino acid sequence of SEQ ID NO:101; or at least 80, 85, 90, 100, 200, or 300 contiguous amino acids of SEQ ID NO:107, or the corresponding full-length sequences or derivatives thereof. The nucleic acid may be isolated from a natural source by cDNA cloning or by subtractive hybridization. The natural source may be mammalian, preferably human, blood, semen, or tissue, and the nucleic acid may be synthesized by the triester method or by using an automated DNA synthesizer.

The term "mammal" refers preferably to such organisms as mice, rats, rabbits, guinea pigs, sheep, and goats, more preferably to cats, dogs, monkeys, and apes, and most preferably to humans.

In yet other preferred embodiments, the nucleic acid is a conserved or unique region, for example those useful for: the design of hybridization probes to facilitate identification and cloning of additional polypeptides, the design of PCR probes to facilitate cloning of additional polypeptides, obtaining antibodies to polypeptide regions, and designing antisense oligonucleotides.

By "conserved nucleic acid regions", are meant regions present on two or more nucleic acids encoding a kinase polypeptide, to which a particular nucleic acid sequence can hybridize under lower stringency conditions. Examples of lower stringency conditions suitable for screening for nucleic acid encoding kinase polypeptides are provided in Abe, et al. (J. Biol. Chem. 19:13361–13368, 1992), hereby incorporated by reference herein in its entirety, including any drawings, figures, or tables. Preferably, conserved regions differ by no more than 5 out of 20 nucleotides, even more preferably 2 out of 20 nucleotides or most preferably 1 out of 20 nucleotides.

By "unique nucleic acid region" is meant a sequence present in a nucleic acid coding for a kinase polypeptide that is not present in a sequence coding for any other naturally occurring polypeptide. Such regions preferably encode 32 (preferably 40, more preferably 45, most preferably 55) or more contiguous amino acids set forth in the amino acid sequence of SEQ ID NO:5, SEQ ID NO:6, or SEQ ID NO:7, or the corresponding full-length amino acid sequence; 250 (preferably 255, more preferably 260, most preferably 270) or more contiguous amino acids set forth in the amino acid sequence SEQ ID NO:13, SEQ ID NO:14, or SEQ ID NO:15, or SEQ ID NO:105, or the corresponding full-length amino acid sequence; 27 (preferably 30, more preferably 40, most preferably 45) or more contiguous amino acids set forth in the amino acid sequence SEQ ID NO:18; 16 (preferably 20, more preferably 25, most preferably 35) or more contiguous amino acids set forth in the amino acid sequence SEQ ID NO:22, SEQ ID NO:23, SEQ ID NO:24, SEQ ID NO:29, SEQ ID NO:31, or SEQ ID NO:103, or the corresponding full-length amino acid sequence; 6 (preferably 10, more preferably 15, most preferably 25) or more contiguous amino acids set forth in the amino acid sequence of SEQ ID NO:97 or SEQ ID NO:99, 22 (preferably 30, more preferably 35, most preferably 45) or more contiguous amino acids set forth in the amino acid sequence of SEQ ID NO:101, or the corresponding full-length amino acid sequence; or 78 (preferably 80, more preferably 85, most preferably 90) or more contiguous amino acids set forth in the amino acid sequence SEQ ID NO:107, or functional derivatives thereof. In particular, a unique nucleic acid region is preferably of mammalian origin.

A second aspect of the invention features a nucleic acid probe for the detection of nucleic acid encoding a kinase polypeptide in a sample, wherein said polypeptide is selected from the group consisting of STLK2, STLK3, STLK4, STLK5, STLK6, STLK7, ZC1, ZC2, ZC3, ZC4, KHS2, SULU1, SULU3, GEK2, PAK4, and PAK5. Preferably, the nucleic acid probe encodes a kinase polypeptide that is a fragment of the protein encoded by the amino acid sequence set forth in SEQ ID NO:5, SEQ ID NO:6, SEQ ID NO:7, SEQ ID NO:13, SEQ ID NO:14, SEQ ID NO:15, SEQ ID NO:18, SEQ ID NO:22, SEQ ID NO:23, SEQ ID NO:24, SEQ ID NO:29, SEQ ID NO:31, SEQ ID NO:97, SEQ ID NO:99, SEQ ID NO:101, SEQ ID NO:103, SEQ ID NO:105, or SEQ ID NO:107, or the corresponding full-length amino acid sequences, not to include fragments consisting only of amino acids 1–22 of SEQ ID NO:13 or amino acids 1–33 of SEQ ID NO:107. The nucleic acid probe contains a nucleotide base sequence that will hybridize to a sequence set forth in SEQ ID NO:1, SEQ ID NO:2, SEQ ID NO:3, SEQ ID NO:9, SEQ ID NO:10, SEQ ID NO:11, SEQ ID NO:17, SEQ ID NO:19, SEQ ID NO:20, SEQ ID NO:21, SEQ ID NO:27, SEQ ID NO:96, SEQ ID NO:98, SEQ ID NO:100, SEQ ID NO:102, SEQ ID NO:104, or SEQ ID NO:106, or the corresponding full-length sequence, or a functional derivative thereof.

In preferred embodiments, the nucleic acid probe hybridizes to nucleic acid encoding at least 6, 12, 75, 90, 105, 120, 150, 200, 250, 300 or 350 contiguous amino acids of the sequence set forth in SEQ ID NO:5, SEQ ID NO:6, SEQ ID NO:7, SEQ ID NO:13, SEQ ID NO:14, SEQ ID NO:15, SEQ ID NO:18, SEQ ID NO:22, SEQ ID NO:23, SEQ ID NO:24, SEQ ID NO:29, SEQ ID NO:31 SEQ ID NO:97, SEQ ID NO:99, SEQ ID NO:101, SEQ ID NO:103, SEQ ID NO:105, or SEQ ID NO:107, or the corresponding full-length amino acid sequence, or functional derivatives thereof.

Methods for using the probes include detecting the presence or amount of kinase RNA in a sample by contacting the sample with a nucleic acid probe under conditions such that hybridization occurs and detecting the presence or amount of the probe bound to kinase RNA. The nucleic acid duplex formed between the probe and a nucleic acid sequence coding for a kinase polypeptide may be used in the identification of the sequence of the nucleic acid detected (Nelson et al., in Nonisotopic DNA Probe Techniques, Academic Press, San Diego, Kricka, ed., p. 275, 1992, hereby incorporated by reference herein in its entirety, including any drawings, figures, or tables). Kits for performing such methods may be constructed to include a container means having disposed therein a nucleic acid probe.

In a third aspect, the invention describes a recombinant cell or tissue comprising a nucleic acid molecule encoding a kinase polypeptide selected from the group consisting of STLK2, STLK3, STLK4, STLK5, STLK6, STLK7, ZC1, ZC2, ZC3, ZC4, KHS2, SULU1, SULU3, GEK2, PAK4, and PAK5. In such cells, the nucleic acid may be under the control of the genomic regulatory elements, or may be under the control of exogenous regulatory elements including an exogenous promoter. By "exogenous" it is meant a promoter that is not normally coupled in vivo transcriptionally to the coding sequence for the kinase polypeptides.

The polypeptide is preferably a fragment of the protein encoded by the amino acid sequence set forth in SEQ ID NO:5, SEQ ID NO:6, SEQ ID NO:7, SEQ ID NO:13, SEQ ID NO:14, SEQ ID NO:15, SEQ ID NO:18, SEQ ID NO:22, SEQ ID NO:23, SEQ ID NO:24, SEQ ID NO:29, SEQ ID NO:31, SEQ ID NO:97, SEQ ID NO:99, SEQ ID NO:101, SEQ ID NO:103, SEQ ID NO:105, or SEQ ID NO:107, or the corresponding full-length amino acid sequence, not to include fragments consisting only of amino acids 1–22 of SEQ ID NO:13 or amino acids 1–33 of SEQ ID NO:107. By "fragment," is meant an amino acid sequence present in a kinase polypeptide. Preferably, such a sequence comprises at least 32, 45, 50, 60, 100, 200, or 300 contiguous amino acids of SEQ ID NO:5, SEQ ID NO:6, or SEQ ID NO:7, or of the corresponding full-length amino acid sequence; at least 250, 255, 275, 300, or 400 contiguous amino acids of SEQ ID NO:13, SEQ ID NO:14, SEQ ID NO:15, OR SEQ ID NO:105, or of the corresponding full-length amino acid sequence; at least 27, 30, 35, 40, 50, 100, 200, or 300 contiguous amino acids of SEQ ID NO:18; at least 16, 25, 35, 50, 100, 200, or 300 contiguous amino acids of SEQ ID NO:22, SEQ ID NO:23, SEQ ID NO:24, SEQ ID NO:29, SEQ ID NO:31 or SEQ ID NO:103, or of the corresponding full-length amino acid sequence; 6 (preferably 10, more preferably 15, most preferably 25) or more contiguous amino acids set forth in the amino acid sequence of SEQ ID NO:97 or SEQ ID NO:99, 22 (preferably 30, more preferably 35, most preferably 45) or more contiguous amino acids set forth in the amino acid sequence of SEQ ID NO:101; at least 78, 85, 90, 100, 200, or 300 contiguous amino acids of SEQ ID NO:107, or the corresponding full-length amino acid sequence; or a functional derivative thereof.

In a fourth aspect the invention features an isolated, enriched, or purified kinase polypeptide selected from the group consisting of STLK2, STLK3, STLK4, STLK5, STLK6, STLK7, ZC1, ZC2, ZC3, ZC4, KHS2, SULU1, SULU3, GEK2, PAK4, and PAK5.

By "isolated" in reference to a polypeptide is meant a polymer of amino acids (2 or more amino acids) conjugated to each other, including polypeptides that are isolated from a natural source or that are synthesized. The isolated polypeptides of the present invention are unique in the sense that they are not found in a pure or separated state in nature. Use of the term "isolated" indicates that a naturally occurring sequence has been removed from its normal cellular environment. Thus, the sequence may be in a cell-free solution or placed in a different cellular environment. The term does not imply that the sequence is the only amino acid chain present, but that it is essentially free (about 90–95% pure at least) of non-amino acid material naturally associated with it.

By the use of the term "enriched" in reference to a polypeptide is meant that the specific amino acid sequence constitutes a significantly higher fraction (2–5 fold) of the total amino acid sequences present in the cells or solution of interest than in normal or diseased cells or in the cells from which the sequence was taken. This could be caused by a person by preferential reduction in the amount of other amino acid sequences present, or by a preferential increase in the amount of the specific amino acid sequence of interest, or by a combination of the two. However, it should be noted that enriched does not imply that there are no other amino acid sequences present, just that the relative amount of the sequence of interest has been significantly increased. The term significant here is used to indicate that the level of increase is useful to the person making such an increase, and generally means an increase relative to other amino acid sequences of about at least 2-fold, more preferably at least 5- to 10-fold or even more. The term also does not imply that there is no amino acid sequence from other sources. The other source of amino acid sequences may, for example, comprise amino acid sequence encoded by a yeast or bacterial genome, or a cloning vector such as pUC19. The term is meant to cover only those situations in which man has intervened to increase the proportion of the desired amino acid sequence.

It is also advantageous for some purposes that an amino acid sequence be in purified form. The term "purified" in reference to a polypeptide does not require absolute purity (such as a homogeneous preparation); instead, it represents an indication that the sequence is relatively purer than in the natural environment. Compared to the natural level this level should be at least 2–5 fold greater (e.g., in terms of mg/mL). Purification of at least one order of magnitude, preferably two or three orders, and more preferably four or five orders of magnitude is expressly contemplated. The substance is preferably free of contamination at a functionally significant level, for example 90%, 95%, or 99% pure.

In preferred embodiments, the kinase polypeptide is a fragment of the protein encoded by the amino acid sequence set forth in SEQ ID NO:5, SEQ ID NO:6, SEQ ID NO:7, SEQ ID NO:13, SEQ ID NO:14, SEQ ID NO:15, SEQ ID NO:18, SEQ ID NO:22, SEQ ID NO:23, SEQ ID NO:24, SEQ ID NO:29, SEQ ID NO:31, SEQ ID NO:97, SEQ ID NO:99, SEQ ID NO:101, SEQ ID NO:103, SEQ ID NO:105, or SEQ ID NO:107, or the corresponding full-length amino acid sequences, not to include fragments consisting only of amino acids 1–22 of SEQ ID NO:13 or amino acids 1–33 of SEQ ID NO:107. Preferably, the kinase polypeptide contains at least 32, 45, 50, 60, 100, 200, or 300 contiguous amino acids of SEQ ID NO:5, SEQ ID NO:6, or SEQ ID NO:7, or the corresponding full-length amino acid sequence; at least 250, 255, 275, 300, or 400 contiguous amino acids of SEQ ID NO:13, SEQ ID NO:14, SEQ ID NO:15, or SEQ ID NO:105, or the corresponding full-length amino acid sequence; at least 27, 30, 35, 40, 50, 100, 200, or 300 contiguous amino acids of SEQ ID NO:18; at least 16, 25, 35, 50, 100, 200, or 300 contiguous amino acids of SEQ ID NO:22, SEQ ID NO:23, SEQ ID NO:24, SEQ ID NO:29, SEQ ID NO:31, or SEQ ID NO:.103, or the corresponding full-length amino acid sequence; 6 (preferably 10, more preferably 15, most preferably 25) or more contiguous amino acids set forth in the amino acid sequence of SEQ ID NO:97 or SEQ ID NO:99, 22 (preferably 30, more preferably 35, most preferably 45) or more contiguous amino acids set forth in the amino acid sequence of SEQ ID NO:101, or the corresponding full-length amino acid sequence; or at least 78, 85, 90, 100, 200, or 300 contiguous amino acids of SEQ ID NO:107, or a functional derivative thereof.

In preferred embodiments, the kinase polypeptide comprises an amino acid sequence having (a) the amino acid sequence set forth in SEQ ID NO:5, SEQ ID NO:6, SEQ ID NO:7, SEQ ID NO:13, SEQ ID NO:14, SEQ ID NO:15, SEQ ID NO:18, SEQ ID NO:22, SEQ ID NO:23, SEQ ID NO:24, SEQ ID NO:29, SEQ ID NO:31, SEQ ID NO:97, SEQ ID NO:99, SEQ ID NO:101, SEQ ID NO:103, SEQ ID NO:105, or SEQ ID NO:107; (b) the amino acid sequence set forth in SEQ ID NO:5, SEQ ID NO:6, SEQ ID NO:7, SEQ ID NO:13, SEQ ID NO:14, SEQ ID NO:15, SEQ ID NO:18, SEQ ID NO:22, SEQ ID NO:23, SEQ ID NO:24, SEQ ID NO:29, SEQ ID NO:31, SEQ ID NO:97, SEQ ID NO:99, SEQ ID NO:103, SEQ ID NO:105, or SEQ ID NO:107, except that it lacks one or more, but not all, of the following segments of amino acid residues: 1–21, 22–274, or 275–416 of SEQ ID NO:5, 1–31, 32–308, 309–489 or 490–516 of SEQ ID NO:6, 1–178 or 179–414 of SEQ ID NO:7, 1–22, 23–289, 290–526, 527–640, 641–896, or 897–1239 of SEQ ID NO:13, 1–255, 256–442, 443–626, 627–954, or 955–1297 of SEQ ID NO:14, 1–255, 256–476, 477–680, 681–983, or 984–1326 of SEQ ID NO:15, 1–13, 14–273, 274–346, 347–534, or 535–894 of SEQ ID NO:18, 1–21, 22–277, 278–427, 428–637, 638–751, or 752–898 of SEQ ID NO:22, 1–66, 67–215, 216–425, 426–539, 540–786, or 787–887 of SEQ ID NO:23, 1–25, 26–273, 274–422, 423–632, or 633–748 of SEQ ID NO:24, 1–51, 52–224, 225–393, 394–658, or 659–681 of SEQ ID NO:29, 1–25, 26–281, 282–430, 431–640, 641–754, 755–901, or 902–1001 of SEQ ID NO:31, 1–10, 11–321, or 322–373 of SEQ ID NO:97, 1–57, 58–369, or 370–418 of SEQ ID NO:99, 1–52, 53–173, 174–307, 308–572, or 573–591 of SEQ ID NO:103, 1–24, 25–289, 290–397, 398–628, 629–668, 669–872, or 873–1227 of SEQ ID NO:105, or 1–33, 34–294, 295–337, 338–472, 473–724, or 725–968 of SEQ ID NO:107; (c) the amino acid sequence set forth in SEQ ID NO:5, SEQ ID NO:6, SEQ ID NO:7, SEQ ID NO:13, SEQ ID NO:14, SEQ ID NO:15, SEQ ID NO:18, SEQ ID NO:22, SEQ ID NO:23, SEQ ID NO:24, SEQ ID NO:29, SEQ ID NO:97, SEQ ID NO:99, SEQ ID NO:103, SEQ ID NO:105, or SEQ ID NO:107 from amino acid residues 1–21, 22–274, or 275–416 of SEQ ID NO:5, 1–31, 32–308, 309–489, or 490–516 of SEQ ID NO:6, 1–178 or 179–414 of SEQ ID NO:7, 23–289, 290–526, 527–640, 641–896, or 897–1239 of SEQ ID NO:13, 1–255, 256–442, 443–626, 627–954, or 955–1297 of SEQ ID NO:14, 1–255, 256–476, 477–680, 681–983, or 984–1326 of SEQ ID NO:15, 1–13, 14–273, 274–346, 347–534, or 535–894 of SEQ ID NO:18, 1–21, 22–277, 278–427, 428–637, 638–751, or 752–898 of SEQ ID NO:22, 1–66, 67–215, 216–425, 426–539, 540–786, or 787–887 of SEQ ID NO:23, 1–25, 26–273, 274–422, 423–632, or 633–748 of SEQ ID NO:24, 1–51, 52–224, 225–393, 394–658, or 659–681 of SEQ ID NO:29, 1–25, 26–273, 274–422, 423–632, 633–746, 747–993, or 994–1093 of SEQ ID NO:31, 1–10, 11–321, or 322–373 of SEQ ID NO:97, 1–57, 58–369, or 370–418 of SEQ ID NO:99, 1–52, 53–173, 174–307, 308–572, or 573–591 of SEQ ID NO:103, 1–24, 25–289, 290–397, 398–628, 629–668, 669–872, or 873–1227 of SEQ ID NO:105, or 1–33, 34–294, 295–337, 338–472, 473–724, or 725–968 of SEQ ID NO:107; or (d) the amino acid sequence set forth in SEQ ID NO:5, SEQ ID NO:6, SEQ ID NO:7, SEQ ID NO:13, SEQ ID NO:14, SEQ ID NO:15, SEQ ID NO:18, SEQ ID NO:22, SEQ ID NO:23, SEQ ID NO:24, SEQ ID NO:29, SEQ ID NO:31, SEQ ID NO:97, SEQ ID NO:99, SEQ ID NO:101, SEQ ID NO:103, SEQ ID NO:105, or SEQ ID NO:107, except that it lacks one or more, but not all, of the domains selected from the group consisting of a C-terminal domain, a catalytic domain, an N-terminal domain, a spacer region, a proline-rich region, a coiled-coil structure region, an insert-, and a C-terminal tail.

The polypeptide can be isolated from a natural source by methods well-known in the art. The natural source may be mammalian, preferably human, blood, semen, or tissue, and the polypeptide may be synthesized using an automated polypeptide synthesizer. The isolated, enriched, or purified kinase polypeptide is preferably: a STLK2, STLK3, STLK4, STLK5, STLK6, or STLK7 polypeptide; a ZC1, ZC2, ZC3, or ZC4 polypeptide; a KHS2 polypeptide; a SULU1 or SULU3 polypeptide; a GEK2 polypeptide; or a PAK4 or PAK5 polypeptide.

In some embodiments the invention includes a recombinant kinase polypeptide selected from the group consisting of STLK2, STLK3, STLK4, STLK5, STLK6, STLK7, ZC1, ZC2, ZC3, ZC4, KHS2, SULU1, SULU3, GEK2, PAK4, and PAK5. By "recombinant kinase polypeptide" is meant a polypeptide produced by recombinant DNA techniques such that it is distinct from a naturally occurring polypeptide either in its location (e.g., present in a different cell or tissue than found in nature), purity or structure. Generally, such a recombinant polypeptide will be present in a cell in an amount different from that normally observed in nature.

In a fifth aspect, the invention features an antibody (e.g., a monoclonal or polyclonal antibody) having specific binding affinity to a kinase polypeptide or a kinase polypeptide domain or fragment where the polypeptide is selected from the group consisting of STLK2, STLK3, STLK4, STLK5, STLK6, STLK7, ZC1, ZC2, ZC3, ZC4, KHS2, SULU1, SULU3, GEK2, PAK4, and PAK5. By "specific binding affinity" is meant that the antibody binds to the target kinase polypeptide with greater affinity than it binds to other polypeptides under specified conditions. Antibodies or antibody fragments are polypeptides that contain regions that can bind other polypeptides. The term "specific binding affinity" describes an antibody that binds to a kinase polypeptide with greater affinity than it binds to other polypeptides under specified conditions.

The term "polyclonal" refers to antibodies that are heterogenous populations of antibody molecules derived from the sera of animals immunized with an antigen or an antigenic functional derivative thereof. For the production of polyclonal antibodies, various host animals may be immunized by injection with the antigen. Various adjuvants may be used to increase the immunological response, depending on the host species.

"Monoclonal antibodies" are substantially homogenous populations of antibodies to a particular antigen. They may be obtained by any technique which provides for the production of antibody molecules by continuous cell lines in culture. Monoclonal antibodies may be obtained by methods known to those skilled in the art (Kohler et al., Nature 256:495–497, 1975, and U.S. Pat. No. 4,376,110, both of which are hereby incorporated by reference herein in their entirety including any figures, tables, or drawings).

The term "antibody fragment" refers to a portion of an antibody, often the hyper variable region and portions of the surrounding heavy and light chains, that displays specific binding affinity for a particular molecule. A hyper variable region is a portion of an antibody that physically binds to the polypeptide target.

Antibodies or antibody fragments having specific binding affinity to a kinase polypeptide of the invention may be used in methods for detecting the presence and/or amount of kinase polypeptide in a sample by probing the sample with the antibody under conditions suitable for kinase-antibody immunocomplex formation and detecting the presence and/or amount of the antibody conjugated to the kinase polypeptide. Diagnostic kits for performing such methods may be constructed to include antibodies or antibody fragments specific for the kinase as well as a conjugate of a binding partner of the antibodies or the antibodies themselves.

An antibody or antibody fragment with specific binding affinity to a kinase polypeptide of the invention can be isolated, enriched, or purified from a prokaryotic or eukaryotic organism. Routine methods known to those skilled in the art enable production of antibodies or antibody fragments, in both prokaryotic and eukaryotic organisms. Purification, enrichment, and isolation of antibodies, which are polypeptide molecules, are described above.

Antibodies having specific binding affinity to a kinase polypeptide of the invention may be used in methods for detecting the presence and/or amount of kinase polypeptide in a sample by contacting the sample with the antibody under conditions such that an immunocomplex forms and detecting the presence and/or amount of the antibody conjugated to the kinase polypeptide. Diagnostic kits for performing such methods may be constructed to include a first container containing the antibody and a second container having a conjugate of a binding partner of the antibody and a label, such as, for example, a radioisotope. The diagnostic kit may also include notification of an FDA approved use and instructions therefor.

In a sixth aspect, the invention features a hybridoma which produces an antibody having specific binding affinity to a kinase polypeptide or a kinase polypeptide domain, where the polypeptide is selected from the group consisting of STLK2, STLK3, STLK4, STLK5, STLK6, STLK7, ZC1, ZC2, ZC3, ZC4, KHS2, SULU1, SULU3, GEK2, PAK4, and PAK5. By "hybridoma" is meant an immortalized cell line that is capable of secreting an antibody, for example an antibody to a kinase of the invention. In preferred embodiments, the antibody to the kinase comprises a sequence of amino acids that is able to specifically bind a kinase polypeptide of the invention.

In a seventh aspect, the invention features a kinase polypeptide binding agent able to bind to a kinase polypeptide selected from the group consisting of STLK2, STLK3, STLK4, STLK6, STLK7, STLK5, ZC1, ZC2, ZC3, ZC4, KHS2, SULU1, SULU3, GEK2, PAK4, and PAK5. The binding agent is preferably a purified antibody that recognizes an epitope present on a kinase polypeptide of the invention. Other binding agents include molecules that bind to kinase polypeptides and analogous molecules that bind to a kinase polypeptide. Such binding agents may be identified by using assays that measure kinase binding partner activity, such as those that measure PDGFR activity.

The invention also features a method for screening for human cells containing a kinase polypeptide of the invention or an equivalent sequence. The method involves identifying the novel polypeptide in human cells using techniques that are routine and standard in the art, such as those described herein for identifying the kinases of the invention (e.g., cloning, Southern or Northern blot analysis, in situ hybridization, PCR amplification, etc.).

In an eighth aspect, the invention features methods for identifying a substance that modulates kinase activity comprising the steps of: (a) contacting a kinase polypeptide selected from the group consisting of STLK2, STLK3, STLK4, STLK5, STLK6, STLK7, ZC1, ZC2, ZC3, ZC4, KHS2, SULU1, SULU3, GEK2, PAK4, and PAK5 with a test substance; (b) measuring the activity of said polypeptide; and (c) determining whether said substance modulates the activity of said polypeptide.

The term "modulates" refers to the ability of a compound to alter the function of a kinase of the invention. A modulator preferably activates or inhibits the activity of a kinase of the invention depending on the concentration of the compound exposed to the kinase.

The term "activates" refers to increasing the cellular activity of the kinase. The term inhibit refers to decreasing the cellular activity of the kinase. Kinase activity is preferably the interaction with a natural binding partner.

The term "modulates" also refers to altering the function of kinases of the invention by increasing or decreasing the probability that a complex forms between the kinase and a natural binding partner. A modulator preferably increases the probability that such a complex forms between the kinase and the natural binding partner, more preferably increases or decreases the probability that a complex forms between the kinase and the natural binding partner depending on the concentration of the compound exposed to the kinase, and most preferably decreases the probability that a complex forms between the kinase and the natural binding partner.

The term "complex" refers to an assembly of at least two molecules bound to one another. Signal transduction complexes often contain at least two protein molecules bound to one another. For instance, a protein tyrosine receptor protein kinase, GRB2, SOS, RAF, and RAS assemble to form a signal transduction complex in response to a mitogenic ligand.

The term "natural binding partner" refers to polypeptides, lipids, small molecules, or nucleic acids that bind to kinases in cells. A change in the interaction between a kinase and a natural binding partner can manifest itself as an increased or decreased probability that the interaction forms, or an increased or decreased concentration of kinase/natural binding partner complex.

The term "contacting" as used herein refers to mixing a solution comprising the test compound with a liquid medium bathing the cells of the methods. The solution comprising the compound may also comprise another component, such as dimethyl sulfoxide (DMSO), which facilitates the uptake of the test compound or compounds into the cells of the methods. The solution comprising the test compound may be added to the medium bathing the cells by utilizing a delivery apparatus, such as a pipet-based device or syringe-based device.

In a ninth aspect, the invention features methods for identifying a substance that modulates kinase activity in a cell comprising the steps of: (a) expressing a kinase polypeptide in a cell, wherein said polypeptide is selected from the group consisting of STLK2, STLK3, STLK4, STLK5, STLK6, STLK7, ZC1, ZC2, ZC3, ZC4, KHS2, SULU1, SULU3, GEK2, PAK4, and PAK5; (b) adding a test substance to said cell; and (c) monitoring a change in cell phenotype or the interaction between said polypeptide and a natural binding partner.

The term "expressing" as used herein refers to the production of kinases of the invention from a nucleic acid vector containing kinase genes within a cell. The nucleic acid vector is transfected into cells using well known techniques in the art as described herein.

In a tenth aspect, the invention provides methods for treating a disease by administering to a patient in need of such treatment a substance that modulates the activity of a kinase selected from the group consisting of STLK2, STLK3, STLK4, STLK5, STLK6, STLK7, ZC1, ZC2, ZC3, ZC4, KHS2, SULU1, SULU3, GEK2, PAK4, and PAK5. Preferably, the disease is selected from the group consisting of immune-related diseases and disorders, organ transplantation, myocardial infarction, cardiovascular disease, stroke, renal failure, oxidative stress-related neurodegenerative disorders, and cancer. Most preferably, the immune-related diseases and disorders include, but are not limited to, rheumatoid arthritis, artherosclerosis, and autoimmune disorders.

In preferred embodiments, the invention provides methods for treating or preventing a disease or disorder by administering to a patient in need of such treatment a substance that modulates the activity of a kinase polypeptide selected from the group consisting of ZC1, ZC2, ZC3, ZC4, KHS2, PAK4, and PAK5. Preferably, the disease or disorder is selected from the group consisting of rheumatoid arthritis, artherosclerosis, autoimmune disorders, and organ transplantation. The invention also features methods of treating or preventing a disease or disorder by administering to a patient in need of such treatment a substance that modulates the activity of a kinase polypeptide selected from the group consisting of STLK1, STLK2, STLK3, STLK4, STLK5, STLK6, and STLK7. Preferably the disease or disorder is selected from the group consisting of immune-related diseases and disorders, myocardial infarction, cardiomyopathies, stroke, renal failure, and oxidative stress-related neurodegenerative disorders. Most preferably, the immune-related diseases and disorders are selected from the group consisting of rheumatoid arthritis, chronic inflammatory bowel disease, chronic inflammatory pelvic disease, multiple sclerosis, asthma, osteoarthritis, psoriasis, atherosclerosis, rhinitis, autoimmunity, and organ transplantation.

The invention also features methods of treating or preventing a disease or disorder by administering to a patient in need of such treatment a substance that modulates the activity of a kinase polypeptide selected from the group consisting of ZC1, ZC2, ZC3, and ZC4. Preferably the disease is selected from the group consisting of immune-related diseases and disorders, cardiovascular disease, and cancer. Most preferably, the immune-related diseases and disorders are selected from the group consisting of rheumatoid arthritis, chronic inflammatory bowel disease, chronic inflammatory pelvic disease, multiple sclerosis, asthma, osteoarthritis, psoriasis, atherosclerosis, rhinitis, autoimmunity, and organ transplantation.

Substances useful for treatment of kinase-related disorders or diseases preferably show positive results in one or more in vitro assays for an activity corresponding to treatment of the disease or disorder in question (Examples of such assays are provided in the references in section VI, below; and in Example 7, herein). Examples of substances that can be screened for favorable activity are provided and referenced in section VI, below. The substances that modulate the activity of the kinases preferably include, but are not limited to, antisense oligonucleotides and inhibitors of protein kinases, as determined by methods and screens referenced in section VI and Example 7, below.

The term "preventing" refers to decreasing the probability that an organism contracts or develops an abnormal condition.

The term "treating" refers to having a therapeutic effect and at least partially alleviating or abrogating an abnormal condition in the organism.

The term "therapeutic effect" refers to the inhibition or activation factors causing or contributing to the abnormal condition. A therapeutic effect relieves to some extent one or more of the symptoms of the abnormal condition. In reference to the treatment of abnormal conditions, a therapeutic effect can refer to one or more of the following: (a) an increase in the proliferation, growth, and/or differentiation of cells; (b) inhibition (i.e., slowing or stopping) of cell death; (c) inhibition of degeneration; (d) relieving to some extent one or more of the symptoms associated with the abnormal condition; and (e) enhancing the function of the affected population of cells. Compounds demonstrating efficacy against abnormal conditions can be identified as described herein.

The term "abnormal condition" refers to a function in the cells or tissues of an organism that deviates from their normal functions in that organism. An abnormal condition can relate to cell proliferation, cell differentiation, or cell survival.

Abnormal cell proliferative conditions include cancers such as fibrotic and mesangial disorders, abnormal angiogenesis and vasculogenesis, wound healing, psoriasis, diabetes mellitus, and inflammation.

Abnormal differentiation conditions include, but are not limited to neurodegenerative disorders, slow wound healing rates, and slow tissue grafting healing rates.

Abnormal cell survival conditions relate to conditions in which programmed cell death (apoptosis) pathways are activated or abrogated. A number of protein kinases are associated with the apoptosis pathways. Aberrations in the function of any one of the protein kinases could lead to cell immortality or premature cell death.

The term "aberration", in conjunction with the function of a kinase in a signal transduction process, refers to a kinase that is over- or under-expressed in an organism, mutated such that its catalytic activity is lower or higher than wild-type protein kinase activity, mutated such that it can no longer interact with a natural binding partner, is no longer modified by another protein kinase or protein phosphatase, or no longer interacts with a natural binding partner.

The term "administering" relates to a method of incorporating a compound into cells or tissues of an organism. The abnormal condition can be prevented or treated when the cells or tissues of the organism exist within the organism or outside of the organism. Cells existing outside the organism can be maintained or grown in cell culture dishes. For cells harbored within the organism, many techniques exist in the art to administer compounds, including (but not limited to) oral, parenteral, dermal, injection, and aerosol applications. For cells outside of the organism, multiple techniques exist in the art to administer the compounds, including (but not limited to) cell microinjection techniques, transformation techniques, and carrier techniques.

The abnormal condition can also be prevented or treated by administering a compound to a group of cells having an aberration in a signal transduction pathway to an organism. The effect of administering a compound on organism function can then be monitored. The organism is preferably a mouse, rat, rabbit, guinea pig, or goat, more preferably a monkey or ape, and most preferably a human.

In an eleventh aspect, the invention features methods for detection of a kinase polypeptide in a sample as a diagnostic tool for diseases or disorders, wherein the method comprises the steps of: (a) contacting the sample with a nucleic acid probe which hybridizes under hybridization assay conditions to a nucleic acid target region of a kinase polypeptide selected from the group consisting of STLK2, STLK3, STLK4, STLK5, STLK6, STLK7, ZC1, ZC2, ZC3, ZC4, KHS2, SULU1, SULU3, GEK2, PAK4, and PAK5, said probe comprising the nucleic acid sequence encoding the polypeptide, fragments thereof, and the complements of the sequences and fragments; and (b) detecting the presence or amount of the probe target region hybrid as an indication of the disease.

In preferred embodiments of the invention, the disease or disorder is selected from the group consisting of rheumatoid arthritis, artherosclerosis, autoimmune disorders, organ transplantation, myocardial infarction, cardiomyopathies, stroke, renal failure, oxidative stress-related neurodegenerative disorders, and cancer. In other preferred embodiments, the kinase polypeptide is selected from the group consisting of PAK4 and PAK5, or the polypeptide is selected from the group consisting of ZC1, ZC2, ZC3, and ZC4, and the disease is cancer.

The kinase "target region" is the nucleotide base sequence set forth in SEQ ID NO:1, SEQ ID NO:2, SEQ ID NO:3, SEQ ID NO:9, SEQ ID NO:10, SEQ ID NO:11, SEQ ID NO:17, SEQ ID NO:19, SEQ ID NO:20, SEQ ID NO:21, SEQ ID NO:27, SEQ ID NO:96, SEQ ID NO:98, SEQ ID NO:100, SEQ ID NO:102, SEQ ID NO:104, or SEQ ID NO:106, or the corresponding full-length sequences, a functional derivative thereof, or a fragment thereof to which the nucleic acid probe will specifically hybridize. Specific hybridization indicates that in the presence of other nucleic acids the probe only hybridizes detectably with the kinase of the invention's target region. Putative target regions can be identified by methods well known in the art consisting of alignment and comparison of the most closely related sequences in the database.

In preferred embodiments the nucleic acid probe hybridizes to a kinase target region encoding at least 6, 12, 75, 90, 105, 120, 150, 200, 250, 300 or 350 contiguous amino acids of the sequence set forth in SEQ ID NO:5, SEQ ID NO:6, SEQ ID NO:7, SEQ ID NO:13, SEQ ID NO:14, SEQ ID NO:15, SEQ ID NO:18, SEQ ID NO:22, SEQ ID NO:23, SEQ ID NO:24, SEQ ID NO:29, SEQ ID NO:31, SEQ ID NO:97, SEQ ID NO:99, SEQ ID NO:101, SEQ ID NO:103, SEQ ID NO:105, or SEQ ID NO:107, or the corresponding full-length amino acid sequence, or a functional derivative thereof. Hybridization conditions should be such that hybridization occurs only with the kinase genes in the presence of other nucleic acid molecules. Under stringent hybridization conditions only highly complementary nucleic acid sequences hybridize. Preferably, such conditions prevent hybridization of nucleic acids having more than 1 or 2 mismatches out of 20 contiguous nucleotides. Such conditions are defined supra.

The diseases for which detection of kinase genes in a sample could be diagnostic include diseases in which kinase nucleic acid (DNA and/or RNA) is amplified in comparison to normal cells. By "amplification" is meant increased numbers of kinase DNA or RNA in a cell compared with normal cells. In normal cells, kinases are typically found as single copy genes. In selected diseases, the chromosomal location of the kinase genes may be amplified, resulting in multiple copies of the gene, or amplification. Gene amplification can lead to amplification of kinase RNA, or kinase RNA can be amplified in the absence of kinase DNA amplification.

"Amplification" as it refers to RNA can be the detectable presence of kinase RNA in cells, since in some normal cells there is no basal expression of kinase RNA. In other normal cells, a basal level of expression of kinase exists, therefore in these cases amplification is the detection of at least 1–2-fold, and preferably more, kinase RNA, compared to the basal level.

The diseases that could be diagnosed by detection of kinase nucleic acid in a sample preferably include cancers. The test samples suitable for nucleic acid probing methods of the present invention include, for example, cells or nucleic acid extracts of cells, or biological fluids. The samples used in the above-described methods will vary based on the assay format, the detection method and the nature of the tissues, cells or extracts to be assayed. Methods for preparing nucleic acid extracts of cells are well known in the art and can be readily adapted in order to obtain a sample that is compatible with the method utilized.

In a final aspect, the invention features a method for detection of a kinase polypeptide in a sample as a diagnostic tool for a disease or disorder, wherein the method comprises: (a) comparing a nucleic acid target region encoding the kinase polypeptide in a sample, where the kinase polypeptide is selected from the group consisting of STLK2, STLK3, STLK4, STLK5, STLK6, STLK7, ZC1, ZC2, ZC3, ZC4, KHS2, SULU1, SULU3, GEK2, PAK4, and PAK5, or one or more fragments thereof, with a control nucleic acid target region encoding the kinase polypeptide, or one or more fragments thereof; and (b) detecting differences in sequence or amount between the target region and the control target region, as an indication of the disease or disorder. Preferably, the disease or disorder is selected from the group consisting of immune-related diseases and disorders, organ transplantation, myocardial infarction, cardiovascular disease, stroke, renal failure, oxidative stress-related neurodegenerative disorders, and cancer. Immune-related diseases and disorders include, but are not limited to, those discussed previously.

The term "comparing" as used herein refers to identifying discrepancies between the nucleic acid target region isolated from a sample, and the control nucleic acid target region. The discrepancies can be in the nucleotide sequences, e.g. insertions, deletions, or point mutations, or in the amount of a given nucleotide sequence. Methods to determine these discrepancies in sequences are well-known to one of ordinary skill in the art. The "control" nucleic acid target region refers to the sequence or amount of the sequence found in normal cells, e.g. cells that are not diseased as discussed previously.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. For example, in some instances the nucleotide sequence of the ZC4 kinase polypeptide may not be part of a preferred embodiment.

The summary of the invention described above is not limiting and other features and advantages of the invention will be apparent from the following detailed description of the invention, and from the claims.

BRIEF DESCRIPTION OF THE FIGURES

FIGS. 1A, 1B, and 1C show a multiple sequence alignment of the amino acid sequences (SEQ ID NOS 84–85, 5–7, respectively, in order of appearance) of the STE20-STE20 family kinases.

FIGS. 2A and 2B show a multiple sequence alignment of the amino acid sequences (SEQ ID NOS 84, 86–87 & 8, respectively, in order of appearance) of the STE20-STLK5 family kinases.

Figure 3A:
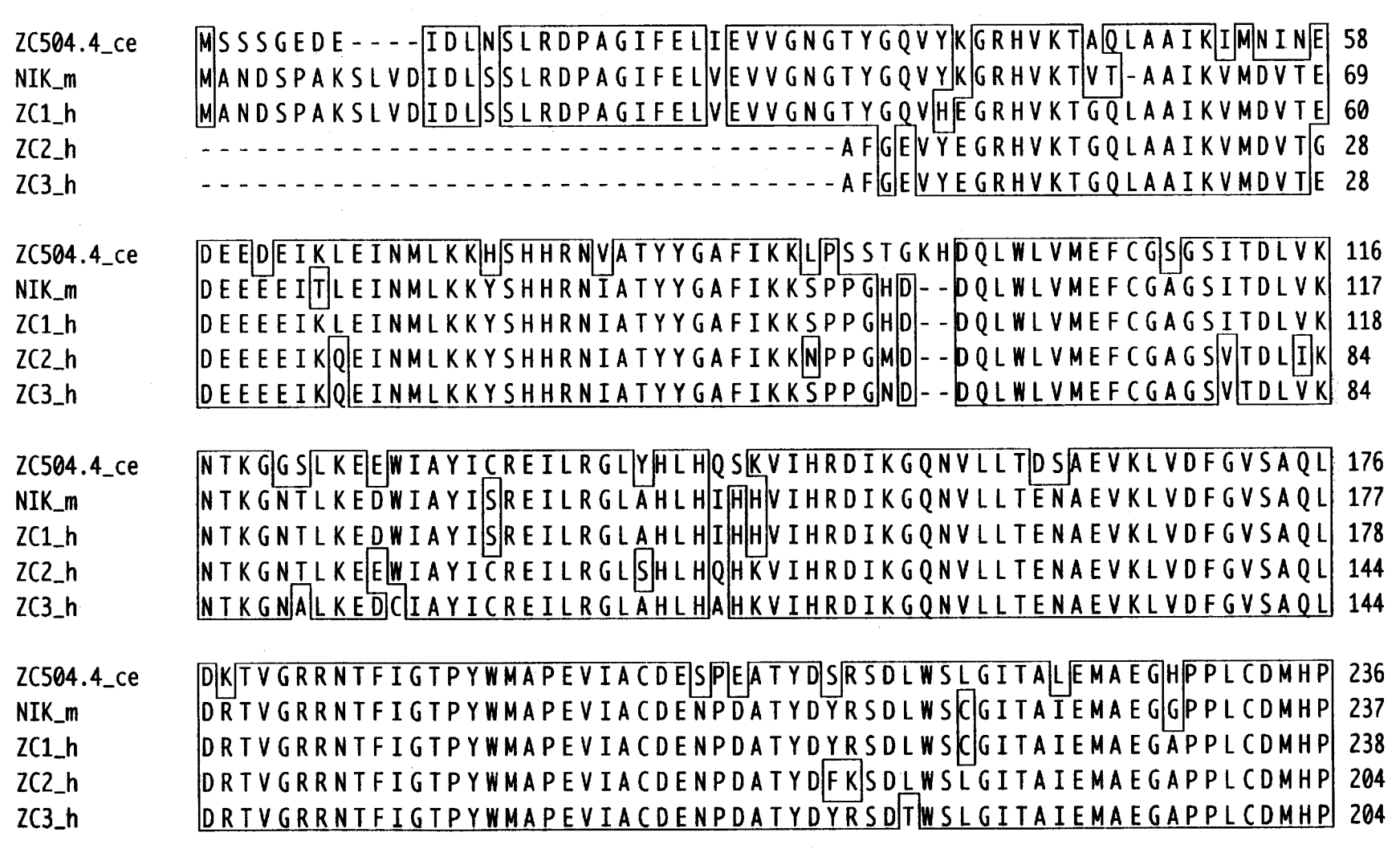
Figure 3D:
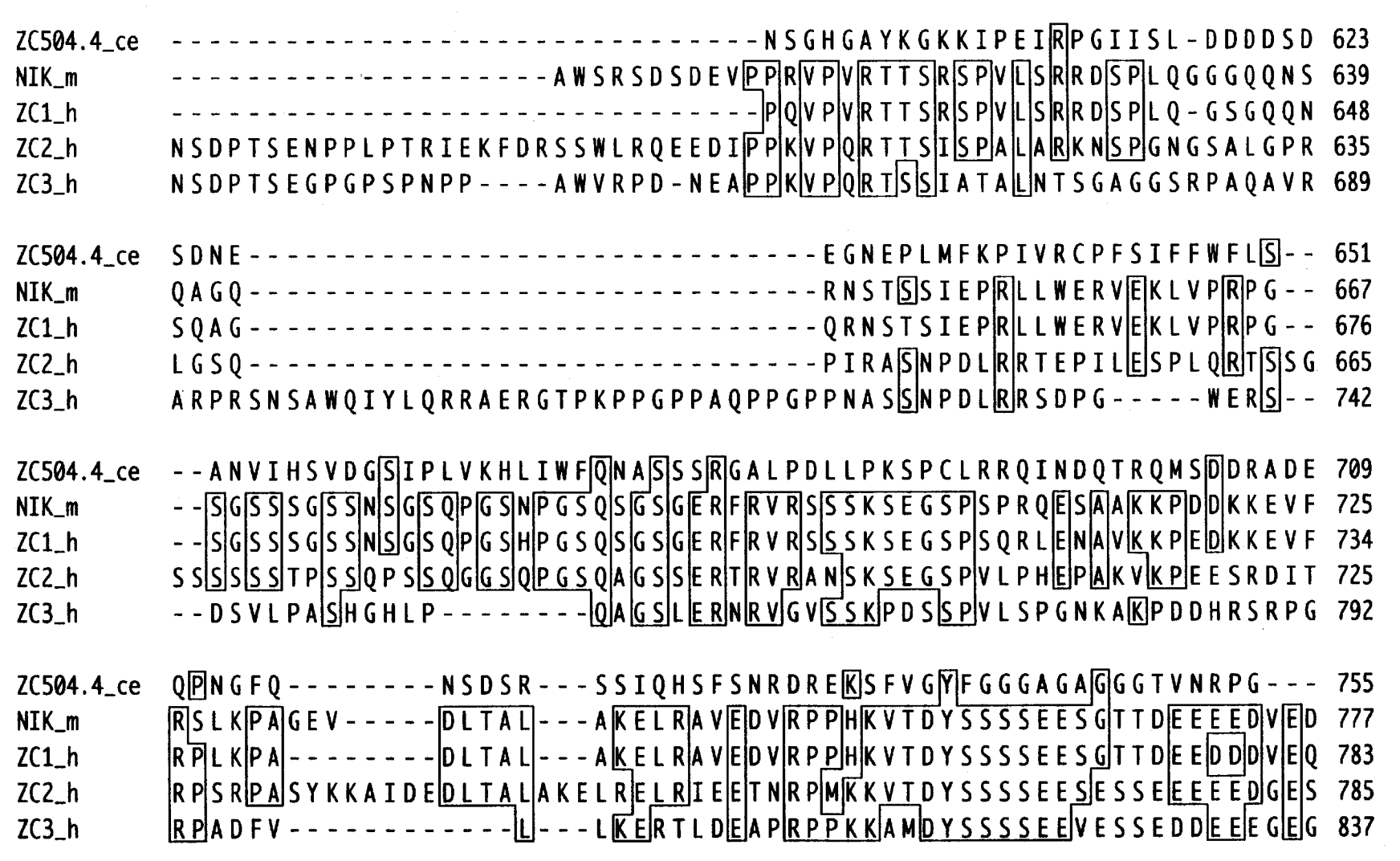
Figure 3F:
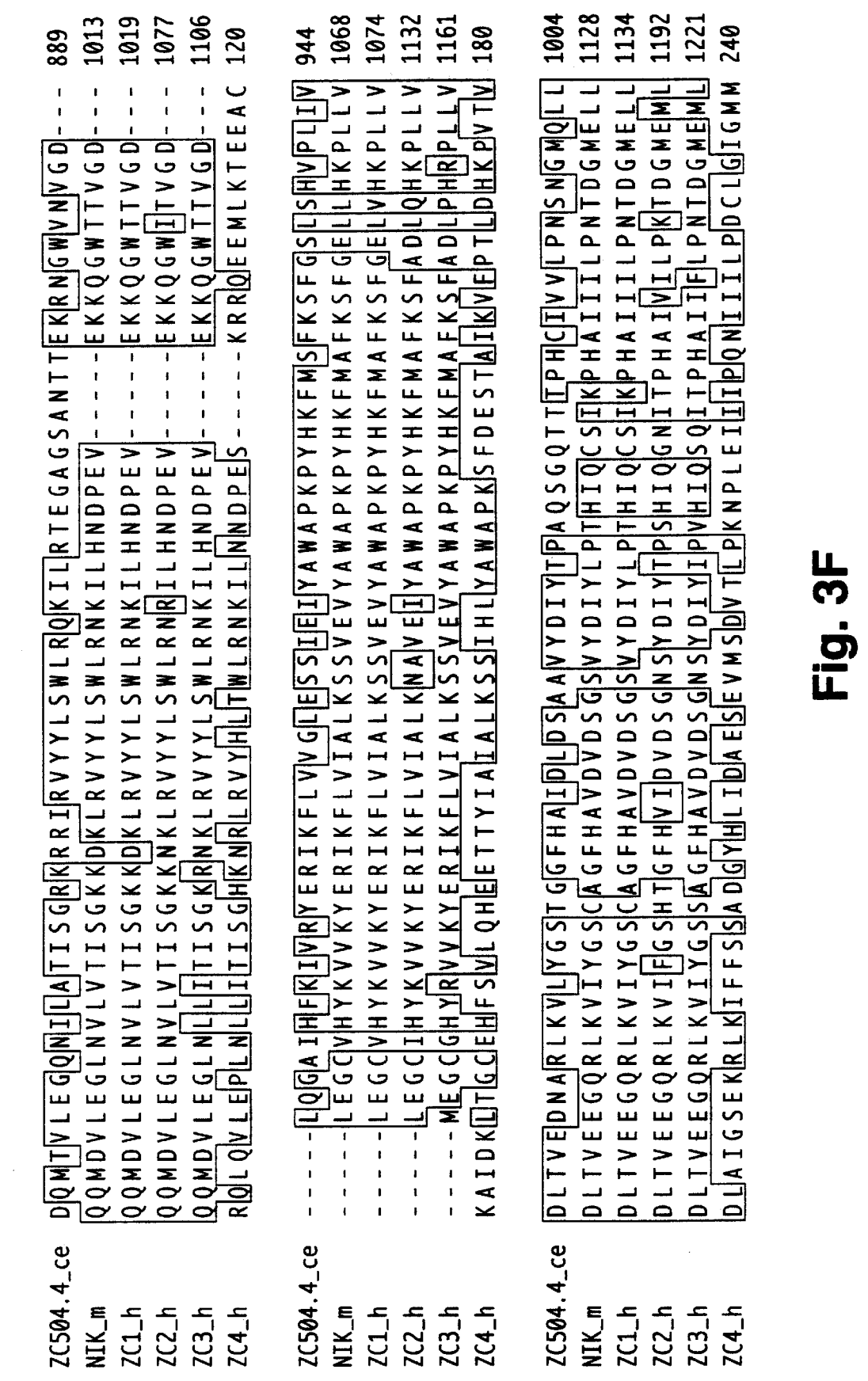

FIGS. 3A, 3B, 3C, 3D, 3E, 3F, and 3G show a multiple sequence alignment of the amino acid sequences (SEQ ID NOS 88–89, 13–16, respectively, in order of appearance) of STE20-ZC family kinases.

FIGS. 4A, 4B, and 4C show a pairwise sequence (SEQ ID NOS 91 & 18, respectively, in order of appearance) alignment of STE20-KHS family kinases.

FIGS. 5A, 5B, 5C, and 5D show a multiple sequence alignment of the amino acid sequences (SEQ ID NOS 90, 22, 24 & 151 respectively, in order of appearance) of STE20-SULU family kinases.

FIGS. 6A, 6B, and 6C show a pairwise sequence (SEQ ID NOS 92 & 26, respectively, in order of appearance) alignment of STE20-GEK family kinases FIGS. 7A, 7B, and 7C show a multiple sequence alignment of the amino acid sequences (SEQ ID NOS 93–95, 29–30 respectively, in order of appearance) of STE20-PAK family kinases.

FIGS. 8A, 8B, 8C, 8D, 8E, 8F and 8G show the amino acid sequences of human STLK2 (SEQ ID NO:5), human STLK3 (SEQ ID NO:6), human STLK4 (SEQ ID NO:7), human STLK5 (SEQ ID NO:8), human ZC1 (SEQ ID NO:13), human ZC2 (SEQ ID NO:14), human ZC3 (SEQ ID NO:15), human ZC4 (SEQ ID NO:16), human KHS2 (SEQ ID NO:18), human SULU1 (SEQ ID NO:22), human SULU3 (SEQ ID NO:23), murine SULU3 (SEQ ID NO:24), human GEK2 (SEQ ID NO:26), human PAK4 (SEQ ID NO:29), and human PAK5 (SEQ ID NO30).

FIGS. 9A, 9B, 9C, 9D, 9E, 9F, 9G, 9H, 9I, 9J, 9K, 9L, 9M, 9N, 9O, 9P, 9Q, 9R, 9S, 9T, 9U, and 9V nucleic acid sequences of human STLK2 (SEQ ID NO:1), human STLK3 (SEQ ID NO:2), human STLK4 (SEQ ID NO:3), human STLK5 (SEQ ID NO:4), human ZC1 (SEQ ID NO:9), human ZC2 (SEQ ID NO:10), human ZC3 (SEQ ID NO:11), human ZC4 (SEQ ID NO:12), human KHS2 (SEQ ID NO:17), human SULU1 (SEQ ID NO:19), human SULU3 (SEQ ID NO:20), murine SULU3 (SEQ ID NO:21), human GEK2 (SEQ ID NO:25), human PAK4 (SEQ ID NO:27), and human PAK5 (SEQ ID NO:28).

FIGS. 10A, 10B, and 10C show the full-length amino acid sequences of human STLK5 (SEQ ID NO: 97), human PAK5 (SEQ ID NO:103), and human ZC4 (SEQ ID NO:105), as well as the partial amino acid sequences of human full-length STLK6 (SEQ ID NO: 99) and human STLK7 (SEQ ID NO:101) and human GEK2 (SEQ ID NO:107).

Figure 11D:
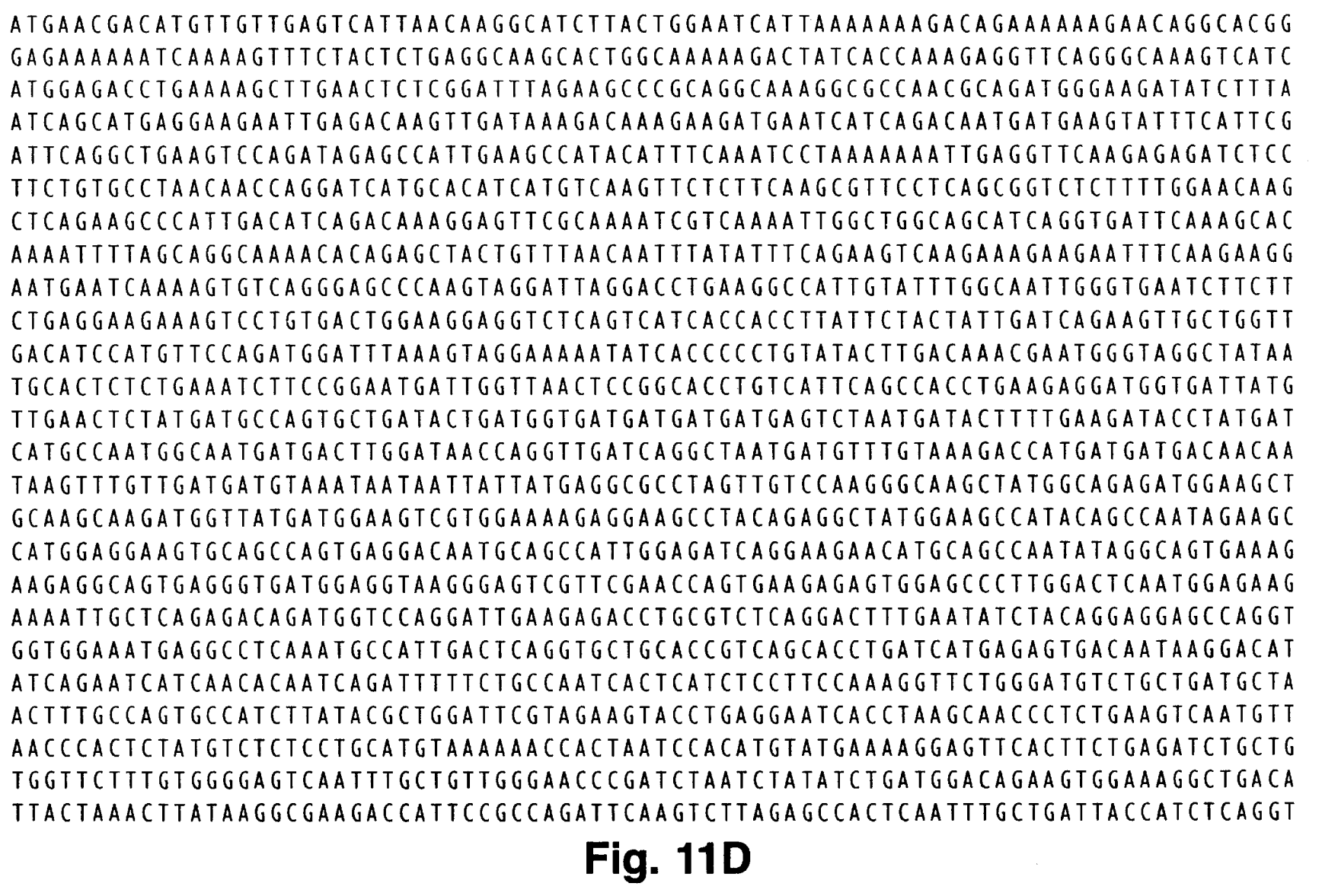
Figure 11F:
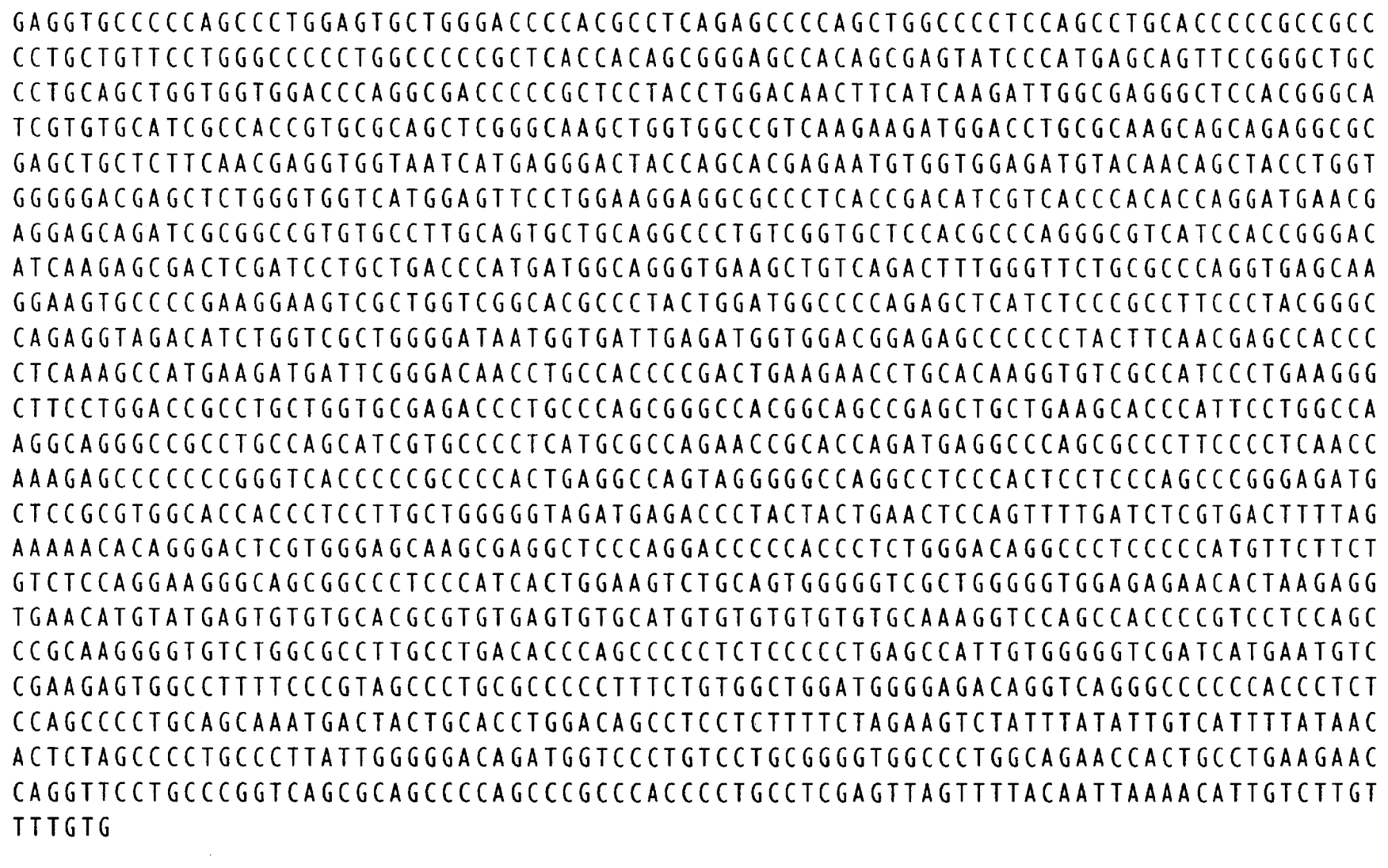

FIGS. 11A, 11B, 11C, 11D, 11E, 11F, 11G, and 11H show the full-length nucleic acid sequences of human STLK5 (SEQ ID NO:96), human PAK5 (SEQ ID NO:102), and human ZC4 (SEQ ID NO:104), as well as the partial nucleic acid sequences of human STLK6 (SEQ ID NO: 98) and human STLK7 (SEQ ID NO: 100) and human GEK2 (SEQ ID NO: 106).

Figure 12A:
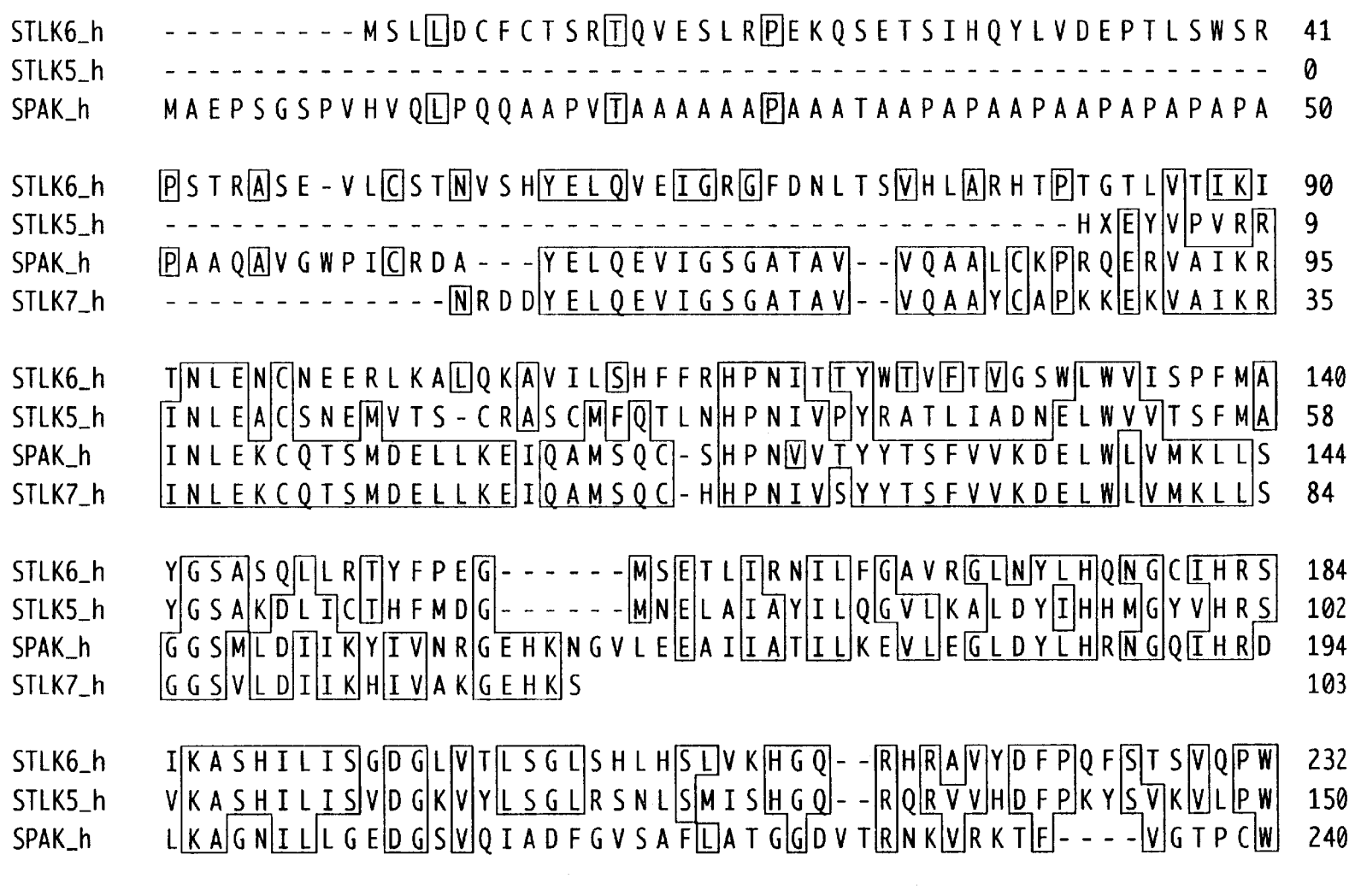

FIGS. 12A, and 12B show a multiple sequence alignment among human SPAK (SEQ ID NO: 153), human STLK6 (SEQ ID NO: 99), human STLK7 (SEQ ID NO: 101) and full-length human STLK5 (SEQ ID NO: 152).

FIGS. 13A, 13B, and 13C show a multiple sequence alignment among human PAK1 (SEQ ID NO: 93), human PAK4 (SEQ ID NO: 29) and human PAK5 (SEQ ID NO: 103).

FIGS. 14A, 14B, and 14C show a pair-wise sequence alignment between human ZC1 (SEQ ID NO:15) and human ZC4 (SEQ ID NO:105).

FIGS. 15A, 15B, and 15C show a pair-wise sequence alignment between LOK1 (SEQ ID NO: 154) and full-length GEK2 (SEQ ID NO: 155).

DETAILED DESCRIPTION OF THE INVENTION

The present invention relates in part to kinase polypeptides, nucleic acids encoding such polypeptides, cells containing such nucleic acids, antibodies to such polypeptides, assays utilizing such polypeptides, and methods relating to all of the foregoing. The present invention is based upon the isolation and characterization of new kinase polypeptides. The polypeptides and nucleic acids may be produced using well-known and standard synthesis techniques when given the sequences presented herein.

The recent elucidation of the DNA sequence of *Saccharomyces cerevesiae* has provided the first complete example of the genetic information contained in a simple eukaryotic organism. Analysis of this yeast genome revealed that it contains at least 113 protein kinases. These kinases were further subdivided into several structurally related groups. One of these newly defined groups was termed the STE20-family to represent its founding member STE20, which is a protein kinase involved in the yeast pheromone response pathway that initiates a protein kinase cascade in response to a G-protein mediated signal. *S. cerevesiae* has two additional members of this family, CLA4, and YOL113W (HRA655).

Several mammalian homologues have recently been identified that belong to the STE20-family, including SOK-1 (human STE20), GC-kinase, KHS, HPK1, NIK, SLK, GEK, PAK1, PAK65, MST1, and CDC7. Furthermore, the Drosophila and the *C. elegans* genome efforts have identified additional protein kinases which belong to the STE20-family, yet have structurally unique extracatalytic domains, including ZC5044 and SULU kinases from *C. elegans*, and NINAC of Drosophila.

STE20-related protein kinases have been implicated as regulating a variety of cellular responses, including response to growth factors or cytokines, oxidative-, UV-, or irradiation-related stress pathways, inflammatory signals (i.e., TNFα), apoptotic stimuli (i.e., Fas), T and B cell costimulation, the control of cytoskeletal architecture, and cellular transformation. Typically, the STE20-related kinases serve as upstream regulators of MAPK cascades. Examples include: HPK1, a protein-serine/threonine kinase (STK) that possesses a STE20-like kinase domain that activates a protein kinase pathway leading to the stress-activated protein kinase SAPK/JNK; PAK1, an STK with an upstream CDC42-binding domain that interacts with Rac and plays a role in cellular transformation through the Ras-MAPK pathway; and murine NIK, which interacts with upstream receptor tyrosine kinases and connects with downstream STE11-family kinases.

The STE20-kinases possess a variety of non-catalytic domains that are believed to interact with upstream regulators. Examples include proline-rich domains for interaction with SH3-containing proteins, or specific domains for interaction with Rac, Rho, and Rab small G-proteins. These interactions may provide a mechanism for cross-talk between distinct biochemical pathways in response to external stimuli such as the activation of a variety of cell surface receptors, including tyrosine kinases, cytokine receptors, TNF receptor, Fas, T cell receptors, CD28, or CD40.

I. The Nucleic Acids of the Invention

Included within the scope of this invention are the functional equivalents of the herein-described isolated nucleic acid molecules. The degeneracy of the genetic code permits substitution of certain codons by other codons that specify the same amino acid and hence would give rise to the same protein. The nucleic acid sequence can vary substantially since, with the exception of methionine and tryptophan, the known amino acids can be coded for by more than one codon. Thus, portions or all of the kinase genes of the invention could be synthesized to give a nucleic acid sequence significantly different from that shown in SEQ ID NO:1, SEQ ID NO:2, SEQ ID NO:3, SEQ ID NO:9, SEQ ID NO:10, SEQ ID NO:11, SEQ ID NO:17, SEQ ID NO:19, SEQ ID NO:20, SEQ ID NO:21, SEQ ID NO:27, SEQ ID NO:96, SEQ ID NO:98, SEQ ID NO:100, SEQ ID NO:102, SEQ ID NO:104, and SEQ ID NO:106. The encoded amino acid sequence thereof would, however, be preserved.

In addition, the nucleic acid sequence may comprise a nucleotide sequence which results from the addition, deletion or substitution of at least one nucleotide to the 5'-end and/or the 3'-end of the nucleic acid formula shown in SEQ ID NO:1, SEQ ID NO:2, SEQ ID NO:3, SEQ ID NO:9, SEQ ID NO:10, SEQ ID NO:11, SEQ ID NO:17, SEQ ID NO:19, SEQ ID NO:20, SEQ ID NO:21, SEQ ID NO:27, SEQ ID NO:96, SEQ ID NO:98, SEQ ID NO:100, SEQ ID NO:102, SEQ ID NO:104, or SEQ ID NO:106, or a derivative thereof. Any nucleotide or polynucleotide may be used in this regard, provided that its addition, deletion or substitution does not alter the amino acid sequence of SEQ ID NO:5, SEQ ID NO:6, SEQ ID NO:7, SEQ ID NO:13, SEQ ID NO:14, SEQ ID NO:15, SEQ ID NO:18, SEQ ID NO:22, SEQ ID NO:23, SEQ ID NO:24, SEQ ID NO:29, SEQ ID NO:97, SEQ ID NO:99, SEQ ID NO:101, SEQ ID NO:103, SEQ ID NO:105, or SEQ ID NO:107, which is encoded by the nucleotide sequence. For example, the present invention is intended to include any nucleic acid sequence resulting from the addition of ATG as an initiation codon at the 5'-end of the inventive nucleic acid sequence or its derivative, or from the addition of TTA, TAG or TGA as a termination codon at the 3'-end of the inventive nucleotide sequence or its derivative. Moreover, the nucleic acid molecule of the present invention may, as necessary, have restriction endonuclease recognition sites added to its 5'-end and/or 3'-end.

Such functional alterations of a given nucleic acid sequence afford an opportunity to promote secretion and/or processing of heterologous proteins encoded by foreign nucleic acid sequences fused thereto. All variations of the nucleotide sequence of the kinase genes of the invention and fragments thereof permitted by the genetic code are, therefore, included in this invention.

Further, it is possible to delete codons or to substitute one or more codons with codons other than degenerate codons to produce a structurally modified polypeptide, but one which has substantially the same utility or activity as the polypeptide produced by the unmodified nucleic acid molecule. As recognized in the art, the two polypeptides are functionally equivalent, as are the two nucleic acid molecules that give rise to their production, even though the differences between the nucleic acid molecules are not related to the degeneracy of the genetic code.

Mammalian STLK2

The full-length human STLK2 cDNA (SEQ ID NO:1) is 3268 bp long and consists of a 1248 bp open reading frame (ORF) flanked by a 181 bp 5' untranslated region (UTR; 1–181) and a 1784 bp 3' UTR (1433–3216) that is followed by a 52 nucleotide polyadenylated region. A polyadenylation signal (AATAAA) is found at positions (3193–3198). The sequence flanking the first ATG conforms to the Kozak consensus (Kozak, M., Nucleic Acids Res. 15, 8125–8148 (1987)) for an initiating methionine, and is believed to be the translational start site for STLK2. Furthermore, human STLK2 and the related SOK-1 and MST3 proteins conserve the amino acid sequence immediately following this presumed initiating methionine.

Several EST fragments span the complete STLK2 sequence with AA191319 at the 5' end and W16504 at the 3' end.

Mammalian STLK3

The partial human STLK3 cDNA (SEQ ID NO:2) is 3030 bp long and consists of a 1548 bp ORF flanked by a 1476 bp 3' UTR (1550–3025) and a 5 nucleotide polyadenylated region. A potential polyadenylation signal (AATAAA) begins at position 3004. Since the coding region is open throughout the 5' extent of this sequence, this is apparently a partial cDNA clone lacking the N-terminal start methionine.

Multiple EST fragments span the complete STLK3 sequence with AA278967 at the 5' end and AA628477 and others at the 3' end.

Mammalian STLK4

The partial human STLK4 cDNA (SEQ ID NO:3) is 3857 bp long and consists of a 1242 bp ORF flanked by a 2596 bp 3' UTR (1244–3839) and an 18 nucleotide polyadenylated region. A potential polyadenylation signal (AATAAA) is found at positions 2181–3822. Since the coding region is open throughout the 5' extent of this sequence, this is apparently a partial cDNA clone lacking the N-terminal start methionine. A near full-length murine STLK4 cDNA is represented in the 1773 bp EST AA117438. It extends an additional 21 nucleotides 5' of the human STLK4 consensus, but since its coding region is open throughout the 5' extent of the sequence, this is also apparently a partial cDNA clone lacking the N-terminal start methionine.

Several EST fragments span the complete STLK3 sequence with AA297759 at the 5' end and AA100484 and others at the 3' end.

Mammalian STLK5

The full-length human STLK5 cDNA (SEQ ID NO:96) is 2110 bp long and consists of a 1119 bp ORF flanked by a 229 bp 5' UTR and a 762 bp 3' UTR. The sequence flanking the first ATG conforms to the Kozak consensus (supra) for an initiating methionine, and is believed to be the translational start site for STLK5. Several EST fragments span the complete STLK5 sequence with AA297059 and F07734 at the 5' end, and R46686 and F03423 and others at the 3' end.

Mammalian STLK6

The full-length human STLK6 cDNA (SEQ ID NO:98) is 2,001 bp long and consists of a 1,254 bp ORF flanked by a 75 bp 5' UTR and a 673 bp 3' UTR. The sequence flanking the first ATG conforms to the Kozak consensus (supra) for an initiating methionine, and is believed to be the translational start site for STLK6.

Mammalian STLK7

The partial human STLK7 cDNA (SEQ ID NO:100) is 311 bp long and consists of a 309 bp ORF. Since the coding region is open throughout both the 5' and 3' extent of this sequence, this is apparently a partial cDNA clone lacking the N-terminal start methionine and C-terminal stop codon.

Mammalian ZC1

The full-length human ZC1 cDNA (SEQ ID NO:9) is 3798 bp long and consists of a 3717 bp ORF (7–3723) flanked by a 6 bp 5' UTR and a 75 bp (3724–3798) 3' UTR. No polyadenylation signal (AATAAA) or polyadenylated region are present in the 3' UTR. The sequence flanking the first ATG conforms to the Kozak consensus for an initiating methionine, and is believed to be the translational start site for human ZC1.

Multiple EST fragments (W81656) match the 3' end of the human ZC1 gene, but at the time of filing, the inventors believe that none exist in GenBank or the EST database that match its 5' end.

Mammalian ZC2

The partial human ZC2 cDNA (SEQ ID NO:10) is 4055 bp long and consists of a 3891 bp ORF (1–3891) and a 164 bp (3892–4055) 3' UTR. Since the coding region is open throughout the 5' extent of this sequence, this is apparently a partial cDNA clone lacking the N-terminal start methionine. No polyadenylation signal (AATAAA) or polyadenylated region are present in the 3' UTR.

Multiple EST fragments (R51245) match the 3' end of the human ZC2 gene, but at the time of filing, the inventors believe that none exist in GenBank or the EST database that match its 5' end.

Mammalian ZC3

The partial human ZC3 cDNA (SEQ ID NO:11) is 4133 bp long and consists of a 3978 bp ORF (1–3978) and a 152 bp (3979–4133) 3' UTR region. Since the coding region is open throughout the 5' extent of this sequence, this is apparently a partial cDNA clone lacking the N-terminal start methionine. No polyadenylation signal (AATAAA) or polyadenylated region are present in the 3' UTR.

Multiple EST fragments (R54563) match the 3' end of the human ZC3 gene, but at the time of filing, the inventors believe that none exist in GenBank or the EST database that match its 5' end.

Mammalian ZC4

The full-length human ZC4 cDNA (SEQ ID NO:104) is 3,684 bp long and was originally assembled from X chromosome genomic DNA sequence.

Multiple EST fragments (R98571) match the 3' end of the human ZC4 gene, but at the time of filing, the inventors believe that none exist in GenBank or the EST database that match its 5' end. ZC4 gene is also contained within the human genomic clone Z83850.

Mammalian KHS2

The full-length human KHS2 cDNA (SEQ ID NO:17) is 4023 bp long and consists of a 2682 bp ORF (6–2687) flanked by a 5 bp (1–5) 5' UTR and a 1336 bp (2688–4023) 3' UTR. A potential polyadenylation signal (AATAAA) is found at positions 4008–4013. No polyadenylated region is present in the 3' UTR. The sequence flanking the first ATG conforms to the Kozak consensus for an initiating methionine, and is believed to be the translational start site for human KHS2.

Multiple EST fragments match the 5' end (AA446022) as well as the 3' end (R37625) of the human KHS2 gene.

Mammalian SULU1

The full-length human SULU1 cDNA (SEQ ID NO:19) is 4177 bp long and consists of a 2694 bp ORF (415–3108) flanked by a 414 bp (1–414) 5' UTR and a 1069 bp (3109–4177) 3' UTR followed by a 19 nucleotide polydenylated region. A potential polyadenylation signal (AATAAA) is found at positions 4164–4169. The sequence flanking the first ATG conforms to the Kozak consensus for an initiating methionine, and is believed to be the translational start site for human SULU1.

Multiple EST fragments match the 5' end (N27153) as well as the 3' end (R90908) of the human SULU1 gene.

Mammalian (Murine) SULU3

The partial murine SULU3 cDNA (SEQ ID NO:21) is 2249 bp long and consists of a 2244 bp ORF (6–2249) flanked by a 5 bp (1–5) 5' UTR. The sequence flanking the first ATG conforms to the Kozak consensus for an initiating methionine, and is believed to be the translational start site for murine SULU3. The 3' end of the murine SULU3 cDNA shares 90% DNA sequence identity over 1620 nucleotides with human SULU3, suggesting that these two genes are functional orthologues.

One EST fragment (AA446022) matches the 3' end of the partial murine SULU3 gene, but at the time of filing, the inventors believe that none exist in GenBank or the EST database that match its 5' end.

Mammalian (Human) SULU3

The partial human SULU3 cDNA (SEQ ID NO:20) is 3824 bp long and consists of a 2358 bp ORF (2–2359) flanked by a 1465 bp (2360–3824) 3' UTR followed by a 19 nucleotide polydenylated region. A potential polyadenylation signal (AATAAA) is found at positions 2602–2607. Since the coding region is open throughout the 5' extent of this sequence, this is apparently a partial cDNA clone lacking the N-terminal start methionine. The 5' end of the human SULU3 cDNA shares 90% DNA sequence identity over 1620 nucleotides with murine SULU3, suggesting that these two genes are functional orthologues.

Multiple EST fragments (R02283) match the 3' end of the human SULU3 gene, but at the time of filing, the inventors believe that none exist in GenBank or the EST database that match its 5' end.

Mammalian GEK2

The full-length human GEK2 cDNA (SEQ ID NO:106) is 2962 bp long and consists of a 2737 bp ORF (59–2795) flanked by a 58 bp (1–58) 5' UTR. The sequence flanking the first ATG conforms to the Kozak consensus for an initiating methionine, and is believed to be the translational start site for human GEK2.

Multiple EST fragments (AA465671) match the 5' end, but at the time of filing, the inventors believe that only one (AA380492) matches the 3' end of the human GEK2 gene.

Mammalian PAK4

The full-length human PAK4 cDNA (SEQ ID NO:27) is 3604 bp long and consists of a 2043 bp ORF (143–2185) flanked by a 142 bp (1–142) 5' UTR and a 1419 3' UTR followed by a 22 nucleotide polydenylated region. A potential polyadenylation signal (AATTAAA) is found at positions 3582–3588. The sequence flanking the first ATG conforms to the Kozak consensus for an initiating methionine, and is believed to be the translational start site for human PAK4.

Multiple EST fragments (AA535791) match the 3' end of the human PAK4 gene, but at the time of filing, the inventors believe that none exist in GenBank or the EST database that match its 5' end.

Mammalian PAK5

The full-length human PAK5 cDNA (SEQ ID NO:102) is 2806 bp long and consists of a 1773 bp ORF flanked by a 201 bp 5' UTR and a 833 bp 3' UTR. The sequence flanking the first ATG conforms to the Kozak consensus (supra) for an initiating methionine, and is believed to be the translational start site for PAK5.

Multiple EST fragments (AA442867) match the 3' end of the human PAK5 gene, but at the time of filing, the inventors believe that none exist in GenBank or the EST database that match its 5' end.

II. Nucleic Acid Probes, Methods, and Kits for Detection of STE20-Related Kinases A nucleic acid probe of the present invention may be used to probe an appropriate chromosomal or cDNA library by usual hybridization methods to obtain other nucleic acid molecules of the present invention. A chromosomal DNA or cDNA library may be prepared from appropriate cells according to recognized methods in the art (cf. "Molecular Cloning: A Laboratory Manual", second edition, Cold Spring Harbor Laboratory, Sambrook, Fritsch, & Maniatis, eds., 1989).

In the alternative, chemical synthesis can be carried out in order to obtain nucleic acid probes having nucleotide sequences which correspond to N-terminal and C-terminal portions of the amino acid sequence of the polypeptide of interest. The synthesized nucleic acid probes may be used as primers in a polymerase chain reaction (PCR) carried out in accordance with recognized PCR techniques, essentially according to PCR Protocols, "A Guide to Methods and Applications", Academic Press, Michael, et al., eds., 1990, utilizing the appropriate chromosomal or cDNA library to obtain the fragment of the present invention.

One skilled in the art can readily design such probes based on the sequence disclosed herein using methods of computer alignment and sequence analysis known in the art ("Molecular Cloning: A Laboratory Manual", 1989, supra). The hybridization probes of the present invention can be labeled by standard labeling techniques such as with a radiolabel, enzyme label, fluorescent label, biotin-avidin label, chemiluminescence, and the like. After hybridization, the probes may be visualized using known methods.

The nucleic acid probes of the present invention include RNA, as well as DNA probes, such probes being generated using techniques known in the art. The nucleic acid probe may be immobilized on a solid support. Examples of such solid supports include, but are not limited to, plastics such as polycarbonate, complex carbohydrates such as agarose and sepharose, and acrylic resins, such as polyacrylamide and latex beads. Techniques for coupling nucleic acid probes to such solid supports are well known in the art.

The test samples suitable for nucleic acid probing methods of the present invention include, for example, cells or nucleic acid extracts of cells, or biological fluids. The samples used in the above-described methods will vary based on the assay format, the detection method and the nature of the tissues, cells or extracts to be assayed. Methods for preparing nucleic acid extracts of cells are well known in the art and can be readily adapted in order to obtain a sample which is compatible with the method utilized.

One method of detecting the presence of nucleic acids of the invention in a sample comprises (a) contacting said sample with the above-described nucleic acid probe under conditions such that hybridization occurs, and (b) detecting the presence of said probe bound to said nucleic acid molecule. One skilled in the art would select the nucleic acid probe according to techniques known in the art as described above. Samples to be tested include but should not be limited to RNA samples of human tissue.

A kit for detecting the presence of nucleic acids of the invention in a sample comprises at least one container means having disposed therein the above-described nucleic acid probe. The kit may further comprise other containers comprising one or more of the following: wash reagents and reagents capable of detecting the presence of bound nucleic acid probe. Examples of detection reagents include, but are not limited to radiolabelled probes, enzymatic labeled probes (horseradish peroxidase, alkaline phosphatase), and affinity labeled probes (biotin, avidin, or steptavidin).

In detail, a compartmentalized kit includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the test sample, a container which contains the probe or primers used in the assay, containers which contain wash reagents (such as phosphate buffered saline, Tris-buffers, and the like), and containers which contain the reagents used to detect the hybridized probe, bound antibody, amplified product, or the like. One skilled in the art will readily recognize that the nucleic acid probes described in the present invention can readily be incorporated into one of the established kit formats which are well known in the art.

III. DNA Constructs Comprising a STE20-Related Nucleic Acid Molecule and Cells Containing These Constructs The present invention also relates to a recombinant DNA molecule comprising, 5' to 3', a promoter effective to initiate transcription in a host cell and the above-described nucleic acid molecules. In addition, the present invention relates to a recombinant DNA molecule comprising a vector and an above-described nucleic acid molecule. The present invention also relates to a nucleic acid molecule comprising a transcriptional region functional in a cell, a sequence complementary to an RNA sequence encoding an amino acid sequence corresponding to the above-described polypeptide, and a transcriptional termination region functional in said cell. The above-described molecules may be isolated and/or purified DNA molecules.

The present invention also relates to a cell or organism that contains an above-described nucleic acid molecule and thereby is capable of expressing a polypeptide. The polypeptide may be purified from cells which have been altered to express the polypeptide. A cell is said to be "altered to express a desired polypeptide" when the cell, through genetic manipulation, is made to produce a protein which it normally does not produce or which the cell normally produces at lower levels. One skilled in the art can readily adapt procedures for introducing and expressing either genomic, cDNA, or synthetic sequences into either eukaryotic or prokaryotic cells.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene sequence expression. The precise nature of the regulatory regions needed for gene sequence expression may vary from organism to organism, but shall in general include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like.

If desired, the non-coding region 3' to the sequence encoding a kinase of the invention may be obtained by the above-described methods. This region may be retained for its transcriptional termination regulatory sequences, such as termination and polyadenylation. Thus, by retaining the 3'-region naturally contiguous to the DNA sequence encoding a kinase of the invention, the transcriptional termination signals may be provided. Where the transcriptional termination signals are not satisfactorily functional in the expression host cell, then a 3' region functional in the host cell may be substituted.

Two DNA sequences (such as a promoter region sequence and a sequence encoding a kinase of the invention) are said to be operably linked if the nature of the linkage between the two DNA sequences does not (1) result in the introduction of a frame-shift mutation, (2) interfere with the ability of the promoter region sequence to direct the transcription of a gene sequence encoding a kinase of the invention, or (3) interfere with the ability of the gene sequence of a kinase of the invention to be transcribed by the promoter region sequence. Thus, a promoter region would be operably linked to a DNA sequence if the promoter were capable of effecting transcription of that DNA sequence. Thus, to express a gene encoding a kinase of the invention, transcriptional and translational signals recognized by an appropriate host are necessary.

The present invention encompasses the expression of a gene encoding a kinase of the invention (or a functional derivative thereof) in either prokaryotic or eukaryotic cells. Prokaryotic hosts are, generally, very efficient and convenient for the production of recombinant proteins and are, therefore, one type of preferred expression system for kinases of the invention. Prokaryotes most frequently are represented by various strains of $E.$ $coli$. However, other microbial strains may also be used, including other bacterial strains.

In prokaryotic systems, plasmid vectors that contain replication sites and control sequences derived from a species compatible with the host may be used. Examples of suitable plasmid vectors may include pBR322, pUC118, pUC119 and the like; suitable phage or bacteriophage vectors may include γgt10, γgt11 and the like; and suitable virus vectors may include pMAM-neo, pKRC and the like. Preferably, the selected vector of the present invention has the capacity to replicate in the selected host cell.

Recognized prokaryotic hosts include bacteria such as $E.$ $coli$, Bacillus, Streptomyces, Pseudomonas, Salmonella, Serratia, and the like. However, under such conditions, the polypeptide will not be glycosylated. The prokaryotic host must be compatible with the replicon and control sequences in the expression plasmid.

To express a kinase of the invention (or a functional derivative thereof) in a prokaryotic cell, it is necessary to operably link the sequence encoding the kinase of the invention to a functional prokaryotic promoter. Such promoters may be either constitutive or, more preferably, regulatable (i.e., inducible or derepressible). Examples of constitutive promoters include the int promoter of bacteriophage λ, the bla promoter of the β-lactamase gene sequence of pBR322, and the cat promoter of the chloramphenicol acetyl transferase gene sequence of pPR325, and the like. Examples of inducible prokaryotic promoters include the major right and left promoters of bacteriophage λ ($P_L$ and $P_R$), the trp, recA, λacZ, λacI, and gal promoters of $E.$ $coli$, the α-amylase (Ulmanen et al., J. Bacteriol. 162:176–182, 1985) and the ζ-28-specific promoters of $B.$ $subtilis$ (Gilman et al., Gene Sequence 32:11–20, 1984), the promoters of the bacteriophages of Bacillus (Gryczan, In: The Molecular Biology of the Bacilli, Academic Press, Inc., NY, 1982), and Streptomyces promoters (Ward et al., Mol. Gen. Genet. 203:468–478, 1986). Prokaryotic promoters are reviewed by Glick (Ind. Microbiot. 1:277–282, 1987), Cenatiempo (Biochimie 68:505–516, 1986), and Gottesman (Ann. Rev. Genet. 18:415–442, 1984).

Proper expression in a prokaryotic cell also requires the presence of a ribosome-binding site upstream of the gene sequence-encoding sequence. Such ribosome-binding sites are disclosed, for example, by Gold et al. (Ann. Rev. Microbiol. 35:365–404, 1981). The selection of control sequences, expression vectors, transformation methods, and the like, are dependent on the type of host cell used to express the gene. As used herein, "cell", "cell line", and "cell culture" may be used interchangeably and all such designations include progeny. Thus, the words "transformants" or "transformed cells" include the primary subject cell and cultures derived therefrom, without regard to the number of transfers. It is also understood that all progeny may not be precisely identical in DNA content, due to deliberate or inadvertent mutations. However, as defined, mutant progeny have the same functionality as that of the originally transformed cell.

Host cells which may be used in the expression systems of the present invention are not strictly limited, provided that they are suitable for use in the expression of the kinase polypeptide of interest. Suitable hosts may often include eukaryotic cells. Preferred eukaryotic hosts include, for example, yeast, fungi, insect cells, mammalian cells either in vivo, or in tissue culture. Mammalian cells which may be useful as hosts include. HeLa cells, cells of fibroblast origin such as VERO or CHO-K1, or cells of lymphoid origin and their derivatives. Preferred mammalian host cells include SP2/0 and J558L, as well as neuroblastoma cell lines such as IMR 332, which may provide better capacities for correct post-translational processing.

In addition, plant cells are also available as hosts, and control sequences compatible with plant cells are available, such as the cauliflower mosaic virus 35S and 19S, and nopaline synthase promoter and polyadenylation signal sequences. Another preferred host is an insect cell, for example the Drosophila larvae. Using insect cells as hosts, the Drosophila alcohol dehydrogenase promoter can be used (Rubin, Science 240:1453–1459, 1988). Alternatively, baculovirus vectors can be engineered to express large amounts of kinases of the invention in insect cells (Jasny, Science 238:1653, 1987; Miller et al., In: Genetic Engineering, Vol. 8, Plenum, Setlow et al., eds., pp. 277–297, 1986).

Any of a series of yeast expression systems can be utilized which incorporate promoter and termination elements from the actively expressed sequences coding for glycolytic enzymes that are produced in large quantities when yeast are grown in mediums rich in glucose. Known glycolytic gene sequences can also provide very efficient transcriptional control signals. Yeast provides substantial advantages in that it can also carry out post-translational modifications. A number of recombinant DNA strategies exist utilizing strong promoter sequences and high copy number plasmids which can be utilized for production of the desired proteins in yeast. Yeast recognizes leader sequences on cloned mammalian genes and secretes peptides bearing leader sequences (i.e., pre-peptides). Several possible vector systems are available for the expression of kinases of the invention in a mammalian host.

A wide variety of transcriptional and translational regulatory sequences may be employed, depending upon the nature of the host. The transcriptional and translational regulatory signals may be derived from viral sources, such as adenovirus, bovine papilloma virus, cytomegalovirus, simian virus, or the like, where the regulatory signals are associated with a particular gene sequence which has a high level of expression. Alternatively, promoters from mammalian expression products, such as actin, collagen, myosin, and the like, may be employed. Transcriptional initiation regulatory signals may be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation.

Expression of kinases of the invention in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et al., J. Mol. Appl. Gen. 1:273–288, 1982); the TK promoter of Herpes virus (McKnight, Cell 31:355–365, 1982); the SV40 early promoter (Benoist et al., Nature (London) 290:304–31, 1981); and the yeast gal4 gene sequence promoter (Johnston et al., Proc. Natl. Acad. Sci. (USA) 79:6971–6975, 1982; Silver et al., Proc. Natl. Acad. Sci. (USA) 81:5951–5955, 1984).

Translation of eukaryotic mRNA is initiated at the codon which encodes the first methionine. For this reason it is preferable to ensure that the linkage between a eukaryotic promoter and a DNA sequence which encodes a kinase of the invention (or a functional derivative thereof) does not contain any intervening codons which are capable of encoding a methionine (i.e., AUG). The presence of such codons results either in the formation of a fusion protein (if the AUG codon is in the same reading frame as the kinase of the invention coding sequence) or a frame-shift mutation (if the AUG codon is not in the same reading frame as the kinase of the invention coding sequence).

A nucleic acid molecule encoding a kinase of the invention and an operably linked promoter may be introduced into a recipient prokaryotic or eukaryotic cell either as a non-replicating DNA or RNA molecule, which may either be a linear molecule or, more preferably, a closed covalent circular molecule. Since such molecules are incapable of autonomous replication, the expression of the gene may occur through the transient expression of the introduced sequence. Alternatively, permanent expression may occur through the integration of the introduced DNA sequence into the host chromosome.

A vector may be employed which is capable of integrating the desired gene sequences into the host cell chromosome. Cells which have stably integrated the introduced DNA into their chromosomes can be selected by also introducing one or more markers which allow for selection of host cells which contain the expression vector. The marker may provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements may also be needed for optimal synthesis of mRNA. These elements may include splice signals, as well as transcription promoters, enhancers, and termination signals. cDNA expression vectors incorporating such elements include those described by Okayama (Mol. Cell. Biol. 3:280-, 1983).

The introduced nucleic acid molecule can be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred prokaryotic vectors include plasmids such as those capable of replication in *E. coli* (such as, for example, pBR322, ColE1, pSC101, pACYC 184, πVX; "Molecular Cloning: A Laboratory Manual", 1989, supra). Bacillus plasmids include pC194, pC221, pT127, and the like (Gryczan, In: The Molecular Biology of the Bacilli, Academic Press, NY, pp. 307–329, 1982). Suitable Streptomyces plasmids include p1J101 (Kendall et al., J. Bacteriol. 169:4177–4183, 1987), and streptomyces bacteriophages such as φC31 (Chater et al., In: Sixth International Symposium on Actinomycetales Biology, Akademiai Kaido, Budapest, Hungary, pp. 45–54, 1986). Pseudomonas plasmids are reviewed by John et al. (Rev. Infect. Dis. 8:693–704, 1986), and Izaki (Jpn. J. Bacteriol. 33:729–742, 1978).

Preferred eukaryotic plasmids include, for example, BPV, vaccinia, SV40, 2-micron circle, and the like, or their derivatives. Such plasmids are well known in the art (Botstein et al., Miami Wntr. Symp. 19:265–274, 1982; Broach, In: "The Molecular Biology of the Yeast Saccharomyces: Life Cycle and Inheritance", Cold Spring Harbor Laboratory, Cold Spring Harbor, N.Y., p. 445–470, 1981; Broach, Cell 28:203–204, 1982; Bollon et al., J. Clin. Hematol. Oncol. 10:39–48, 1980; Maniatis, In: Cell Biology: A Comprehensive Treatise, Vol. 3, Gene Sequence Expression, Academic Press, NY, pp. 563–608, 1980).

Once the vector or nucleic acid molecule containing the construct(s) has been prepared for expression, the DNA construct(s) may be introduced into an appropriate host cell by any of a variety of suitable means, i.e., transformation, transfection, conjugation, protoplast fusion, electroporation, particle gun technology, calcium phosphate-precipitation, direct microinjection, and the like. After the introduction of the vector, recipient cells are grown in a selective medium, which selects for the growth of vector-containing cells. Expression of the cloned gene(s) results in the production of a kinase of the invention, or fragments thereof. This can take place in the transformed cells as such, or following the induction of these cells to differentiate (for example, by administration of bromodeoxyuracil to neuroblastoma cells or the like). A variety of incubation conditions can be used to form the peptide of the present invention. The most preferred conditions are those which mimic physiological conditions.

IV. The Proteins of the Invention

A variety of methodologies known in the art can be utilized to obtain the polypeptides of the present invention. The polypeptides may be purified from tissues or cells that naturally produce the polypeptides. Alternatively, the above-described isolated nucleic acid fragments could be used to express the kinases of the invention in any organism. The samples of the present invention include cells, protein extracts or membrane extracts of cells, or biological fluids. The samples will vary based on the assay format, the detection method, and the nature of the tissues, cells or extracts used as the sample.

Any eukaryotic organism can be used as a source for the polypeptides of the invention, as long as the source organism naturally contains such polypeptides. As used herein, "source organism" refers to the original organism from which the amino acid sequence of the subunit is derived, regardless of the organism the subunit is expressed in and ultimately isolated from.

One skilled in the art can readily follow known methods for isolating proteins in order to obtain the polypeptides free of natural contaminants. These include, but are not limited to: size-exclusion chromatography, HPLC, ion-exchange chromatography, and immuno-affinity chromatography.

Mammalian STLK2

Analysis of the deduced amino acid sequence predicts STLK2 to be an intracellular serine/threonine kinase, lacking both a signal sequence and transmembrane domain. STLK2 contains a 21 amino acid N-terminal domain, a 253 amino acid catalytic domain with all the motifs characteristic of a serine/threonine kinase, followed by a 142 amino acid C-terminal domain.

STLK2 is most closely related to human STE20-subfamily kinases, MST3 (GB:AF024636) and SOK-1 (GB:X99325) and a C. elegans kinase yk34b11.5 (GB:U53153) sharing 72.7%, 68.7%, and 69.3% amino acid identity, respectively.

The 21 amino acid N-terminal domain of human STLK2 is 71.4% identical to the N-terminus of MST3 (GB:AF024636) Human STLK2 lacks a glycine residue at position 2, and is therefore unlikely to undergo myristylation. A Smith-Waterman search of the nonredundant protein database does not reveal any significant homologies that might suggest a potential function for this domain.

The 253 amino acid catalytic domain of human STLK2 is most related to human SOK-1 (X99325), MST3 (GB:AF024636), C. elegans yk32b11.5 (GB:U53153), and STLK3 (SEQ ID NO:6) sharing 88.9%, 87.4%, 78.3%, and 49% amino identity respectively, placing it in the STLK-subfamily of STE20-related kinases. The STLK2 kinase domain displayed lesser homology to other STE20-related kinases including: 55.9% to human MST2 (GB:U26424), 49.2% to human GCK (GB:U07349), 49.2% to human KHS1 (GB:U77129), and 44.2% to human HPK1 (GB:U66464). The activation loop of human STLK2 catalytic domain is identical to that of human SOK-1 and MST3 including the presence of four potential threonine phosphorylation sites that could serve an autoregulatory role on kinase activity.

The 142 amino acid C-terminal domain of human STLK2 is most related to human SOK-1 (X99325), MST3 (GB:AF024636), and C. elegans yk32b11.5 (GB:U53153), sharing 39.9%, 39.9%, and 33.3% amino acid identity, respectively. This C-terminal domain shares some significant amino acid similarity to the C-terminal domains of the related human STLK3 (SEQ ID NO:6) and STLK4 (SEQ ID NO:7).

The C-terminus of the related human SOK-1 (GB:X99325) kinase has been shown to be inhibitory to the catalytic activity of this kinase (Pombo, C. M., Bonventre, J. V., Molnar, A., Kyriakis, J. and Force, T. EMBO J. 15, 4537–4546 (1996)). Based on the sequence identity between the C-termini of human SOK-1 (GB:X99325) and human STLK2 (39.2%), the C-terminus of human STLK2 may also function as an inhibitory domain for its kinase.

Mammalian STLK3

The 3030 bp human STLK3 nucleotide sequence of the partial cDNA clone encodes a polypeptide of 516 amino acids (SEQ ID NO:6) with a predicted molecular mass of 56,784 daltons. Analysis of the deduced amino acid sequence predicts STLK3 to be an intracellular serine/threonine kinase, lacking both a signal sequence and transmembrane domain, however the cDNA clone lacks an initiating ATG, so the full extent of it N-terminus is not known. STLK3 contains a 31 amino acid N-terminal domain, a 277 amino acid catalytic domain with all the motifs characteristic of a serine/threonine kinase, followed by a 181 amino acid C-terminal domain containing a 25 amino acid insert and a 27 amino acid tail relative to the sequence of human STLK2.

STLK3 is most closely related to human STE20-subfamily kinases, STLK4 (SEQ ID. NO:7), MST3 (GB:AF024636), SOK-1 (GB:X99325) and STLK2 (SEQ ID NO:5) sharing 71.1%, 37.6%, 38.1%, and 38.4% amino acid identity respectively.

The 31 amino acid N-terminal domain of human STLK3 lacked any significant amino acid sequence homologies using a Smith-Waterman search of the nonredundant protein database, other than sequence similarity to proline-alanine repeats.

The 277 amino acid catalytic domain of human STLK3 is most related to human STLK4 (SEQ ID NO:7), SOK-1 (GB:X99325), MST3 (GB:AF024636), and STLK2 (SEQ ID NO:5) sharing 88.2%, 49.2%, 49%, and 49% amino acid identity, respectively. It also shares strong homology to other STKs from lower organisms including 51.7% to A. thaliana (GB:AC002343), 43.1% to A. thaliana (GB:Z97336), 42.1% to A. thaliana (GB:U96613), and 43.3% to C. elegans (GB:U53153). The activation loop of the human STLK3 catalytic domain conserves three potential threonine phosphorylation sites with other members of the STLK-subfamily of STE20-related kinases (human STE20, MST3, STLK2, STLK4) that could serve an autoregulatory role on kinase activity.

The 181 amino acid C-terminal domain of human STLK3 shares 55.5% amino acid identity to human STLK4 (SEQ ID NO:7), and is 100% identical to a partial human cDNA DCHT (GB:AF017635). The C-terminal domain of human STLK3 contains a 26 amino acid insert relative to human STE20. A similar (87.5% amino acid identity) 26 amino acid insert is also present in human STLK4.

The 27 amino acid C-terminal tail of human STLK3 shares 77.8% amino acid identity to human STLK4, but is absent from other STLK-family members. This high degree of homology between the C-tail of two STLK-family members suggests they may be involved in an as yet unidentified protein-protein interaction.

The weak sequence homology between the C-termini of human STLK3 and STE20, suggests it may also function as an inhibitory domain for its kinase.

Mammalian STLK4

The 3857 bp human STLK4 nucleotide sequence of the partial cDNA clone encodes a polypeptide of 414 amino acids (SEQ ID NO:7) with a predicted molecular mass of 45,451 daltons. Analysis of the deduced amino acid sequence predicts STLK4 to be an intracellular serine/threonine kinase, lacking both a signal sequence and transmembrane domain, however the cDNA clone lacks an initiating ATG, so the full extent of it N-terminus is not known. The partial STLK4 protein sequence contains a 178 amino acid catalytic domain corresponding to the C-terminal motifs. VI–XI of a serine/threonine kinase, followed by a 236 amino acid C-terminal domain containing two inserts of 25 and 41 amino acids each, relative to the sequence of human STLK2.

STLK4 is most closely related to human STE20-subfamily kinases, STLK3 (SEQ ID. NO 6), MST3 (GB:AF024636), STLK2 (SEQ ID NO:5), and SOK-1 (GB:X99325) sharing 71.0%, 46.8%, 43.9%, and 37.7% amino acid identity, respectively.

The 178 amino acid catalytic domain of human STLK4 is most related to human STLK3 (SEQ ID NO. 7), SOK-1 (GB:X99325), MST3 (GB:AF024636), STLK2 (SEQ ID NO:5), and MST1 (GB:U18297), sharing 88.2%, 54.2%, 54.0%, 53.7 and 45.7% amino acid identity, respectively. It also shares strong homology to other STKs from lower organisms including 56.9% to *A. thaliana* (GB:AC002343), 52.5% to *C. elegans* (GB:U53153), 46.2% to *A. thaliana* (GB:Z97336) and 45.7% to *A. thaliana* (GB:U96613). The activation loop of the human STLK4 catalytic domain conserves three potential threonine phosphorylation sites with other members of the STLK-subfamily of STE20-related kinases (human STE20, MST3, STLK2 and STLK3) that could serve an autoregulatory role on kinase activity.

The 236 amino acid C-terminal domain of human STLK4 shares 58.1% amino acid identity to both human STLK3 (SEQ ID NO:6) and to a partial human cDNA, DCHT (GB:AF017635). The C-terminal domain of human STLK4 contains a 25 amino acid insert relative to human SOK-1 and shares 87.5% amino acid identity to an insert present in human STLK3.

The weak sequence homology between the C-termini of human STLK4 and STE20, suggests it may also function as an inhibitory domain for its kinase.

Mammalian STLK5

The full-length 2110 bp human STLK5 cDNA encodes a polypeptide of 373 amino acids (SEQ ID NO:97) with a predicted molecular mass of 41,700 daltons. Analysis of the deduced amino acid sequence predicts STLK5 to be an intracellular STE20-subfamily kinase, lacking both a signal sequence and transmembrane domain. STLK5 contains a 10 amino acid N-terminal domain, a 311 amino acid catalytic domain with all the motifs characteristic of a serine/threonine kinase, and a 52 amino acid C-terminal domain.

STLK5 is most closely related to the human STE20-subfamily kinases STLK6 (SEQ ID No. 99) and SPAK (AF099989), sharing 51% and 33% amino acid identity, respectively, over its full extent. It also shares significant homology to database entries from *Arabidopsis thaliana* (GB:AC002343) and *C.elegans* (GB:AL023843, GB:AL023843).

The 10 amino acid N-terminal domain of human STLK5 does not reveal any significant homologies to the protein database.

The 311 amino acid catalytic domain of human STLK5 shares 51% and 34% identity to STLK6 and SPAK, respectively. The catalytic domain of STLK5 contains a 45 amino acid insert between kinase subdomains X and XI relative to human STE20. Multiple human EST fragments as well as a murine EST (GB:AA575647) contain this insert providing evidence that this region is an integral part of STLK5.

The 52 amino acid C-terminal tail of human STLK5 shares 41.3% amino acid identity to human SOK-1 (GB:X99325). The weak sequence homology between the C-termini of human STLK5 and STE20, suggests it may also function as an inhibitory domain for its kinase.

Mammalian STLK6

The 2,001 bp human STLK6 nucleotide sequence of the complete cDNA encodes a polypeptide of 418 amino acids (SEQ ID NO:99) with a predicted molecular mass of 47,025 daltons. Analysis of the deduced amino acid sequence predicts STLK6 to be an intracellular STE20-subfamily kinase, lacking both a signal sequence and transmembrane domain. STLK6 contains a 57 amino acid N-terminal domain, a 312 amino acid catalytic domain with all the motifs characteristic of a serine/threonine kinase, followed by a 49 amino acid C-terminal domain.

STLK6 is most closely related to human STE20-subfamily kinases STLK5 (SEQ ID NO:97), STLK7 (SEQ ID NO:101), and SPAK (AF099989), sharing 50%, 35%, and 30% amino acid identity over its full extent. It also shares significant homology to database entries from *Arabidopsis thaliana* (GB:AC002343) and *C.elegans* (GB:U53153).

The 57 amino acid N-terminal domain of human STLK6 does not reveal any significant homologies in the protein database.

The 312 amino acid catalytic domain of human STLK6 shares 51 and 30% identity to human STLK5 and SPAK, respectively.

The 49 amino acid C-terminal tail of human STLK6 shares low amino acid sequence identity (29%) with STLK5 and SPAK.

Mammalian STLK7

The 311 bp human STLK7 nucleotide sequence of the partial cDNA encodes a polypeptide of 103 amino acids (SEQ ID NO:101). Analysis of the deduced amino acid sequence predicts STLK7 to be an internal fragment of an intracellular STE20-family kinase. This sequence lacks the N- and C-terminal portions of STLK7 and contains only the N-terminal 103 amino acids of the predicted catalytic domain.

Human STLK7 is most closely related to human STE20-subfamily kinases SPAK (AF099989), STLK5 (SEQ ID NO:97), and STLK6 (SEQ ID NO:99), sharing 86%, 38%, and 35% amino acid identity within this region of the kinase domain. It also shares significant homology to database entries from *Arabidopsis thaliana* (GB:AC002343) and *Drosophila melanogaster* (GB:AF006640).

Mammalian ZC1

The 3798 bp human ZC1 nucleotide sequence encodes a polypeptide of 1239 amino acids (SEQ ID NO:13) with a predicted molecular mass of 142,140 daltons. Analysis of the deduced amino acid sequence predicts ZC1 to be an intracellular serine/threonine kinase, lacking both a signal sequence and transmembrane domain. The full-length ZC1 protein contains a 22 amino acid N-terminus, a 267 amino acid catalytic domain with all the motifs characteristic of a serine/threonine kinase, a 237 amino acid region predicted to form a coiled-coil structure, a 114 amino acid proline-rich region, a 256 amino acid spacer region, followed by a 343 amino acid C-terminal domain containing a potential Rab/Rho-binding region.

ZC1 is most closely related to the human STE20-subfamily kinases ZC2 (SEQ ID NO:14), ZC3 (SEQ ID NO:15), and ZC4 (SEQ ID NO:16), sharing 61.7%, 60.9%, and 43.8% amino acid identity, respectively. ZC1 also shares 45.5% amino acid identity to a *C. elegans* kinase encoded by the cosmid ZC504.4 (GB:Z50029). ZC1 exhibits. 90.0% amino acid homology to murine NIK (GB:U88984), suggesting it may be the human orthologue of this STK.

The 22 amino acid N-terminal domain of human ZC1 is 58.8% identical to the *C. elegans* kinase encoded by the cosmid ZC504.4 (GB:Z50029), and 100% identical to murine NIK (GB:U88984). Human ZC1 lacks a glycine residue at position 2, and is therefore unlikely to undergo myristylation. A Smith-Waterman search of the nonredundant protein database does not reveal any significant homologies that might suggest a potential function for this domain.

The 267 amino acid catalytic domain of human ZC1 is most related to human STE20-subfamily kinases, ZC3 (SEQ ID NO:15), ZC2 (SEQ ID NO:14), KHS2 (SEQ ID NO:18), SOK-1 (GB:X99325), GCK (GB:U07349), and GEK2 (SEQ ID NO:107), and to the *C. elegans* kinase encoded by the cosmid ZC504.4 (GB:Z50029) sharing 90.6%, 90.2%, 50.6%, 47.4%, 45.4%, 42.5% and 82.6% amino acid identity, respectively. The ZC1 kinase domain shares 98.1% identity to murine NIK (GB:U88984). ZC1 contains the potential "TPY" regulatory phosphorylation site in its activation loop. This "TPY" motif is conserved in other STE20-related kinases, including ZC2, ZC3, ZC4, GEK2, KHS2, SULU1, SULU3, PAK4 and PAK5.

Immediately C-terminal to the kinase domain of human ZC1 is a 237 amino acid region predicted to form a coiled-coil structure based on the Lupas algorithm (Lupas, A. Meth. Enzymol. 266, 513–525 (1996)). This region of ZC1 is most related to human STE20-subfamily kinases, ZC3 (SEQ ID NO:15), ZC2 (SEQ ID NO:14), and GEK2 (SEQ ID NO:107), as well as to human PITSLRE (GB:U04824) sharing 65.5%, 65.4%, 25.3%, and 29.0% amino acid identity, respectively. The ZC1 coiled-coil domain also shares 90.6% amino acid homology to murine NIK. The *C. elegans* homologue ZC504.4 shares 32.2% sequence identity over this region.

Within the predicted coiled-coil domain of human ZC1, and the related ZC3, is a region predicted to form a leucine zipper (Leu-X6-Leu-X6-Leu-X6-Leu-X20-Leu-X6-Leu) (SEQ ID NO: 149). The fact that this leucine repeat exists within a predicted coiled-coil structure suggests that the leucine zipper may have a high probability of serving as a dimerization interface (Hirst, J. D. et al Protein Engineering 9 657–662 (1996)) mediating a potential inter- or intramolecular dimerization of human ZC1.

The 114 amino acid proline-rich region of human ZC1 is most related to human STE20-subfamily kinases, ZC2 (SEQ ID NO:14) and ZC3 (SEQ ID NO:15), sharing 35.8%, and 24.9%, respectively. The ZC1 proline-rich domain shares 36.4% amino acid homology to murine NIK (GB:U88984). Three potential "PxxP" (SEQ ID NO:148) SH3 domain-binding motifs (I, II and III) are found within the proline-rich region of human ZC1. Motif I is conserved in human ZC1 and *C. elegans* ZC504.4 (GB:Z50029). Motif II is conserved in ZC1, ZC2, ZC3, ZC4 and *C. elegans* ZC504.4. Motif III is conserved in ZC1, ZC2, ZC3 and ZC4. Motifs II and m of murine NIK have been shown to bind the SH3 motif of the adaptor molecule Nck (Su, Y-C. et al, EMBO J. 16, 1279–1290 (1997)). From this evidence, human ZC1 may have the potential to bind to Nck or other SH3 or WW domain-containing proteins and participate in growth factor-induced signaling pathways.

The 256 amino acid spacer region of human ZC1 is most related to human STE20-subfamily kinases, ZC2 (SEQ ID NO:14) and ZC3 (SEQ ID NO:15), as well as to human PITSLRE (GB:U04824), sharing 59.9%, 33.1%, 29.6%, and 26.4% amino acid identity, respectively. It also shares 59.9% amino acid homology to murine NIK. The *C. elegans* homologue ZC504.4 has only limited sequence similarity in this spacer region.

The 343 amino acid C-terminal of human ZC1 is most related to human STE20-subfamily kinases, ZC3 (SEQ ID NO:15), ZC2 (SEQ ID NO:14), and ZC4 (SEQ ID NO:16), sharing 89.2%, 88.9%, and 42.3%, amino acid identity, respectively. The ZC1 C-terminal domain also shares 98.8% amino acid identity to murine NIK. The *C. elegans* homologue ZC504.4 also shares 68.7% amino acid identity with the C-tail of human ZC1. A lower, yet significant, homology is also evident to human KHS2 (SEQ ID NO:18), GCK (GB:U07349), and murine citron (GB:U07349) with 26.6%, 23.1% and 36.2% amino acid identity, respectively. GCK is a STE20-family kinase whose C-terminal domain has been shown to bind the small G-protein Rab8 (Ren, M. et al., Proc. Natl. Acad. Sci. 93, 5151–5155 (1996)). Citron is a non-kinase Rho-binding protein (Madaule, P. et al., FEBS Lett. 377, 243–238 (1995)).

The sequence similarity of the C-terminal region of ZC1 to proteins that have potential Rab- or Rho-binding domains suggests that ZC1 may signal through a small G-protein-dependant pathway.

Mammalian ZC2

The 4055 bp human ZC2 nucleotide sequence of the partial cDNA encodes a polypeptide of 1297 amino acids (SEQ ID NO:14) with a predicted molecular mass of 147,785 daltons. Analysis of the deduced amino acid sequence predicts ZC2 to be an intracellular serine/threonine kinase, lacking both a signal sequence and transmembrane domain, however the cDNA clone lacks an initiating ATG, so the full extent of it N-terminus is not known. The N-terminally truncated ZC2 protein contains a 255 amino acid catalytic domain with all the motifs characteristic of a serine/threonine kinase, a 187 amino acid region predicted to form a coiled-coil structure, a 184 amino acid proline-rich region, a 328 amino acid spacer region, followed by a 343 amino acid C-terminal domain containing a potential Rab/Rhb-binding region.

ZC2 is most closely related to the human STE20-subfamily kinases ZC3 (SEQ ID NO:15), ZC1 (SEQ ID NO:13), and ZC4 (SEQ ID NO:16), sharing 88.3%, 61.7%, and 41.9% amino acid identity, respectively, and shares 41.7% amino acid identity to a *C. elegans* kinase encoded by the cosmid ZC504.4 (GB:Z50029).

The 255 amino acid catalytic domain of human ZC2 is most related to human STE20-subfamily kinases, ZC1 (SEQ ID NO:13), ZC3 (SEQ ID NO:15), SOK-1 (GB:X99325), KHS2 (SEQ ID NO:18), MST1 (GB:U18297), and GCK (GB:U07349), and to the *C. elegans* kinase encoded by the cosmid ZC504.4 (GB:Z50029) sharing 90.2%, 89.8%, 49.0%, 48.6%, 47.9%, 45.0 and 76.7% amino acid identity, respectively. ZC2 contains the potential "TPY" regulatory phosphorylation site in its activation loop. This "TPY" motif is conserved in other STE20-related kinases, including ZC1, ZC3, ZC4, GEK2, KHS2, SULU1, SULU3, PAK4 and PAK5.

Immediately C-terminal to the kinase domain of human ZC2 is a 187 amino acid region predicted to form a coiled-coil structure based on the Lupas algorithm (supra). This region of ZC2 is most related to human STE20-subfamily kinases, ZC1 (SEQ ID NO:13), ZC3 (SEQ ID NO:15), and GEK2 (SEQ ID NO:107), as well as to human PITSLRE (GB:U04824), sharing 65.8%, 61.5%, 29.7% and 29.6% amino acid identity, respectively. The *C. elegans* homologue ZC504.4 shares 30.8% sequence identity over this region. Human ZC2 lacks the potential leucine zipper found in ZC1 as a consequence of a 29 amino acid deletion relative to ZC1 and ZC3.

The 184 amino acid proline-rich region of human ZC2 is most related to human STE20-subfamily kinases, ZC3 (SEQ ID NO:15) and ZC1 (SEQ ID NO:13), sharing 35.9% and 28.6%, amino acid identity, respectively. Significant homology is also evident to the murine WW domain-binding protein WBP7 (GB:U92455), and to the human SH3 domain-binding protein 3BP-1 (GB:X87671), with 27.7% and 25.3% amino acid identity, respectively.

ZC2 contains two of the potential "PxxP" (SEQ ID NO: 148) SH3 domain-binding motifs (II and III) found within the proline-rich region of human ZC1. Motif II is conserved in ZC1, ZC3, ZC4 and *C. elegans* ZC504.4, and Motif II is conserved in ZC1, ZC3 and ZC4. Motifs II and III of murine NIK have been shown to bind the SH3 motif of the adaptor molecule Nck. From this evidence, human ZC1 may have the potential to bind to Nck or other SH3 or WW domain-containing proteins, and to participate in growth factor-induced signaling pathways.

The 328 amino acid spacer region of human ZC2 is most related to human STE20-subfamily kinases ZC1 (SEQ ID NO:13) and ZC3 (SEQ ID NO:15), and to murine NIK (GB:U88984), sharing 31.6%, 26.9% and 25.9% amino acid identity, respectively. The *C. elegans* homologue ZC504.4 has only limited sequence similarity in this spacer region.

The 343 amino acid C-terminal of human ZC2 is most related to human STE20-subfamily kinases ZC1 (SEQ ID NO:13), ZC3 (SEQ ID NO:15) and ZC4 (SEQ ID NO:16), and to murine NIK (GB:U88984), sharing 88.9%, 88.3%, 41.9%, and 88.0%, amino acid identity, respectively. The *C. elegans* homologue, ZC504.4, also shares 67.2% amino acid identity with the C-tail of human ZC2. A lower, yet significant, homology is also evident to human GCK (GB:U07349), murine citron (GB:U07349), and the *S. cerevisiae* ROM2 protein (GB:U19103), a Rho1 GDP/GTP exchange factor, with 22.3%, 22.2% and 21.9% amino acid identity, respectively.

The sequence similarity of the C-terminal region of ZC2 to proteins that have potential Rab- or Rho-binding domains suggests that ZC2, like ZC1, may also signal through a small G-protein-dependant pathway.

Mammalian ZC3

The 4133 bp human ZC3 nucleotide sequence of the partial cDNA encodes a polypeptide of 1326 amino acids (SEQ ID NO:15) with a predicted molecular mass of 149,906 daltons. Analysis of the deduced amino acid sequence predicts ZC3 to be an intracellular serine/threonine kinase, lacking both a signal sequence and transmembrane domain, however the cDNA clone lacks an initiating ATG, so the full extent of it N-terminus is not known. The N-terminally truncated ZC3 protein contains a 255 amino acid catalytic domain with all the motifs characteristic of a serine/threonine kinase: a 221 amino acid region predicted to form a coiled-coil structure, a 204 amino acid proline-rich region, and a 303 amino acid spacer region followed by a 343 amino acid C-terminal domain containing a potential Rab/Rho-binding region.

ZC3 is most closely related to the human STE20-subfamily kinases ZC1 (SEQ ID NO:13), ZC2 (SEQ ID NO:14), and ZC4 (SEQ ID NO:16), sharing 62.0%, 61.0%, and 42.5% amino acid identity, respectively and shares 46.7% amino acid identity to a *C. elegans* kinase encoded by the cosmid ZC504.4 (GB:Z50029).

The 255 amino acid catalytic domain of human ZC3 is most related to human STE20-subfamily kinases, ZC1 (SEQ ID NO:13), ZC2 (SEQ ID NO:14), SOK-1 (GB:X99325), KHS2 (SEQ ID NO:18), GCK (GB:U07349), SULU1 (SEQ ID NO:22), and GEK2 (SEQ ID NO:107), and to the *C. elegans* kinase encoded by the cosmid ZC504.4 (GB:Z50029) sharing 90.6%, 89.3%, 49.0%, 48.3%, 45.0%, 43.1%, 42.3% and 76.7% amino acid identity, respectively. ZC1 contains the potential "TPY" regulatory phosphorylation site in its activation loop. This "TPY" motif is conserved in other STE20-related kinases, including ZC1, ZC2, GEK2, KHS2, SULU1, SULU3, PAK4 and PAK5.

Immediately C-terminal to the kinase domain of human ZC3 is a 221 amino acid region predicted to form a coiled-coil structure based on the Lupas algorithm (supra). This region of ZC3 is most homologous to human STE20-subfamily kinases, ZC1 (SEQ ID NO:13), ZC2 (SEQ ID NO:14), and GEK2 (SEQ ID NO:107), sharing 66.9%, 61.5%, and 27.5% identity, as well as to rat PLC-beta (GB:A45493) and human PITSLRE (GB:H54024) sharing 29.6% and 25.9% amino acid identity, respectively. The *C. elegans* homologue ZC504.4 shares 26.8% sequence identity over this region.

Within the predicted coiled-coil domain of human ZC3, and the related ZC1, is a region predicted to form a leucine zipper (Leu-X6-Leu-X6-Leu-X6-Leu-X20-Leu-X6-Leu) (SEQ ID NO: 149). The fact that this leucine repeat exists within a predicted coiled-coil structure suggests that the leucine zipper may have a high probability of serving as a dimerization interface (Hirst, J. D. et al Protein Engineering 9 657–662 (1996)) mediating a potential inter- or intra-molecular dimerization of human ZC3.

The 204 amino acid proline-rich region of human ZC3 is most related to human STE20-subfamily kinases, ZC1 (SEQ ID NO:13) and ZC2 (SEQ. ID NO:14), sharing 66.9% and 61.5% amino acid identity, respectively.

ZC3 contains two of the potential "PxxP" (SEQ ID NO: 148) SH3 domain-binding motifs (II and III) found within the proline-rich region of human ZC1. Motif II is conserved in ZC1, ZC2, ZC4 and *C. elegans* ZC504.4; Motif III is conserved in ZC1, ZC2 and ZC4. Motifs II and III of murine NIK have been shown to bind the SH3 motif of the adaptor molecule Nck. From this evidence, human ZC3 may have the potential to bind to Nck or other SH3 or WW domain-containing proteins and participate in growth factor-induced signaling pathways.

The 303 amino acid spacer region of human ZC3 is most related to human STE20-subfamily kinases, ZC1 (SEQ ID NO:13) and ZC2 (SEQ ID NO:14) sharing 30.1%, and 27.1% amino acid identity, respectively. The *C. elegans* homologue ZC504.4 lacks nearly the entire spacer region of ZC3.

The 343 amino acid C-terminal of human ZC3 is most related to human STE20-subfamily kinases, ZC1 (SEQ ID NO:13), ZC2 (SEQ ID NO:14) and ZC4 (SEQ ID NO:16), sharing 89.2%, 88.9%, and 42.5%, amino acid identity, respectively. The *C. elegans* homologue ZC504.4 also shares 67.2% amino acid identity with the C-tail of human ZC3. A lower, yet significant, homology is also evident to human GCK (GB:U07349), as well as to the non-kinases murine citron (GB:U07349) and the *S. cerevisiae* ROM2 protein (GB:U19103), a Roh1 GDP/GTP exchange factor, with 21.6%, 32.4% and 22.9% amino acid identity, respectively.

The sequence similarity of the C-terminal region of ZC3 to proteins that have potential Rab- or Rho-binding domains suggests that ZC3, like ZC1 and ZC2, may signal through a small G-protein-dependant pathway.

Mammalian ZC4

The 3,684 bp human ZC4 nucleotide sequence of the complete cDNA encodes a polypeptide of 1,227 amino acids (SEQ ID NO:105) with a predicted molecular mass of 138,205 Daltons. Analysis of the deduced amino acid sequence predicts ZC4 to be an intracellular STE20-subfamily kinase, lacking both a signal sequence and a transmembrane domain. The full-length ZC4 protein contains a 25 amino acid N-terminus, a 265 amino acid catalytic domain with all the motifs characteristic of a serine/threonine kinase, a 108 amino acid region predicted to form a coiled-coil structure, a 231 amino acid proline-rich region, a 40 amino acid region predicted to form a coiled-coil structure spacer region, a 204 amino acid spacer region (domain B), followed by a 355 amino acid C-terminal domain containing a potential Rab/Rho-binding region (domain C).

ZC4 is most closely related to human ZC1 (SEQ ID NO:13, also known as human HGK, human KIAA0687, murine NIK, human AC005035, human NIK, and *C. elegans* MIG-15), ZC2 (SEQ ID NO:14, similar to partial sequence human KIAA0551), and ZC3 (SEQ ID NO:15). An assembled genomic fragment in the database (Z83850) is identical to ZC4, except for inappropriate identification of the exon boundaries. (Abo et al. (1998) EMBO J. 17: 6527–6540.)

The 25 amino acid N-terminal domain of human ZC4 shares weak homology to human ZC1 in its C-terminal extent, but otherwise does not reveal any significant homologies to the protein database.

The 265 amino acid catalytic domain of human ZC4 is most related to human ZC1 (SEQ ID NO:13), ZC3 (SEQ ID NO:15), and ZC2 (SEQ ID NO:14), sharing 63%, 64% and 62% amino acid identity, respectively.

Immediately C-terminal to the kinase domain of human ZC4 is a 108 amino acid region predicted to form a coiled-coil structure based on the Lupas algorithm (supra). This region is most related to human ZC1 (SEQ ID NO:13), ZC3 (SEQ ID NO:15), and ZC2 (SEQ ID NO:14), sharing 29%, 25% and 20% amino acid identity, respectively.

The 231 amino acid proline-rich region of human ZC4 does not reveal any significant homologies to the protein database. This region of ZC4 contains two "PxxP" (SEQ ID NO: 148) motifs that could potentially bind to proteins containing SH3 or WW domains and allow ZC4 to participate in growth factor activated signaling pathways. In addition, within the pro-rich domain of human ZC4 is a region predicted to form a leucine zipper (Leu-X6-Leu-X6-Leu-X6-Leu-X20-Leu-X6-Leu) (SEQ ID NO: 149) which may serve as a dimerization interface. The ZC STE20 subfamily kinases (ZC1, ZC2 and ZC3) have similarly located "PxxP" (SEQ ID NO: 148) motifs and potential Leu zippers.

Immediately C-terminal to the proline-rich region of human ZC4 is a 40 amino acid region also predicted to form a coiled-coil structure based on the Lupas algorithm. This region of human ZC4 does not reveal any significant homologies to the protein database.

The 204 amino acid acidic- and serine-rich domain "B" of ZC4 does not reveal any significant homologies to the protein database.

The 355 amino acid C-terminal of human ZC4 is most related to human ZC1 (SEQ ID NO:13), ZC3 (SEQ ID NO:15), and ZC2 (SEQ ID NO:14), sharing 43%, 42% and 42% amino acid identity, respectively.

The sequence similarity of the C-terminal region of ZC4 to proteins that have potential Rab- or Rho-binding domains suggests that ZC4, like other ZC-subfamily STE20 kinases, may signal through a small G-protein-dependant pathway.

Mammalian KHS2

The 4023 bp human KHS2 nucleotide sequence encodes a polypeptide of 894 amino acids (SEQ ID NO:18) with a predicted molecular mass of 101,327 daltons. Analysis of the deduced amino acid sequence predicts KHS2 to be an intracellular serine/threonine kinase, lacking both a signal sequence and transmembrane domain. The full-length KHS2 protein contains a 13 amino acid N-terminus, a 260 amino acid catalytic domain with all the motifs characteristic of a serine/threonine kinase, a 73 amino acid spacer region, a 188 proline-rich region, followed by a 360 amino acid C-terminal domain containing a potential Rab/Rho-binding-site.

KHS2 is most closely related to the human STE20-subfamily kinases KHS1 (GB:U177129), GCK (GB:U07349), and HPK1 (GB:U07349), sharing 65.5%, 51.9%, and 44.9% amino acid identity, respectively and shares 38.5% amino acid identity to a *C. elegans* STK (GB:U55363).

The 13 amino acid N-terminal domain of human KHS2 does not reveal any significant homologies that might suggest a potential function for this domain when examined by a Smith-Waterman alignment to the nonredundant protein database. Human KHS2 lacks a glycine residue at position 2, and is therefore unlikely to undergo myristylation.

The 260 amino acid catalytic domain of human KHS2 is most related to human STE20-subfamily kinases KHS1 (GB:U177129), GCK (GB:U07349), HPK1 (GB:U66464), SOK-1 (GB:X99325), MST1 (GB:U18297), ZC1 (SEQ ID NO:13), and to the *C. elegans* kinase (GB:U55363), sharing 85.4%, 75.1%, 67.7%, 51.4%, 48.1%, 49.8% and 72.0% amino acid identity, respectively. KHS2 contains the potential "TPY" regulatory phosphorylation site in its activation loop. This "TPY" motif is conserved in other STE20-related kinases, including ZC1, ZC2, ZC3, ZC4, GEK2, SULU1, SULU3, PAK4 and PAK5.

The 73 amino acid spacer region of human KHS2 is most related to human STE20-subfamily kinases, KHS1 (GB:U177129), HPK1 (GB:U66464) and GCK (GB:U07349), sharing 60.3%, 43.5% and 44.0%, amino acid identity, respectively.

The 188 amino acid proline-rich region of human KHS2 is most related to human STE20-subfamily kinases, HPK1 (GB:U66464), GCK (GB:U07349) and KHS1 (GB:U177129), sharing 33.3%, 31.9% and 31.4%, amino acid identity, respectively.

Two potential "PxxP" (SEQ ID NO: 148) SH3 domain-binding motifs (I and II) are found within the proline-rich region of human KHS2. Motif I is conserved with human KHS1 and HPK1; motif II is conserved with GCK and KHS2. A 192 amino acid region of human KPK1 containing motif II has been shown to bind to the C-terminal SH3 motif of the adaptor molecule Grb2 (Anafi, M et al, J. Biol. Chem. J. 272, 27804–27811 (1997)). Human KHS2 may bind SH3 or WW domain-containing proteins through this proline-rich region.

The 360 amino acid C-terminal of human KHS2 is most related to KHS1 (GB:U177129), GCK (GB:U07349) and HPK1 (GB:U66464), and to the *C. elegans* kinase (GB:U55363), sharing 74.9%, 54.8%, 42.9%, and 31.0%, amino acid identity, respectively. GCK is a STE20-family kinase whose C-terminal domain has been shown to bind the small G-protein Rab8 (Ren, M. et al., Proc. Natl. Acad. Sci. 93, 5151–5155 (1996)).

Mammalian SULU1

The 4196 bp human SULU1 nucleotide sequence encodes a polypeptide of 898 amino acids (SEQ ID NO:22) with a predicted molecular mass of 105,402 daltons. Analysis of the deduced amino acid sequence predicts SULU1 to be an intracellular serine/threonine kinase, lacking both a signal sequence and transmembrane domain. The full-length SULU1 protein contains a 21 amino acid N-terminus, a 256 amino acid catalytic domain with all the motifs characteristic of a serine/threonine kinase, a 150 amino acid spacer region, a 210 amino acid region predicted to form a coiled-coil structure, a 114 amino acid spacer region and a 147 amino acid C-terminal domain predicted to form a coiled-coil structure.

SULU1 is most closely related to the STE20-subfamily kinases murine SULU3 (SEQ ID NO:24), human SULU3 (SEQ ID NO:23), and to the C. elegans kinase SULU (GB:U11280), sharing 68.9%, 72.2% and 38.2% amino acid identity, respectively.

The 21 amino acid N-terminal domain of human SULU1 is most related to murine SULU3 (SEQ ID NO:24) and to the C. elegans kinase SULU (GB:U11280), sharing 86.3% and 62.3% amino acid identity. Human SULU1 lacks a glycine residue at position 2, and is therefore unlikely to undergo myristoylation. A Smith-Waterman search of the nonredundant protein database does not reveal any significant homologies that might suggest a potential function for this domain.

The 256 amino acid catalytic domain of human SULU1 is most related to murine SULU3 (SEQ ID NO:24), and to human SOK-1 (GB:X99325), STLK2 (SEQ ID NO:5), MST1 (GB:U18297), PAK1 (GB:U24152), ZC2 (SEQ ID NO:14), and KHS2 (SEQ ID NO:18) sharing 86.3%, 48.1%, 46.9%, 45.2%, 43.3%, 43.1% and 42.0% amino acid identity, respectively. The C. elegans SULU STK (GB:U11280) shares 62.3% sequence identity over this region. SULU1 contains the potential "TPY" regulatory phosphorylation site in its activation loop. This "TPY" motif is conserved in other STE20-related kinases, including ZC1, ZC2, ZC3, ZC4, GEK2, KHS2, SULU3, PAK4 and PAK5.

The 150 amino acid spacer region of human SULU1 is most related to human SULU3 (SEQ ID NO:23) and to the C. elegans kinase (GB:U11280), sharing 53.5% and 10.4% amino acid identity, respectively.

Immediately C-terminal to the spacer region of human SULU1 is a 210 amino acid region predicted to form a coiled-coil structure based on the Lupas algorithm. This region of SULU1 is most related to SULU3 (SEQ ID NO:23), the C. elegans SULU kinase (GB:U11280), GEK2 (SEQ ID NO:107) and ZC1 (SEQ ID NO:13), sharing 68.6%, 26.8%, 23.2%, and 22.8% amino acid identity, respectively.

The 114 amino acid spacer region human SULU1 is most related to human SULU3 (SEQ ID NO:24) with 73.7% amino acid sequence identity. A lower, yet significant, homology is also evident to murine PITSLRE (GB:U04824) and DLK (GB:A55318), human ZC1 (SEQ ID NO:13) and GEK2 (SEQ ID NO:107), as well as to the C. elegans SULU STK (GB:U11280) sharing 39.7%, 35.4%, 29.5%, 23.6% and 37.6% amino acid identity, respectively.

Immediately C-terminal to the second spacer region of human SULU1 is a 147 amino acid region predicted to form a coiled-coil structure based on the Lupas algorithm. This region of SULU1 is most related to human SULU3 (SEQ ID NO:24), ZC1 (SEQ ID NO:13) and GEK2 (SEQ ID NO:107), as well as to the C. elegans SULU STK (GB:U11280), sharing 73.3%, 28.4%, 26.1% and 39.5%, amino acid identity, respectively.

Mammalian (Human) SULU3

The 3824 bp partial cDNA human SULU3 nucleotide sequence encodes a polypeptide of 786 amino acids (SEQ ID NO:23) with a predicted molecular mass of 92,037 daltons. Analysis of the deduced amino acid sequence predicts SULU3 to be an intracellular serine/threonine kinase lacking a transmembrane domain. The N-terminally truncated human SULU3 protein contains a 66 amino acid partial catalytic domain followed by a 149 amino acid spacer region, a 210 amino acid region predicted to form a coiled-coil structure, a second spacer region of 114 amino acids, a 247 amino acid C-terminal region predicted to form a second coiled-coil structure and a 100 amino acid C-terminal tail.

Human SULU3 is most closely related murine SULU3 (SEQ ID NO:24), human SULU1 (SEQ ID NO:22), and to the C. elegans SULU kinase (GB:U11280), sharing 66.3%, 68.9% and 32.9% amino acid identity, respectively. The high sequence homology between murine and human SULU3 suggests that these two proteins are orthologs of each other.

The 66 amino acid partial catalytic domain of human SULU3 is most related to murine SULU3 (SEQ ID NO:24), and to the human STE20 subfamily kinases ZC1 (SEQ ID NO:13), STE20 (GB:X99325), KHS1(GB:U177129) and GEK2 (SEQ ID NO:107), as well as to the C. elegans SULU kinase (GB:U11280), sharing 83.3%, 47.0%, 45.5%, 43.5%, 41.8% and 55.6% amino acid identity, respectively.

The 149 amino acid spacer region of human SULU3 is most related to murine SULU3 (SEQ ID NO:24), human STE20 (GB:X99325), MST1 (GB:U18297), and to the C.elegans SULU kinase (GB:U11280) sharing 98.7%, 21.9% and 21.8% amino acid identity, respectively.

Immediately C-terminal to the first spacer region of human SULU3 is a 210 amino acid region predicted to form a coiled-coil structure based on the Lupas algorithm. This region of SULU3 is most related to murine SULU3 (SEQ ID NO:24), and to human SULU1 (SEQ ID NO:22), ZC1 (SEQ ID NO:13) and GEK2 (SEQ ID NO:107), as well as to the C. elegans SULU kinase (GB:U11280), sharing 99.5%, 68.6%, 27.4% and 22.5% amino acid identity, respectively.

The 114 amino acid second spacer region of human SULU3 is most related to murine SULU3 (SEQ ID NO:24), and to human SULU1 (SEQ ID NO:22) GEK2 (SEQ ID NO:107), and ZC1 (SEQ ID NO:13), as well as to the C. elegans SULU kinase (GB:U11280), sharing 99.1%, 73.7%, 24.6%, 24.1% and 41.2% amino acid identity, respectively.

Immediately C-terminal to the second spacer region of human SULU3 is a 247 amino acid region predicted to form a coiled-coil structure based on the Lupas algorithm (supra). This region of SULU3 is most related to human SULU1 (SEQ ID NO:22) and ZC1 (SEQ ID NO:13) as well as to rat PKN-(GB:D26180) murine p160 ROCK1 (GB:U58512), and the C. elegans SULU kinase (GB:U11280), sharing 73.7%, 26.7%, 24.0% and 21.0% amino acid identity, respectively.

The 100 amino acid C-tail of human SULU3 is most related to a human prion protein (GB:L38993), with 45.0% amino acid identity.

Mammalian (Murine) SULU3

The 2249 bp murine, partial cDNA SULU3 nucleotide sequence encodes a polypeptide of 748 amino acids (SEQ ID NO:24) with a predicted molecular mass of 87,520 daltons. Analysis of the deduced amino acid sequence predicts SULU3 to be an intracellular serine/threonine kinase, lacking both a signal sequence and transmembrane domain. The partial murine SULU3 protein contains a 25 amino acid N-terminus, a 248 amino acid catalytic domain with all the motifs characteristic of a serine/threonine kinase, a 149 amino acid spacer region, a 210 amino acid region predicted to form a coiled-coil structure, and a 116 amino acid spacer region.

Murine SULU3 is most closely related to human SULU3 (SEQ ID NO:23) and SULU1 (SEQ ID NO:22), as well as to the *C. elegans* SULU kinase (GB:U11280), sharing 97.0%, 72.3% and 38.4% amino acid identity, respectively. The high sequence homology between murine and human SULU3 suggests that these two proteins are orthologs.

The 25 amino acid N-terminal domain of murine SULU3 is most related to human SULU1 (SEQ ID NO:22) and to the *C. elegans* SULU kinase (GB:U11280), sharing 70.0% and 44.4% amino acid identity, respectively.

Murine SULU3 lacks a glycine residue at position 2, and is therefore-unlikely to undergo myristoylation. A Smith-Waterman search of the nonredundant protein database does not reveal any significant homologies that might suggest a potential function for this domain.

The 248 amino acid catalytic domain of murine SULU3 is most related to human SULU1 (SEQ ID NO:22), STE20 (GB:X99325), ZC1 (SEQ ID NO:13), and KHS1 (GB:U77129), as well as to the *C. elegans* SULU kinase (GB:U11280), sharing 86.7%, 46.6%, 43.3%, 59.4% amino acid identity, respectively. Murine SULU3 contains the potential "TPY" regulatory phosphorylation site in its activation loop. This "TPY" motif is conserved in other STE20-related kinases, including ZC2, ZC3, ZC4, GEK2, KHS2, SULU1, SULU3, PAK4 and PAK5.

The 149 amino acid spacer of murine SULU3 is most related to human SULU3 (SEQ ID NO:23), SULU1 (SEQ ID NO:22), and STE20 (GB:X99325), as well as to the *C. elegans* SULU (GB:U11280) and the *S. cerevisiae* STE20 (GB:L04655) kinases, sharing 98.7%, 53.4%, 21.9%, 59.4% and 21.9% amino acid identity, respectively.

Immediately C-terminal to the spacer region of murine SULU3 is a 210 amino acid region predicted to form a coiled-coil structure based on the Lupas algorithm. This region of murine SULU3 is most related to human SULU3 (SEQ ID NO:23), ZC1 (SEQ ID NO:13), and GEK2 (SEQ ID NO:107), as well as to the *C. elegans* SULU kinase (GB:U11280), sharing 99.5%, 27.4%, 22.5% and 29.2% amino acid identity, respectively.

The 116 amino acid C-terminal spacer region of murine SULU3 is most related to human SULU3 (SEQ ID NO:23), GEK2 (SEQ ID NO:107), and ZC1 (SEQ ID NO:13), well as to the *C. elegans* SULU kinase (GB:U11280), sharing 98.3%, 24.6%, 24.1% and 40.5% amino acid identity, respectively.

Mammalian (Murine/human) SULU3

The 2249 bp murine SULU3 and the 3824 bp human SULU3 cDNAs contain a 1620 nucleotide overlap (541 amino acids) with 90% and 98% DNA and amino acid sequence identity, respectively. Owing to the high degree of sequence identity in this extended overlap, we propose that these are functional orthologues of a single gene. The combined murine/human 4492 bp SULU3 sequence encodes a polypeptide of 1001 amino acids (SEQ ID NO:31) with a predicted molecular mass of 116,069 daltons. Analysis of the deduced amino acid sequence predicts SULU3 to be an intracellular serine/threonine kinase, lacking both a signal sequence and transmembrane domain. SULU3 contains a 25 amino acid N-terminus, a 248 amino acid catalytic domain with all the motifs characteristic of a serine/threonine kinase, a 149 amino acid spacer region, a 210 amino acid region predicted to form a coiled-coil structure and a second spacer region of 114 amino acids, a 247 amino acid C-terminal region predicted to form a second coiled-coil structure and a 100 amino acid C-terminal tail. The murine SULU3 clone lacks the region from the second C-terminal coiled-coil to the C-terminus, whereas the human clone lacks the N-terminal domain, and all but 66 amino acids of the 248 amino acid kinase domain.

SULU3 is most closely related to SULU1 (SEQ ID NO:22) and the *C. elegans* SULU kinase (GB:U11280) sharing 72.3% and 38.4% amino acid identity, respectively.

The 25 amino acid N-terminal domain of SULU3 is most related to human SULU1 (SEQ ID NO:22) and to the *C. elegans* SULU kinase (GB:U11280), sharing 70.0% and 44.4% amino acid identity, respectively SULU3 lacks a glycine residue at position 2, and is therefore unlikely to undergo myristylation. A Smith-Waterman search of the nonredundant protein database does not reveal any significant homologies that might suggest a potential function for this domain.

The 248 amino acid catalytic domain of SULU3 is most related to human SULU1 (SEQ ID NO:22), SOK-1 (GB:X99325), ZC1 (SEQ ID NO:13), KHS1 (GB:U77129) and the *C. elegans* SULU kinase (GB:U11280), sharing 86.7%, 46.6%, 43.3%, 42.0% and 59.4% amino acid identity, respectively. SULU3 contains the potential "TPY" regulatory phosphorylation site in its activation loop. This "TPY" motif is conserved in other STE20-related kinases, including ZC2, ZC3, ZC4, GEK2, KHS2, SULU1, PAK4 and PAK5.

The 149 amino acid spacer of SULU3 is most related to SULU1 (SEQ ID NO:22) and SOK-1 (GB:X99325), and to the *C. elegans* SULU (GB:U11280), and *S. cerevisiae* STE20 (GB:L04655) kinases, sharing 53.4%, 21.9%, 59.4% and 21.9% amino acid identity, respectively.

Immediately C-terminal to the spacer region of SULU3 is a 210 amino acid region predicted to form a coiled-coil structure based on the Lupas algorithm. This region is most related to ZC1 (SEQ ID NO:13), GEK2 (SEQ ID NO:107), and the *C. elegans* SULU kinase (GB:U11280), sharing 27.4% 22.5% and 29.2% amino acid identity, respectively.

The 114 amino acid spacer region of SULU3 is most related to human SULU1 (SEQ ID NO:22), GEK2 (SEQ ID NO:107), ZC1 (SEQ.ID NO:13), and to the *C. elegans* SULU kinase (GB:U11280), sharing 73.7%, 24.6%, 24.1% and 41.2% amino acid identity, respectively.

Immediately C-terminal to the second spacer region of SULU3 is a 247 amino acid region predicted to form a coiled-coil structure based on the Lupas algorithm. This region of SULU3 is most related to human SULU1 (SEQ ID NO:22) and ZC1 (SEQ ID NO:13), as well as to rat PKN (GB:D26180), murine p160 ROCK1 (GB:U58512) and the *C. elegans* SULU kinase (GB:U11280), sharing 73.7%, 26.7%, 24.0%, 21.0% and 37.6% amino acid identity, respectively.

The 100 amino acid C-tail of SULU3 is most related to a human prion protein (GB:L38993) with 45.0% amino acid identity.

Mammalian GEK2

The 2926 bp human GEK2 nucleotide sequence of the complete cDNA encodes a polypeptide of 968 amino acids (SEQ ID NO:107) with a predicted molecular mass of 112,120 daltons. Analysis of the deduced amino acid sequence predicts GEK2 to be an intracellular serine/threonine kinase, lacking both a signal sequence and transmembrane domain. The complete GEK2 protein contains a 33 amino acid N-terminus, a 261 amino acid catalytic domain with all the motifs characteristic of a serine/threonine kinase, a 43 amino acid spacer region, a 135 amino acid proline-rich region, a 252 amino acid region predicted to form a coiled-coil structure followed by a 244 amino acid region also predicted to form a coiled-coil structure.

GEK2 is most closely related to rat AT1-46 (GB:U33472) (a partial cDNA that extends from the middle of the first potential coiled-coil domain of GEK2 to the C-terminus), murine LOK (GB:D89728), *Xenopus laevis* polo-like kinase 1 (GB:AF100165), and human SLK (GB:AB002804), sharing 91.3%, 88.5%, 65.0%, and 44.7% amino acid identity, respectively. The high sequence homology between human GEK2, murine LOK and rat AT1-46 suggests that human GEK2 is a highly related protein to the rodent forms, or alternatively, its orthologue. Recently, a full-length version of GEK2 was reported (STK10 or human LOK AB015718). The 968 amino acid sequence is 99% identical to GEK2 (SEQ ID NO:107).

The 33 amino acid N-terminal domain of human GEK2 is most related to murine LOK (GB:D89728) and to human SLK (GB:AB002804), sharing 100% and 54.5% amino acid identity, respectively.

Human GEK2 lacks a glycine residue at position 2, and is therefore unlikely to undergo myristylation. A Smith-Waterman search of the nonredundant protein database does not reveal any significant homologies that might suggest a potential function for this domain.

The 261 amino acid catalytic domain of human GEK2 is most related to murine LOK (GB:D89728), rat AT1-46 (GB:D89728) and human SLK (GB:AB002804) as well as to a *C. elegans* kinase (GB:Z81460), sharing 97.7%, 90.8%, 54.5% and 55.9% amino acid identity, respectively. GEK2 contains the potential "TPY" regulatory phosphorylation site in its activation loop. This "TPY" motif is conserved in other STE20-related kinases, including ZC2, ZC3, ZC4, GEK2, KHS2, SULU1, SULU3, PAK4 and PAK5.

The 43 amino acid spacer region of human GEK2 is most related to murine LOK (GB:D89728) and to human SLK, sharing 83.7% and 77.6% amino acid identity, respectively.

The 135 amino acid proline-rich region of human GEK2 is most related to murine LOK (GB:D89728) with 66.2% amino acid identity, respectively. Within the proline-rich region of human GEK2 is a potential "PxxP" (SEQ ID NO: 148) SH3-binding domain conserved with murine LOK.

Immediately C-terminal to the proline-rich region of human GEK2 is a 252 amino acid region predicted to form a coiled-coil structure based on the Lupas algorithm. This region of human GEK2 is most related to rat AT1-46 (GB:D89728), murine LOK (GB:D89728) and human SLK (GB:AB002804), and ZC2 (SEQ ID NO:14), sharing 90.8%, 86.9%, 42.2%, and 29.7% amino acid identity, respectively.

Immediately C-terminal to the predicted coiled-coil structure of human GEK2 is a second potential coiled-coil structure of 244 amino acids predicted based on the Lupas algorithm. This region of human GEK2 is most related to rat AT1-46 (GB:D89728) and murine LOK (GB:D89728) as well as to human SLK (GB:AB002804) and ZC1 (SEQ ID NO:13), sharing 91.8%, 92.6%, 70.4% and 26.7% amino acid identity, respectively. The *C. elegans* kinase (GB:Z81460) shares 31.5% amino acid sequence identity over this region.

Mammalian PAK4

The 3604 bp human PAK4 nucleotide sequence encodes a polypeptide of 681 amino acids (SEQ ID NO:29) with a predicted molecular mass of 74,875 daltons. Analysis of the deduced amino acid sequence predicts PAK4 to be an intracellular serine/threonine kinase, lacking both a signal sequence and transmembrane domain. The full-length PAK4 protein contains a 51 amino acid N-terminus predicted to contain a rac-binding motif, a 173 amino acid insert relative to the known mammalian PAK proteins, a 169 amino acid spacer region, a 265 amino acid catalytic domain with all the motifs characteristic of a serine/threonine kinase and a 23 amino acid C-terminal tail.

PAK4 is most closely related to human PAK5 (SEQ ID NO:30), PAK1 (GB:U24152), and PAK65 (GB:U25975), as well as to a *C. elegans* kinase (GB:Z74029), sharing 76.8%, 49.5%, 49.8%, and 34.6% amino acid identity, respectively.

The 51 amino acid N-terminal domain of human PAK4 is most related to human PAK1 (GB:U24152), and PAK65 (GB:U25975), as well as to a *C.elegans* kinase (GB:Z74029), sharing 50.0%, 50.0% and 49.0% amino acid identity, respectively.

The 10 amino acid region at positions 13–23 of human PAK4 fits the consensus for a Cdc42/Rac-binding motif (SXPX4-6HXXH) (SEQ ID NO: 150) (Burbelo, P. D., Dreschel, D. and Hall, A. J. Bio. Chem. 270, 29071–29074 (1995)).

The 173 amino acid insert of human PAK4, relative to the known mammalian PAK proteins, is most related to a *C. elegans* kinase (GB:Z74029) with 39.0% amino acid identity. A Smith-Waterman search of the nonredundant protein database does not reveal any significant homologies that might suggest a potential function for this region.

The 169 amino acid spacer of human PAK4 does not reveal any significant homologies that might suggest a potential function for this region.

The equivalent spacer region in PAK1 binds to the guanine nucleotide exchange factor PIX (Manser, E. et al (1998) Molecular Cell, 1, 183–192). Since PAK4 differs substantially from PAK1 over this region, the spacer domain of PAK4 may differ in its guanine nucleotide exchange factor binding specificity, relative to PAK1.

The 265 amino acid catalytic domain of human PAK4 is most related to human PAK5 (SEQ ID NO:30), PAK1 (GB:U24152), GCK (GB:U07349), SOK-1 (GB:X99325), and SLK (GB:AB002804), as well as to the *C. elegans* (GB:Z74029), and *S. cerevisiae* STE20-related kinases (GB:L04655), sharing 95.9%, 51.7%, 41.3%, 39.8%, 37.4%, 60.2% and 47.9% amino acid identity, respectively. PAK4 contains the potential "TPY" regulatory phosphorylation site in its activation loop. This "TPY" motif is conserved in other STE20-related kinases, including ZC1, ZC2, ZC3, ZC4, GEK2, KHS2, SULU1, SULU3 and PAK5.

The 23 amino acid C-tail of human PAK4 contains a sequence that is homologous to a G-protein beta subunit binding site (Leeuw, T. et al. Nature, 391, 191–195 (1998)). PAK4 has, therefore, the potential to be activated by both Cdc42- as well as G-protein-dependant pathways.

Mammalian PAK5

The 2,806 bp human PAK5 nucleotide sequence of the complete cDNA encodes a polypeptide of 591 amino acids (SEQ ID NO:103) with a predicted molecular mass of 64,071 Daltons. Analysis of the deduced amino acid sequence predicts PAK5 to be an intracellular STE20-subfamily kinase, lacking both a signal sequence and transmembrane domain. The full-length PAK5 protein contains a 52 amino acid N-terminus predicted to contain a p21 (small G-protein) binding domain (PDB or CRIB), a 121 amino acid insert relative to the known mammalian PAK proteins, a 134 amino spacer region, a 265 amino acid catalytic domain with all the motifs characteristic of a serine/threonine kinase and a 19 amino acid C-terminal tail.

PAK5 is most closely related to Human PAK4 (SEQ ID NO:29), *Drosophila melanogaster* PAK (also known as "mushroom bodies tiny") (AJ011578), C45B11.1b from *C.*

*elegans* (Z74029), and human PAK3 (Q13177) sharing 48% (327/674 aa), 50% (330/651 aa), 43% (234/435 aa excluding gap), and 47% (190/405 aa excluding gap) amino acid identity, respectively. Recently, a full length version of PAK5 Was reported (PAK4 AF005046) whose 591 amino acid sequence is identical to PAK5 (SEQ ID NO:103). (Abo, et al. (1998) EMBO J. 17:6527–6540).

The 52 amino acid N-terminal domain of human PAK5 is most related to human PAK4 (SEQ ID NO:29), *Drosophila melanogaster* PAK (AJ011578), C45B11.1b from *C. elegans* (Z74029), and human PAK3 (Q13177), sharing 65%, 57%, 54%, and 53% amino acid identity, respectively.

The 11 amino acid region at positions 12–22 of human PAK5 (FIG. 10A) fits the consensus for a small G-protein binding domain (PDB or CRIB) (SXPX4-6HXXH) (SEQ ID NO: 150) (Burbelo, P. D., Dreschel, D. and Hall, A. J. Bio. Chem. 270, 29071–29074 (1995), hereby incorporated by reference herein in its entirety including any figures, tables, or drawings.).

The 121 amino acid insert of human PAK5 shares 43% amino acid identity with a similar domain from PAK4 (SEQ ID NO:29), but that is absent from other known PAKs.

The equivalent spacer region in PAK1 binds to the guanine nucleotide exchange factor PIX (Manser, E. et al (1998) Molecular Cell, 1, 183–192 hereby incorporated by reference herein in its entirety including any drawings, figures, or tables.). Since PAK5 differs substantially from PAK1 over this region, the spacer domain of PAK5 may differ in its guanine nucleotide exchange factor binding specificity, relative to PAK1.

The 134 amino acid collagen-like region of human PAK5 shares 34% amino acid identity to pro-α I type collagen from several species and is not present in other known PAKs.

The 265 amino acid catalytic domain of human PAK5 is most related to human PAK4 (SEQ ID NO:29), *Drosophila melanogaster* PAK (AJ011578), C45B11.1b from *C. elegans* (Z74029), and human PAK3 (Q13177), sharing 78%, 80%, 61%, and 55% amino acid identity, respectively. PAK5 also contains the potential "TPY" regulatory phosphorylation site in its activation loop. This "TPY" motif is conserved in other STE20-related kinases, including ZC1, ZC2, ZC3, ZC4, GEK2, KHS2, SULU1, SULU3 and PAK4.

The 19 amino acid C-tail shares 80% amino acid identity to a PAK-like homologue identified from genomic DNA (AL031652). Furthermore, this C-terminal region of human PAK5 contains a sequence that is homologous to a G-protein beta subunit binding site (Leeuw, T. et al. Nature, 391, 191–195 (1998) hereby incorporated by reference herein in its entirety including any figures, tables, or drawings). PAK5 has, therefore, the potential to be activated by both, Cdc42 as well as G-protein-dependant pathways.

V. Antibodies Hybridomas, Methods of Use and Kits for Detection of STE20-Related Kinases The present invention relates to an antibody having binding affinity to a kinase of the invention. The polypeptide may have the amino acid sequence set forth in SEQ ID NO:5, SEQ ID NO:6, SEQ ID NO:7, SEQ ID NO:13, SEQ ID NO:14, SEQ ID NO:15, SEQ ID NO:18, SEQ ID NO:22, SEQ ID NO:23, SEQ ID NO:24, SEQ ID NO:29, SEQ ID NO:97, SEQ ID NO:99, SEQ ID NO:101, SEQ ID NO:103, SEQ ID NO:105, or SEQ ID NO:107, or a functional derivative thereof, or at least 9 contiguous amino acids thereof (preferably, at least 20, 30, 35, or 40 or more contiguous amino acids thereof).

The present invention also relates to an antibody having specific binding affinity to a kinase of the invention. Such an antibody may be isolated by comparing its binding affinity to a kinase of the invention with its binding affinity to other polypeptides. Those which bind selectively to a kinase of the invention would be chosen for use in methods requiring a distinction between a kinase of the invention and other polypeptides. Such methods could include, but should not be limited to, the analysis of altered kinase expression in tissue containing other polypeptides.

The STE20-Related kinases of the present invention can be used in a variety of procedures and methods, such as for the generation of antibodies, for use in identifying pharmaceutical compositions, and for studying DNA/protein interaction.

The kinases of the present invention can be used to produce antibodies or hybridomas. One skilled in the art will recognize that if an antibody is desired, such a peptide could be generated as described herein and used as an immunogen. The antibodies of the present invention include monoclonal and polyclonal antibodies, as well fragments of these antibodies, and humanized forms. Humanized forms of the antibodies of the present invention may be generated using one of the procedures known in the art such as chimerization or CDR grafting.

The present invention also relates to a hybridoma which produces the above-described monoclonal antibody, or binding fragment thereof. A hybridoma is an immortalized cell line which is capable of secreting a specific monoclonal antibody.

In general, techniques for preparing monoclonal antibodies and hybridomas are well known in the art (Campbell, "Monoclonal Antibody Technology: Laboratory Techniques in Biochemistry and Molecular Biology," Elsevier Science Publishers, Amsterdam, The Netherlands, 1984; St. Groth et al., J. Immunol. Methods 35:1–21, 1980). Any animal (mouse, rabbit, and the like) which is known to produce antibodies can be immunized with the selected polypeptide. Methods for immunization are well known in the art. Such methods include subcutaneous or intraperitoneal injection of the polypeptide. One skilled in the art will recognize that the amount of polypeptide used for immunization will vary based on the animal which is immunized, the antigenicity of the polypeptide and the site of injection.

The pblypeptide may be modified or administered in an adjuvant in order to increase the peptide antigenicity. Methods of increasing the antigenicity of a polypeptide are well known in the art. Such procedures include coupling the antigen with a heterologous protein (such as globulin or β-galactosidase) or through the inclusion of an adjuvant during immunization.

For monoclonal antibodies, spleen cells from the immunized animals are removed, fused with myeloma cells, such as SP2/0-Agl4 myeloma cells, and allowed to become monoclonal antibody producing hybridoma cells. Any one of a number of methods well known in the art can be used to identify the hybridoma cell which produces an antibody with the desired characteristics. These include screening the hybridomas with an ELISA assay, western blot analysis, or radioimmunoassay (Lutz et al., Exp. Cell Res. 175:109–124, 1988). Hybridomas secreting the desired antibodies are cloned and the class and subclass are determined using procedures known in the art (Campbell, "Monoclonal Antibody Technology: Laboratory Techniques in Biochemistry and Molecular Biology", supra, 1984).

For polyclonal antibodies, antibody-containing antisera is isolated from the immunized animal and is screened for the presence of antibodies with the desired specificity using one of the above-described procedures. The above-described antibodies may be detectably labeled. Antibodies can be detectably labeled through the use of radioisotopes, affinity labels (such as biotin, avidin, and the like), enzymatic labels (such as horse radish peroxidase, alkaline phosphatase, and the like) fluorescent labels (such as FITC or rhodamine, and the like), paramagnetic atoms, and the like. Procedures for accomplishing such labeling are well-known in the art, for example, see Sternberger et al., J. Histochem. Cytochem. 18:315, 1970; Bayer et al., Meth. Enzym. 62:308-, 1979; Engval et al., Immunol. 109:129-, 1972; Goding, J. Immunol. Meth. 13:215-, 1976. The labeled antibodies of the present invention can be used for in vitro, in vivo, and in situ assays to identify cells or tissues which express a specific peptide.

The above-described antibodies may also be immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., "Handbook of Experimental Immunology" 4th Ed., Blackwell Scientific Publications, Oxford, England, Chapter 10, 1986; Jacoby et al., Meth. Enzym. 34, Academic Press, N.Y., 1974). The immobilized antibodies of the present invention can be used for in vitro, in vivo, and in situ assays as well as in immunochromotography.

Furthermore, one skilled in the art can readily adapt currently available procedures, as well as the techniques, methods and kits disclosed herein with regard to antibodies, to generate peptides capable of binding to a specific peptide sequence in order to generate rationally designed antipeptide peptides (Hurby et al., "Application of Synthetic Peptides: Antisense Peptides", In Synthetic Peptides, A User's Guide, W.H. Freeman, NY, pp. 289–307, 1992; Kaspczak et al., Biochemistry 28:9230–9238, 1989).

Anti-peptide peptides can be generated by replacing the basic amino acid residues found in the peptide sequences of the kinases of the invention with acidic residues, while maintaining hydrophobic and uncharged polar groups. For example, lysine, arginine, and/or histidine residues are replaced with aspartic acid or glutamic acid and glutamic acid residues are replaced by lysine, arginine or histidine.

The present invention also encompasses a method of detecting a STE20-related kinase polypeptide in a sample, comprising: (a) contacting the sample with an above-described antibody, under conditions such that immunocomplexes form, and (b) detecting the presence of said antibody bound to the polypeptide. In detail, the methods comprise incubating a test sample with one or more of the antibodies of the present invention and assaying whether the antibody binds to the test sample. Altered levels of a kinase of the invention in a sample as compared to normal levels may indicate disease.

Conditions for incubating an antibody with a test sample vary. Incubation conditions depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion based Ouchterlony, or rocket immunofluorescent assays) can readily be adapted to employ the antibodies of the present invention. Examples of such assays can be found in Chard ("An Introduction to Radioimmunoassay and Related Techniques" Elsevier Science Publishers, Amsterdam, The Netherlands, 1986), Bullock et al. ("Techniques in Immunocytochemistry," Academic Press, Orlando, Fla. Vol. 1, 1982; Vol. 2, 1983; Vol. 3, 1985), Tijssen ("Practice and Theory of Enzyme Immunoassays: Laboratory Techniques in Biochemistry and Molecular Biology," Elsevier Science Publishers, Amsterdam, The Netherlands, 1985).

The immunological assay test samples of the present invention include cells, protein or membrane extracts of cells, or biological fluids such as blood, serum, plasma, or urine. The test samples used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is testable with the system utilized.

A kit contains all the necessary reagents to carry out the previously described methods of detection. The kit may comprise: (i) a first container means containing an above-described antibody, and (ii) second container means containing a conjugate comprising a binding partner of the antibody and a label. In another preferred embodiment, the kit further comprises one or more other containers comprising one or more of the following: wash reagents and reagents capable of detecting the presence of bound antibodies.

Examples of detection reagents include, but are not limited to, labeled secondary antibodies, or in the alternative, if the primary antibody is labeled, the chromophoric, enzymatic, or antibody binding reagents which are capable of reacting with the labeled antibody. The compartmentalized kit may be as described above for nucleic acid probe kits. One skilled in the art will readily recognize that the antibodies described in the present invention can readily be incorporated into one of the established kit formats which are well known in the art.

VI. Isolation of Compounds Which Interact With STE20-Related Kinases

The present invention also relates to a method of detecting a compound capable of binding to a STE20-related kinase of the invention comprising incubating the compound with a kinase of the invention and detecting the presence of the compound bound to the kinase. The compound may be present within a complex mixture, for example, serum, body fluid, or cell extracts.

The present invention also relates to a method of detecting an agonist or antagonist of kinase activity or kinase binding partner activity comprising incubating cells that produce a kinase of the invention in the presence of a compound and detecting changes in the level of kinase activity or kinase binding partner activity. The compounds thus identified would produce a change in activity indicative of the presence of the compound. The compound may be present within a complex mixture, for example, serum, body fluid, or cell extracts. Once the compound is identified it can be isolated using techniques well known in the art.

The present invention also encompasses a method of agonizing (stimulating) or antagonizing kinase associated activity in a mammal comprising administering to said mammal an agonist or antagonist to a kinase of the invention in an amount sufficient to effect said agonism or antagonism. A method of treating diseases in a mammal with an agonist or antagonist of STE20-related kinase activity comprising administering the agonist or antagonist to a mammal in an amount sufficient to agonize or antagonize STE20-related kinase associated functions is also encompassed in the present application.

In an effort to discover novel treatments for diseases, biomedical researchers and chemists have designed, synthesized, and tested molecules that inhibit the function of protein kinases. Some small organic molecules form a class of compounds that modulate the function of protein kinases. Examples of molecules that have been reported to inhibit the function of protein kinases include, but are not limited to, bis monocyclic, bicyclic or heterocyclic aryl compounds (PCT WO 92/20642, published Nov. 26, 1992 by Maguire et al.), vinylene-azaindole derivatives (PCT WO 94/14808, published Jul. 7, 1994 by Ballinari et al.), 1-cyclopropyl-4-pyridyl-quinolones (U.S. Pat. No. 5,330,992), styryl compounds (U.S. Pat. No. 5,217,999), styryl-substituted pyridyl compounds (U.S. Pat. No. 5,302,606), certain quinazoline derivatives (EP Application No. 0 566 266 A1), seleoindoles and selenides (PCT WO 94/03427, published Feb. 17, 1994 by Denny et al.), tricyclic polyhydroxylic compounds (PCT WO 92/21660, published Dec. 10, 1992 by Dow), and benzylphosphonic acid compounds (PCT WO 91/15495, published Oct. 17, 1991 by Dow et al).

Compounds that can traverse cell membranes and are resistant to acid hydrolysis are potentially advantageous as therapeutics as they can become highly bioavailable after being administered orally to patients. However, many of these protein kinase inhibitors only weakly inhibit the function of protein kinases. In addition, many inhibit a variety of protein kinases and will cause multiple side-effects as therapeutics for diseases.

Some indolinone compounds, however, form classes of acid resistant and membrane permeable organic molecules. WO 96/22976 (published Aug. 1, 1996 by Ballinari et al.) describes hydrosoluble indolinone compounds that harbor tetralin, naphthalene, quinoline, and indole substituents fused to the oxindole ring. These bicyclic substituents are in turn substituted with polar moieties including hydroxylated alkyl, phosphate, and ether moieties. U.S. patent application Ser. Nos. 08/702,232, filed Aug. 23, 1996, entitled "Indolinone Combinatorial Libraries and Related Products and Methods for the Treatment of Disease" by Tang et al. (Lyon & Lyon Docket No. 221/187) and 08/485,323, filed Jun. 7, 1995, entitled "Benzylidene-Z-Indoline Compounds for the Treatment of Disease" by Tang et al. (Lyon & Lyon Docket No. 223/298) and International Patent Publication WO 96/22976, published Aug. 1, 1996 by Ballinari et al., all of which are incorporated herein by reference in their entirety, including any drawings, describe indolinone chemical libraries of indolinone compounds harboring other bicyclic moieties as well as monocyclic moieties fused to the oxindole ring. Applications 08/702,232, filed Aug. 23, 1996, entitled "Indolinone Combinatorial Libraries and Related Products and Methods for the Treatment of Disease" by Tang et al. (Lyon & Lyon Docket No. 221/187), 08/485,323, filed Jun. 7, 1995, entitled "Benzylidene-Z-Indoline Compounds for the Treatment of Disease" by Tang et al. (Lyon & Lyon Docket No. 223/298), and WO 96/22976, published Aug. 1, 1996 by Ballinari et al. teach methods of indolinone synthesis, methods of testing the biological activity of indolinone compounds in cells, and inhibition patterns of indolinone derivatives.

Other examples of substances capable of modulating kinase activity include, but are not limited to, tyrphostins, quinazolines, quinoxolines, and quinolines. The quinazolines, tyrphostins, quinolines, and quinoxolines referred to above include well known compounds such as those described in the literature. For example, representative publications describing quinazolines include Barker et al., EPO Publication No. 0 520 722 A1; Jones et al., U.S. Pat. No. 4,447,608; Kabbe et al., U.S. Pat. No. 4,757,072; Kaul and Vougioukas, U.S. Pat. No. 5, 316,553; Kreighbaum and Comer, U.S. Pat. No. 4,343,940; Pegg and Wardleworth, EPO Publication No. 0 562 734 A1; Barker et al., *Proc. of Am. Assoc. for Cancer Research* 32:327 (1991); Bertino, J. R., *Cancer Research* 3:293–304 (1979); Bertino, J. R., *Cancer Research* 9(2 part 1):293–304 (1979); Curtin et al., *Br. J. Cancer* 53:361–368 (1986); Fernandes et al., *Cancer Research* 43:1117–1123 (1983); Ferris et al. *J. Org. Chem.* 44(2):173–178; Fry et al., *Science* 265:1093–1095 (1994); Jackman et al., *Cancer Research* 51:5579–5586 (1981); Jones et al. *J. Med. Chem.* 29(6):1114–1118; Lee and Skibo, *Biochemistry* 26(23):7355–7362 (1987); Lemus et al., *J. Org. Chem.* 54:3511–3518 (1989); Ley and Seng, *Synthesis* 1975:415–522 (1975); Maxwell et al., *Magnetic Resonance in Medicine* 17:189–196 (1991); Mini et al., *Cancer Research* 45:325–330 (1985); Phillips and Castle, *J. Heterocyclic Chem.* 17(19):1489–1596 (1980); Reece et al., *Cancer Research* 47(11):2996–2999 (1977); Sculier et al., *Cancer Immunol. and Immunother.* 23:A65 (1986); Sikora et al., *Cancer Letters* 23:289–295 (1984); Sikora et al., *Analytical Biochem.* 172:344–355 (1988); all of which are incorporated herein by reference in their entirety, including any drawings.

Quinoxaline is described in Kaul and Vougioukas, U.S. Pat. No. 5,316,553, incorporated herein by reference in its entirety, including any drawings.

Quinolines are described in Dolle et al., *J. Med. Chem.* 37:2627–2629 (1994); MaGuire, *J. Med. Chem.* 37:2129–2131 (1994); Burke et al., *J. Med. Chem.* 36:425–432 (1993); and Burke et al. BioOrganic Med. Chem. Letters 2:1771–1774 (1992), all of which are incorporated by reference in their entirety, including any drawings.

Tyrphostins are described in Allen et al., *Clin. Exp. Immunol.* 91:141–156 (1993); Anafi et al., *Blood* 82:12:3524–3529 (1993); Baker et al., *J. Cell Sci.* 102:543–555 (1992); Bilder et al., *Amer. Physiol. Soc.* pp. 6363–6143:C721–C730 (1991); Brunton et al., *Proceedings of Amer. Assoc. Cancer Rsch.* 33:558 (1992); Bryckaert et al., *Experimental Cell Research* 199:255–261 (1992); Dong et al., *J. Leukocyte Biology* 53:53–60 (1993); Dong et al., *J. Immunol.* 151(5):2717–2724 (1993); Gazit et al., *J. Med. Chem.* 32:2344–2352 (1989); Gazit et al., "*J. Med. Chem.* 36:3556–3564 (1993); Kaur et al., *Anti-Cancer Drugs* 5:213–222 (1994); Kaur et al., King et al., *Biochem. J.* 275:413–418 (1991); Kuo et al., *Cancer Letters* 74:197–202 (1993); Levitzki, A., *The FASEB J.* 6:3275–3282 (1992); Lyall et al., *J. Biol. Chem.* 264:14503–14509 (1989); Peterson et al., *The Prostate* 22:335–345 (1993); Pillemer et al., *Int. J. Cancer* 50:80–85 (1992); Posner et al., *Molecular Pharmacology* 45:673–683 (1993); Rendu et al., *Biol. Pharmacology* 44(5):881–888,(1992); Sauro and Thomas, *Life Sciences* 53:371–376 (1993); Sauro and Thomas, *J. Pharm. and Experimental Therapeutics* 267(3):119–1125 (1993); Wolbring et al., *J. Biol. Chem.* 269(36):22470–22472 (1994); and Yoneda et al., *Cancer Research* 51:4430–4435 (1991); all of which are incorporated herein by reference in their entirety, including any drawings.

Other compounds that could be used as modulators include oxindolinones such as those described in U.S. patent application Ser. No. 08/702,232 filed Aug. 23, 1996, incorporated herein by reference in its entirety, including any drawings.

VII. Biological Significance, Applications and Clinical Relevance of Novel STE20-Related Kinases Human STLK2, STLK3, STLK4, STLK5, STLK6, and STLK7

STLK2, STLK4, STLK5, STLK6 and STLK7 belong to an expanding family of intracellular STKs that have varying degrees of sequence homology to SOK-1, a kinase implicated in oxidative stress agents (Pombo, C M et al, EMBO J. (17) 4537–4546, 1996). Our data shows that STLK2 is expressed highly in hematopoietic cells. Therefore, STLK2 may participate in the oxidative response pathway during inflammation. In addition, STLK2 could also be a possible component in the signaling pathways leading to T cell activation. High levels of STLK2 in several tumor cell lines could also imply that STLK2 might be involved in tumorigenesis.

STLK2 is most closely related to two human STE20-subfamily kinases: MST3 and SOK-1. MST3 is a 52,000 daltons cytoplasmic kinase that is ubiquitously expressed with its highest levels of expression found in heart, skeletal muscle and pancreas. The serine/threonine kinase activity of MST3 is activated by phosphorylation. Unlike SOK-1, MST3 prefers $Mn^{++}$ over $Mg^{++}$ and can use both GTP and ATP as phosphate donors. MST3 may undergo dimerization. No agonists have yet been identified that activate MST3. The downstream signaling mechanism of this kinase is unknown (Schinkmann, K and Blenis, J. (1997) J. Biol. Chem. 272, 28695–28703).

SOK-1 is a 50,000 daltons cytoplasmic kinase expressed predominantly in testis, large intestine, brain and stomach and to a lesser extent in heart and lung. SOK-1 is also expressed in the germinal center B-cell line (RAMOS) and in a mature B cell line (HS Sultan). The serine/threonine kinase activity of SOK-1 is activated by phosphorylation. The C-terminus of SOK-1 has been shown to be inhibitory to the catalytic activity of this kinase. The only agonists known to activate SOK-1 are oxidant agents, like $H_2O_2$ and menadione, a quinone that is a potent intracellular generator of reactive oxygen species (Pombo, C. M. et al. EMBO J. 15, 4537–4546). SOK-1 is also activated by chemical anoxia through the generation of reactive oxygen species and release of calcium into the cytoplasm from intracellular stores. SOK-1, therefore, may play an important role in ischemia, the cause of myocardial infarction, stroke and acute renal failure (Pombo, C. M. et al. J. Biol. Chem. 272, 29372–29379 (1997)). The activity of SOK-1 in the response to oxidant stress is inversely correlated with the activity of the stress-activated protein kinases (SAPKs): elevated SOK-1 activity correlates with absent SAPK activity and vice-versa. SOK-1 does not activate any of the four MAP kinase pathways, SAPKS, p38, ERK-1 or MEK-5/ERK-5 (Pombo, C. M. et al. EMBO J. 15, 4537–4546). The downstream signaling mechanism of this kinase remains unknown.

STLK2 is expressed in a wide variety of immune cell types and tissues including thymus, dendrocytes, mast cells, monocytes, B cells (primary, Jurkat, RPMI, SR), T cells (CD8/CD4+, TH1, TH2, CEM, MOLT4) and megakaryocytes (K562), whereas STLK3 is restricted to thymus and STLK4 is predominantly expressed in thymus, T cells (CD4/CD8+, TH1, CEM) and B cells (Jurkat, RPMI). Consequently, these STKs might participate in the oxidative response pathway during inflammation, reperfusion injury (stroke, surgery, shock), TNFα-mediated signaling, insulin desensitization, atherogenesis, vascular injury, T or B cell costimulation, or alternatively, participate in other MAPK-related signal transduction processes.

TLK5 is more distantly related to this STE20-subfamily including SOK-1 and STLK2, STLK3 and STLK4. STLK5, may therefore mediate a signaling pathway that is distinct from the oxidative stress response pathway.

The high degree of sequence homology in the C-termini of SOK-1, STLK2, STLK3, STLK4, STLK5, and STLK6 raises the possibility that these novel STKs, like SOK-1, may be subject to autoinhibition through a conserved C-terminal motif.

Human ZC1, ZC2, ZC3 and ZC4

ZC1 is a good candidate for any disease in which tyrosine kinase, cytokine, or heterotrimeric G-protein coupled receptors have been implicated. The mouse homologue binds to NCK, and is recruited to activated PDGF (Su et al., EMBO 16: 1279–1290, 1997). The Drosophila homolog has been shown to bind to TRAF2, implicating it in TNF-α signaling (Liu et al., (1999) Curr. Biol. 9:101–104, 1999)). While ZC1 does not contain the exact NCK- and TRAF2-binding domains, it is likely to bind to related proteins.

Of the ZC subfamily of STE20-related protein kinases, ZC1 has very broad over-expression in many tumor types, suggesting that it may be involved in cellular growth, transformation, or tumor progression. A truncated form of ZC1 containing only the C-terminal putative MEKK1-binding domain was found to reduce the number of foci generated by H-Ras-V12 in Rat Intestinal Epithelial cells (RIE-1). These data indicate that ZC1 may play a role in the ability for these cells to overcome contact inhibition and anchorage-dependent growth.

The ZC1 homolog, Misshapen (msn) in *Drosophila melanogaster* was cloned as a result of complementing a mutation in a developmental pathway required for dorsal closure, a process involving changes in cell shape and position in the embryo (Treisman et al. Gene 186 119–125, 1997). A *D. melanogaster* homolog of the JNK1/JNK2 kinases from mammals was shown to function downstream of msn in the dorsal-closure signaling pathway (Su et al. Genes Dev. 12:2371–2380, 1998).

While ZC1 could be involved in multiple aspects of tumorigenesis, by analogy with Drosophila, the role of misshapen in dorsal closure suggests a critical role in the regulation of the cytoskeleton for the processes of cell attachment, cell movement and perhaps migration.

The association of the ZC1 family members msn and NIK with TRAF2 may indicate a role for this kinase in cell survival and/or in apoptosis. The ZC1 family contains a highly conserved domain that in the mouse homolog, NIK, has been shown to bind to MEKK1 (Mitogen-activated/Extracellular-regulated Kinase Kinase 1) (Su et al., (1997) EMBO 16(6):1279–90). MEKK1 is involved in cell survival and/or apoptosis in several systems (Schlesinger et al., Front. Biosci. 3:D1181–6, 1998). Depending on the context, MEKK1 appears to be upstream of either the ERK1/MAPK or the JNK/SAPK pathway [Schlesinger et al., (1998 Front. Biosci. 3:D1181–6). Three homologues of ZC1: murine NIK (NCK-interacting kinase) (Su et al. EMBO 16:1279–90, 1–997), Drosophila msn (Liu et al. Curr. Biol. 9:101–104, 1999) and human HGK (HPK/GCK-like kinase) (Yao et al., J. Biol. Chem. 274:2118–25, 1999) have all been shown to activate the JNK pathway when over-expressed in 293T cells.

ZC1 shares a high degree of homology with these other family members in both the kinase domain and the "MEKK"-binding domains, yet it differs in the intervening region, which contains several putative binding domains for upstream signaling adapter molecules (e.g. NCK, TRAF2). Unlike the other family members, ZC1 does not appear to activate the JNK pathway in 293T cells as seen by its ability to induce expression of either a JUN or ATF2-driven luciferase gene. Upon co-transfection into these cells with HA-tagged JNK, modest activation of JNK was detected. ZC1 also modestly activated co-transfected ERK1. Both the ERK and the JNK activation were very slight compared with the positive controls in the assay (activated forms of MEK1 and MEKK1, respectively). In both cases, activation required the full-length kinase. While the kinase domain alone is up to 5× more active in autophosphorylation and in phosphorylation of MBP, it does not lead to activation of these potential downstream kinases. Based on the strong sequence homology of ZC1 with the other family members, it is very likely that ZC1 will be important for either JNK or ERK activation once the proper context is found.

ZC1 profoundly inhibits ERK1 kinase expression in co-transfection assays. This effect is dependent on ZC1 kinase activity, occurring with the wild-type and the kinase domain alone, but not with the kinase-dead mutant even though all three forms of ZC1 are expressed at similar levels. This may suggest a role for this kinase in transcriptional or post-transcriptional regulation.

ZC1 may be an important component in the signaling pathways mediated by the co-stimulatory receptor CD28 in T cells and/or by the pro-inflammatory cytokine TNFα, since co-transfection of the wild-type ZC1 activated the RE/AP-luciferase and NFκB-luciferase reporter genes. While our data showed that ZC1 strongly activates NFκB in T-cells, no activation of NFκB driven luciferase was detectable in NIH 3T3 cells. A recent paper (J. Biol. Chem. 274:2118–25; 1999.) has shown that a human ZC1 splicing isoform, HGK, is involved in the TNFα-signaling pathways.

Given the importance of T cell activation in autoimmunity and transplantation, as well as the key role that TNFα plays in inflammatory diseases, it is possible that ZC1 could be a therapeutic target for immunological diseases which include but are not limited to: rheumatoid arthritus, chronic inflammatory bowel diseases (ie Crohn's disease), chronic inflammatory pelvic disease, multiple sclerosis, asthma, osteoarthritis, psoriasis, atherosclerosis, rhinitis, and autoimmunity as well as organ transplantation and cardio-vascular diseases.

ZC1 appears to be the human orthologue of murine NIK and possibly an orthologue of a C. elegans STE20-subfamily kinase encoded by the ZC504.4 cosmid.

Murine NIK is a 140,000 daltons kinase that is most highly expressed in brain and heart. NIK interacts with the SH3 domains of the adaptor molecule Nck through its proline-rich regions found in the C-terminal extra-catalytic region. The specific regions that mediate this interaction are two PxxP (SEQ ID NO: 148) motifs that are nearly uniformly conserved between NIK, ZC1,2,3 and the C. elegans STE20 ZC504.4 kinase. In addition, NIK binds MEKK1 through its 719 amino acid C-terminal (Su, Y-C. et al. (1997) EMBO J. 16, 1279–1290). MEKK1 is a membrane-associated kinase responsible for activating MKK4 (also known as SEK1), which in turn activates SAPK (Yan, M et al. (1994) Nature, 372, 798–800). NIK may function as a kinase that links growth factor activated pathways and the stress-response pathway mediated by SAPKs. According to this hypothesis, activation of growth factor receptors leads to receptor tyrosine phosphorylation, Nck binding to the phosphorylated tyrosines via its SH2 domain, NIK redistribution to a membrane compartment via binding to the SH3 domain of Nck, and juxtaposition to the membrane-associated MEKK1. The NIK-MEKK1 interaction would, in this fashion, turn on the SAPK pathway in response to growth factor stimulation (Su, Y-C. et al. (1997) EMBO J. 16, 1279–1290).

Given the high homology between ZC1, ZC2, ZC3, and ZC4 STKs and NIK, it is conceivable that these kinases may each function to connect growth factor- and stress-activated signaling pathways. The heterogeneity that the ZC kinases exhibit within their putative SH3-binding domain could provide signaling specificity in terms of the nature of the adaptor molecule that they bind. The high level of sequence conservation in the C-termini of the ZC1, ZC2 and ZC3 strongly suggests that these human kinases, like murine NIK, also may bind to MEKK1 and activate SAPKs. The ZC kinases also display strong homology at their C-termini to protein domains that bind small GTPase proteins such as Rab, Rho and Rac. For example, the C-termini of ZC1 is 36.2% identical to citron, a murine Rho-binding protein, and 23.1% identical to the rab-binding region of GC kinase. This suggests that, in addition to adaptor molecules, small GTPase proteins may also mediate membrane association and activation of the ZC kinases. The presence of a potential coiled-coil region located immediately C-terminal to the catalytic region strongly suggests that the ZC kinases may also be subject to regulation via homo or heterodimerization events.

The C. elegans STE20 ZC504.4 kinase is the product of the mig-15 gene. The product of this gene has been implicated in several developmental processes such as epidermal development, Q neuroblast migrations and muscle arm targeting in the developing worm (Zhu, X. and Hedgecock E. (1997) Worm Breeder's Gazette 14, 76). The high level of sequence conservation between the ZC kinases and the ZC504.4 C. elegans kinase will make C. elegans a valuable model organism to study, through epistatic analysis, the signaling properties of the human ZC kinases.

Human KHS2

KHS1 (kinase homologous to SPS1/STE20) is a 100,000 dalton cytoplasmic STK that is expressed ubiquitously. KHS1 has been implicated in the mechanism of SAPK activation in response to inflammatory cytokines such as TNFα as well as to ultraviolight light, which also uses the TNF signaling pathway. TNFα binding to its receptors (TNFR1 and TNFR2) results in the sequential association with the receptor C-tail of multiple signaling molecules including TNFR1-associated death domain protein (TRADD), Fas-associated death domain protein (FADD or MORT1), TNFR-associated factor 2 (TRAF2), and the STK RIP (receptor interacting protein). The TRADD-TRAF2 interaction is mediated by a conserved region present at the C-terminus of TRAF2, the TRAF domain. Activation of the NFκB and SAPK pathways is mediated by the ring finger motif present at the N-terminus of TRAF2 (Curr. Opinion in Cell. Biol. (1997) 9:247–251). KHS1 is activated by TNFα stimulation in a TRAF2-dependant manner and inhibition of KHS1 blocks TNFα-induced SAPK activation but not NFκB activation. The mechanism by which TRAF2 activates KHS1 is not known. Cotransfection of TRAF2- and KHS1-expressing constructs in 293T cells failed to reveal a direct association between these two molecules. KHS1 activates the SAPK pathway by a direct association with the constitutively active kinase MEKK1. MEKK1 subsequently activates SEK1, which in turn activates SAPK. Neither the MAPK nor the p38 kinase pathways are activated by KHS1 (Shi, C-S and Kehrl. J. H. (1997) J. Biol. Chem. 272, 32102–32107). In addition to its catalytic domain, downstream signaling of KHS1 requires its conserved C-terminus (Diener, K. et al (1997) Proc. Natl. Acad. Sci. 94, 9687–9692).

GCK (germinal center kinase) is a constitutively active 97,000 dalton STK that is broadly expressed. GCK may participate in B-cell differentiation since its expression is localized to the germinal center within lymphoid follicles. GCK activates the SAPK pathway in response to TNFα via activation of SEK1. The upstream activators of GCK in response to cytokines as well as the immediate downstream target of this kinase are unknown. The C-terminus of GCK is sufficient to activate SEK1 (Pombo, C. M. et al (1995) Nature, 377, 750–754).

The murine orthologue of GCK, rab8ip (rab8-interacting protein), is a 97,000 dalton protein that fractionates with both the soluble cytoplasmic fraction as well as with a salt-sensitive fraction associated with the basolateral membrane of the trans-Golgi region in polarized MDCK epithelial cells. The C-terminus of rab8ip binds to rab8, a small GTP-binding protein required for vesicular transport from the Golgi apparatus (Ren, M. et al. (1996) Proc. Natl. Acad. Sci. 93, 5151–5155). In addition to inducing the transcriptional activation of cytokines like IL2 via SAPK, GCK may also promote the rab-dependent release of secretory proteins in response to TNFα (Buccione, R. et al (1995) Mol. Bio. Cell 6, 291).

HPK1 (hematopoietic protein kinase) is a constitutively active 90,000 dalton STK restricted to hematopoietic cells. HPK1 activates the SAPK pathway by directly binding to and activating MEKK1 (Hu, M. et al (1996) Genes and Dev. 10:2251–2264) as well as the ubiquitously expressed mixed-lineage kinase MLK-3 (Kiefer, F. et al (1996) EMBO J. 15:7013–7025). This function of HPK1 requires, in contrast to GCK, both its kinase domain as well as its C-terminus. The upstream activators of HPK1 remain unknown. HPK1 also plays a key role as a mediator of transforming growth factor-β (TGFβ) signaling. HPK1 activates the TGFb-activated kinase (TAK), which in turn stimulates the SAPK pathway by phosphorylating SEK1 (Wang W. et al (1997) J. Biol. Chem. 272:22771–22775).

KHS2 is expressed in thymus, dendrocytes and monocytes. KHS2 could have a complementary function to that of KHS1 as a mediator of SAPK activation in the cellular response to inflammatory cytokines. KHS2 could have the potential to interact directly with TRAF2 since a STK with the predicted molecular weight of KHS2 (approximately 101,000 daltons) is found in the TNFR-TRAF2 complex upon TNFα stimulation (VanArsdale, T. and Ware, C. F. (1994) J. Immunol. 153, 3043–3050). The presence of a putative binding domain for Rab or a Rab-like molecule at the C-terminus of KHS2 indicates that KHS2, in addition to having a potential role in the TRAF2-dependant TNFα cytokine response, could also mediate signaling events that utilize small GTPase proteins. Alternatively, the binding of a small GTPase protein to the C-terminus of KHS2 may be required for its potential TRAF2-dependant signaling to a downstream kinase such as MEKK1.

Human GEK2, SULU1 and SULU3

A recent report (Y-W Qian et al., Science 282:1701–1704, 1998) described xPlkk1 as the activator of Plx1 (the Xenopus Polo kinase). In Xenopus oocytes, the STK Plkk1 can phosphorylate and activate Plx1 STK (the mammalian Polo kinase or PLK). A dominant-negative (kinase-dead) form of xPlkk1 prevents Plx1 activation and delays germinal vesicle breakdown. Yet another unidentified kinase is probably responsible for xPlkk1 activation during mitosis.

The homology through the entire length of the xPlkk1 protein with GEK2 suggests that GEK2 might represent the human homologue for xPlkk1. Based on this, GEK2 might be upstream of PLK in mammalian cells. In addition, based on the phage display screen results using the SULU1 coiled-coil2 domain as bait, SULU1 might also interact in vivo with GEK2 and therefore regulate GEK2 (and/or SLK through the coiled-coil domain) activation leading to PLK activation and mitosis.

If such a cascade of events is required for mitosis in mammalian cells, interruption of this signaling cascade at any point might block mitosis and could be beneficial for cancer treatment.

A recently cloned STE20-subfamily kinase, rat TAO1, is most likely the rodent orthologue of human SULU3 (Hutchinson, M. et al. J. Biol. Chem 273:28625–28632, 1998). TAO1 activates MEK3, 4 and 6 in vitro, while in transfected cells it associates and activates only MEK3, resulting in phosphorylation and activation of p38. These results implicate TAO1 (SULU3) in the regulation of the p38 containing stress-responsive MAP kinase pathway.

Human SULU1 is weakly expressed in hematopoietic sources whereas SULU3 is found in B-cells and TH1-restricted T cells . These mammalian SULU STKs display strong homology to the C. elegans SULU kinase. The role that this kinase plays in nematode development is unknown. The strong sequence homology between the catalytic domain of mammalian SULU kinases and other STE20-subfamily kinases such as SOK-1 (human STE20) and KHS2 suggests that the mammalian kinases may participate in the stress-response pathway. The potential coiled-coil domains found at the C-terminus of the SULU kinases may play a role in the regulation of this kinase.

Murine LOK (lymphocyte-oriented kinase) is a constitutively activated STK of approximately 130,000 daltons that is predominantly expressed in spleen, thymus and bone marrow (Kuramochi, S. et al (1997) J. Biol. Chem. 272: 22679–22684) as well as in meiotic testicular and primordial germ cells. The LOK1 gene is located in chromosome 11 of the mouse near the wr locus, a region that is associated with reproductive and neurological defects (Yanagisawa, M. et al (1996) Mol. Reprod. and Dev. 45:411–420). LOK does not activate any of the known MAPK pathways (ERK, JNK and p38) nor the NFkB pathway. The upstream signaling elements of LOK as well as the extracellular stimuli that utilize this kinase to elicit a biological response are also unknown (Kuramochi, S. et al (1997) J. Biol. Chem. 272: 22679–22684).

Human GEK2 is highly related to murine LOK, but based on sequence divergence in the non-catalytic domain, it appears to be a distinct member of this STE20-subfamily. GEK2 may signal through a pathway that remains to be defined. The presence of potential coiled-coil regions at the C-terminus of GEK2 could play a key role in regulating the functions of this kinase.

Human PAK4 and PAK5

The p21 activated protein kinases (PAK) are a closely related subgroup of the STE20 family of serine/threonine kinases. Extensive genetic and biochemical analysis of the budding yeast STE20 has shown the critical role this serine/threonine kinase plays at the juncture of several important intracellular pathways required to appropriately respond to extracellular signals. STE20 links the transcriptional response by mediating the activation of the appropriate downstream MAPK pathway as well as coupling changes in cellular morphology via its control of the actin cytoskeleton.

A hallmark of the PAK subgroup is their small G protein-binding domain (PBD) that confers G protein-dependent activation upon this group of kinases. Via the PBD, PAKs bind to activated small G proteins resulting in the derepression of the PAK's intrinsic kinase activity.

Until recently, there were three known PAK kinases: PAK1, a 68 kD protein whose expression is restricted expression to brain, muscle, and spleen; PAK2 (PAKI, PAK65), a 62 kD protein whose expression is ubiquitous; and PAK3, a 65kD protein whose expression is restricted to the brain. Similar to STE20, the mammalian PAKs (1, 2, and 3) have been shown to respond to extracellular signals (growth factors, mitogens, cytokines and a variety of cellular stresses) (Bagrodia, et al. (1995). J. Biol. Chem. 270: 22731–22737; Zhang, S., et al. (1995). J. Biol. Chem. 270: 23934–23936, Frost, J. et al. (1998) J. Biol. Chem. 273: 28191–28198; Galisteo, M. et al. (1996) J. Biol. Chem. 271: 20997–21000), and are linked to TCR activation (Yablonski, D., et al. (1998) EMBO J. 17: 5647–5657), and heterotrimeric G protein-coupled receptors (Knaus, U. et al. (1995) Science 269: 221–223).

The PAKs were originally identified as effectors for members of the Rho family of small G proteins (such as Rac and Cdc42), hence their name, p21-activated kinases (PAK) (Manser et al Nature 367:40–46). The recruitment of the PAKs to the appropriate intracellular location is critical to their function. Attempts to elucidate the role played by PAKs in intracellular signaling and morphological changes is complicated due to the complex interactions by which they can be recruited by such factors as activated small G proteins (rac, cdc42), adaptors (nck) and exchange proteins (PIX, Cool).

The adaptor molecule, Nck, is constitutively bound via its SH3 domain to the proline-rich motif in the N-terminal portion of PAK1. Binding of the Nck-PAK complex to activated growth factor receptors in response to growth factor stimulation provides a mechanism to link growth factor-stimulated and stress-response pathways (Galisteo, M. et al. (1996) J. Biol. Chem. 271:20997–21000).

The PBD found at the N-terminus of PAK1 is responsible for its high-affinity interaction with the GTP-bound forms of Cdc42 and Rac (Burbelo, P. et al. (1995) J. Biol. Chem. 270:29071–29074). The exact mechanism through which the small GTPases activate PAKs may involve, in part, association of the kinase with activated growth factor receptors through guanine nucleotide exchange factors (GEFs). GEFs activate small GTPases by catalyzing the formation of their GTP-bound state, thereby promoting their association with, and activation of, PAKs. The known mammalian PAK kinases, as well as Drosophila and *C. elegans* PAKs, all conserve an N-terminal extracatalytic motif responsible for a high-affinity interaction with the GEF, PIX. The PAK-Cdc42 interaction and subsequent PAKs occurs as a PIX/PAK complex (Manser, E. et al. (1998) Molecular Cell, 1, 183–192).

PAK signaling stimulated by heterotrimeric G proteins is mediated through the interaction between a short conserved amino acid region located at the C-terminus of PAK1 with the G-protein β-subunit (Leeuw, T. et al. (.1998) Nature, 391: 191–195).

A variety of studies have indicated that the human PAKs are involved in mediating the activation of stress-activated protein kinase pathways (JNK and to lesser extent p38). PAKs are also potential mediators in the crosstalk between the pathways regulated by the Rho family of small G proteins and the signaling pathways directly downstream of Ras leading to the activation of the ERK pathway (Bagrodia, et al. (1995). J. Biol. Chem. 270: 22731–22737; Zhang, S., et al. (1995). J. Biol. Chem. 270: 23934–23936; Brown, J., et al. (1996) Curr Biol. 6:598–60596; Frost, J., et al. (1996). Mol. Cell. Biol. 16: 3707–3713).

PAK1 has been implicated in phosphorylating a regulatory site in MEK1 that is necessary for MEK1's ability to interact with Raf1 (Frost, et al. (1997) EMBO J. 16:6426–6438). PAK3 has been shown to phosphorylate Raf1 on a site that is important for Raf1 activity (King, A., et al. (1998). Nature 396: 180–183).

PAKs play an important role in controlling morphological changes in cell shape mediated by the actin cytoskeleton. Such morphological changes are required for cellular functions ranging from cell division and proliferation to cell motility and vesicle transport. PAK activity has been implicated in the localized assembly (leading edge) and disassembly (retracting edge) of focal adhesions necessary for cell motility (Frost J. et al (1998) J. Biol. Chem. 273:28191–28198).

PAK2 may have a role in the morphological changes induced during apoptosis (Membrane and morphological changes in apoptotic cells regulated by caspase-mediated activation of PAK2. (Rudel, T. (1997) Science. 276:1571–4)), and PAK1 may be important in preventing apoptosis (Faure S, et al. (1997) EMBO J. (1997) 16:5550–61). In addition to overcoming mitogen- and anchorage-independent growth, tumor cells need to escape the programmed cell death that accompanies deregulated cell growth. Thus, inhibition of PAKs may be effective in triggering apoptosis in tumors.

A direct requirement for PAKs in the transformation of mammalian cells has been shown for PAK1 and PAK2. Kinase-dead alleles of PAK1 block ras transformation of RAT1 and Schwann cells (Tang, Y., et al. (1997) Mol. Cell. Biol. 17, 4454–4464). Dominant-negative alleles of PAK2 have been shown to interfere with ras-mediated transformation of mammalian cells (Osada, S., (1997) FEBS Lett 404:227–233) Mutations in PAK3 have been implicated in nonsyndromic X-linked mental retardation suggesting a role for PAK3 in cognitive function (Allen, K. et al. (1998) Nat. Genet. 20: 25–30). PAK1 has been implicated in neurite outgrowth in PC12 cells (Daniels, R. et al. (1998) EMBO J. 17: 754–764; Nikolic, M. et al. (1998) Nature 395:194–198).

Finally, PAK-like STKs may also play a role in AIDS pathogenesis since the myristoylated 27 kD membrane-associated HIV Nef gene product directly interacts with and activates these kinases via cdc42 and Rac. The Nef-mediated activation of PAK-like STKs correlates with the induction of high viral titers and the development of AIDS in infected hosts (Cullen, B. R. (1996) Curr. Biol. 6:1557–1559).

Our results show that PAK4 is expressed in thymus, dendrocytes, mast cells, monocytes, as well as in T cells (TH2-restricted cells and MOLT4) and the B cell line RPMI. PAK5 is found in mast cells and in the T cell line MOLT4. These data suggest potential roles for PAK4 and PAK5 in the immune system.

PAK4 and PAK5 share with the known PAKs a potential cdc42-binding motif at their N-termini. Both PAK4 and PAK5 display sequence homology in their C-termini to a motif responsible for an interaction between PAK1 and the β-subunit of heterotrimic G-proteins (amino acid residues 665–676 in PAK4, and amino acid residues 386–398 in PAK5). Consequently, PAK4, and possibly PAK5, could mediate signaling events originating from growth factors as well as from ligands that stimulate G-protein-linked receptors.

PAK4 conserves a leucine (leu 44), that when mutated to a phenylalanine renders the kinase activity of human PAK1 constitutively active, bypassing its cdc42-binding requirement for activation (Brown J. et al (1996) Current Biol. 6:598–605). PAK5 contains an isoleucine at the equivalent position. Therefore, the mechanism by which cdc42 potentially activates human PAK1, PAK4, and possibly PAK5, may be very similar.

PAK4 and PAK5 however, lack the PIX-binding motif, and consequently cdc42-activating GEFs other than PIX (for example Dbl and Cool) must be responsible for the activation of these kinases. Alternatively, PAK4 and PAK5 may be activated by another GTPase, such as Rac1 which uses the Tiam1 GEF for its activation to the GTP-bound state.

PAK4 and PAK5 also lack the PxxP (SEQ ID NO: 148) motif responsible for the Nck-PAK1 association. Between the PBD or cdc42-binding N-terminal motifs and the putative GEF-binding regions, PAK4 and PAK5 have long insertions (185 and 123 amino acids for PAK4 and PAK5, respectively) relative to PAK1. This region probably confers different binding characteristics to adaptor molecules and/or GEFs from those exhibited by known mammalian PAKs.

PAKs have been shown to be upstream in pathways leading to activation of both the JNK (Bagrodia, S., et al. (1995) J. Biol. Chem. 270: 22731–22737) and ERK kinase pathways (Brown, J., et al. (1996). Curr Biol. 6:598–605). PAK1 was shown to synergize with ras in activation of the ERK pathway through phosphorylation of MEK1 (Frost, J. et al. (1997). EMBO J. 16:6426–6438). Our data shows that MEK1 serves as an in vitro substrate for PAK4, suggesting a potential role for PAK4 in the activation of the ERK pathway and mitogenesis.

PAK5 may also have a mitogenic role, and be linked to cancer, based on its expression profile (elevated RNA and protein levels in a wide variety of tumor cell lines), its interaction with cdc42 via its PBD, and the ability of a kinase-dead allele (Lys350, 351 Ala) to block ras transformation of NIH3T3 cells. Thus, a screen for small molecule inhibitors of PAK5 kinase activity may yield compounds with therapeutic potential for intervention in cancer derived from a wide variety of tissue types.

PAK4 and PAK5 may also play a role in HIV pathogenesis as potential mediators of Nef signaling, since none of the known PAKs correspond to the PAK-like kinase shown to interact with, and be activated by, the HIV nef protein (Lu, X. et al (1996) Current Biology 6:1677–1684)

The 3' untranslated region of PAK4 contains a CA repeat that is prone to undergo expansion. CA dinucleotide repeat instability has been associated with disease (Toren, M. Z. et al (1998) Am. J. Hematol. 57: 148–152), and expansion of such repeat in the 3' untranslated region of PAK4 could implicate this kinase in as yet unknown pathologies.

Clinical Applications

Human STLK2, STLK3, STLK4, STLK5, STLK6, and STLK7

STLK3, STLK5, STLK6 and STLK7, as well as other homologues of the STLK subfamily of STE20 protein kinases such as STLK4, may play an important role as mediators of the immune response. Thus, they are targets for the development of specific small molecule inhibitors to treat immunological diseases, including, but not limited to, rheumatoid arthritis, chronic inflammatory bowel diseases (e.g. Crohn's disease), chronic inflammatory pelvic disease, multiple sclerosis, asthma, osteoarthritis, psoriasis, atherosclerosis, rhinitis and autoimmunity, as well as in organ transplantation. Other diseases include cardiovascular diseases.

The human STLKs may also play an important role in cell growth regulation. Thus, they are targets for developing small molecule kinase inhibitors for the treatment of cancer and metastases. STLK5 maps to a chromosomal region frequently amplified in a variety of tumors including those from non-small cell lung cancer, breast cancer and peripheral nerve tumors. This suggests that STLK5 could play a role in the development, maintenance, or progression of human tumors.

The potential role of human STLKs 2,3, and 4 in mediating oxidative stress strongly suggests that drugs targeting these kinases could prove useful in the treatment of myocardial infarction, arrhythmia and other cardiomyopathies, stroke, renal failure, oxidative stress-related neurodegenerative disorders such amyotrophic lateral sclerosis, Parkinson's disease and Leigh syndrome, a necrotizing mitochondrial encephalopathy, as well.

Human ZC1, ZC2, ZC3, and ZC4

ZC1 may be a component of the CD28-signaling pathway and therefore important in T cell activation. As such, ZC1 as well as other ZC subfamily kinases, are targets for the development of specific small molecule inhibitors to treat immunological diseases, including, but not limited to, rheumatoid arthritis, chronic inflammatory bowel diseases (e.g. Crohn's disease), chronic inflammatory pelvic disease, multiple sclerosis, asthma, osteoarthritis, psoriasis, atherosclerosis, rhinitis and autoimmunity, as well as organ transplantation. Other diseases include cardiovascular diseases.

ZC1 and ZC2 are also implicated in cell growth regulation. Thus, ZC subfamily kinases are targets for developing small molecule inhibitors for the treatment of cancer and metastases. ZC2 maps to a chromosomal region frequently amplified in a variety of tumors including those from non-small cell lung cancer, small cell lung cancer, and cervical cancer. This suggests that ZC2 could play a role in the development, maintenance, or progression of human tumors.

The role of human ZC1, ZC2, ZC3, and ZC4 in the inflammatory and stress-response pathways, strongly suggests that drugs targeting these kinases could have strong immunosuppressive actions. These drugs can prove valuable for the treatment of rheumatoid arthritis, artherosclerosis, autoimmune disorders and organ transplantation among others. At least one very important class of immunosuppresants, corticosteroids, functions by blocking SAPK activation at an as yet undefined site on this pathway (Swantek, J. L. et al (1997) Mol. Cell. Biol. (1997) 6274–6282). Other immunosuppresive drugs like the pyridinyl imidazoles specifically target the p38 kinases (Kumar, S. et al (1997) Biochem. Biophys. Res. Commun. 235: 533–528). Drug targeting of the MAPK and p38 pathways could lead to the development of novel immunosuppresants.

Human SULU and GEK

The potential role of these novel STE20-related protein kinases in the control of mitosis strongly suggests that agents that specifically inhibit these kinases could be useful for cancer and metastases treatment.

The close homology of human STLK5, GEK2, SULU1 and SULU3 to STE20-subfamily kinases involved in the stress and oxidative response pathway strongly suggests that drugs targeting these kinases may also be useful as immunosuppressants as well as to treat ischemic disorders.

Human KHS2

The role of human KHS2 in the inflammatory and stress-response pathways, strongly suggests that drugs targeting this and related kinases could have strong immunosuppressive actions. These drugs can prove valuable for the treatment of rheumatoid arthritis, artherosclerosis, autoimmune disorders and organ transplantation among others. At least one very important class of immunosuppresants, corticosteroids, functions by blocking SAPK activation at an as yet undefined site on this pathway (Swantek, J. L. et al (1997) Mol. Cell. Biol. (1997) 6274–6282). Other immunosuppresive drugs like the pyridinyl imidazoles specifically target the p38 kinases (Kumar, S. et al (1997) Biochem.

Biophys. Res. Commun. 235: 533–528). Drug targeting of the MAPK and p38 pathways could lead to the development of novel immunosuppressants.

Human PAK Family

PAK5 has a role in cancer based on its expression profile (elevated RNA and protein levels in wide variety of tumor lines), its interaction with Cdc42 via its PBD, and the ability of the kinase-dead allele of PAK5 (Lys350, 351Ala) to block ras transformation of NIH3T3 cells. Thus, a screen for small molecule inhibitors of PAK5 kinase activity may yield compounds with therapeutic potential for intervention in cancers and metastases derived from a wide range of tissue types.

PAK5 maps to a chromosomal region frequently amplified in a variety of tumors including those from non-small cell lung cancer, and small cell lung cancer. These findings suggest that PAK5 could play a role in the development, maintenance, or progression of human tumors and/or metastases.

The role of human PAK4, and PAK5 in the inflammatory and stress-response pathways also strongly suggests that drugs targeting these kinases could have strong immunosuppressive actions. These drugs can prove valuable for the treatment of rheumatoid arthritis, artherosclerosis, autoimmune disorders and organ transplantation among others. At least one very important class of immunosuppresants, corticosteroids, functions by blocking SAPK activation at an as yet undefined site on this pathway (Swantek, J. L. et al (1997) Mol. Cell. Biol. (1997) 6274–6282). Other immunosuppresive drugs like the pyridinyl imidazoles specifically target the p38 kinases (Kumar, S. et al (1997) Biochem. Biophys. Res. Commun. 235: 533–528). Drug targeting of the MAPK and p38 pathways could lead to the development of novel immunosuppresants. In addition, drugs targeting PAK4 or PAK5 could prove useful as immunosuppresants as well as in AIDS treatment.

VIII. Transgenic Animals

A variety of methods are available for the production of transgenic animals associated with this invention. DNA can be injected into the pronucleus of a fertilized egg before fusion of the male and female pronuclei, or injected into the nucleus of an embryonic cell (e.g., the nucleus of a two-cell embryo) following the initiation of cell division (Brinster et al., Proc. Nat. Acad. Sci. USA 82: 4438–4442, 1985). Embryos can be infected with viruses, especially retroviruses, modified to carry inorganic-ion receptor nucleotide sequences of the invention.

Pluripotent stem cells derived from the inner cell mass of the embryo and stabilized in culture can be manipulated in culture to incorporate nucleotide sequences of the invention. A transgenic animal can be produced from such cells through implantation into a blastocyst that is implanted into a foster mother and allowed to come to term. Animals suitable for transgenic experiments can be obtained from standard commercial sources such as Charles River (Wilmington, Mass.), Taconic (Germantown, N.Y.), Harlan Sprague Dawley (Indianapolis, Ind.), etc.

The procedures for manipulation of the rodent embryo and for microinjection of DNA into the pronucleus of the zygote are well known to those of ordinary skill in the art (Hogan et al., supra). Microinjection procedures for fish, amphibian eggs and birds are detailed in Houdebine and Chourrout (Experientia 47: 897–905, 1991). Other procedures for introduction of DNA into tissues of animals are described in U.S. Pat. No. , 4,945,050 (Sandford et al., Jul. 30, 1990).

By way of example only, to prepare a transgenic mouse, female mice are induced to superovulate. Females are placed with males, and the mated females are sacrificed by $CO_2$ asphyxiation or cervical dislocation and embryos are recovered from excised oviducts. Surrounding cumulus cells are removed. Pronuclear embryos are then washed and stored until the time of injection. Randomly cycling adult female mice are paired with vasectomized males. Recipient females are mated at the same time as donor females. Embryos then are transferred surgically. The procedure for generating transgenic rats is similar to that of mice (Hammer et al., Cell 63:1099–1112, 1990).

Methods for the culturing of embryonic stem (ES) cells and the subsequent production of transgenic animals by the introduction of DNA into ES cells using methods such as electroporation, calcium phosphate/DNA precipitation and direct injection also are well known to those of ordinary skill in the art (Teratocarcinomas and Embryonic Stem Cells, A Practical Approach, E. J. Robertson, ed., IRL Press, 1987).

In cases involving random gene integration, a clone containing the sequence(s) of the invention is co-transfected with a gene encoding resistance. Alternatively, the gene encoding neomycin resistance is physically linked to the sequence(s) of the invention. Transfection and isolation of desired clones are carried out by any one of several methods well known to those of ordinary skill in the art (E. J. Robertson, supra).

DNA molecules introduced into ES cells can also be integrated into the chromosome through the process of homologous recombination (Capecchi, Science 244: 1288–1292, 1989). Methods for positive selection of the recombination event (i.e., neo resistance) and dual positive-negative selection (i.e., neo resistance and gancyclovir resistance) and the subsequent identification of the desired clones by PCR have been described by Capecchi, supra and Joyner et al. (Nature 338: 153–156, 1989), the teachings of which are incorporated herein in their entirety including any drawings. The final phase of the procedure is to inject targeted ES cells into blastocysts and to transfer the blastocysts into pseudopregnant females. The resulting chimeric animals are bred and the offspring are analyzed by Southern blotting to identify individuals that carry the transgene. Procedures for the production of non-rodent mammals and other animals have been discussed by others (Houdebine and Chourrout, supra; Pursel et al., Science 244:1281–1288, 1989; and Simms et al., Bio/Technology 6:179–183, 1988).

Thus, the invention provides transgenic, nonhuman mammals containing a transgene encoding a kinase of the invention or a gene effecting the expression of the kinase. Such transgenic nonhuman mammals are particularly useful as an in vivo test system for studying the effects of introduction of a kinase, or regulating the expression of a kinase (i.e., through the introduction of additional genes, antisense nucleic acids, or ribozymes).

A "transgenic animal" is an animal having cells that contain DNA which has been artificially inserted into a cell, which DNA becomes part of the genome of the animal which develops from that cell. Preferred transgenic animals are primates, mice, rats, cows, pigs, horses, goats, sheep, dogs and cats. The transgenic DNA may encode human STE20-related kinases. Native expression in an animal may be reduced by providing an amount of anti-sense RNA or DNA effective to reduce expression of the receptor.

IX. Gene Therapy

STE20-related kinases or their genetic sequences will also be useful in gene therapy (reviewed in Miller, Nature 357:455–460, 1992). Miller states that advances have resulted in practical approaches to human gene therapy that have demonstrated positive initial results. The basic science of gene therapy is described in Mulligan (Science 260:926–931, 1993).

In one preferred embodiment, an expression vector containing STE20-related kinase coding sequence is inserted into cells, the cells are grown in vitro and then infused in large numbers into patients. In another preferred embodiment, a DNA segment containing a promoter of choice (for example a strong promoter) is transferred into cells containing an endogenous gene encoding kinases of the invention in such a manner that the promoter segment enhances expression of the endogenous kinase gene (for example, the promoter segment is transferred to the cell such that it becomes directly linked to the endogenous kinase gene).

The gene therapy may involve the use of an adenovirus containing kinase cDNA targeted to a tumor, systemic kinase increase by implantation of engineered cells, injection with kinase-encoding virus, or injection of naked kinase DNA into appropriate tissues.

Target cell populations may be modified by introducing altered forms of one or more components of the protein complexes in order to modulate the activity of such complexes. For example, by reducing or inhibiting a complex component activity within target cells, an abnormal signal transduction event(s) leading to a condition may be decreased, inhibited, or reversed. Deletion or missense mutants of a component, that retain the ability to interact with other components of the protein complexes but cannot function in signal transduction may be used to inhibit an abnormal, deleterious signal transduction event.

Expression vectors derived from viruses such as retroviruses, vaccinia virus, adenovirus, adeno-associated virus, herpes viruses, several RNA viruses, or bovine papilloma virus, may be used for delivery of nucleotide sequences (e.g., cDNA) encoding recombinant kinase of the invention protein into the targeted cell population (e.g., tumor cells). Methods which are well known to those skilled in the art can be used to construct recombinant viral vectors containing coding sequences (Maniatis et al., Molecular Cloning: A Laboratory Manual, Cold Spring Harbor Laboratory, N.Y., 1989; Ausubel et al., Current Protocols in Molecular Biology, Greene Publishing Associates and Wiley Interscience, N.Y., 1989). Alternatively, recombinant nucleic acid molecules encoding protein sequences can be used as naked DNA or in a reconstituted system e.g., liposomes or other lipid systems for delivery to target cells (e.g., Feigner et al., Nature 337:387–8, 1989). Several other methods for the direct transfer of plasmid DNA into cells exist for use in human gene therapy and involve targeting the DNA to receptors on cells by complexing the plasmid DNA to proteins (Miller, supra).

In its simplest form, gene transfer can be performed by simply injecting minute amounts of DNA into the nucleus of a cell, through a process of microinjection (Capecchi, Cell 22:479–88, 1980). Once recombinant genes are introduced into a cell, they can be recognized by the cell's normal mechanisms for transcription and translation, and a gene product will be expressed. Other methods have also been attempted for introducing DNA into larger numbers of cells. These methods include: transfection, wherein DNA is precipitated with $CaPO_4$ and taken into cells by pinocytosis (Chen et al., Mol. Cell Biol. 7:2745–52, 1987); electroporation, wherein cells are exposed to large voltage pulses to introduce holes into the membrane (Chu et al., Nucleic Acids Res. 15:1311–26, 1987); lipofection/liposome fusion, wherein DNA is packaged into lipophilic vesicles which fuse with a target cell (Felgner et al., Proc. Natl. Acad. Sci. USA. 84:7413–7417, 1987); and particle bombardment using DNA bound to small projectiles (Yang et al., Proc. Natl. Acad. Sci. 87:9568–9572, 1990). Another method for introducing DNA into cells is to couple the DNA to chemically modified proteins.

It has also been shown that adenovirus proteins are capable of destabilizing endosomes and enhancing the uptake of DNA into cells. The admixture of adenovirus to solutions containing DNA complexes, or the binding of DNA to polylysine covalently attached to adenovirus using protein crosslinking agents substantially improves the uptake and expression of the recombinant gene (Curiel et al., Am. J. Respir. Cell. Mol. Biol., 6:247–52, 1992).

As used herein "gene transfer" means the process of introducing a foreign nucleic acid molecule into a cell. Gene transfer is commonly performed to enable the expression of a particular product encoded by the gene. The product may include a protein, polypeptide, anti-sense DNA or RNA, or enzymatically active RNA. Gene transfer can be performed in cultured cells or by direct administration into animals. Generally gene transfer involves the process of nucleic acid contact with a target cell by non-specific or receptor mediated interactions, uptake of nucleic acid into the cell through the membrane or by endocytosis, and release of nucleic acid into the cytoplasm from the plasma membrane or endosome. Expression may require, in addition, movement of the nucleic acid into the nucleus of the cell and binding to appropriate nuclear factors for transcription.

As used herein "gene therapy" is a form of gene transfer and is included within the definition of gene transfer as used herein and specifically refers to gene transfer to express a therapeutic product from a cell in vivo or in vitro. Gene transfer can be performed ex vivo on cells which are then transplanted into a patient, or can be performed by direct administration of the nucleic acid or nucleic acid-protein complex into the patient.

In another preferred embodiment, a vector having nucleic acid sequences encoding a STE20-related kinase polypeptide is provided in which the nucleic acid sequence is expressed only in specific tissue. Methods of achieving tissue-specific gene expression are set forth in International Publication No. WO 93/09236, filed Nov. 3, 1992 and published May 13, 1993.

In all of the preceding vectors set forth above, a further aspect of the invention is that the nucleic acid sequence contained in the vector may include additions, deletions or modifications to some or all of the sequence of the nucleic acid, as defined above.

In another preferred embodiment, a method of gene replacement is set forth. "Gene replacement" as used herein means supplying a nucleic acid sequence which is capable of being expressed in vivo in an animal and thereby providing or augmenting the function of an endogenous gene which is missing or defective in the animal.

X. Administration of Substances

Methods of determining the dosages of compounds to be administered to a patient and modes of administering compounds to an organism are disclosed in U.S. application Ser. No. 08/702,282, filed Aug. 23, 1996 and International patent publication number WO 96/22976, published Aug. 1, 1996, both of which are incorporated herein by reference in their entirety, including any drawings, figures, or tables. Those skilled in the art will appreciate that such descriptions are applicable to the present invention and can be easily adapted to it.

The proper dosage depends on various factors such as the type of disease being treated, the particular composition being used, and the size and physiological condition of the patient. Therapeutically effective doses for the compounds described herein can be estimated initially from cell culture and animal models. For example, a dose can be formulated in animal models to achieve a circulating concentration range that initially takes into account the $IC_{50}$ as determined in cell culture assays. The animal model data can be used to more accurately determine useful doses in humans.

Plasma half-life and biodistribution of the drug and metabolites in the plasma, tumors, and major organs can be also be determined to facilitate the selection of drugs most appropriate to inhibit a disorder. Such measurements can be carried out. For example, HPLC analysis can be performed on the plasma of animals treated with the drug and the location of radiolabeled compounds can be determined using detection methods such as X-ray, CAT scan, and MRI. Compounds that show potent inhibitory activity in the screening assays, but have poor pharmacokinetic characteristics, can be optimized by altering the chemical structure and retesting. In this regard, compounds displaying good pharmacokinetic characteristics can be used as a model.

Toxicity studies can also be carried out by measuring the blood cell composition. For example, toxicity studies can be carried out in a suitable animal model as follows: 1) the compound is administered to mice (an untreated control mouse should also be used); 2) blood samples are periodically obtained via the tail vein from one mouse in each treatment group; and 3) the samples are analyzed for red and white blood cell counts, blood cell composition, and the percent of lymphocytes versus polymorphonuclear cells. A comparison of results for each dosing regime with the controls indicates if toxicity is present.

At the termination of each toxicity study, further studies can be carried out by sacrificing the animals (preferably, in accordance with the American Veterinary Medical Association guidelines Report of the American Veterinary Medical Assoc. panel on Euthanasia, *Journal of American Veterinary Medical Assoc.*, 202:229–249, 1993). Representative animals from each treatment group can then be examined by gross necropsy for immediate evidence of metastasis, unusual illness, or toxicity. Gross abnormalities in tissue are noted, and tissues are examined histologically. Compounds causing a reduction in body weight or blood components are less preferred, as are compounds having an adverse effect on major organs. In general, the greater the adverse effect the less preferred the compound.

For the treatment of cancers the expected daily dose of a hydrophobic pharmaceutical agent is between 1 to 500 mg/day, preferably 1 to 250 mg/day, and most preferably 1 to 50 mg/day. Drugs can be delivered less frequently provided plasma levels of the active moiety are sufficient to maintain therapeutic effectiveness.

Plasma levels should reflect the potency of the drug. Generally, the more potent the compound the lower the plasma levels necessary to achieve efficacy.

EXAMPLES

The examples below are not limiting and are merely representative of various aspects and features of the present invention. The examples below demonstrate the isolation and characterization of the STE20-related kinases of the invention.

Example 1

Isolation of cDNAs Encoding Mammalian STE20-Related Protein Kinases

Materials and Methods

Identification of Novel Clones

Total RNAs were isolated using the Guanidine Salts/Phenol extraction protocol of Chomczynski and Sacchi (P. Chomczynski and N. Sacchi, Anal. Biochem. 162, 156 (1987)) from primary human tumors, normal and tumor cell lines, normal human tissues, and sorted human hematopoietic cells. These RNAs were used to generate single-stranded cDNA using the Superscript Preamplification System (GIBCO BRL, Gaithersburg, Md.; Gerard, G F et al. (1989), FOCUS 11, 66) under conditions recommended by the manufacturer. A typical reaction used 10 $\mu$g total RNA with 1.5 $\mu$g oligo(dT)$_{12-18}$ in a reaction volume of 60 $\mu$L. The product was treated with RNaseH and diluted to 100 $\mu$L with $H_2O$. For subsequent PCR amplification, 1–4 $\mu$L of this sscDNA was used in each reaction.

Degenerate oligonucleotides were synthesized on an Applied Biosystems 3948 DNA synthesizer using established phosphoramidite chemistry, precipitated with ethanol and used unpurified for PCR. The sequence of some of the degenerate oligonucleotide primers and the amino acid motif they encode is as follows:

TRK1 5'-CTGAATTCGGNGCNTTYGGNAARGT-3' (SEQ ID NO:32) GAFGKV (sense) (SEQ ID NO:37)

TRK4 5'-GCTGGATCCYTCNGGNGGCATCCA-3' (SEQ ID NO:33) WMPPE (antisense) (SEQ ID NO:38)

ROS1 5'-GCNTTYGGNGARGTNTAYGARGG-3' (SEQ ID NO:34) AFGEVYEG (sense) (SEQ ID NO:39)

CCK4b 5'-GCTGGATCCYTCNGGNSWCATCCA-3' (SEQ ID NO:35) WMSPE (antisense) (SEQ ID NO:40)

CCK4c 5'-GAGTTYGGNGARGTNTTYYTNGC-3' (SEQ ID NO:36) EFGEVYEG (sense) (SEQ ID NO:41)

These primers were derived from the sense and antisense strands of conserved motifs within the catalytic domain of several protein kinases. Degenerate nucleotide residue designations are: N=A, C, G, or T; R=A or G; Y=C or T; H=A, C or T not G; D A, G or T not C; S=C or G; and W=A or T.

PCR reactions were performed using degenerate primers applied to multiple single-stranded cDNAs. The primers were added at a final concentration of 5 $\mu$M each to a mixture containing 10 mM TrisHCl, pH 8.3, 50 mM KCl, 1.5 mM $MgCl_2$, 200 $\mu$M each deoxynucleoside triphosphate, 0.001% gelatin, 1.5 U AmpliTaq DNA Polymerase (Perkin-Elmer/Cetus), and 1–4 $\mu$L cDNA. Following 3 min denaturation at 95° C., the cycling conditions were 94° C. for 30 s, 50° C. for 1 min, and 72° C. for 1 min 45 s for 35 cycles. PCR fragments migrating between 300–350 bp were isolated from 2% agarose gels using the GeneClean Kit (Bio101), and T-A cloned into the pCRII vector (Invitrogen Corp. U.S.A.) according to the manufacturer's protocol.

Colonies were selected for mini plasmid DNA-preparations using Qiagen columns and the plasmid DNA was sequenced using a cycle sequencing dye-terminator kit with AmpliTaq DNA Polymerase, FS (ABI, Foster City, Calif.). Sequencing reaction products were run on an ABI Prism 377 DNA Sequencer, and analyzed using the BLAST alignment algorithm (Altschul, S. F. et al., J. Mol. Biol. 215: 403–10).

Additional PCR strategies were employed to connect various PCR fragments or ESTs using exact or near exact oligonucleotide primers as detailed in the results section for each cDNA. PCR conditions were as described above except the annealing temperatures were calculated for each oligo pair using the formula: Tm=4(G+C)+2(A+T).

Isolation of cDNA Clones:

Human cDNA libraries were probed with PCR or EST fragments corresponding to STE20-related genes. Probes were $^{32}$P-labeled by random priming and used at $2 \times 10^6$ cpm/mL following standard techniques for library screening. Pre-hybridization (3 h) and hybridization (overnight) were conducted at 42° C. in 5×SSC, 5×Denhart's solution, 2.5% dextran sulfate, 50 mM $Na_2PO_4$/$NaHPO_4$, pH 7.0, 50% formamide with 100 mg/mL denatured salmon sperm DNA. Stringent washes were performed at 65° C. in 0.1× SSC and 0.1% SDS. DNA sequencing was carried out on both strands using a cycle sequencing dye-terminator kit with AmpliTaq DNA Polymerase, FS (ABI, Foster City, Calif.). Sequencing reaction products were run on an ABI Prism 377 DNA Sequencer.

Makegene Bioinformatics EST Assembler

The EST reports were downloaded from ncbi (National Institute for Biotechnology Information). After uncompressing the files, the program 'report2est' was scripted to extract the following information: 1) EST names, 2) GenBank Accession numbers, 3) GenBank gi numbers, 4) Clone Id numbers, 5) the nucleotide sequences of the ESTs 6) the organism, 7) the library name, 8) the name of the lab, and 9) the institution. The output of 'report2est' is a file in FASTA format with all of the information listed above in the first line of each entry except the sequence, which is listed in the second line of each entry. The resulting file is formatted for BLAST using 'pressdb' (available as part of the ncbi tool kit).

To build a gene or part of a gene from ESTs, the program 'makegene' was developed. Input to this program is a query sequence and the organism/species for which a gene is to be built. An initial search of the formatted EST database described above is performed using BLAST (blastn). Any results that contain warnings, such as polyA tails or other repeat elements, are eliminated from future queries. The program 'blast_parse_reports' was developed to extract the FASTA header line from the search results and the output is then filtered to extract only FASTA header lines for the desired species.

The initial results, having been filtered for warnings and species, go into a loop in which searches against the database are repeated until no new ESTs are found. The loop consists of the following steps: 1) when possible the names of both ends of the ESTs are extracted from the database by searching using the 'Clone Id' field or the part of the ' EST name' field before the .r or .s postscript, 2) any ESTs that have been used as queries in previous loops are removed from the current query by the program 'subtract', 3) the resulting list of ESTs is used to extract the sequences from the database by the program batch_parse_fasta, 4) BLAST is run against the database using each sequence, 5) the output files from BLAST containing warnings are removed, 6) the results are filtered by species, and 7) the loop is reentered if there are new ESTs found in the previous pass through the loop.

The ESTs chosen by 'makegene' are used as input for the program 'mpd2_cluster' (Hide, W., Burke, J, and Davison, D. U. of Houston, unpublished) which clusters overlapping sequences. The programs 'contig' (Kerlavage, T., TIGR, unpublished), 'gde2mult' and 'gde2sing' (Smith, S. W., et al., CABIOS 10, 671–675 (1994)), are used to make an alignment and consensus sequence of the overlapping ESTs.

RESULTS cDNA Cloning and Characterization of STLK2

The human STLK2 cDNA sequence is composed of two overlapping EST fragments, AA191319 and W16504, that were identified using a Smith-Waterman search of the EST database with STLK1 (MST3 GB:AF024636) as a query. The complete sequence of both clones was determined and used to generate the full-length human STL2 sequence.

EST clone AA191319 contains a 1327 bp insert and an ORF of 1146 bp (382 amino acids). EST clone W16504 contains a 2474 bp insert (not including the poly-A tail) and an ORF of 687 bp (382 amino acids) The full-length human STLK2 cDNA (SEQ ID NO. 1) is 3268 bp long. AA191319 spans positions 1–1327 and W16504 positions 743–3216. The overlap between these two clones exhibits 100% sequence identity. The human STLK2 cDNA constains a 1248 bp ORF flanked by a 181 bp 5' UTR (1–181) and a 1784 bp 3' UTR (1433–3216) that is followed by a 52 nucleotide polyadenylated region. A polyadenylation signal (AATAAA) is found at positions 3193–3198. The sequence flanking the first ATG conforms to the Kozak consensus for an initiating methionine, and is believed to be the translational start site for STLK2. Furthermore, human STLK2, and the related SOK-1 and MST3 proteins, conserve the amino acid sequence immediately following this presumed initiating methionine.

Several EST fragments span the complete STLK2 sequence with AA191319 at the 5' end and W16504 at the 3' end.

All searches against the public nucleic acid database (NRN) and protein database (NRP) were conducted using the Smith-Waterman gap alignment program ((Smith, T F and Waterman, M S (1981) J. Mol. Biol, 147, 195–197).) with the PAM100 matrix and gap open and extension penalties of 14:1, respectively.

cDNA Cloning and Characterization of STLK3

A mammalian STLK3 clone, 135-31-19, was first identified from a PCR screen with the degenerate oligos, TRK1 and TRK4, applied to a sscDNA generated from adult rat brain substantia nigra. Sequence analysis of the 457 bp insert indicated that it represented a novel member of the STE20-subfamily of STKS.

A Smith-Waterman search of the EST database with the rat STLK3 fragment and human STLK1 (MST3 GB:AF024636) as queries identified several overlapping ESTs spanning most of the human STLK3 cDNA sequence. A Makegene analysis generated a 3037 bp contig from approximately 44 EST sequences. Since the 3' ESTs were not commercially available, a pair of primers (5'-CACAGAAACGGTCAGATTCAC-3' (SEQ ID NO: 42) and 5'-GATCAGGGTGACATCAAGGGAC-3' (SEQ ID NO: 43)) were derived from this region to generate PCR clone 3R21-20-6 from human fetal liver sscDNA. This clone and EST AA278967 were fully sequenced to generate the full-length STLK2 cDNA sequence.

AA278967 is a 837 bp EST isolated by the IMAGE consortium from cDNA made from CD20+/IgD-germinal center B cells sorted from human tonsillar cells.

PCR clone 3R21-20-6 was isolated from human fetal sscDNA and contains a 1116 bp insert, including a 1086 bp ORF encoding the 362 C-terminal amino acids of STLK3.

The full-length human STLK3 cDNA (SEQ ID NO. 2) is 3030 bp long. AA278967 spans positions 1–814 and 3R21-20-6 spans positions 464–1579. The overlap between these two clones exhibits 100% sequence identity. The remaining 1452 bp of 3' UTR is derived from an assembly of multiple unconfirmed EST fragments.

The near full-length human STLK3 cDNA (SEQ ID NO.2) is 3030 bp long and consists of a 1548 bp ORF flanked by a 1476 bp 3' UTR (1550–3025) and a 5 nucleotide polyadenylated region. A polyadenylation signal (AATAAA) begins at position 3004. Since the coding region is open throughout the 5' extent of this sequence, this is apparently a partial cDNA clone lacking the N-terminal start methionine. Six copies of a "GGCCCC" repeat were observed in positions 21–67. Five independent ESTs (AA150838, AA286879, AA251679, AA252004, AA278967) showed the same repeat, suggesting that this sequence may be an integral region of the human STLK3 gene. Stronger evidence for this being the case is provided by the sequence of the murine orthologue of STLK3 represented by a 876 bp EST W20737.

Multiple EST fragments span the complete STLK3 sequence with AA278967 at the 5' end and AA628477 and others at the 3' end.

cDNA Cloning and Characterization of STLK4

The human STLK4 cDNA sequence is composed of two overlapping EST fragments, AA297759 and AA100484, that were identified using a Smith-Waterman search of the EST database with STLK1 (MST3 GB:AF024636) as a query. The complete sequence of both clones was determined and used to generate the near full-length human STLK4 sequence.

AA100484 is an IMAGE consortium cDNA clone isolated from the T-84 colonic epithelium cell line. It has an insert of 3694 bp and a coding region of 1146 bp (382 amino acids). A Smith-Waterman sequence alignment against the NRN database showed this EST to be 71.4% identical to the human STE20-like kinase (GB:X99325).

W16504 is an IMAGE consortium clone isolated from a human fetal heart cDNA library. It has an insert length of 2474 bp (not including the poly-A tail) and a coding region of 687 bp (229 amino acids). A Smith-Waterman sequence alignment of W16504 against the NRN database showed this EST to be 69.2% identical to the human STE20-like kinase (GB:X99325).

The full-length human STLK2 cDNA (SEQ ID NO. 1) is 3268 bp long. AA191319 spans positions 1–1327, and W16504 positions 743–3216. The overlap between these two clones is 585 bp long with 100% sequence identity.

AA100484 is an IMAGE consortium cDNA clone isolated from the T-84 colonic epithelium cell line. AA100484 covers the bulk of Human STLK4 with its 3694 bp, which spans positions 146–3839 of SEQ ID NO:3. A second EST, AA297759, isolated from a Jurkat T cell cDNA library, spans positions 1–271 of the human STLK4 contig. The two ESTs overlap over a 126 bp stretch that has only one nucleotide discrepancy at position 149 (G in AA297759 and T in AA100484). A T at this position was chosen for the SEQ ID NO:3 based on sequence data generated from A100484. The 5' 145 bp of human STLK4 contains three sequencing ambiguities (N's in SEQ ID.NO:3) arising from sequence errors in the GenBank entry for AA297759. Three amino acid sequence ambiguities in the N-terminus of human STLK4 are present also in SEQ ID NO:7 as a consequence of the sequence inaccuracies from the EST entry.

The coding region of human STLK4 is 1242 bp long (2–1243), capable of encoding a 414 amino acid polypeptide, and is followed by a 2596 nucleotide 3' UTR (1244–3839). Human STLK4 ends in a polyadenylated stretch that has 18 adenines (3840–3857). A polyadenylation signal (AATAAA) is found between positions 3822–3827.

Targeted-PCR cloning identified one rat orthologue of human STLK4, clone 135-31-19. In addition, one murine orthologue of human STLK4 was recognized in the EST database as AA117483. None of these orthologues add additional N-terminal sequence to the human STLK4.

The near full-length human STLK4 cDNA (SEQ ID NO.3) is 3857 bp long and consists of a 1242 bp ORF flanked by a 2596 bp 3' UTR (1244–3839) and an 18 nucleotide polyadenylated region. Polyadenylation signals (AATAAA) begin at positions 2181 and 3822. Since the coding region is open throughout the 5' extent of this sequence, this is apparently a partial cDNA clone lacking the N-terminal start methionine. A near full-length murine STLK4 cDNA is represented in the 1773 bp EST AA117438. It extends an additional 21 nucleotides 5' of the human STLK4 consensus, but since its coding region is open throughout the 5' extent of the sequence, this is also probably a partial cDNA clone lacking the N-terminal start methionine.

Several EST fragments span the complete STLK3 sequence with AA297759 at the 5' end and AA100484 and others at the 3' end.

cDNA Cloning and Characterization of STLK5

The human STLK5 cDNA sequence is composed of four overlapping sequences, AI418298, 2R96-13-1, 3R25-45-3 and R46685. A human STLK5 clone, F07734, was first identified using a Smith-Waterman search of the EST database with SPS_sc (U33057) as a query.

AI418298 is an IMAGE consortium cDNA clone with an 895 bp insert.

PCR clone 2R96-13-1 was isolated from human brain sscDNA using primers 5'-CTCATCTGTACACACTTCATGG (SEQ ID NO:44) and 5'-GATTCCCACACTGTAGATGTC (SEQ ID NO:45) derived from F07734. 2R96-13-1 contains a 330 bp insert and an ORF of 330 bp (110 amino acids).

EST clone R46685 was identified using a Smith-Waterman search of the EST database with the C-terminus of SPS_sc (GB:U33057) as query. Sequence analysis of the 1047 bp insert identified this EST to contain an ORF of 285 bp (95 amino acids) encoding the C-terminus of human STLK5.

PCR clone 3R25-45-3 was isolated from human fetal brain sscDNA using primers 5'-GGCCCTCGACTACATCCACCACAT (SEQ ID NO:46) and 5'-CAACGAAACTAACACAGCATAAGG (SEQ ID NO:47) derived from 2R96-13-1 and R46685, respectively. 3R25-45-3 contains a 330 bp insert and an ORF of 750 bp (250 amino acids).

The full-length human STLK5 cDNA (SEQ ID NO:96) is 2110 bp long and consists of a 1119 bp ORF flanked by a 229 bp 5' UTR and a 762 bp 3' UTR. The sequence flanking the first ATG conforms to the Kozak consensus (supra) for an initiating methionine, and is believed to be the translational start site for STLK5.

Several EST fragments span the complete STLK5 sequence with AA297059 and F07734 at the 5' end and R46686 and F03423 and others at the 3' end.

STLK5 displays a 100% match over a 41 bp stretch (position 2–42, SEQ ID NO. 97) to a human CpG island repeat (Z61277).

cDNA Cloning and Characterization of STLK6

Human STLK6 was first identified in the translated EST database (AA219667) as a novel serine threonine kinase.

The partial human STLK6 cDNA (SEQ ID NO:98) is 2,001 bp long and consists of a 1,254 bp ORF flanked by a 75 bp 5' UTR and a 673 bp 3' UTR. The sequence flanking the first ATG conforms to the Kozak consensus (Kozak, M., Nucleic Acids Res. 15, 8125–8148 (1987)) for an initiating methionine, and is believed to be the translational start site for STLK6.

At the time of filing, inventors believe that STLK6 does not have any significant match in the nucleic acid database.

cDNA Cloning and Characterization of STLK7

Human STLK7 was first identified in the translated EST database (AA988954) as a novel serine threonine kinase. The original clone was not available through public sources, so a PCR fragment amplified from the sequence of AA988954 yielded 5R54-21-2.

The partial human STLK7 cDNA (SEQ ID NO:100) is 311 bp long and consists of a 309 bp ORF. Since the coding region is open throughout the 5' and 3' extent of this sequence, this appears to be a partial cDNA clone lacking the N-terminal start methionine and C-terminal stop codon.

STLK7 shares 80% sequence identity to human SPAK (AF099989) over a 167 bp region and 50% nucleotide sequence identity to SLTK7 (SEQ ID NO. 101) over 391 nucleotides.

cDNA Cloning and Characterization of ZC1

The human ZC1 cDNA sequence is composed of two overlapping PCR clones, 3R25-24-2 and R65-12-2.

A human ZC1 clone, 125-33-5, was first identified from a PCR screen with degenerate oligos, TRK1 and TRK4, applied to sscDNA generated from human small airway epithelial cells (Clontech). Sequence analysis of the 503 bp insert identified a 501 bp ORF (167 amino acids) with the potential to encode a novel human STK related to the C. elegans ZC504.4 gene product.

PCR clone 3R25-24-2 was isolated from human SNB19 glioblastoma sscDNA using primers 5'-ATGGCGAACGACTCTCCCGCGAA (SEQ ID NO:48) and 5'-ACACCAAAATCAACAAGTTTCACCTC (SEQ ID NO:49) derived from the N-terminus of a murine orthologue of ZC1 (NIK, GB:U88984) and the original human ZC1 clone 125-33-5, respectively. 3R25-24-2 contains a 527 bp insert and an ORF of 519 bp (173 amino acids).

PCR clone R65-12-2 was isolated as follows: A Smith-Waterman search of the EST database with the C. elegans ZC504.4 gene (GB:Z50029) as a query identified a human EST (W81656) whose ORF is related to the C. elegans gene and terminates in an identical residue (Trp). A primer was designed 3' to this stop codon (5'-AGTTACAAGGAATTCCAAGTTCT (SEQ ID NO:50)) and used in a PCR reaction with a primer derived from the original human ZC1 clone 125-33-5 (5'-ATGAAGAGGAAGAAATCAAACTG (SEQ ID NO:51)) using sscDNA from human SNB19 glioblastoma as a template. PCR clone R65-12-2 was identified and was found to contain a 3611 bp insert with a 3534 bp ORF encoding the C-terminal portion of human ZC1 (1178 amino acids).

The full-length human ZC1 cDNA (SEQ ID NO. 9) is 3798 bp long. Clone 3R25-24-2 spans positions 1–527, and clone R65-12-2 spans positions 188–3798. The overlap between these two clones exhibits 100% sequence identity. The human ZC1 contains a 3717 bp ORF (17–3723) flanked by a 6 bp 5' UTR and a 75 bp (3724–3798) 3' UTR. No polyadenylation signal (AATAAA) or polyadenylated region are present in the 3' UTR. The sequence flanking the first ATG conforms to the Kozak consensus for an initiating methionine, and is believed to be the translational start site for human ZC1.

Multiple EST fragments (W81656) match the 3' end of the human ZC1 gene, but at the time of filing, the inventors believe that none exist in GenBank or the EST database that match its 5' end.

cDNA Cloning and Characterization of ZC2

The human ZC2 cDNA sequence is composed of four overlapping PCR clones, G75-31-17, R65-24-6, 2R28-8-1, and R99-6-10.

A human ZC2 clone, G75-31-17, was first identified from a PCR screen with degenerate oligos, ROS1 (5'-GCNTTYGGNGARGTNTAYGARGG (SEQ ID NO:34)) and CCK4b (5'-GCTGGATCCYTCNGGNSWCATCCA (SEQ ID NO:35)), applied to sscDNA generated from the human HLT383 primary non-small cell lung cancer tissue. Sequence analysis of the 492 bp insert identified a 492 ORF (164 amino acids) with the potential to encode a novel human STK related to the C. elegans ZC504.4 gene product.

PCR clone R99-6-10 was isolated as follows: A Smith-Waterman search of the EST database with C. elegans ZC504.4 gene (GB:Z50029) as a query identified two overlapping human EST fragments (AA115844 and R51245) whose ORFs were related to the C. elegans gene and terminate in an identical residue (Trp). A primer was designed 3' to the stop codon found in R51245 (5'-AGATGGACTGTACTGGGAGG (SEQ ID NO:52)) and used in a PCR reaction with a primer derived from AA115844 (5'-ACTTTGTGCAGCTCTGTGGG (SEQ ID NO:53)) using human fetal brain sscDNA as a template. PCR clone R99-6-10 was identified and was found to contain a 1095 bp insert with a 930 bp ORF encoding the C-terminal portion of human ZC2 (310 amino acids).

PCR clone R65-24-6 was isolated from human HT29 colon cancer cell line sscDNA using primers 5'-AAGGTTATGGATGTCACAGGG (SEQ ID NO:54) and 5'-AGATGGACTGTACTGGGAGG (SEQ ID NO:52) derived from G75-31-17 and R51245, respectively. The 3' primer used in this PCR reaction mispaired between positions 1634–1653 of this gene leading to the formation of a truncated product. R65-24-6 contains a 1593 bp insert and an ORF of 1593 bp (531 amino acids).

PCR clone 2R28-8-1 was isolated from human colon cancer cell line HT29 sscDNA using primers 5'-CTCACAAGGTTGCCAACAGG (SEQ ID NO:55) and 5'-AGTCCCCACCAGAAGGTTTAC (SEQ ID NO:56) derived from R65-24-6 and R99-6-10, respectively. 2R28-8-1 contains a 1538 bp insert and an ORF of 1536 bp (512 amino acids).

The partial human ZC2 cDNA (SEQ ID NO. 10) is 4055 bp long. Clone G75-31-17 spans positions 1–492, clone R65-24-6 spans positions 58–1650, clone 2R28-8-1 spans positions 1466–3003 and clone R99-6-10 spans positions 2961–4055. The overlaping regions between these clones exhibit 100% sequence identity except for a single guanine (G75-31-17) to adenosine (R65-24-6) mismatch at position 280 resulting in a Glu to Lys change. Based on the presence of an acidic residue in this position in human ZC1 and ZC3 and C. elegans ZC504.4, the sequence encoding the Glu is probably correct. The human ZC2 gene contains a 3891 bp ORF (1–3891) flanked by 164 bp (3892–4055) 3' UTR. No polyadenylation signal (AATAAA) or polyadenylated region is present in the 3' UTR.

Multiple EST fragments (R51245) match the 3' end of the human ZC2 gene, but at the time of filing, the inventors believe that none exist in GenBank or the EST database that match its 5' end.

cDNA Cloning and Characterization of ZC3

The human ZC3 cDNA sequence is composed of four overlapping PCR clones, G75-30-30, 3R33-5-3, 3R19-17-6, and R99-43-11.

A human ZC3 clone, G75-30-30, was first identified from a PCR screen with degenerate oligos, ROS1 and CCK4b, applied to sscDNA generated from a human HLT370 primary non-small cell lung cancer tissue. Sequence analysis of the 492 bp insert identified a 492 ORF (164 amino acids) with the potential to encode a novel human STK related to the C. elegans ZC504.4 gene product.

PCR clone R99-43-11 was isolated as follows: A Smith-Waterman search of the EST database with the C. elegans ZC504.4 gene (GB:Z50029) as a query identified a human EST (R54563) whose ORF is related to the C. elegans gene and terminates in an identical residue (Trp). A primer was designed 3' to the stop codon found in R54563 (5'-TCAGGGGTCAGAGGTCACG (SEQ ID NO:57)) and used in a PCR reaction with a primer derived from the 5' end of R54563 (5'-CCCAAACCCTACCACAAATTC (SEQ ID NO:58)) using sscDNA from human fetal brain as a template. PCR clone R99-43-11 was identified and was found to contain a 719 bp insert with a 564 bp ORF encoding the C-terminal portion of human ZC3 (188 amino acids).

PCR clone 3R19-17-6 was isolated from human A549 lung cancer cell line sscDNA using primers 5'-CCCCCGGGAAACGATGACCA (SEQ ID NO:59) and 5'-AGCCGCTGCCCCTCCTCTACTGT (SEQ ID NO:60) derived from G75-30-30 and R99-43-11, respectively. The 3' primer used in this PCR reaction mispriming leading to the formation of a truncated product. 3R19-17-6 contains a 1172 bp insert and an ORF of 1170 bp (390 amino acids).

PCR clone 3R33-5-3 was isolated from human A549 lung cancer cell line sscDNA using primers 5'-ACCGCAACATCGCCACCTACTAC (SEQ ID NO:61) and 5'-CTCGACGTCGTGGACCACC (SEQ ID NO:62) derived from G75-30-30 and 3R19-17-6, respectively. 3R33-5-3 contains a 2465 bp insert and an ORF of 2463 bp (821 amino acids).

The full-length human ZC3 cDNA (SEQ ID NO. 11) is 4133 bp long. Clone G75-30-30 spans positions 1–483, clone 3R33-5-3 spans positions 134–2598, clone 3R19-17-6 spans positions 2356–3512 and clone R99-43-11 spans positions 3415–4133. The overlaps between these clones exhibit 100% sequence identity. The human ZC3 gene contains a 3978 bp ORF (1–3978) flanked by a 152 bp 3' UTR (3979–4133). No polyadenylation signal (AATAAA) or polyadenylated region is present in the 3' UTR.

Multiple EST fragments (R54563) match the 3' end of the human ZC3 gene, but at the time of filing, the inventors believe that none exist in GenBank or the EST database that match its 5' end.

cDNA Cloning and Characterization of ZC4

The human ZC4 cDNA sequence, represented by PCR fragment 3R25-27-1, was first identified in the human genomic cosmid 82J11 (GB:Z833850) containing exon sequences that displayed strong homology to the ZC504.4 C. elegans gene.

PCR clone 3R25-27-1 was isolated from human fetal liver sscDNA and primers 5'-CAATGTTAACCCACTCTATGTCTC (SEQ ID NO:63) and 5'-AGTTTGCCGATGTTTTTCTTTTC (SEQ ID NO:64) derived from a potential ORF (positions 25729–25852) from the 82J11 cosmid and from an EST (R98571) encoding the C-terminus of the human ZC4 gene, respectively.

The partial human ZC4 cDNA (SEQ ID NO.12) is 1459 bp long and consists of a 1047 bp ORF (2–1048) flanked by a 411 bp (1049–1459) 3' UTR region. No polyadenylation signal (AATAAA) or polyadenylated region is present in the 3' UTR.

The N-terminal coding sequence for ZC4_h was extended by building a contiguous DNA sequence of 233, 137 bp containing Z83850 and four other sequences: cU84B10 and cU230B10 (from the Sanger Human Genome Sequencing Project) and Z97356 and Z69734 (available from the National Institute for Biotechnology Information). The position of each sequence in the contig is represented in the table below.

| Accession | Length | Start | End |
| --- | --- | --- | --- |
| cU84B10 | 43273 | 0 | 43273 |
| Z97356 | 21848 | 43171 | 65018 |
| Z69734 | 37077 | 63073 | 100149 |
| cU230B10 | 11841 | 88416 | 100256 |
| Z83850 | 132981 | 100156 | 233137 |

Sequences in ZC4 genomic contig.

The 233,137 bp contig was analyzed for exons using the programs FGENES 1.5 and FGENESH, human gene structure prediction software available from The Sanger Centre.

The resulting human ZC4 coding sequence (SEQ ID NO:104) is 3,681 bp long (excluding the stop codon) and encodes for a STE20 kinase of 1227 amino acids.

cDNA Cloning and Characterization of KHS2

The human KHS2 cDNA sequence is composed of four overlapping clones, 3R25-51-2, 3R16-34-2, 3R16-31-2, and T79916.

A human KHS2 clone, AA250855, was first identified using a Smith-Waterman search of the EST database with KHS1 (GB:U77129) as a query. Sequence analysis of the 1112 bp insert identified a 618 bp ORF (206 amino acids) with the potential to encode a novel STK related to the human KHS1 gene product. Using AA250855 as a query, a second EST (AA446022) was found whose sequence was shown to contain the initiator methionine for human KHS2 based on a comparison with KHS1.

PCR clone 3R25-51-2 was isolated from human testicular cancer sscDNA using primers 5'-CCGCCATGAACCCCGGCTT (SEQ ID NO:65) and 5'-CGATTGCCAAAGACCGTGTCA (SEQ ID NO:66) derived from AA446022 and AA250855, respectively. 3R25-51-2 contains an 850 bp insert and an ORF of 849 bp (283 amino acids).

EST clone, T79916, was identified using a Smith-Waterman search of the EST database with the C-terminus of KHS1 (GB:U77129) as a query. Sequence analysis of the 2107 bp insert identified this EST to contain an ORF of 345 bp (115 amino acids disrupted by a single stop codon) encoding the C-terminus of human KHS2, followed by 1762 bp 3' UTR.

PCR clone 3R16-34-2 was isolated from human testis sscDNA using primers 5'-AGAAGTTGCAGCTGTTGAGAGGA (SEQ ID NO:67) and 5'-TATGGCCCGTGTAAGGATTTC (SEQ ID NO:68) derived from AA250885 and T79916, respectively. 3R16-34-2 contains an 1516 bp insert and an ORF of 1128 bp (376 amino acids).

PCR clone 3R16-31-2 was isolated from normal human colon sscDNA using primers 5'-GTGCCAGAAGTGTTGTGTTGTAA (SEQ ID NO:69) and 5'-TATGGCCCGTGTAAGGATTTC (SEQ ID NO:68) derived from EST T79916. 3R16-31-2 contains a 728 bp insert and an ORF of 669 bp (223 amino acids). This clone lacked the stop codon present within EST T79916 (postion 2662 in the KHS2 sequence).

The full-length human KHS2 cDNA (SEQ ID NO.17) is 4023 bp long. Clone 3R25-51-2 spans positions 1–855, clone AA250885 spans positions 336–923, clone 3R16-34-2 spans positions 545–2061, and clone T79916 spans positions 1917–4023. The overlaping regions between these clones exhibit 100% sequence identity, except for 4 nucleotide differences, two of which are silent, a third corrects the internal stop codon at position 2662, and the fourth at position 247 (T to C change) results in a Pro to Leu change. The human KHS2 cDNA contains a 2682 bp ORF (6–2687) flanked by a 5 bp (1–5) 5' UTR and a 1336 bp (2688–4023) 3' UTR. A potential polyadenylation signal (AATAAA) is found at positions 4008–4013. No polyadenylated region is present in the 3' UTR. The sequence flanking the first ATG is in a poor context for translational initiation, however, a 134 bp 5' UTR sequence from EST AA446022 did not reveal any additional ATG's and displayed two in-frame stop codons 5' to the putative start ATG for human KHS2.

Multiple EST fragments match the 5' end (AA446022) as well as the 3' end (R37625) of the human KHS2 gene.

cDNA Cloning and Characterization of SULU1

The human SULU1 cDNA sequence is composed of three overlapping clones, N40091, 2R90-1-1 and R90907.

A human SULU1 clone, N40091, was first identified using a Smith-Waterman search of the EST database with the *C. elegans* SULU gene (GB:U32275) as a query. Sequence analysis of the 1321 bp insert identified a 906 bp ORF (302 amino acids) with the potential to encode a novel human STK related to the *C. elegans* SULU gene product.

EST clone R90907 was first identified using a Smith-Waterman search of the EST database with the 3' end of the *C. elegans* SULU gene (GB:U32275) as a query. Sequence analysis of the 1647 bp insert identified a 578 bp ORF (192 amino acids) with the potential to encode the C-terminus of the human SULU1 gene product.

PCR clone 2R90-1-1 was isolated from human HT29 colon cancer cell sscDNA using primers 5'-TATTGAATTGGCGGAACGGAAG (SEQ ID NO:70) and 5'-TTGTTTTGTGCTCATTCTTTGGAG (SEQ ID NO:71) derived from N40091 and R90907, respectively. 2R90-1-1 contains a 1625 bp insert and an ORF of 1623 bp (541 amino acids).

The full-length human SULU1 cDNA (SEQ ID NO.19) is 4177 bp long. Clone N40091 spans positions 1-1321, clone 2R90-1-1 spans positions 1048–2671, and clone R90907 spans positions 2531–4177. The overlaping regions between these clones exhibit 100% sequence identity. The human SULU1 cDNA contains a 2694 bp ORF (415–3108) flanked by a 414 bp (1–414) 5' UTR and a 1069 bp (3109–4177) 3' UTR followed by a 19 nucleotide polydenylated region. A potential polyadenylation signal (AATAAA) is found at positions 4164–4169. The sequence flanking the first ATG conforms to the Kozak consensus for an initiating methionine, and is believed to be the translational start site for human SULU1.

Multiple EST fragments match the 5' end (N27153) as well as the 3, end (R90908) of the human SULU1 gene.

cDNA Cloning and Characterization of Murine SULU3

The murine SULU3 cDNA sequence is represented by PCR fragment 2R92-1-6.

A murine SULU3 clone, G83-4-5, was first identified from a PCR screen with degenerate oligos, CCK4c and CCK4b, applied to sscDNA generated from murine day-12 embryos. Sequence analysis of the 473 bp insert identified a 471 ORF (157 amino acids) with the potential to encode a novel human STK related to the *C. elegans* SULU gene (GB:U32275) product. The antisense strand of G83-4-5 is identical at the nucleic acid level to the 5' UTR of the murine ets1 protooncogenic transcription factor (GB:X53953). This homology is likely the result of a cloning artifact attached to the 5'-end of the database entry for murine ets1.

PCR clone 3R19-17-6 was isolated from human A549 cell sscDNA using primers 5'-CCCCCGGGAAACGATGACCA (SEQ ID NP:59) and 5'-AGCCGCTGCCCCTCCTCTACTGT (SEQ ID NO:60) derived from G75-30-30 and R99-43-11, respectively. The 3' primer used in this PCR reaction misprimed leading to the formation of a truncated product. 3R19-17-6 contains a 1172 bp insert and an ORF of 1170 bp (390 amino acids).

PCR clone 2R92-1-6 was isolated from murine d8 embryo sscDNA using primers 5'-ACCGCAACATCGCCACCTACTAC (SEQ ID NO:61) and 5'-GATTGCTTTGTGCTCATTCTTTGG (SEQ ID NO:72) derived from the 5' UTR of the ets1 gene and the human EST AA234623, respectively. The latter (shown herein) encodes the C-terminus of human SULU3. 2R92-1-6 contains a 2249 bp insert and an ORF of 2244 bp (748 amino acids).

The partial murine SULU3 cDNA (SEQ ID NO.21) is 2249 bp long and consists of a 2244 bp ORF (6–2249) flanked by a 5 bp (1–5) 5' UTR. The sequence flanking the first ATG conforms to the Kozak consensus for an initiating methionine, and is believed to be the translational start site for murine SULU3.

One EST fragment (AA446022) matches the 3' end of the partial murine SULU3 gene, but at the time of filing, the inventors believe that none exist in GenBank or the EST database that match its 5' end.

cDNA Cloning and Characterization of Human SULU3

The human SULU3 cDNA sequence is composed of two overlapping clones, 2R90-22-1 and AA234623.

A human SULU3 clone, AA234623, was first identified using a Smith-Waterman search of the EST database with the *C. elegans* SULU gene (GB:U32275) as a query. Sequence analysis of the 2652 bp insert identified a 1185 bp ORF (395 amino acids) with the potential to encode the C-terminus of a novel human STK related to the *C. elegans* SULU gene product.

PCR clone 2R90-22-1 was isolated from human SKMel128 melanoma cell line sscDNA using primers 5'-TATTGAATTGGCGGAACGGAAG (SEQ ID NO:70) and 5'-TTGTTCTAAGAGTGCCCTCCG (SEQ ID NO:73) derived from the murine SULU3 2R92-1-6 clone and from AA234623, respectively. 2R92-1-6 contains a 1897 bp insert and an ORF of 1896 bp (632 amino acids).

The partial human SULU3 cDNA (SEQ ID NO.20) is 3824 bp long. Clone 2R90-22-1 spans positions 1–1897 and clone AA234623 spans positions 1173. The overlaping region between these clones exhibits 100% sequence identity. The human SULU3 cDNA contains a 2358 bp ORF (2–2359) flanked by a 1465 bp (2360–3824) 3' UTR followed by a 19 nucleotide polydenylated region. A potential polyadenylation signal (AATAAA) is found at positions 2602–2607. Since the coding region is open throughout the 5' extent of this sequence, this is apparently a partial cDNA clone lacking the N-terminal start methionine.

Multiple EST fragments (R02283) match the 3' end of the human SULU3 gene, but at the time of filing, the inventors believe that none exist in GenBank or the. EST database that match its 5' end.

cDNA Cloning and Characterization of GEK2

The human GEK2 cDNA sequence is composed of three overlapping clones, AA459448, 3R25-48-1 and GEK2_h#3.

A human GEK2 clone, AA459448, was first identified using a Smith-Waterman search of the EST database with the human SLK gene (GB:AB002804) as a query. Sequence analysis of the 1286 bp insert identified a 1227 bp ORF (409 amino acids) with the potential to encode the N-terminus of a novel human STK related to the human SLK gene product. An additional Smith-Waterman search using the C-terminus of the SLK gene as a query yielded three additional EST's, AA323687, AA380492 and AA168869, that encode the C-terminal region of human GEK2.

PCR clone 2R98-41-17 was isolated from human testis sscDNA using primers 5'-AAGACCATGCCGTGCGCCG (SEQ ID NO:74) and 5'-ATTCCTTCAGGTTCTGGTTATGG (SEQ ID NO:75) derived from AA323687 and from AA380492, respectively. 2R98-41-17 contains a 851 bp insert and an ORF of 849 bp (283 amino acids).

PCR clone GEK2_h#3 was isolated from human sscDNA made from the H23 tumor cell line using primers 5'-GCAGCAAGTGGAGAAGATGG (SEQ ID NO:109) and 5'-GGAAGCATCCCCAGAGCTGTAG (SEQ ID NO:110) derived from the sequence of clone 3R25-48-1 and from the 3' end of murine LOK (GB:D89728), respectively. GEK2_h#3 contains a 1042bp insert and an ORF of 1041 bp (347 amino acids).

The full-length human GEK2 cDNA (SEQ ID NO:106) is 2962 bp long. Clone AA459448 spans positions 1–1286, clone 3R25-48-1 spans positions 1100–2449 and clone GEK2_h#3 spans positions 1920–2962. The overlapping regions between these clones exhibit 100% sequence identity.

The human GEK2 cDNA contains a 2904 bp ORF (59–2962) flanked by a 58 bp (1–58) 5' UTR. The sequence flanking the first ATG conforms to the Kozak consensus for an initiating methionine, and is believed to be the translational start site for human GEK2.

Multiple EST fragments (AA465671) match the 5' end of the sequence, but only one (AA380492) matches the 3' end of the human GEK2 gene.

cDNA Cloning and Characterization of PAK4

The human PAK4 cDNA sequence is represented by clone SNB2#1.

A human PAK4 clone, R88460, was first identified using a Smith-Waterman search of the EST database with the human PAK gene (GB:U24152) as a query. Sequence analysis of the 2332 bp insert identified a 930 bp ORF (310 amino acids) with the potential to encode the C-terminus of a novel human STK related to the human PAK gene product.

cDNA clone SNB2#1 was isolated from human glioblastoma cell line SNB75 cDNA library using a probe derived from R88460. SNB2#1 contains a 3604 bp insert and an ORF of 2043 bp (681 amino acids).

The full-length human PAK4 cDNA (SEQ ID NO.27) is 3604 bp long and consists of a 2043 bp ORF (143–2185) flanked by a 142 bp (1–142) 5' UTR and a 1419 3' UTR followed by a 22 nucleotide polyadenylated region. A potential polyadenylation signal (AATTAAA) is found at positions 3582–3588. The sequence flanking the first ATG conforms to the Kozak consensus for an initiating methionine, and is believed to be the translational start site for human PAK4. The 3' UTR of the PAK4 gene contains a GT dinucleotide repeat prone to undergo expansion based on the number of repeats found in clones SNB#1 and R88460, 32 and 23, respectively. Several neurologic disorders have been correlated with the expansion of di- or tri-nucleotide repeats similar to those found in the PAK4 sequence, suggesting PAK4 may also be a disease target and that this repeat in its 3' UTR may serve as a diagnostic marker.

Multiple EST fragments (AA535791) match the 3' end of the human PAK4 gene, but at the time of filing, the inventors believe that none exist in GenBank or the EST database that match its 5' end.

cDNA Cloning and Characterization of PAK5

The full-length human PAK5 cDNA sequence is composed of two overlapping clones, H450#1-1 and SNB8#5.

A human PAK5 clone, R18825, was first identified using a Smith-Waterman search of the EST database with the human PAK4 gene as a query. Sequence analysis of the 1248 bp insert identified a 420 bp ORF (140 amino acids) with the potential to encode the C-terminus of a novel human STK related to the human PAK4 gene product.

cDNA clone SNB8#5 was isolated from human SNB75 cDNA library using a probe derived from R18825. SNB2#1 contains a 2028 bp insert and an ORF of 1194 bp (398 amino acids) The partial human PAK5 cDNA (SEQ ID NO.28) is 2028 bp long and consists of a 1194 bp ORF (2–1195) flanked by an 833 bp (1196–2028) 3' UTR followed by a 22 nucleotide polydenylated region. A potential polyadenylation signal (AATTAAA) is found at positions 2004–2010. Since the coding region is open throughout the 5' extent of this sequence, this is apparently a partial cDNA clone lacking the N-terminal start methionine.

Clone H460#1-1 was isolated from a human lung H460 cDNA library using a probe derived from the partial SNB2#1 cDNA clone described above. Sequence analysis of the 2526 bp insert identified a 1773 bp ORF (592 amino acids) with the potential to encode a full-length PAK5.

The human PAK5 cDNA (SEQ ID NO:102) is 2,806 bp long and consists of a 1,773 bp ORF flanked by a 201 bp 5' UTR and a 833 bp 3' UTR. The sequence flanking the first ATG conforms to the Kozak consensus (Kozak, M., Nucleic Acids Res. 15, 8125–8148 (1987)) for an initiating methionine, and is believed to be the translational start site for PAK5.

PAK5 shares 99% sequence identity over 2795 bp to a recent database entry, AF005046. These sequences are presumed to be from the same gene, with minor polymorphic variations.

Example 2

Expression Analysis of Mammalian STE20-Related Protein Kinases

Materials and Methods

Northern Blot Analysis

Northern blots were prepared by running 10 µg total RNA isolated from 60 human tumor cell lines (HOP-92, EKVX, NCI-H23, NCI-H226, NCI-H322M, NCI-H460, NCI-H522, A549, HOP-62, OVCAR-3, OVCAR-4, OVCAR-5, OVCAR-8, IGROV1, SK-OV-3, SNB-19, SNB-75, U251, SF-268, SF-295, SF-539, CCRF-CEM, K-562, MOLT-4, HL-60, RPMI 8226, SR, DU-145, PC-3, HT-29, HCC-2998, HCT-116, SW620, Colo 205, HTC15, KM-12, UO-31, SN12C, A498, CaKi1, RXF-393, ACHN, 786-0, TK-10, LOX IMVI, Malme-3M, SK-MEL-2, SK-MEL-5, SK-MEL-28, UACC-62, UACC-257, M14, MCF-7, MCF-7/ADR RES, Hs578T, MDA-MB-231, MDA-MB-435, MDA-N, BT-549, T47D), from 22 human adult tissues (thymus, lung, duodenum, colon, testis, brain, cerebellum, cortex, salivary gland, liver, pancreas, kidney, spleen, stomach, uterus, prostate, skeletal muscle, placenta, mammary gland, bladder, lymph node, adipose tissue), and 2 human fetal normal tissues (fetal liver, fetal brain), on a denaturing formaldehyde 1.2% agarose gel and transferring to nylon membranes.

Filters were hybridized with random primed [$\alpha^{32}P$]dCTP-labeled probes synthesized from the inserts of several of the STE20-related kinase genes. Hybridization was performed at 42° C. overnight in 6xSSC, 0.1% SDS, 1xDenhardt's solution, 100 µg/mL denatured herring sperm DNA with 1–2×10$^6$ cpm/mL of $^{32}$P-labeled DNA probes. The filters were washed in .0.1×SSC/0.1% SDS, 65° C., and exposed on a Molecular Dynamics phosphorimager.

Quantitative PCR Analysis

RNA was isolated from a variety of normal human tissues and cell lines. Single stranded cDNA was synthesized from 10 µg of each RNA as described above using the Superscript Preamplification System (GibcoBRL). These single strand templates were then used in a 25 cycle PCR reaction with primers specific to each clone. Reaction products were electrophoresed on 2% agarose gels, stained with ethidium bromide and photographed on a UV light box. The relative intensity of the STK-specific bands were estimated for each sample.

DNA Array Based Expression Analysis

Plasmid DNA array blots were prepared by loading 0.5 µg denatured plasmid for each STE20-related kinase on a nylon membrane. The [α$^{32}$P]dCTP labeled single stranded DNA probes were synthesized from the total RNA isolated from several human immune tissue sources or tumor cells (thymus, dendrocytes, mast cells, monocytes, B cells (primary, Jurkat, RPMI8226, SR), T cells (CD8/CD4+, TH1, TH2, CEM, MOLT4), K562 (megakaryocytes). Hybridization was performed at 42° C. for 16 hours in 6×SSC, 0.1% SDS, 1×Denhardt's solution, 100 µg/mL denatured herring sperm DNA with 106 cpm/mL of [α$^{32}$P]dCTP labeled single stranded probe. The filters were washed in 0.1×SSC/0.1% SDS, 65° C., and exposed for quantitative analysis on a Molecular Dynamics phosphorimager.

RESULTS

Distribution of STE20-Related Gene Transcripts in Normal Tissues and Tumor Cell Lines ZC1, ZC2, and ZC3 RNA expression was analyzed by quantitative PCR from multiple human normal tissues, cultured primary epithelial and endothelial cells, and tumor cell lines. The results are summarized in Tables 1 and 2, with relative expression values ranging from 0 (undetectable) to 23 (very strong). An "x" refers to sample not tested. ZC1, ZC2, and ZC3 were all expressed at very low levels in most normal human tissues, however ZC1 and ZC2 were more abundant in cultured epithelial cells and ZC3 in normal kidney and breast tissue.

Expression of these 3 genes was also examined in a panel of human tumor cell lines representing a diverse sampling of tumor types (Table 2). ZC1 and ZC2 showed strong expression in cell lines from most melanomas and renal tumors and from some non-small cell lung cancers and colon tumors. ZC3 expression was consistently lower in the tumor cell lines except for high expression in most breast cancers and leukemias. The robust overexpression ZC1, ZC2, and ZC3 in tumor cells versus normal tissues may provide an attractive target for oncology drug development.

Expression of all the novel STE20-related kinases was examined in a panel of human immune tissues/cells by hybridization to a DNA array blot containing plasmids encoding each of these genes. STLK2 was broadly expressed in all 14 immune samples, whereas STLK4 and PAK4 were highly expressed in a subset of 6–7 of the samples (Table 3). Several other kinases (SULU3, ZC4, KHS2) had more restricted expression, while others were expressed in only a single immune source (STLK3, thymus; ZC1, dendrocytes; ZC3, monocytes; PAK5, mast cells and MOLT4), and several more were absent from all the immune sources assayed (GEK2, SULU1, ZC2, STLK5). These expression patterns were quite distinct among members of the same subfamily (i.e., ZC1, ZC2, ZC3 and ZC4, or PAK1, PAK2, PAK3, PAK4, PAK5). This analysis suggests that some of these kinases may be candidate targets for various immune disorders, and that some, which are more broadly expressed, may mediate functions vital to the basic biology of most proliferating cells.

TABLE 1

Z-C1, ZC2 and ZC3 Expression in Normal Human Tissues and Cells

| Sample | | ZC1 | ZC2 | ZC3 |
|---|---|---|---|---|
| NORMAL | | | | |
| Brain | Tiss | 2.8 | 0.6 | 0.9 |
| Duod | Tiss | 3.8 | 1.5 | 0.3 |
| Heart | Tiss | 1.2 | 0.3 | 0.0 |
| Kidney | Tiss | 0.7 | 0.0 | 7.0 |
| Lung | Tiss | 1.6 | 0.2 | 0.0 |
| Pancreas | Tiss | 2.0 | 0.4 | 2.5 |
| Placenta | Tiss | 1.4 | 0.0 | 0.0 |
| Sal gl. | Tiss | 3.0 | 0.3 | 3.2 |
| Sk mus. | Tiss | 2.3 | 0.1 | 0.1 |
| Spleen | Tiss | 0.4 | 0.0 | x |
| Stomach | Tiss | 0.8 | 0.0 | 0.0 |
| Thymus | Tiss | 3.5 | 0.4 | 1.5 |
| Cereb | Tiss | 2.8 | 1.1 | 4.4 |
| Liver | Tiss | 1.8 | 0.0 | 0.4 |
| Uterus | Tiss | 1.6 | 0.0 | 1.4 |
| Prostate | Tiss | 1.4 | 0.0 | 1.6 |
| Testis | Tiss | x | x | 5.8 |
| f Brain | Tiss | x | x | 3.1 |
| Mam gl | Tiss | x | x | 7.2 |
| HCAEC | ENDO | 1.0 | 0.0 | 0.0 |
| HMVEC-d | ENDO | 0.7 | 0.0 | 0.4 |
| HMVEC-L | ENDO | 2.2 | 1.6 | 1.8 |
| HPAEC | ENDO | 9.3 | 5.3 | 6.4 |
| HMEC | EPI | 4.1 | 2.3 | 1.9 |
| RPTEC. | EPI | 3.6 | 2.2 | 0.2 |
| HRCE | EPI | 5.3 | 3.5 | 1.3 |
| HSAE | EPI | 0.9 | 3.3 | 4.8 |

TABLE 2

ZC1, ZC2 and ZC3 Expression in Tumor Cell lLnes

| Sample | Origin | ZC1 | ZC2 | ZC3 |
|---|---|---|---|---|
| HOP-92 | Lung | 9.3 | 7.2 | 3.3 |
| EKVX | Lung | 10.7 | 3.7 | 3.5 |
| NCI-H23 | Lung | 5.8 | 6.3 | 4.1 |
| NCI-H226 | Lung | 6.5 | 6.8 | 3.3 |
| NCI-H322M | Lung | 3.5 | 5.8 | 4.9 |
| NCI-H460 | Lung | 4.5 | 3.7 | 2.9 |
| NCI-H522 | Lung | 4.7 | 3.3 | 4.6 |
| A549/ATCC | Lung | 3.8 | 3.6 | 4.1 |
| HOP-62 | Lung | 4.3 | 3.8 | 4.2 |
| OVCAR-3 | Ovary | 2.9 | 3.1 | 1.5 |
| OVCAR-4 | Ovary | 3.3 | 1.0 | 3.8 |
| OVCAR-5 | Ovary | 2.6 | 3.6 | 2.2 |
| OVCAR-8 | Ovary | 3.6 | 2.0 | 4.7 |
| IGROV1 | Ovary | 3.8 | 1.7 | 3.2 |
| SK-OV-3 | Ovary | 4.9 | 0.0 | 3.5 |
| SNB-19 | CNS | 5.1 | 5.4 | 4.2 |
| SNB-75 | CNS | 2.5 | 0.9 | 0.7 |
| U251 | CNS | 1.5 | 1.2 | 0.6 |
| SF-268 | CNS | 5.8 | 2.7 | 3.0 |
| SF-295 | CNS | 6.4 | 1.1 | 3.2 |
| SF-539 | CNS | 5.1 | 2.9 | 4.3 |
| CCRF-CEM | Leuk | 3.4 | 2.7 | 3.1 |
| K-562 | Leuk | 4.1 | 6.3 | 4.3 |
| MOLT-4 | Leuk | 7.1 | 3.4 | 4.2 |
| HL-60 | Leuk | x | x | 0.4 |
| RPMI 8226 | Leuk | 0.5 | 0.2 | 1.4 |
| SR | Leuk | 3.5 | 7.2 | 5.4 |
| DU-145 | Pro | x | x | 3.4 |
| PC-3 | Pro | x | x | 3.4 |
| HT-29 | Colon | 2.4 | 5.9 | 6.6 |

TABLE 2-continued

ZC1, ZC2 and ZC3 Expression in Tumor Cell lLnes

| Sample | Origin | ZC1 | ZC2 | ZC3 |
|---|---|---|---|---|
| HCC-2998 | Colon | 2.4 | 3.8 | 3.0 |
| HCT 116 | Colon | 2.2 | 2.1 | 5.4 |
| SW-620 | Colon | 7.8 | 12.1 | 3.1 |
| COLO 205 | Colon | 9.1 | 16.2 | 3.0 |
| HCT-15 | Colon | 13.8 | 4.9 | 2.5 |
| KM-12 | Colon | 7.0 | 13.2 | 3.1 |
| UO-31 | Colon | 10.4 | 10.6 | 0.9 |
| SN12C | Renal | 8.1 | 3.4 | 2.8 |
| A498 | Renal | 6.2 | 3.1 | 2.9 |
| Caki-1 | Renal | 9.2 | 14.4 | 2.3 |
| RXF 393 | Renal | 10.6 | 4.8 | 2.8 |
| ACHN | Renal | 9.3 | 6.0 | 3.9 |
| 786-0 | Renal | 8.8 | 15.6 | 5.6 |
| TK-10 | Renal | 20.9 | 21.2 | 5.0 |
| LOX IMVI | Mel | 2.3 | 2.4 | 3.3 |
| Malme-3M | Mel | x | x | 2.2 |
| SK-MEL-2 | Mel | 15.7 | 14.1 | 2.9 |
| SK-MEL-5 | Mel | 7.9 | 7.0 | 0.0 |
| SK-MEL-28 | Mel | 16.5 | 23.1 | 0.0 |
| UACC-62 | Mel | 12.1 | 18.3 | 5.3 |
| UACC-257 | Mel | 10.8 | 9.4 | 6.2 |
| M14 | Mel | 4.4 | 0.9 | 7.9 |
| MCF7 | Breast | 4.8 | 1.3 | 7.7 |
| MCF-7/ADR | Breast | 8.8 | 3.4 | 7.7 |
| Hs 578T | Breast | 6.9 | 2.6 | 5.7 |
| MDA-MB-231 | Breast | 5.7 | 1.9 | 6.4 |
| MDA-MB-435 | Breast | 4.8 | 6.7 | 9.1 |
| MDA-N | Breast | 7.3 | 6.3 | 9.1 |
| BT-549 | Breast | 3.6 | 1.9 | 8.0 |
| T-47D | Breast | 0.4 | 12.3 | 9.3 |

Transcript size from Northern data

| Kinase | (kb) |
|---|---|
| STLK2 | 3.8 |
| STLK4 | 5.0 |
| ZC1 | 6.9/4.7 |
| ZC2 | 6.0/8.0 |
| ZC4 | 5 |
| KHS2 | 4.4 |
| SULU1 | 4.5 |
| SULU3 | 10.0 |
| GEK2 | 5.5 |
| PAK4 | 4.8 |
| PAK5 | 3.5 |

STLK2is widely expressed; the highest expression levels were found in placenta, spleen and PBL.

STLK4 is also widely expressed in normal tissues including heart, brain, placenta, lung, liver, skeletal muscle, kidney, pancreas, spleen, thymus, prostate, testis, ovary, small intestine colon, and peripheral blood lymphocytes. STLK4 was also detected in Jurkat T cells.

ZC1 is highly overexpressed in the following human cancer cell lines: HOP-92, EKVX, NCI-H23, NCI-H226, NCI-H322M, NCI-H522, A549, HOP-62 (lung); OVCAR-3, OVCAR-4, OVCAR-5 (ovary); SNB-19, U251, SF-268, SF-295, SF-539 (CNS); K-562, RPMI-8226 (leukemia); DU-145, PC-3 (prostate); HT-29, HCC-2998, HCT-116, SW620, COLO-205, HCT-15, KM-12 (colon); UO-31, CAKi-1, RXF-393, 786-0, TK-10 (renal); LOXIMVI, Malme-3M, SK-MEL-2, SK-MEL-28, UACC-62, UACC-

TABLE 3

STE20-related kinase expression in a human immune panel

| KINASE | thymus | Dendrocytes | Mast cells | Monocytes | B cells | CD8+ CD4+ | TH1 | TH2 |
|---|---|---|---|---|---|---|---|---|
| GEK2 | 350 | 350 | 350 | 350 | 350 | 350 | 350 | 350 |
| SULU1 | 350 | 350 | 350 | 350 | 350 | 350 | 350 | 350 |
| SULU3 | 350 | 350 | 350 | 350 | 12149 | 350 | 5115 | 350 |
| STLK2 | 117770 | 13771 | 27620 | 92036 | 18305 | 39109 | 5408 | 3564 |
| STLK3 | 8624 | 350 | 350 | 350 | 350 | 350 | 350 | 350 |
| STLK4 | 8524 | 350 | 350 | 350 | 350 | 8685 | 5642 | 350 |
| STLK5 | xxx | xxx | xxx | xxx | 350 | 350 | 350 | xxx |
| ZC1 | 350 | 3377 | 350 | 350 | 350 | 350 | 350 | 350 |
| ZC2 | 350 | 350 | 350 | 350 | 350 | 350 | 350 | 350 |
| ZC3 | 350 | 350 | 350 | 20156 | 350 | 350 | 350 | 350 |
| ZC4 | xxx | xxx | xxx | xxx | 350 | 350 | 350 | xxx |
| KHS2 | 8766 | 2508 | 350 | 56575 | 350 | 350 | 350 | 350 |
| PAK4 | 32658 | 7684 | 3729 | 100948 | 350 | 350 | 350 | 1604 |
| PAK5 | 350 | 350 | 4905 | 350 | 350 | 350 | 350 | 350 |

| KINASE | CEM (T cell) | MOLT4 (T cell) | JURKAT (B cell) | RPMI8226 (B cell) | SR (B cell) | K562 (MO) |
|---|---|---|---|---|---|---|
| GEK2 | 350 | 350 | 350 | 350 | 350 | 350 |
| SULU1 | 350 | 350 | 350 | 350 | 350 | 350 |
| SULU3 | 350 | 350 | 350 | 350 | 350 | 350 |
| STLK2 | 47236 | 53262 | 47605 | 22560 | 65936 | 30390 |
| STLK3 | 350 | 350 | 350 | 350 | 350 | 350 |
| STLK4 | 3648 | 350 | 26772 | 1570 | 350 | 350 |
| STLK5 | 350 | 350 | 350 | xxx | 350 | 350 |
| ZC1 | 350 | 350 | 350 | 350 | 350 | 350 |
| ZC2 | 350 | 350 | 350 | 350 | 350 | 350 |
| ZC3 | 350 | 350 | 350 | 350 | 350 | 350 |
| ZC4 | 1094 | 7813 | 14945 | xxx | 350 | 6385 |
| KHS2 | 350 | 350 | 350 | 350 | 350 | 350 |
| PAK4 | 350 | 10246 | 350 | 3229 | 350 | 350 |
| PAK5 | 350 | 12672 | 350 | 350 | 350 | 350 |

257, M14 (melanoma); and MCF-7, MCF-7/ADR, HIS 578T, MDA-MB-231, MDA-MB-431, MDA-N, BT-549, T-47D (breast).

ZC2 is expressed in brain and testis. It is highly overexpressed in the following human cancer cell lines: TK-10 (renal); SK-MEL-28, UACC-62 (melanoma); T47D (breast).

Moderate expression in HOP92 (lung); OVCAR4, IGROV1 (ovary); DNB75, U251 (brain); K-562 (leukemia); and COL0205 (colon).

SULU1 is overexpressed in the following human cancer cell lines: HOP-92, EKVX, NCI-H23, NCI-H226, NCI-H322M, NCI-H522, A549, HOP-62 (lung); OVCAR-3, OVCAR-4, OVCAR-5, SK-OV-3 (ovary); SNB-19, U251, SF-268, SF-295, SF-539 (CNS); K-562, RPMI-8226 (leukemia); DU-145, PC-3 (prostate); HT-29, HCC-2998, HCT-116, SW620, COLO-205, HCT-15, KM-12 (colon); UO-31, CAKi-1, RXF-393, 786-0, TK-10 (renal); LOX, IMVI, Malme-3M, SK-MEL-2, SK-MEL-28, UACC-62, UACC-257, M14 (melanoma); MCF-7, MCF-7/ADR, HIS 578T, MDA-MB-231, MDA-MB-431, MDA-N, BT-549, T-47D (breast) SULU3 showed a broad pattern of expression in the normal tissue panel of RNAs.

GEK2 was expressed in spleen, thymus and testis. Expression was high in the cell lines RBL-2H3 and H441.

PAK4 was expressed in the normal tissues: brain, testis and prostate, and in the human cancer cell lines: HNCI-H23 (lung); OVCAR-3 (ovary); SNB-19, U251 (CNS); RPMI-8226 (leukemia); DU-145 (prostate); COLO-205, HCT-15 (colon).

PAK5 showed weak expression levels in the normal tissues: brain, testes, bladder, colon, adrenal medulla, spleen, fetal liver, breast, cerebral cortex, cerebellum, thymus, salivary gland, lung, stomach, duodenum, uterus, prostate, skeletal muscle and placenta. PAK5 was overexpressed in the human cancer cell lines: HOP-92, EKVX, NCI-H23, NCI-H226, NCI-H322M, NCI-H522, A549, HOP-62 (lung); OVCAR-3, OVCAR-4, OVCAR-5, SK-OV-3 (ovary); SNB-19, U251, SF-268, SF-295, SF-539 (CNS); K-562, RPMI-8226 (leukemia); DU-145, PC-3 (prostate); HT-29, HCC-2998, HCT-116, SW620, COLO-205, HCT-15, KM-12 (colon); UO-31, CAKi-1, RXF-393, 786-0, TK-10 (renal); LOXIMVI, Malme-3M, SK-MEL-2, SK-MEL-28, UACC-62, UACC-257, M14 (melanoma); MCF-7, MCF-7/ADR, HIS 578T, MDA-MB-231, MDA-MB-431, MDA-N, BT-549, T-47D (breast).

Example 3

STE20-Related Protein Kinase Gene Expression Vector Construction

Materials and Methods

Expression Vector Construction Several expression constructs were generated for some of the human STE20-related cDNAs including: a) full-length clones in a pcDNA expression vector; b) a GST-fusion construct containing the catalytic domain of the novel STE20-related kinase fused to the C-terminal end of a GST expression cassette; and c) a full-length clone containing a Lys to Ala (K to A) mutation at the predicted ATP binding site within the kinase domain, inserted in the pcDNA vector.

The "K to A" mutants of the STE20-related kinase might function as dominant negative constructs, and will be used to elucidate the function of these novel STKs.

RESULTS

Constructs for ZC1, ZC2, ZC3, SULU1, SULU3, PAK4 and PAK5 have been generated.

Numerous additional constructs have been generated for the various STE20-subfamily kinases, including full length, kinase inactive and tagged versions. In addition, the following three constructs were designed for specific applications based on their unique domain structure:

Construct 1: SULU1-coiled-coil2
Vector: pGEX-4T
Insert: Coiled-coil2
Sequence: Amino acids 752–898
Purpose: phage display
Result: Interacts with GEK2 CC1
Construct 2: SULU3-coiled-coil2
Vector: pGEX4T
Insert:- coiled-coil 2 domain fused to GST
Sequence range of insert: amino acids 802–898 of SEQ
Purpose: phage display
Result: Interacts with coiled-coiled region of human SLK
Construct 3: PAK5 Dominant Negative
Vector: pCAN5
Insert: Full length coding sequence of human PAK5 containing the following mutation: K350,351A (Lys at aa positions 350 and 351 changed to Ala).
Purpose: to determine role of human PAK5 kinase activity in cell growth and transformation.
Result: Interferes with Ras transformation.

Example 4

Generation of Specific Immunoreagents to STE20-Related Protein Kinases

Materials and Methods

Specific immunoreagents were raised in rabbits against KLH- or MAP-conjugated synthetic peptides corresponding to the human STE20-related kinases. C-terminal peptides were conjugated to KLH with glutaraldehyde, leaving a free C-terminus. Internal peptides were MAP-conjugated with a blocked N-terminus. Additional immunoreagents can also be generated by immunizing rabbits with the bacterially expressed GST-fusion proteins containing the cytoplasmic domains of each novel STK.

The various immune sera are first tested for reactivity and selectivity to recombinant protein, prior to testing for endogenous sources.

Western Blots

Proteins in SDS PAGE are transferred to immobilon membrane. The washing buffer is PBST (standard phosphate-buffered saline pH 7.4+0.1% tritonx100). Blocking and antibody incubation buffer is PBST+5% milk. Antibody dilutions varied from 1:1000 to 1:2000.

RESULTS

Three SULU1 antisera (against both 539A (SEQ ID NO: 79) and 540A (SEQ ID NO: 78)) and two SULU3 antisera (542A) (SEQ ID NO: 81) reacted specifically with the peptide antigens. Antisera binding was competable with peptide. Experiments with extracts from cells transfected with epitope-tagged SULU1 and SULU3 genes are underway.

Antisera against the PAK4 C-terminal peptide 554A (SEQ ID NO: 82) reacted with purified Gst-PAK4 and detected a protein of the correct molecular weight from tissue culture cells. Specific immunoprecipitation experiments are ongoing to determine the reactivity with native protein.

Similar immunization and antisera testing experiments are underway for each of the other novel STE20-kinases.

STE20-Related Protein Kinase Peptide Immunogens and Their Specificity in Recognizing Endogenous Protein by Western Blots or Immunoprecipitations.

| Protein | Sequence | Aa positions | Conj | West. | IP |
|---|---|---|---|---|---|
| STLK2 | EKFQKCSADESP (SEQ ID NO:111) | 405–416 | KLH | Y | Y |
| STLK4 | SISNSELFPTTDPVGT (SEQ ID NO:112) | 252–267 | KLH | Y | Y |
| SULU1 | LDFPKEDYR (SEQ ID NO:113) | 890–898 | KLH | Y | Y |
| SULU1 | HGDPRPEPRPTQ (SEQ ID NO:114) | 409–420 | KLH | Y | Y |
| SULU3 | PSTNRAGSLKDPEC (SEQ ID NO:115) | 2–14 | KLH | N | ND |
| SULU3 | DPRTRASDPQSPPQVSRHK (SEQ ID NO:116) | 411–429 | KLH | ND | ND |
| PAK4 | CLVPLIQLYRKQTSTC (SEQ ID NO:117) | 666–680 | KLH | ND | Y |
| PAK5 | PLMRQNRTR (SEQ ID NO:118) | 390–398 | KLH | Y | Y |
| PAK5 | SGDRRRAGPEKRPKSS (SEQ ID NO:119) | 148–163 | KLH | Y | Y |
| PAK5 | (C) RRKSLVGTPYWMAPE (SEQ ID NO:120) | 471–485 | KLH | Y | ND |

ND = not done yet

STE20-Related Protein Kinase GST Fusion Protein Immunogens and Their Specificity in Recognizing Endogenous Protein by Western Blots or Immunoprecipitations.

| Protein | domain | Aa positions | West. | IP |
|---|---|---|---|---|
| ZC1 | Coiled-coil/pro/B/C | 350–867 | Y | Y |
| ZC1 | B | 615–732 | Y | Y |
| ZC2 | Coiled-coil/pro/B | 348–762 | ND | ND |
| ZC2 | B | 658–762 | Y | Y |
| PAK4 | Nterm | 252–426 | ND | ND |
| PAK4 | Kinase/Cterm | 350–681 | ND | Y |
| PAK5 | A/ Nterm | 53–330 | ND | ND |
| PAK5 | A/Nterm | 53–309 | ND | ND |

ND = not done yet

The 50 kD STLK2 protein was expressed highly in several hematopoietic cell lines including Jurkat, pGL10, Ramos, A20, WEHI-231, K562, HEL and freshly isolated thymocytes from C57/BL6 mice. High levels of STLK2 expression were also detected in several tumor cell lines including Calu6, Colo205, LS180, MDAM231 and A549.

The 160 kD ZC1 protein was detected in Jurkat T cells, Colo205, HCT116, RIE-1, 293T, MDAMB231, and SK-MEL28.

The 170 kD ZC2 protein was detected in SK-Mel28 and UACC-62.

Elevated levels of the 64 kD PAK5 protein were confirmed in the breast cancer cell lines MDA-231 and MCF-7, and in the lung cancer cell line A549.

Example 5

Recombinant Expression and Biological Assays for STE20-related Protein Kinases

Materials and Methods

Transient Expression of the Ste20-Related Kinases in Mammalian Cells

The pcDNA expression plasmids (10 μg DNA/100 mm plate) containing the STE20-related kinase constructs are introduced into 293 cells with lipofectamine (Gibco BRL). After 72 hours, the cells are harvested in 0.5 mL solubilization buffer (20 mM HEPES, pH 7.35, 150 mM NaCl, 10% glycerol, 1% Triton X-100, 1.5 mM $MgCl_2$, 1 mM EGTA, 2 mM phenylmethylsulfonyl fluoride, 1 μg/mL aprotinin). Sample aliquots were resolved by SDS polyacrylamide gel electrophoresis (PAGE) on 6% acrylamide/0.5% bisacrylamide gels and electrophoretically transferred to nitrocellulose. Non-specific binding was blocked by preincubating blots in Blotto (phosphate buffered saline containing 5% w/v non-fat dried milk and 0.2% v/v nonidet P-40 (Sigma)), and recombinant protein was detected using the various anti-peptide or anti-GST-fusion specific antisera.

In Vitro Kinase Assays

Three days after transfection with the STE20-related kinase expression contructs, a 10 cm plate of 293 cells was washed with PBS and solubilized on ice with 2 mL PBSTDS containing phosphatase inhibitors (10 mM $NaHPO_4$, pH 7.25, 150 mM NaCl, 1% Triton X-100, 0.5% deoxycholate, 0.1% SDS, 0.2% sodium azide, 1 mM NaF, 1 mM EGTA, 4 mM sodium orthovanadate, 1% aprotinin, 5 μg/mL leupeptin). Cell debris was removed by centrifugation (12000×g, 15 min, 4° C.) and the lysate was precleared by two successive incubations with 50 μL of a 1:1 slurry of protein A sepharose for 1 hour each. One-half mL of the cleared supernatant was reacted with 10 μL of protein A purified kinase-specific antisera (generated from the GST fusion protein or antipeptide antisera) plus 50 μL of a 1:1 slurry of protein A-sepharose for 2 hr at 4° C. The beads were then washed 2 times in PBSTDS, and 2 times in HNTG (20 mM HEPES, pH 7.5/150 mM NaCl, 0,1% Triton X-100, 10% glycerol).

The immunopurified kinases on sepharose beads were resuspended in 20 μL HNTG plus 30 mM $MgCl_2$, 10 mM $MnCl_2$, and 20 μCi [$\alpha^{32}P$]ATP (3000 Ci/mmol). The kinase reactions were run for 30 min at room temperature, and stopped by addition of HNTG supplemented with 50 mM EDTA. The samples were washed 6 times in HNTG, boiled 5 min in SDS sample buffer and analyzed by 6% SDS-PAGE followed by autoradiography. Phosphoamino acid analysis was performed by standard 2D methods on $^{32}P$-labeled bands excised from the SDS-PAGE gel.

Similar assays were performed on bacterially expressed GST-fusion constructs of the kinases.

ZC1 Assay buffer: 20 mM Tris pH 7.4, 200 mM NaCl, 0.5 mM DTT, 3 mM MgCl2, 0.3 mM MnCl2, 100μM 32PγATP.

Substrates: myelin basic protein (MBP) at 0.28 mg/mL and phosphorylated ZC1 peptide RTVGRRNTFIGT-PPYWMAPE (SEQ ID NO:121) at 17 M (bold underlined residue shows site of phosphorylation).

At higher concentrations of $MgCl_2$ (3 mM); the activity of ZC1 (both full-length and recombinant kinase domain) is up to 10-fold greater towards exogenous substrate MBP. In contrast, the autophosphorylation and the phosphorylation of the activation loop peptide substrate are both inhibited. Mn++ does not inhibit the autophosphorylation and the peptide phosphorylation by the truncated kinase domain form. However, both the MBP phosphorylation, Mn++-preferring activity AND the autophosphorylating, Mg++-preferring activity are eliminated with mutation of the ATP-binding lysine in ZC1 (Lys54Ala) indicating that both activities are attributable to the ZC1 kinase domain.

SULU1 Assay buffer: This buffer is identical to that for ZC1, except for 5 mM MgCl2. Under these conditions, other STE20 family members (PAK4, ZC1) were inhibited for autophosphorylation and required reducing the [Mn] to <0.3 mM for an efficient autophosphorylation reaction.

Substrates: MBP, phosvitin, or α-casein at 0.28 mg/mL.

PAK4, PAK5 Assay Buffer: 20 mM Hepes pH 7.2, 130 mM KCl, 10 mM MgCl2, 1 mM NaF 20 mM B-glycerolphosphate, 0.5 mM DTT, 50 μM ATP, 0.5 μCi $^{32}$PγATP.

Substrates: MBP at 0.28 mg/mL and peptide substrates derived from PAK5 activation loop at 2.5 μM.

STLK2 Assay buffer: Similar to that described above, except for the inclusion of 5 mM $MgCl_2$, 5 mM $MnCl_2$ and 5 μCi $^{32}$PγATP.

Transformation (PAK Experiments)

Low-passage NIH3T3 fibroblasts displaying normal morphology (flat, non-refractile cellular morphology), as well as low rates of spontaneous transformation, were used in transformation assays. NIH3T3 cells were maintained in Dulbecco's modified Eagle's medium supplemented with 10% (v/v) fetal calf serum, penicillin (100 U/mL) and streptomycin (100 U/mL) and kept in an humidified incubator at 37° C. and 5% $CO_2$.

Cells were transfected with DNA-lipid complexes. As per manufacturer instructions, lipofectamine was utilized to transfect NIH3T3 cells. All transfections were with equal amounts of plasmid DNA (DNA from the appropriate expression vector without insert was used to give equivalent amounts of DNA per transfection). 1 μg of activated allele of H-Ras was co-transfected with increasing amounts of various alleles of PAK5.

Foci were scored after 3 weeks by fixing 10 min in 10% methanol, 10% acetic acid for 10 min, followed by staining with 0.4% (w/v) crystal violet in 10% methanol for 10 min and washing with deionized water and drying at room temperature.

Transfections, Stimulations, and Luciferase Assays (ZC1 Experiments)

Cells (107) were transiently transfected by electroporation using a Gene Pulser (Bio-Rad Labs) with the setting of 960° F. and 250 V. 20–40 hours later, transfected cells (about $10^5$) were stimulated with various stimuli. After a 6-hour stimulation, cells were lysed, and luciferase activities were measured using the MicroLumatPlus (EG&G Berthold). (J. Exp. Med. 183:611–620, 1996, hereby incorporated by reference herein in its entirety including any drawings, tables, or figures.)

RESULTS

| Protein expression and kinase activity of novel STE20-related protein kinases | | | | |
|---|---|---|---|---|
| Protein | Observed size (kD) | Predicted Size (kD) | In vitro Kinase activity | Endogenous Kinase activity |
| STLK2 | 50 | 46 | y | y |
| STLK4 | 55 | 50 | y | ND |
| ZC1 | 160 | 140 | y | y |
| ZC2 | 170 | 150 | y | y |
| KRS2 | ND | 101 | ND | ND |
| SULU1 | 119 | 105 | y | y |
| SULU3 | 140 | 115 | ND | Y |
| PAK4 | 80 | 75 | y | y |
| PAK5 | 64 | 64 | y | y |

ZC1: Regulation of Kinase Activity

ZC1 is constitutively active as a full-length kinase when expressed either in vitro (TNT rabbit reticulocyte system) or in NIH 3T3, 293T, or H1299 tissue culture cells. The endogenously expressed kinase is also active when immunoprecipitated from carcinoma cell lines.

ZC1 Signaling Pathways

Using human leukemic T cell line Jurkat as a model system, the impact of cotransfected wild-type ZC1 on the activation of two reporter genes, RE/AP-luciferase and NFκB luciferase, was examined. RE/AP is a composite in the IL-2 gene promoter containing both a NFκB-like site and an AP-1 site.

Optimal activation of both RE/AP-luciferase and NFκB-luciferase reporter genes in Jurkat T cells requires signals generated from stimulation of both T cell receptor and the costimulator receptor CD28. Cotransfection of wild-type ZC1 with either the RE/AP-luciferase or the NFκB-luciferase reporter results in the activation of RE/AP or NFκB when costimulated with the anti-T cell receptor monoclonal antibody or the pharmacological reagents PMA and ionomycin that bypass proximal T cell receptor. No activation was seen when costimulated with an anti-CD28 monoclonal antibody.

These results suggest that wild-type ZC1, when overexpressed, was replacing a CD28-specific signal to activate RE/AP or NFkB. These results imply that ZC1 is involved in the CD28 signaling pathway. Since NFκB is one of the major pathways also activated by the pro-inflammatory cytokine TNF-α signaling, it is also likely that ZC1 may be a component in the TNF-α signaling pathways.

PAK5: Design of Specific Peptide Substrates

To aid in the development of in vitro kinase assays for screening small molecule libraries to identify specific inhibitors, the search for specific peptide substrates for PAK5 was undertaken.

The rationale used to design such peptides is based on the hypothesis that upon binding activated small G protein, PAK5 undergoes a conformational change that results in derepression of its kinase activity followed by autophosphorylation on the activation loop resulting in a fully active kinase. The site of autophosphorylation for related family members has been identified by biochemical and/or genetic means (e.g. Wu, C, et al. J. Biol. Chem 270:15984–15992 and Szczepanowska, et al. Proc. Natl. Acad. Sci 94, 8503–8508, 1997). Specific peptide substrates for PAK5 were designed from the sequence of the activation loop of this kinase.

An activation loop PAK5 peptide phosphorylated on the Thr residue of the TPY motif served as a high-affinity substrate for PAK5.

PAK5 Activation Loop Peptides as Kinase Substrates

| Peptide # | Kinase | Sequence | Aa | SEQ ID | Kinase | substrate |
|---|---|---|---|---|---|---|
| 1 | PAK5 | (C)RRKSLVGTPYWMAPE | 471–485 | 120 | PAK5 | yes |
| 2 | PAK5 | (C)RRKSLVG<u>T</u>PYWMAPE | 471–485 | 120 | PAK5 | yes |
| 3 | PAK5 | (C)RRK<u>S</u>LVGTPYWMAPE | 471–485 | 120 | PAK5 | no |
| 4 | KHS1 | KRKSFIGTPYWMAPE | 171–185 | 122 | PAK5 | yes |
| 5 | STLK2 | KRNTFVGTPFWMAPE | 175–189 | 123 | PAK5 | poor |
| 6 | SULU1 | PANSFVGTPYWMAPE | 174–188 | 124 | PAK5 | poor |
| 7 | ZC1 | RRNTFIGTPYWMAPE | 184–198 | 125 | PAK5 | poor |
| 8 | ZC1 | RRNTFIG<u>T</u>PYWMAPE | 184–198 | 126 | PAK5 | poor |
| 9 | STLK4 | RNKVRKTFVGTPCWMAPE | 66–83 | 127 | PAKS | poor |
| 10 | PAK5 | (C)RRKSLVG<u>T</u>PYWMMAPE | 471–485 | 120 | PAK4 | yes |

Note: underlined/bold reside was phosphorylated

| Peptide # | Kinase | Notes |
|---|---|---|
| 1 | PAK5 | Equally well as MBB |
| 2 | PAK5 | High Km for PAK5 (1–10 μM) |
| 3 | PAK5 | S is the site of phosphorylation |
| 4 | KHS1 | Similar to peptide 1 |
| 5 | STLK2 | |
| 6 | SULU1 | |
| 7 | ZC1 | |
| 8 | ZC1 | Better than 7 |
| 9 | STLK4 | |
| 10 | PAK5 | Same Km as phosph. by PAK5 |

PAK5: Transformation

Transformation of low-passage NIH3T3 cells by ras in the presence or absence of various alleles of PAK5 showed that the dominant negative, kinase-dead allele of PAK5 was able to block ras transformation of NIH3T3 cells. Thus, PAK5 activity is required for ras transformation of NIH3T3 cells. Inhibition of PAK5 activity may have therapeutic value as an anti-proliferative agent for treating cancer.

PAK4 and PAK5: Interaction with Cdc42

PAK4 interacts with CDC42 small G-protein but not Rac, RhoA, or Ras as determined by co-transfection of recombinant genes and detection by kinase assays. PAK5 also interacts with Cdc42. Coding sequences of activated alleles of small G proteins (ras, Cdc42, Rac, Rho) tagged with a Myc epitope were transiently expressed in 293T cells, various alleles of 35S-labeled PAK5 tagged with HA epitope were expressed in vitro with the reticulocyte (TNT) system.

Example 6

Chromosomal Localization of Ste20-Related Protein Kinases

Materials And Methods

STE20 protein kinases STLK3, STLK4, ZC1, ZC2, ZC3, KHS2, SULU1, PAK4, and PAK5 were mapped using the GeneBridge 4 Radiation Hybrid Panel, RH02.05 (Research Genetics). The GeneBridge 4 Panel consists of 91 hybrid panel samples, in addition to one human positive control (HFL), and one hamster negative control (A23). The standard reaction conditions used to test and conduct PCR reactions using the GeneBridge 4 Panel are available from Research Genetics.

Oligonucleotide sequences (all 5' to 3') used for PCR mapping were:

STLK3: CTCCCATTTCCTAGCAAAATCA (SEQ ID NO: 128),

AGAGGCAGTATTGTCAGATGTA (SEQ ID NO:129)

STLK4: CCACACATGCGTATCTCTGTTG (SEQ ID NO:130),

TTGCTAGAATTCACATCAGGTACA (SEQ ID NO:131)

ZC1: ATCCCTGGATCACACTGCTTCT (SEQ ID NO:132),

CAAGGTGTTCTTTGCCTCTGTT (SEQ ID NO:133)

ZC2: AGATGGACTGTACTGGGAGGG (SEQ ID NO:134),

AGAAGAGCACTTGGCACTTATC (SEQ ID NO:135)

ZC3: CATCATGAACTGGTGACGGG (SEQ ID NO:136),

CCAGTGAAATCAAACCAGTAAAA (SEQ ID NO:137)

SULU1: CAAAACCTGGCCGTCTCTTCTATT (SEQ ID NO:138),

ATTTGTGCTACTGGGATTCTGTG (SEQ ID NO:139)

KHS2: GAATAGCGGTACCATGATAGAATA (SEQ ID NO:140),

TACCAAAAAGAGCCAAAAGTGTG (SEQ ID NO:141)

PAK4: CTCAGTATTCTCTCCAAAGATTG (SEQ ID NO:142),

GATGTTCTCTCCATTCTGTAAAG (SEQ ID NO:143)

PAK5: CATCACTGGAAGTCTGCAGTG (SEQ ID NO:144),

CAGGTGCAGTAGTCATTTGC (SEQ ID NO:145)

Positive reactions were assigned a score of "1", negative reactions are assigned a score of "0", and ambiguous reactions are assigned a score of "2". Results were submitted to the Whitehead Institute (www@genome.wi.mit.edu) for position analysis. Chromosomal localizations for ZC4, SULU3, STLK2, STLK5 and STLK6 were available publicly (for example, from Unigene). The chromosomal locations of GEK2 and STLK7 have not been determined.

| STLK2 h | Xq25–27.1 | (Public) |
| STLK3 | 2q31.3 | (Sugen) |
| STLK4 h | 3p22.3–p22.2 | (Sugen) |
| STLK5 h | 17q23.2–24.2 | (Public) |
| STLK6 h | 2q32.2–q33.3 | (Public) |
| STLK7 h | NA | |

-continued

| | | |
|---|---|---|
| ZC1 h | 2p11.2 | (Sugen) |
| ZC2 h | 3q26.31–3q26.32 | (Sugen) |
| ZC3 h | 17p13.2–13.3 | (Sugen) |
| ZC4 h | Xq22 | (Public) |
| KHS2 h | 2p22–2p22.2 | (Sugen) |
| SULU1 h | 12q24.21 | (Sugen) |
| SULU3 h | 17p11.2 | (Public) |
| GEK2 h | NA | |
| PAK4 h | 15q14 | (Sugen) |
| PAK5 h | 19q13.2–q13.3 | (Sugen) |

Many of the STE 20 kinases were mapped to regions associated with various human cancers, as shown below.

The regions were also cross-checked with the Mendalian Inheritance in Man database, which tracks genetic information for many human diseases, including cancer. References for association of the mapped sites with chromosomal abnormalities found in human cancer can be found in: Knuutila, et al., Am J Pathol, 1998, 152:1107–1123, hereby incorporated herein be reference in its entirety including any figures, tables, or drawings. Association of these mapped regions with other diseases is documented in the Online Mendalian Inheritance in Man (OMIM).

STLK2 h, Xq25-27.1, (Public)
Osteosarcoma, Xq25-qter, 2 of 31.
Lymphoproliferative syndrome, X-linked (OMIM No. 308240)
human STLK3, 2q31.3, (Sugen)
Squamous cell carcinoma of Head and Neck, 3 of 30.
STLK4 h, 3p22.3-p22.2, (Sugen)
Mantle cell lymphoma 3p14-p22 1 of 27
Squamous cell carcinoma of Head and Neck 3p22-p24 1 of 14
Cardiomyopathy, dilated (OMIM 601154)
STLK5 h, 17q23.2-24.2, (Public)
Cervical cancer, 17q, 1 of 30
Gastroesophageal junction adenocarcinoma xenograft, 17q, 1 of 5
Breast carcinoma, 17q12-qter, 1 of 16
Bladder carcinoma, 17q22-q23, 1 of 1
Breast carcinoma, 17q22-q25, 8 of 101
Non-small cell lung cancer, 17q24-q25, 6 of 50
Testis, 17q24-qter, 2 of 11
Malignant peripheral nerve sheath tumors, 17q24-qter, 5 of 7
Alzheimer disease, susceptibility to (OMIM 106180)
STLK6 h, 2q32.2-q33.3, (Public)
Non-small cell lung cancer, 2q31-q32, 1 of 50
Squamous cell carcinoma of Head and Neck, 2q31-q33, 3 of 30
Small cell lung cancer, 2q32-q35, 1 of 22
ZC1 h, 2p11.2, (Sugen)
non-small cell lung cancer, 2pter-q13, 1 of 10
non-small cell lung cancer, 2pter-q21, 1 of 10
Pulmonary alveolar proteinosis, congenital (OMIM 178640).
ZC2 h, 3q26.31-3q26.32, (Sugen)
Non-small cell lung cancer, 3q26.1-q26.3, 26 of 103
Cervical cancer, 3q26.1-q27, 4 of 30
Small cell lung cancer, 3q26.3-qter, 3 of 35
Squamous cell carcinoma of Head and Neck, 3q26.3-qter, 3 of 13
Marginal zone B-cell lymphoma, 3q26-q27, 1 of 25
Parosteal osteosarcoma, 3q26-q28, 1 of 1
Gastrointestinal stromal tumor, 3q26-q29, 1 of 16
Mantle cell lymphoma, 3q26-q29, 1 of 5
ZC3 h 17p13.2-13.3 (Sugen)
Malignant fibrous histiocytoma of soft tissue, 17p, 2 of 58
Leiomyosarcoma, 17p, 7 of 29
Non-small cell lung cancer, 17p, 1 of 50
ZC4 h, Xq22, (Public)
Diffuse large cell lymphoma, Xq22-ter, 1 of 32
Deafness, X-linked 1, progressive. (OMIM 304700).
KHS2 h, 2p22-2p22.2, (Sugen)
Synovial sarcoma, 2p21-q14, 1_of_67
Follicular lymphoma, 2p22-p24, 1_of_46
Colorectal cancer, hereditary, nonpolyposis, type 1,
Ovarian cancer (MSH2, COCA1, FCC1). (OMIM 120435).
SULU1h, 12q24.21 (Sugen)
Neuroglial tumors, 12q22-qter, 1_of_15
Gastroesophageal junction adenocarcinoma, 12q23-qter, 1 of 5.
Non-small cell lung cancer, 12q24.1-24.3, 2 of 50.
SULU3 h 17p11.2 (Public)
Malignant fibrous histiocytoma of soft tissue, 17p, 2_of_58
Leiomyosarcoma, 17p, 7_of_29
non-small cell lung cancer, 17p, 1_of_50
Diffuse large cell lymphoma, 17p11.2, 1_of_32
Osteosarcoma, 17p11.2-p12, 4_of_31
PAK4 h:15q14 (Sugen)
Schizophrenia, (OMIM 118511).
PAK5 h:19q13.2-q13.3 (Sugen)
Follicular lymphoma, 19q13, 1 of 46*
Mantle cell lymphoma, 19q13, 1 of 5
Hepatocellular carcinoma, 19q13.1, 2 of 50
Small cell lung cancer, 19q13.1, 10 of 35
Breast carcinoma, 19q13.1-qter, 1 of 33
cervical cancer, 19q13.1-qter, 1 of 30
Testis, 19q13.1-qter, 1 of 11
Chondrosarcoma, 19q13.2, 1 of 29
Malignant fibrous histiocytoma of soft tissue, 19q13.2-qter, 2 of 58
Non-small cell lung cancer, 19qcen-q13.3, 6 of 104.

Example 7

Demonstration of Gene Amplification by Southern Blotting

Materials and Methods

Nylon membranes were purchased from Boehringer Mannheim. Denaturing solution contains 0.4 M NaOH and 0.6 M NaCl. Neutralization solution contains 0.5 M Tris-HCL, pH 7.5 and 1.5 M NaCl. Hybridization solution contains 50% formamide, 6×SSPE, 2.5×Denhardt's solution, 0.2 mg/mL denatured salmon DNA, 0.1 mg/mL yeast tRNA, and 0.2% sodium dodecyl sulfate. Restriction enzymes were purchased from Boehringer Mannheim. Radiolabeled probes were prepared using the Prime-it II kit by Stratagene. The beta actin DNA fragment used for a probe template was purchased from Clontech.

Genomic DNA was isolated from 20 different tumor cell lines: MCF-7, MDA-MB-231, Calu-6, A549, HCT-15, HT-29, Colo 205, LS-180, DLD-1, HCT-116, PC3, CAPAN-2, MIA-PaCa-2, PANC-1, AsPc-1, BxPC-3, OVCAR-3, SKOV3, SW 626 and PA-1, and from two normal cell lines: human mammary epithelial cells and human umbilical vein endothelial cells.

A 10 µg aliquot of each genomic DNA sample was digested with EcoRI restriction enzyme and a separate 10 µg sample was digested with HindIII restriction enzyme. The restriction-digested DNA samples were loaded onto a 0.7% agarose gel and, following electrophoretic separation, the DNA was capillary-transferred to a nylon membrane by standard methods (Sambrook, J. et al (1989) Molecular Cloning: A Laboratory Manual, Cold Spring Harbor Laboratory).

PAK5 Amplicon:

A 600 base pair fragment (EcoRI-SacI) of the PAK5 gene was used as a template for a radiolabeled DNA probe which was hybridized to the blots at 42° C. for 48 hours in hybridization solution using standard methods (supra). The blots were exposed to a phosphorimager screen for 4 days, then scanned and analyzed using a Molecular Dynamics Storm 840 phosphorimager. The relative mass and gene copy number values of the PAK5 DNA fragments were calculated from the band density values obtained. The blots were re-hybridized with a radiolabeled probe copied from a fragment of human beta actin DNA and developed as above to confirm the sample mass loading equivalency.

RESULTS

The PAK5 gene was determined to exhibit 3-fold amplification compared to the normal DNA copy number in PANC-1 (pancreatic epithelioid carcinoma) and OVCAR-3 (ovarian adenocarcinoma) human cell lines, and approximately 2 times the normal copy number in the BxPC-3 (primary pancreatic adenocarcinoma) human cell line.

Similar Southern analyses can be performed for other STE20 kinases.

Example 8

Detection of Protein-protein Interaction Through Phage Display

Materials And Methods

Phage display provides a method for isolating molecular interactions based on affinity for a desired bait. cDNA fragments cloned as fusions to phage coat proteins are displayed on the surface of the phage. Phage(s) interacting with a bait are enriched by affinity purification and the insert DNA from individual clones is analyzed.

T7 Phage Display Libraries

All libraries were constructed in the T7Select1-1b vector (Novagen) according to the manufacturer's directions.

Bait Presentation

Protein domains to be used as baits were generated as C-terminal fusions to GST and expressed in E. coli. Peptides were chemically synthesized and biotinylated at the N-terminus using a long chain spacer biotin reagent.

Selection

Aliquots of refreshed libraries ($10^{10}$–$10^{12}$ pfu) supplemented with PanMix and a cocktail of E. coli inhibitors (Sigma P-8465) were incubated for 1–2 hrs at room temperature with the immobilized baits. Unbound phage was extensively washed (at least 4 times) with wash buffer.

After 3–4 rounds of selection, bound phage was eluted in 100 µL of 1% SDS and plated on agarose plates to obtain single plaques.

Identification of Insert DNAs

Individual plaques were picked into 25 µL of 10 mM EDTA and the phage was disrupted by heating at 70° C. for 10 min. 2 µL of the disrupted phage were added to 50 µL PCR reaction mix. The insert DNA was amplified by 35 rounds of thermal cycling (94° C., 50 sec; 50° C., 1 min; 72° C., 1 min).

Composition of Buffer

10×PanMix

5% Triton X100

10% non-fat dry milk (Carnation)

10 mM EGTA 250 mM NaF

250 µg/mL Heparin (sigma)

250 µg/mL sheared, boiled salmon sperm DNA (sigma)

0.05% Na azide

Prepared in PBS

Wash Buffer

PBS supplemented with:

0.5% NP-40

25 µl g/mL heparin

PCR Reaction Mix 1.0 mL 10×PCR buffer (Perkin-Elmer, with 15 mM Mg)

0.2 mL each dNTPs (10 mM stock)

0.1 mL T7UP primer (15 pmol/µL) GGAGCTGTCGTAT-TCCAGTC (SEQ ID NO:146)

0.1 mL T7DN primer (15 pmol/µL) AACCCCTCAA-GACCCGTTTAG (SEQ ID NO:147)

0.2 mL 25 mM $MgCl_2$ or $MgSO_4$ to compensate for EDTA

Q.S. to 10 mL with distilled water

Add 1 unit of Taq polymerase per 50 µL reaction

LIBRARY: T7 Select1-H441

RESULTS

Phage display baits and interactors

| Bait | Domain | Aa | Patent SEQ ID | CDNA library | Interactor | Sequence Range & SEQ ID |
|---|---|---|---|---|---|---|
| SULU1 | Coiled-coil2 | 752–898 | 22 | H441 | GEK2 cc dom (1) | 677–820 SEQ #26 |
| SULU3 | Coiled-coil2 | 755–898 | 23 | H441 | SLK isoform | M83780 |

(1) SULU1 ccl also interacted to a lesser extent with the coiled-coil domain of an SLK isoform.

The phage display data suggest potential interactions of SULU3 with SLK and SULU1 with GEK2 through their coiled-coil domains. Therefore two members of the SULU subfamily of STE20 kinases interact with two members of a separate STE20 family, the prototype being SLK.

These results suggest a specificity in the interaction, and imply that these STE20 kinases may interact with each other through homo- and hetero-dimerization. Alternatively SULU-related kinases could act immediately up- or downstream of the SLK-related kinases in a signaling cascade.

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed.

In particular, although some formulations described herein have been identified by the excipients added to the formulations, the invention is meant to also cover the final formulation formed by the combination of these excipients. Specifically, the invention includes formulations in which one to all of the added excipients undergo a reaction during formulation and are no longer present in the final formulation, or are present in modified forms.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

Other embodiments are within the following claims.

What is claimed is:

1. An isolated, enriched, or purified PAK5 polypeptide fragment, in said fragment is the amino acid sequence SEQ ID NO: 30.

2. The PAK5 polypeptide fragment of claim 1, wherein said polypeptide fragment is isolated, purified, or enriched from a mammal.

3. The PAK5 polypeptide fragment of claim 2, wherein said mammal is a human.

4. A PAK5 polypeptide fragment consisting of at least 12 contiguous amino acid residues of the polypeptide fragment of claim 1.

5. A PAK5 polypeptide fragment consisting of at least 15 contiguous amino acid residues of the polypeptide fragment of claim 1.

6. A PAK5 polypeptide fragment consisting of at least 20 contiguous amino acid residues of the polypeptide fragment of claim 1.

7. A PAK5 polypeptide fragment consisting of at least 30 contiguous amino acid residues of the polypeptide fragment of claim 1.

8. A PAK5 polypeptide fragment consisting of at least 120 contiguous amino acid residues of the polypeptide fragment of claim 1.

9. A PAK5 polypeptide fragment consisting of at least 125 contiguous amino acid residues of the polypeptide fragment of claim 1.

10. A PAK5 polypeptide fragment consisting of at least 130 contiguous amino acid residues of the polypeptide fragment of claim 1.

11. A PAK5 polypeptide fragment consisting of at least 200 contiguous amino acid residues of the polypeptide fragment of claim 1.

12. A PAK5 polypeptide fragment consisting of at least 300 contiguous amino acid residues of the polypeptide fragment of claim 1.

13. A PAK5 polypeptide fragment consisting of amino acid residues 1–114 of the polypeptide fragment of claim 1.

14. A PAK5 polypeptide fragment consisting of amino acid residues 115–379 of the polypeptide fragment of claim 1.

15. A PAK5 polypeptide fragment consisting of amino acid residues 380–398 of the polypeptide fragment of claim 1.

* * * * *